United States Patent
Lee et al.

(10) Patent No.: US 10,508,088 B2
(45) Date of Patent: Dec. 17, 2019

(54) METHODS USING HDAC11 INHIBITORS

(71) Applicant: FORMA Therapeutics, Inc., Watertown, MA (US)

(72) Inventors: Jennifer Lee, Arlington, MA (US); Nicholas Barczak, Waterford, CT (US); Jaime A. Escobedo, Natick, MA (US); Chiara Conti, Belmont, MA (US); Bingsong Han, Westwood, MA (US); David R. Lancia, Jr., Boston, MA (US); Cuixian Liu, Madison, CT (US); Matthew W. Martin, Arlington, MA (US); Pui Yee Ng, Waltham, MA (US); Aleksandra Rudnitskaya, Roslindale, MA (US); Jennifer R. Thomason, Clinton, MA (US); Xiaozhang Zheng, Lexington, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/202,207

(22) Filed: Nov. 28, 2018

(65) Prior Publication Data

US 2019/0084945 A1 Mar. 21, 2019

Related U.S. Application Data

(63) Continuation of application No. 15/789,869, filed on Oct. 20, 2017, now abandoned.
(Continued)

(51) Int. Cl.
| | | |
|---|---|---|
| *C07D 263/58* | (2006.01) |
| *A61P 35/00* | (2006.01) |
| *A61K 31/403* | (2006.01) |
| *A61K 31/404* | (2006.01) |
| *A61K 31/4178* | (2006.01) |
| *A61K 31/4184* | (2006.01) |
| *A61K 31/4188* | (2006.01) |
| *A61K 31/4192* | (2006.01) |
| *A61K 31/422* | (2006.01) |
| *A61K 31/423* | (2006.01) |
| *A61K 31/4245* | (2006.01) |
| *A61K 31/427* | (2006.01) |
| *A61K 31/428* | (2006.01) |
| *A61K 31/435* | (2006.01) |
| *A61K 31/437* | (2006.01) |
| *A61K 31/438* | (2006.01) |
| *A61K 31/4439* | (2006.01) |
| *A61K 31/4709* | (2006.01) |
| *A61K 31/4985* | (2006.01) |
| *A61K 31/506* | (2006.01) |

(Continued)

(52) U.S. Cl.
CPC ......... *C07D 263/58* (2013.01); *A61K 31/403* (2013.01); *A61K 31/404* (2013.01); *A61K 31/4178* (2013.01); *A61K 31/4184* (2013.01); *A61K 31/4188* (2013.01); *A61K 31/4192* (2013.01); *A61K 31/422* (2013.01); *A61K 31/423* (2013.01); *A61K 31/427* (2013.01); *A61K 31/428* (2013.01); *A61K 31/4245* (2013.01); *A61K 31/435* (2013.01); *A61K 31/437* (2013.01); *A61K 31/438* (2013.01); *A61K 31/4439* (2013.01); *A61K 31/4709* (2013.01); *A61K 31/4985* (2013.01); *A61K 31/506* (2013.01); *A61K 31/52* (2013.01); *A61K 31/5377* (2013.01); *A61K 31/5383* (2013.01); *A61K 45/06* (2013.01); *A61P 35/00* (2018.01); *C07C 53/06* (2013.01); *C07D 209/40* (2013.01); *C07D 209/54* (2013.01); *C07D 221/20* (2013.01); *C07D 235/30* (2013.01); *C07D 277/82* (2013.01); *C07D 401/04* (2013.01); *C07D 401/06* (2013.01); *C07D 401/14* (2013.01); *C07D 403/04* (2013.01); *C07D 403/06* (2013.01); *C07D 405/04* (2013.01); *C07D 413/06* (2013.01); *C07D 413/12* (2013.01); *C07D 413/14* (2013.01); *C07D 417/06* (2013.01); *C07D 473/00* (2013.01); *C07D 487/04* (2013.01); *C07D 491/056* (2013.01); *C07D 491/107* (2013.01); *C07D 498/04* (2013.01)

(58) Field of Classification Search
None
See application file for complete search history.

(56) References Cited

U.S. PATENT DOCUMENTS

| | | |
|---|---|---|
| 2005/0159347 A1 | 7/2005 | DiMartino |
| 2011/0160399 A1 | 6/2011 | Nagase et al. |

(Continued)

FOREIGN PATENT DOCUMENTS

| | | |
|---|---|---|
| CN | 105131082 A | 12/2015 |
| WO | WO-2005/071079 A1 | 8/2005 |

(Continued)

OTHER PUBLICATIONS

American Cancer Society, Cancer Facts & Figures, 7 pages 2016. URL: www.cancer.org/acs/groups/content/@research/documents/document/acspc-047079.pdf [Retrieved Aug. 2, 2018].
(Continued)

*Primary Examiner* — Heidi Reese
(74) *Attorney, Agent, or Firm* — Choate, Hall & Stewart LLP; Michael A. Shinall; Nicholas J. Pace

(57) ABSTRACT

The present invention provides methods and uses of inhibitors of histone deacetylase 11 (HDAC11) in the treatment of diseases and/or disorders, such as, for example, cell proliferative diseases.

11 Claims, 17 Drawing Sheets

Specification includes a Sequence Listing.

Related U.S. Application Data

(60) Provisional application No. 62/410,767, filed on Oct. 20, 2016, provisional application No. 62/410,766, filed on Oct. 20, 2016, provisional application No. 62/410,768, filed on Oct. 20, 2016.

(51) Int. Cl.

| | |
|---|---|
| *A61K 31/52* | (2006.01) |
| *A61K 31/5377* | (2006.01) |
| *A61K 31/5383* | (2006.01) |
| *A61K 45/06* | (2006.01) |
| *C07C 53/06* | (2006.01) |
| *C07D 209/40* | (2006.01) |
| *C07D 209/54* | (2006.01) |
| *C07D 221/20* | (2006.01) |
| *C07D 235/30* | (2006.01) |
| *C07D 277/82* | (2006.01) |
| *C07D 401/04* | (2006.01) |
| *C07D 401/06* | (2006.01) |
| *C07D 401/14* | (2006.01) |
| *C07D 403/04* | (2006.01) |
| *C07D 403/06* | (2006.01) |
| *C07D 405/04* | (2006.01) |
| *C07D 413/06* | (2006.01) |
| *C07D 413/12* | (2006.01) |
| *C07D 413/14* | (2006.01) |
| *C07D 417/06* | (2006.01) |
| *C07D 473/00* | (2006.01) |
| *C07D 487/04* | (2006.01) |
| *C07D 491/056* | (2006.01) |
| *C07D 491/107* | (2006.01) |
| *C07D 498/04* | (2006.01) |

(56) References Cited

U.S. PATENT DOCUMENTS

| | | |
|---|---|---|
| 2011/0237663 A1 | 9/2011 | Mascagni et al. |
| 2014/0039059 A1 | 2/2014 | Oldoni et al. |
| 2014/0045850 A1 | 2/2014 | Mallais et al. |
| 2016/0222026 A1 | 8/2016 | Deziel et al. |
| 2018/0127386 A1 | 5/2018 | Lee et al. |
| 2019/0084946 A1 | 3/2019 | Lee et al. |

FOREIGN PATENT DOCUMENTS

| | | |
|---|---|---|
| WO | WO-2007/038073 A2 | 4/2007 |
| WO | WO-2010/034693 A1 | 4/2010 |
| WO | WO-2014/096386 A1 | 6/2014 |
| WO | WO-2018/075959 A1 | 4/2018 |

OTHER PUBLICATIONS

Buglio, D. et al., HDAC11 plays an essential role in regulating OX40 ligand expression in Hodgkin lymphoma, Blood, 117(10): 2910-2917 (2011).

Cheng, F. et al., Divergent Roles of Histone Deacetylase 6 (HDAC6) and Histone Deacetylase 11 (HDAC11) on the Transcriptional Regulation of IL10 in Antigen Presenting Cells, Mol Immunol., 60(1):44-53 (2014).

Deubzer, H. et al., HDAC11 is a novel drug target in carcinomas, Int J Cancer, 132(9): 2200-2208 (2013).

Dokmanovic, M. et al., Histone Deacetylase Inhibitors: Overview and Perspectives, Mol Cancer Res., 981-989 (2007).

Ganai, S. et al., Histone deacetylase inhibitor pracinostat in doublet therapy: a unique strategy to improve therapeutic efficacy and to tackle herculean cancer chemoresistance, Pharmaceutical Biology, 54(9): 1926-1935 (2016).

Gao, L. et al., Cloning and Functional Characterization of HDAC11, a Novel Member of the Human Histone Deacetylase Family, J Biol Chem., 277(28): 25748-25755 (2002).

Gobert, M. et al., Regulatory T Cells Recruited through CCL22/CCR4 Are Selectively Activated in Lymphoid Infiltrates Surrounding Primary Breast Tumors and Lead to an Adverse Clinical Outcome, Cancer Res., 69: 2000-2009 (2009).

International Search Report for Ganai, S. et al., Histone deacetylase inhibitor pracinostat in doublet therapy: a unique strategy to improve therapeutic efficacy and to tackle herculean cancer chemoresistance, Pharmaceutical Biology, 54(9): 1926-1935 (2016)., 6 pages, ISA/US (dated Feb. 12, 2018).

Joshi, P. et al., The functional interactome landscape of the human histone deacetylase family, Molecular Systems Biology, 9(672): 1-21 (2013).

Lozada, E.M. et al., Acetylation and deacetylation of Cdc25A constitutes a novel mechanism for modulating Cdc25A functions with implications for cancer, Oncotarget, 7(15): 20425-20439 (2016).

Martin, M.W et al., Discovery of novel N-hydroxy-2-arylisoindoline-4-carboxamides as potent and selective inhibitors of HDAC11, Bioorganic & Medicinal Chemistry Letters, 28(12): 2143-2147 (2018).

Sahakian, E. et al., Histone deacetylase 11: A novel epigenetic regulator of myeloid derived suppressor cell expansion and function, Mol Immunol., 63(2): 579-85 (2015).

Sonbol, M.B. et al., Comprehensive review of JAK inhibitors in myeloproliferative neoplasms, Ther Adv Hematol., 4(1): 15-35 (2013).

Villagra, A. et al., The histone deacetylase HDAC11 regulates the expression of interleukin 10 and immune tolerance, Nat Immunol., 10(1): 92-100 (2009).

Watanabe, Y. et al., Dendrite Development Regulated by the Schizophrenia-Associated Gene FEZ1 Involves the Ubiquitin Proteasome System, Cell Rep., 7(2): 552-564 (2014).

Weina, K. et al., SOX2 and cancer: current research and its implications in the clinic, Clin and Translational Med., 3(19): 1-10 (2014).

Wong, et al., Chromatin unfolding by Cdt1 regulates MCM loading via opposing functions of HBO1 and HDAC11-geminin, Cell Cycle., 9(21): 4351-63 (2010).

Written Opinion for PCT/US2017/057715, 9 pages, ISA/US (dated Feb. 12, 2018).

Zdanov, S. et al., Mutant KRAS conversion of conventional T cells into regulatory T cells, Cancer Immunol Res., 38 pages (Feb. 15, 2016), URL: http://cancerimmunolres.aacrjournals.org/content/early/2016/02/13/2326-6066.CIR-15-0241 [Retrieved Aug. 2, 2018].

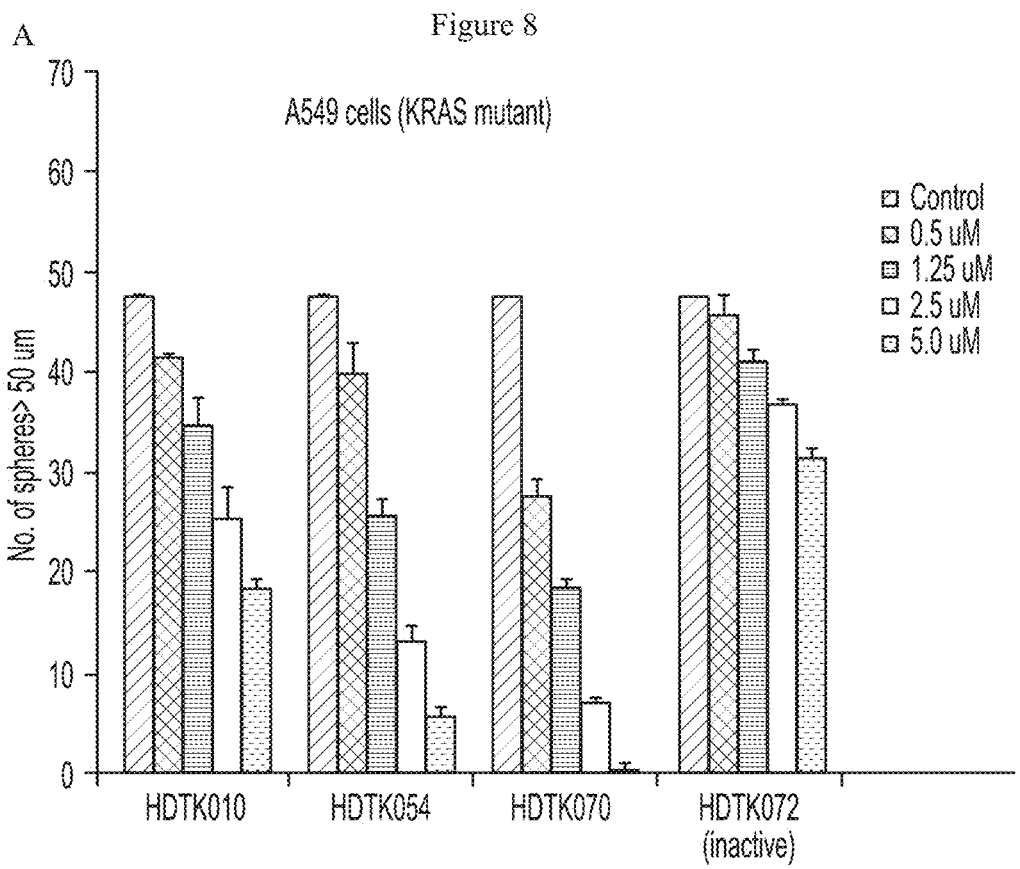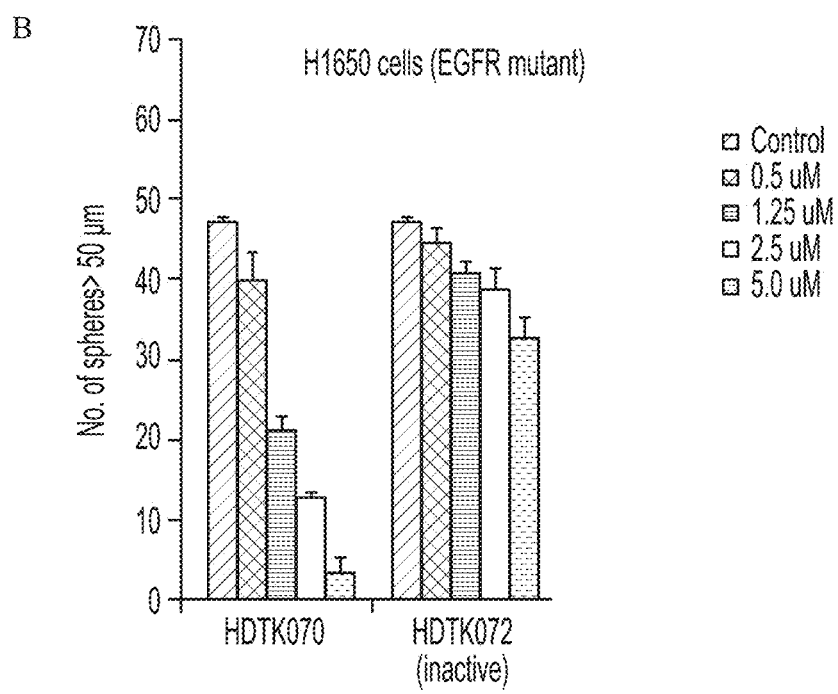
Figure 8

Figure 12
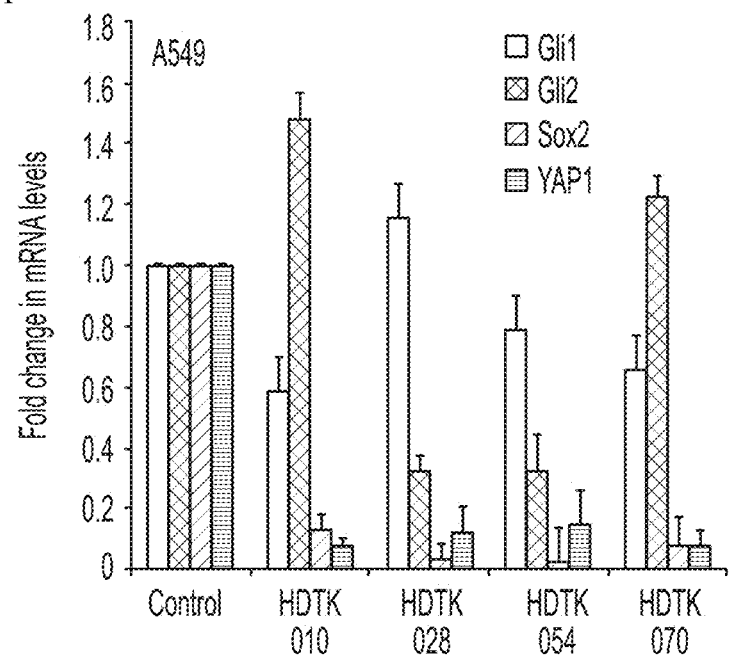
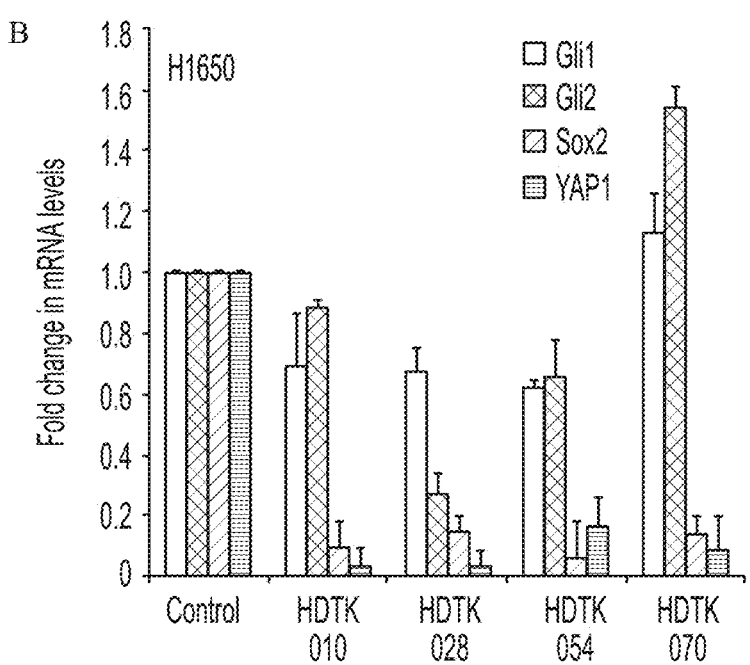

Figure 15

| HDTK # | Name | Structure |
|---|---|---|
| HDTK010 | 3-((5,6-dichlorobenzo[d]oxazol-2-yl)amino)-N-hydroxybenzamide | 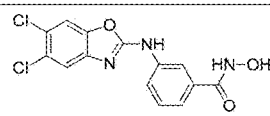 |
| HDTK028 | N-hydroxy-1,1-dimethyl-2-(6-(trifluoromethyl)-1H-benzo[d]imidazol-2-yl)isoindoline-4-carboxamide | 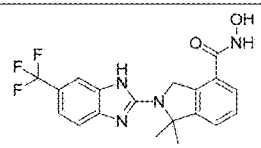 |
| HDTK029 | 1'-(4-chloro-3-(trifluoromethyl)benzyl)-N-hydroxy-2'-oxo-1,3-dihydrospiro[indene-2,3'-pyrrolidine]-4-carboxamide | 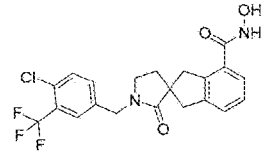 |
| HDTK054 | (S)-1'-(4-chloro-3-(trifluoromethyl)benzyl)-N-hydroxy-2'-oxo-1,3-dihydrospiro[indene-2,3'-pyrrolidine]-4-carboxamide | 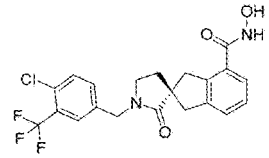 |
| HDTK070 | N-hydroxy-1,1-dimethyl-2-(5-(trifluoromethyl)pyrazin-2-yl)isoindoline-4-carboxamide | 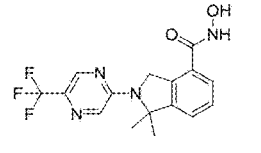 |

METHODS USING HDAC11 INHIBITORS

CROSS REFERENCE TO RELATED APPLICATIONS

This application is a continuation of U.S. application Ser. No. 15/789,869 filed Oct. 20, 2017, which claims the benefit of U.S. Provisional Application Ser. No. 62/410,766 filed Oct. 20, 2016, 62/410,767 filed Oct. 20, 2016, and 62/410,768 filed Oct. 20, 2016, the contents of all of which are hereby incorporated by reference in their entirety.

REFERENCE TO SEQUENCE LISTING

This application contains a Sequence Listing which has been submitted electronically in ASCII format and is hereby incorporated by reference in its entirety. Said ASCII copy, created, Oct. 19, 2017, is named FOTH039_ST25.txt and is 10.6 KB in size.

FIELD OF THE INVENTION

The present invention relates to inhibitors of histone deacetylase 11 (HDAC11) useful in the treatment of certain diseases and/or disorders, including diseases and disorders associated with cell proliferation (e.g., cancers) and/or diseases and disorders associated with increased expression of genes associated with stem cell activity. The present disclosure provides, at least in part, methods and compositions for treating or preventing diseases and/or disorders that include a HDAC11 inhibitor.

BACKGROUND OF THE INVENTION

Diseases associated with cell proliferation, such as cancer, remain a serious public health problem. For example, about 595,690 people in the United States of America are expected to die of cancer in 2016 alone according to the American Cancer Society, Cancer Facts & Figures 2016 (www.cancer.org/acs/groups/content/@research/documents/document/acspc-047079.pdf). While many targets have been identified as associated with certain cancers, it has been challenging to develop selective therapies. Accordingly, there remains a need for effective, safe and selective methods of treating diseases and/or disorders associated with cell proliferation.

BRIEF SUMMARY OF THE INVENTION

The present disclosure provides compounds and methods for treatment or prevention of diseases and/or disorders associated with cell proliferation and/or associated with amplification of genes associated with stem cell activity. The present disclosure encompasses the recognition that HDAC11 inhibitors may have potential benefit for treatment of diseases and/or disorders associated with cell proliferation and/or associated with activation (e.g., amplification) of genes associated with stem cell activity. In some embodiments, a disease or disorder associated with cell proliferation and/or associated with activation (e.g., amplification) of genes associated with stem cell activity is a cancer.

Cancers for treatment with a HDAC11 inhibitor include, but are not limited to, gastro-intestinal cancers, nervous system cancers, esophageal squamous cell carcinomas, oral squamous cell carcinomas, skin cancers, lung cancers, breast cancers, squamous cell carcinomas, lung adenocarcinomas, non-small cell lung cancer, small cell lung cancer, prostate cancers, sinonasal cancers, leukemias, lymphomas (Hodgkin's and non-Hodgkin's), myelomas and myeloproliferative disorders. In some embodiments, a cancer is associated with activation of JAK/STAT signaling. In some embodiments, a cancer is associated with activation of a Signal Transducer and Activator of Transcription (STAT), such as, for example, STAT1, STAT2, STAT3, STAT4, STAT5 (STAT5A and STAT5B), and/or STAT6. In some embodiments, activation of a STAT transcription factor is associated with an increase in gene expression and/or a decrease in protein phosphorylation. In some embodiments, a cancer is associated with activation of STAT3. In some certain embodiments, a cancer associated with activation of STAT3 is breast cancer. In some embodiments, a cancer is associated with activation of SRY (sex determining region Y)-box 2 (SOX2). In some embodiments, activation of SOX2 is an increase in SOX2 gene expression.

The present disclosure provides methods of treating cancer, wherein one or more cancer cells exhibit stem cell-like properties. In some embodiments, methods comprise administering to a patient in need thereof an effective amount of a HDAC11 inhibitor. In some embodiments, one or more cancer cells that exhibit stem cell-like properties is associated with increased expression (e.g., gene amplification) or activity of a marker for a cancer stem cell. In some embodiments, a marker for a cancer stem cell is activation of one or more components of a JAK/STAT signaling pathway. In some embodiments, a marker for a cancer stem cell is increased expression (e.g., gene amplification) or activity of SOX2. In some embodiments, a marker for a cancer stem cell is increased expression (e.g., gene amplification) or activity of STAT3.

In some embodiments, the present disclosure provides methods of treating diseases and/or disorders associated with HDAC11. Diseases and/or disorders associated with HDAC11 include, e.g., cell proliferation diseases or disorders having cancer cells that exhibit cancer stem cell properties and/or are associated with amplification of genes associated with cancer stem cell activity.

In some embodiments, a disease and/or disorder for treatment with a HDAC11 inhibitor is a myeloproliferative neoplasm (MPN). In some embodiments, MPNs for treatment with a HDAC11 inhibitor include, but are not limited to, polycythemia vera (PV), essential thrombocythemia (ET) and primary myelofibrosis (PMF).

In some embodiments, a cell responsive to treatment with a HDAC11 inhibitor is a cancer stem cell (CSC). In some embodiments, a cell responsive to treatment with a HDAC11 inhibitor is cell associated with expression of a CSC marker. In some embodiments, a CSC marker is activation of one or more components of a JAK/STAT signaling pathway (e.g., SOX2 and/or STAT3).

In some embodiments, the present disclosure provides a method of inhibiting and/or reducing proliferation of a stem cell-like cancer cell in a patient having cancer, comprising administering to a HDAC11 inhibitor as described herein to the patient. In some embodiments, a stem cell-like cancer is associated with activation of JAK/STAT signaling. In some embodiments, a stem cell-like cancer is associated with a gene amplification of SOX2. In some embodiments, a stem cell-like cancer is associated with activation of STAT3.

In some embodiments, a cancer is a lung cancer (e.g., adenocarcinoma of the lung, NSCLC), a hematological cancer (e.g., a leukemia, a lymphoma, a myeloma and a myeloproliferative disorder), a skin cancer, a breast cancer, a squamous cell carcinoma, a gastro-intestinal cancer (e.g., esophageal cancer, gastric cancer), a uterine cancer, a prostrate cancer and/or a nervous system cancer.

In some embodiments, the present disclosure provides a method of treating a hematological cancer comprising administering to a patient an effective amount of a HDAC11 inhibitor. In some embodiments, a hematological cancer is a myeloproliferative disorder, a lymphoma, a leukemia, and/or myeloma. In some embodiments, a hematological cancer is a myeloproliferative disorder. In certain embodiments, a myeloproliferative disorder is polycythemia vera, essential thrombocythemia, myelofibrosis, chronic myelogenous leukemia, chronic neutrophilic leukemia, chronic eosinophilic leukemia, or mastocytosis.

In some embodiments, a HDAC11 inhibitor is a siRNA, a shRNA, an antibody agent, or a chemical compound (e.g., a small molecule). In some embodiments, a HDAC11 inhibitor is a chemical compound that is a small molecule. In some embodiments, a small molecule HDAC11 inhibitor is at least 10-fold selective for the inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In some embodiments, a small molecule HDAC11 inhibitor is at least 10-fold selective for the inhibition of HDAC11 over each of HDAC1, HDAC2, HDAC3, HDAC4, HDAC5, HDAC6, HDAC7, HDAC8, HDAC9 and HDAC10. In some embodiments, a HDAC11 inhibitor is specific for human HDAC11.

The present disclosure also encompasses the recognition that inhibition of HDAC11 may be beneficial for treatment or prevention of inflammatory and/or autoimmune diseases. In some embodiments, a disease or disorder for treatment with a HDAC11 inhibitor is an immune or inflammatory disorder, which may be acute or chronic. In some embodiments, a disease or disorder for treatment with a HDAC11 inhibitor is inflammatory bowel disease, psoriasis, rheumatoid arthritis, multiple sclerosis, and/or Alzheimer's disease.

In some embodiments, methods described herein may include administration of one, two, three or more HDAC11 inhibitors.

In some embodiments, methods described herein may further include administering a JAK2 inhibitor to a patient in need thereof. In some embodiments, a JAK2 inhibitor is a siRNA, a shRNA, an antibody agent, or a chemical compound. In certain embodiments, a JAK2 inhibitor is JAK2 inhibitor is ruxolitinib, baricitinib, CYT387, lestaurtinib, or pacritinib.

In some embodiments, a HDAC11 inhibitor is administered to a patient that has been or will be administered a JAK2 inhibitor, such that the patient receives treatment with both. In some embodiments, a JAK2 inhibitor is administered to a patient that has been or will be administered a HDAC11 inhibitor, such that the patient receives treatment with both.

In some embodiments, the present disclosure provides a method of treating a patient having a myeloproliferative disorder that include administering to a patient in need thereof a HDAC11 inhibitor and a JAK2 inhibitor. In some embodiments, a myeloproliferative disorder is polycythemia vera, essential thrombocythemia, myelofibrosis, chronic myelogenous leukemia, chronic neutrophilic leukemia, chronic eosinophilic leukemia, or mastocytosis.

In some embodiments, methods described herein may further comprise administering a hedgehog pathway inhibitor to the patient. In some embodiments, a hedgehog pathway inhibitor is vismodegib, erismodegib, BMS-833923, glasdegib, taladegib, or saridegib. In some embodiments, a HDAC11 inhibitor is administered to a patient that has been or will be administered a hedgehog pathway inhibitor, such that the patient receives treatment with both. In some embodiments, a hedgehog pathway inhibitor is administered to a patient that has been or will be administered a HDAC11 inhibitor, such that the patient receives treatment with both.

In certain embodiments, a HDAC11 inhibitor is a siRNA, a shRNA, an antibody agent, or a chemical compound. In some embodiments, a chemical compound is a small molecule that is at least 10-fold selective for the inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10).

In some embodiments, the present disclosure provides a method for treating a patient having a myeloproliferative disorder resistant to a JAK2 inhibitor, where the method includes administering a HDAC11 inhibitor to the patient. In some embodiments, a myeloproliferative disorder is polycythemia vera, essential thrombocythemia, myelofibrosis, chronic myelogenous leukemia, chronic neutrophilic leukemia, chronic eosinophilic leukemia, or mastocytosis.

In certain embodiments, the HDAC11 inhibitor is a siRNA, a shRNA, an antibody agent, or a chemical compound. In some embodiments, a chemical compound is a small molecule that is at least 10-fold selective for the inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10).

In some embodiments, the present disclosure provides a method of treating a patient having a myeloproliferative disorder, where the method includes administering to a patient a HDAC11 inhibitor and a hedgehog pathway inhibitor. In some embodiments, a myeloproliferative disorder is polycythemia vera, essential thrombocythemia, myelofibrosis, chronic myelogenous leukemia, chronic neutrophilic leukemia, chronic eosinophilic leukemia, or mastocytosis. In certain embodiments, a HDAC11 inhibitor is a siRNA, a shRNA, an antibody agent, or a chemical compound. In some embodiments, a chemical compound is a small molecule that is at least 10-fold selective for the inhibition of HDAC11 over other histone deacetylase isoforms (e.g., HDAC1, HDAC2, HDAC3, HDAC4, HDAC5, HDAC6, HDAC7, HDAC8, HDAC9 and/or HDAC10). In some embodiments, a hedgehog pathway inhibitor is vismodegib, erismodegib, BMS-833923, glasdegib, taladegib, or saridegib.

In some embodiments, the present disclosure provides a method of treating cancer wherein one or more cancer cells exhibit stem cell-like properties, where the method includes treating a patient with a first line therapy and administering to the patient a HDAC11 inhibitor, whereby any cancer cells surviving from the first line therapy are reduced or eliminated after treatment with the HDAC11 inhibitor.

In some embodiments, a cancer is a lung cancer (e.g., adenocarcinoma of the lung, NSCLC), a hematological cancer (e.g., a leukemia, a lymphoma, a myeloma and a myeloproliferative disorder), a skin cancer, a breast cancer, a squamous cell carcinoma, gastro-intestinal cancer (e.g., esophageal cancer, gastric cancer), a uterine cancer, a prostrate cancer and/or a nervous system cancer. In some embodiments, a cancer is esophageal squamous cell carcinoma, oral squamous cell carcinoma, lung squamous cell carcinoma, lung adenocarcinoma, non-small cell lung cancer, small cell lung cancer and/or sinonasal cancer. In certain embodiments, the cancer is breast cancer. In certain embodiments, a HDAC11 inhibitor is a siRNA, a shRNA, an antibody agent, or a chemical compound. In some embodiments, a chemical compound is a small molecule that is at least 10-fold selective for the inhibition of HDAC11 over other histone deacetylase isoforms (e.g., HDAC1, HDAC2, HDAC3, HDAC4, HDAC5, HDAC6, HDAC7, HDAC8, HDAC9 and/or HDAC10). In certain embodiments, a first line therapy is resection, radiation, and/or stem cell transplant.

In some embodiments, a HDAC11 compound used in accordance with the present disclosure is of Formulae I, I', or II, as defined herein.

In some embodiments, the present disclosure provides a compound of Formula I:

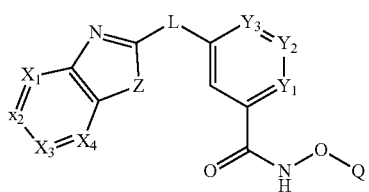

(I)

wherein each of $Y_1$, $Y_2$, $Y_3$, Q, L, Z, $X_1$, $X_2$, $X_3$, and $X_4$ is as defined herein.

In some embodiments, the present disclosure provides a compound of Formula I':

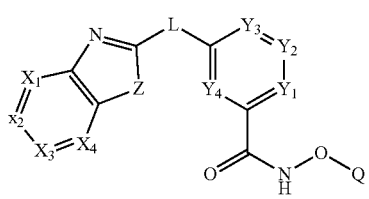

(I')

wherein each of $Y_1$, $Y_2$, $Y_3$, $Y_4$, Q, L, Z, $X_1$, $X_2$, $X_3$, and $X_4$ is as defined herein.

In some embodiments, the present disclosure provides a compound of Formula II:

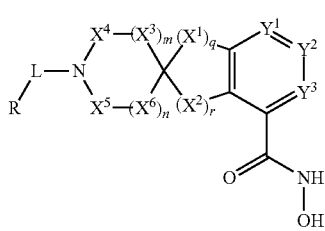

(II)

wherein each of $Y^1$, $Y^2$, $Y^3$, R, L, m, n, q, r, $X^1$, $X^2$, $X^3$, $X^4$, $X^5$, and $X^6$ is as defined herein.

BRIEF DESCRIPTION OF THE DRAWING

The Drawing included herein, which is composed of the following Figures, is for illustration purposes only and not for limitation.

FIG. 8 shows growth inhibition of (A) A549 and (B) H1650 stem-like cancer cells with increasing concentrations of HDAC11 inhibitors. For each sample: control—leftmost column, 0.5 µM—second column from left, 1.25 µM—third column from left (center), 2.5 µM—second column from right, 5.0 µM—rightmost column.

FIG. 12 shows that treatment with HDAC11 inhibitors resulted in decreased expression of SOX2 in (A) A549 and (B) H1650 cell lines. For control and each HDAC11 inhibitor, fold change in mRNA levels for each gene was measures: Gli1—leftmost column, Gli2—second column from left, Sox2—second column from right, YAP1—rightmost column.

FIG. 15 shows several exemplary HDAC11 inhibitors.

DETAILED DESCRIPTION

Figure 1:
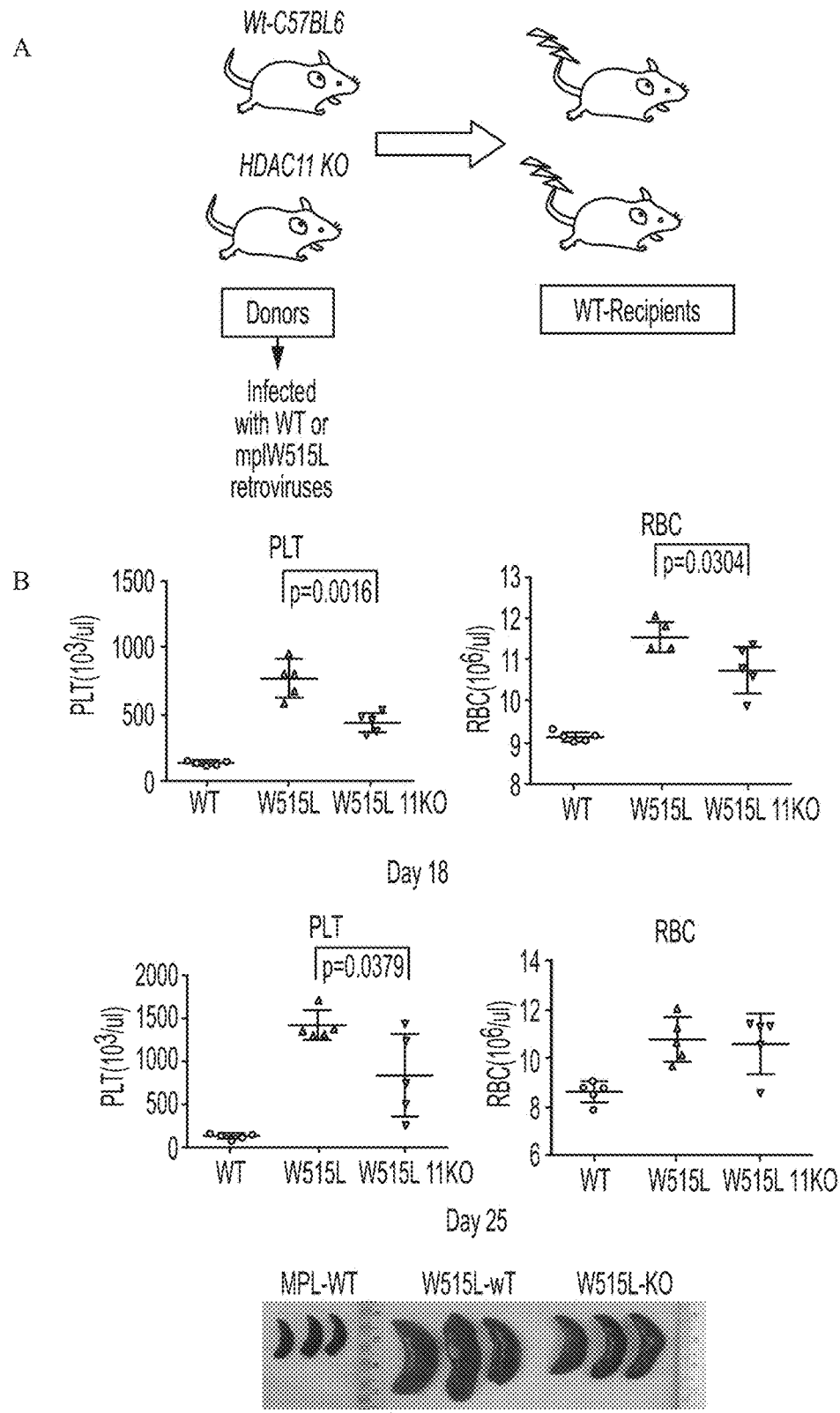
FIG. 1 shows that disease burden was reduced by HDAC11 deficiency in a bone marrow transplant MPN model. (A) depicts a schematic representation of the experimental protocol and (B) depicts platelet and red blood cell counts and images of spleens from mice.

HDAC11 interacts with or regulates RNA splicing-related proteins (e.g., SMN1, Dicer1, Gemin3, and Gemin4), cell cycle-related proteins (e.g., Cdt1, BubR1, and Cdc25), and immune cell signaling proteins (e.g., IL-10 and OX40 ligand). Accordingly, inhibition of HDAC11 can have downstream effects that can play a role in the development of certain diseases such as cell proliferative diseases. The present disclosure provides methods for using inhibitors of HDAC11 to treat cell proliferative diseases and disorders including MPNs, hematological malignancies, and solid tumor malignancies. The present disclosure also provides methods for using inhibitors of HDAC11 to treat cell proliferation diseases or disorders having cancer cells that exhibit cancer stem cell properties and/or are associated with amplification of genes associated with cancer stem cell activity (e.g., SOX2 and STAT3).

The present invention is based in part on the discovery that HDAC11 inhibitors prevent growth and survival of JAK2 and myeloproliferative leukemia gene (MPL) mutant cell lines and patient-derived samples. Furthermore, as discussed in detail herein, knockout of HDAC11 reduces thrombocytosis and erythrocytosis in a MPN model using MPL mutant bone marrow transplant mice. The present invention is also based in part on the discovery that HDAC11 inhibitors prevent the growth of stem cell-like cancer cells and also decrease the expression of certain stem cell transcription factors such as SOX2 and STAT3.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

Certain Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "inhibitor" as used herein encompasses molecules that block, inhibit, and/or decrease the expression or activity of HDAC11. As used herein, an inhibitor may be a polypeptide, polynucleotide, antibody, or a chemical compound. Examples of HDAC11 activity include deacetylase function and associating with a protein complex or transcription regulator, such as a promoter.

The phrases "interacts with" and "associates with" are used interchangeably herein to describe proteins that form a multi-protein complex via non-covalent interactions. In some embodiments, HDAC11 co-precipitates with a protein with which it is associated.

An "effective amount" when used in connection with an inhibitor is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent (e.g., HDAC11 inhibitor or JAK2 inhibitor) from one organ, or portion of the body, to another organ, or portion of the body of a subject.

The term "treating" with regard to a subject, refers to improving at least one symptom of the subject's disorder. Treating includes curing, improving, or at least partially ameliorating the disorder and/or symptoms related to the disorder.

The term "disorder" is used in this disclosure to mean, and is used interchangeably with, the terms disease, condition, or illness, unless otherwise indicated.

The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

The term "administer", "administering", or "administration" as used in this disclosure refers to either directly administering a therapeutic agent such as a compound or pharmaceutically acceptable salt of the compound or a composition to a subject, or administering a prodrug derivative or analog of the therapeutic agent to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more (e.g., 10, 9, 8, 7, 6, 5, 4, 3, 2, or 1) mismatches with respect to the target RNA. Variations at any location within the oligomer are included. In certain embodiments, variations in sequence near the termini of an oligomer are generally preferable to variations in the interior, and if present, are may be within about 10, 9, 8, 7, 6, 5, 4, 3, 2, or 1 nucleotides of the 5' and/or 3' terminus.

By "isolated" is meant a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, an isolated substance or entity is "pure". As used herein, a substance or entity is "pure" if it is substantially or essentially free from components that normally accompany it in its native state. In some embodiments, a substance and/or entity is about 80%, about 85%, about 90%, about 91%, about 92%, about 93%, about 94%, about 95%, about 96%, about 97%, about 98%, about 99%, or more than about 99% pure. For example, an "isolated polynucleotide" or "isolated oligonucleotide," as used herein, may refer to a polynucleotide that has been purified or removed from the sequences that flank it in a naturally-occurring state, e.g., a DNA fragment that has been removed from the sequences that are normally adjacent to the fragment. In another example, an "isolated polypeptide" or "isolated antibody," as used herein, may refer to a polypeptide (e.g., an antibody) that has been purified or removed from one or more components of its naturally-occurring environment.

The term "reduce" or "inhibit" may relate generally to the ability of one or more inhibitors of the invention to "decrease" a relevant biological activity or cellular response, such as catalytic activity or a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of MPNs. A "decrease" in a biological activity may be "statistically significant" as compared to the biological activity produced by no inhibitor or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

"Homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology," John Wiley & Sons Inc, 1994-1998, Chapter 15.

"dsRNA" refers to a ribonucleic acid molecule having a duplex structure comprising two complementary and antiparallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides. The term "dsRNA" also includes "siRNA" or short interfering RNA.

By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

A wild-type gene or gene product is that which is most frequently observed in a population and is thus arbitrarily designed the "normal" or "wild-type" form of the gene.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "alkylaryl" refers to aryl groups connected to an adjacent alkyl wherein the linkage is located at the alkyl end. A "($C_1$-$C_6$)alkylaryl" refers to a group that contains a $C_1$-$C_6$ alkyl group bonded to an aryl group. Accordingly, groups such as benzyl, phenylethyl, or mesitylenyl constitute exemplary representatives of alkylaryl of the present invention.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have a saturated, unsaturated or partially saturated ring fused with an aromatic ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have a saturated, unsaturated or partially saturated ring fused with an aromatic ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon containing 1-12 carbon atoms. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propanyl, n-butynyl, iso-butynyl, pentynyl, or hexynyl. An alkynyl group can be unsubstituted or substituted.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered non-aromatic rings containing carbon and heteroatoms taken from oxygen, phosphorous, nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The rings can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. A $C_5$-$C_{12}$ spirocycle is a spirocycle containing between 5 and 12 carbon atoms.

The term "spirocycloalkenyl" means a carbogenic bicyclic ring system containing 5-12 atoms with both ring systems connected through a single atom and wherein at least one ring contains a carbon-carbon double bond. The rings can be different in size and nature, or identical in size and nature. One or both rings may contain a double-bond. One or both of the rings in a spirocycloalkenyl can further be fused to another carbocyclic, heterocyclic, aromatic, or heteroaromatic ring.

The term "spirocyclic heterocycle," "spiroheterocyclyl," or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

Histone Deacetylases and HDAC11

Histone deacetylases (HDAC, EC number 3.5.1) are a group of hydrolases removing the acetyl group from an ε-N-acetyl lysine amino acid of a histone or other substrate protein. Depending on sequence identity and domain organization, HDACs have been classified into class I (including HDAC1-3 and 8), class IIa (HDAC4, 5, 7, 9), class IIb (HDAC 6 and 10), class III (including sirtuins) and class IV (HDAC11) (Dokmanovic et al, 2007, Mol Cancer Res October 5; 981-989).

HDAC11 is a class IV histone deacetylase (HDAC). HDAC11 is highly expressed in brain, heart, skeletal muscle, kidney and testis and primarily localized in the nucleus (Gao et al, J Biol Chem. 2002, Jul. 12; 277(28): 25748-55). Without wishing to be bound by theory, histone deacetylation may provide a tag for epigenetic repression and play an important role in transcriptional regulation, cell cycle progression and developmental events. Additionally, HDAC substrates are not restricted to histones, and HDACs have been shown to function in numerous cell regulatory pathways. For example, HDAC11 has been reported to deacetylate or associate with cell cycle-related proteins including Cdt1, Geminin (Wong et al, Cell Cycle. 2010, Nov. 1; 9(21):4351-63), BubR1 (Watanabe et al, Cell Rep. 2014, Apr. 24; 7(2):552-64), and Cdc25 (Lozada et al, Oncotarget. 2016, March 7). HDAC11 was also reported to function in RNA splicing as part of the survival of motor neuron (SMN) complex in association with SMN1, Dicer1, Gemin3, and Gemin4 (Joshi et al, Mol Syst Biol. 2013, 9:672). HDAC11 has also been reported to function in regulating dendrite growth (Watanabe et al, Cell Rep. 2014, Apr. 24; 7(2):552-64).

HDAC11 may play a role in certain cancers (Deubzer et al, Int J Cancer. 2013, May 1; 132(9):2200-8; WO 2005/071079; WO 2007/038073), such as, for example, Hodgkin lymphoma (Buglio et al, Blood. 2011, Mar. 10; 117(10): 2910-7).

Alternative splicing of HDAC11 results in multiple transcript variants. In some embodiments, an inhibitor of HDAC11 may selectively inhibit one or more variants of HDAC11.

In some embodiments, an inhibitor of HDAC11 selectively inhibits activity of a HDAC11 that is or comprises a sequence of any one of SEQ ID NO: 13-15. In some embodiments, an inhibitor of HDAC11 selectively inhibits activity of a HDAC11 that is or comprises a sequence that is 80%, 85%, 90%, 91%, 92%, 93%, 94%, 95%, 96%, 97%, 98%, or 99% identical to any one of SEQ ID NO: 13-15.

```
-human HDAC11 isoform 1
                                          SEQ ID NO: 13
MLHTTQLYQH VPETRWPIVY SPRYNITFMG LEKLHPFDAG

KWGKVINFLK EEKLLSDSML VEAREASEED LLVVHTRRYL

NELKWSFAVA TITEIPPVIF LPNFLVQRKV LRPLRTQTGG

TIMAGKLAVE RGWAINVGGG FHHCSSDRGG GFCAYADITL

AIKFLFERVE GISRATIIDL DAHQGNGHER DFMDDKRVYI

MDVYNRHIYP GDRFAKQAIR RKVELEWGTE DDEYLDKVER

NIKKSLQEHL PDVVVYNAGT DILEGDRLGG LSISPAGIVK

RDELVFRMVR GRRVPILMVT SGGYQKRTAR IIADSILNLF

GLGLIGPESP SVSAQNSDTP LLPPAVP

-human HDAC11 isoform 2
                                          SEQ ID NO: 14
MGLEKLHPFD AGKWGKVINF LKEEKLLSDS MLVEAREASE

EDLLVVHTRR YLNELKRKVL RPLRTQTGGT IMAGKLAVER

GWAINVGGGF HHCSSDRGGG FCAYADITLA IKFLFERVEG

ISRATIIDLD AHQGNGHERD FMDDKRVYIM DVYNRHIYPG

DRFAKQAIRR KVELEWGTED DEYLDKVERN IKKSLQEHLP

DVVVYNAGTD ILEGDRLGGL SISPAGIVKR DELVFRMVRG

RRVPILMVTS GGYQKRTARI IADSILNLFG LGLIGPESPS

VSAQNSDTPL LPPAVP

-human HDAC11 isoform 3
                                          SEQ ID NO: 15
MLHTTQLYQH VPETRWPIVY SPRYNITFMG LEKLHPFDAG

KWGKVINFLK EEKLLSDSML VEAREASEED LLVVHTRRYL

NELKFLFERV EGISRATIID LDAHQGNGHE RDFMDDKRVY

IMDVYNRHIY PGDRFAKQAI RRKVELEWGT EDDEYLDKVE

RNIKKSLQEH LPDVVVYNAG TDILEGDRLG GLSISPAGIV

KRDELVFRMV RGRRVPILMV TSGGYQKRTA RIIADSILNL

FGLGLIGPES PSVSAQNSDT PLLPPAVP
```

HDAC11 Inhibitors

In certain embodiments, methods of the present disclosure directed to modulating the activity of HDAC11 are practiced using an agent that inhibits HDAC11 expression and/or activity. For example, in certain embodiments, such a modulator specifically reduces or inhibits HDAC11's ability to associate with a protein complex. In other embodiments, an agent reduces expression of HDAC11. In some embodiments, agents that modulate (e.g. inhibit) HDAC11 are polynucleotides, polypeptides, peptides, peptide nucleic acids, antibodies and fragments thereof, small molecules, inorganic compounds and/or organic compounds. In some embodiments, agents that modulate (e.g. inhibit) HDAC11 include antagonists of HDAC11.

HDAC11 inhibitors include any molecule that reduces HDAC11 expression or activity. In certain embodiments, inhibitors interfere with HDAC11 activity by any of a variety of means including, e.g., inhibiting HDAC11 associating with a protein complex or inhibiting deacetylase activity.

Any HDAC11 inhibitors known in the art may be used in the methods described herein. Examples of HDAC11 inhibitors include, but are not limited to, HDTK010, HDTK028, HDTK029, HDTK054, HDTK070, commercially available shRNA (e.g., Sigma-Aldrich), commercially available siRNA (e.g., Sigma-Aldrich and Qiagen), commercially available Clustered regular interspaced short palindromic repeats-CRISPR associated protein 9-single guide RNA (CRISPR-Cas9-sgRNA) (e.g., Origene) and commercially available anti-HDAC11 antibodies (e.g., Abcam and Sigma-Aldrich).

In some embodiments, a HDAC11 inhibitor is a small molecule. In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 over one, two, three, four, five, six, seven, eight, or more other histone deacetylase isoforms (e.g., HDAC1, HDAC2, HDAC3, HDAC4, HDAC5, HDAC6, HDAC7, HDAC8, HDAC9 and/or HDAC10). In certain embodiments, a HDAC11 inhibitor is at least 10-fold selective for HDAC11 over other histone deacetylase isoforms. In certain embodiments, the HDAC11 inhibitor is a small molecule that is at least 200-fold selective for HDAC11 over other histone deacetylase isoforms. In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 each of HDAC1, HDAC2, HDAC3, HDAC4, HDAC5, HDAC6, HDAC7, HDAC8, HDAC9 and HDAC10.

Peptides and Polypeptides

In some embodiments, methods of the disclosure are practiced using peptide or polypeptide inhibitors of HDAC11. In some embodiments, a HDAC11 inhibitor is a peptide or polypeptide inhibitor of HDAC11.

In some embodiments, activity of HDAC11 is altered by over expression of a dominant negative inhibitor of HDAC11. Dominant negative inhibitors of HDAC11 are typically mutant forms of HDAC11, which reduce or block the activity of wild type HDAC11, e.g., by competing for associating with a protein complex or promoter but failing to deacetylate a target protein. Examples of various HDAC11 dominant negative inhibitors include a mutant HDAC11 having reduced ability to associate with a protein complex and a mutant HDAC11 that associates with the protein complex but fails to deacetylate a target protein. For example, one dominant negative is a HDAC11 having one or more amino acid substitutions in the catalytic domain, such that the mutant HDAC11 associates with the relevant protein complex but exhibits reduced deacetylation activity.

Polynucleotides

Various polynucleotides are contemplated for use as modulators of HDAC11 expression and/or activity. In certain embodiments, polynucleotide inhibitors of HDAC11 are antisense RNA, or RNA interference (RNAi) reagents designed to specifically target HDAC11, according to methods known and available in the art. Other polynucleotide inhibitors include, e.g., targeting vectors designed for integration into the genome and suitable for deleting all or a portion of a HDAC11 allele or mutating a HDAC11 allele, e.g., through insertional mutagenesis.

Antisense

In some embodiments, a HDAC11 inhibitor is an antisense RNA directed to HDAC11 polynucleotides, or other components of the HDAC11 signaling cascade. Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, antisense constructs have been described that inhibit and can be used to treat a variety of abnormal cellular proliferations, e.g. cancer (U.S. Pat. Nos. 5,747,470; 5,591,317 and 5,783,683).

The term "target sequence" refers to a portion of the target DNA or RNA against which the oligonucleotide or antisense agent is directed, that is, the sequence to which the oligonucleotide will hybridize by Watson-Crick base pairing of a complementary sequence.

The term "targeting sequence" or "antisense targeting sequence" refers to the sequence in an oligonucleotide or other antisense agent that is complementary (meaning, in addition, substantially complementary) to the target sequence. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least 90% sequence homology, and preferably at least 95% sequence homology, with the target sequence.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

Therefore, in certain embodiments, oligonucleotide sequences that comprise all, or a portion of, any sequence that is capable of specifically binding to a HDAC11 target polynucleotide sequence, or a complement thereof may be used in the methods described herein. In another embodiment, an oligonucleotide sequence comprises all, or a portion of, any sequence that is capable of specifically binding to a HDAC11 polynucleotide sequence, or a complement thereof. In some embodiments, an antisense oligonucleotides comprise DNA or derivatives thereof. In another embodiment, an oligonucleotides comprise RNA or derivatives thereof. Antisense oligonucleotides may be modified DNAs comprising a phosphorothioated modified backbone. Also, oligonucleotide sequences may comprise peptide nucleic acids or derivatives thereof. In each case, as appropriate, compositions can comprise a sequence region that is complementary to one or more portions of a HDAC11 target gene or polynucleotide sequence. In some embodiments, compositions can comprise a sequence region that is completely complementary one or more portions of a HDAC11 target gene or polynucleotide sequence.

Methods of producing antisense molecules are known in the art and can be readily adapted to produce an antisense molecule that targets HDAC11. Selection of antisense compositions specific for a given sequence is based upon analysis of the chosen target sequence and determination of secondary structure, Tm, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

RNAi Molecules

RNA interference methods using RNAi molecules also may be used to disrupt the expression of a gene or polynucleotide of interest, including a HDAC11 gene. RNAi is an evolutionarily conserved gene-silencing mechanism, originally discovered in studies of the nematode *Caenorhabditis elegans* (Lee et al., Cell 75:843, 1993; Reinhart et al., Nature 403:901, 2000). It may be triggered by introducing dsRNA into cells expressing the appropriate molecular machinery, which then degrades the corresponding endogenous mRNA. Without wishing to be bound by theory, the RNAi mechanism involves conversion of dsRNA into short RNAs that direct ribonucleases to homologous mRNA targets (summarized, for example, by Ruvkun, Science 2294:797, 2001).

In some embodiments, a HDAC11 inhibitor is a RNAi oligonucleotide. In some embodiments a RNAi oligonucleotide is single stranded. In some embodiments, a RNAi oligonucleotide is double stranded.

In certain embodiments, methods provided herein may utilize double-stranded ribonucleic acid (dsRNA) molecules as modulating agents, for inhibiting HDAC11. dsRNAs generally comprise two single strands. In some embodiments, one strand of the dsRNA comprises a nucleotide sequence that is substantially identical to a portion of the target gene or target region (the "sense" strand), and the other strand (the "complementary" or "antisense" strand) comprises a sequence that is substantially complementary to a portion of the target region. The strands are sufficiently complementary to hybridize to form a duplex structure. In certain embodiments, the complementary RNA strand may be less than 30 nucleotides, less than 25 nucleotides in length, or even 19 to 24 nucleotides in length. In some embodiments, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, the dsRNA may further comprise at least one chemically modified nucleotide. In certain embodiments, a dsRNA comprising a single-stranded overhang of 1 to 4 nucleotides may comprise a molecule wherein the unpaired nucleotide of the single-stranded overhang that is directly adjacent to the terminal nucleotide pair contains a purine base. In some embodiments, the last complementary nucleotide pairs on both ends of a dsRNA are a G-C pair, or, at least two of the last four terminal nucleotide pairs are G-C pairs.

Certain embodiments of the present disclosure may comprise micro RNAs (miRNAs). In some embodiments, a HDAC11 inhibitor is a miRNA. miRNAs represent a large group of small RNAs produced naturally in organisms, some of which regulate the expression of target genes. miRNAs are formed from an approximately 70 nucleotide single-stranded hairpin precursor transcript by Dicer. (V. Ambros et al. Current Biology 13:807, 2003). miRNAs are not translated into proteins, but instead bind to specific messenger RNAs, thereby blocking translation. Without wishing to be bound by theory, it is thought that miRNAs base-pair imprecisely with their targets to inhibit translation. Certain miRNAs may be transcribed as hairpin RNA precursors, which are then processed to their mature forms by Dicer enzyme.

Certain embodiments of the present disclosure may employ short-interfering RNAs (siRNA). In some embodiments, a HDAC11 inhibitor is a siRNA. In certain embodiments, the first strand of the double-stranded oligonucleotide contains two more nucleoside residues than the second strand. In other embodiments, the first strand and the second strand have the same number of nucleosides; however, the first and second strands are offset such that the two terminal nucleosides on the first and second strands are not paired with a residue on the complimentary strand. In certain instances, the two nucleosides that are not paired are thymidine resides.

In instances where HDAC11 inhibiting agent is or comprises siRNA, the agent should include a region of sufficient homology to the target region, and be of sufficient length in terms of nucleotides, such that the siRNA agent, or a fragment thereof, can mediate down regulation of the target RNA. It will be understood that the term "ribonucleotide" or "nucleotide" can, in the case of a modified RNA or nucleotide surrogate, also refer to a modified nucleotide, or surrogate replacement moiety at one or more positions. Thus, a siRNA agent is or includes a region which is at least partially complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments include one or more mismatches with respect to the target RNA, typically 10, 8, 6, 5, 4, 3, 2, or fewer mismatches. In some embodiments, matches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the overall double-strand character of the molecule.

In addition, a siRNA modulating agent may be modified or include nucleoside surrogates. Single stranded regions of a siRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of a siRNA agent, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents may include, for example, molecules that are long enough to trigger the interferon response (which can be cleaved by Dicer (Bernstein et al., Nature, 409:363-366, 2001) and enter a RISC(RNAi-induced silencing complex)), in addition to molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter RNAi agents herein. "siRNA agent or shorter RNAi agent" as used refers to an siRNA agent that is sufficiently short that it does not induce a deleterious interferon response in a human cell, e.g., it has a duplexed region of less than 60 but preferably less than 50, 40, or 30 nucleotide pairs. An siRNA modulating agent, or a cleavage product thereof, can down regulate a target gene, e.g., by inducing RNAi with respect to a target RNA, such as HDAC11 mRNA.

Each strand of an siRNA modulating agent can be equal to or less than 35, 30, 25, 24, 23, 22, 21, or 20 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA modulating agent may have one or more of the following properties: it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA; it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, a siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a C3'-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide.

A "single strand RNAi agent" as used herein, is an RNAi agent which is made up of a single molecule. It may include a duplexed region, formed by intra-strand pairing, e.g., it may be, or include, a hairpin or pan-handle structure. Single strand RNAi modulating agents are preferably antisense with regard to the target molecule. A single strand RNAi agent should be sufficiently long that it can enter the RISC and participate in RISC mediated cleavage of a target mRNA. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents, e.g., short hairpin RNA (shRNA), may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

Certain modulating agents utilized according to the methods provided herein may comprise RNAi oligonucleotides such as chimeric oligonucleotides, or "chimeras," which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides may be formed as composite structures of two or more oligonucleotides, modified oligonucleotides, oligonucleotides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013,830, 5,149,797, 5,220,007, 5,256,775, 5,366,878, 5,403,711, 5,491,133, 5,565,350, 5,623,065, 5,652,355, 5,652,356, 5,700,922, and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

In some embodiments, HDAC11 modulating agents, such as RNAi agents, relate to an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, naptha-lenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, a non-natural nucleobase is difluorotolyl. A wide variety of ligands are known in the art and are amenable to the present invention. For example, a ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, a ligand is a steroid or aromatic compound. In certain instances, the ligand is cholesteryl.

In other embodiments, a RNAi agent is an oligonucleotide tethered to a ligand for the purposes of improving cellular targeting and uptake. For example, a RNAi agent may be tethered to an antibody, or antigen binding fragment thereof. As an additional example, an RNAi agent may be tethered to a specific ligand binding molecule, such as a polypeptide or polypeptide fragment that specifically binds a particular cell-surface receptor.

In some embodiments, a HDAC11 modulating agent comprises a non-natural nucleobase. In certain embodiments, a non-natural nucleobase is difluorotolyl, nitroimidazolyl, nitroindolyl, or nitropyrrolyl. In certain embodiments, HDAC11 modulating agents provided herein relate to a double-stranded oligonucleotide sequence, wherein only one of the two strands contains a non-natural nucleobase. In certain embodiments, HDAC11 modulating agents as used herein relate to a double-stranded oligonucleotide sequence, wherein both of the strands independently comprise at least one non-natural nucleobase.

In certain instances, a ribose sugar moiety that naturally occurs in nucleosides is replaced with a hexose sugar. In some certain embodiments, a hexose sugar is an allose, altrose, glucose, mannose, gulose, idose, galactose, talose, or a derivative thereof. In some certain embodiments, a hexose is a D-hexose. In certain instances, a ribose sugar moiety that naturally occurs in nucleosides is replaced with a polycyclic heteroalkyl ring or cyclohexenyl group. In certain instances, a polycyclic heteroalkyl group is a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane. In certain embodiments, the backbone of an oligonucleotide has been modified to improve the therapeutic or diagnostic properties of the oligonucleotide compound. In certain embodiments, at least one of the bases or at least one of the sugars of the oligonucleotide has been modified to improve the therapeutic or diagnostic properties of the oligonucleotide compound. In instances when the oligonucleotide is double stranded, the two strands may be complementary, partially complementary, or chimeric oligonucleotides.

Examples of modified RNAi agents envisioned for use in the methods of the present disclosure include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. Modified oligonucleotides that do not have a phosphorus atom in their intersugar backbone can also be considered to be oligonucleotides. Specific oligonucleotide chemical modifications are described below. It is not necessary for all positions in a given compound to be uniformly modified, and in fact more than one of the following modifications may be incorporated in a single oligonucleotide compound or even in a single nucleotide thereof.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents that teach the preparation of the above phosphorus atom-containing linkages include, but are not limited to, U.S. Pat. Nos. 3,687,808, 4,469,863, 4,476,301, 5,023,243, 5,177,196, 5,188,897, 5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, 5,625,050, and 5,697,248, each of which is herein incorporated by reference.

Examples of modified internucleoside linkages or backbones that do not include a phosphorus atom therein (i.e., oligonucleotides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, and 5,677,439, each of which is herein incorporated by reference.

In other examples of oligonucleotide mimetics, both the sugar and the internucleoside linkage, i.e., the backbone, of the nucleoside units may be replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082, 5,714,331, and 5,719,262, each of which is herein incorporated by reference. Further teaching of PNA compounds can be found in Nielsen et al., Science, 1991, 254, 1497.

In certain instances, the RNAi agents for use with the methods provided herein may be modified by non-ligand group. A number of non-ligand molecules have been conjugated to oligonucleotides in order to enhance the activity, cellular distribution, cellular targeting, or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 86:6553-56, 1989), cholic acid (Manoharan et al., Bioorg. Med. Chem. Lett. 4:1053, 1994), a thioether, e.g., hexyl-5-tritylthiol (Manoharan et al., Ann. N.Y. Acad. Sci., 660:306, 1992; Manoharan et al., Bioorg. Med. Chem. Let., 3:2765, 1993), a thiocholesterol (Oberhauser et al., Nucl. Acids Res., 20:533, 1992), an aliphatic chain, e.g., dodecandiol or undecyl residues (Saison-Behmoaras et al., EMBO J. 10:111, 1991; Kabanov et al., FEBS Lett. 259:327, 1990; Svinarchuk et al., Biochimie. 75:49, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651, 1995; Shea et al., Nucl. Acids Res. 18:3777, 1990), a polyamine or a polyethylene glycol chain (Manoharan et al., Nucleosides & Nucleotides. 14:969, 1995), or adamantane acetic acid (Manoharan et al., Tetrahedron Lett. 36:3651, 1995), a palmityl moiety (Mishra et al., Biochim. Biophys. Acta. 1264:229, 1995), or an octadecylamine or hexylamino-carbonyl-oxycholesterol moiety (Crooke et al., J. Pharmacol. Exp. Ther. 277:923, 1996). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Additional examples of modulating agents, such as RNAi oligonucleotides, may be found in U.S. Application Publication Nos. 2007/0275465, 2007/0054279, 2006/0287260, 2006/0035254, 2006/0008822, which are incorporated by reference.

CRISPR

In some embodiments, a gene editing system can be used to silence, enhance or mutate the HDAC11 gene. Any gene editing systems known in the art may be used in the methods of the present disclosure. In certain embodiments, a gene editing system is a CRISPR/Cas system. CRISPR/Cas systems have been modified for use in gene editing (silencing, enhancing or changing specific genes) in eukaryotes such as mice or primates. Wiedenheft et al., 2012. Nature 482: 331-8. This is accomplished by introducing into the eukaryotic cell a plasmid containing a specifically designed CRISPR and one or more appropriate Cas. The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the HDAC11 CRISPR/Cas system, the spacers are derived from the HDAC11 gene sequence. RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. 2010. Science 327: 167-170; Makarova et al. 2006 Biology Direct 1:7. The spacers thus serve as templates for RNA molecules, analogously to siRNAs. Pennisi 2013. Science 341: 833-836.

In certain embodiments, artificial CRISPR systems can be generated which inhibit HDAC11 using technology known in the art, e.g., that is described in U.S. patent application Ser. No. 13/842,859 (published as US 20140068797). Such HDAC11-inhibitory CRISPR system can include a guide RNA (gRNA) comprising a HDAC11-targeting domain, i.e, a nucleotide sequence that is complementary to a HDAC11 DNA strand, and a second domain that interacts with an RNA-directed nuclease.

Knockout Constructs

In certain embodiments, the activity of HDAC11 is altered by mutating a gene encoding the HDAC11 molecule. A variety of methods of mutating an endogenous gene are known and available in the art, including, e.g., insertional mutagenesis and knockout methods. Accordingly, the disclosure provides methods of knocking out one or more alleles of a HDAC11 gene. It is understood that knockout vectors in accordance with the present disclosure include any vector capable of disrupting expression or activity of a HDAC11 gene, including, in certain embodiments, targeting vectors.

In preferred methods, targeting vectors are used to selectively disrupt a HDAC11 gene. Knockout vectors include those that alter gene expression, for example, by disrupting a regulatory element of a HDAC11 gene, including, e.g., inserting a regulatory element that reduces gene expression or deleting or otherwise reducing the activity of an endogenous element that positively affects transcription of the target gene. In other embodiments, knockout vectors can disrupt, e.g., delete or mutate, the 5' region, 3' region or coding region of a HDAC11 gene. In some embodiments, knockout vectors delete a region or the entirety of the coding region of a HDAC11 gene. In certain embodiments, knockout vectors delete a region of a HDAC11 gene, while in other embodiments; they insert exogenous sequences into a HDAC11 gene. In addition, in certain embodiments, including those using replacement vectors, knockout vectors both remove a region of a gene and introduce an exogenous sequence.

Targeting vectors in accordance with the present disclosure include all vectors capable of undergoing homologous recombination with an endogenous HDAC11 gene, including replacement vectors. Targeting vectors include all those used in methods of positive selection, negative selection, positive-negative selection, and positive switch selection. Targeting vectors employing positive, negative, and positive-negative selection are well known in the art and representative examples are described in Joyner, A. L., Gene Targeting: A Practical Approach, 2nd Ed. (2000) and references cited therein.

Antibody Agents

In some embodiments, antibody agents that specifically bind HDAC11 can be used in accordance with the methods described herein. In some embodiments, an antibody agent that specifically binds to HDAC11 and inhibits its catalytic activity. As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present disclosure is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

An antibody agent is said to "specifically bind," "immunologically bind," and/or is "immunologically reactive" to a polypeptide of the disclosure if it reacts at a detectable level (within, for example, an ELISA assay) with the polypeptide, and does not react detectably with unrelated polypeptides under similar conditions. Antibodies are considered to specifically bind to a target polypeptide when the binding affinity is at least $1\times10^{-7}$ M or, preferably, at least $1\times10^{-8}$ M. In some embodiments, a HDAC11 inhibitory agent is an antibody agent that specifically binds the catalytic domain of HDAC11.

Antibody agents for use in accordance with the present disclosure include, but are not limited to, monoclonal antibodies, chimeric antibodies, humanized antibodies, fully human antibodies, single chain antibodies, Fab fragments, and scFv fragments. An example of an anti-HDAC11 antibody is described in WO 2014/096386.

Antibody agents may be prepared by any of a variety of techniques known to those of ordinary skill in the art. See, e.g., Harlow and Lane, Antibodies: A Laboratory Manual, Cold Spring Harbor Laboratory, 1988. In general, antibodies can be produced by cell culture techniques, including the generation of monoclonal antibodies via conventional techniques known in the art, or via transfection of antibody genes into suitable bacterial or mammalian cell hosts, in order to allow for the production of recombinant antibodies. Monoclonal antibodies (Mabs) specific for an antigenic polypeptide of interest may be prepared, for example, using the technique of Kohler and Milstein, Eur. J. Immunol. 6:511-519, 1976, and improvements thereto. Methods of making chimeric and humanized antibodies are well known in the art, (See, e.g., U.S. Pat. No. 4,816,567, International Application No. WO84/03712, respectively).

In certain embodiments, methods of preparing monoclonal antibodies involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides in accordance with the present disclosure may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab)2" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent VH::VL heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("scFv") polypeptide is a covalently linked VH::VL heterodimer which is expressed from a gene fusion including VH- and VL-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, each of the above-described antibody agents can include a heavy chain and a light chain complementarity-determining region (CDR) set, respectively interposed between a heavy chain and a light chain framework region which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

Fab or F(ab')2 fragments may be wholly animal or human derived, or they may be in chimeric form, such that the constant domains are derived from the constant regions of human immunoglobulins and the variable regions are derived from the parent murine mAb. Alternatively, the Fv, Fab, or F(ab')2 may be humanized, so that only the complementarity determining regions (CDR) are derived from an animal mAb, and the constant domains and the framework regions of the variable regions are of human origin. These chimeric and humanized fragments are less immunogenic than their wholly animal counterparts, and thus more suitable for in vivo use, especially over prolonged periods.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is may be accepted as the human framework region (FR) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

Humanization generally aims to retain high affinity for the antigen of interest and other favorable biological properties. To achieve this goal, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Humanized or fully human antibodies in accordance with the present disclosure may be prepared according to the methods described in U.S. Pat. Nos. 5,770,429, 5,833,985, 5,837,243, 5,922,845, 6,071,517, 6,096,311, 6,111,166, 6,270,765, 6,303,755, 6,365,116, 6,410,690, 6,682,928, and 6,984,720.

Phage display technology (McCafferty et al., Nature 348: 552-553 (1990)) can also be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell.

Phage display can be performed in a variety of formats; for their review see, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

Phage display may be used to generate synthetic antibodies or human antibodies according to various methods. For example, in certain embodiments, phage display is utilized to produce a library of fully human antibodies or fragments thereof, which may be screened for their ability to bind a target polypeptide, such as HDAC11. The screening of such libraries is commercially available, e.g., by Morphosys (Munich, Germany). Libraries of human antibodies and methods of use thereof are described, e.g., in U.S. Pat. Nos. 7,049,135, 6,828,422, 6,753,138, 6,706, and 484, 6,696,248, and U.S. Patent Application Publication Nos. 2006/0121563, 2006/0003334, and 2004/0157291, all assigned to Morphosys.

Additional methods of generating and screening human antibody libraries using phage display are described, e.g., in Steukers, M. et al., J Immunol Methods. 2006 Mar. 20; 310(1-2):126-35; Huang L. et al., J. Leukoc. Biol. Vol 80. 2006 October; Wassaf, D. et al., Anal Biochem. 2006 Apr. 15; 351(2):241-53; Shrivastava A, et al., Protein Eng Des Sel. 2005 September; 18(9):417-24; Schoonbroodt S. et al., Nucleic Acids Res. 2005 May 19; 33(9); Hogan S, et al., Biotechniques. 2005 April; 38(4):536, 538; Hoet R M, et al., Nat Biotechnol. 2005 March; 23(3):344-8; Huang L, et al., J Mol Recognit. 2005 Feb. 10; Blaise L, et al., Gene. 2004 Nov. 24; 342(2):211-8; Fleming T, et al., J. Mol. Recognit. 2004 17:1-9; Jostock, et al., J Immunol Methods. 2004 June; 289(1-2):65-80; Kelley B, et al., J Chro. 4 Jun. 2004 2004; 1038(1-2):121-130; Ladner R C, et al., Drug Discovery Today. June 2004; 9(12):525-529; Williams A, Baird L G, Transfus Apheresis Sci. December 2003; 29(3):255-258; van den Beucken T, et al., FEBS Lett. Jul. 10 2003; 546(2-3):288-294. Jul. 10 2003; 546(2-3):288-294; Sato A., Biopolymers. July 2003; 71(3):316; and Nixon A E., Biopolymers. July 2003; 71(3):302, 398.

In some embodiments, an antibody or fragment thereof inhibits HDAC11 activity by binding to HDAC11 and, e.g., blocking the catalytic domain, and thereby inhibiting the deacetylase activity.

Small Molecules

In some embodiments, HDAC11 inhibitors for use in accordance with the present disclosure are chemical compounds, including large or small inorganic or organic molecules. In some embodiments, HDAC11 modulating agents in accordance with the present disclosure are small organic molecules, or derivatives or analogs thereof.

In certain embodiments, a HDAC11 modulating agent includes a protecting group. The term "protecting group" refers to chemical moieties that block at least some reactive moieties and prevent such groups from participating in chemical reactions until the protective group is removed (or "cleaved"). Examples of blocking/protecting groups are described, e.g., in Greene and Wuts, Protective Groups in Organic Synthesis, 3rd Ed., John Wiley & Sons, New York, N.Y., 1999.

Any of the HDAC11-inhibiting chemical compounds may possess one or more chiral centers and each center may exist in the R or S configuration. In some embodiments, a chiral center exists in the R configuration. In some embodiments, a chiral center exists in the S configuration. HDAC11-inhibiting chemical compounds of the present disclosure include all diastereomeric, enantiomeric, and epimeric forms as well as mixtures thereof. Stereoisomers may be obtained, if desired, by methods known in the art as, for example, the separation of stereoisomers by chiral chromatographic columns. HDAC11-inhibiting chemical compounds may further include of N-oxides, crystalline forms (also known as polymorphs), and pharmaceutically acceptable salts, as well as active metabolites of any inhibitor. All tautomers are included within the scope of the HDAC11 modulating agents presented herein. In addition, HDAC11-inhibiting chemical compounds agents described herein can exist in unsolvated as well as solvated forms with pharmaceutically acceptable solvents such as water, ethanol, and the like. The solvated forms of HDAC11-inhibiting chemical compounds are also included within the present disclosure.

In some embodiments, a small molecule inhibitor binds to HDAC11. In some embodiments, a small molecule binds to the catalytic domain of HDAC11 and interferes with or reduces its deacetylase activity or its ability to associate with other proteins to form a complex. In some embodiments, a small molecule HDAC11 inhibitor is at least 10-fold selective for the inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In other embodiments, a small molecule inhibitor of HDAC11 is at least 200-fold selective for HDAC11 over other isoforms of histone deacetylases. In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In some embodiments, a small molecule HDAC11 inhibitor is at least 10-fold selective for the inhibition of HDAC11 over each of HDAC1, HDAC2, HDAC3, HDAC4, HDAC5, HDAC6, HDAC7, HDAC8, HDAC9 and HDAC10. In some embodiments, a HDAC11 inhibitor is specific for human HDAC11.

Inhibitors of HDAC11, including small organic compounds, may be identified according to routine screening procedures available in the art, e.g., using commercially available libraries of such compounds. Exemplary inhibitors of HDAC11 are described in further detail below.

Aminobenzimidazoles and Related Compounds

In one embodiment of the invention, compounds of Formula I are described:

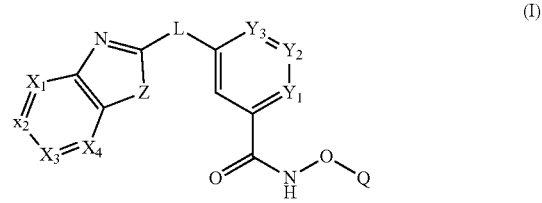

(I)

and pharmaceutically acceptable salts thereof wherein:

Q is —H, —OC(O)NR$^6$(C$_1$-C$_6$)alkylaryl, or —OC(O)O(C$_1$-C$_6$)alkylaryl;

Z is —CH$_2$—, O, S or NR$^6$;

X$_1$, X$_2$, X$_3$, and X$_4$ are each independently, at each occurrence, N or CR$^1$;

Y$_1$, Y$_2$, and Y$_3$ are each independently N or CR$^1$;

L is NR$^6$, O, or —(CR$^1$R$^2$)$_p$—;

R$^1$ and R$^2$ are independently, at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —OH, —OR$^3$, halogen, —NO$_2$, —CN, —NHC$_1$-C$_6$alkyl, —N(C$_1$-C$_6$alkyl)$_2$, —S(O)$_2$NH$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, —N(C$_1$-C$_6$alkyl)S(O)$_2$C$_1$-C$_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^3$, —R$^5$, —SR$^3$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocycle, aryl, or heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or two occurrences of R$^1$, when on adjacent atoms, can combine to form a cycloalkyl, a heterocycle, aryl, heteroaryl containing 1-5 heteroatoms selected from the group consisting of N, S, P and O, or a cycloalkenyl, each optionally substituted with one or more independent occurrences of R$^3$ and R$^4$;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, oxo, or —(CHR$^5$)$_p$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —C(O)OC$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_p$N(C$_1$-C$_6$alkyl)$_2$;

R$^6$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$NR$^3$R$^4$ wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

and p is 0, 1, 2, 3, 4, 5, or 6.

In some embodiments, compounds of Formula I' are described:

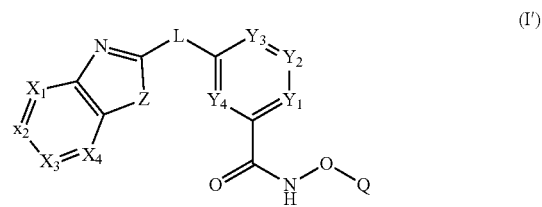

(I')

wherein Y$_4$ is N or CR$^1$, and all other variables are as defined above for Formula I and described in classes and subclasses herein. Unless otherwise stated, references herein to Formula I include reference to Formula I'.

In some embodiments, for compounds of Formula I, one of Y$_1$, Y$_2$ or Y$_3$ is N and the other two of Y$_1$, Y$_2$ or Y$_3$ are each independently CR$^1$. In other embodiments, two of Y$_1$, Y$_2$ or Y$_3$ are N and the other one of Y$_1$, Y$_2$ or Y$_3$ is CR$^1$. In some embodiments, R$^1$ is H.

In some embodiments, Y$_1$, Y$_2$ and Y$_3$ are CH; X$_1$, X$_2$, X$_3$ and X$_4$ are each CR$^1$; and R$^1$ is independently, at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —OH, halogen, —NO$_2$, —CN, —NHC$_1$-C$_6$alkyl, —N(C$_1$-C$_6$alkyl)$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, —N(C$_1$-C$_6$alkyl)S(O)$_2$C$_1$-C$_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocycle, aryl, or heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or two occurrences of R$^1$, when on adjacent atoms, can combine to form a cycloalkyl, a heterocycle, aryl, heteroaryl containing 1-5 heteroatoms selected from the group consisting of N, S, P and O, or a cycloalkenyl, each optionally substituted with one or more independent occurrences of R$^3$ and R$^4$;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —C(O)OC$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_p$N(C$_1$-C$_6$alkyl)$_2$.

In some embodiments, for compounds of Formula I, L is S. In other embodiments, for compounds of Formula I, L is O. In other embodiments for compounds of Formula I, L is NR$^6$.

In one or more embodiments, compounds of Formula I-A are provided:

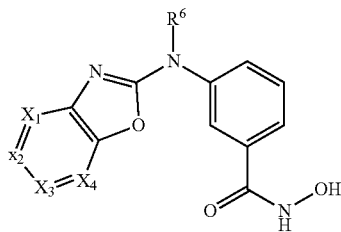

I-A wherein X$_1$, X$_2$, X$_3$, X$_4$, and R$^6$ are as described generally above and in classes, subclasses, and species herein.

In one or more embodiments, compounds of Formula I-B are provided:

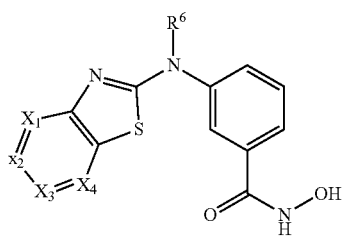

I-B wherein X$_1$, X$_2$, X$_3$, X$_4$, and R$^6$ are as described generally above and in classes, subclasses, and species herein.

In one or more embodiments, compounds of Formula I-C are provided:

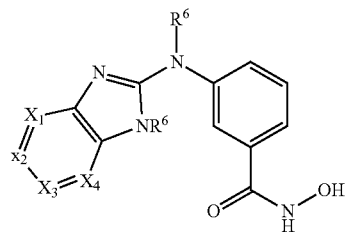

I-C wherein X$_1$, X$_2$, X$_3$, X$_4$, and R$^6$ are as described generally above and in classes, subclasses, and species herein.

In some embodiments for compounds of Formulae I, I-A, I-B, or I-C, X$_1$ and X$_4$ are both N, and X$_2$ and X$_3$ are each independently CR$^1$. In some embodiments for compounds of Formulae I, I-A, I-B, or I-C, X$_2$ and X$_4$ are both N, and X$_1$ and X$_3$ are each independently CR$^1$. In some embodiments for compounds of Formulae I, I-A, I-B, or I-C, X$_1$ is N and X$_2$, X$_3$ and X$_4$ are each independently CR$^1$.

In some embodiments for compounds of Formulae I, I-A, I-B, or I-C, each occurrence of R$^6$ is independently H, —C$_1$-C$_6$alkyl, —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$NR$^3$R$^4$ wherein each alkyl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl. In some embodiments, for compounds of Formulae I, I-A, I-B, or I-C, each occurrence of R$^6$ is independently H, —(CHR$^5$)$_p$NR$^3$R$^4$, or C$_1$-C$_6$alkyl optionally substituted with one or more substituents selected from —OH, halogen, —NO$_2$, oxo, —CN, —R$^5$, —O(C$_1$-C$_6$)alkyl, —NH(C$_1$-C$_6$) alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, or —N(C$_1$-C$_6$alkyl)S(O)R$^5$.

For each of the embodiments described above for compounds of Formulae I, I-A, I-B, or I-C, each independent occurrence of R$^1$ is halogen, —CF$_3$, —OH, —CN, —SO$_2$(C$_1$-C$_3$alkyl), phenyl, C$_1$-C$_3$alkyl, C$_1$-C$_3$alkoxy, pyridyl, —C(O)C$_1$-C$_3$alkyl, —OC$_1$-C$_3$alkyl, —(C$_1$-C$_3$alkyl)O(C$_1$-C$_3$alkyl), —OCF$_3$ or —OCH$_2$phenyl.

In some embodiments, in any of the above-embodiments for compounds of Formula I, I-A, I-B, or I-C, Q is —H.

In one or more embodiments, a compound of Formula I can be selected from one of the compounds in Table I-1:

TABLE I-1

| Example | Structure | Name |
|---|---|---|
| HDTK010 | ![structure] | 3-((5,6-dichlorobenzo[d]oxazol-2-yl)amino)-N-hydroxybenzamide |

TABLE I-1-continued

| Example | Structure | Name |
|---|---|---|
| 2-1 | 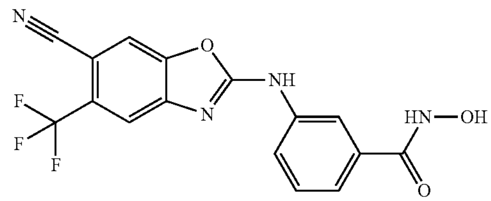 [SMILES: N#Cc1cc2oc(Nc3cccc(C(=O)NO)c3)nc2cc1C(F)(F)F] | 3-((6-cyano-5-(trifluoromethyl)benzo[d]oxazol-2-yl)amino)-N-hydroxybenzamide |
| 3-1 | 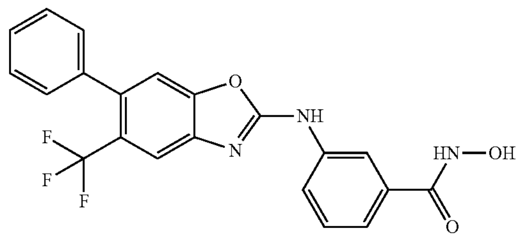 | N-hydroxy-3-((6-phenyl-5-(trifluoromethyl)benzo[d]oxazol-2-yl)amino)benzamide |
| 4-1 | 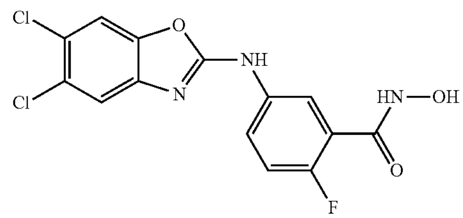 [SMILES: O=C(NO)c1cc(Nc2nc3cc(Cl)c(Cl)cc3o2)ccc1F] | 5-((5,6-dichlorobenzo[d]oxazol-2-yl)amino)-2-fluoro-N-hydroxybenzamide |
| 4-2 | 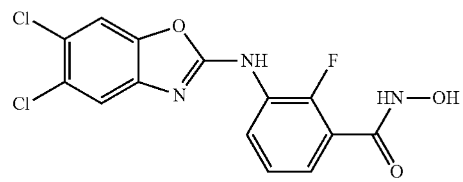 [SMILES: O=C(NO)c1cccc(Nc2nc3cc(Cl)c(Cl)cc3o2)c1F] | 3-((5,6-dichlorobenzo[d]oxazol-2-yl)amino)-2-fluoro-N-hydroxybenzamide |
| 4-3 | 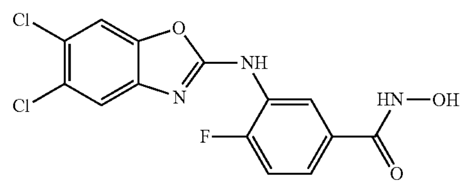 [SMILES: O=C(NO)c1ccc(F)c(Nc2nc3cc(Cl)c(Cl)cc3o2)c1] | 3-((5,6-dichlorobenzo[d]oxazol-2-yl)amino)-4-fluoro-N-hydroxybenzamide |
| 4-4 | 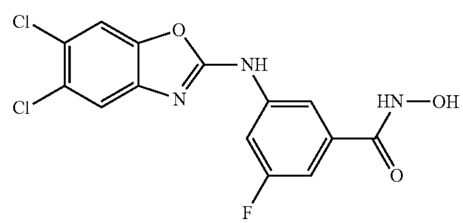 [SMILES: O=C(NO)c1cc(F)cc(Nc2nc3cc(Cl)c(Cl)cc3o2)c1] | 3-((5,6-dichlorobenzo[d]oxazol-2-yl)amino)-5-fluoro-N-hydroxybenzamide |
| 4-5 | 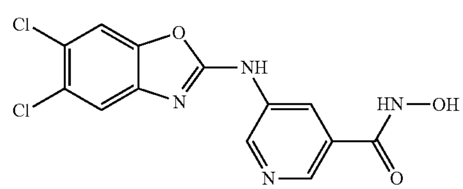 [SMILES: O=C(NO)c1cncc(Nc2nc3cc(Cl)c(Cl)cc3o2)c1] | 5-((5,6-dichlorobenzo[d]oxazol-2-yl)amino)-N-hydroxynicotinamide |

TABLE I-1-continued

| Example | Structure | Name |
|---|---|---|
| 4-6 | 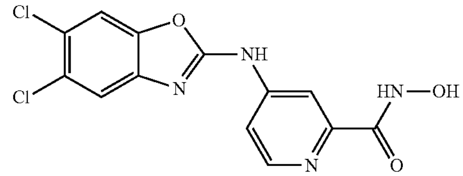 | 4-((5,6-dichlorobenzo[d]oxazol-2-yl)amino)-N-hydroxypicolinamide |
| 4-7 | 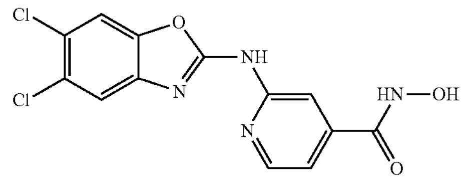 | 2-((5,6-dichlorobenzo[d]oxazol-2-yl)amino)-N-hydroxyisonicotinamide |
| 4-8 | 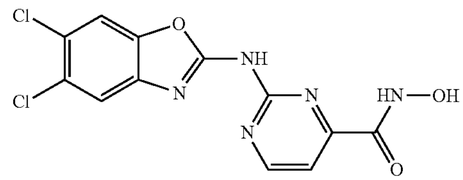 | 2-((5,6-dichlorobenzo[d]oxazol-2-yl)amino)-N-hydroxypyrimidine-4-carboxamide |
| 5-1 | 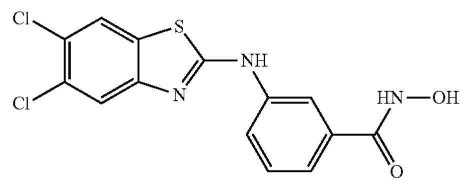 | 3-((5,6-dichlorobenzo[d]thiazol-2-yl)amino)-N-hydroxybenzamide |
| 6-1 | 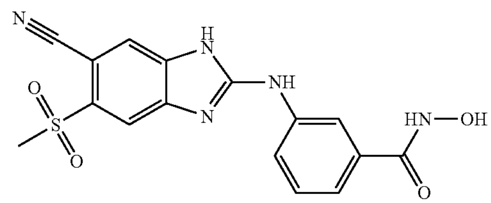 [SMILES: CS(=O)(=O)c1cc2nc(Nc3cccc(C(=O)NO)c3)[nH]c2cc1C#N] | 3-((6-cyano-5-(methylsulfonyl)-1H-benzo[d]imidazol-2-yl)amino)-N-hydroxybenzamide |
| 7-1 | 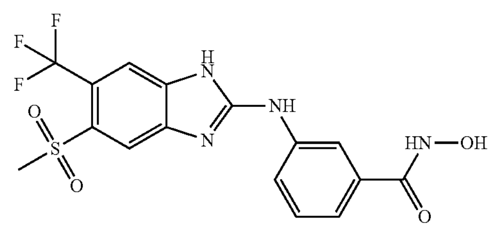 [SMILES: CS(=O)(=O)c1cc2nc(Nc3cccc(C(=O)NO)c3)[nH]c2cc1C(F)(F)F] | N-hydroxy-3-((5-(methylsulfonyl)-6-(trifluoromethyl)-1H-benzo[d]imidazol-2-yl)amino)benzamide |
| 8-1 | 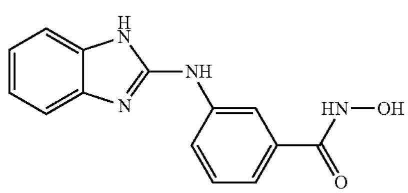 [SMILES: O=C(NO)c1cccc(Nc2nc3ccccc3[nH]2)c1] | 3-((1H-benzo[d]imidazol-2-yl)amino)-N-hydroxybenzamide |
| 9-1 | 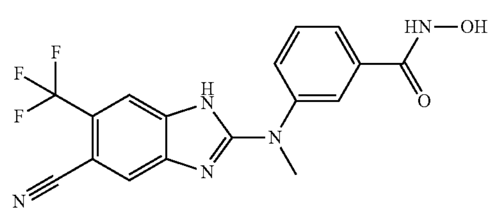 [SMILES: CN(c1cccc(C(=O)NO)c1)c1nc2cc(C#N)c(C(F)(F)F)cc2[nH]1] | 3-((5-cyano-6-(trifluoromethyl)-1H-benzo[d]imidazol-2-yl)(methyl)amino)-N-hydroxybenzamide |

TABLE I-1-continued

| Example | Structure | Name |
|---|---|---|
| 10-1 | 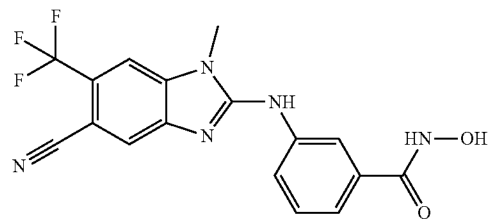 [SMILES: Cn1c(Nc2cccc(C(=O)NO)c2)nc2cc(C#N)c(C(F)(F)F)cc21] | 3-((5-cyano-1-methyl-6-(trifluoromethyl)-1H-benzo[d]imidazol-2-yl)amino)-N-hydroxybenzamide |
| 11-1 | 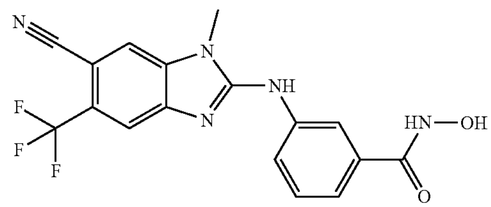 [SMILES: Cn1c(Nc2cccc(C(=O)NO)c2)nc2cc(C(F)(F)F)c(C#N)cc21] | 3-((6-cyano-1-methyl-5-(trifluoromethyl)-1H-benzo[d]imidazol-2-yl)amino)-N-hydroxybenzamide |
| 12-1 | 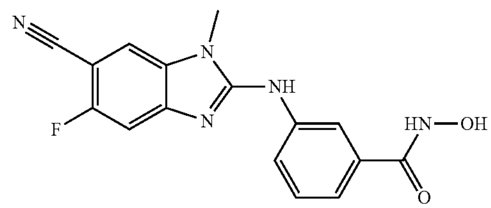 [SMILES: Cn1c(Nc2cccc(C(=O)NO)c2)nc2cc(F)c(C#N)cc21] | 3-((6-cyano-5-fluoro-1-methyl-1H-benzo[d]imidazol-2-yl)amino)-N-hydroxybenzamide |
| 13-1 | 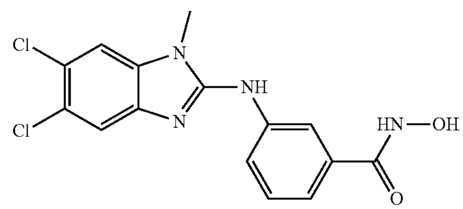 [SMILES: Cn1c(Nc2cccc(C(=O)NO)c2)nc2cc(Cl)c(Cl)cc21] | 3-((5,6-dichloro-1-methyl-1H-benzo[d]imidazol-2-yl)amino)-N-hydroxybenzamide |
| 14-1 | 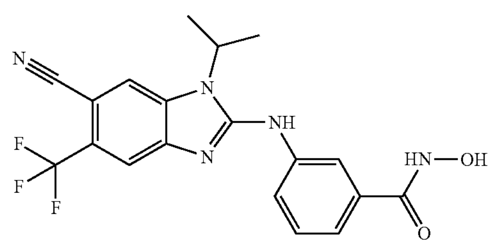 [SMILES: CC(C)n1c(Nc2cccc(C(=O)NO)c2)nc2cc(C(F)(F)F)c(C#N)cc21] | 3-((6-cyano-1-isopropyl-5-(trifluoromethyl)-1H-benzo[d]imidazol-2-yl)amino)-N-hydroxybenzamide |
| 15-1 | 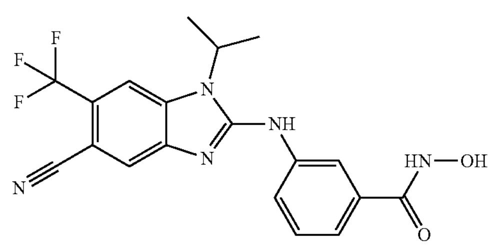 [SMILES: CC(C)n1c(Nc2cccc(C(=O)NO)c2)nc2cc(C#N)c(C(F)(F)F)cc21] | 3-((5-cyano-1-isopropyl-6-(trifluoromethyl)-1H-benzo[d]imidazol-2-yl)amino)-N-hydroxybenzamide |
| 16-1 | 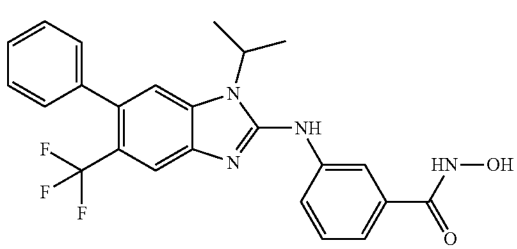 [SMILES: CC(C)n1c(Nc2cccc(C(=O)NO)c2)nc2cc(C(F)(F)F)c(-c3ccccc3)cc21] | N-hydroxy-3-((1-isopropyl-6-phenyl-5-(trifluoromethyl)-1H-benzo[d]imidazol-2-yl)amino)benzamide |

TABLE I-1-continued

| Example | Structure | Name |
|---|---|---|
| 16-2 | 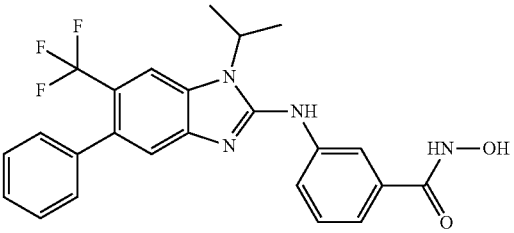 [SMILES: CC(C)n1c(Nc2cccc(C(=O)NO)c2)nc2cc(-c3ccccc3)c(C(F)(F)F)cc21] | N-hydroxy-3-((1-isopropyl-5-phenyl-6-(trifluoromethyl)-1H-benzo[d]imidazol-2-yl)amino)benzamide |
| 17-1 | 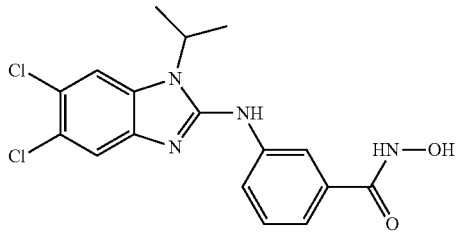 [SMILES: CC(C)n1c(Nc2cccc(C(=O)NO)c2)nc2cc(Cl)c(Cl)cc21] | 3-((5,6-dichloro-1-isopropyl-1H-benzo[d]imidazol-2-yl)amino)-N-hydroxybenzamide |
| 18-1 | 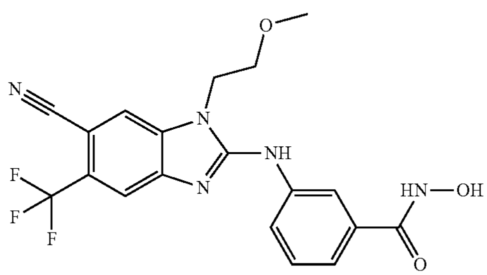 [SMILES: COCCn1c(Nc2cccc(C(=O)NO)c2)nc2cc(C(F)(F)F)c(C#N)cc21] | 3-((6-cyano-1-(2-methoxyethyl)-5-(trifluoromethyl)-1H-benzo[d]imidazol-2-yl)amino)-N-hydroxybenzamide |
| 19-1 | 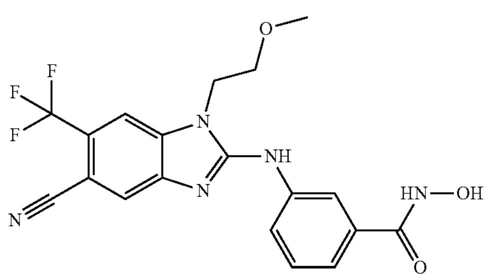 [SMILES: COCCn1c(Nc2cccc(C(=O)NO)c2)nc2cc(C#N)c(C(F)(F)F)cc21] | 3-((5-cyano-1-(2-methoxyethyl)-6-(trifluoromethyl)-1H-benzo[d]imidazol-2-yl)amino)-N-hydroxybenzamide |
| 20-1 | 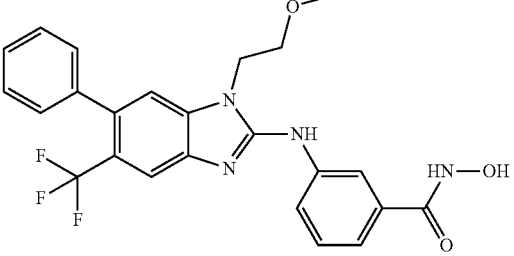 | N-hydroxy-3-((1-(2-methoxyethyl)-6-phenyl-5-(trifluoromethyl)-1H-benzo[d]imidazol-2-yl)amino)benzamide |
| 20-2 | 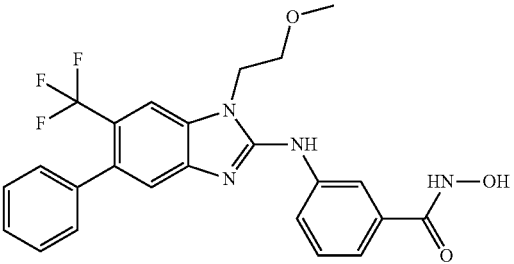 [SMILES: COCCn1c(Nc2cccc(C(=O)NO)c2)nc2cc(-c3ccccc3)c(C(F)(F)F)cc21] | N-hydroxy-3-((1-(2-methoxyethyl)-5-phenyl-6-(trifluoromethyl)-1H-benzo[d]imidazol-2-yl)amino)benzamide |

TABLE I-1-continued

| Example | Structure | Name |
|---|---|---|
| 21-1 | 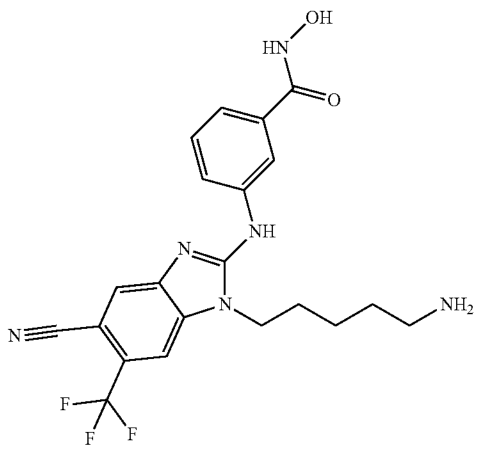 [SMILES: N#Cc1cc2nc(Nc3cccc(C(=O)NO)c3)n(CCCCCN)c2cc1C(F)(F)F] | 3-((1-(5-aminopentyl)-5-cyano-6-(trifluoromethyl)-1H-benzo[d]imidazol-2-yl)amino)-N-hydroxybenzamide |
| 22-1 | 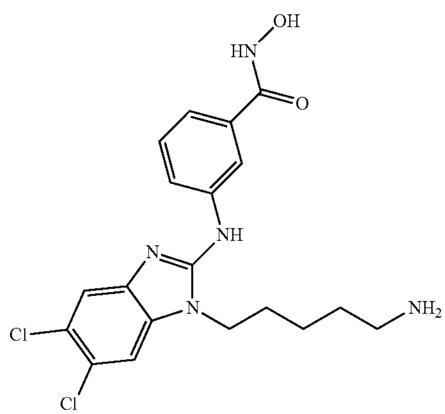 [SMILES: NCCCCCn1c(Nc2cccc(C(=O)NO)c2)nc2cc(Cl)c(Cl)cc21] | 3-((1-(5-aminopentyl)-5,6-dichloro-1H-benzo[d]imidazol-2-yl)amino)-N-hydroxybenzamide |
| 22-2 | 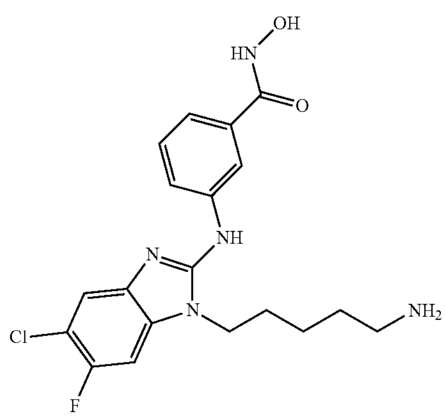 [SMILES: NCCCCCn1c(Nc2cccc(C(=O)NO)c2)nc2cc(Cl)c(F)cc21] | 3-((1-(5-aminopentyl)-5-chloro-6-fluoro-1H-benzo[d]imidazol-2-yl)amino)-N-hydroxybenzamide |
| 23-1 | 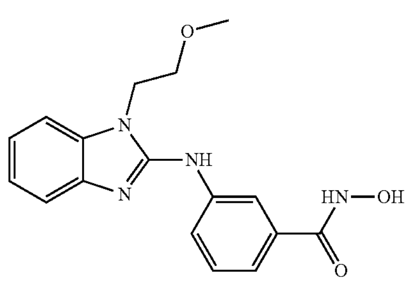 [SMILES: COCCn1c(Nc2cccc(C(=O)NO)c2)nc2ccccc21] | N-hydroxy-3-((1-(2-methoxyethyl)-1H-benzo[d]imidazol-2-yl)amino)benzamide |

TABLE I-1-continued

| Example | Structure | Name |
|---|---|---|
| 23-2 | 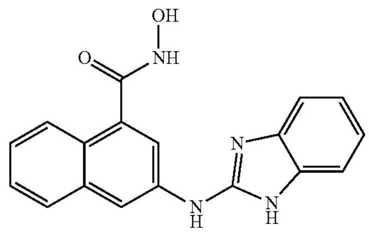 [SMILES: O=C(NO)c1cc(Nc2nc3ccccc3[nH]2)cc2ccccc12] | 3-((1H-benzo[d]imidazol-2-yl)amino)-N-hydroxy-1-naphthamide |
| 23-3 | 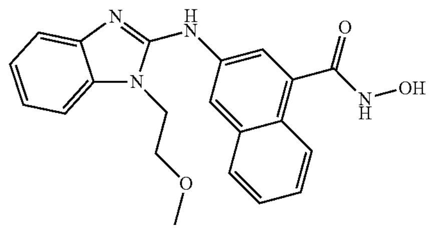 [SMILES: COCCn1c(Nc2cc(C(=O)NO)c3ccccc3c2)nc2ccccc21] | N-hydroxy-3-((1-(2-methoxyethyl)-1H-benzo[d]imidazol-2-yl)amino)-1-naphthamide |
| 23-4 | 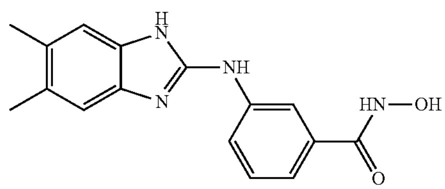 [SMILES: Cc1cc2nc(Nc3cccc(C(=O)NO)c3)[nH]c2cc1C] | 3-((5,6-dimethyl-1H-benzo[d]imidazol-2-yl)amino)-N-hydroxybenzamide |
| 24-1 | 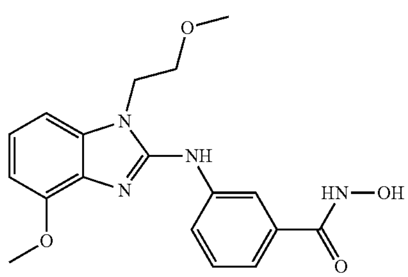 [SMILES: COCCn1c(Nc2cccc(C(=O)NO)c2)nc2c(OC)cccc21] | N-hydroxy-3-((4-methoxy-1-(2-methoxyethyl)-1H-benzo[d]imidazol-2-yl)amino)benzamide |
| 24-2 | 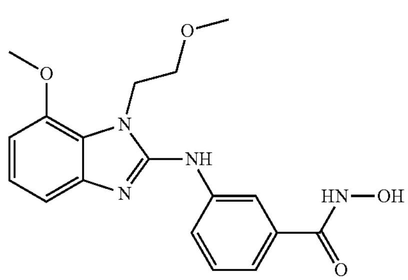 [SMILES: COCCn1c(Nc2cccc(C(=O)NO)c2)nc2cccc(OC)c21] | N-hydroxy-3-((7-methoxy-1-(2-methoxyethyl)-1H-benzo[d]imidazol-2-yl)amino)benzamide |
| 25-1 | 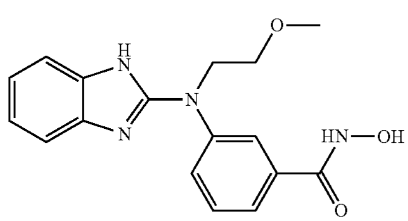 [SMILES: COCCN(c1cccc(C(=O)NO)c1)c1nc2ccccc2[nH]1] | 3-((1H-benzo[d]imidazol-2-yl)(2-methoxyethyl)amino)-N-hydroxybenzamide |

TABLE I-1-continued

| Example | Structure | Name |
| --- | --- | --- |
| 26-1 | 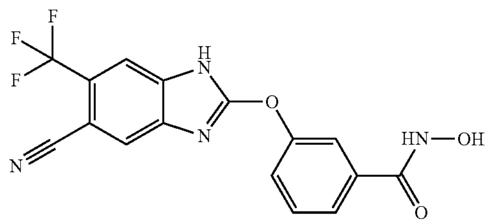 [SMILES: N#Cc1cc2nc(Oc3cccc(C(=O)NO)c3)[nH]c2cc1C(F)(F)F] | 3-((5-cyano-6-(trifluoromethyl)-1H-benzo[d]imidazol-2-yl)oxy)-N-hydroxybenzamide |
| 27-1 | 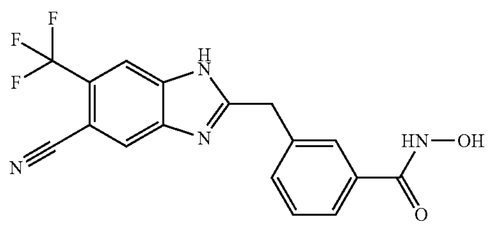 [SMILES: N#Cc1cc2nc(Cc3cccc(C(=O)NO)c3)[nH]c2cc1C(F)(F)F] | 3-((5-cyano-6-(trifluoromethyl)-1H-benzo[d]imidazol-2-yl)methyl)-N-hydroxybenzamide |
| 27-2 | 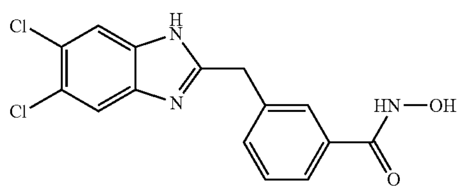 [SMILES: O=C(NO)c1cccc(Cc2nc3cc(Cl)c(Cl)cc3[nH]2)c1] | 3-((5,6-dichloro-1H-benzo[d]imidazol-2-yl)methyl)-N-hydroxybenzamide |
| 28-1 | 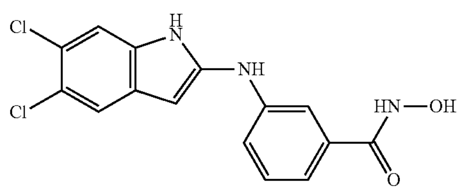 [SMILES: O=C(NO)c1cccc(Nc2cc3cc(Cl)c(Cl)cc3[nH]2)c1] | 3-((5,6-dichloro-1H-indol-2-yl)amino)-N-hydroxybenzamide |
| 29-1 | 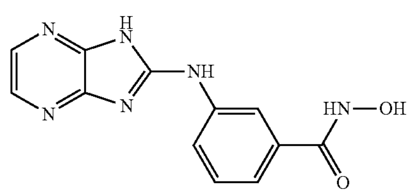 [SMILES: O=C(NO)c1cccc(Nc2nc3nccnc3[nH]2)c1] | 3-((1H-imidazo[4,5-b]pyrazin-2-yl)amino)-N-hydroxybenzamide |
| 30-1 | 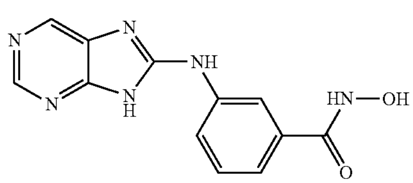 [SMILES: O=C(NO)c1cccc(Nc2nc3cncnc3[nH]2)c1] | 3-((9H-purin-8-yl)amino)-N-hydroxybenzamide |
| 31-1 | 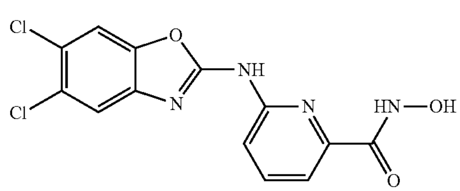 [SMILES: O=C(NO)c1cccc(Nc2nc3cc(Cl)c(Cl)cc3o2)n1] | 6-((5,6-dichlorobenzo[d]oxazol-2-yl)amino)-N-hydroxypicolinamide |
| 32-1 | 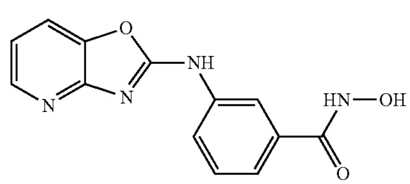 [SMILES: O=C(NO)c1cccc(Nc2nc3ncccc3o2)c1] | N-hydroxy-3-(oxazolo[4,5-b]pyridin-2-ylamino)benzamide |

TABLE I-1-continued

| Example | Structure | Name |
| --- | --- | --- |
| 32-2 | 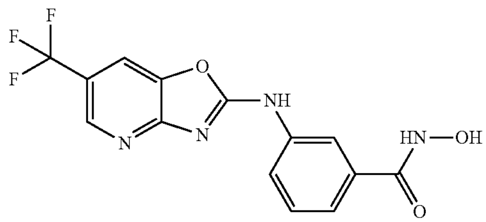 [SMILES: O=C(NO)c1cccc(Nc2nc3ncc(C(F)(F)F)cc3o2)c1] | N-hydroxy-3-((6-(trifluoromethyl)oxazolo[4,5-b]pyridin-2-yl)amino)benzamide |
| 33-1 | 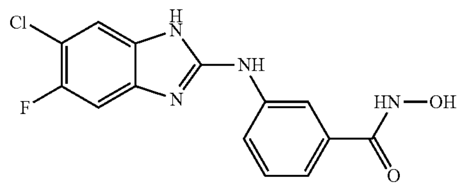 [SMILES: O=C(NO)c1cccc(Nc2nc3cc(F)c(Cl)cc3[nH]2)c1] | 3-((6-chloro-5-fluoro-1H-benzo[d]imidazol-2-yl)amino)-N-hydroxybenzamide |
| 33-10 | 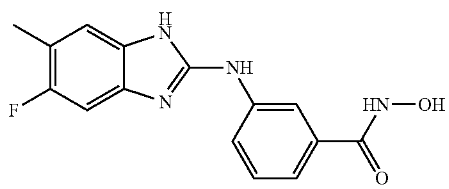 [SMILES: Cc1cc2[nH]c(Nc3cccc(C(=O)NO)c3)nc2cc1F] | 3-((5-fluoro-6-methyl-1H-benzo[d]imidazol-2-yl)amino)-N-hydroxybenzamide |
| 33-11 | 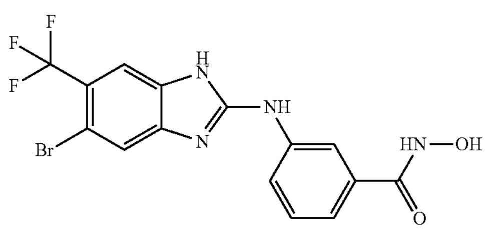 [SMILES: O=C(NO)c1cccc(Nc2nc3cc(Br)c(C(F)(F)F)cc3[nH]2)c1] | 3-((5-bromo-6-(trifluoromethyl)-1H-benzo[d]imidazol-2-yl)amino)-N-hydroxybenzamide |
| 33-12 | 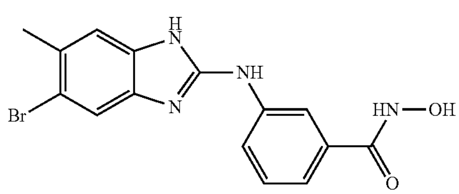 | 3-((5-bromo-6-methyl-1H-benzo[d]imidazol-2-yl)amino)-N-hydroxybenzamide |
| 33-13 | 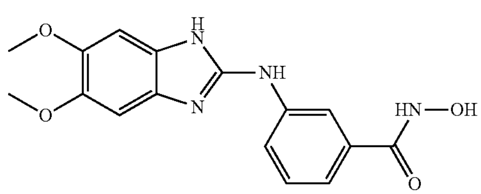 [SMILES: COc1cc2nc(Nc3cccc(C(=O)NO)c3)[nH]c2cc1OC] | 3-((5,6-dimethoxy-1H-benzo[d]imidazol-2-yl)amino)-N-hydroxybenzamide |
| 33-14 | 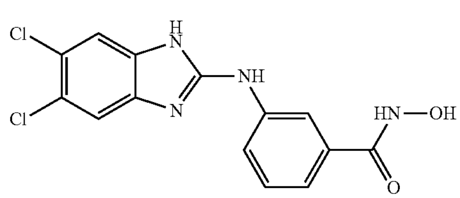 [SMILES: O=C(NO)c1cccc(Nc2nc3cc(Cl)c(Cl)cc3[nH]2)c1] | 3-((5,6-dichloro-1H-benzo[d]imidazol-2-yl)amino)-N-hydroxybenzamide |

TABLE I-1-continued

| Example | Structure | Name |
|---|---|---|
| 33-15 | 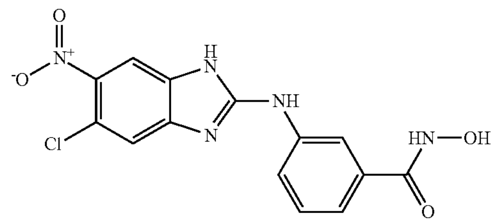 | 3-((5-chloro-6-nitro-1H-benzo[d]imidazol-2-yl)amino)-N-hydroxybenzamide |
| 33-16 | 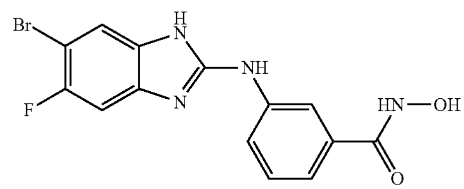 | 3-((6-bromo-5-fluoro-1H-benzo[d]imidazol-2-yl)amino)-N-hydroxybenzamide |
| 33-17 | 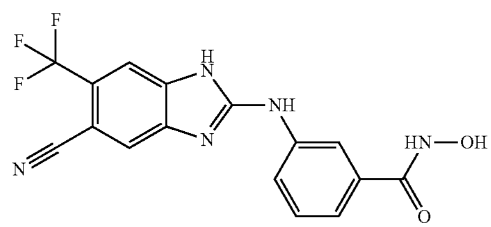 [SMILES: N#Cc1cc2nc(Nc3cccc(C(=O)NO)c3)[nH]c2cc1C(F)(F)F] | 3-((5-cyano-6-(trifluoromethyl)-1H-benzo[d]imidazol-2-yl)amino)-N-hydroxybenzamide |
| 33-18 | 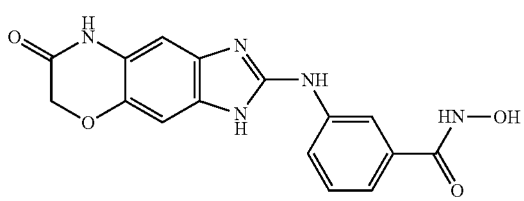 [SMILES: O=C1COc2cc3[nH]c(Nc4cccc(C(=O)NO)c4)nc3cc2N1] | N-hydroxy-3-((7-oxo-3,6,7,8-tetrahydroimidazo[4',5':4,5]benzo[1,2-b][1,4]oxazin-2-yl)amino)benzamide |
| 33-19 | 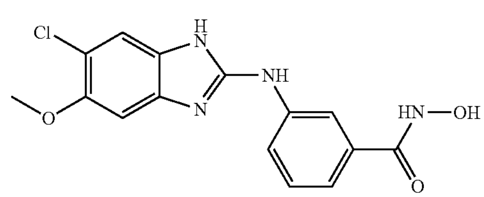 [SMILES: COc1cc2nc(Nc3cccc(C(=O)NO)c3)[nH]c2cc1Cl] | 3-((6-chloro-5-methoxy-1H-benzo[d]imidazol-2-yl)amino)-N-hydroxybenzamide |
| 33-2 | 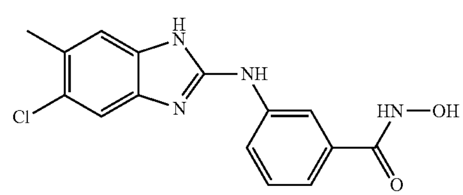 | 3-((5-chloro-6-methyl-1H-benzo[d]imidazol-2-yl)amino)-N-hydroxybenzamide |
| 33-20 | 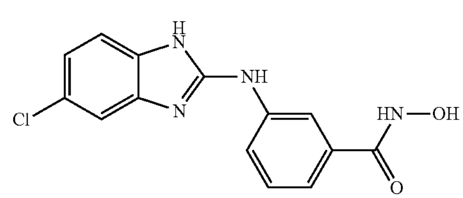 [SMILES: O=C(NO)c1cccc(Nc2nc3cc(Cl)ccc3[nH]2)c1] | 3-((5-chloro-1H-benzo[d]imidazol-2-yl)amino)-N-hydroxybenzamide |

TABLE I-1-continued

| Example | Structure | Name |
|---|---|---|
| 33-21 | 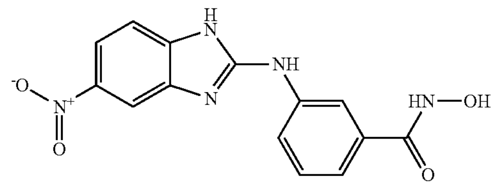 | N-hydroxy-3-((5-nitro-1H-benzo[d]imidazol-2-yl)amino)benzamide |
| 33-22 | 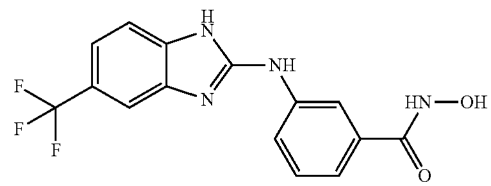 [SMILES: O=C(NO)c1cccc(Nc2nc3cc(C(F)(F)F)ccc3[nH]2)c1] | N-hydroxy-3-((5-(trifluoromethyl)-1H-benzo[d]imidazol-2-yl)amino)benzamide |
| 33-23 | 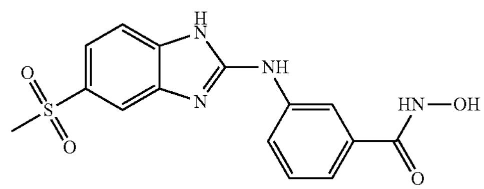 [SMILES: CS(=O)(=O)c1ccc2[nH]c(Nc3cccc(C(=O)NO)c3)nc2c1] | N-hydroxy-3-((5-(methylsulfonyl)-1H-benzo[d]imidazol-2-yl)amino)benzamide |
| 33-24 | 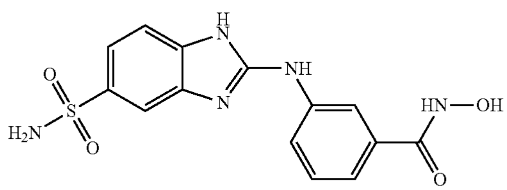 [SMILES: NS(=O)(=O)c1ccc2[nH]c(Nc3cccc(C(=O)NO)c3)nc2c1] | N-hydroxy-3-((5-sulfamoyl-1H-benzo[d]imidazol-2-yl)amino)benzamide |
| 33-3 | 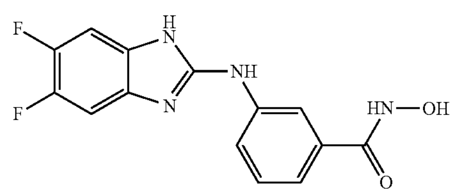 [SMILES: O=C(NO)c1cccc(Nc2nc3cc(F)c(F)cc3[nH]2)c1] | 3-((5,6-difluoro-1H-benzo[d]imidazol-2-yl)amino)-N-hydroxybenzamide |
| 33-4 | 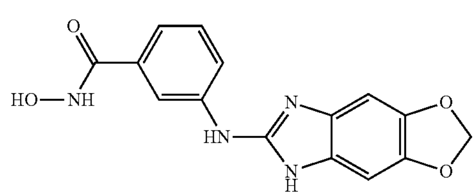 [SMILES: O=C(NO)c1cccc(Nc2nc3cc4c(cc3[nH]2)OCO4)c1] | 3-((5H-[1,3]dioxolo[4',5':4,5]benzo[1,2-d]imidazol-6-yl)amino)-N-hydroxybenzamide |
| 33-5 | 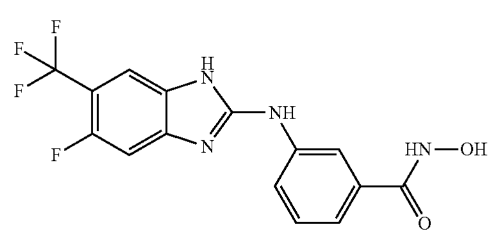 [SMILES: O=C(NO)c1cccc(Nc2nc3cc(F)c(C(F)(F)F)cc3[nH]2)c1] | 3-((5-fluoro-6-(trifluoromethyl)-1H-benzo[d]imidazol-2-yl)amino)-N-hydroxybenzamide |

TABLE I-1-continued

| Example | Structure | Name |
|---|---|---|
| 33-6 | 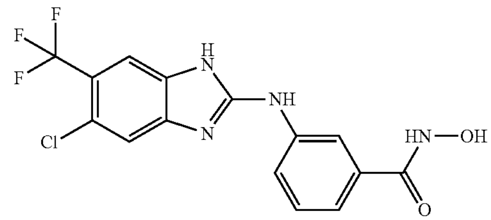 [SMILES: O=C(NO)c1cccc(Nc2nc3cc(Cl)c(C(F)(F)F)cc3[nH]2)c1] | 3-((5-chloro-6-(trifluoromethyl)-1H-benzo[d]imidazol-2-yl)amino)-N-hydroxybenzamide |
| 33-7 | 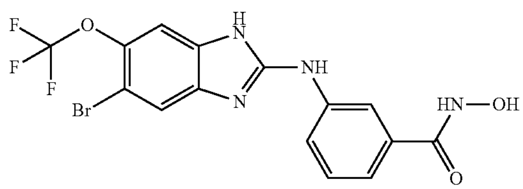 [SMILES: O=C(NO)c1cccc(Nc2nc3cc(Br)c(OC(F)(F)F)cc3[nH]2)c1] | 3-((5-bromo-6-(trifluoromethoxy)-1H-benzo[d]imidazol-2-yl)amino)-N-hydroxybenzamide |
| 33-8 | 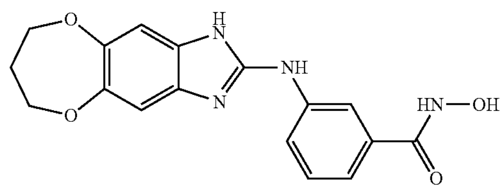 [SMILES: O=C(NO)c1cccc(Nc2nc3cc4c(cc3[nH]2)OCCCO4)c1] | 3-((7,8-dihydro-1H,6H-[1,4]dioxepino[2',3':4,5]benzo[1,2-d]imidazol-2-yl)amino)-N-hydroxybenzamide |
| 33-9 | 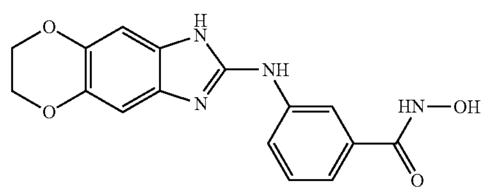 [SMILES: O=C(NO)c1cccc(Nc2nc3cc4c(cc3[nH]2)OCCO4)c1] | 3-((6,7-dihydro-1H-[1,4]dioxino[2',3':4,5]benzo[1,2-d]imidazol-2-yl)amino)-N-hydroxybenzamide |
| 34-1 | 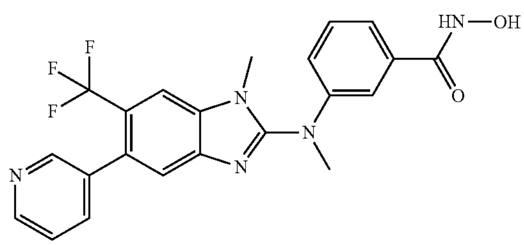 [SMILES: CN(c1cccc(C(=O)NO)c1)c1nc2cc(-c3cccnc3)c(C(F)(F)F)cc2n1C] | N-hydroxy-3-(methyl(1-methyl-5-(pyridin-3-yl)-6-(trifluoromethyl)-1H-benzo[d]imidazol-2-yl)amino)benzamide |
| 34-2 | 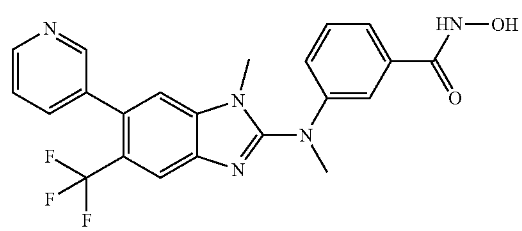 [SMILES: CN(c1cccc(C(=O)NO)c1)c1nc2cc(C(F)(F)F)c(-c3cccnc3)cc2n1C] | N-hydroxy-3-(methyl(1-methyl-6-(pyridin-3-yl)-5-(trifluoromethyl)-1H-benzo[d]imidazol-2-yl)amino)benzamide |
| 34-3 | 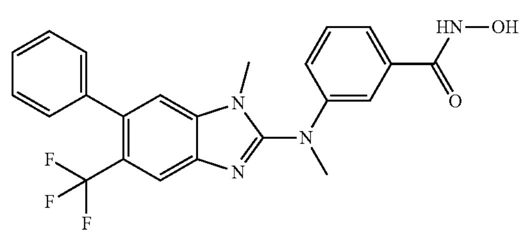 [SMILES: CN(c1cccc(C(=O)NO)c1)c1nc2cc(C(F)(F)F)c(-c3ccccc3)cc2n1C] | N-hydroxy-3-(methyl(1-methyl-6-phenyl-5-(trifluoromethyl)-1H-benzo[d]imidazol-2-yl)amino)benzamide |

TABLE I-1-continued

| Example | Structure | Name |
|---|---|---|
| 35-1 | 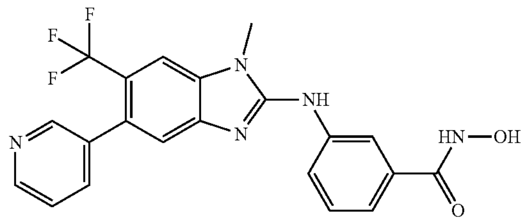 [SMILES: Cn1c(Nc2cccc(C(=O)NO)c2)nc2cc(-c3cccnc3)c(C(F)(F)F)cc21] | N-hydroxy-3-((1-methyl-5-(pyridin-3-yl)-6-(trifluoromethyl)-1H-benzo[d]imidazol-2-yl)amino)benzamide |
| 35-2 | 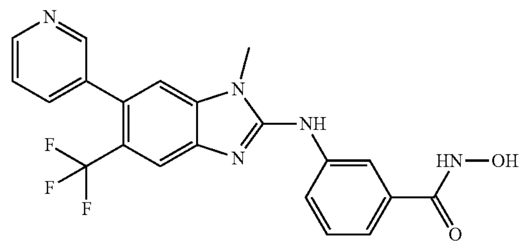 [SMILES: Cn1c(Nc2cccc(C(=O)NO)c2)nc2cc(C(F)(F)F)c(-c3cccnc3)cc21] | N-hydroxy-3-((1-methyl-6-(pyridin-3-yl)-5-(trifluoromethyl)-1H-benzo[d]imidazol-2-yl)amino)benzamide |
| 35-3 | 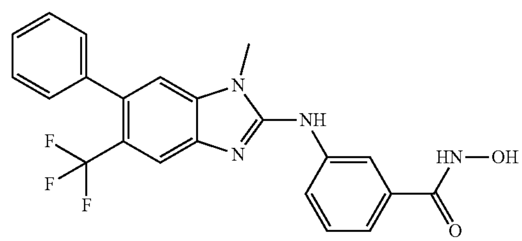 [SMILES: Cn1c(Nc2cccc(C(=O)NO)c2)nc2cc(C(F)(F)F)c(-c3ccccc3)cc21] | N-hydroxy-3-((1-methyl-6-phenyl-5-(trifluoromethyl)-1H-benzo[d]imidazol-2-yl)amino)benzamide |
| 36-1 | 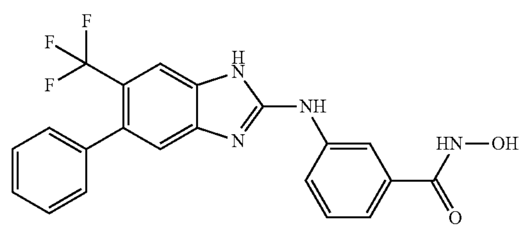 [SMILES: O=C(NO)c1cccc(Nc2nc3cc(-c4ccccc4)c(C(F)(F)F)cc3[nH]2)c1] | N-hydroxy-3-((5-phenyl-6-(trifluoromethyl)-1H-benzo[d]imidazol-2-yl)amino)benzamide |
| 36-10 | 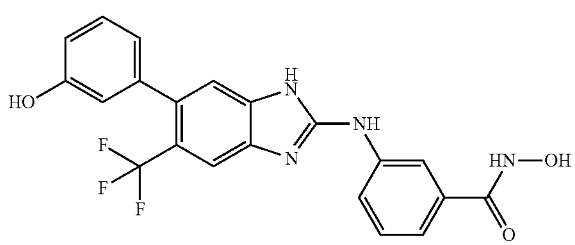 [SMILES: O=C(NO)c1cccc(Nc2nc3cc(C(F)(F)F)c(-c4cccc(O)c4)cc3[nH]2)c1] | N-hydroxy-3-((6-(3-hydroxyphenyl)-5-(trifluoromethyl)-1H-benzo[d]imidazol-2-yl)amino)benzamide |
| 36-11 | 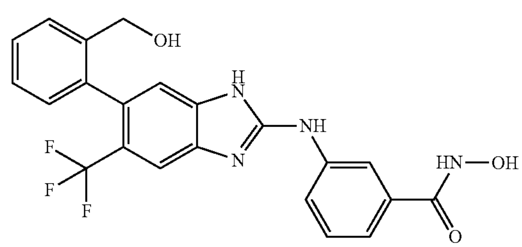 [SMILES: O=C(NO)c1cccc(Nc2nc3cc(C(F)(F)F)c(-c4ccccc4CO)cc3[nH]2)c1] | N-hydroxy-3-((6-(2-(hydroxymethyl)phenyl)-5-(trifluoromethyl)-1H-benzo[d]imidazol-2-yl)amino)benzamide |

TABLE I-1-continued

| Example | Structure | Name |
|---|---|---|
| 36-12 | 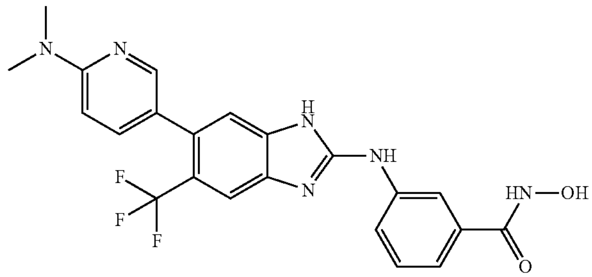 [SMILES: CN(C)c1ccc(-c2cc3[nH]c(Nc4cccc(C(=O)NO)c4)nc3cc2C(F)(F)F)cn1] | 3-((6-(6-(dimethylamino)pyridin-3-yl)-5-(trifluoromethyl)-1H-benzo[d]imidazol-2-yl)amino)-N-hydroxybenzamide |
| 36-13 | 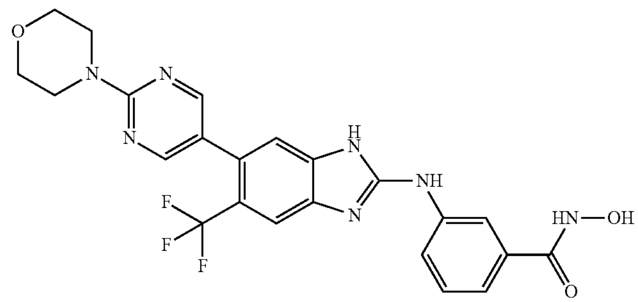 [SMILES: O=C(NO)c1cccc(Nc2nc3cc(C(F)(F)F)c(-c4cnc(N5CCOCC5)nc4)cc3[nH]2)c1] | N-hydroxy-3-((6-(2-morpholinopyrimidin-5-yl)-5-(trifluoromethyl)-1H-benzo[d]imidazol-2-yl)amino)benzamide |
| 36-14 | 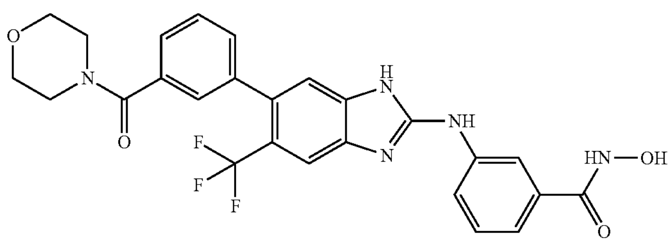 [SMILES: O=C(NO)c1cccc(Nc2nc3cc(C(F)(F)F)c(-c4cccc(C(=O)N5CCOCC5)c4)cc3[nH]2)c1] | N-hydroxy-3-((6-(3-(morpholine-4-carbonyl)phenyl)-5-(trifluoromethyl)-1H-benzo[d]imidazol-2-yl)amino)benzamide |
| 36-15 | 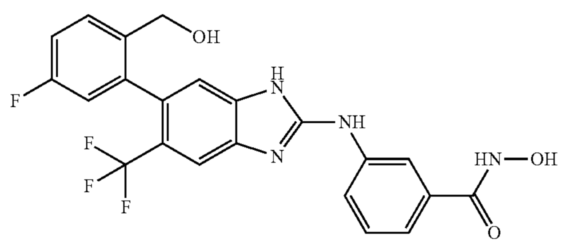 [SMILES: O=C(NO)c1cccc(Nc2nc3cc(C(F)(F)F)c(-c4cc(F)ccc4CO)cc3[nH]2)c1] | 3-((6-(5-fluoro-2-(hydroxymethyl)phenyl)-5-(trifluoromethyl)-1H-benzo[d]imidazol-2-yl)amino)-N-hydroxybenzamide |
| 36-16 | 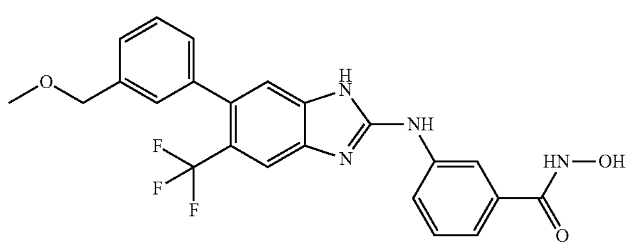 [SMILES: COCc1cccc(-c2cc3[nH]c(Nc4cccc(C(=O)NO)c4)nc3cc2C(F)(F)F)c1] | N-hydroxy-3-((6-(3-(methoxymethyl)phenyl)-5-(trifluoromethyl)-1H-benzo[d]imidazol-2-yl)amino)benzamide |
| 36-17 | 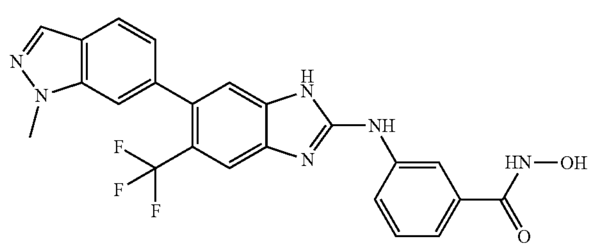 [SMILES: Cn1ncc2ccc(-c3cc4[nH]c(Nc5cccc(C(=O)NO)c5)nc4cc3C(F)(F)F)cc21] | N-hydroxy-3-((6-(1-methyl-1H-indazol-6-yl)-5-(trifluoromethyl)-1H-benzo[d]imidazol-2-yl)amino)benzamide |

TABLE I-1-continued

| Example | Structure | Name |
|---|---|---|
| 36-18 | 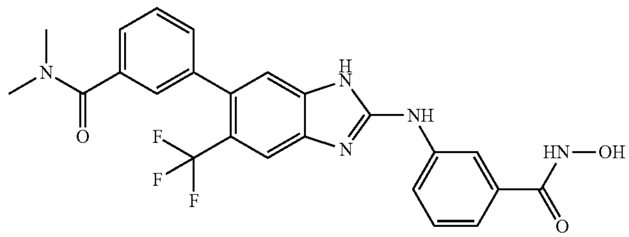 [SMILES: CN(C)C(=O)c1cccc(-c2cc3[nH]c(Nc4cccc(C(=O)NO)c4)nc3cc2C(F)(F)F)c1] | 3-(2-((3-(hydroxycarbamoyl)phenyl)amino)-5-(trifluoromethyl)-1H-benzo[d]imidazol-6-yl)-N,N-dimethylbenzamide |
| 36-19 | 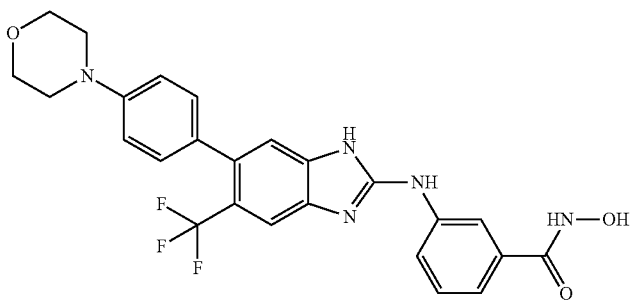 [SMILES: O=C(NO)c1cccc(Nc2nc3cc(C(F)(F)F)c(-c4ccc(N5CCOCC5)cc4)cc3[nH]2)c1] | N-hydroxy-3-((6-(4-morpholinophenyl)-5-(trifluoromethyl)-1H-benzo[d]imidazol-2-yl)amino)benzamide |
| 36-2 | 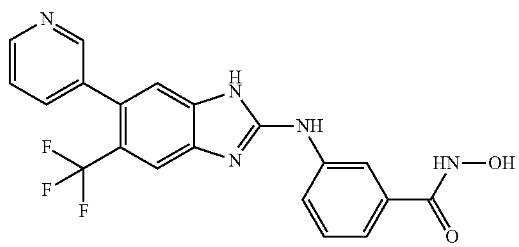 [SMILES: O=C(NO)c1cccc(Nc2nc3cc(C(F)(F)F)c(-c4cccnc4)cc3[nH]2)c1] | N-hydroxy-3-((6-(pyridin-3-yl)-5-(trifluoromethyl)-1H-benzo[d]imidazol-2-yl)amino)benzamide |
| 36-20 | 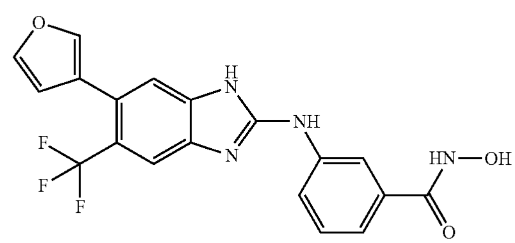 [SMILES: O=C(NO)c1cccc(Nc2nc3cc(C(F)(F)F)c(-c4ccoc4)cc3[nH]2)c1] | 3-((6-(furan-3-yl)-5-(trifluoromethyl)-1H-benzo[d]imidazol-2-yl)amino)-N-hydroxybenzamide |
| 36-3 | 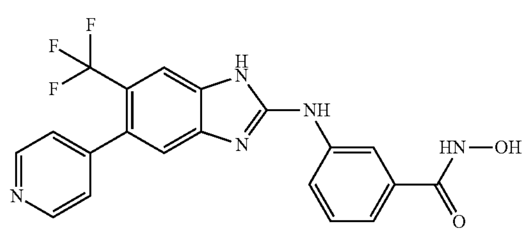 [SMILES: O=C(NO)c1cccc(Nc2nc3cc(-c4ccncc4)c(C(F)(F)F)cc3[nH]2)c1] | N-hydroxy-3-((5-(pyridin-4-yl)-6-(trifluoromethyl)-1H-benzo[d]imidazol-2-yl)amino)benzamide |
| 36-4 | 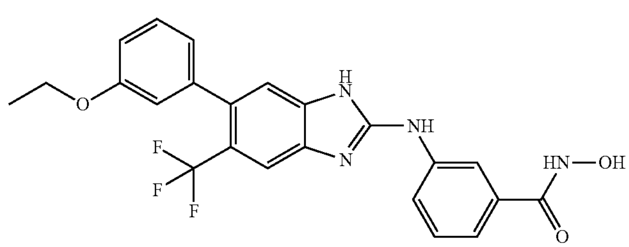 [SMILES: CCOc1cccc(-c2cc3[nH]c(Nc4cccc(C(=O)NO)c4)nc3cc2C(F)(F)F)c1] | 3-((6-(3-ethoxyphenyl)-5-(trifluoromethyl)-1H-benzo[d]imidazol-2-yl)amino)-N-hydroxybenzamide |

TABLE I-1-continued

| Example | Structure | Name |
|---|---|---|
| 36-5 | 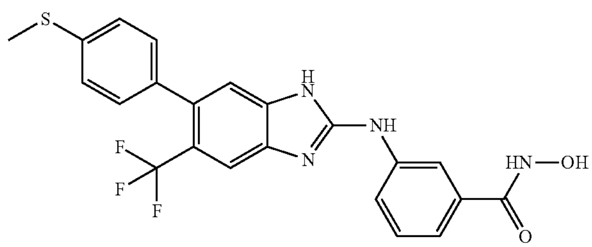 [SMILES: CSc1ccc(-c2cc3[nH]c(Nc4cccc(C(=O)NO)c4)nc3cc2C(F)(F)F)cc1] | N-hydroxy-3-((6-(4-(methylthio)phenyl)-5-(trifluoromethyl)-1H-benzo[d]imidazol-2-yl)amino)benzamide |
| 36-6 | 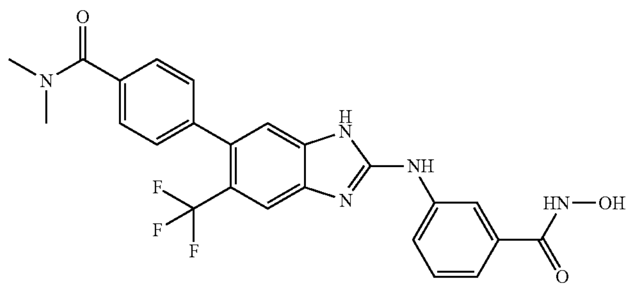 [SMILES: CN(C)C(=O)c1ccc(-c2cc3[nH]c(Nc4cccc(C(=O)NO)c4)nc3cc2C(F)(F)F)cc1] | 4-(2-((3-(hydroxycarbamoyl)phenyl)amino)-5-(trifluoromethyl)-1H-benzo[d]imidazol-6-yl)-N,N-dimethylbenzamide |
| 36-7 | 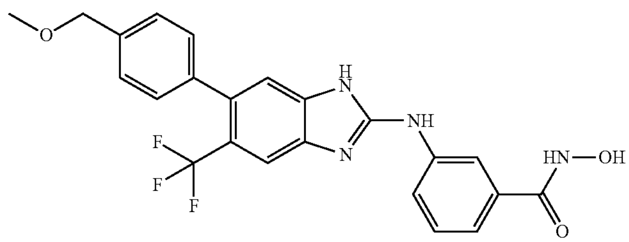 [SMILES: COCc1ccc(-c2cc3[nH]c(Nc4cccc(C(=O)NO)c4)nc3cc2C(F)(F)F)cc1] | N-hydroxy-3-((6-(4-(methoxymethyl)phenyl)-5-(trifluoromethyl)-1H-benzo[d]imidazol-2-yl)amino)benzamide |
| 36-8 | 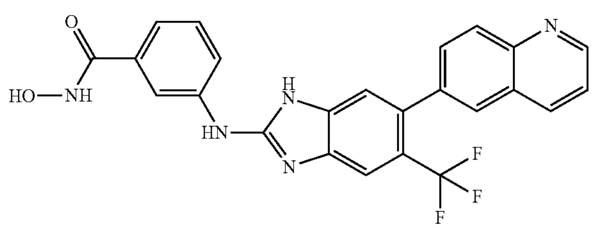 [SMILES: O=C(NO)c1cccc(Nc2nc3cc(C(F)(F)F)c(-c4ccc5ncccc5c4)cc3[nH]2)c1] | N-hydroxy-3-((6-(quinolin-6-yl)-5-(trifluoromethyl)-1H-benzo[d]imidazol-2-yl)amino)benzamide |
| 36-9 | 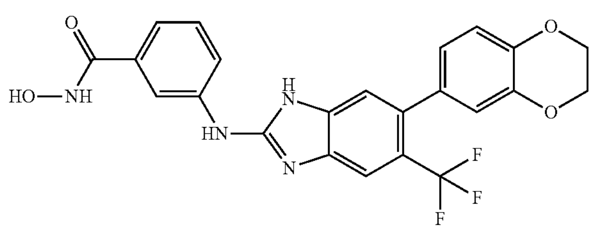 [SMILES: O=C(NO)c1cccc(Nc2nc3cc(C(F)(F)F)c(-c4ccc5c(c4)OCCO5)cc3[nH]2)c1] | 3-((6-(2,3-dihydrobenzo[b][1,4]dioxin-6-yl)-5-(trifluoromethyl)-1H-benzo[d]imidazol-2-yl)amino)-N-hydroxybenzamide |
| 37-1 | 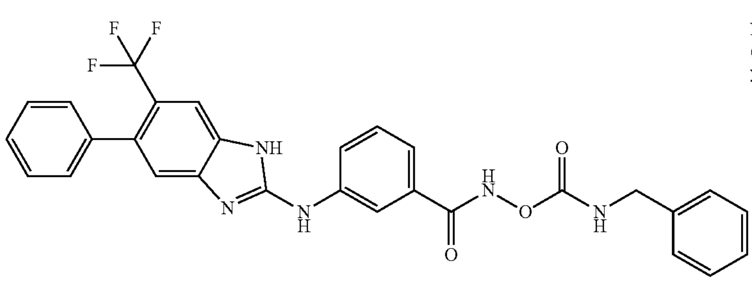 [SMILES: O=C(NCc1ccccc1)ONC(=O)c1cccc(Nc2nc3cc(-c4ccccc4)c(C(F)(F)F)cc3[nH]2)c1] | N-((benzylcarbamoyl)oxy)-3-((5-phenyl-6-(trifluoromethyl)-1H-benzo[d]imidazol-2-yl)amino)benzamide |

TABLE I-1-continued

| Example | Structure | Name |
|---|---|---|
| 37-2 | (structure shown) | N-((benzylcarbamoyl)oxy)-3-((5-cyano-6-(trifluoromethyl)-1H-benzo[d]imidazol-2-yl)(methyl)amino)benzamide | or a pharmaceutically acceptable salt thereof.

Methods of Synthesizing the Disclosed Compounds

The compounds of the present invention may be made by a variety of methods, including standard chemistry. Suitable synthetic routes are depicted in the schemes given below.

The compounds of Formula I may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the Formula I can be synthesized using the methods described below, together with synthetic methods known in the art of synthetic organic chemistry, or variations thereon as appreciated by those skilled in the art. These methods include but are not limited to those methods described below.

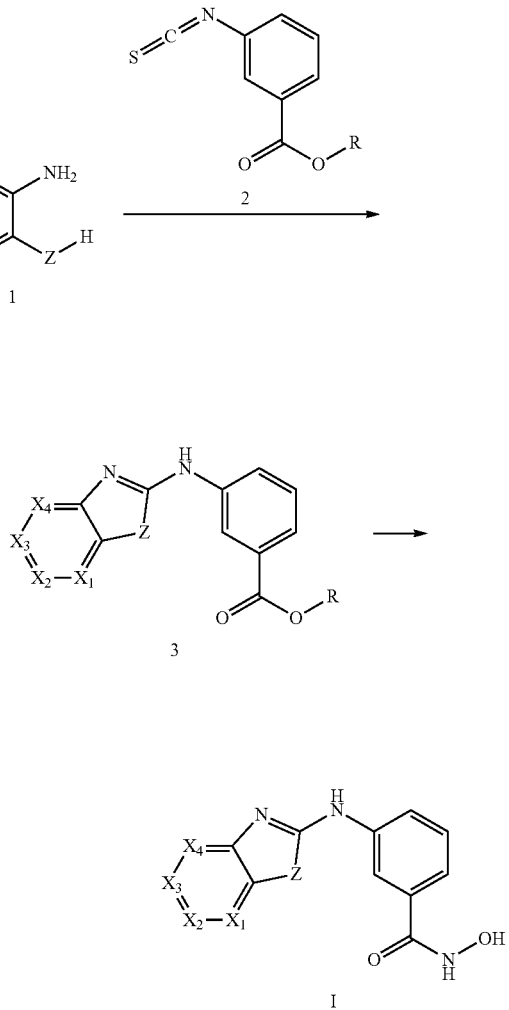

General Scheme I-1 wherein $X_1$, $X_2$, $X_3$, $X_4$, and Z are described herein.

A general way of preparing the compounds of the present invention using an amine 1 is outlined in General Scheme I-1. Condensation and cyclization of amine 1 with compound 2 will provide the carboxylate 3. A final condensation of compound 3 with a hydroxyamine will generally provide the compounds of formula I.

General Scheme II-1

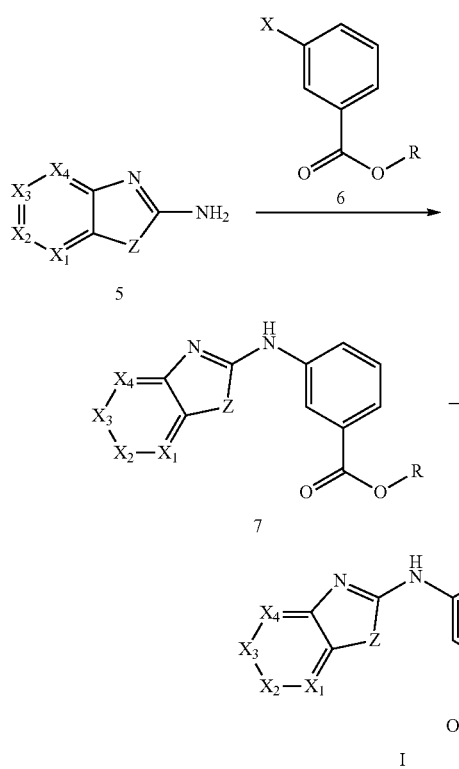

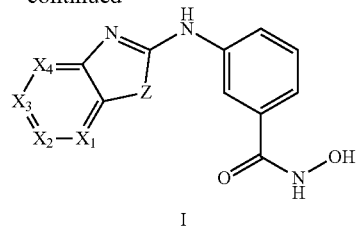

wherein $X_1$, $X_2$, $X_3$, $X_4$, and Z are described herein.

Another general way of preparing the compounds of the present invention is outlined in General Scheme II-1. Cross-coupling of amine 1 with compound 6 under standard conditions using metal-catalyzed coupling will provide the carboxylate 7. A final condensation of compound 7 with a hydroxyamine will generally provide the compounds of formula I.

General Scheme III-1

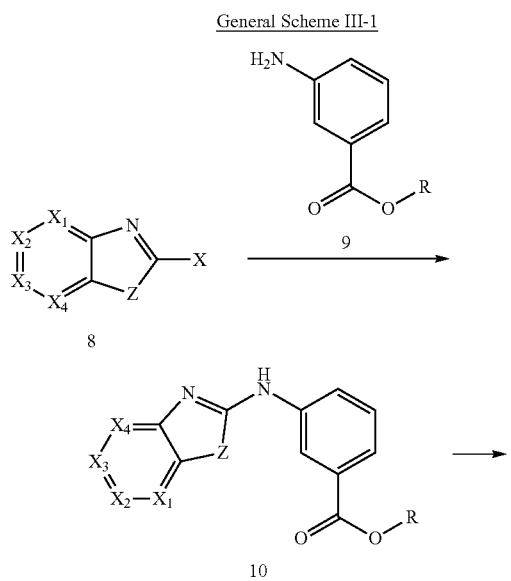

wherein $X_1$, $X_2$, $X_3$, $X_4$, and Z are described herein.

Another general way of preparing the compounds of the present invention is outlined in General Scheme III-1. Cross-coupling of compound 1 with amine 9 under standard conditions using metal-catalyzed coupling will provide the carboxylate 10. A final condensation of compound 10 with a hydroxyamine will generally provide the compounds of formula I.

Spirocycles

One aspect of the invention relates to compounds of Formula II:

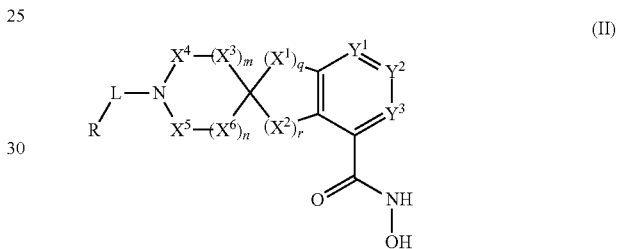

and pharmaceutically acceptable salts thereof, wherein:

$X^1$, $X^2$, $X^3$, $X^4$, $X^5$, and $X^6$ are each independently, at each occurrence, —$CR^1R^2$—, —$NR^3$—, —O—, —C(O)—, —S(O)$_2$—, —S(O)—, or —S—;

$Y^1$, $Y^2$, and $Y^3$ are each independently N or $CR^1$;

L is a bond, —$(CR^1R^2)_p$—, —C(O)$NR^3$—, —S(O)$_2$—, —S(O)$_2NR^3$—, —S(O)—, —S(O)$NR^3$—, —C(O)$(CR^1R^2)_pO$—, or —C(O)$(CR^1R^2)_p$—;

R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO$_2$, —CN, —$R^1$, —$R^2$, —$SR^3$, —$OR^3$, —$NHR^3$, —$NR^3R^4$, —S(O)$_2NR^3R^4$, —S(O)$_2R^1$, —C(O)$R^1$, —C(O)$OR^1$, —$NR^3$S(O)$_2R^1$, —S(O)$R^1$, —S(O)$NR^3R^4$, —$NR^3$S(O)$R^1$, heterocycle, aryl, or heteroaryl;

$R^1$ and $R^2$ are independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —NO$_2$, —CN, —NH$C_1$-$C_6$alkyl, —N($C_1$-$C_6$alkyl)$_2$, —S(O)$_2$N($C_1$-$C_6$alkyl)$_2$, —N($C_1$-$C_6$alkyl)S(O)$_2R^5$, —S(O)$_2$($C_1$-$C_6$alkyl), —($C_1$-$C_6$alkyl)S(O)$_2R^5$, —C(O)$C_1$-$C_6$alkyl, —C(O)O$C_1$-$C_6$alkyl, —N($C_1$-$C_6$alkyl) S(O)$_2C_1$-$C_6$alkyl, or —(CHR$^5$)$_p$NR$^3R^4$, wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^3$, —$NHR^3$, —$NR^3R^4$, —$S(O)_2N(R^3)_2$—, —$S(O)_2R^5$, —$C(O)R^5$, —$C(O)OR^5$, —$NR^3S(O)_2R^5$, —$S(O)R^5$, —$S(O)NR^3R^4$, —$NR^3S(O)R^5$, heterocycle, aryl, or heteroaryl;

or $R^1$ and $R^2$ can combine with the carbon atom to which they are both attached to form a spirocycle, spiroheterocycle, or spirocycloalkenyl;

or $R^1$ and $R^2$, when on adjacent atoms, can combine to form a cycloalkyl, a heterocycle, aryl, heteroaryl containing 1-5 heteroatoms selected from the group consisting of N, S, P and O, or a cycloalkenyl;

or $R^1$ and $R^2$, when on non-adjacent atoms, can combine to form an optionally bridging cycloalkyl, an optionally bridging heterocycle, or an optionally bridging cycloalkenyl;

$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —$S(O)_2N(C_1$-$C_6$alkyl$)_2$, —$S(O)_2(C_1$-$C_6$alkyl), —$(C_1$-$C_6$alkyl$)S(O)_2R^5$, —$C(O)C_1$-$C_6$alkyl, —$C(O)OC_1$-$C_6$alkyl, or —$(CHR^5)_pN(C_1$-$C_6$alkyl$)_2$, wherein each alkyl, alkenyl, cycloalkenyl, alkynyl, cycloalkyl, heterocyclyl, aryl, and heteroaryl is optionally substituted with one or more substituents selected from —OH, halogen, —$NO_2$, oxo, —CN, —$R^5$, —$O(C_1$-$C_6$)alkyl, —$NH(C_1$-$C_6$)alkyl, —$N(C_1$-$C_6$alkyl$)_2$, —$S(O)_2N(C_1$-$C_6$alkyl$)_2$, —$S(O)_2NHC_1$-$C_6$alkyl, —$C(O)C_1$-$C_6$alkyl, —$C(O)OC_1$-$C_6$alkyl, —$N(C_1$-$C_6$alkyl$)S(O)_2C_1$-$C_6$alkyl, —$S(O)R^5$, —$S(O)N(C_1$-$C_6$alkyl$)_2$, —$N(C_1$-$C_6$alkyl$)S(O)R^5$, heterocycle, aryl, or heteroaryl;

$R^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —$NO_2$, —CN, —$NHC_1$-$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$C(O)OC_1$-$C_6$alkyl, —$N(C_1$-$C_6$alkyl$)SO_2C_1$-$C_6$alkyl, —$S(O)(C_1$-$C_6$alkyl), —$S(O)N(C_1$-$C_6$alkyl$)_2$, —$N(C_1$-$C_6$alkyl$)S(O)(C_1$-$C_6$alkyl) or —$(CH_2)_pN(C_1$-$C_6$alkyl$)_2$;

p is 0, 1, 2, 3, 4, 5, or 6;
n is 0, 1, 2, 3, or 4;
m is 0, 1, or 2;
q is 1 or 2;
r is 1 or 2;
wherein the sum q+r≤3 and
wherein the sum m+n≤4.

In one or more embodiments, n is 0 and m is 1. In one or more embodiments, n is 1 and m is 1. In one or more embodiments, q is 1 and r is 1. In one or more embodiments, q is 2 and r is 1. In one or more embodiments, q is 1 and r is 2. In one or more embodiments, q is 1, r is 1, m is 0 and n is 1. In one or more embodiments, q is 1, r is 1, m is 1 and n is 1. In one or more embodiments, q is 1, r is 1, m is 2 and n is 1. In one or more embodiments, q is 1, r is 1, m is 1 and n is 2. In one or more embodiments, $X^5$ is C(O). In one or more embodiments, $X^4$ is C(O).

In some embodiments, $X^1$ is —$CH_2$—. In some embodiments, $X^1$ is —$CH_2$—, and $X^2$ is —$CH_2$—. In some embodiments, $X^1$ is —$CH_2$—, $X^2$ is —$CH_2$—, and $X^3$ is —$CH_2$—. In some embodiments, $X^1$ is —$CH_2$—, $X^2$ is —$CH_2$—, $X^3$ is —$CH_2$—, and $X^4$ —$CH_2$—. In some embodiments, $X^1$ is —$CH_2$—, $X^2$ is —$CH_2$—, $X^3$ is —$CH_2$—, $X^4$ is —$CH_2$—, and $X^5$ is —$CH_2$—. In some embodiments, $X^1$ is —$CH_2$—, $X^2$ is —$CH_2$—, $X^3$ is —$CH_2$—, $X^4$ is —$CH_2$—, $X^5$ is —$CH_2$—, and $X^6$ is —$CH_2$—.

In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, and m is 0. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 2. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 2. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is m is 0, n is 1, q is 1, and r is 2.

In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —$CH_2$—, $X^2$ is —$CH_2$—, $X^3$ is —$CH_2$—, $X^4$ is —$CH_2$—, $X^5$ is —$CH_2$—, $X^6$ is m is 0, n is 1, q is 2, and r is 1.

In some embodiments, $X^1$ is —O—. In some embodiments, $X^1$ is —O—, and $X^2$ is —$CH_2$—. In some embodiments, $X^1$ is —O—, $X^2$ is —$CH_2$—, and $X^3$ is —$CH_2$—. In some embodiments, $X^1$ is —O—, $X^2$ is —$CH_2$—, $X^3$ is —$CH_2$—, and $X^4$ —$CH_2$—. In some embodiments, $X^1$ is —O—, $X^2$ is —$CH_2$—, $X^3$ is —$CH_2$—, $X^4$ is —$CH_2$—, and $X^5$ is —$CH_2$—. In some embodiments, X1 is —O—, $X^2$ is —$CH_2$—, $X^3$ is —$CH_2$—, $X^4$ is —$CH_2$—, $X^5$ is —$CH_2$—, and $X^6$ is —$CH_2$—.

In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, and m is 0. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 2. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 2. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 2.

In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —O—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 2, and r is 1.

In some embodiments, $X^1$ is —O—, and $X^2$ is —O—. In some embodiments, $X^1$ is —O—, $X^2$ is —O—, and $X^3$ is —$CH_2$—. In some embodiments, $X^1$ is —O—, $X^2$ is —O—, $X^3$ is —$CH_2$—, and $X^4$ —$CH_2$—. In some embodiments, $X^1$ is —O—, $X^2$ is —O—, $X^3$ is —$CH_2$—, $X^4$ is —$CH_2$—, and $X^5$ is —$CH_2$—. In some embodiments, X1 is —O—, $X^2$ is —O—, $X^3$ is —$CH_2$—, $X^4$ is —$CH_2$—, $X^5$ is —$CH_2$—, and $X^6$ is —$CH_2$—.

In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, and m is 0. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 1, n is 0, q is 1, and r is. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 1, n is 1, q is 1, and r is. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 0, n is 1, q is 1, and r is 2.

In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —O—, $X^2$ is —O—, $X^3$ is —$CH_2$—, $X^4$ is —$CH_2$—, $X^5$ is —$CH_2$—, $X^6$ is —$CH_2$—, m is 0, n is 1, q is 2, and r is 1.

In some embodiments, $X^1$ is —$CH_2$—, and $X^2$ is —O—. In some embodiments, $X^1$ is —$CH_2$—, $X^2$ is —O—, and $X^3$ is —$CH_2$—. In some embodiments, $X^1$ is —$CH_2$—, $X^2$ is —O—, $X^3$ is —$CH_2$—, and $X^4$ —$CH_2$—. In some embodiments, $X^1$ is —$CH_2$—, $X^2$ is —O—, $X^3$ is —$CH_2$—, $X^4$ is —$CH_2$—, and $X^5$ is —$CH_2$—. In some embodiments, $X^1$ is —$CH_2$—, $X^2$ is —O—, $X^3$ is —$CH_2$—, $X^4$ is —$CH_2$—, $X^5$ is —$CH_2$—, and $X^6$ is —$CH_2$—.

In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, and m is 0. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 1, n is 0, q is 1, and r is 2. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 1, n is 1, q is 1, and r is 2. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 0, n is 1, q is 1, and r is 2.

In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —$CH_2$—, $X^2$ is —O—, $X^3$ is —$CH_2$—, $X^4$ is —$CH_2$—, $X^5$ is —$CH_2$—, $X^6$ is —$CH_2$—, m is 0, n is 1, q is 2, and r is 1.

In some embodiments, $X^1$ is —$NR^3$—. In some embodiments, $X^1$ is —$NR^3$—, and $X^2$ is —$CH_2$—. In some embodiments, $X^1$ is —$NR^3$—, $X^2$ is —$CH_2$—, and $X^3$ is —$CH_2$—. In some embodiments, $X^1$ is —$NR^3$—, $X^2$ is —$CH_2$—, $X^3$ is —$CH_2$—, and $X^4$ —$CH_2$—. In some embodiments, $X^1$ is —$NR^3$—, $X^2$ is —$CH_2$—, $X^3$ is —$CH_2$—, $X^4$ is —$CH_2$—, and $X^5$ is —$CH_2$—. In some embodiments, $X^1$ is —$NR^3$—, $X^2$ is —$CH_2$—, $X^3$ is —$CH_2$—, $X^4$ is —$CH_2$—, $X^5$ is —$CH_2$—, and $X^6$ is —$CH_2$—.

In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, and m is 0. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 2. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 2. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 2.

In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —$NR^3$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 2, and r is 1.

In some embodiments, $X^1$ is —S(O)—. In some embodiments, $X^1$ is —S(O)—, and $X^2$ is —$CH_2$—. In some embodiments, $X^1$ is —S(O)—, $X^2$ is —$CH_2$—, and $X^3$ is —$CH_2$—. In some embodiments, $X^1$ is —S(O)—, $X^2$ is —$CH_2$—, $X^3$ is —$CH_2$—, and $X^4$ —$CH_2$—. In some embodiments, $X^1$ is —S(O)—, $X^2$ is —$CH_2$—, $X^3$ is —$CH_2$—, $X^4$ is —$CH_2$—, and $X^5$ is —$CH_2$—. In some embodiments, $X^1$ is —S(O)—, $X^2$ is —$CH_2$—, $X^3$ is —$CH_2$—, $X^4$ is —$CH_2$—, $X^5$ is —$CH_2$—, and $X^6$ is —$CH_2$—.

In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, and m is 0. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —S(O)—, $X^2$ is —$CH_2$—, $X^3$ is —$CH_2$—, $X^4$ is —$CH_2$—, $X^5$ is $X^6$ is —$CH_2$—, m is 0, n is 0, q is 1, and r is 1.

In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 2. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 2. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 2.

In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —S(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 2, and r is 1.

In some embodiments, $X^1$ is —$S(O)_2$—. In some embodiments, $X^1$ is —$S(O)_2$—, and $X^2$ is —$CH_2$—. In some embodiments, $X^1$ is —$S(O)_2$—, $X^2$ is —$CH_2$—, and $X^3$ is —$CH_2$—. In some embodiments, $X^1$ is —$S(O)_2$—, $X^2$ is —$CH_2$—, $X^3$ is —$CH_2$—, and $X^4$ —$CH_2$—. In some embodiments, $X^1$ is —$S(O)_2$—, $X^2$ is —$CH_2$—, $X^3$ is —$CH_2$—, $X^4$ is —$CH_2$—, and $X^5$ is —$CH_2$—. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, and $X^6$ is —$CH_2$—.

In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, and m is 0. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 1.

In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 2. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 2. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 1, and r is 2.

In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 2, and r is 1. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 2, and r is 1. In some embodiments, $X^1$ is —$S(O)_2$—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 1, q is 2, and r is 1.

In some embodiments, $X^1$ is —C(O)—. In some embodiments, $X^1$ is —C(O)—, and $X^2$ is —$CH_2$—. In some embodiments, $X^1$ is —C(O)—, $X^2$ is —$CH_2$—, and $X^3$ is —$CH_2$—. In some embodiments, $X^1$ is —C(O)—, $X^2$ is —$CH_2$—, $X^3$ is —$CH_2$—, and $X^4$ —$CH_2$—. In some embodiments, $X^1$ is —C(O)—, $X^2$ is —$CH_2$—, $X^3$ is —$CH_2$—, $X^4$ is —$CH_2$—, and $X^5$ is —$CH_2$—. In some embodiments, $X^1$ is —C(O)—, $X^2$ is —$CH_2$—, $X^3$ is —$CH_2$—, $X^4$ is —$CH_2$—, $X^5$ is —$CH_2$—, and $X^6$ is —$CH_2$—.

In some embodiments, $X^1$ is —C(O)—, $X^2$ is —$CH_2$—, $X^3$ is —$CH_2$—, $X^4$ is —$CH_2$—, $X^5$ is —$CH_2$—, $X^6$ is —$CH_2$—, and m is 0. In some embodiments, $X^1$ is —C(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, and n is 0. In some embodiments, $X^1$ is —C(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, and q is 1. In some embodiments, $X^1$ is —C(O)—, $X^2$ is —$CH_2$—, $X^3$ is —$CH_2$—, $X^4$ is —$CH_2$—, $X^5$ is —$CH_2$—, $X^6$ is —$CH_2$—, m is 0, n is 0, q is 1, and r is 1.

In some embodiments, $X^1$ is —C(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 0, q is 1, and r is 1. In some embodiments, $X^1$ is —C(O)—, $X^2$ is —$CH_2$—, $X^3$ is —$CH_2$—, $X^4$ is —$CH_2$—, $X^5$ is —$CH_2$—, $X^6$ is —$CH_2$—, m is 1, n is 1, q is 1, and r is 1. In some embodiments, $X^1$ is —C(O)—, $X^2$ is $X^3$ is $X^4$ is $X^5$ is $X^6$ is —$CH_2$—, m is 0, n is 1, q is 1, and r is 1.

In some embodiments, $X^1$ is —C(O)—, $X^2$ is —CH$_2$—, $X^3$ is —CH$_2$—, $X^4$ is —CH$_2$—, $X^5$ is —CH$_2$—, $X^6$ is —CH$_2$—, m is 1, n is 0, q is 1, and r is 2. In some embodiments, $X^1$ is —C(O)—, $X^2$ is —CH$_2$—, $X^3$ is —CH$_2$—, $X^4$ is —CH$_2$—, $X^5$ is —CH$_2$—, $X^6$ is —CH$_2$—, m is 1, n is 1, q is 1, and r is 2. In some embodiments, $X^1$ is —C(O)—, $X^2$ is —CH$_2$—, $X^3$ is —CH$_2$—, $X^4$ is —CH$_2$—, $X^5$ is —CH$_2$—, $X^6$ is —CH$_2$—, m is 0, n is 1, q is 1, and r is 2.

In some embodiments, $X^1$ is —C(O)—, $X^2$ is —CH$_2$—, $X^3$ is —CH$_2$—, $X^4$ is —CH$_2$—, $X^5$ is —CH$_2$—, $X^6$ is —CH$_2$—, m is 1, n is 0, q is 2, and r is 1. In some embodiments, $X^1$ is —C(O)—, $X^2$ is —CH$_2$—, $X^3$ is —CH$_2$—, $X^4$ is —CH$_2$—, $X^5$ is —CH$_2$—, $X^6$ is —CH$_2$—, m is 1, n is 1, q is 2, and r is 1. In some embodiments, $X^1$ is —C(O)—, $X^2$ is —CH$_2$—, $X^3$ is —CH$_2$—, $X^4$ is —CH$_2$—, $X^5$ is —CH$_2$—, $X^6$ is —CH$_2$—, m is 0, n is 1, q is 2, and r is 1.

In some embodiments, $X^1$ is —CH$_2$—, and $X^2$ is —NR$^3$—. In some embodiments, $X^1$ is —CH$_2$—, $X^2$ is —NR$^3$—, and $X^3$ is —CH$_2$—. In some embodiments, $X^1$ is —CH$_2$—, $X^2$ is —NR$^3$—, $X^3$ is —CH$_2$—, and $X^4$ —CH$_2$—. In some embodiments, $X^1$ is —CH$_2$—, $X^2$ is —NR$^3$—, $X^3$ is —CH$_2$—, $X^4$ is —CH$_2$—, and $X^5$ is —CH$_2$—. In some embodiments, $X^1$ is —CH$_2$—, $X^2$ is —NR$^3$—, $X^3$ is —CH$_2$—, $X^4$ is —CH$_2$—, $X^5$ is —CH$_2$—, and $X^6$ is —CH$_2$—.

In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, and m is 0. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 0, and n is 0. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 0, n is 0, and q is 1. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 0, n is 0, q is 1, and r is 1.

In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 1, n is 0, q is 1, and r is 1. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 1, n is 1, q is 1, and r is 1. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 0, n is 1, q is 1, and r is 1.

In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 1, n is 0, q is 1, and r is 2. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 1, n is 1, q is 1, and r is 2. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 0, n is 1, q is 1, and r is 2.

In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 1, n is 0, q is 2, and r is 1. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 1, n is 1, q is 2, and r is 1. In some embodiments, $X^1$ is —CH$_2$—, $X^2$ is —NR$^3$—, $X^3$ is —CH$_2$—, $X^4$ is —CH$_2$—, $X^5$ is —CH$_2$—, $X^6$ is —CH$_2$—, m is 0, n is 1, q is 2, and r is 1.

In some embodiments, $X^1$ is —CH$_2$—, and $X^2$ is —S(O)—. In some embodiments, $X^1$ is —CH$_2$—, $X^2$ is —S(O)—, and $X^3$ is —CH$_2$—. In some embodiments, $X^1$ is —CH$_2$—, $X^2$ is —S(O)—, $X^3$ is —CH$_2$—, and $X^4$ —CH$_2$—. In some embodiments, $X^1$ is —CH$_2$—, $X^2$ is —S(O)—, $X^3$ is —CH$_2$—, $X^4$ is —CH$_2$—, and $X^5$ is —CH$_2$—. In some embodiments, $X^1$ is —CH$_2$—, $X^2$ is —S(O)—, $X^3$ is —CH$_2$—, $X^4$ is —CH$_2$—, $X^5$ is —CH$_2$—, and $X^6$ is —CH$_2$—.

In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, and m is 0. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 0, and n is 0. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 0, n is 0, and q is 1. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 0, n is 0, q is 1, and r is 1.

In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 1, n is 0, q is 1, and r is 1. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 1, n is 1, q is 1, and r is 1. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 0, n is 1, q is 1, and r is 1.

In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 1, n is 0, q is 1, and r is 2. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 1, n is 1, q is 1, and r is 2. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 0, n is 1, q is 1, and r is 2.

In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 1, n is 0, q is 2, and r is 1. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 1, n is 1, q is 2, and r is 1. In some embodiments, $X^1$ is —CH$_2$—, $X^2$ is —S(O)—, $X^3$ is —CH$_2$—, $X^4$ is —CH$_2$—, $X^5$ is —CH$_2$—, $X^6$ is —CH$_2$—, m is 0, n is 1, q is 2, and r is 1.

In some embodiments, $X^1$ is —CH$_2$—, and $X^2$ is —S(O)$_2$—. In some embodiments, $X^1$ is —CH$_2$—, $X^2$ is —S(O)$_2$—, and $X^3$ is —CH$_2$—. In some embodiments, $X^1$ is —CH$_2$—, $X^2$ is —S(O)$_2$—, $X^3$ is —CH$_2$—, and $X^4$ —CH$_2$—. In some embodiments, $X^1$ is —CH$_2$—, $X^2$ is —S(O)$_2$—, $X^3$ is —CH$_2$—, $X^4$ is —CH$_2$—, and $X^5$ is —CH$_2$—. In some embodiments, $X^1$ is —CH$_2$—, $X^2$ is —S(O)$_2$—, $X^3$ is —CH$_2$—, $X^4$ is —CH$_2$—, $X^5$ is —CH$_2$—, and $X^6$ is —CH$_2$—.

In some embodiments, $X^1$ is —CH$_2$—, $X^2$ is —S(O)$_2$—, $X^3$ is —CH$_2$—, $X^4$ is —CH$_2$—, $X^5$ is —CH$_2$—, $X^6$ is —CH$_2$—, and m is 0. In some embodiments, $X^1$ is —CH$_2$—, $X^2$ is —S(O)$_2$—, $X^3$ is —CH$_2$—, $X^4$ is —CH$_2$—, $X^5$ is —CH$_2$—, $X^6$ is —CH$_2$—, m is 0, and n is 0. In some embodiments, $X^1$ is —CH$_2$—, $X^2$ is —S(O)$_2$—, $X^3$ is —CH$_2$—, $X^4$ is —CH$_2$—, $X^5$ is —CH$_2$—, $X^6$ is —CH$_2$—, m is 0, n is 0, and q is 1. In some embodiments, $X^1$ is —CH$_2$—, $X^2$ is —S(O)$_2$—, $X^3$ is —CH$_2$—, $X^4$ is —CH$_2$—, $X^5$ is —CH$_2$—, $X^6$ is —CH$_2$—, m is 0, n is 0, q is 1, and r is 1.

In some embodiments, $X^1$ is —CH$_2$—, $X^2$ is —S(O)$_2$—, $X^3$ is —CH$_2$—, $X^4$ is —CH$_2$—, $X^5$ is —CH$_2$—, $X^6$ is —CH$_2$—, m is 1, n is 0, q is 1, and r is 1. In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 1, n is 1, q is 1, and r is 1. In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 0, n is 1, q is 1, and r is 1.

In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 1, n is 0, q is 1, and r is 2. In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 1, n is 1, q is 1, and r is 2. In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 0, n is 1, q is 1, and r is 2.

In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 1, n is 0, q is 2, and r is 1. In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 1, n is 1, q is 2, and r is 1. In some embodiments, X$^1$ is —CH$_2$—, X$^2$ is —S(O)$_2$—, X$^3$ is —CH$_2$—, X$^4$ is —CH$_2$—, X$^5$ is —CH$_2$—, X$^6$ is —CH$_2$—, m is 0, n is 1, q is 2, and r is 1.

In some embodiments, X$^1$ is —CH$_2$—, and X$^2$ is —C(O)—. In some embodiments, X$^1$ is —CH$_2$—, X$^2$ is —C(O)—, and X$^3$ is —CH$_2$—. In some embodiments, X$^1$ is —CH$_2$—, X$^2$ is —C(O)—, X$^3$ is —CH$_2$—, and X$^4$ is —CH$_2$—. In some embodiments, X$^1$ is —CH$_2$—, X$^2$ is —C(O)—, X$^3$ is —CH$_2$—, X$^4$ is —CH$_2$—, and X$^5$ is —CH$_2$—. In some embodiments, X$^1$ is —CH$_2$—, X$^2$ is —C(O)—, X$^3$ is —CH$_2$—, X$^4$ is —CH$_2$—, X$^5$ is —CH$_2$—, and X$^6$ is —CH$_2$—.

In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, and m is 0. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 0, and n is 0. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 0, n is 0, and q is 1. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 0, n is 0, q is 1, and r is 1.

In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 1, n is 0, q is 1, and r is 1. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 1, n is 1, q is 1, and r is 1. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 0, n is 1, q is 1, and r is 1.

In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 1, n is 0, q is 1, and r is 2. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 1, n is 1, q is 1, and r is 2. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 0, n is 1, q is 1, and r is 2.

In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 1, n is 0, q is 2, and r is 1. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 1, n is 1, q is 2, and r is 1. In some embodiments, X$^1$ is —CH$_2$—, X$^2$ is —C(O)—, X$^3$ is —CH$_2$—, X$^4$ is —CH$_2$—, X$^5$ is —CH$_2$—, X$^6$ is —CH$_2$—, m is 0, n is 1, q is 2, and r is 1.

In some embodiments, Y$^1$ is —CH—. In some embodiments, Y$^2$ is —CH—. In some embodiments, Y$^3$ is —CH—. In some embodiments, Y$^1$ is —N—. In some embodiments, Y$^2$ is —N—. In some embodiments, Y$^3$ is —N—. In some embodiments, Y$^1$ is —CH—, Y$^2$ is —CH—, and, and Y$^3$ is —CH—. In some embodiments, Y$^1$ is —N—, Y$^2$ is —CH—, and, and Y$^3$ is —N—. In some embodiments, Y$^1$ is —N—, Y$^2$ is —N—, and, and Y$^3$ is —CH—. In some embodiments, Y$^1$ is —CH—, Y$^2$ is —N—, and, and Y$^3$ is —CH—. In some embodiments, Y$^1$ is —CH—, Y$^2$ is —N—, and, and Y$^3$ is —N—.

In some embodiments, X$^4$ is —C(O)— and X$^1$, X$^2$, X$^3$, X$^5$, X$^6$ are —CH$_2$—. In some embodiments, X$^4$ is —C(O)—, X$^1$, X$^2$, X$^3$, X$^5$, X$^6$ are —CH$_2$—, m is 0 and n is 0. In some embodiments, X$^4$ is —C(O)—, X$^1$, X$^2$, X$^3$, X$^5$, X$^6$ are —CH$_2$—, m is 1 and n is 0. In some embodiments, X$^4$ is —C(O)—, X$^1$, X$^2$, X$^3$, X$^5$, X$^6$ are —CH$_2$—, m is 0 and n is 1. In some embodiments, X$^4$ is —C(O)—, X$^1$, X$^2$, X$^3$, X$^5$, X$^6$ are —CH$_2$—, m is 1 and n is 1.

In some embodiments, X$^4$ is —C(O)—, X$^1$, X$^2$, X$^3$, X$^5$, X$^6$ are —CH$_2$—, m is 0, n is 0, q is 1 and r is 1. In some embodiments, X$^4$ is —C(O)—, X$^1$, X$^2$, X$^3$, X$^5$, X$^6$ are —CH$_2$—, m is 1, n is 0, q is 1 and r is 1. In some embodiments, X$^4$ is —C(O)—, X$^1$, X$^2$, X$^3$, X$^5$, X$^6$ are —CH$_2$—, m is 0, n is 1, q is 1 and r is 1. In some embodiments, X$^4$ is —C(O)—, X$^1$, X$^2$, X$^3$, X$^5$, X$^6$ are —CH$_2$—, m is 1, n is 1, q is 1 and r is 1.

In some embodiments, X$^4$ is —C(O)—, X$^1$, X$^2$, X$^3$, X$^5$, X$^6$ are —CH$_2$—, m is 0, n is 0, q is 2 and r is 1. In some embodiments, X$^4$ is —C(O)—, X$^1$, X$^2$, X$^3$, X$^5$, X$^6$ are —CH$_2$—, m is 1, n is 0, q is 2 and r is 1. In some embodiments, X$^4$ is —C(O)—, X$^1$, X$^2$, X$^3$, X$^5$, X$^6$ are —CH$_2$—, m is 0, n is 1, q is 2 and r is 1. In some embodiments, X$^4$ is —C(O)—, X$^1$, X$^2$, X$^3$, X$^5$, X$^6$ are —CH$_2$—, m is 1, n is 1, q is 2 and r is 1.

In some embodiments, X$^4$ is —C(O)—, X$^1$, X$^2$, X$^3$, X$^5$, X$^6$ are —CH$_2$—, m is 0, n is 0, q is 1 and r is 2. In some embodiments, X$^4$ is —C(O)—, X$^1$, X$^2$, X$^3$, X$^5$, X$^6$ are —CH$_2$—, m is 1, n is 0, q is 1 and r is 2. In some embodiments, X$^4$ is —C(O)—, X$^1$, X$^2$, X$^3$, X$^5$, X$^6$ are —CH$_2$—, m is 0, n is 1, q is 1 and r is 2. In some embodiments, X$^4$ is —C(O)—, X$^1$, X$^2$, X$^3$, X$^5$, X$^6$ are —CH$_2$—, m is 1, n is 1, q is 1 and r is 2.

In some embodiments, X$^4$ is —S(O)— and X$^1$, X$^2$, X$^3$, X$^5$, X$^6$ are —CH$_2$—. In some embodiments, X$^4$ is —S(O)—, X$^1$, X$^2$, X$^3$, X$^5$, X$^6$ are —CH$_2$—, m is 0 and n is 0. In some embodiments, X$^4$ is —S(O)—, X$^1$, X$^2$, X$^3$, X$^5$, X$^6$ are —CH$_2$—, m is 1 and n is 0 In some embodiments, X$^4$ is —S(O)—, X$^1$, X$^2$, X$^3$, X$^5$, X$^6$ are —CH$_2$—, m is 0 and n is 1. In some embodiments, X$^4$ is —S(O)—, X$^1$, X$^2$, X$^3$, X$^5$, X$^6$ are —CH$_2$—, m is 1 and n is 1.

In some embodiments, X$^4$ is —S(O)—, X$^1$, X$^2$, X$^3$, X$^5$, X$^6$ are —CH$_2$—, m is 0, n is 0, q is 1 and r is 1. In some embodiments, X$^4$ is —S(O)—, X$^1$, X$^2$, X$^3$, X$^5$, X$^6$ are —CH$_2$—, m is 1, n is 0, q is 1 and r is 1. In some embodiments, X$^4$ is —S(O)—, X$^1$, X$^2$, X$^3$, X$^5$, X$^6$ are —CH$_2$—, m is 0, n is 1, q is 1 and r is 1. In some embodiments, X$^4$ is —S(O)—, X$^1$, X$^2$, X$^3$, X$^5$, X$^6$ are —CH$_2$—, m is 1, n is 1, q is 1 and r is 1.

In some embodiments, X$^4$ is —S(O)—, X$^1$, X$^2$, X$^3$, X$^5$, X$^6$ are —CH$_2$—, m is 0, n is 0, q is 2 and r is 1. In some embodiments, X$^4$ is —S(O)—, X$^1$, X$^2$, X$^3$, X$^5$, X$^6$ are —CH$_2$—, m is 1, n is 0, q is 2 and r is 1. In some embodiments, X$^4$ is —S(O)—, X$^1$, X$^2$, X$^3$, X$^5$, X$^6$ are —CH$_2$—, m is 0, n is 1, q is 2 and r is 1. In some embodiments, X$^4$ is —S(O)—, X$^1$, X$^2$, X$^3$, X$^5$, X$^6$ are —CH$_2$—, m is 1, n is 1, q is 2 and r is 1.

In some embodiments, X$^4$ is —S(O)—, X$^1$, X$^2$, X$^3$, X$^5$, X$^6$ are —CH$_2$—, m is 0, n is 0, q is 1 and r is 2. In some embodiments, X$^4$ is —S(O)—, X$^1$, X$^2$, X$^3$, X$^5$, X$^6$ are —CH$_2$—, m is 1, n is 0, q is 1 and r is 2. In some embodiments, X$^4$ is —S(O)—, X$^1$, X$^2$, X$^3$, X$^5$, X$^6$ are —CH$_2$—, m is 0, n is 1, q is 1 and r is 2. In some embodiments, X$^4$ is —S(O)—, X$^1$, X$^2$, X$^3$, X$^5$, X$^6$ are —CH$_2$—, m is 1, n is 1, q is 1 and r is 2.

In some embodiments, X$^4$ is —S(O)$_2$—, and X$^1$, X$^2$, X$^3$, X$^5$, X$^6$ are —CH$_2$—. In some embodiments, X$^4$ is —S(O)$_2$—, X$^1$, X$^2$, X$^3$, X$^5$, X$^6$ are —CH$_2$—, m is 0 and n is 0. In some embodiments, X$^4$ is —S(O)$_2$—, X$^1$, X$^2$, X$^3$, X$^5$, X$^6$ are —CH$_2$—, m is 1 and n is 0. In some embodiments, X$^4$ is —S(O)$_2$—, X$^1$, X$^2$, X$^3$, X$^5$, X$^6$ are —CH$_2$—, m is 0 and n is 1. In some embodiments, X$^4$ is —S(O)$_2$—, X$^1$, X$^2$, X$^3$, X$^5$, X$^6$ are —CH$_2$—, m is 1 and n is 1.

In some embodiments, X$^4$ is —S(O)$_2$—, X$^1$, X$^2$, X$^3$, X$^5$, X$^6$ are —CH$_2$—, m is 0, n is 0, q is 1 and r is 1. In some embodiments, X$^4$ is —S(O)$_2$—, X$^1$, X$^2$, X$^3$, X$^5$, X$^6$ are —CH$_2$—, m is 1, n is 0, q is 1 and r is 1. In some embodiments, X$^4$ is —S(O)$_2$—, X$^1$, X$^2$, X$^3$, X$^5$, X$^6$ are —CH$_2$—, m is 0, n is 1, q is 1 and r is 1. In some embodiments, X$^4$ is —S(O)$_2$—, X$^1$, X$^2$, X$^3$, X$^5$, X$^6$ are —CH$_2$—, m is 1, n is 1, q is 1 and r is 1.

In some embodiments, X$^4$ is —S(O)$_2$—, X$^1$, X$^2$, X$^3$, X$^5$, X$^6$ are —CH$_2$—, m is 0, n is 0, q is 2 and r is 1. In some embodiments, X$^4$ is —S(O)$_2$—, X$^1$, X$^2$, X$^3$, X$^5$, X$^6$ are —CH$_2$—, m is 1, n is 0, q is 2 and r is 1. In some embodiments, X$^4$ is —S(O)$_2$—, X$^1$, X$^2$, X$^3$, X$^5$, X$^6$ are —CH$_2$—, m is 0, n is 1, q is 2 and r is 1. In some embodiments, X$^4$ is —S(O)$_2$—, X$^1$, X$^2$, X$^3$, X$^5$, X$^6$ are —CH$_2$—, m is 1, n is 1, q is 2 and r is 1.

In some embodiments, X$^4$ is —S(O)$_2$—, X$^1$, X$^2$, X$^3$, X$^5$, X$^6$ are —CH$_2$—, m is 0, n is 0, q is 1 and r is 2. In some embodiments, X$^4$ is —S(O)$_2$—, X$^1$, X$^2$, X$^3$, X$^5$, X$^6$ are —CH$_2$—, m is 1, n is 0, q is 1 and r is 2. In some embodiments, X$^4$ is —S(O)$_2$—, X$^1$, X$^2$, X$^3$, X$^5$, X$^6$ are —CH$_2$—, m is 0, n is 1, q is 1 and r is 2. In some embodiments, X$^4$ is —S(O)$_2$—, X$^1$, X$^2$, X$^3$, X$^5$, X$^6$ are —CH$_2$—, m is 1, n is 1, q is 1 and r is 2.

In some embodiments, X$^4$ is —C(O)—, X$^1$ is —O—, and X$^2$, X$^3$, X$^5$, X$^6$ are —CH$_2$—. In some embodiments, X$^4$ is —C(O)—, X$^1$ is —O—, and X$^2$, X$^3$, X$^5$, X$^6$ are —CH$_2$—, m is 0 and n is 0. In some embodiments, X$^4$ is —C(O)—, X$^1$ is —O—, and X$^2$, X$^3$, X$^5$, X$^6$ are —CH$_2$—, m is 1 and n is 0. In some embodiments, X$^4$ is —C(O)—, X$^1$ is —O—, and X$^2$, X$^3$, X$^5$, X$^6$ are —CH$_2$—, m is 0 and n is 1. In some embodiments, X$^4$ is —C(O)—, X$^1$ is —O—, and X$^2$, X$^3$, X$^5$, X$^6$ are —CH$_2$—, m is 1 and n is 1.

In some embodiments, X$^4$ is —C(O)—, X$^1$ is —O—, and X$^2$, X$^3$, X$^5$, X$^6$ are —CH$_2$—, m is 0, n is 0, q is 1 and r is 1. In some embodiments, X$^4$ is —C(O)—, X$^1$ is —O—, and X$^2$, X$^3$, X$^5$, X$^6$ are —CH$_2$—, m is 1, n is 0, q is 1 and r is 1. In some embodiments, X$^4$ is —C(O)—, X$^1$ is —O—, and X$^2$, X$^3$, X$^5$, X$^6$ are —CH$_2$—, m is 0, n is 1, q is 1 and r is 1. In some embodiments, X$^4$ is —C(O)—, X$^1$ is —O—, and X$^2$, X$^3$, X$^5$, X$^6$ are —CH$_2$—, m is 1, n is 1, q is 1 and r is 1.

In some embodiments, X$^4$ is —C(O)—, X$^1$ is —O—, and X$^2$, X$^3$, X$^5$, X$^6$ are —CH$_2$—, m is 0, n is 0, q is 2 and r is 1. In some embodiments, X$^4$ is —C(O)—, X$^1$ is —O—, and X$^2$, X$^3$, X$^5$, X$^6$ are —CH$_2$—, m is 1, n is 0, q is 2 and r is 1. In some embodiments, X$^4$ is —C(O)—, X$^1$ is —O—, and X$^2$, X$^3$, X$^5$, X$^6$ are —CH$_2$—, m is 0, n is 1, q is 2 and r is 1. In some embodiments, X$^4$ is —C(O)—, X$^1$ is —O—, and X$^2$, X$^3$, X$^5$, X$^6$ are —CH$_2$—, m is 1, n is 1, q is 2 and r is 1.

In some embodiments, X$^4$ is —C(O)—, X$^1$ is —O—, and X$^2$, X$^3$, X$^5$, X$^6$ are —CH$_2$—, m is 0, n is 0, q is 1 and r is 2. In some embodiments, X$^4$ is —C(O)—, X$^1$ is —O—, and X$^2$, X$^3$, X$^5$, X$^6$ are —CH$_2$—, m is 1, n is 0, q is 1 and r is 2. In some embodiments, X$^4$ is —C(O)—, X$^1$ is —O—, and X$^2$, X$^3$, X$^5$, X$^6$ are —CH$_2$—, m is 0, n is 1, q is 1 and r is 2. In some embodiments, X$^4$ is —C(O)—, X$^1$ is —O—, and X$^2$, X$^3$, X$^5$, X$^6$ are —CH$_2$—, m is 1, n is 1, q is 1 and r is 2.

In some embodiments, X$^4$ is —S(O)—, X$^1$ is —O—, and X$^2$, X$^3$, X$^5$, X$^6$ are —CH$_2$—. In some embodiments, X$^4$ is —S(O)—, X$^1$ is —O—, and X$^2$, X$^3$, X$^5$, X$^6$ are —CH$_2$—, m is 0 and n is 0. In some embodiments, X$^4$ is —S(O)—, X$^1$ is —O—, and X$^2$, X$^3$, X$^5$, X$^6$ are —CH$_2$—, m is 1 and n is 0. In some embodiments, X$^4$ is —S(O)—, X$^1$ is —O—, and X$^2$, X$^3$, X$^5$, X$^6$ are —CH$_2$—, m is 0 and n is 1. In some embodiments, X$^4$ is —S(O)—, X$^1$ is —O—, and X$^2$, X$^3$, X$^5$, X$^6$ are —CH$_2$—, m is 1 and n is 1.

In some embodiments, X$^4$ is —S(O)—, X$^1$ is —O—, and X$^2$, X$^3$, X$^5$, X$^6$ are —CH$_2$—, m is 0, n is 0, q is 1 and r is 1. In some embodiments, X$^4$ is —S(O)—, X$^1$ is —O—, and X$^2$, X$^3$, X$^5$, X$^6$ are —CH$_2$—, m is 1, n is 0, q is 1 and r is 1. In some embodiments, X$^4$ is —S(O)—, X$^1$ is —O—, and X$^2$, X$^3$, X$^5$, X$^6$ are —CH$_2$—, m is 0, n is 1, q is 1 and r is 1. In some embodiments, X$^4$ is —S(O)—, X$^1$ is —O—, and X$^2$, X$^3$, X$^5$, X$^6$ are —CH$_2$—, m is 1, n is 1, q is 1 and r is 1.

In some embodiments, X$^4$ is —S(O)—, X$^1$ is —O—, and X$^2$, X$^3$, X$^5$, X$^6$ are —CH$_2$—, m is 0, n is 0, q is 2 and r is 1. In some embodiments, X$^4$ is —S(O)—, X$^1$ is —O—, and X$^2$, X$^3$, X$^5$, X$^6$ are —CH$_2$—, m is 1, n is 0, q is 2 and r is 1. In some embodiments, X$^4$ is —S(O)—, X$^1$ is —O—, and X$^2$, X$^3$, X$^5$, X$^6$ are —CH$_2$—, m is 0, n is 1, q is 2 and r is 1. In some embodiments, X$^4$ is —S(O)—, X$^1$ is —O—, and X$^2$, X$^3$, X$^5$, X$^6$ are —CH$_2$—, m is 1, n is 1, q is 2 and r is 1.

In some embodiments, X$^4$ is —S(O)—, X$^1$ is —O—, and X$^2$, X$^3$, X$^5$, X$^6$ are —CH$_2$—, m is 0, n is 0, q is 1 and r is 2. In some embodiments, X$^4$ is —S(O)—, X$^1$ is —O—, and X$^2$, X$^3$, X$^5$, X$^6$ are —CH$_2$—, m is 1, n is 0, q is 1 and r is 2. In some embodiments, X$^4$ is —S(O)—, X$^1$ is —O—, and X$^2$, X$^3$, X$^5$, X$^6$ are —CH$_2$—, m is 0, n is 1, q is 1 and r is 2. In some embodiments, X$^4$ is —S(O)—, X$^1$ is —O—, and X$^2$, X$^3$, X$^5$, X$^6$ are —CH$_2$—, m is 1, n is 1, q is 1 and r is 2.

In some embodiments, X$^4$ is —S(O)$_2$—, X$^1$ is —O—, and X$^2$, X$^3$, X$^5$, X$^6$ are —CH$_2$—. In some embodiments, X$^4$ is —S(O)$_2$—, X$^1$ is —O—, and X$^2$, X$^3$, X$^5$, X$^6$ are —CH$_2$—, m is 0 and n is 0. In some embodiments, X$^4$ is —S(O)$_2$—, X$^1$ is —O—, and X$^2$, X$^3$, X$^5$, X$^6$ are —CH$_2$—, m is 1 and n is 0. In some embodiments, X$^4$ is —S(O)$_2$—, X$^1$ is —O—, and X$^2$, X$^3$, X$^5$, X$^6$ are —CH$_2$—, m is 0 and n is 1. In some embodiments, X$^4$ is —S(O)$_2$—, X$^1$ is —O—, and X$^2$, X$^3$, X$^5$, X$^6$ are —CH$_2$—, m is 1 and n is 1.

In some embodiments, X$^4$ is —S(O)$_2$—, X$^1$ is —O—, and X$^2$, X$^3$, X$^5$, X$^6$ are —CH$_2$—, m is 0, n is 0, q is 1 and r is 1. In some embodiments, X$^4$ is —S(O)$_2$—, X$^1$ is —O—, and X$^2$, X$^3$, X$^5$, X$^6$ are —CH$_2$—, m is 1, n is 0, q is 1 and r is 1. In some embodiments, X$^4$ is —S(O)$_2$—, X$^1$ is —O—, and X$^2$, X$^3$, X$^5$, X$^6$ are —CH$_2$—, m is 0, n is 1, q is 1 and r is In some embodiments, $X^4$ is —S(O)$_2$—, $X^1$ is —O—, and $X^2$, $X^3$, $X^5$, $X^6$ are —CH$_2$—, m is 1, n is 1, q is 1 and r is 1.

In some embodiments, $X^4$ is —S(O)$_2$—, $X^1$ is —O—, and $X^2$, $X^3$, $X^5$, $X^6$ are —CH$_2$—, m is 0, n is 0, q is 2 and r is 1. In some embodiments, $X^4$ is —S(O)$_2$—, $X^1$ is —O—, and $X^2$, $X^3$, $X^5$, $X^6$ are —CH$_2$—, m is 1, n is 0, q is 2 and r is 1. In some embodiments, $X^4$ is —S(O)$_2$—, $X^1$ is —O—, and $X^2$, $X^3$, $X^5$, $X^6$ are —CH$_2$—, m is 0, n is 1, q is 2 and r is 1. In some embodiments, $X^4$ is —S(O)$_2$—, $X^1$ is —O—, and $X^2$, $X^3$, $X^5$, $X^6$ are —CH$_2$—, m is 1, n is 1, q is 2 and r is 1.

In some embodiments, $X^4$ is —S(O)$_2$—, $X^1$ is —O—, and $X^2$, $X^3$, $X^5$, $X^6$ are —CH$_2$—, m is 0, n is 0, q is 1 and r is 2. In some embodiments, $X^4$ is —S(O)$_2$—, $X^1$ is —O—, and $X^2$, $X^3$, $X^5$, $X^6$ are —CH$_2$—, m is 1, n is 0, q is 1 and r is 2. In some embodiments, $X^4$ is —S(O)$_2$—, $X^1$ is —O—, and $X^2$, $X^3$, $X^5$, $X^6$ are —CH$_2$—, m is 0, n is 1, q is 1 and r is 2. In some embodiments, $X^4$ is —S(O)$_2$—, $X^1$ is —O—, and $X^2$, $X^3$, $X^5$, $X^6$ are —CH$_2$—, m is 1, n is 1, q is 1 and r is 2.

In some embodiments, $X^4$ is —C(O)—, $X^2$ is —O—, and $X^1$, $X^3$, $X^5$, $X^6$ are —CH$_2$—. In some embodiments, $X^4$ is —C(O)—, $X^2$ is —O—, and $X^1$, $X^3$, $X^5$, $X^6$ are —CH$_2$—, m is 0 and n is 0. In some embodiments, $X^4$ is —C(O)—, $X^2$ is —O—, and $X^1$, $X^3$, $X^5$, $X^6$ are —CH$_2$—, m is 1 and n is 0. In some embodiments, $X^4$ is —C(O)—, $X^2$ is —O—, and $X^1$, $X^3$, $X^5$, $X^6$ are —CH$_2$—, m is 0 and n is 1. In some embodiments, $X^4$ is —C(O)—, $X^2$ is —O—, and $X^1$, $X^3$, $X^5$, $X^6$ are —CH$_2$—, m is 1 and n is 1.

In some embodiments, $X^4$ is —C(O)—, $X^2$ is —O—, and $X^1$, $X^3$, $X^5$, $X^6$ are —CH$_2$—, m is 0, n is 0, q is 1 and r is 1. In some embodiments, $X^4$ is —C(O)—, $X^2$ is —O—, and $X^1$, $X^3$, $X^5$, $X^6$ are —CH$_2$—, m is 1, n is 0, q is 1 and r is 1. In some embodiments, $X^4$ is —C(O)—, $X^2$ is —O—, and $X^1$, $X^3$, $X^5$, $X^6$ are —CH$_2$—, m is 0, n is 1, q is 1 and r is 1. In some embodiments, $X^4$ is —C(O)—, $X^2$ is —O—, and $X^1$, $X^3$, $X^5$, $X^6$ are —CH$_2$—, m is 1, n is 1, q is 1 and r is 1.

In some embodiments, $X^4$ is —C(O)—, $X^2$ is —O—, and $X^1$, $X^3$, $X^5$, $X^6$ are —CH$_2$—, m is 0, n is 0, q is 2 and r is 1. In some embodiments, $X^4$ is —C(O)—, $X^2$ is —O—, and $X^1$, $X^3$, $X^5$, $X^6$ are —CH$_2$—, m is 1, n is 0, q is 2 and r is 1. In some embodiments, $X^4$ is —C(O)—, $X^2$ is —O—, and $X^1$, $X^3$, $X^5$, $X^6$ are —CH$_2$—, m is 0, n is 1, q is 2 and r is 1. In some embodiments, $X^4$ is —C(O)—, $X^2$ is —O—, and $X^1$, $X^3$, $X^5$, $X^6$ are —CH$_2$—, m is 1, n is 1, q is 2 and r is 1.

In some embodiments, $X^4$ is —C(O)—, $X^2$ is —O—, and $X^1$, $X^3$, $X^5$, $X^6$ are —CH$_2$—, m is 0, n is 0, q is 1 and r is 2. In some embodiments, $X^4$ is —C(O)—, $X^2$ is —O—, and $X^1$, $X^3$, $X^5$, $X^6$ are —CH$_2$—, m is 1, n is 0, q is 1 and r is 2. In some embodiments, $X^4$ is —C(O)—, $X^2$ is —O—, and $X^1$, $X^3$, $X^5$, $X^6$ are —CH$_2$—, m is 0, n is 1, q is 1 and r is 2. In some embodiments, $X^4$ is —C(O)—, $X^2$ is —O—, and $X^1$, $X^3$, $X^5$, $X^6$ are —CH$_2$—, m is 1, n is 1, q is 1 and r is 2.

In some embodiments, $X^4$ is —S(O)—, $X^2$ is —O—, and $X^1$, $X^3$, $X^5$, $X^6$ are —CH$_2$—. In some embodiments, $X^4$ is —S(O)—, $X^2$ is —O—, and $X^1$, $X^3$, $X^5$, $X^6$ are —CH$_2$—, m is 0 and n is 0. In some embodiments, $X^4$ is —S(O)—, $X^2$ is —O—, and $X^1$, $X^3$, $X^5$, $X^6$ are —CH$_2$—, m is 1 and n is 0. In some embodiments, $X^4$ is —S(O)—, $X^2$ is —O—, and $X^1$, $X^3$, $X^5$, $X^6$ are —CH$_2$—, m is 0 and n is 1. In some embodiments, $X^4$ is —S(O)—, $X^2$ is —O—, and $X^1$, $X^3$, $X^5$, $X^6$ are —CH$_2$—, m is 1 and n is 1.

In some embodiments, $X^4$ is —S(O)—, $X^2$ is —O—, and $X^1$, $X^3$, $X^5$, $X^6$ are —CH$_2$—, m is 0, n is 0, q is 1 and r is 1. In some embodiments, $X^4$ is —S(O)—, $X^2$ is —O—, and $X^1$, $X^3$, $X^5$, $X^6$ are —CH$_2$—, m is 1, n is 0, q is 1 and r is 1. In some embodiments, $X^4$ is —S(O)—, $X^2$ is —O—, and $X^1$, $X^3$, $X^5$, $X^6$ are —CH$_2$—, m is 0, n is 1, q is 1 and r is 1. In some embodiments, $X^4$ is —S(O)—, $X^2$ is —O—, and $X^1$, $X^3$, $X^5$, $X^6$ are —CH$_2$—, m is 1, n is 1, q is 1 and r is 1.

In some embodiments, $X^4$ is —S(O)—, $X^2$ is —O—, and $X^1$, $X^3$, $X^5$, $X^6$ are —CH$_2$—, m is 0, n is 0, q is 2 and r is 1. In some embodiments, $X^4$ is —S(O)—, $X^2$ is —O—, and $X^1$, $X^3$, $X^5$, $X^6$ are —CH$_2$—, m is 1, n is 0, q is 2 and r is 1. In some embodiments, $X^4$ is —S(O)—, $X^2$ is —O—, and $X^1$, $X^3$, $X^5$, $X^6$ are —CH$_2$—, m is 0, n is 1, q is 2 and r is 1. In some embodiments, $X^4$ is —S(O)—, $X^2$ is —O—, and $X^1$, $X^3$, $X^5$, $X^6$ are —CH$_2$—, m is 1, n is 1, q is 2 and r is 1.

In some embodiments, $X^4$ is —S(O)—, $X^2$ is —O—, and $X^1$, $X^3$, $X^5$, $X^6$ are —CH$_2$—, m is 0, n is 0, q is 1 and r is 2. In some embodiments, $X^4$ is —S(O)—, $X^2$ is —O—, and $X^1$, $X^3$, $X^5$, $X^6$ are —CH$_2$—, m is 1, n is 0, q is 1 and r is 2. In some embodiments, $X^4$ is —S(O)—, $X^2$ is —O—, and $X^1$, $X^3$, $X^5$, $X^6$ are —CH$_2$—, m is 0, n is 1, q is 1 and r is 2. In some embodiments, $X^4$ is —S(O)—, $X^2$ is —O—, and $X^1$, $X^3$, $X^5$, $X^6$ are —CH$_2$—, m is 1, n is 1, q is 1 and r is 2.

In some embodiments, $X^4$ is —S(O)$_2$—, $X^2$ is —O—, and $X^1$, $X^3$, $X^5$, $X^6$ are —CH$_2$—. In some embodiments, $X^4$ is —S(O)$_2$—, $X^2$ is —O—, and $X^1$, $X^3$, $X^5$, $X^6$ are —CH$_2$—, m is 0 and n is 0. In some embodiments, $X^4$ is —S(O)$_2$—, $X^2$ is —O—, and $X^1$, $X^3$, $X^5$, $X^6$ are —CH$_2$—, m is 1 and n is 0. In some embodiments, $X^4$ is —S(O)$_2$—, $X^2$ is —O—, and $X^1$, $X^3$, $X^5$, $X^6$ are —CH$_2$—, m is 0 and n is 1. In some embodiments, $X^4$ is —S(O)$_2$—, $X^2$ is —O—, and $X^1$, $X^3$, $X^5$, $X^6$ are —CH$_2$—, m is 1 and n is 1.

In some embodiments, $X^4$ is —S(O)$_2$—, $X^2$ is —O—, and $X^1$, $X^3$, $X^5$, $X^6$ are —CH$_2$—, m is 0, n is 0, q is 1 and r is 1. In some embodiments, $X^4$ is —S(O)$_2$—, $X^2$ is —O—, and $X^1$, $X^3$, $X^5$, $X^6$ are —CH$_2$—, m is 1, n is 0, q is 1 and r is 1. In some embodiments, $X^4$ is —S(O)$_2$—, $X^2$ is —O—, and $X^1$, $X^3$, $X^5$, $X^6$ are —CH$_2$—, m is 0, n is 1, q is 1 and r is 1. In some embodiments, $X^4$ is —S(O)$_2$—, $X^2$ is —O—, and $X^1$, $X^3$, $X^5$, $X^6$ are —CH$_2$—, m is 1, n is 1, q is 1 and r is 1.

In some embodiments, $X^4$ is —S(O)$_2$—, $X^2$ is —O—, and $X^1$, $X^3$, $X^5$, $X^6$ are —CH$_2$—, m is 0, n is 0, q is 2 and r is 1. In some embodiments, $X^4$ is —S(O)$_2$—, $X^2$ is —O—, and $X^1$, $X^3$, $X^5$, $X^6$ are —CH$_2$—, m is 1, n is 0, q is 2 and r is 1. In some embodiments, $X^4$ is —S(O)$_2$—, $X^2$ is —O—, and $X^1$, $X^3$, $X^5$, $X^6$ are —CH$_2$—, m is 0, n is 1, q is 2 and r is 1. In some embodiments, $X^4$ is —S(O)$_2$—, $X^2$ is —O—, and $X^1$, $X^3$, $X^5$, $X^6$ are —CH$_2$—, m is 1, n is 1, q is 2 and r is 1.

In some embodiments, $X^4$ is —S(O)$_2$—, $X^2$ is —O—, and $X^1$, $X^3$, $X^5$, $X^6$ are —CH$_2$—, m is 0, n is 0, q is 1 and r is 2. In some embodiments, $X^4$ is —S(O)$_2$—, $X^2$ is —O—, and $X^1$, $X^3$, $X^5$, $X^6$ are —CH$_2$—, m is 1, n is 0, q is 1 and r is 2. In some embodiments, $X^4$ is —S(O)$_2$—, $X^2$ is —O—, and $X^1$, $X^3$, $X^5$, $X^6$ are —CH$_2$—, m is 0, n is 1, q is 1 and r is 2. In some embodiments, $X^4$ is —S(O)$_2$—, $X^2$ is —O—, and $X^1$, $X^3$, $X^5$, $X^6$ are —CH$_2$—, m is 1, n is 1, q is 1 and r is 2.

In one or more embodiments, the compound is of the Formula II-A:

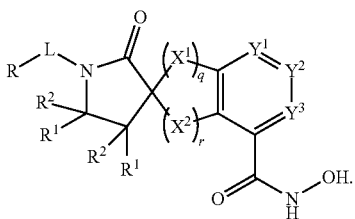

In one or more embodiments, the compound is of the Formula II-B:

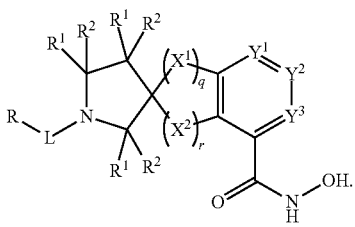

In one or more embodiments, the compound is of the Formula II-C:

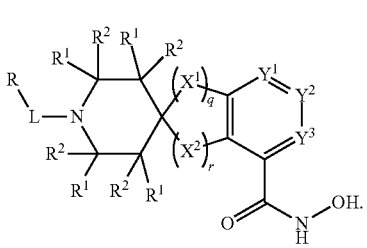

In one or more embodiments, the compound is of the Formula II-D:

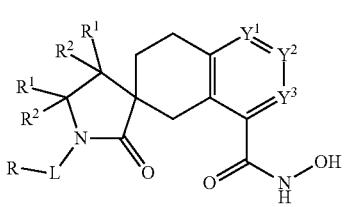

In one or more embodiments, the compound is of the Formula II-E:

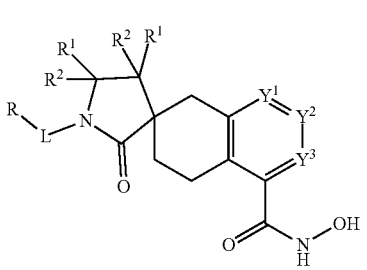

For each of the embodiments described above for compounds of Formula II, II-A, II-B, II-C, II-D, or II-E, L is selected from a bond, —CH$_2$—, —(CH$_2$)$_2$—, —(CH$_2$)$_3$—, —C(O)—, —S(O)$_2$—, —C(O)NR$^3$—, or —C(O)CH$_2$—. For each of the embodiments described above for compounds of Formula II, II-A, II-B, II-C, II-D, or II-E, L is selected from a bond, —CH$_2$—, or —C(O)—. For each of the embodiments for compounds of Formula II, II-A, II-B, II-C, II-D, or II-E, L is selected from a bond. For each of the embodiments for compounds of Formula II, II-A, II-B, II-C, II-D, or II-E, L is selected from —CH$_2$—. For each of the embodiments for compounds of Formula II, II-A, II-B, II-C, II-D, or II-E, L is selected from —C(O)—.

For each of the embodiments described above for compounds of Formula II, II-A, II-B, II-C, II-D, or II-E, R is hydrogen or an optionally substituted group selected from C$_1$-C$_6$alkyl, aryl, C$_3$-C$_8$ cycloalkyl, heterocyclyl, or heteroaryl containing 1-5 heteroatoms selected from the group consisting of N, S, P, or O. For each of the embodiments described above for compounds for Formula II, II-A, II-B, II-C, II-D, or II-E, R is hydrogen or an optionally substituted group selected from phenyl, C$_1$-C$_6$alkyl, cyclopropyl, cyclobutyl, cyclopentyl, cyclohexyl, pyridyl, or morpholinyl. For each of the embodiments described above for compounds of Formula II, II-A, II-B, II-C, II-D, or II-E, R is phenyl optionally substituted with one or more independent occurrences of halogen, CF$_3$, —SO$_2$CH$_3$, phenyl, C$_1$-C$_3$ alkyl, C$_1$-C$_3$alkoxy, pyridyl, —OCF$_3$ or —OCH$_2$phenyl.

In one or more embodiments, the compound is of the Formula II-A-i:

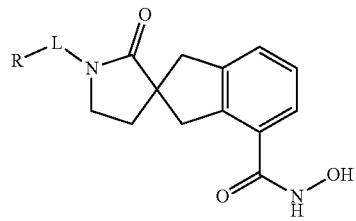

In one or more embodiments, the compound is of the Formula II-B-i:

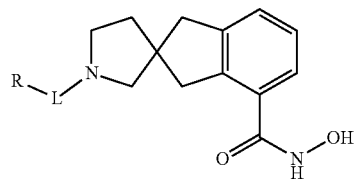

In one or more embodiments, the compound is of the Formula II-C-i:

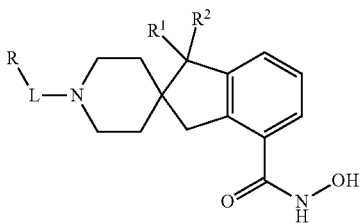

(II-C-i)

In one or more embodiments, the compound is of the Formula II-C-ii:

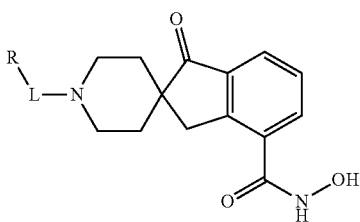

(II-C-ii)

In one or more embodiments, the compound is of the Formula II-D-i:

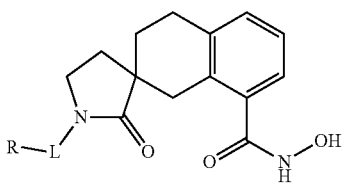

(II-D-i)

In one or more embodiments, the compound is of the Formula II-E-i:

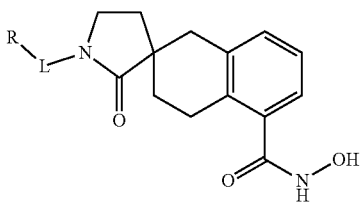

(II-E-i)

For each of the embodiments described above for compounds of Formula II, II-B-i, II-C-i, II-D-i, or II-E-i, L is selected from a bond, —CH$_2$—, —(CH$_2$)$_2$—, —(CH$_2$)$_3$—, —C(O)—, —S(O)$_2$—, —C(O)NR$^3$—, or —C(O)CH$_2$—. For each of the embodiments described above for compounds of Formula II, II-A-i, II-B-i, II-C-i, II-D-i, or II-E-i, L is selected from a bond, —CH$_2$—, or —C(O)—. For each of the embodiments for compounds of Formula II, II-A-i, II-B-i, II-C-i, II-C-ii, II-D-i, or II-E-i, L is selected from a bond. For each of the embodiments for compounds of Formula II, II-A-i, II-B-i, II-C-i, II-C-ii, II-D-i, or II-E-i, L is selected from —CH$_2$—. For each of the embodiments for compounds of Formula II, II-A-i, II-B-i, II-C-i, II-C-ii, II-D-i, or II-E-i, L is selected from —C(O)—.

For each of the embodiments described above for compounds of Formula II, II-B-i, II-C-i, II-C-ii, II-D-i, or II-E-i, R is hydrogen or an optionally substituted group selected from C$_1$-C$_6$alkyl, aryl, C$_3$-C$_8$ cycloalkyl, heterocyclyl, or heteroaryl containing 1-5 heteroatoms selected from the group consisting of N, S, P, or O. For each of the embodiments described above for compounds for Formula II, II-A-i, II-B-i, II-C-i, II-C-ii, II-D-i, or II-E-i, R is hydrogen or an optionally substituted group selected from phenyl, C$_1$-C$_6$alkyl, cyclopropyl, cyclobutyl, cyclopentyl, cyclohexyl, pyridyl, or morpholinyl. For each of the embodiments described above for compounds of Formula II, II-A-i, II-B-i, II-C-i, II-C-ii, II-D-i, or II-E-i, R is phenyl optionally substituted with one or more independent occurrences of halogen, CF$_3$, —SO$_2$CH$_3$, phenyl, C$_1$-C$_3$ alkyl, C$_1$-C$_3$alkoxy, pyridyl, —OCF$_3$ or —OCH$_2$phenyl.

In one or more embodiments, a compound of Formula II can be selected from:

1'-(4-chlorobenzyl)-N-hydroxy-2'-oxo-1,3-dihydrospiro[indene-2,3'-pyrrolidine]-4-carboxamide (II-1);

N-hydroxy-1'-methyl-2'-oxo-1,3-dihydrospiro[indene-2,3'-pyrrolidine]-4-carboxamide (II-2);

(R)-1'-(4-chloro-3-(trifluoromethyl)benzyl)-N-hydroxy-2'-oxo-1,3-dihydrospiro[indene-2,3'-pyrrolidine]-4-carboxamide (II-3);

(S)-1'-(4-chloro-3-(trifluoromethyl)benzyl)-N-hydroxy-2'-oxo-1,3-dihydrospiro[indene-2,3'-pyrrolidine]-4-carboxamide (HDTK054);

1'-(3-fluoro-4-(trifluoromethyl)benzyl)-N-hydroxy-2'-oxo-1,3-dihydrospiro[indene-2,3'-pyrrolidine]-4-carboxamide (II-5);

N-hydroxy-2'-oxo-1'-(4-(trifluoromethyl)benzyl)-1,3-dihydrospiro[indene-2,3'-pyrrolidine]-4-carboxamide (II-6);

1'-(4-fluorobenzyl)-N-hydroxy-2'-oxo-1,3-dihydrospiro[indene-2,3'-pyrrolidine]-4-carboxamide (II-7);

N-hydroxy-1'-(4-(methylsulfonyl)benzyl)-2'-oxo-1,3-dihydrospiro[indene-2,3'-pyrrolidine]-4-carboxamide (II-8);

1'-cyclopropyl-N-hydroxy-2'-oxo-1,3-dihydrospiro[indene-2,3'-pyrrolidine]-4-carboxamide (II-9);

1'-(cyclobutylmethyl)-N-hydroxy-2'-oxo-1,3-dihydrospiro[indene-2,3'-pyrrolidine]-4-carboxamide (II-10);

N-hydroxy-2'-oxo-1'-(4-(trifluoromethyl)phenyl)-1,3-dihydrospiro[indene-2,3'-pyrrolidine]-4-carboxamide (II-11);

N-hydroxy-2'-oxo-1'-(3-(trifluoromethyl)phenyl)-1,3-dihydrospiro[indene-2,3'-pyrrolidine]-4-carboxamide (II-12);

N-hydroxy-2'-oxo-1'-(2-(trifluoromethyl)phenyl)-1,3-dihydrospiro[indene-2,3'-pyrrolidine]-4-carboxamide (II-13);

1'-benzyl-N-hydroxy-2'-oxo-1,3-dihydrospiro[indene-2,3'-pyrrolidine]-4-carboxamide (II-14);

N-hydroxy-2'-oxo-1'-(3-phenylpropyl)-1,3-dihydrospiro[indene-2,3'-pyrrolidine]-4-carboxamide (II-15);

1'-([1,1'-biphenyl]-4-ylmethyl)-N-hydroxy-2'-oxo-1,3-dihydrospiro[indene-2,3'-pyrrolidine]-4-carboxamide (II-16);

N-hydroxy-1'-(3-methylbenzyl)-2'-oxo-1,3-dihydrospiro[indene-2,3'-pyrrolidine]-4-carboxamide (II-17);

1'-([1,1'-biphenyl]-3-ylmethyl)-N-hydroxy-2'-oxo-1,3-dihydrospiro[indene-2,3'-pyrrolidine]-4-carboxamide (II-18);

N-hydroxy-1'-(4-methoxybenzyl)-2'-oxo-1,3-dihydrospiro[indene-2,3'-pyrrolidine]-4-carboxamide (II-19);

N-hydroxy-1'-(3-methoxybenzyl)-2'-oxo-1,3-dihydrospiro[indene-2,3'-pyrrolidine]-4-carboxamide (II-20);

1'-(2,6-dichlorobenzyl)-N-hydroxy-2'-oxo-1,3-dihydrospiro[indene-2,3'-pyrrolidine]-4-carboxamide (II-21);

1'-(2,3-dichlorobenzyl)-N-hydroxy-2'-oxo-1,3-dihydrospiro[indene-2,3'-pyrrolidine]-4-carboxamide (II-22);

N-hydroxy-1'-(2-methylbenzyl)-2'-oxo-1,3-dihydrospiro[indene-2,3'-pyrrolidine]-4-carboxamide (II-23);

N-hydroxy-2'-oxo-1'-(pyridin-3-ylmethyl)-1,3-dihydrospiro[indene-2,3'-pyrrolidine]-4-carboxamide (II-24);

1'-(2-chlorobenzyl)-N-hydroxy-2'-oxo-1,3-dihydrospiro[indene-2,3'-pyrrolidine]-4-carboxamide (II-25);

1'-(3-fluorobenzyl)-N-hydroxy-2'-oxo-1,3-dihydrospiro[indene-2,3'-pyrrolidine]-4-carboxamide (II-26);

N-hydroxy-2'-oxo-1'-(4-(trifluoromethoxy)benzyl)-1,3-dihydrospiro[indene-2,3'-pyrrolidine]-4-carboxamide (II-27);

1'-(3,5-difluorobenzyl)-N-hydroxy-2'-oxo-1,3-dihydrospiro[indene-2,3'-pyrrolidine]-4-carboxamide (II-28);

N-hydroxy-2'-oxo-1'-(2-(trifluoromethyl)benzyl)-1,3-dihydrospiro[indene-2,3'-pyrrolidine]-4-carboxamide (II-29);

1'-(3-chlorobenzyl)-N-hydroxy-2'-oxo-1,3-dihydrospiro[indene-2,3'-pyrrolidine]-4-carboxamide (II-30);

N-hydroxy-2'-oxo-1'-(3-(trifluoromethyl)benzyl)-1,3-dihydrospiro[indene-2,3'-pyrrolidine]-4-carboxamide (II-31);

N-hydroxy-2'-oxo-1'-(2-(trifluoromethoxy)benzyl)-1,3-dihydrospiro[indene-2,3'-pyrrolidine]-4-carboxamide (II-32);

1'-(3-bromobenzyl)-N-hydroxy-2'-oxo-1,3-dihydrospiro[indene-2,3'-pyrrolidine]-4-carboxamide (II-33);

N-hydroxy-2'-oxo-1'-((2-phenylthiazol-4-yl)methyl)-1,3-dihydrospiro[indene-2,3'-pyrrolidine]-4-carboxamide (II-34);

1'-(2,4-difluorobenzyl)-N-hydroxy-2'-oxo-1,3-dihydrospiro[indene-2,3'-pyrrolidine]-4-carboxamide (II-35);

N-hydroxy-1'-(2-methoxybenzyl)-2'-oxo-1,3-dihydrospiro[indene-2,3'-pyrrolidine]-4-carboxamide (II-36);

1'-([1,1'-biphenyl]-2-ylmethyl)-N-hydroxy-2'-oxo-1,3-dihydrospiro[indene-2,3'-pyrrolidine]-4-carboxamide (II-37);

1'-(3,4-dichlorobenzyl)-N-hydroxy-2'-oxo-1,3-dihydrospiro[indene-2,3'-pyrrolidine]-4-carboxamide (II-38);

1'-(3,4-dimethylbenzyl)-N-hydroxy-2'-oxo-1,3-dihydrospiro[indene-2,3'-pyrrolidine]-4-carboxamide (II-39);

1'-(3,5-dimethoxybenzyl)-N-hydroxy-2'-oxo-1,3-dihydrospiro[indene-2,3'-pyrrolidine]-4-carboxamide (II-40);

1'-(4-(benzyloxy)benzyl)-N-hydroxy-2'-oxo-1,3-dihydrospiro[indene-2,3'-pyrrolidine]-4-carboxamide (II-41);

N-hydroxy-2'-oxo-1'-(3-(trifluoromethoxy)benzyl)-1,3-dihydrospiro[indene-2,3'-pyrrolidine]-4-carboxamide (II-42);

1'-(2-fluoro-3-(trifluoromethyl)benzyl)-N-hydroxy-2'-oxo-1,3-dihydrospiro[indene-2,3'-pyrrolidine]-4-carboxamide (II-43);

1'-(cyclohexylmethyl)-N-hydroxy-2'-oxo-1,3-dihydrospiro[indene-2,3'-pyrrolidine]-4-carboxamide (II-44);

1'-(2,5-dichlorobenzyl)-N-hydroxy-2'-oxo-1,3-dihydrospiro[indene-2,3'-pyrrolidine]-4-carboxamide (II-45);

N-hydroxy-2'-oxo-1'-((3-phenylisoxazol-5-yl)methyl)-1,3-dihydrospiro[indene-2,3'-pyrrolidine]-4-carboxamide (II-46);

1'-((6-(1H-pyrazol-1-yl)pyridin-3-yl)methyl)-N-hydroxy-2'-oxo-1,3-dihydrospiro[indene-2,3'-pyrrolidine]-4-carboxamide (II-47);

N-hydroxy-2'-oxo-1'-((6-(trifluoromethyl)pyridin-3-yl)methyl)-1,3-dihydrospiro[indene-2,3'-pyrrolidine]-4-carboxamide (II-48);

N-hydroxy-2'-oxo-1'-((5-(tetrahydro-2H-pyran-4-yl)-1,2,4-oxadiazol-3-yl)methyl)-1,3-dihydrospiro[indene-2,3'-pyrrolidine]-4-carboxamide (II-49);

1'-((3,5-dimethylisoxazol-4-yl)methyl)-N-hydroxy-2'-oxo-1,3-dihydrospiro[indene-2,3'-pyrrolidine]-4-carboxamide (II-50);

N-hydroxy-2'-oxo-1'-((6-(trifluoromethyl)pyridin-2-yl)methyl)-1,3-dihydrospiro[indene-2,3'-pyrrolidine]-4-carboxamide (II-51);

N-hydroxy-1'-(2-morpholinoethyl)-2'-oxo-1,3-dihydrospiro[indene-2,3'-pyrrolidine]-4-carboxamide (II-52);

N-hydroxy-2'-oxo-1'-41-phenyl-1H-1,2,3-triazol-4-yl)methyl)-1,3-dihydrospiro[indene-2,3'-pyrrolidine]-4-carboxamide (II-53);

N-hydroxy-1'-(4-(methylsulfonyl)benzyl)-2'-oxo-1,3-dihydrospiro[indene-2,3'-pyrrolidine]-4-carboxamide (II-54);

1'-(cyclopropylmethyl)-N-hydroxy-2'-oxo-1,3-dihydrospiro[indene-2,3'-pyrrolidine]-4-carboxamide (II-55);

N-hydroxy-1'-(4-(trifluoromethyl)benzyl)-1,3-dihydrospiro[indene-2,3'-pyrrolidine]-4-carboxamide (II-56);

1'-cyclopropyl-N-hydroxy-1,3-dihydrospiro[indene-2,3'-pyrrolidine]-4-carboxamide (II-57);

N-hydroxy-1'-(4-(trifluoromethyl)benzoyl)-1,3-dihydrospiro[indene-2,3'-pyrrolidine]-4-carboxamide (II-58);

1'-acetyl-N-hydroxy-1,3-dihydrospiro[indene-2,3'-pyrrolidine]-4-carboxamide (II-59);

1'-acetyl-N-hydroxy-1,3-dihydrospiro[indene-2,4'-piperidine]-4-carboxamide (II-60);

1'-(4-chlorobenzoyl)-N-hydroxy-1,3-dihydrospiro[indene-2,4'-piperidine]-4-carboxamide (II-61);

1'-(4-chlorobenzyl)-N-hydroxy-1,3-dihydrospiro[indene-2,4'-piperidine]-4-carboxamide (II-62);

1'-cyclopropyl-N-hydroxy-1,3-dihydrospiro[indene-2,4'-piperidine]-4-carboxamide (II-63);

1'-benzyl-N-hydroxy-1,3-dihydrospiro[indene-2,4'-piperidine]-4-carboxamide (II-64);

1'-benzyl-N-hydroxy-1-oxo-1,3-dihydrospiro[indene-2,4'-piperidine]-4-carboxamide (II-65);

1'-benzyl-N,1-dihydroxy-1,3-dihydrospiro[indene-2,4'-piperidine]-4-carboxamide (II-66);

1'-(4-chloro-3-(trifluoromethyl)benzyl)-N-hydroxy-2'-oxo-3,4-dihydro-1H-spiro[naphthalene-2,3'-pyrrolidine]-8-carboxamide (II-67);

1'-(3-fluoro-4-(trifluoromethyl)benzyl)-N-hydroxy-2'-oxo-3,4-dihydro-1H-spiro[naphthalene-2,3'-pyrrolidine]-8-carboxamide (II-68);

1'-(4-chlorobenzyl)-N-hydroxy-2'-oxo-3,4-dihydro-1H-spiro[naphthalene-2,3'-pyrrolidine]-8-carboxamide (II-69);

N-hydroxy-2'-oxo-1'-(4-(trifluoromethyl)benzyl)-3,4-dihydro-1H-spiro[naphthalene-2,3'-pyrrolidine]-8-carboxamide (II-70);

N-hydroxy-2'-oxo-1'-(4-(trifluoromethyl)phenyl)-3,4-dihydro-1H-spiro[naphthalene-2,3'-pyrrolidine]-8-carboxamide (II-71);

N-hydroxy-2'-oxo-1'-(3-(trifluoromethyl)phenyl)-3,4-dihydro-1H-spiro[naphthalene-2,3'-pyrrolidine]-8-carboxamide (II-72);

N-hydroxy-2'-oxo-1'-(2-(trifluoromethyl)phenyl)-3,4-dihydro-1H-spiro[naphthalene-2,3'-pyrrolidine]-8-carboxamide (II-73);

N8-hydroxy-N1',N1'-dimethylspiro[chromane-2,4'-piperidine]-1',8-dicarboxamide (II-74);

1'-(4-fluorobenzoyl)-N-hydroxyspiro[chromane-2,4'-piperidine]-8-carboxamide (II-75);

1'-(cyclohexylsulfonyl)-N-hydroxyspiro[chromane-2,4'-piperidine]-8-carboxamide (II-76);

N-hydroxy-1'-(4-methyltetrahydro-2H-pyran-4-carbonyl)spiro[chromane-2,4'-piperidine]-8-carboxamide (II-77);

N-hydroxy-1'-(1-(3-(trifluoromethyl)phenyl)cyclopropane-1-carbonyl)spiro[chromane-2,4'-piperidine]-8-carboxamide (II-78);

N-hydroxy-1'-(2-phenylacetyl)spiro[chromane-2,4'-piperidine]-8-carboxamide (II-79);

1'-(4-fluorobenzyl)-N-hydroxyspiro[chromane-2,4'-piperidine]-8-carboxamide (II-80);

1'-cyclohexyl-N-hydroxyspiro[chromane-2,4'-piperidine]-8-carboxamide (II-81);

N-hydroxy-1'-(5-(trifluoromethyl)pyridin-2-yl)spiro[chromane-2,4'-piperidine]-8-carboxamide (II-82);

1'-(3-fluoro-4-methylphenyl)-N-hydroxyspiro[chromane-2,4'-piperidine]-8-carboxamide (II-83);

1'-(4-chloro-3-(trifluoromethyl)benzyl)-N-hydroxy-2'-oxo-3,4-dihydro-1H-spiro[naphthalene-2,3'-pyrrolidine]-5-carboxamide (II-84);

N-hydroxy-2'-oxo-1'-(4-(trifluoromethyl)benzyl)-3,4-dihydro-1H-spiro[naphthalene-2,3'-pyrrolidine]-5-carboxamide (II-85);

1'-(3-fluoro-4-(trifluoromethyl)benzyl)-N-hydroxy-2'-oxo-3,4-dihydro-1H-spiro[naphthalene-2,3'-pyrrolidine]-5-carboxamide (II-86);

1'-(4-chlorobenzyl)-N-hydroxy-2'-oxo-3,4-dihydro-1H-spiro[naphthalene-2,3'-pyrrolidine]-5-carboxamide (II-87);

N-hydroxy-2'-oxo-1'-(4-(trifluoromethyl)phenyl)-3,4-dihydro-1H-spiro[naphthalene-2,3'-pyrrolidine]-5-carboxamide (II-88);

N-hydroxy-2'-oxo-1'-(3-(trifluoromethyl)phenyl)-3,4-dihydro-1H-spiro[naphthalene-2,3'-pyrrolidine]-5-carboxamide (II-89);

N-hydroxy-2'-oxo-1'-(2-(trifluoromethyl)phenyl)-3,4-dihydro-1H-spiro[naphthalene-2,3'-pyrrolidine]-5-carboxamide (II-90);

1'-acetyl-N-hydroxyspiro[chromane-2,4'-piperidine]-5-carboxamide (II-91);

N-hydroxy-1'-phenylspiro[chromane-2,4'-piperidine]-5-carboxamide (II-92) or

1'-(4-fluorophenyl)-N-hydroxyspiro[chromane-2,4'-piperidine]-5-carboxamide (II-93), or a pharmaceutically acceptable salt thereof.

Methods of Synthesizing the Disclosed Compounds

The compounds of the present invention may be made by a variety of methods, including standard chemistry. Suitable synthetic routes are depicted in the schemes given below.

The compounds of Formula II may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula II.

Those skilled in the art will recognize if a stereocenter exists in the compounds of Formula II. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present invention can be prepared in a number of ways well known to those skilled in the art of organic synthesis. By way of example, compounds of the Formula II can be synthesized using the methods described below, together with synthetic methods known in the art of synthetic organic chemistry, or variations thereon as appreciated by those skilled in the art. These methods include but are not limited to those methods described below.

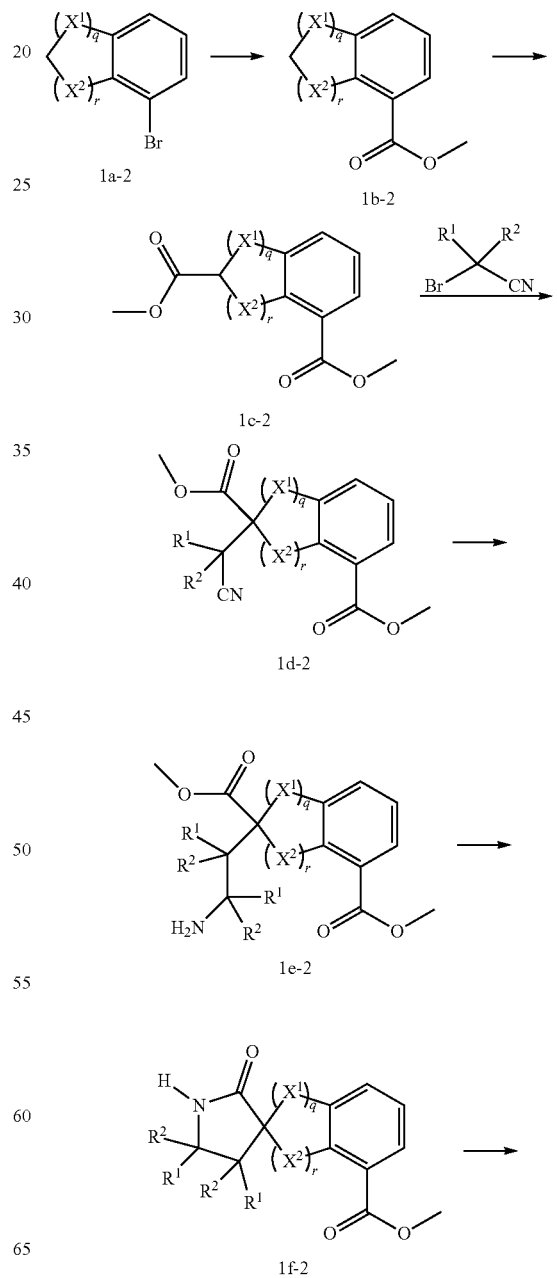

Scheme 1-2. General Synthesis of Compounds of Formula II-A

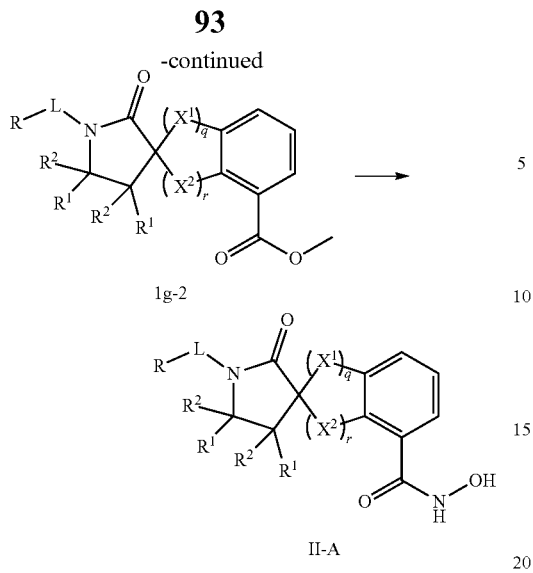

1g-2

II-A wherein L and R are defined as in Formula (II).

A general method of preparing target molecules of Formula (II-A) by using Intermediates 1a-2, 1b-2, 1c-2, 1d-2, 1e-2, 1f-2, and 1g-2 is outlined in Scheme 1-2. Carbonylation of the starting material (1a-2), for instance in the presence of a metal catalyst, e.g., [1,1'-Bis(diphenylphosphino)ferrocene]dichloropalladium(II) (Pd(dppf)Cl$_2$), carbon monoxide, and a base, e.g., triethylamine (Et$_3$N), provides ester 1b-2. Further carbonylation of 1b-2, for instance using a base, e.g., sodium hydride (NaH), in the presence of dimethyl carbonate affords Intermediate 1c-2, which can be alkylated by treatment with a halo-nitrile in the presence of a base to provide Intermediates 1d-2. Reduction, for example, with hydrogen gas in the presence of platinum (IV) oxide (PtO$_2$), acetic acid, and methanol (MeOH), can provide alkyl amine 1e-2. Spiro-lactams 1f-2 can be obtained, for example, by treatment of 1e-2 with ammonia (NH$_3$) in MeOH. Addition of the R-L moiety can be achieved via standard methods of, for instance, alkylation, arylation, acylation, urea formation, or sulfonation. For example, alkylation of 1f-2 with an alkyl halide in the presence of a base, e.g., NaH, can provide compounds of Intermediates 1g-2. Alternatively, arylation of 1f-2 with an aryl halide in the presence of a metal catalyst, e.g., copper (I) iodide (CuI), a diamine ligand, and a base, can also provide compounds of Intermediates 1g-2. Treatment of 1g-2 with hydroxylamine and a base, e.g., sodium hydroxide (NaOH), can provide compounds of Formula (II-A).

Scheme 2-2. General Synthesis of Compounds of Formula II-B

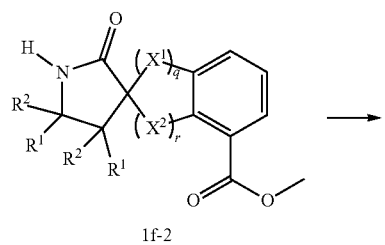

1f-2

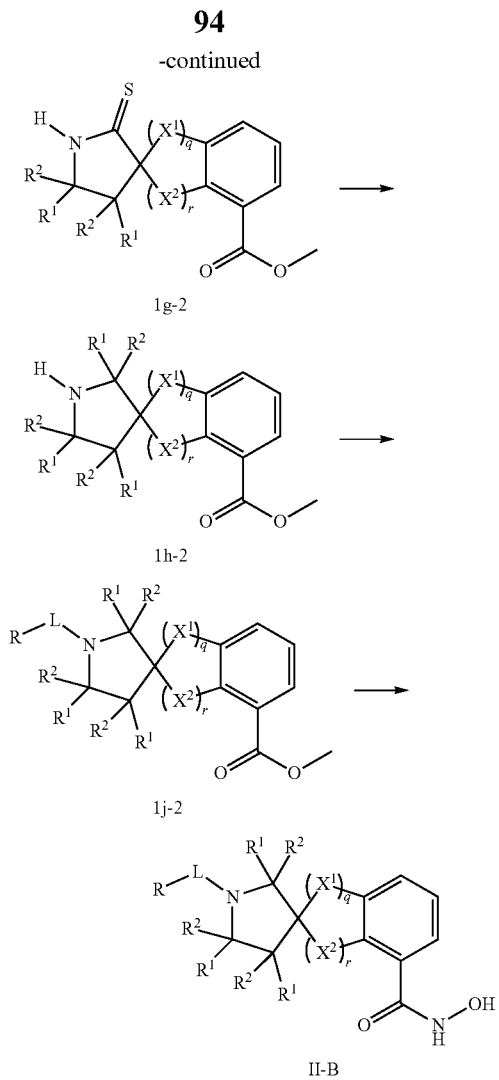

1g-2

1h-2

1j-2

II-B wherein L and R are defined as in Formula (II).

A general method of preparing target molecules of Formula (II-B) by using Intermediates 1f-2, 1g-2, 1h-2, and 1j-2 is outlined in Scheme 2-2. Spiro-amines 1h-2 can be obtained via reduction of thiolactams 1g-2 by treatment of 1f-2 with 2,4-bis(4-methoxyphenyl)-2,4-dithioxo-1,3,2,4-dithiadiphosphetane (Lawesson reagent), followed by sodium borohydride (NaBH$_4$) in the presence of, for instance, nickel (II) chloride hexahydrate (NiCl$_2$.6H$_2$O). Addition of the R-L moiety to achieve Intermediates 1j-2 can be achieved via standard methods of alkylation, arylation, acylation, urea formation, or sulfonation. Treatment of 1j-2 with hydroxylamine and a base, e.g., NaOH, can provide compounds of Formula (II-B).

Scheme 3-2. General Synthesis of Compounds of Formula II-C

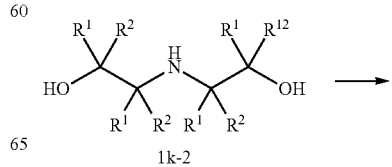

1k-2

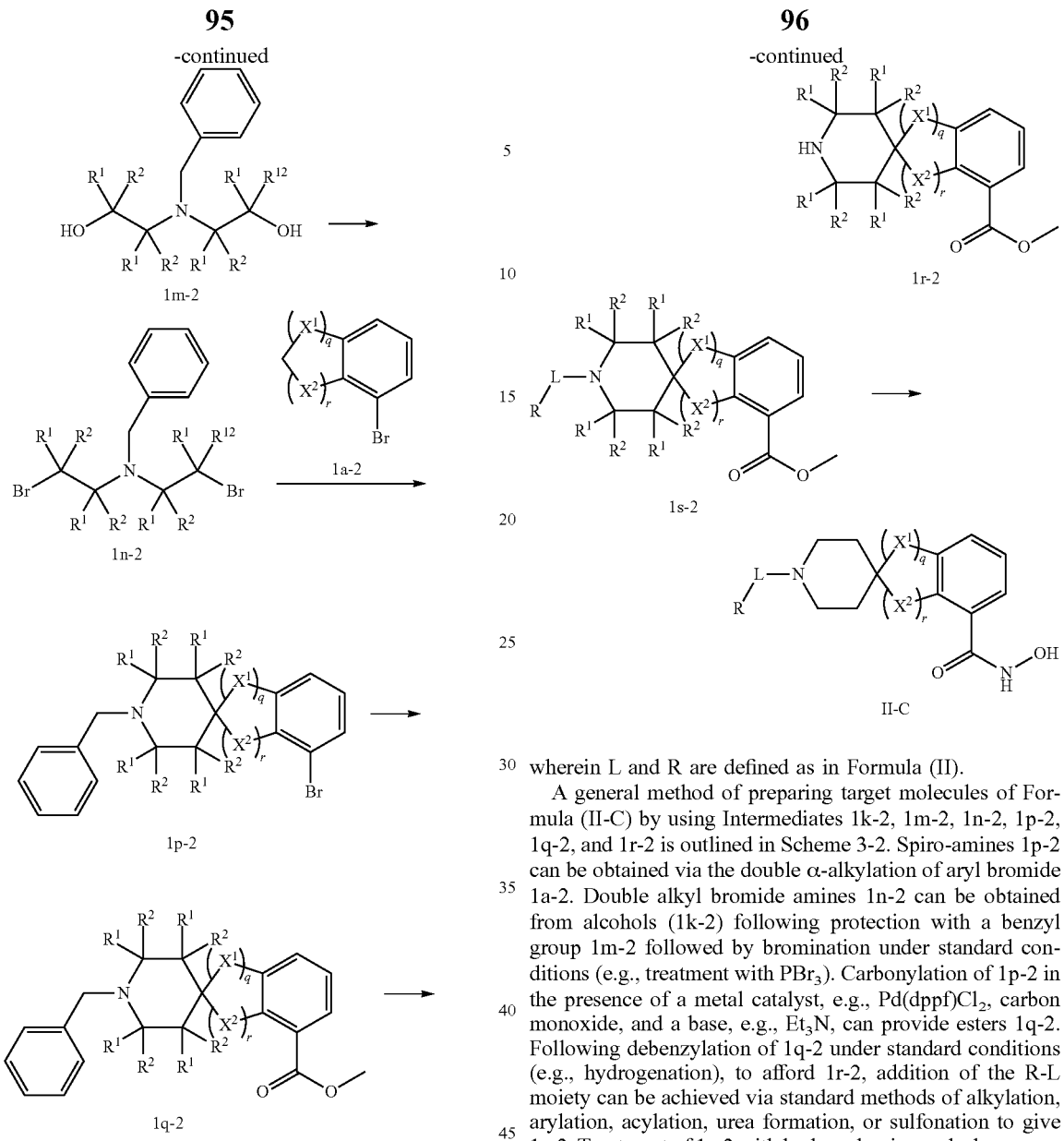

wherein L and R are defined as in Formula (II).

A general method of preparing target molecules of Formula (II-C) by using Intermediates 1k-2, 1m-2, 1n-2, 1p-2, 1q-2, and 1r-2 is outlined in Scheme 3-2. Spiro-amines 1p-2 can be obtained via the double α-alkylation of aryl bromide 1a-2. Double alkyl bromide amines 1n-2 can be obtained from alcohols (1k-2) following protection with a benzyl group 1m-2 followed by bromination under standard conditions (e.g., treatment with PBr₃). Carbonylation of 1p-2 in the presence of a metal catalyst, e.g., Pd(dppf)Cl₂, carbon monoxide, and a base, e.g., Et₃N, can provide esters 1q-2. Following debenzylation of 1q-2 under standard conditions (e.g., hydrogenation), to afford 1r-2, addition of the R-L moiety can be achieved via standard methods of alkylation, arylation, acylation, urea formation, or sulfonation to give 1s-2. Treatment of 1s-2 with hydroxylamine and a base, e.g., NaOH, can provide compounds of Formula (II-C).

Scheme 4-2. General Synthesis of Compounds of Formula II-A1 and II-A2.

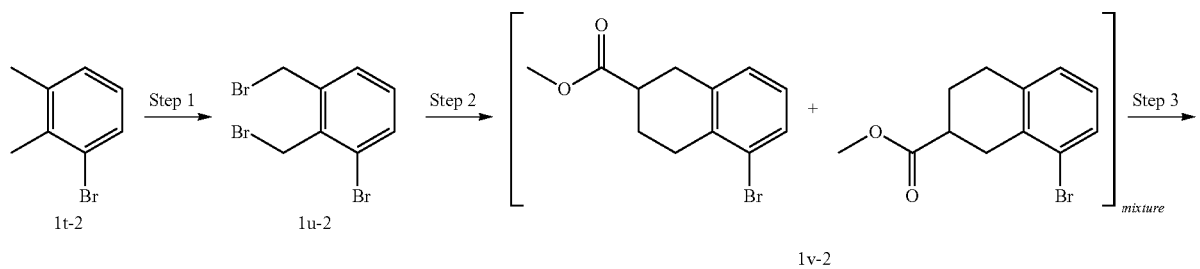

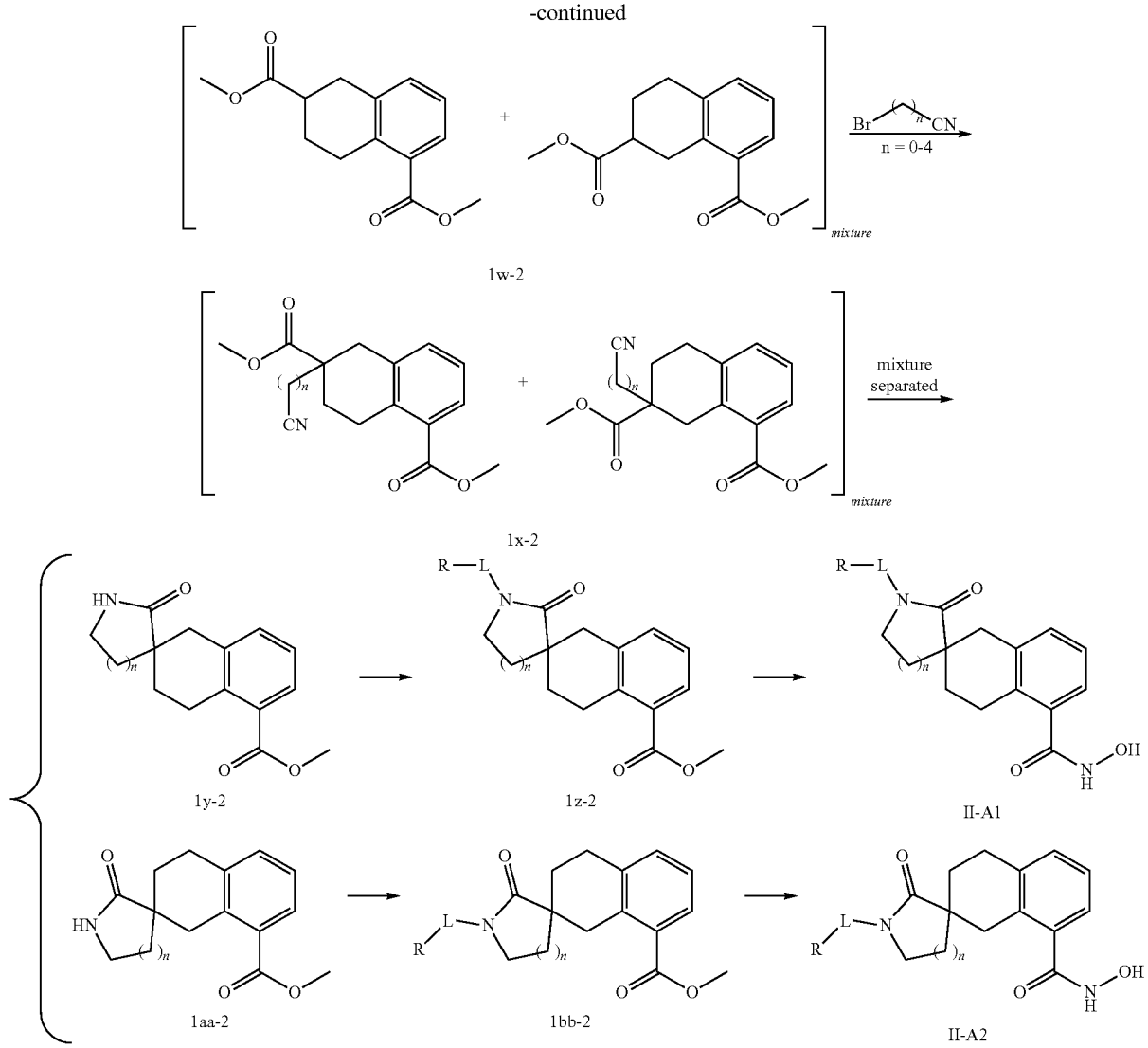

wherein L and R are defined as in Formula (II).

Another general method of preparing target molecules of Formulae II-A (e.g., II-A1 and II-A2) by using Intermediates 1t-2, 1u-2, 1v-2, 1w-2, 1x-2, 1y-2, 1z-2, 1aa-2, and 1bb-2 is outlined in Scheme 4-2. Double bromination of 1-bromo-2,3-dimethylbenzene (1t-2), followed by in situ generation of a reactive diene from 1u-2, for example, in the presence of sodium iodide, to undergo a Diels-Alder cycloaddition with methyl acrylate can afford a regioisomeric mixture of tetrahydronaphthalenes 1v-2. Carbonylation of 1v-2 in the presence of a metal catalyst, e.g., Pd(dppf)Cl$_2$, carbon monoxide, and a base, e.g., Et$_3$N, can provide esters 1w-2, which can be alkylated by treatment with a halo-nitrile in the presence of a base to provide Intermediates 1x-2. Reduction, for example, with hydrogen gas in the presence of PtO$_2$, acetic acid, and MeOH, can be followed by treatment with NH$_3$ in MeOH to provide spirolactams 1y-2 and 1aa-2, which can be separated by column chromatography. Addition of the R-L moiety can be achieved via standard methods of alkylation, acylation, urea formation, sulfonation or arylation. For example, alkylation of 1y-2 or 1aa-2 with an alkyl halide in the presence of a base, e.g., NaH, can provide compounds of Intermediates 1z-2 and 1bb-2. Alternatively, arylation of 1y-2 or 1aa-2 with an aryl boronic acid in the presence of a metal catalyst, e.g., copper (II) acetate (Cu(OAc)$_2$), and a base, can also provide compounds of Intermediates 1z-2 or 1bb-2. Treatment of 1z-2 or 1bb-2 with hydroxylamine and a base, e.g., NaOH, can provide compounds of Formulae (II-A1) and (II-A2).

Scheme 5-2. General Synthesis of Compounds of Formula II-C1

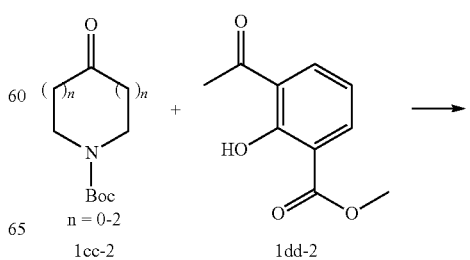

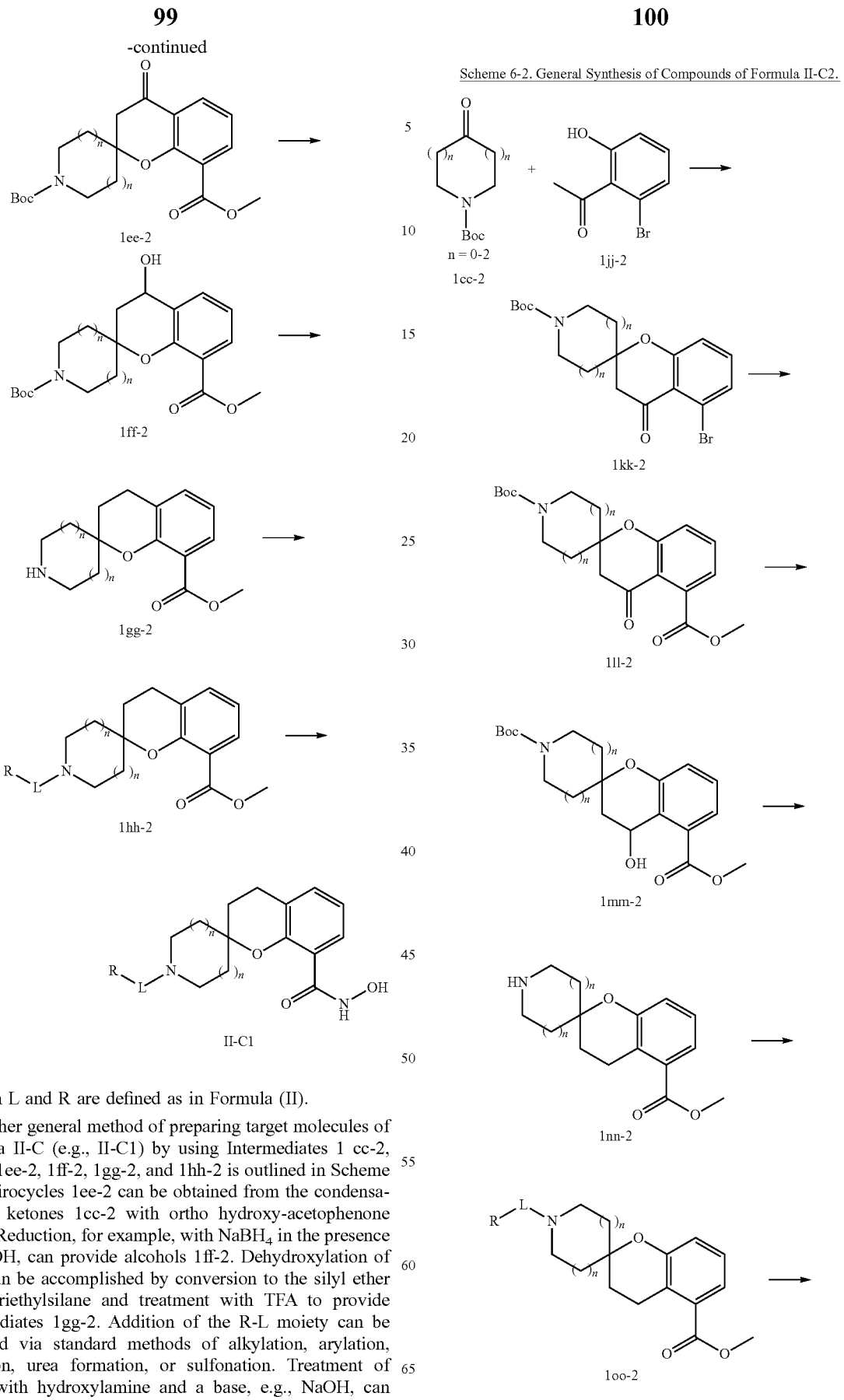

wherein L and R are defined as in Formula (II).

Another general method of preparing target molecules of Formula II-C (e.g., II-C1) by using Intermediates 1 cc-2, 1dd-2, 1ee-2, 1ff-2, 1gg-2, and 1hh-2 is outlined in Scheme 5-2. Spirocycles 1ee-2 can be obtained from the condensation of ketones 1cc-2 with ortho hydroxy-acetophenone 1dd-2. Reduction, for example, with NaBH$_4$ in the presence of MeOH, can provide alcohols 1ff-2. Dehydroxylation of 1ff-2 can be accomplished by conversion to the silyl ether using triethylsilane and treatment with TFA to provide Intermediates 1gg-2. Addition of the R-L moiety can be achieved via standard methods of alkylation, arylation, acylation, urea formation, or sulfonation. Treatment of 1hh-2 with hydroxylamine and a base, e.g., NaOH, can provide compounds of Formula (II-C1).

-continued

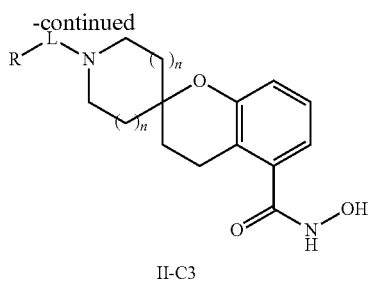

II-C3 wherein L and R are defined as in Formula (II).

Another general method of preparing target molecules of Formula II-C (e.g., II-C2) by using Intermediates 1cc-2, 1jj-2, 1kk-2, 1ll-2, 1mm-2, 1nn-2, and 1oo-2 is outlined in Scheme 6-2. Spirocycles 1kk-2 can be obtained from the condensation of ketones 1cc-2 with ortho hydroxy-acetophenone 1jj-2. Carbonylation of 1kk-2 in the presence of a metal catalyst, e.g., PdCl$_2$, carbon monoxide, and a diphosphine, can provide esters 1ll-2. Reduction, for example, with NaBH$_4$ in the presence of MeOH, can provide alcohols 1mm-2. Dehydroxylation of 1mm-2 can be accomplished by conversion to the silyl ether using triethylsilane and treatment with TFA to provide Intermediates 1nn-2. Addition of the R-L moiety can be achieved via standard methods of alkylation, arylation, acylation, urea formation, or sulfonation. Treatment of 1oo-2 with hydroxylamine and a base, e.g., NaOH, can provide compounds of Formula (II-C2).

Methods of Using HDAC11 Inhibitors

The present disclosure provides methods of administering an effective amount of a therapeutic agent described herein (e.g., a HDAC11 inhibitor) to a subject in need of treatment. In some embodiments are provided methods of treating a disease associated with HDAC11 modulation in a subject in need thereof. In some embodiments, a method involves administering to a patient in need of treatment for diseases or disorders associated with HDAC11 an effective amount of a HDAC11 inhibitor. In some embodiments, a disease for treatment can be, but is not limited to, a cell proliferative disease, a cancer, a neurodegenerative disease, a neurodevelopmental disease, an inflammatory or autoimmune disease, an infection, a metabolic disease, a hematologic disease, or a cardiovascular disease.

In some embodiments, a method of treating a cell proliferative disease comprises administering a HDAC11 inhibitor to a subject. In some embodiments, an effective amount (e.g., a therapeutic amount) of a HDAC11 inhibitor is administered.

In any of the methods described herein, a HDAC11 inhibitor of any class may be used. In some embodiments, a HDAC11 inhibitor is a siRNA, a shRNA, an antibody agent, or a chemical compound (e.g., a small molecule). In some embodiments, a HDAC11 inhibitor is a siRNA, a shRNA, an antibody agent, or a chemical compound (e.g., a small molecule). In some embodiments, a HDAC11 inhibitor is a chemical compound that is a small molecule. In some embodiments, a small molecule HDAC11 inhibitor is at least 10-fold selective for the inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In some embodiments, a small molecule HDAC11 inhibitor is at least 10-fold selective for the inhibition of HDAC11 over each of HDAC1, HDAC2, HDAC3, HDAC4, HDAC5, HDAC6, HDAC7, HDAC8, HDAC9 and HDAC10. In some embodiments, a HDAC11 inhibitor is specific for human HDAC11.

Cancers

In some embodiments are provided methods to treat cell proliferative diseases or disorders, such as, for example, cancer. Generally, in the context of the present disclosure, a cancer can be understood as abnormal or unregulated cell growth within a patient. In some embodiments, a cancer can include, but is not limited to, hematological malignancy, lung cancer, ovarian cancer, breast cancer, prostate cancer, pancreatic cancer, hepatocellular cancer, renal cancer, melanoma, and leukemias such as acute myeloid leukemia and acute lymphoblastic leukemia. Additional cancer types include T-cell lymphoma (e.g., cutaneous T-cell lymphoma, peripheral T-cell lymphoma), Hodgkin lymphoma, and multiple myeloma.

In some embodiments, the present disclosure encompasses the recognition that HDAC11 inhibitors may be beneficial for targeting cancer stem cells (CSCs). CSCs are cancer cells found within tumors or hematological cancers that possess characteristics associated with normal stem cells, specifically the ability to give rise to all cell types found in a particular cancer sample. As a result, CSCs may generate tumors through the stem cell processes of self-renewal and differentiation and can thus potentially persist in tumors causing relapse and metastasis by giving rise to new tumors. Specific therapies targeted at CSCs would be beneficial for the treatment of patients, particularly those with metastatic disease, however a challenge to development of therapies targeted at CSCs is the identification of specific CSC markers to help identify therapies that can target certain CSCs specifically. In some embodiments, a HDAC11 inhibitor can specifically target CSCs. In some embodiments, a HDAC11 inhibitor may specifically target cancer cells that exhibit cancer stem cell properties and/or are associated with gene amplification of genes associated with cancer stem cell activity.

In some embodiments, the present disclosure provides a method of treating a cancer wherein one or more cancer cells exhibit stem cell-like properties. In some embodiments, the cancer is associated with a gene amplification of SOX2. In some embodiments, the cancer associated with a gene amplification of SOX2 is esophageal squamous cell carcinoma, oral squamous cell carcinoma, lung, squamous cell carcinoma, lung adenocarcinoma, non-small cell lung cancer, small cell lung cancer or sinonasal cancer.

In some embodiments, the present disclosure provides methods for inhibiting expression of SOX2 in a stem-like cancer cell in a patient having a cancer, comprising administering a HDAC11 inhibitor to the patient. Sex determining region Y-Box 2 (SOX2) is a gene that encodes for a transcription factor belonging to the SOX gene family and has been described as an essential embryonic stem cell gene and as a necessary factor for induced cellular reprogramming. Recent research has indicated that SOX2 is frequently overexpressed in a variety of human cancers and acts as an oncogene to confer certain stem cell properties to carcinoma cells. Consequently, there has been a great deal of interest about the role of SOX2 in the clinic and potential therapeutic targets to selectively target SOX2-expressing cancer cells (Weina et al, Clin and Translational Med. 2014, July; 3:19), however it has been challenging to identify selective targets and therapies for SOX2-expressing cancer cells. Accordingly, there remains a need for effective, safe and selective methods of treating diseases or disorders associated with gene amplification of SOX2. In some embodiments, a SOX2-expressing cancer is lung cancer, hematological cancer or breast cancer. In some embodiments, a hematological cancer is MPN, lymphoma, or leukemia. In some embodiments, a cancer is esophageal squamous cell carcinoma, oral squamous cell carcinoma, lung, squamous cell carcinoma, lung adenocarcinoma, non-small cell lung cancer, small cell lung cancer or sinonasal cancer.

In some embodiments, a cancer for treatment with a HDAC11 is a cancer that is associated with a gene activation of STAT3. In some embodiments, a cancer associated with a gene activation of STAT3 is breast cancer.

In some embodiments, treating proliferative diseases or disorders can include any cancer where there is evidence of an increase in Treg/effector T cell ratio, and/or an increase in absolute Treg number, and/or increased expression of T cell tolerance-related genes. In some embodiments, an increase in Treg number can in the periphery, in the tumor microenvironment, and/or tertiary lymphoid structures. Such proliferative diseases or disorders can include, but are not limited to: any Kras mutant carrying tumor (http://cancerimmunolres.aacrjournals.org/content/early/2016/02/13/2326-6066.CIR-15-0241.long); renal cell carcinoma; lung carcinoma; cervical cancer; prostate cancer; ovarian cancer; head and neck cancer; lymphoma; colorectal cancer, non-small cell lung carcinoma; breast cancers (Gobert, M. et al. (2009) Cancer Res. 69, 2000-2009); and bladder cancer.

In some embodiments, a cell proliferation disease is a hematological malignancy. Hematological malignancies include, but are not limited to, leukemia (e.g., acute lymphocytic leukemia (ALL), acute myelogenous leukemia (AML), chronic lymphocytic leukemia (CLL), chronic myelogenous leukemia (CML), acute monocytic leukemia (AMoL)), lymphoma (e.g., Hodgkin's lymphoma (HL) and Non-Hodgkin's lymphoma (NHL)), and myeloma (e.g., multiple myeloma).

In some embodiments, a cell proliferation disease is a solid tumor. Examples of solid tumors include, but are not limited to, sarcomas, carcinomas, lung cancer, ovarian cancer, breast cancer, prostate cancer, pancreatic cancer, hepatocellular cancer, renal cancer, and melanoma. In some embodiments, a solid tumor is benign. In some embodiments, a solid tumor is malignant.

In some embodiments, a cell proliferation disease is a myeloproliferative neoplasm (MPN). Myeloproliferative neoplasms are hematological diseases characterized by excessive and chronic production of mature cells from one or several myeloid lineages (Sonbol et al, Ther Adv Hematol. 2013, February; 4(1):15-35). MPNs include, but are not limited to, polycythemia vera (PV), essential thrombocythemia (ET), primary myelofibrosis (PMF), chronic myelogenous leukemia (CIVIL), chronic neutrophilic leukemia (CNL), and chronic eosinophilic leukemia (CEL).

MPNs are often associated with mutations in JAK2 or MPL. Current treatments for MPNs include the use of Janus kinase 2 (JAK2) inhibitors such as ruxolitinib; however, some cells remain refractory to treatment with JAK2 inhibitors. Moreover, current therapies treat the symptoms rather than the disease. While class I and/or class II HDAC inhibitors have been suggested for treating certain MPNs (WO 2010/034693, US 2011/0237663, and US 2014/0039059), pan-HDAC inhibitors can result in cellular toxicity due to the large role HDACs play in regulating transcription. Accordingly, there remains a need for effective, safe, and selective methods of treating cell proliferative diseases, particularly MPNs.

In certain embodiments, a MPN for treatment with a HDAC11 inhibitor is selected from PV, ET, and PMF. In certain embodiments, a MPN is PV. In certain embodiments, a MPN is ET. In certain embodiments, a MPN is PMF.

Inflammatory and Autoimmune Diseases

The present disclosure encompasses the recognition that inhibition of HDAC11 may be beneficial for treatment or prevention of inflammatory and/or autoimmune diseases. Without wishing to be bound to theory, it is envisioned that inhibition of HDAC11 may exert effects on immune cell regulation (e.g., T cells, B cells, macrophages, and/or antigen presenting cells (APC)). For example, the protein interactome of HDAC11 in T cells suggests a wide variety of substrates and biological processes (Joshi et al, Mol Syst Biol. 2013, 9:672). HDAC11 also regulates interleukin 10 (IL-10) expression in antigen presenting cells and myeloid-derived suppressor cells (Villagra et al, Nat Immunol. 2009, January; 10(1):92-100; Cheng et al, Mol Immunol. 2014, July; 60(1):44-53; Sahakian et al, Mol Immunol. 2015, February; 63(2):579-85). HDAC11 also plays a role in regulating OX40 ligand in antigen presenting cells (Buglio et al, Blood. 2011, Mar. 10; 117(10):2910-7).

In some embodiments, a disease or disorder for treatment with a HDAC11 inhibitor is an immune or inflammatory disorder, which may be acute or chronic. Examples of immune and inflammatory disorders include inflammatory bowel disease, psoriasis, rheumatoid arthritis, multiple sclerosis, and Alzheimer's disease.

Combination Therapies

A HDAC11 inhibitor may be administered alone or in combination with other drugs (e.g., as an adjuvant). For example, one or more HDAC11 inhibitors can be in combination with other agents for treatment or prevention of diseases disclosed herein.

In some embodiments, a HDAC11 inhibitor is administered in combination with at least one other anticancer agent, including, for example, any chemotherapeutic agent known in the art, ionizing radiation, small molecule anticancer agents, surgery and/or biological therapies (e.g., antibody agents, viruses, gene therapies, cell-based therapies, etc.).

In some embodiments, a method for inhibiting proliferation of a neoplastic cell in a patient having a MPN comprising administering a combination of a HDAC11 inhibitor and a JAK2 inhibitor to the patient. In some embodiments, a HDAC11 inhibitor and JAK2 inhibitor are co-administered. In another embodiment, the HDAC11 inhibitor and JAK2 inhibitor are administered separately. In some embodiments, a HDAC11 inhibitor and JAK2 inhibitor are administered in series. In some embodiments, a HDAC11 inhibitor is administered prior to the JAK2 inhibitor. In another embodiment, the JAK2 inhibitor is administered prior to the HDAC11 inhibitor. In some embodiments, a MPN is PV, ET and/or MPF. In some embodiments, a HDAC11 inhibitor is a polypeptide, a polynucleotide, a siRNA, a shRNA, an antibody agent, or a chemical compound. In some embodiments, a JAK2 inhibitor is a polypeptide, a polynucleotide, a siRNA, a shRNA, an antibody agent, or a chemical compound. In some embodiment, a JAK2 inhibitor is ruxolitinib, baricitinib, CYT387, lestaurtinib, or pacritinib. In some embodiments, a JAK2 inhibitor is JAK2 inhibitor is ruxolitinib, baricitinib, CYT387, lestaurtinib, or pacritinib.

In some embodiments, the present disclosure provides a method for reducing tumor burden in a patient having a myeloproliferative neoplasm, comprising administering a combination of a HDAC11 inhibitor and a JAK2 inhibitor to the patient. In some embodiments, a HDAC11 inhibitor and JAK2 inhibitor are co-administered. In another embodiment, the HDAC11 inhibitor and JAK2 inhibitor are administered separately. In some embodiments, a HDAC11 inhibitor and JAK2 inhibitor are administered in series. In some embodiments, a HDAC11 inhibitor is administered prior to the JAK2 inhibitor. In another embodiment, a JAK2 inhibitor is administered prior to the HDAC11 inhibitor. In some embodiments, a HDAC11 inhibitor is administered to a patient that has been or will be administered a JAK2 inhibitor, such that the patient receives treatment with both. In some embodiments, a JAK2 inhibitor is administered to a patient that has been or will be administered a HDAC11 inhibitor, such that the patient receives treatment with both. In some embodiments, a MPN is PV, ET and/or MPF. In some embodiments, a HDAC11 inhibitor is a polypeptide, a polynucleotide, a siRNA, a shRNA, an antibody agent, or a chemical compound. In some embodiments, a JAK2 inhibitor is a polypeptide, a polynucleotide, a siRNA, a shRNA, an antibody agent, or a chemical compound. In some embodiments, a JAK2 inhibitor is JAK2 inhibitor is ruxolitinib, baricitinib, CYT387, lestaurtinib, or pacritinib. In some embodiments, a JAK2 inhibitor is ruxolitinib.

In some embodiments, the present disclosure provides a method for inhibiting proliferation of a cell resistant to a JAK2 inhibitor in a patient having a MPN, comprising administering a HDAC11 inhibitor to the patient. In some embodiments, a MPN is PV, ET and/or MPF. In some embodiments, a HDAC11 inhibitor is a polypeptide, a polynucleotide, a siRNA, a shRNA, an antibody agent, or a chemical compound. In some embodiments, a JAK2 inhibitor is a polypeptide, a polynucleotide, a siRNA, a shRNA, an antibody agent, or a chemical compound. In some embodiments, a JAK2 inhibitor is ruxolitinib, baricitinib, CYT387, lestaurtinib, or pacritinib. In some embodiments, a JAK2 inhibitor is ruxolitinib.

In some embodiments, the present disclosure provides a method for inducing cell cycle arrest in a patient having a MPN, comprising administering a combination of a HDAC11 inhibitor and a JAK2 inhibitor to the patient. In some embodiments, a HDAC11 inhibitor and a JAK2 inhibitor are co-administered. In other embodiments, a HDAC11 inhibitor and a JAK2 inhibitor are administered separately. In some embodiments, a HDAC11 inhibitor and a JAK2 inhibitor are administered in series. In some embodiments, a HDAC11 inhibitor is administered prior to administration of a JAK2 inhibitor. In other embodiments, a JAK2 inhibitor is administered prior to a HDAC11 inhibitor. In some embodiments, a HDAC11 inhibitor is administered to a patient that has been or will be administered a JAK2 inhibitor, such that the patient receives treatment with both. In some embodiments, a JAK2 inhibitor is administered to a patient that has been or will be administered a HDAC11 inhibitor, such that the patient receives treatment with both. In some embodiments, a MPN is PV, ET and/or MPF. In some embodiments, a HDAC11 inhibitor is a polypeptide, a polynucleotide, a siRNA, a shRNA, an antibody agent, or a chemical compound. In some embodiments, a JAK2 inhibitor is a polypeptide, a polynucleotide, a siRNA, a shRNA, an antibody agent, or a chemical compound. In some embodiments, a JAK2 inhibitor is ruxolitinib, baricitinib, CYT387, lestaurtinib, or pacritinib. In some embodiments, a JAK2 inhibitor is ruxolitinib. In some embodiments, a cell cycle is arrested at G1.

In some embodiments, the HDAC11 inhibitor is a polypeptide, a polynucleotide, a siRNA, a shRNA, an antibody agent, or a chemical compound. In some embodiments, the method further comprises administering a JAK2 inhibitor. In some embodiments, the JAK2 inhibitor is a polypeptide, a polynucleotide, a siRNA, a shRNA, an antibody agent, or a chemical compound. In some embodiments, the JAK2 inhibitor is ruxolitinib, baricitinib, CYT387, lestaurtinib, or pacritinib. In some embodiments, the JAK2 inhibitor is ruxolitinib.

In some embodiments, a method further comprises administering a hedgehog pathway inhibitor. In some embodiments, the hedgehog pathway inhibitor is vismodegib, erismodegib, BMS-833923, glasdegib, taladegib, or saridegib. In some embodiments, a HDAC11 inhibitor is administered to a patient that has been or will be administered a hedgehog pathway inhibitor, such that the patient receives treatment with both. In some embodiments, a hedgehog pathway inhibitor is administered to a patient that has been or will be administered a HDAC11 inhibitor, such that the patient receives treatment with both.

In some embodiments, a method for inhibiting expression of SOX2 in a stem-like cancer cell in a patient in need thereof are provided, comprising administering a HDAC11 inhibitor in combination with one or more additional therapeutic agents. In some embodiments, a cancer is lung cancer, hematological cancer or breast cancer. In some embodiments, a hematological cancer is MPN, lymphoma, or leukemia. In some embodiments, a cancer is esophageal squamous cell carcinoma, oral squamous cell carcinoma, lung, squamous cell carcinoma, lung adenocarcinoma, non-small cell lung cancer, small cell lung cancer or sinonasal cancer. In some embodiments, a HDAC11 inhibitor is a polypeptide, a polynucleotide, a siRNA, a shRNA, an antibody agent, or a chemical compound.

In some embodiments, a method for inhibiting expression of SOX2 in a stem-like cancer cell in a patient in thereof comprises administering a HDAC11 inhibitor in combination with a JAK2 inhibitor. In some embodiments, a JAK2 inhibitor is a polypeptide, a polynucleotide, a siRNA, a shRNA, an antibody agent, or a chemical compound. In some embodiments, a JAK2 inhibitor is ruxolitinib, baricitinib, CYT387, lestaurtinib, or pacritinib. In some embodiments, a JAK2 inhibitor is ruxolitinib.

In some embodiments, a method for inhibiting expression of SOX2 in a stem-like cancer cell in a patient in thereof comprises administering a HDAC11 inhibitor in combination with a hedgehog pathway inhibitor. In some embodiments, a hedgehog pathway inhibitor is vismodegib, erismodegib, BMS-833923, glasdegib, taladegib, or saridegib.

In another embodiment, methods of treating cancer wherein one or more cancer cells exhibit stem cell-like properties are provided comprising treating a patient with a first line therapy; and administering to the patient a HDAC11 inhibitor, whereby any cancer cells surviving from the first line therapy are reduced or eliminated after treatment with the HDAC11 inhibitor. In some embodiments, the cancer is esophageal squamous cell carcinoma, oral squamous cell carcinoma, lung squamous cell carcinoma, lung adenocarcinoma, non-small cell lung cancer, small cell lung cancer or sinonasal cancer. In other embodiments, the cancer is breast cancer. In some embodiments, the HDAC11 inhibitor is a siRNA, a shRNA, an antibody agent, or a chemical compound. In other embodiments, the chemical compound is a small molecule that is at least 10-fold selective for the inhibition of HDAC11 over other histone deacetylase isoforms. In some embodiments, the first line therapy is resection, radiation, or stem cell transplant.

Formulation and Administration

Administration of therapeutic agents encompassed by the present disclosure (e.g., a HDAC11 inhibitor and/or a JAK2 inhibitor or a hedgehog pathway inhibitor) can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, therapeutic agents described herein can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a therapeutic agent and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Therapeutic agents can be also formulated as a suppository that can be prepared from fatty emulsions or suspensions; using polyalkylene glycols such as propylene glycol, as the carrier.

Therapeutic agents can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Therapeutic agents can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In some embodiments, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

The present disclosure provides pharmaceutical compositions comprising a therapeutic agent (e.g., HDAC11 inhibitor) and a pharmaceutically acceptable carrier. The pharmaceutically acceptable carrier can further include an excipient, diluent, or surfactant. The composition, if desired, can also contain one or more additional therapeutically active substances.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Compositions can be prepared according to conventional mixing, granulating or coating methods, respectively, and the present pharmaceutical compositions can contain from about 0.1% to about 99%, from about 5% to about 90%, or from about 1% to about 20% of a therapeutic agent described herein by weight or volume.

A dosage regimen utilizing the therapeutic agent is selected in accordance with a variety of factors including type, species, age, weight, sex and medical condition of the patient; the severity of the condition to be treated; the route of administration; the renal or hepatic function of the patient; and the particular therapeutic agent employed. A physician or veterinarian of ordinary skill in the art can readily determine and prescribe the effective amount of the therapeutic agent required to prevent, counter or arrest the progress of the condition.

Effective dosage amounts of therapeutic agents, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the therapeutic agent, or, in a range of from one amount to another amount in the list of doses. In some embodiments, compositions are in the form of a tablet that can be scored.

Kits

The present disclosure further provides a pharmaceutical pack or kit comprising one or more containers filled with at least one HDAC11 inhibitor as described herein. Kits may be used in any applicable method, including, for example, therapeutically, diagnostically, etc. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In some embodiments, a kit may include one or more reagents for detection (e.g, detection of a HDAC11 inhibitor). In some embodiments, a kit may include a HDAC11 inhibitor in a detectable form (e.g., covalently associated with detectable moiety or entity).

In some embodiments, a HDAC11 inhibitor as provided herein may be included in a kit used for detection and/or treatment of subjects.

The following numbered embodiments, while non-limiting, are exemplary of certain aspects of the present disclosure:

1. A compound of the Formula I:

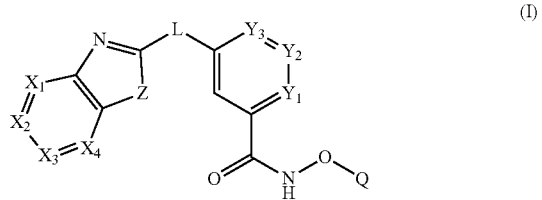

(I)

and pharmaceutically acceptable salts thereof, wherein:

Q is —H, —OC(O)NR$^6$(C$_1$-C$_6$)alkylaryl, or —OC(O)O (C$_1$-C$_6$)alkylaryl

Z is —CH$_2$—, O, S or NR$^6$;

X$_1$, X$_2$, X$_3$, and X$_4$ are each independently, at each occurrence, N or CR$^1$;

Y$_1$, Y$_2$, and Y$_3$ are each independently N or CR$^1$;

L is NR$^6$, O, or —(CR$^1$R$^2$)$_p$—;

R$^1$ and R$^2$ are independently, at each occurrence, —H, —R$^3$, —R$^4$, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —OH, —OR$^{3'}$ halogen, —NO$_2$, —CN, —NHC$_1$-C$_6$alkyl, —N(C$_1$-C$_6$alkyl)$_2$, —S(O)$_2$NH$_2$, —S(O)$_2$N(C$_1$-C$_6$alkyl)$_2$, —N(C$_1$-C$_6$alkyl)S(O)$_2$R$^5$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, —N(C$_1$-C$_6$alkyl)S(O)$_2$C$_1$-C$_6$alkyl, or —(CHR$^5$)$_p$NR$^3$R$^4$, wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^3$, —R$^5$, —SR$^3$, —OR$^3$, —NHR$^3$, —NR$^3$R$^4$, —S(O)$_2$(R$^3$)$_2$—, —S(O)$_2$R$^5$, —C(O)R$^5$, —C(O)OR$^5$, —NR$^3$S(O)$_2$R$^5$, —S(O)R$^5$, —S(O)NR$^3$R$^4$, —NR$^3$S(O)R$^5$, heterocycle, aryl, or heteroaryl;

or R$^1$ and R$^2$ can combine with the carbon atom to which they are both attached to form a spirocycle, spiroheterocycle, or spirocycloalkenyl, each optionally substituted with one or more independent occurrences of R$^3$ and R$^4$;

or two occurrences of R$^1$, when on adjacent atoms, can combine to form a cycloalkyl, a heterocycle, aryl, heteroaryl containing 1-5 heteroatoms selected from the group consisting of N, S, P and O, or a cycloalkenyl, each optionally substituted with one or more independent occurrences of R$^3$ and R$^4$;

R$^3$ and R$^4$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P, and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

R$^5$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, P and O, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —C(O)OC$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_p$N(C$_1$-C$_6$alkyl)$_2$;

R$^6$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from the group consisting of N, S, P and O, —S(O)$_2$N(C$_1$-C$_6$alkyl)$_2$, —S(O)$_2$(C$_1$-C$_6$alkyl), —(C$_1$-C$_6$alkyl)S(O)$_2$R$^5$, —C(O)C$_1$-C$_6$alkyl, —C(O)OC$_1$-C$_6$alkyl, or —(CHR$^5$)$_p$NR$^3$R$^4$ wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH (C$_1$-C$_6$)alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

and p is 0, 1, 2, 3, 4, 5, or 6.

2. The compound of embodiment 1, wherein one of Y$_1$, Y$_2$ or Y$_3$ is N and the other two of Y$_1$, Y$_2$ or Y$_3$ are each independently CR$^1$.

3. The compound of embodiment 1, wherein two of Y$_1$, Y$_2$ or Y$_3$ are N and the other one of Y$_1$, Y$_2$ or Y$_3$ is CR$^1$.

4. The compound of embodiment 2 or 3, wherein R$^1$ is H.

5. The compound of embodiment 1, wherein L is S.

6. The compound of embodiment 1, wherein L is O.

7. The compound of embodiment 1, wherein L is NR$^6$.

8. The compound of embodiment 1, wherein the compound is represented by Formula I-A:

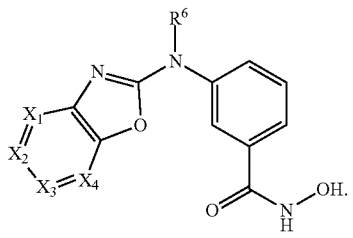

(I-A)

9. The compound of embodiment 1, wherein the compound is represented by Formula I-B:

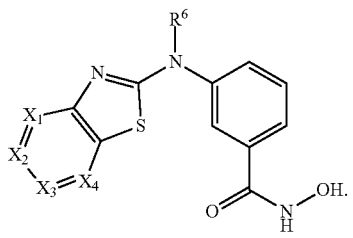

(I-B)

10. The compound of embodiment 1, wherein the compound is represented by Formula I-C:

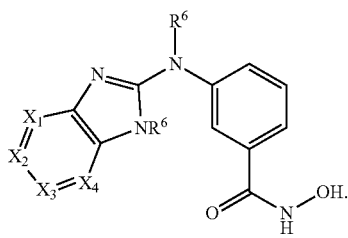

(I-C)

11. The compound of embodiment 1, 8, 9 or 10, wherein $X_1$ and $X_4$ are both N, and $X_2$ and $X_3$ are each independently $CR^1$.
12. The compound of embodiment 1, 8, 9 or 10, wherein $X_2$ and $X_4$ are both N, and $X_1$ and $X_3$ are each independently $CR^1$.
13. The compound of embodiment 1, 8, 9 or 10, wherein $X_1$ is N and $X_2$, $X_3$ and $X_4$ are each independently $CR^1$.
14. The compound of embodiment 1, 8, 9 or 10, wherein each occurrence of $R^6$ is independently H, —$C_1$-$C_6$alkyl, —($C_1$-$C_6$alkyl)S(O)$_2R^5$, —C(O)$C_1$-$C_6$alkyl, —C(O)O$C_1$-$C_6$alkyl, or —(CHR$^5$)$_p$NR$^3R^4$ wherein each alkyl is optionally substituted with one or more substituents selected from —OH, halogen, —NO$_2$, oxo, —CN, —$R^5$, —O($C_1$-$C_6$)alkyl, —NH($C_1$-$C_6$)alkyl, —N($C_1$-$C_6$alkyl)$_2$, —S(O)$_2$N($C_1$-$C_6$alkyl)$_2$, —S(O)$_2$NH$C_1$-$C_6$alkyl, —C(O)$C_1$-$C_6$alkyl, —C(O)O$C_1$-$C_6$alkyl, —N($C_1$-$C_6$alkyl)S(O)$_2C_1$-$C_6$alkyl, —S(O)$R^5$, —S(O)N($C_1$-$C_6$alkyl)$_2$, —N($C_1$-$C_6$alkyl)S(O)$R^5$, heterocycle, aryl, or heteroaryl.
15. The compound of embodiment 14, wherein each occurrence of $R^6$ is independently H, —(CHR$^5$)$_p$NR$^3R^4$, or —$C_1$-$C_6$alkyl optionally substituted with one or more substituents selected from —OH, halogen, —NO$_2$, oxo, —CN, —$R^5$, —O($C_1$-$C_6$)alkyl, —NH($C_1$-$C_6$)alkyl, —N($C_1$-$C_6$alkyl)$_2$, —S(O)$_2$N($C_1$-$C_6$alkyl)$_2$, —S(O)$_2$NH$C_1$-$C_6$alkyl, —C(O)$C_1$-$C_6$alkyl, —C(O)O$C_1$-$C_6$alkyl, —N($C_1$-$C_6$alkyl)S(O)$_2C_1$-$C_6$alkyl, —S(O)$R^5$, —S(O)N($C_1$-$C_6$alkyl)$_2$, or —N($C_1$-$C_6$alkyl)S(O)$R^5$.
16. The compound of embodiment 1, 8, 9 or 10, wherein each independent occurrence of $R^1$ is halogen, —CF$_3$, —OH, —CN, —SO$_2$($C_1$-$C_3$alkyl), phenyl, $C_1$-$C_3$alkyl, $C_1$-$C_3$alkoxy, pyridyl, —C(O)$C_1$-$C_3$alkyl, —O$C_1$-$C_3$alkyl, —($C_1$-$C_3$alkyl)O($C_1$-$C_3$alkyl), —OCF$_3$ or —OCH$_2$phenyl.
17. A compound of the Formula II:

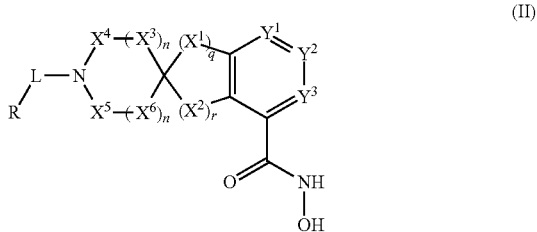

(II)

or a pharmaceutically acceptable salt thereof, wherein:
$X^1$, $X^2$, $X^3$, $X^4$, $X^5$, and $X^6$ are each independently, at each occurrence, —CR$^1R^2$—, —NR$^3$—, —O—, —C(O)—, —S(O)$_2$—, —S(O)—, or —S—;
$Y^1$, $Y^2$, and $Y^3$ are each independently N or CR$^1$;
L is a bond, —(CR$^1R^2$)$_p$—, —C(O)NR$^3$—, —S(O)$_2$—, —S(O)$_2$NR$^3$—, —S(O)—, —S(O)NR$^3$—, —C(O)(CR$^1R^2$)$_p$O—, or —C(O)(CR$^1R^2$)$_p$—;
R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO$_2$, —CN, —$R^2$, —SR$^3$, —OR$^3$, —NHR$^3$, —NR$^3R^4$, —S(O)$_2$NR$^3R^4$, —S(O)$_2R^1$, —C(O)$R^1$, —C(O)OR$^1$, —NR$^3$S(O)$_2R^1$, —S(O)$R^1$, —S(O)NR$^3R^4$, —NR$^3$S(O)$R^1$, heterocycle, aryl, or heteroaryl;
$R^1$ and $R^2$ are independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —NO$_2$, —CN, —NH$C_1$-$C_6$alkyl, —N($C_1$-$C_6$alkyl)$_2$, —S(O)$_2$N($C_1$-$C_6$alkyl)$_2$, —N($C_1$-$C_6$alkyl)S(O)$_2R^5$, —S(O)$_2$($C_1$-$C_6$alkyl), —($C_1$-$C_6$alkyl)S(O)$_2R^5$, —C(O)$C_1$-$C_6$alkyl, —C(O)O$C_1$-$C_6$alkyl, —N($C_1$-$C_6$alkyl)S(O)$_2C_1$-$C_6$alkyl, or —(CHR$^5$)$_p$NR$^3R^4$, wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —$R^5$, —OR$^3$, —NHR$^3$, —NR$^3R^4$, —S(O)$_2$N(R$^3$)$_2$, —S(O)$_2R^5$, —C(O)R$^5$, —C(O)OR$^5$, —NR$^3$S(O)$_2R^5$, —S(O)$R^5$, —S(O)NR$^3R^4$, —NR$^3$S(O)$R^5$, heterocycle, aryl, or heteroaryl;
or $R^1$ and $R^2$ can combine with the carbon atom to which they are both attached to form a spirocycle, spiroheterocycle, or spirocycloalkenyl;
or $R^1$ and $R^2$, when on adjacent atoms, can combine to form a cycloalkyl, cycloalkenyl, heterocycle, aryl, or heteroaryl containing 1-5 heteroatoms selected from the group consisting of N, S, P and O;

or R¹ and R², when on non-adjacent atoms, can combine to form an optionally bridging cycloalkyl, an optionally bridging heterocycle, or an optionally bridging cycloalkenyl;

R³ and R⁴ are independently, at each occurrence, —H, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —S(O)$_2$N($C_1$-$C_6$alkyl)$_2$, —S(O)$_2$($C_1$-$C_6$alkyl), —($C_1$-$C_6$alkyl)S(O)$_2$R⁵, —C(O)$C_1$-$C_6$alkyl, —C(O)O$C_1$-$C_6$alkyl, or —(CHR⁵)$_p$N($C_1$-$C_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R⁵, —O($C_1$-$C_6$)alkyl, —NH($C_1$-$C_6$)alkyl, —N($C_1$-$C_6$alkyl)$_2$, —S(O)$_2$N($C_1$-$C_6$alkyl)$_2$, —S(O)$_2$NH$C_1$-$C_6$alkyl, —C(O)$C_1$-$C_6$alkyl, —C(O)O$C_1$-$C_6$alkyl, —N($C_1$-$C_6$alkyl)S(O)$_2$$C_1$-$C_6$alkyl, —S(O)R⁵, —S(O)N($C_1$-$C_6$alkyl)$_2$, —N($C_1$-$C_6$alkyl)S(O)R⁵, heterocycle, aryl, or heteroaryl;

R⁵ is independently, at each occurrence, —H, —$C_2$-$C_6$alkenyl, $C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —NO$_2$, —CN, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —C(O)$C_1$-$C_6$alkyl, —C(O)O$C_1$-$C_6$alkyl, —N($C_1$-$C_6$alkyl)SO$_2$$C_1$-$C_6$alkyl, —S(O)($C_1$-$C_6$alkyl), —S(O)N($C_1$-$C_6$alkyl)$_2$, —N($C_1$-$C_6$alkyl)S(O)($C_1$-$C_6$alkyl) or —(CH$_2$)$_p$N($C_1$-$C_6$alkyl)$_2$;

p is 0, 1, 2, 3, 4, 5, or 6;

n is 0, 1, 2, 3, or 4;

m is 0, 1, or 2;

q is 1 or 2; and r is 1 or 2;

wherein the sum q+r≤3 and wherein the sum m+n≤4.

18. The compound of embodiment 17, wherein n is 0 and m is 1.

19. The compound of embodiment 17, wherein n is 1 and m is 1.

20. The compound of embodiment 17, wherein q is 1 and r is 1.

21. The compound of embodiment 17, wherein q is 2 and r is 1.

22. The compound of embodiment 17, wherein q is 1 and r is 2.

23. The compound of embodiment 17, wherein q is 1, r is 1, m is 0 and n is 1.

24. The compound of embodiment 17, wherein q is 1, r is 1, m is 1 and n is 1.

25. The compound of embodiment 17, wherein q is 1, r is 1, m is 2 and n is 1.

26. The compound of embodiment 17, wherein q is 1, r is 1, m is 1 and n is 2.

27. The compound of embodiment 17, wherein X⁵ is C(O).

28. The compound of embodiment 17, wherein X⁴ is C(O).

29. The compound of embodiment 17, wherein the compound is of the Formula II-A:

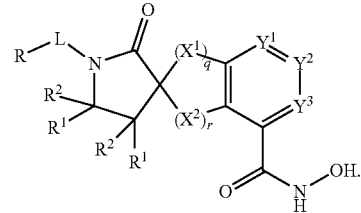

(II-A)

30. The compound of embodiment 17, wherein the compound is of the Formula II-B:

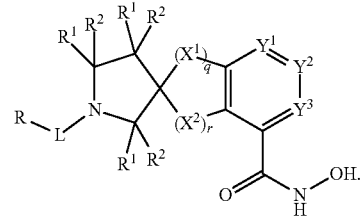

(II-B)

31. The compound of embodiment 17, wherein the compound is of the Formula II-C:

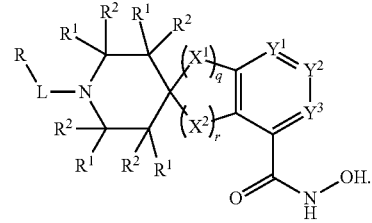

(II-C)

32. The compound of embodiment 17, wherein the compound is of the Formula II-D:

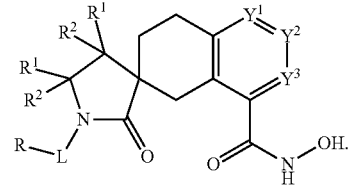

(II-D)

33. The compound of embodiment 17, wherein the compound is of the Formula II-E:

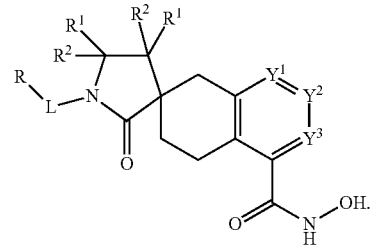

(II-E)

34. The compound of any one of embodiments 29-33, wherein L is selected from a bond, —CH$_2$—, —(CH$_2$)$_2$—, —(CH$_2$)$_3$—, —C(O)—, —S(O)$_2$—, —C(O)NR$^3$—, or —C(O)CH$_2$—.

35. The compound of any one of embodiments 29-33, wherein L is selected from —CH$_2$—, or —C(O)—.

36. The compound of any one of embodiments 29-33, wherein R is hydrogen or an optionally substituted group selected from C$_1$-C$_6$alkyl, aryl, C$_3$-C$_8$ cycloalkyl, heterocyclyl, or heteroaryl containing 1-5 heteroatoms selected from the group consisting of N, S, P, or O.

37. The compound of any one of embodiments 29-33, wherein R is hydrogen or an optionally substituted group selected from phenyl, C$_1$-C$_6$alkyl, cyclopropyl, cyclobutyl, cyclopentyl, cyclohexyl, pyridyl, or morpholinyl.

38. The compound of any one of embodiments 29-33, wherein R is phenyl optionally substituted with one or more independent occurrences of halogen, CF$_3$, —SO$_2$CH$_3$, phenyl, C$_1$-C$_3$ alkyl, C$_1$-C$_3$alkoxy, pyridyl, —OCF$_3$ or —OCH$_2$phenyl.

39. The compound of embodiment 17, wherein the compound is of the Formula II-A-i:

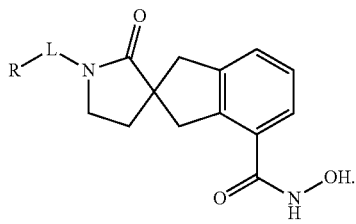

(II-A-i)

40. The compound of embodiment 17, wherein the compound is of the Formula II-B-i:

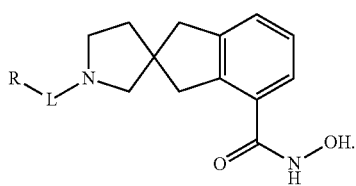

(II-B-i)

41. The compound of embodiment 17, wherein the compound is of the Formula II-C-i or II-C-ii:

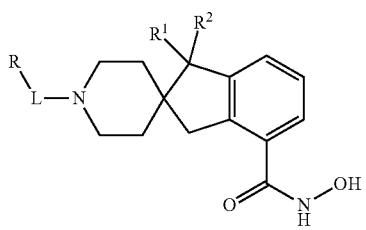

(II-C-i)

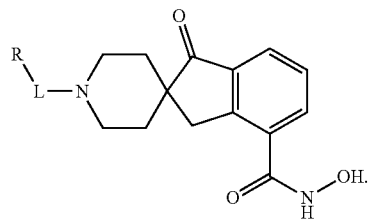

(II-C-ii)

42. The compound of embodiment 17, wherein the compound is of the Formula II-D-i:

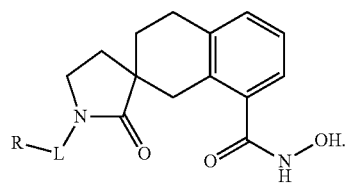

(II-D-i)

43. The compound of embodiment 17, wherein the compound is of the Formula II-E-i:

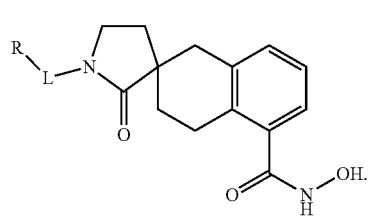

(II-E-i)

44. The compound of any one of embodiments 39-43, wherein L is selected from a bond, —CH$_2$—, —(CH$_2$)$_2$—, —(CH$_2$)$_3$—, —C(O)—, —S(O)$_2$—, —C(O)NR$^3$—, or —C(O)CH$_2$—.

45. The compound of any one of embodiments 39-43, wherein L is selected from —CH$_2$—, or —C(O)—.

46. The compound of any one of embodiments 39-43, wherein R is hydrogen or an optionally substituted group selected from C$_1$-C$_6$alkyl, aryl, C$_3$-C$_8$ cycloalkyl, heterocyclyl, or heteroaryl containing 1-5 heteroatoms selected from the group consisting of N, S, P, or O.

47. The compound of any one of embodiments 39-43, wherein R is hydrogen or an optionally substituted group selected from phenyl, C$_1$-C$_6$alkyl, cyclopropyl, cyclobutyl, cyclopentyl, cyclohexyl, pyridyl, or morpholinyl.

48. The compound of any one of embodiments 39-43, wherein R is phenyl optionally substituted with one or more independent occurrences of halogen, CF$_3$, —SO$_2$CH$_3$, phenyl, C$_1$-C$_3$ alkyl, C$_1$-C$_3$alkoxy, pyridyl, —OCF$_3$ or —OCH$_2$phenyl.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby.

It is to be further understood that resort may be had to various other embodiments, modifications, and equivalents thereof which may suggest themselves to those skilled in the art without departing from the spirit of the present disclosure and/or scope of the appended claims.

Certain abbreviations used in the following Examples and elsewhere herein:
ACN acetonitrile ($CH_3CN$)
AcOH acetic acid
AIBN 2,2'-Azobis(2-methylpropionitrile)
$CH_3CN$ acetonitrile
DCE 1,2-dichloroethane
DCM dichloromethane or methylene chloride
DEA N,N-diethylamine
DIEA N,N-diisopropylethylamine
DMA N,N-Dimethylacetamide
DMF N,N-dimethylformamide
DMSO dimethylsulfoxide
DMTMM 4-(4,6-dimethoxy-1,3,5-triazin-2-yl)-4-methylmorpholinium chloride
dppf bis(diphenylphosphino)ferrocene
EtOAc ethyl acetate
EtOH ethanol
FA formic acid
h hours
HATU 2-(3H-[1,2,3]triazolo[4,5-b]pyridin-3-yl)-1,1,3,3-tetramethylisouronium hexafluorophosphate
HBr hydrogen bromide
HCl hydrogen chloride
HPLC high performance liquid chromatography
LC/MS liquid chromatography/mass spectrometry
LiOH lithium hydroxide
$K_2CO_3$ potassium carbonate
MeOH methanol
MS mass spectrometry
NaOH sodium hydroxide
$Na_2SO_4$ sodium sulfate
$NH_4HCO_3$ ammonium bicarbonate
NMM 4-methylmorpholine
NMP N-Methyl-2-pyrrolidone
$Pd_2(dba)_3$ tris(dibenzylideneacetone)dipalladium
$Pd(dppf)Cl_2$ [1,1'-Bis(diphenylphosphino)ferrocene]dichloropalladium (II)
PMB para-methoxybenzyl
$PPh_3$ triphenylphosphine
rt room temperature
RuPhos 2-Dicyclohexylphosphino-2',6'-diisopropoxybiphenyl
RuPhos 2G Chloro(2-dicyclohexylphosphino-2',6'-diisopropoxy-1,1'-biphenyl)[2-(2'-amino-1,1'-biphenyl)]palladium(II),
TEA triethylamine
TFA trifluoroacetic acid
THF tetrahydrofuran
XantPhos 4,5-Bis(diphenylphosphino)-9,9-dimethylxanthene
XPhos 2-Dicyclohexylphosphino-2',4',6'-triisopropylbiphenyl
XPhos 2G Chloro(2-dicyclohexylphosphino-2',4',6'-triisopropyl-1,1'-biphenyl)[2-(2'-amino-1,1'-biphenyl)]palladium (II)
XPhos 3G Methanesulfonato(2-dicyclohexylphosphino-2',4',6'-tri-i-propyl-1,1'-biphenyl)(2'-amino-1,1'-biphenyl-2-yl)palladium(II) dichloromethane adduct
Materials Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C18 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Unless otherwise noted, proton nuclear magnetic resonance (NMR) spectra were obtained on either: (1) Bruker BBFO ASCEND™400 AVANCE III spectrometer at 400 MHz or (2) Bruker BBFO ULTRASHIELD™300 AVANCE III spectrometer at 300 MHz. Spectra are given in ppm ($\delta$) and coupling constants, J, are reported in Hertz (Hz). Tetramethylsilane (TMS) was used as an internal standard. Mass spectra were collected using a Waters ZQ Single Quad Mass Spectrometer (ion trap electrospray ionization (ESI)).

Example 1

HDAC Inhibition Assays

This example describes in vitro inhibition properties of exemplary HDAC11 inhibitors for various HDACs. HDAC inhibition assays were performed using an electrophoretic mobility shift assay at Nanosyn, Inc. (Santa Clara, Calif.). Full length human recombinant HDAC proteins were expressed in the baculoviral system and purified by affinity chromatography. A human recombinant HDAC3 was co-expressed with nuclear receptor corepressor (Ncor2). The following peptide substrates were used: FAM-RHKK(Ac)-NH2 for HDAC3, HDAC6 and HDAC8; FITC-H3K27(Ac)-NH2 for HDAC1, HDAC2 and HDAC10; FAM-RHKK(trifluor-Ac)-NH2 for HDAC4, HDAC5, HDAC7, HDAC9 and HDAC11. Reactions consisting of compound, enzyme, and substrate were performed in reaction buffer (comprised of 100 mM HEPES, pH7.5, 25 mM KCl, 0.1% bovine serum albumin, 0.01% Triton X-100) at 25° C. and quenched by the addition of termination buffer (100 mM HEPES, pH7.5, 0.01% Triton X-100, 0.05% SDS). The fluorescence intensity of the electrophoretically separated de-acetylated product and substrate peptide were measured and analyzed using the LabChip® 3000 microfluidic electrophoresis instrument (Perkin Elmer/Caliper Life Sciences). The $IC_{50}$ values of inhibitors were determined by fitting the %-inhibition curves with 4 parameter dose-response model using XLfit 4 software (IDBS).

Table 1 shows the activity of exemplary selective HDAC11 inhibitors from three different chemical series.

Exemplary selective HDAC11 inhibitors HDTK010 and HDTK054 display >200-fold selectivity over HDACs 1-10.

Exemplary selective HDAC11 inhibitors HDTK070 and HDTK028 display >1800-fold selectivity over HDACs1-10.

TABLE 1

| Chemical Series | Compound ID | HDAC Biochemical IC50 (µM) | | | | | | | | | | |
|---|---|---|---|---|---|---|---|---|---|---|---|---|
| | | HDAC1 | HDAC2 | HDAC3 | HDAC4 | HDAC5 | HDAC6 | HDAC7 | HDAC8 | HDAC9 | HDAC10 | HDAC11 |
| A | HDTK010 | >10 | >10 | >10 | >10 | >10 | 0.5-1.0 | 5-10 | 0.5-1.0 | >10 | >10 | 0.001-0.005 |
| A (inactive) | HDTK069 | >10 | >10 | >10 | >10 | >10 | >10 | >10 | >10 | >10 | >10 | >10 |
| B | HDTK070 | >10 | >10 | >10 | >10 | >10 | >10 | >10 | 5-10 | >10 | >10 | 0.001-0.005 |
| B | HDTK028 | >10 | >10 | >10 | >10 | >10 | >10 | >10 | 10 | >10 | >10 | 0.001-0.005 |
| B (inactive) | HDTK072 | >10 | >10 | >10 | >10 | >10 | >10 | >10 | >10 | >10 | >10 | >10 |
| C | HDTK054 | >10 | >10 | >10 | >10 | >10 | >10 | >10 | 5-10 | >10 | >10 | 0.01-0.05 |

Example 2

Bone Marrow Transplant Assay

This example describes certain in vivo effects of modulating HDAC11 in vivo, using an exemplary model mouse for MPN disease. Effects of HDAC11 knockout on MPN disease were determined using a MPLW515L mouse bone marrow transplant model. This model was established using procedures as described previously with minor modifications (Pikman et al. PloS Med. 2006). Bone marrow cells were harvested from C57BL/6 donor mice (either wild-type (WT) or HDAC11 knock out (KO) mice) 7 days after 5-fluorouracil injection (150 mg/kg). Cells were then treated with red blood cell lysis buffer and cultured overnight in transplantation medium (RPMI-1640+10% fetal bovine serum (FBS)+6 ng/ml IL-3, 10 ng/ml IL-6 and 10 ng/ml stem-cell factor (SCF)) at 37° C. and 5% CO2. The next day cells were transduced with recombinant retroviruses overexpressing either MPLW515L or MPLWT by spin infection at 2500 rpm for 90 minutes at 30° C. The spin infection was repeated 24 hours later. Cells were then re-suspended in PBS and injected into tail veins of lethally irradiated (2×450 cGy) C57BL/6 recipient mice at 0.8-1.0×106 cells/mouse. Viral constructs used included MSCV-human-MPLW515L-green fluorescent protein (GFP) and MSCV-human-MPLWT-GFP. Peripheral blood cell counts including white blood cells (WBC), platelets (PLT), and red blood cells (RBC) were measured at indicated time points to evaluate disease burden. Spleens were isolated and the weights were measured. Bone marrow cells were collected from two femurs and two tibias. After RBC lysis, cells were lysed for western blot analysis. Cells were lysed in RIPA buffer (Sigma-Aldrich, St. Louis, Mo.) supplemented with protease inhibitors (Roche, Basel, Switzerland) and phosphatase inhibitors (Sigma P5726). Protein concentrations were determined with Pierce BCA protein assay kit (Thermo Fisher Scientific, Waltham, Mass.). Proteins were separated on a 4-12% Bis-Tris gradient electrophoresis gel (Life Technologies, Carlsbad, Calif.) and transferred onto a nitrocellulose membrane. The membrane was then blocked in either 5% nonfat dry milk or 5% bovine serum albumin (BSA) followed by incubation with primary antibodies at 4° C. overnight. Antibodies for p-STAT5 (Abcam 32364), STAT5 (Cell Signaling 9358), p-STAT3 (Cell Signaling 9145) and STAT3 (Cell Signaling 9139) were used. β-actin was used as loading control.

The recipients of the MPL W515L transduced-WT bone marrow displayed splenomegaly and increased platelet and red blood cell count (FIG. 1) compared to MPL WT transduced-WT bone marrow recipients. The recipients of the MPL W515L transduced-HDAC11 KO bone marrow showed amelioration of the disease, with significantly fewer platelets and red blood cells and smaller spleen size in comparison to the recipients of the MPL W515L transduced-WT bone marrow. These results demonstrated that HDAC11 knockout reduces thrombocytosis and erythrocytosis in a MPN mouse model.

Figure 2:
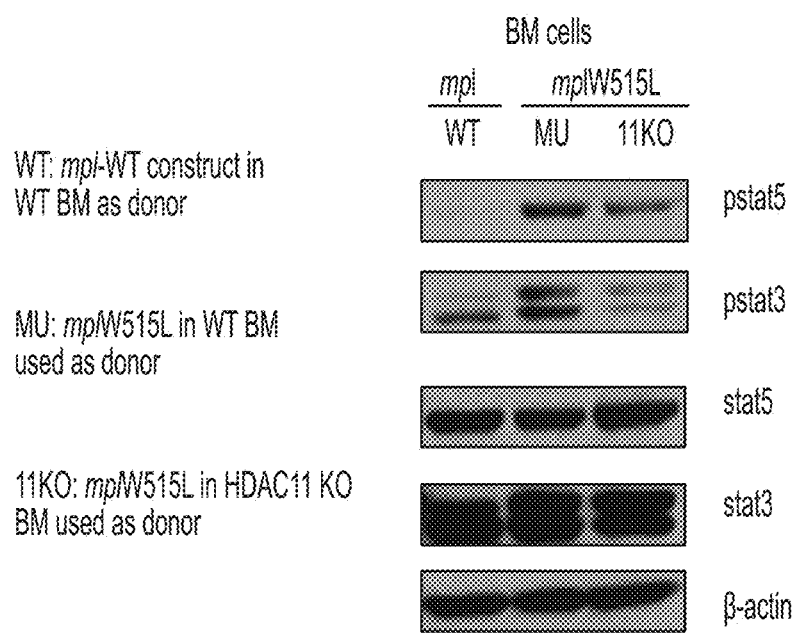
FIG. 2 shows that STAT3 and STAT5 phosphorylation were decreased by HDAC11 deficiency in a bone marrow transplant MPN model.

The amounts of STAT3 and STAT5 phosphorylation were examined by western blots of whole bone marrow samples on Day 34. With WT donor bone marrow cells, transduction of MPL W515L resulted in increased STAT3 and STAT5 phosphorylation, compared to transduction of MPL WT (FIG. 2). Transduction of MPL W515L in the HDAC11 KO donor bone marrow cells resulted in inhibition of STAT3 and STAT5 phosphorylation.

Example 3

Cell Proliferation Assays in Cells Expressing MPL or JAK2 Mutations

This example describes inhibition of in vitro cell proliferation with exemplary HDAC11 inhibitors. The effects of selective HDAC11 inhibitors on cell proliferation were measured in cell lines containing the MPN-associated mutations MPL W515L (Ba/F3 MPL W515L) and JAK2 V617F (Ba/F3 JAK2 V617F, HEL 92.1.7, SET-2). HEL 92.1.7 and SET-2 cells were purchased from the ATCC and DSMZ, respectively. Ba/F3 cells overexpressing either MPLW515L or JAK2V617F, which were cytokine independent, were generated by transforming Ba/F3 cells with retroviruses overexpressing either MPL W515L or JAK2V617F. For survival assays, cells were seeded in 96-well plates at the density of 0.1 million/ml with addition of indicated compounds and incubated at 37° C. for 48 h. CCK8 solution (Dojindo, Rockville, Md.) was added and absorbance at 450 nm was measured after 3 hours of incubation. Readings were normalized to dimethylsulfoxide (DMSO)-treated wells.

Figure 3:
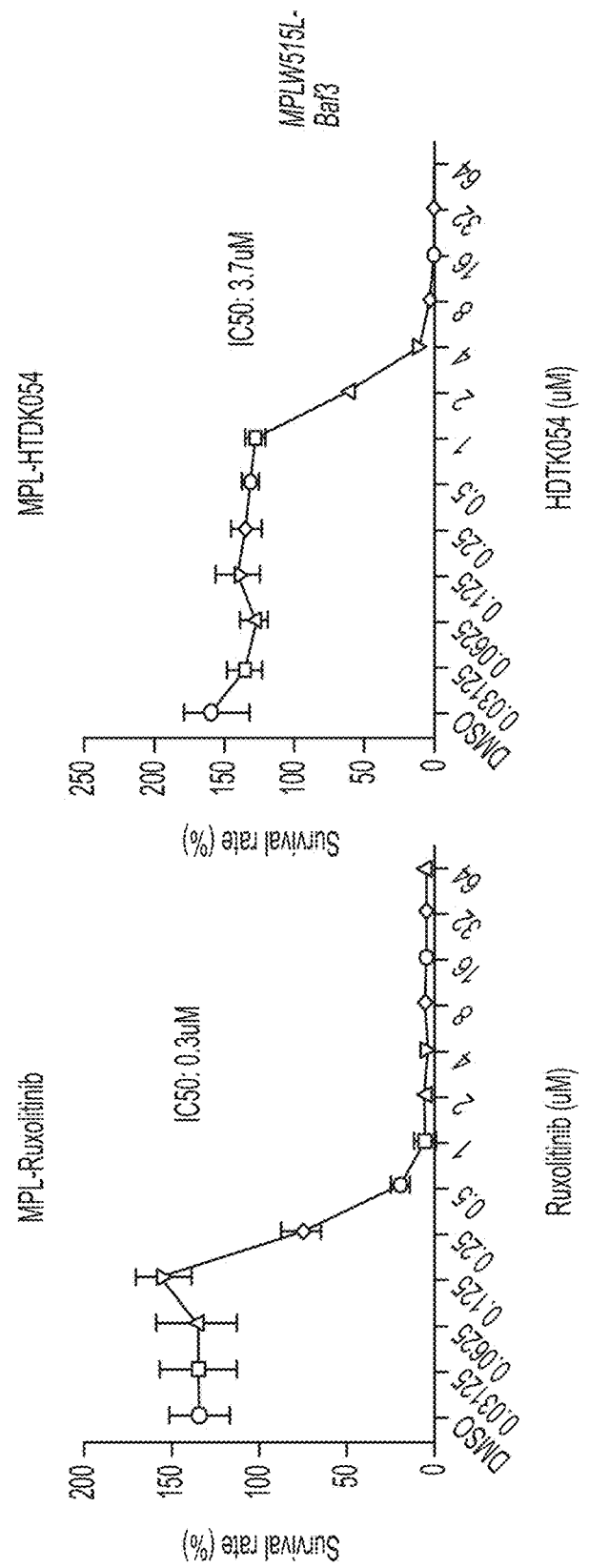
FIG. 3 shows that growth of MPL- or JAK2-mutant expressing cell lines was inhibited by HDAC11 inhibitors.
Figure 3:
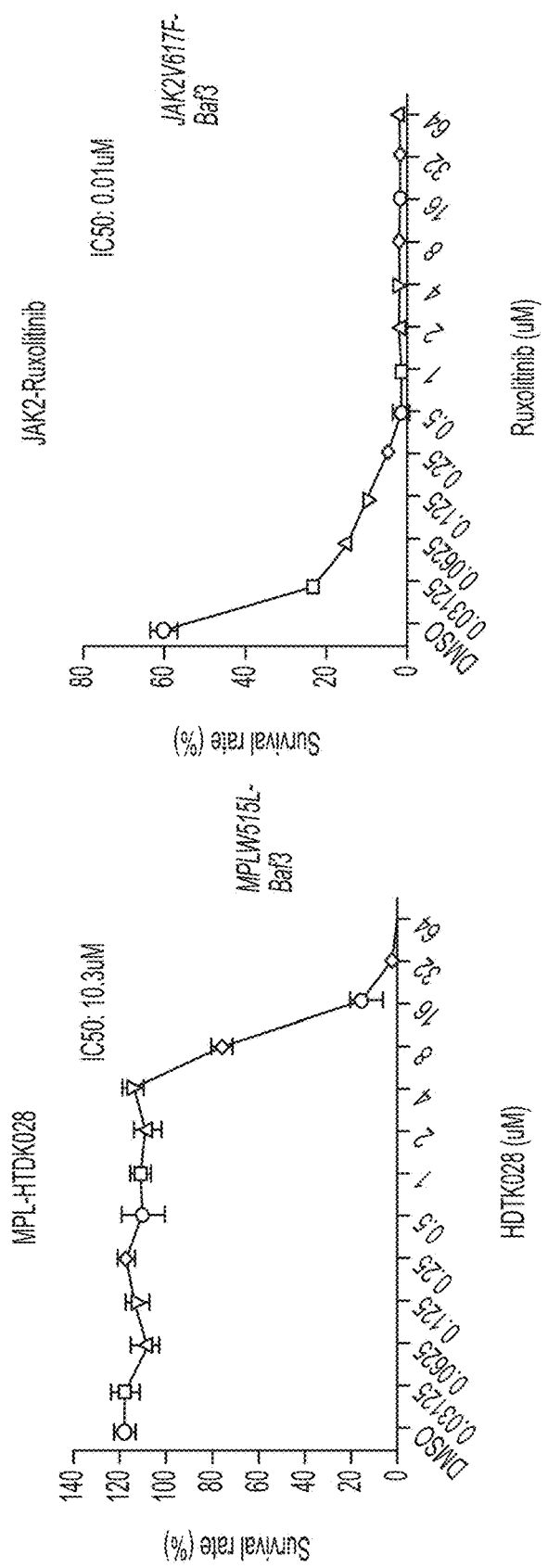
Figure 3:
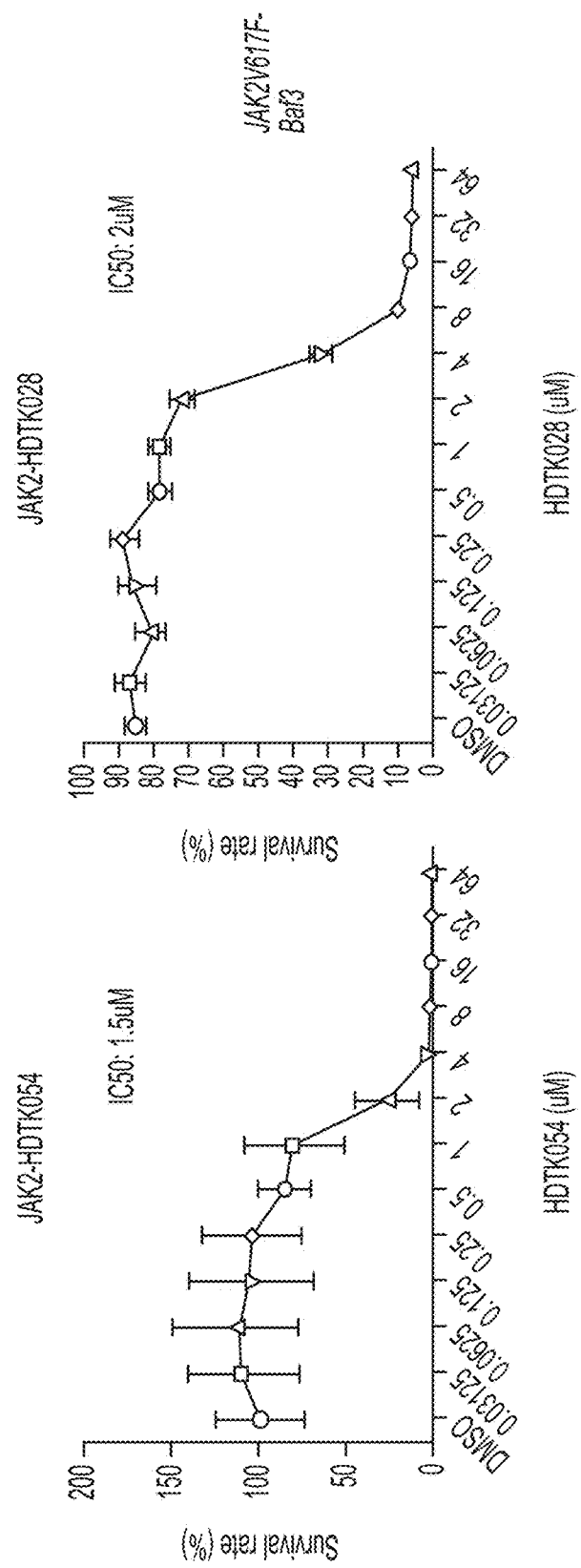
Figure 4:
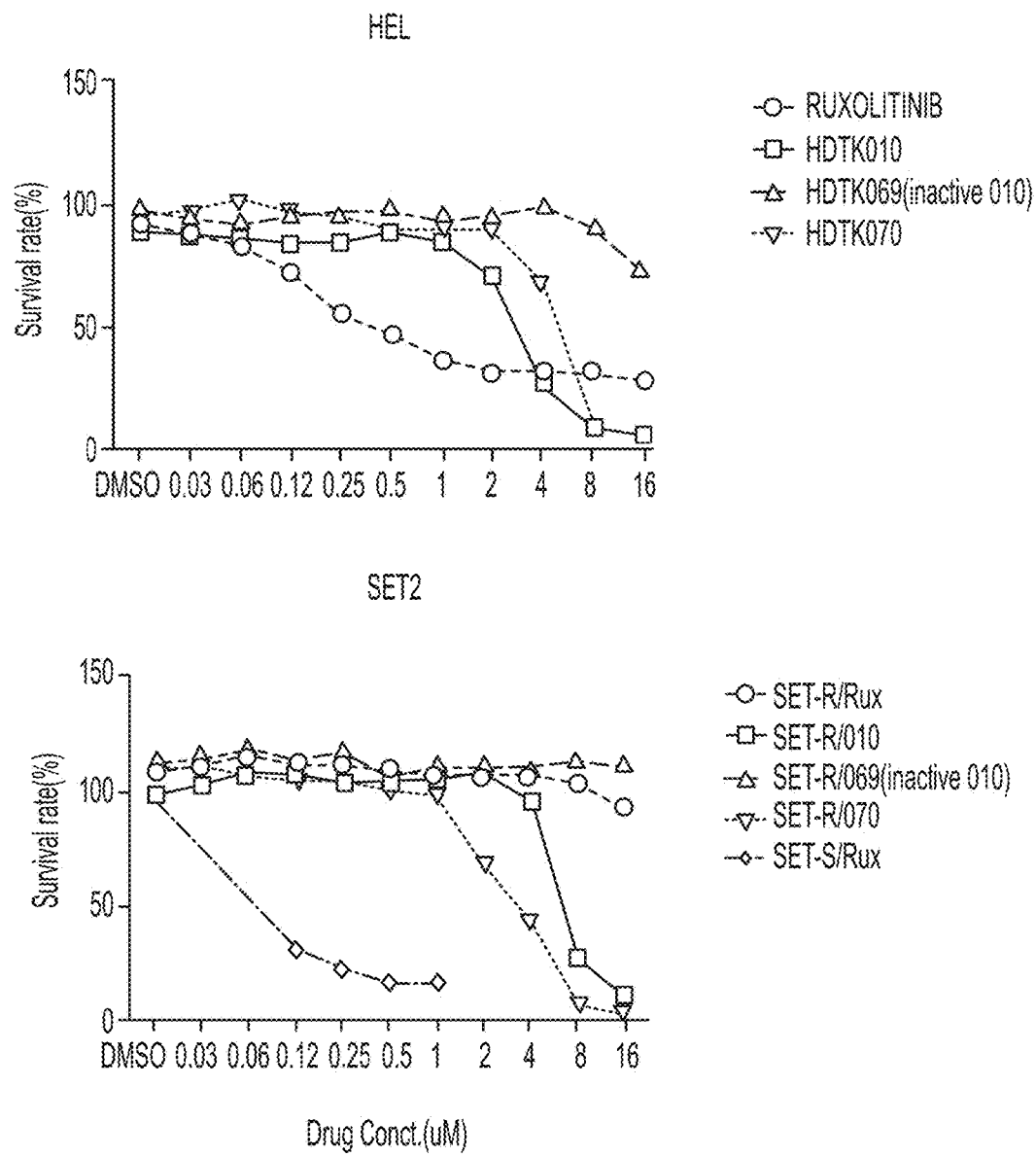
FIG. 4 shows that growth of HEL92.1.7 and SET-2 cell lines was inhibited by HDAC11 inhibitors and ruxolitinib.

Exemplary selective HDAC11 inhibitors HDTK028 and HDTK054 inhibited proliferation of Ba/F3 MPLW515L and Ba/F3 JAK2V617F with IC50 values in the 1-10 range. The exemplary selective inhibitors HDTK010 and HDTK070 inhibited the growth of the HEL 92.1.7 cell line, while an inactive analog HDTK069 did not (FIG. 3). While less potent than the JAK2 inhibitor Ruxolitinib, the exemplary selective HDAC11 inhibitors HDTK010 and HDTK070 inhibited the growth of a SET-2 cell line that was generated to be Ruxolitinib-resistant (FIG. 4).

Example 4

Cell Cycle Assay

This example describes in vitro cell cycle inhibition mediated by an exemplary HDAC11 inhibitor.

The effect of selective HDAC11 compounds on cell cycle was determined using flow cytometry. After treatment, HEL 92.1.7 cells were fixed in 70% ethanol overnight. The next day, cells were washed with PBS and suspended in 4',6-diamidino-2-phenylindole (DAPI)/Triton X-100 staining solution (0.1% Triton X-100, 1 ug/ml DAPI) and kept in dark for 1 hour before measured by a LSRII cytometer (BD Biosciences, San Diego, Calif.). Analysis was performed using ModFit LT software v4.1 (Verity Software House).

Figure 5:
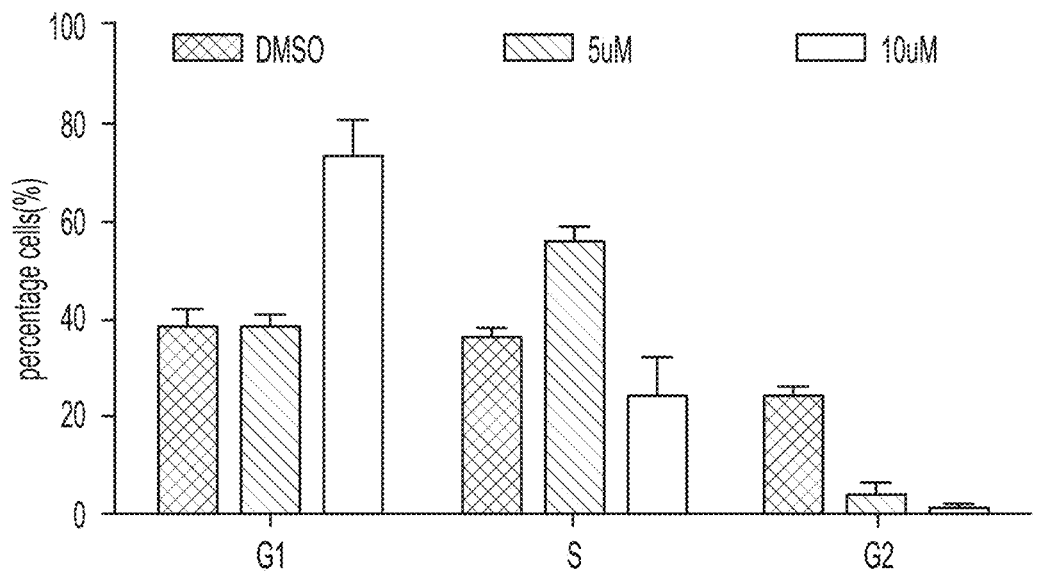
FIG. 5 shows G1 cell cycle arrest in HEL92.1.7 cells after treatment with an HDAC11 inhibitor.

The exemplary selective HDAC11 inhibitor HDTK070 induced G1 cell cycle arrest in HEL 92.1.7 cells after 12 hours of treatment at 10 µM concentration (FIG. 5).

Example 5

STAT3 and STAT5 Pathway Assays

The example describes in vitro cell expression and phosphorylation of certain JAK/STAT pathway polypeptides upon treatment with exemplary HDAC11 inhibitors.

STAT3 and STAT5 Phosphorylation Western Blot Assay

The effects of selective HDAC11 inhibition on STAT3 and STAT3 phosphorylation in HEL 92.1.7 cells were determined by western blot. Cells were treated with HDAC11 inhibitors and lysed in RIPA buffer (Sigma-Aldrich, St. Louis, Mo.) supplemented with protease inhibitors (Roche, Basel, Switzerland) and phosphatase inhibitors (Sigma P5726). Protein concentrations were determined with Pierce BCA protein assay kit (Thermo Fisher Scientific, Waltham, Mass.). Proteins were separated on a 4-12% Bis-Tris gradient electrophoresis gel (Life Technologies, Carlsbad, Calif.) and transferred onto a nitrocellulose membrane. The membrane was then blocked in either 5% nonfat dry milk or 5% BSA followed by incubation with primary antibodies at 4° C. overnight. Antibodies for p-STAT5 (Abcam 32364), STAT5 (Cell Signaling 9358), p-STAT3 (Cell Signaling 9145) and STAT3 (Cell Signaling 9139) were used. β-actin was used as loading control.

Figure 6:
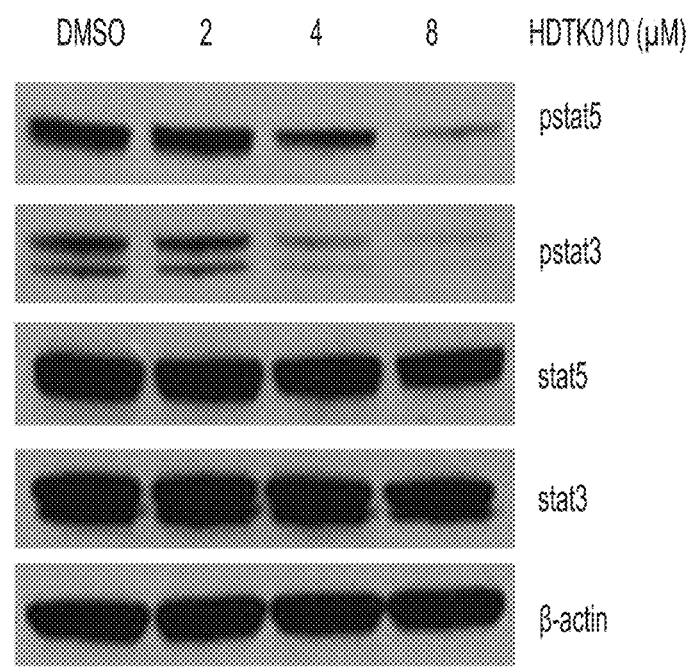
FIG. 6 shows inhibition of STAT3 and STAT5 phosphorylation in HEL92.1.7 cells after treatment with a HDAC11 inhibitor.

As shown in FIG. 6, the exemplary selective HDAC11 inhibitor HDTK010 inhibited STAT3 and STAT5 phosphorylation.

JAK/STAT Signaling Pathway PCR Array

The effects of HDAC11 inhibition on the STAT pathway were further examined using a JAK/STAT Signaling Pathway PCR Array (Qiagen). HEL 92.1.7 cells were treated with HDTK010 for 24 or 48 hours. At the end of treatment, the cells were lysed and total RNA was isolated using the RNeasy Plus Micro Kit following the manufacturer's protocol (Qiagen). RNA (0.5 µg) was converted to cDNA using the iScript reaction mix (BioRad). The cDNA template was mixed with RT2 SYBR Green Mastermix and added to the PCR Array. Reactions were carried out in an Eppendorf Realplex2 ep.gradient Mastercycler and data analyzed per manufacturer's protocol. Results from HDAC11 treatment were compared to DMSO control.

Table 2 lists genes in the JAK/STAT Signaling Pathway with increased expression after HDAC11 inhibitor treatment.

TABLE 2

JAK/STAT Signaling Pathway Genes Modulated by HDAC11 Inhibitor

PDGFR
JUN
IL10RA
CDKN1A

Example 6

Colony Formation Assay from Patient Samples

To determine the effects of selective HDAC11 inhibition on MPN patient samples, the effects of HDAC11 inhibitors were evaluated in a colony formation assay with erythroid or myeloid cells from MPN patients. Peripheral blood was obtained from MPN patients consented through the Moffitt Cancer Center Total Cancer Care protocol (MCC 14690). Blood was treated with HetaSep™ (STEMCELL Technologies, Inc.) to remove the majority of red blood cells. Peripheral blood mononuclear cells (PBMCs) were isolated by ficoll separation. PBMCs (1-4×105) were then plated in 1 mL of methylcellulose medium containing rhSCF, rhIL-3, and granulocyte-macrophage colony-stimulating factor (rhGM-CSF) (MethoCult™ #H4534; STEMCELL Technologies, Inc.). All drug treated samples contained 0.1% DMSO as the final concentration. Cells were incubated at 37° C. and 5% CO2 in a humidified incubator. Colonies were scored 12 to 14 days after plating.

Figure 7:
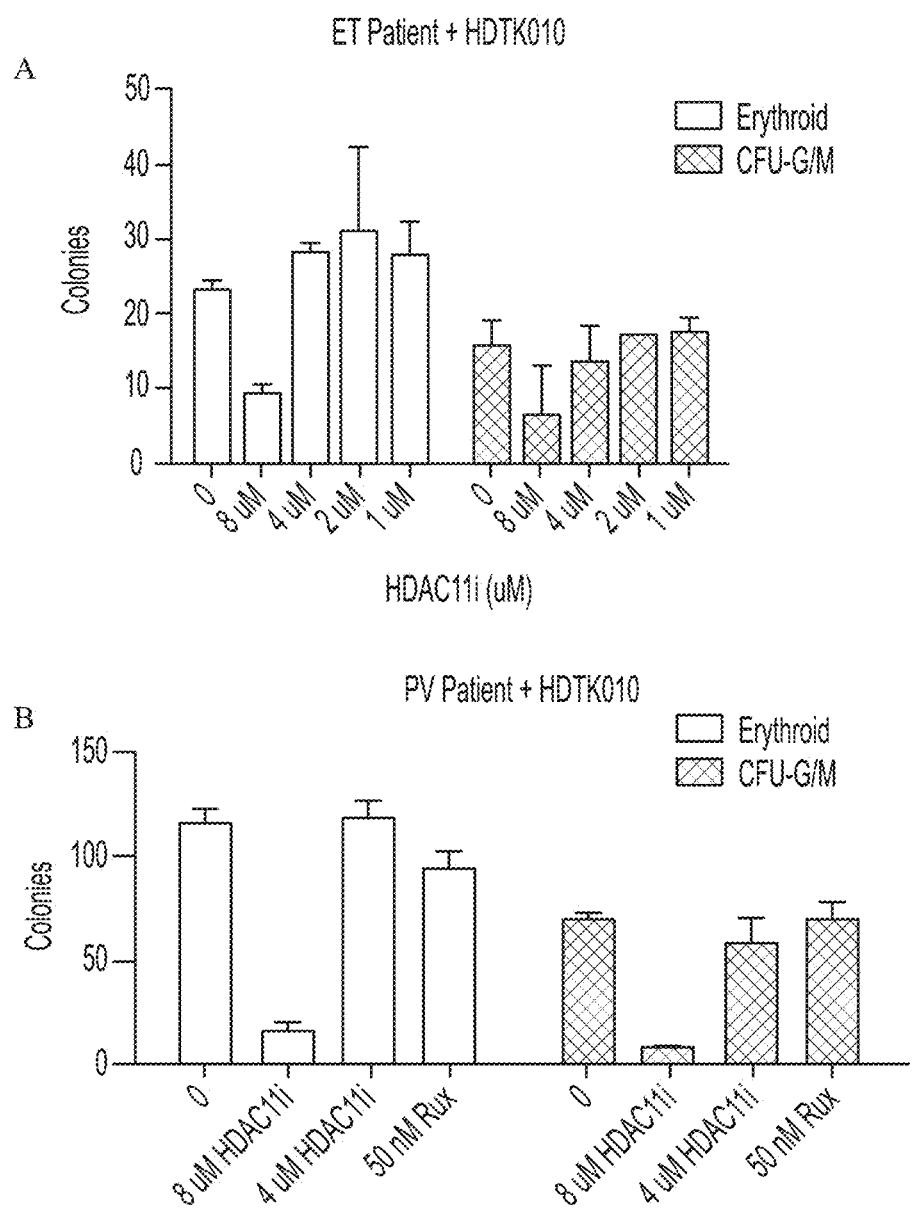
FIG. 7 shows inhibition of colony growth from (A) erythroid and (B) myeloid patient-derived cells after treatment with a HDAC11 inhibitor.

The results from two patient samples are shown in FIG. 7. One patient had essential thrombocytosis (ET), and the other had polycythemia vera (PV) and was also Ruxolitinib resistant. The exemplary selective HDAC11 inhibitor HDTK010 reduced the growth of colonies from both erythroid and myeloid cells.

Example 7

Sphere Formation Assay with Stem-Like Side Population NSCLC Cells

In order to investigate the role of HDAC11 in the self-renewal of stem-like cancer cells, sphere formation assays were conducted with NSCLC side population (SP) stem-like cells. A549 and NCI-H1650 cells were obtained from the ATCC. Asynchronously growing A549 or NCI-H1650 cells were washed once with phosphate buffered saline (PBS) and harvested using Accutase solution (Sigma Aldrich) and resuspended in DMEM-F12K medium (Gibo, Life Technologies) with 2% fetal bovine serum (FBS) at 1×106 cells/ml density. The cells were incubated with 4 µg/ml of Hoechst 33342 dye (Life Technologies) for 90 min at 37° C. in the presence or absence of 1 µM Fumitremorgin C (Sigma-Aldrich) which was used as a control sample to set the gate during sorting. The Hoechst stained cells were sorted using the BD FACSAria cell sorter. The sorted SP cells were plated in 96-well ultra-low adherent plate (Corning Inc) at the cell density of 1000 cells/100 µl/well in stem cell selective medium (DMEM:F12K supplemented with N2 supplement, 10 ng/mL epidermal growth factor (EGF) and 10 ng/ml basic fibroblast growth factor (bFGF) (Sigma-Aldrich) at 37° C. for 7-10 days. The spheres were observed and acquired using EVOS FL microscope system (Life Technologies Inc., USA). The numbers of spheres greater than or equal to 50 µm were counted. To study the effect of the HDAC11 inhibitors, the appropriate concentrations of the compounds were added to the wells on Day 0 and Day 5 and the image acquisition and analysis of the spheres were performed on Day 10. The sphere formation assays were performed twice with triplicates of each treatment in every assay.

As shown in FIG. 8, the exemplary selective HDAC11 inhibitors HDTK010, HDTK054, and HDTK070 prevented growth of the stem-like cancer cells carrying either KRAS (A549) or EGFR (H1650) mutation, while the inactive analog HDTK072 did not.

Example 8

Tube Formation Assay with Stem-Like Side Population NSCLC Cells

The angiogenic tubule assay was performed with the sorted side population cells to analyze vascular mimicry. The H1650 side population cells were sorted as mentioned above and they were further grown on Matrigel (BD Biosciences) to form angiogenic tubule-like structures. 100 µl of thawed Matrigel was layered on the wells of 96-well tissue culture plates and allowed to polymerize at 37° C. for 30 min. Sorted H1650 SP cells were layered (12000 cells/100 µl of Matrigel) on the polymerized matrigel and incubated overnight at 37° C. Tubule formation was assessed under bright field using EVOS FL microscope system and images were acquired with EVOS software (Life Technologies Inc., USA). For the treatment with HDAC11 inhibitors, appropriate concentrations of the compounds were added to the cells when they were seeded on Matrigel for the tubule formation assay.

Figure 9:
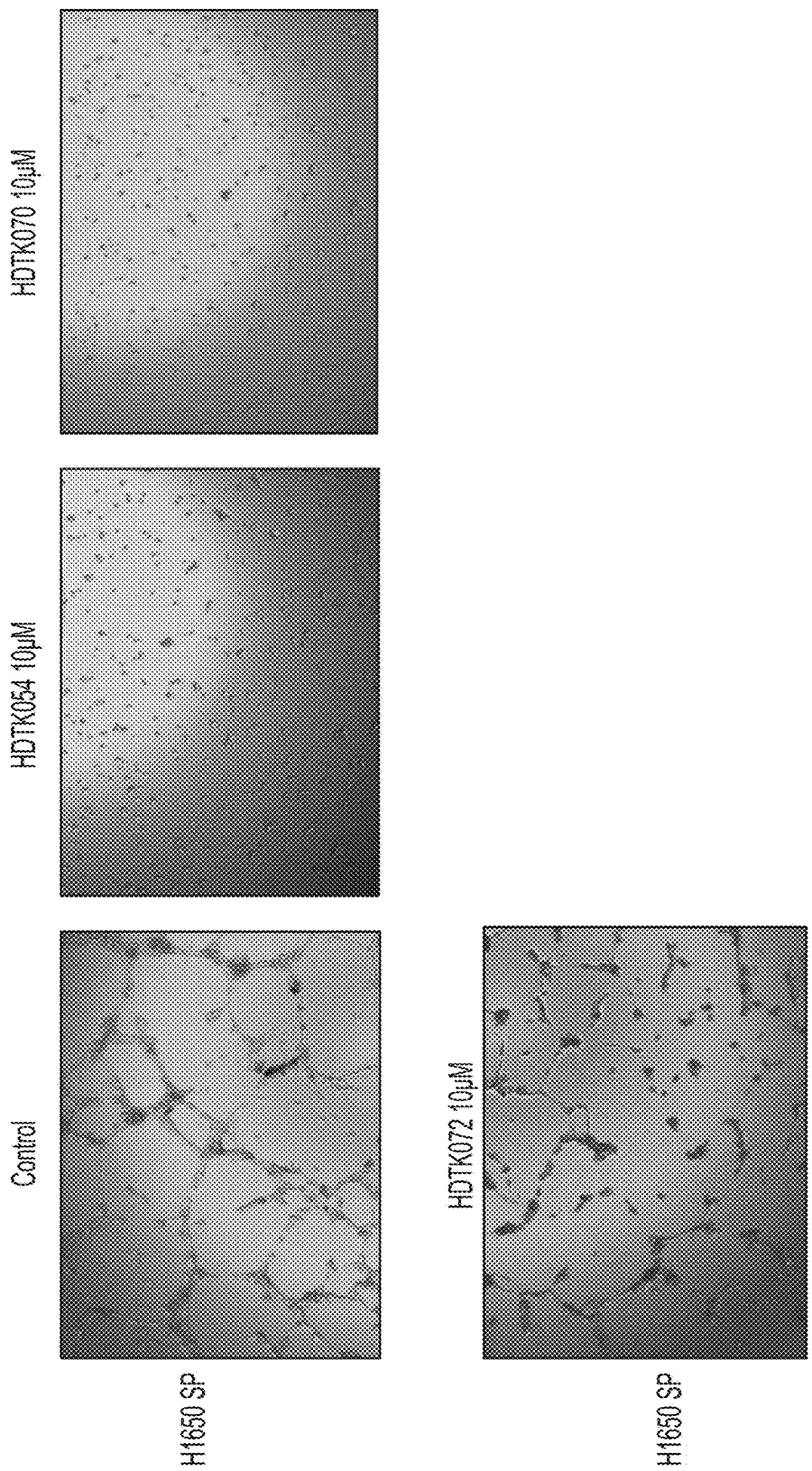
FIG. 9 shows inhibition of tubule formation in H1650 SP cells by HDAC11 inhibitors.

The exemplary selective HDAC11 inhibitors HDTK054 and HDTK070 inhibited tubule formation by the H1650 SP cells, while the inactive analog HDTK072 did not (FIG. 9).

Example 9

Cell Migration Assay

The effects of HDAC11 inhibition on cell migration were determined using a scratch assay. A549 cells (120,000-150,000 cells/2 ml/well) were grown in 6-well tissue culture plates (BD Biosciences). A scratch was made using a sterile 2 µl pipette tip in each well. The 10% FBS containing medium was added to the wells after a wash with DPBS. To assess the effect of the HDAC11 inhibitors on cell migration, the inhibitors were added in the medium at appropriate concentrations. The cells were further incubated at 37° C. The images were taken on Day 0 and after every 24 hours using EVOS FL microscope system and EVOS software (Life Technologies Inc) and the cell migration was compared to the Day 0 of treatment.

Figure 10:
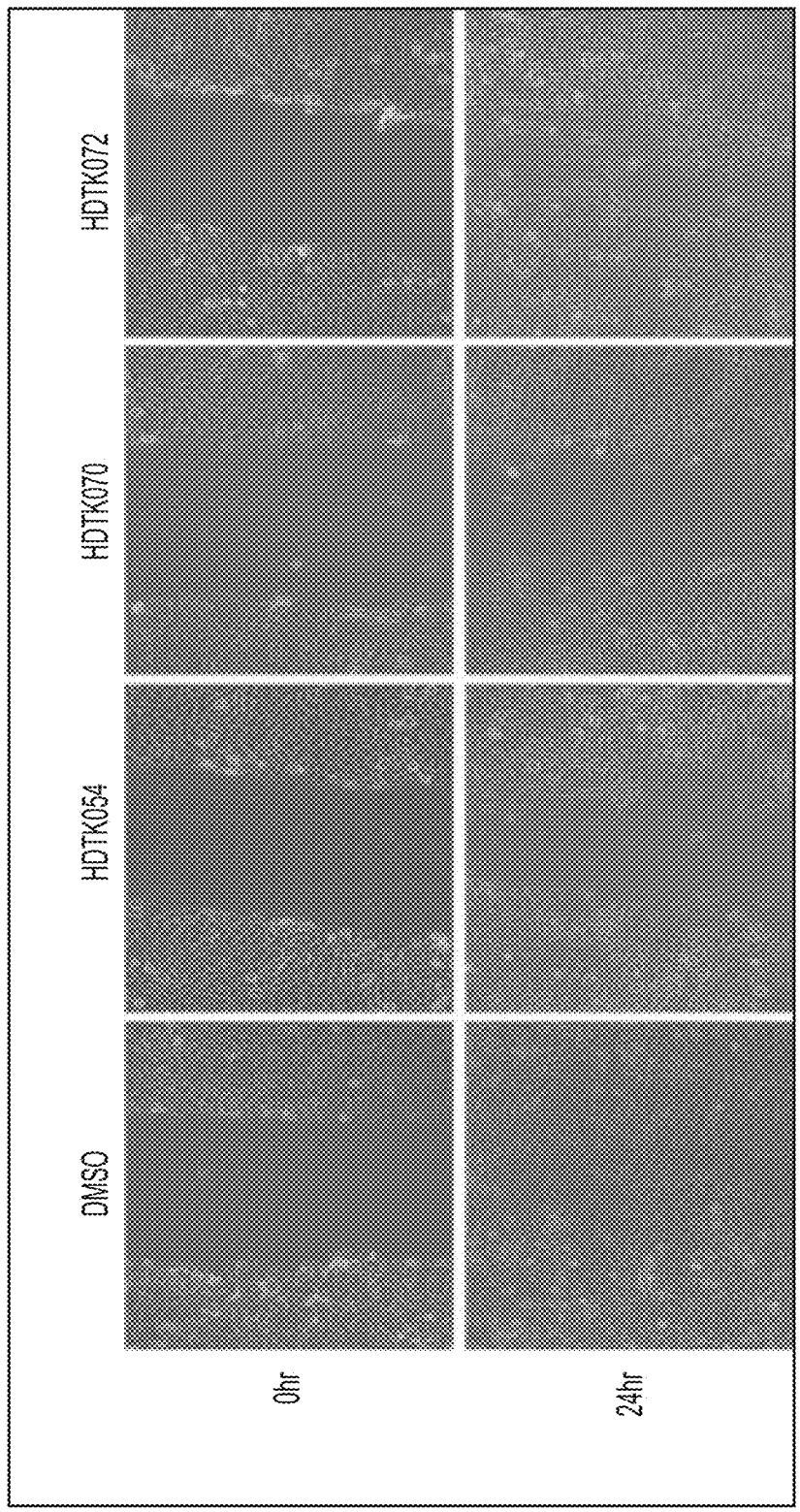
FIG. 10 shows that HDAC11 inhibitors impaired A549 cell migration.

The exemplary selective HDAC11 inhibitors HDTK054 and HDTK070 impaired A549 cell migration, while the effects of the inactive analog HTK072 were similar to the control (FIG. 10).

Example 10

QRT-PCR Assay for Stem Cell Transcription Factors

Given the effects of HDAC11 inhibition on stem-like side population cells, the effects on the expression of stem cell transcription factors was determined using QRT-PCR. A549 or H1650 cells were plated in 60 mm cell culture dishes (120,000 cells). The next day, HDAC11 inhibitors were added at various concentrations and incubated for 72 hours. For the siRNA experiments, A549 cells were plated in 60 mm cell culture dishes (120,000 cells per dish). The siRNAs (Santa Cruz Biotechnologies sc-106896 or ThermoFisher Scientific Cat#4392420) were transfected at a concentration of 100 and 150 pmoles into cells using Oligofectamine reagent (Invitrogen) as per manufacturer's protocol. A non-targeting siRNA (Ambion AM4635) was used as a control for all the transfection experiments. The cells were harvested after 72 hours post transfection. At the end of the treatments, cells were scraped, lysed and total RNA was isolated by RNeasy miniprep kit from Qiagen following the manufacturer's protocol (RNeasy mini kit Cat No. 74104). 1 µg of RNA was converted into cDNA using iScript cDNA synthesis kit (BioRad) in a 20 µl total reaction volume. Levels of mRNA were further analyzed using quantitative real time-PCR (qRT-PCR) that was performed in CFX96 Real time system using BioRad iQ SYBR Green supermix. The reaction was set with 5 µl of SYBR Green, 1 µl of 1 µM Forward primer, 1 µl of 1 µM Reverse primer, 0.5 µl of cDNA and 4.5 µl of water in a total 12 µl reaction. Data was normalized using GAPDH as an internal control and fold change was calculated by $2^{-Delta\text{-}Delta}Ct$ method. First the Delta-Ct was calculated (Delta-Ct=Ct Gene−Ct GAPDH). Next Delta-Delta-Ct was calculated (Delta-Delta-Ct=Delta-Ct treatment−Delta-Ct control). Finally fold change was calculated by $2^{-Delta\text{-}Delta}Ct$.

The primers used for amplification were as follows:

```
YAP1 FP
                                          (SEQ ID NO: 1)
5'-CCCAAGACGGCCAACGTGCC-3',

YAP1 RP
                                          (SEQ ID NO: 2)
5'-ACTGGCCTGTCGGGAGTGGG-3', Annealing Tm-58° C.

Sox2 FP
                                          (SEQ ID NO: 3)
5'-GGGAAATGGGAGGGGTGCAAAAGA-3',

Sox2 RP
                                          (SEQ ID NO: 4)
5'-TTGCGTGAGTGTGGATGGGATTGG-3', Annealing Tm-55°
C.

Oct4 FP
                                          (SEQ ID NO: 5)
5'-ACATCAAAGCTCTGCAGAAAGAACT-3',

Oct4 RP
                                          (SEQ ID NO: 6)
5'-CTG AAT ACC TTC CCAAAT AGA ACC C-3', Annealing
Tm-52° C.

Nanog FP
                                          (SEQ ID NO: 7)
5'-AGAAGGCCTCAGCACCTA-3', Nanog RP
                                          (SEQ ID NO: 8)
5'-GGCCTGATTGTTCCAGGATT-3', Annealing Tm-52° C.

GAPDH FP
                                          (SEQ ID NO: 9)
5'-GGTGGTCTCCTCTGACTTCAACA-3',

GAPDH RP
                                          (SEQ ID NO: 10)
5'-GTTGCTGTAGCCAAATTCGTTGT-3' Annealing Tm-52-60°
C.

Gli1 FP
                                          (SEQ ID NO: 11)
5'-CCCAATCACAAGTCAGGTTCCT-3',

Gli1 RP
                                          (SEQ ID NO: 12)
5'-CCTATGTGAAGCCCTATTTGCC-3' Annealing Tm-57° C.
```

Figure 11:
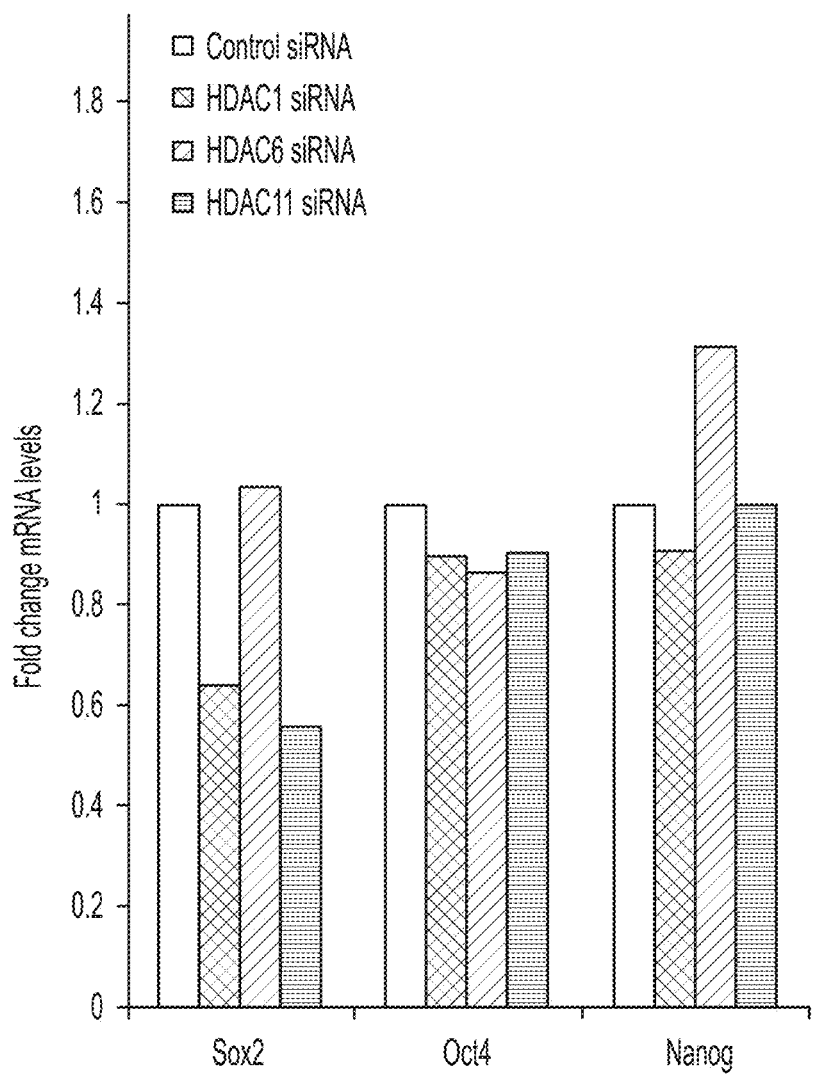
FIG. 11 shows that HDAC11 and HDAC1 knockdown resulted in decreased expression of SOX2. For each gene (Sox2, Oct4 and Nanog) fold change in mRNA levels was measured after knockdown with siRNAs: control—leftmost column, HDAC1 siRNA—second column from left, HDAC6 siRNA—second column from right, HDAC11 siRNA—rightmost column.

HDAC11 and HDAC1 knockdown in A549 cells resulted in decreased expression of Sox2. The expression of two other stem cell transcription factors, Oct4 and Nanog, was unchanged with HDAC1, HDAC6, or HDAC11 knockdown (FIG. 11).

Treatment with exemplary selective HDAC11 inhibitors HDTK010, HDTK028, HDTK054, or HDTK070 also resulted in decreased expression of Sox2 in A549 and H1650 cells. In addition, decreased expression of Gli1 and Yap1 was also observed (FIG. 12).

Example 11

Co-Culture Assay with Cancer Cells and Cancer Associated Fibroblasts

The effects of selective HDAC11 inhibition on cancer cells and cancer associated fibroblasts (CAFs) were determined in a co-culture assay. The cells were first trypsinized and collected in serum containing medium and were further incubated in same media at 37° C. for 15-20 min for recovery. The cells were resuspended in serum free media at 1×106 cells/ml density and stained with 10 uM of cytotracker green (Cancer associated fibroblasts) or cytotracker red dye (H1650 cells) (Life Technologies Inc) at 37° C. for 90 min. The stained cells were washed twice with serum free medium to remove excess dye at 1500 rpm for 5 min. The cytotracker green stained CAFs were mixed with cytotracker red stained H1650 cells in 1:1 ratio and grown in 96-well tissue culture plate overnight. The HDAC11 inhibitors were then added to the mixed adhered cells (CAFs+H1650) at appropriate concentrations. The images were taken on Day 0 and after every 24 hours using EVOS FL microscope system and EVOS software (Life Technologies Inc).

Figure 13:
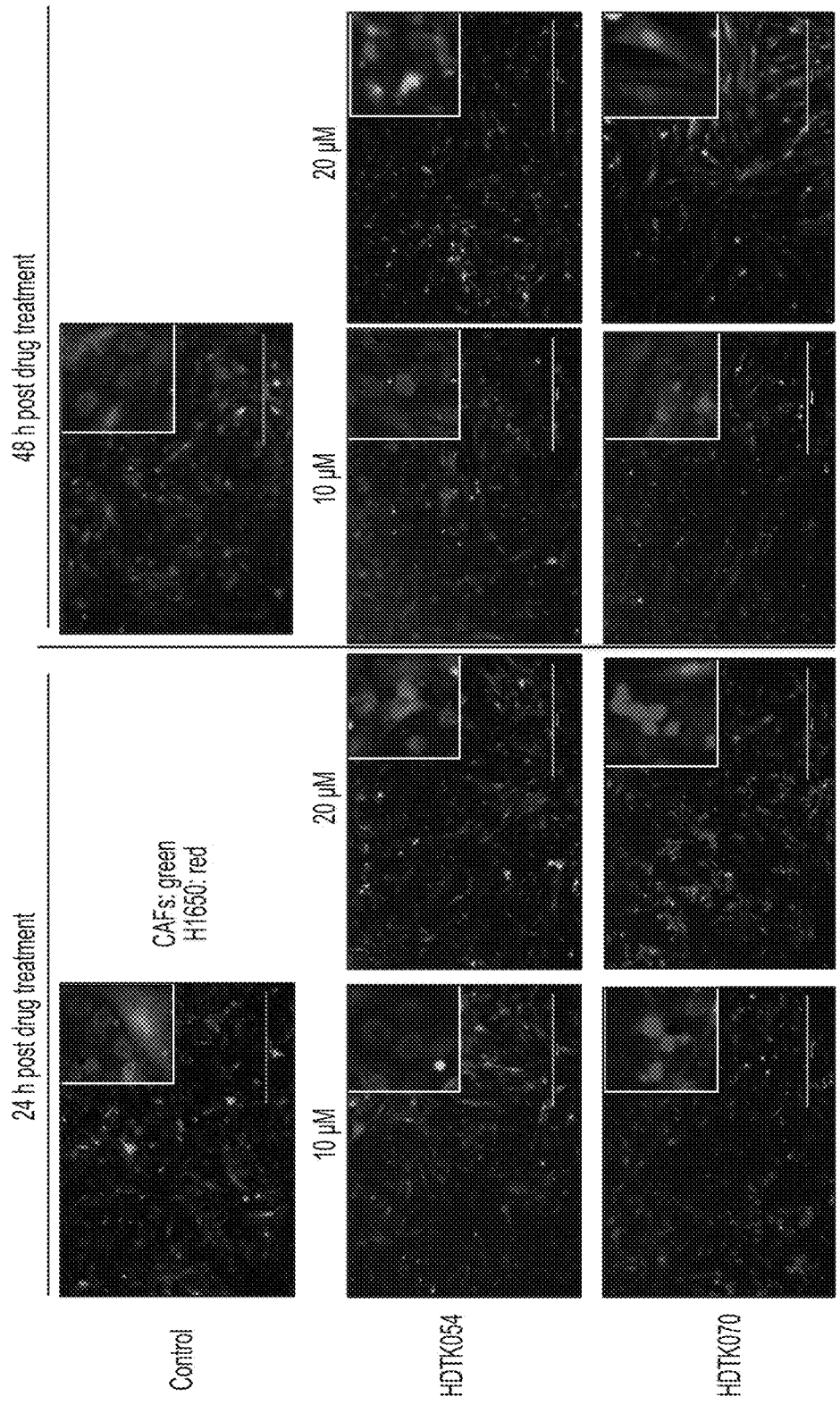
FIG. 13 shows that HDAC11 inhibitor compounds inhibited growth of H1650 cell lines co-cultured with cancer associated fibroblasts.

As shown in FIG. 13, the exemplary selective HDAC11 compounds HDTK054 and HDTK070 inhibit the growth of H1650 cells co-cultured with primary CAFs from human lung cancer with minimal effects on CAFs.

Example 12

Cell Proliferation Assays with Combination Treatment

Selective HDAC11 inhibitors may be useful in combination with other targeted agents, including Jak2 inhibitors and Smoothened inhibitors. The effect of combination with the Smoothened inhibitors GDC-0449 (Vismodegib) and BMS-833923 was tested in lung cancer cell lines. A549 and NCI-H2170 cells were obtained from the ATCC. H2170 is a squamous carcinoma cell line. Cell viability was assessed using MTT reagent (Thiazolyl Blue Tetrazolium Bromide) (Sigma-Aldrich). The cells were grown in 96-well plates at a density of 3000-5000 cells/well in triplicates. The HDAC11 inhibitors were added to the adherent cells at different concentrations and treatment was carried out for 96 hours. After treatments, the cells were incubated with the 1 mg/mL MTT reagent at 37° C. for 1 hour. The reaction was terminated with DMSO that solubilizes the formazan product formed. Absorbance at 590 nm was recorded in a plate reader.

Figure 14:
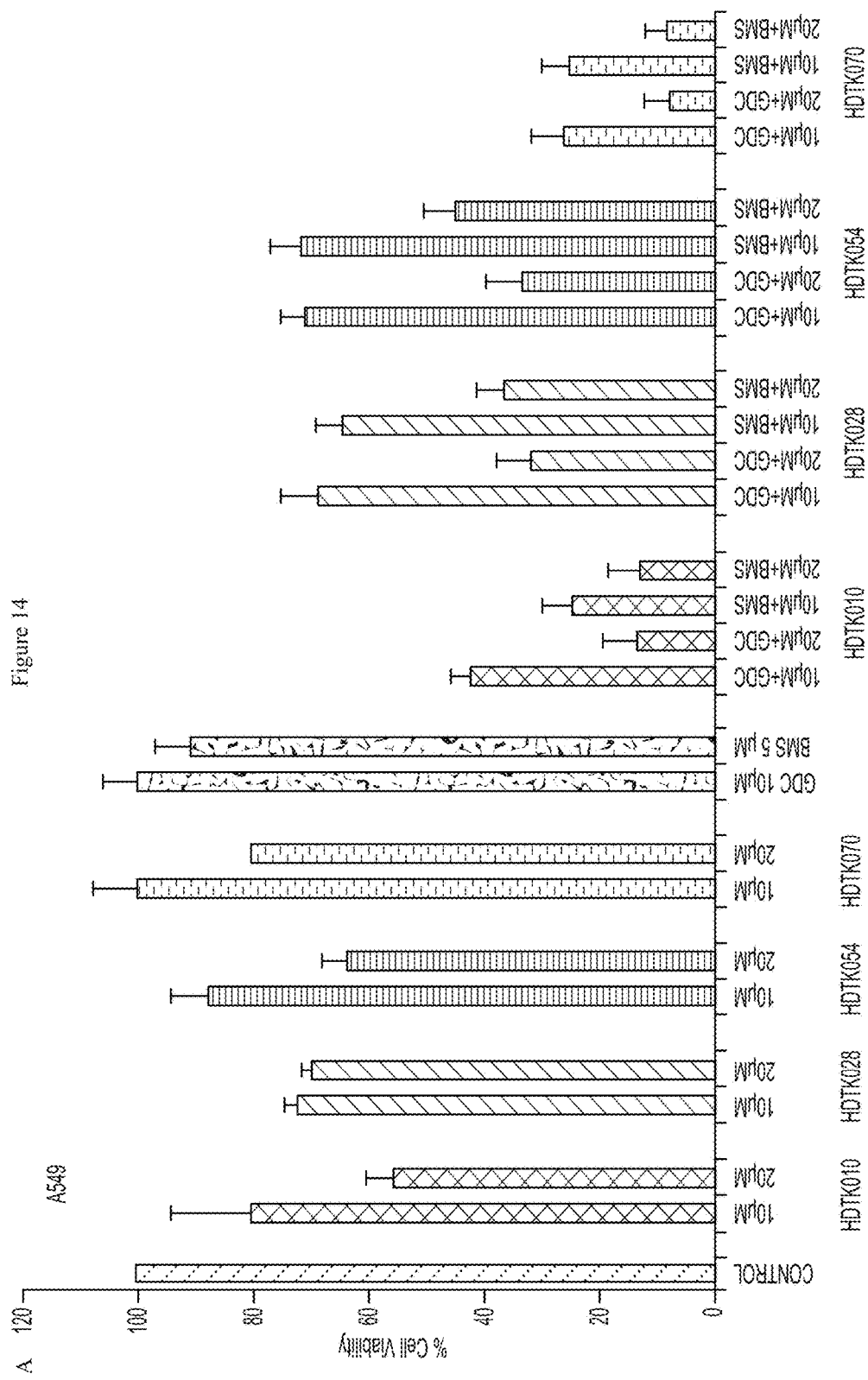
FIG. 14 shows that a combination of HDAC11 inhibitors and Smoothened inhibitors inhibited growth of (A) A549 and (B) H2170 cells.
Figure 14:
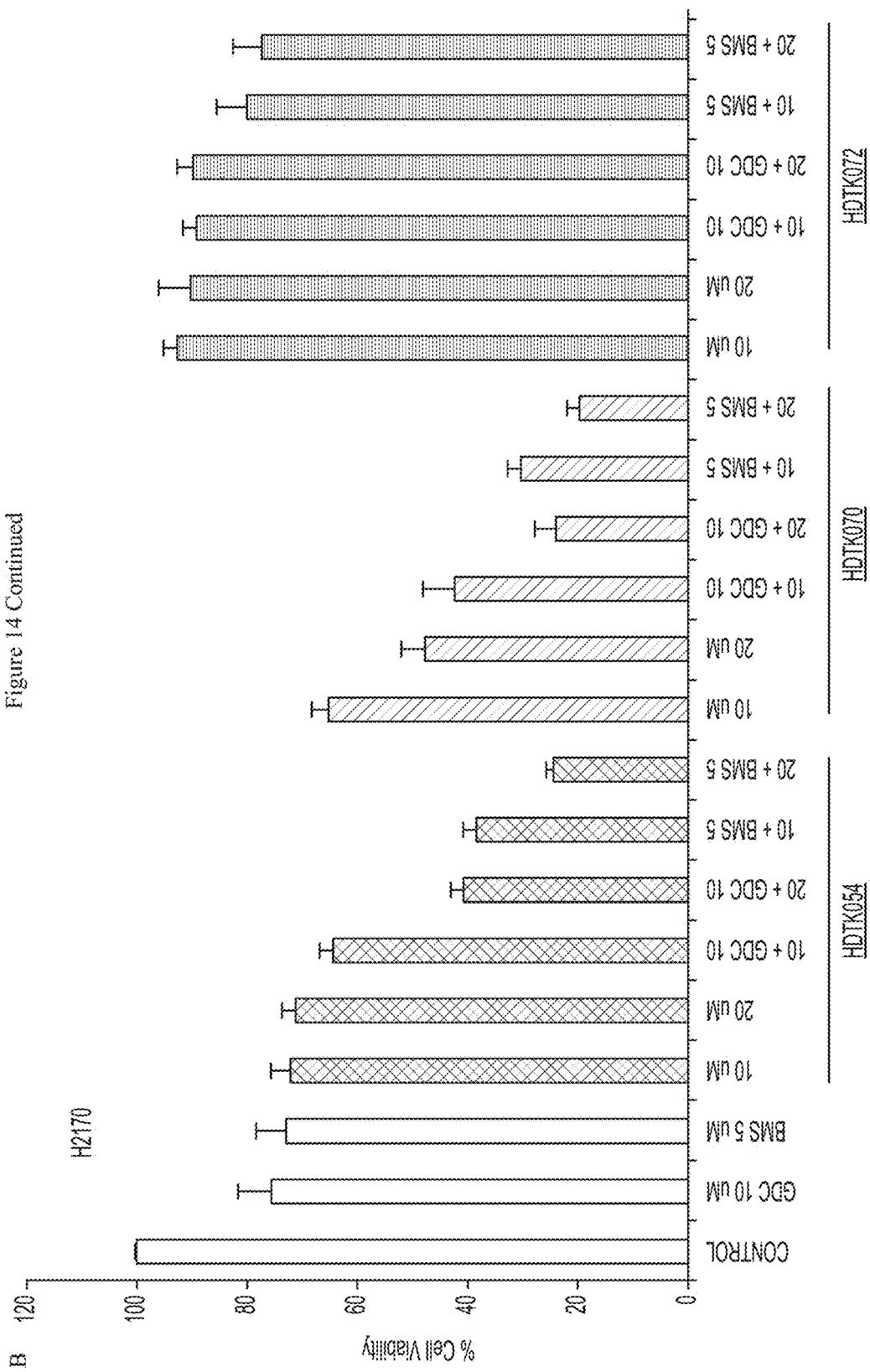

Single agent treatment with the Smoothened inhibitors or exemplary selective HDAC11 inhibitors had minimal effects on cell growth. However, the combination of exemplary selective HDAC11 inhibitors HDTK010, HDTK028, HDTK054 or HDTK070 with the Smoothened inhibitors resulted in decreased cell viability (FIG. 14)

Synthesis of Aminobenzimidazoles and Related Compounds

Example 1-1. 3-(5,6-dichlorobenzo[d]oxazol-2-ylamino)-N-hydroxybenzamide

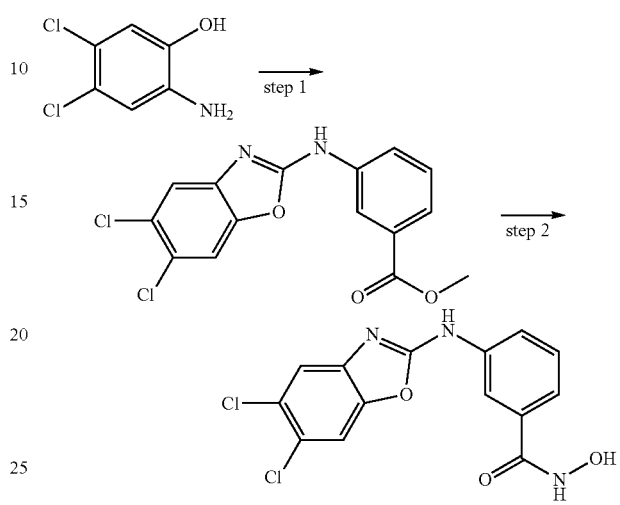

Step 1. Methyl 3-(5,6-dichlorobenzo[d]oxazol-2-ylamino)benzoate

A solution of 2-amino-4,5-dichlorophenol (209 mg, 1.17 mmol) and methyl 3-isothiocyanatobenzoate (226 mg, 1.17 mmol) in THF (17.5 mL) stirred for 3 h at room temperature. Copper (II) sulfate (1.68 g, 11.5 mmol), triethyl amine (0.16 mL, 1.17 mmol), and silica gel (1.68 g) were added, and the resulting mixture stirred overnight at room temperature. The mixture was filtered, and the filtrate was concentrated. The residue was purified vis column chromatography on silica gel (eluting with 10:1, dichloromethane/methanol) to afford methyl 3-(5,6-dichlorobenzo[d]oxazol-2-ylamino)benzoate (100 mg, 25%) as a white solid. MS: (ESI, m/z): 337[M+H]$^+$.

Step 2. 3-(5,6-dichlorobenzo[d]oxazol-2-ylamino)-N-hydroxybenzamide

Hydroxyl amine solution (50% in water, 0.55 mL, 8.9 mmol) and 1 M aqueous sodium hydroxide solution (0.60 mL, 0.60 mmol) were added to a 0° C. solution of methyl 3-(5,6-dichlorobenzo[d]oxazol-2-ylamino)benzoate (100 mg, 0.30 mmol) in THF/MeOH (4:1, 5 mL), and the resulting solution stirred for 2 h at room temperature. The solution was cooled to 0° C., and pH of the mixture was adjusted to 6 with 6 M aqueous HCl solution. The crude product was purified by Prep-HPLC with the following conditions: Column,)(Bridge Prep C18, 5 um, 19×150 mm; Mobile phase A: water with 0.05% TFA; Mobile phase B: ACN; Gradient: 5%-95% B in 2 min; Detector, 254 nm. The collected fraction was lyophilized to give 3-(5,6-dichlorobenzo[d]oxazol-2-ylamino)-N-hydroxybenzamide (3.6 mg, 3%) as an off-white solid. $^1$H-NMR (DMSO, 300 MHz), δ (ppm): 11.22 (s, 1H), 11.05 (s, 1H), 9.06 (s, 1H), 8.08 (s, 1H), 7.95-7.89 (m, 2H), 7.77 (s, 1H), 7.49-7.38 (m, 2H). MS: (ESI, m/z): 338[M+H]$^+$.

Example 2-1. 3-(6-cyano-5-(trifluoromethyl)benzo[d]oxazol-2-ylamino)-N-hydroxybenzamide

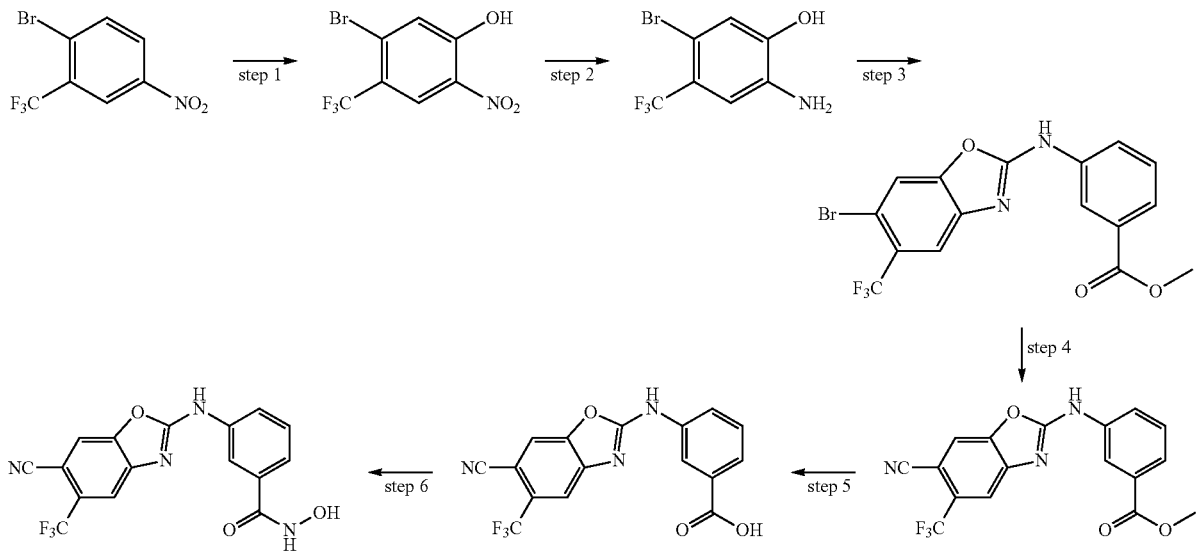

Step 1. 5-bromo-2-nitro-4-(trifluoromethyl)phenol

Potassium tert-butoxide (1.68 g, 14.97 mmol) was added in portions to a −60° C. solution of liquid ammonia (20 mL). A solution of tert-butyl hydroperoxide (590 mg, 6.55 mmol) and 1-bromo-4-nitro-2-(trifluoromethyl)benzene (1.61 g, 5.96 mmol) in tetrahydrofuran (6 mL) was added, and the resulting solution was stirred for 30 min at −30° C. The reaction was then quenched by the addition of 50 mL of saturated aqueous ammonium chloride, and the resulting mixture was extracted with 3×50 mL of ethyl acetate. The combined organic layers were concentrated under vacuum. The crude product was purified by recrystallization from petroleum ether/ethyl acetate (10:1) to give 5-bromo-2-nitro-4-(trifluoromethyl)phenol (1.5 g, 88%) as a yellow solid. MS: (ESI, m/z): 284[M−H]−.

Step 2. 2-amino-5-bromo-4-(trifluoromethyl)phenol

Hydrogen gas was introduced into a mixture of 5-bromo-2-nitro-4-(trifluoromethyl)phenol (500 mg, 1.75 mmol) and Raney nickel (50 mg) in methanol (10 mL), and the reaction mixture stirred for 2 h at room temperature. The solids were filtered out, and the filtrate was concentrated under vacuum to give 2-amino-5-bromo-4-(trifluoromethyl)phenol (430 mg, 96%) as a black solid. MS: (ESI, m/z): 256[M+H]+.

Step 3. Methyl 3-(6-bromo-5-(trifluoromethyl)benzo[d]oxazol-2-ylamino)benzoate A mixture of 2-amino-5-bromo-4-(trifluoromethyl)phenol (330 mg, 1.29 mmol), methyl 3-isothiocyanatobenzoate (300 mg, 1.55 mmol), triethylamine (0.22 mL, 1.59 mmol), copper (II) sulfate (2.2 g), and silica gel (2.8 g) in tetrahydrofuran (30 mL) stirred for 3 h at 50° C. The reaction mixture was filtered, and the filtrate was concentrated under vacuum. The residue was purified via column chromatography on silica gel (eluting with 50% ethyl acetate/petroleum ether) to afford methyl 3-(6-bromo-5-(trifluoromethyl) benzo[d]oxazol-2-ylamino)benzoate (260 mg, 49%) as a yellow solid. MS: (ESI, m/z): 415[M+H]+.

Step 4. Methyl 3-(6-cyano-5-(trifluoromethyl)benzo[d]oxazol-2-ylamino)benzoate A solution of methyl 3-(6-bromo-5-(trifluoromethyl) benzo[d]oxazol-2-ylamino)benzoate (87 mg, 0.21 mmol), zinc cyanide (23 mg, 0.20 mmol), DavePhos (33 mg, 0.08 mmol), Pd$_2$(dba)$_3$ (60 mg, 0.05 mmol) in DMA (5 mL) stirred for 1 h at 90° C. in an oil bath. The resulting mixture was cooled to room temperature and then diluted 30 mL of water. The resulting solution was extracted with 3×50 mL of ethyl acetate, and the combined organic phases were washed with 100 mL of brine, dried over anhydrous sodium sulfate, filtered, and concentrated under vacuum. The residue was purified via column chromatography on silica gel (gradient elution with 20-50% ethyl acetate/petroleum ether) to give methyl 3-(6-cyano-5-(trifluoromethyl)benzo[d]oxazol-2-ylamino)benzoate (65 mg, 86%) as a light yellow solid. MS: (ESI, m/z): 362[M+H]+.

Step 5. 3-(6-cyano-5-(trifluoromethyl)benzo[d]oxazol-2-ylamino)benzoic Acid

A solution of methyl 3-(6-cyano-5-(trifluoromethyl) benzo[d]oxazol-2-ylamino)benzoate (145 mg, 0.40 mmol) 1 M aqueous lithium hydroxide solution (2 mL, 2 mmol) in tetrahydrofuran (2 mL) stirred overnight at room temperature. The pH value of the reaction mixture was adjusted to 5 with 2 M aqueous HCl solution. The resulting solution was diluted with 10 mL of water and extracted with 3×10 mL of ethyl acetate. The combined organic phases were washed with 30 mL of brine, dried over anhydrous sodium sulfate, filtered, and concentrated under vacuum. The residue was purified by reversed phase column with the following conditions: Column: C18 column, 40 g, 20-45 um, 100 A; Mobile phase: water with 0.05% TFA and ACN (20% up to 50% in 30 minutes), 254 & 220 nm. The collected fraction was concentrated under vacuum to give 3-(6-cyano-5-(trifluoromethyl)benzo[d]oxazol-2-ylamino)benzoic acid (103 mg, 74%) as a light yellow solid. MS: (ESI, m/z): 348[M+H]+.

Step 6. 3-(6-cyano-5-(trifluoromethyl)benzo[d]oxazol-2-ylamino)-N-hydroxybenzamide A solution of 3-(6-cyano-5-(trifluoromethyl)benzo[d]oxazol-2-ylamino)benzoic acid (103 mg, 0.30 mmol), NMM (149 mg, 1.48 mmol), hydroxylamine hydrochloride (22 mg, 0.33 mmol), IPCF (0.041 mL, 0.30 mmol) in DMA (3 mL) stirred for 4 h at room temperature. The crude product was purified by Prep-HPLC with the following conditions: Column: Waters HSS C18, 2.1×50 mm, 1.8 um; Mobile Phase A: water/0.05% TFA; Mobile Phase B: ACN/0.05% TFA; Flow rate: 0.7 mL/min; Gradient: 5% B to 95% B in 2.0 min, hold 0.6 min; UV 254 nm. The collected fraction was lyophilized to give 3-(6-cyano-5-(trifluoromethyl)benzo[d]oxazol-2-ylamino)-N-hydroxybenzamide (34.9 mg, 32%) as an off-white solid. $^1$H-NMR (DMSO, 400 MHz), δ (ppm): 11.44 (s, 1H), 11.24 (s, 1H), 9.07 (s, 1H), 8.45 (s, 1H), 8.09 (d, J=10.8 Hz, 2H), 7.93-7.91 (m, 1H), 7.51-7.43 (m, 2H). MS: (ESI, m/z): 363[M+H]$^+$.

Example 3-1. N-hydroxy-3-(6-phenyl-5-(trifluoromethyl)benzo[d]oxazol-2-ylamino)benzamide

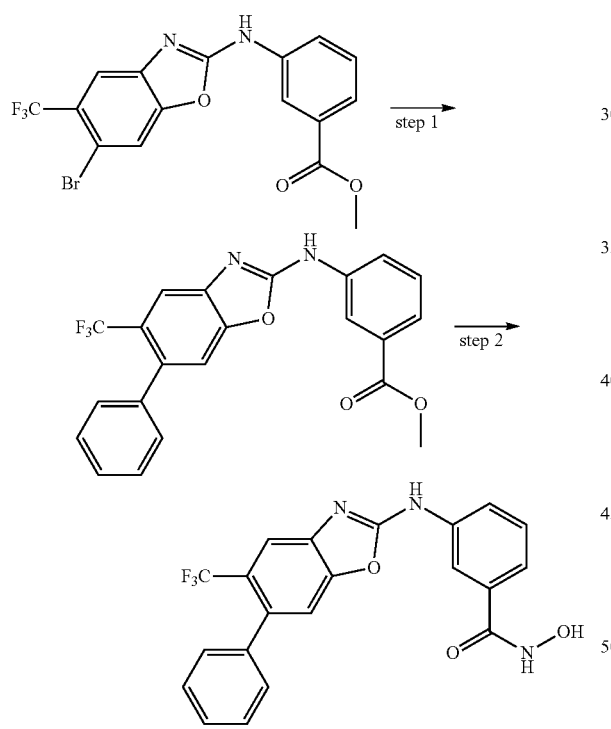

Step 1. Methyl 3-(6-phenyl-5-(trifluoromethyl)benzo[d]oxazol-2-ylamino)benzoate

A solution of methyl 3-(6-bromo-5-(trifluoromethyl)benzo[d]oxazol-2-ylamino)benzoate (80 mg, 0.19 mmol), Pd(PPh$_3$)$_4$ (45 mg, 0.04 mmol), sodium carbonate (41 mg, 0.39 mmol) and phenylboronic acid (26 mg, 0.21 mmol) in 1,4-dioxane (5 mL) stirred for 2 h at 100° C. in an oil bath. The resulting mixture was cooled to room temperature and concentrated under vacuum. The residue was purified via column chromatography on silica gel (gradient elution with 10-50% ethyl acetate/petroleum ether) to give methyl 3-(6-phenyl-5-(trifluoromethyl)benzo[d]oxazol-2-ylamino)benzoate (50 mg, 63%) as a yellow solid. MS: (ESI, m/z): 413 [M+H]$^+$.

Step 2: N-hydroxy-3-(6-phenyl-5-(trifluoromethyl)benzo[d]oxazol-2-ylamino)benzamide Hydroxyl amine solution (50% in water, 0.37 mL, 6.1 mmol) and 1 M aqueous sodium hydroxide solution (0.20 mL, 0.20 mmol) were added to a solution of methyl 3-(6-phenyl-5-(trifluoromethyl)benzo[d]oxazol-2-ylamino)benzoate (40 mg, 0.10 mmol) in THF/MeOH (4:1, 2 mL), and the resulting solution stirred overnight at room temperature. The crude product was purified by prep-HPLC with the following conditions: Column: XBridge RP C18, 19×150 mm, 5 um; Mobile Phase A: water/0.05% TFA, Mobile Phase B: ACN; Flow rate: 25 mL/min; Gradient: 5% B to 50% B in 6.0 min, 254 nm. The collected fraction was lyophilized to give N-hydroxy-3-(6-phenyl-5-(trifluoromethyl)benzo[d]oxazol-2-ylamino)benzamide (11.4 mg, 28%) as off-white solid. $^1$H-NMR (DMSO, 400 MHz), δ (ppm): 11.23 (s, 1H), 11.10 (s, 1H), 8.13 (s, 1H), 7.97-7.91 (m, 2H), 7.58 (s, 1H), 7.50-7.36 (m, 7H). MS: (ESI, m/z): 414[M+H]$^+$.

Example 4-1. 5-(5,6-dichlorobenzo[d]oxazol-2-ylamino)-2-fluoro-N-hydroxybenzamide

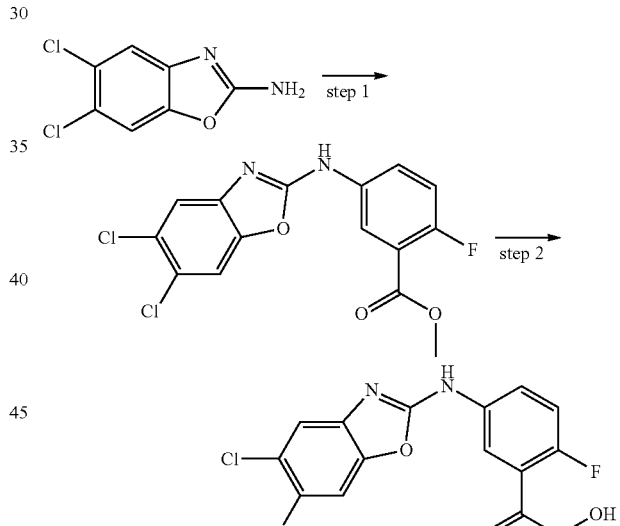

Intermediate 1. 5,6-dichlorobenzo[d]oxazol-2-amine

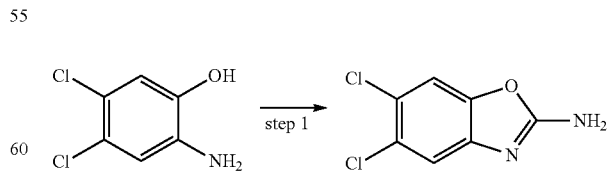

A solution of 2-amino-4,5-dichlorophenol (500 mg, 2.81 mmol), cyanogen bromide (356 mg, 3.36 mmol) in methanol (5 mL) stirred for 6 h at room temperature. The reaction was then poured into 50 mL of 2 M aqueous sodium bicarbonate solution and extracted with 3×20 mL of ethyl acetate. The combined organic phases were washed with 50 mL of brine, dried over anhydrous sodium sulfate, filtered, and concentrated under vacuum. The residue was purified vis column chromatography on silica gel (eluting with 25% ethyl acetate-petroleum ether) to afford 5,6-dichlorobenzo[d]oxazol-2-amine (340 mg, 60%) as a yellow solid. MS: (ESI, m/z): 203 [M+H]+.

Step 1. Methyl 5-(5,6-dichlorobenzo[d]oxazol-2-ylamino)-2-fluorobenzoate

A solution of t-BuBrettPhos (24 mg, 0.049 mmol) and Pd(OAc)$_2$ (5.6 mg, 0.02 mmol) in water (0.05 mL) and tert-butanol (2 mL) was added to a 10-mL sealed tube, and the system was purged and maintained with an inert atmosphere of nitrogen. The resulting solution stirred for 2 min at 110° C. and was then transferred via cannula over 1 minute to a 10-mL sealed tube charged with a solution of 5,6-dichlorobenzo[d]oxazol-2-amine (100 mg, 0.49 mmol), methyl 5-bromo-2-fluorobenzoate (138 mg, 0.59 mmol), and potassium carbonate (104 mg, 0.75 mmol) in tert-butanol (2 mL) under an inert atmosphere of nitrogen. The resulting solution stirred overnight at 110° C. The reaction mixture was cooled to room temperature and then diluted with 15 mL of water. The resulting solution was extracted with 3×15 mL of ethyl acetate, and the combined organic phases were dried over anhydrous sodium sulfate, filtered, and concentrated under vacuum. The residue was purified via column chromatography with silica gel (eluting with ethyl acetate/petroleum ether (1:10)) to give methyl 5-(5,6-dichlorobenzo[d]oxazol-2-ylamino)-2-fluorobenzoate (70 mg, 40%) as a yellow solid. MS: (ESI, m/z): 355[M+H]+.

Step 2. 5-(5,6-dichlorobenzo[d]oxazol-2-ylamino)-2-fluoro-N-hydroxybenzamide Hydroxyl amine solution (50% in water, 0.73 mL, 12 mmol) and 1 M aqueous sodium hydroxide solution (0.40 mL, 0.40 mmol) were added to a solution of methyl 5-(5,6-dichlorobenzo[d]oxazol-2-ylamino)-2-fluorobenzoate (70 mg, 0.20 mmol) in THF/MeOH (4:1, 3 mL), and the resulting solution stirred for 2 h at room temperature. The solids were filtered out, and the crude product was purified by prep-HPLC with the following conditions: Column, Xbridge RP18 5 um, 19×150 mm; mobile phase, water (0.05% TFA) and CH$_3$CN (5% CH$_3$CN up to 35% in 7 min); Detector, UV 220/254 nm. The collected fraction was lyophilized to give 5-(5,6-dichlorobenzo[d]oxazol-2-ylamino)-2-fluoro-N-hydroxybenzamide (11.7 mg, 17%) as an off-white solid. $^1$H-NMR (DMSO, 400 MHz), δ (ppm): 11.12 (s, 1H), 11.03 (s, 1H), 9.27 (s, 1H), 8.00-7.91 (m, 2H), 7.83-7.72 (m, 2H), 7.36-7.31 (m, 1H). MS: (ESI, m/z): 356[M+H]+.

The following compounds were prepared according to the procedures outlined above for 5-(5,6-dichlorobenzo[d]oxazol-2-ylamino)-2-fluoro-N-hydroxybenzamide.

| Ex. | Structure | Name | $^1$H NMR | (ESI, m/z) [M + H]+ |
|---|---|---|---|---|
| 4-2 | 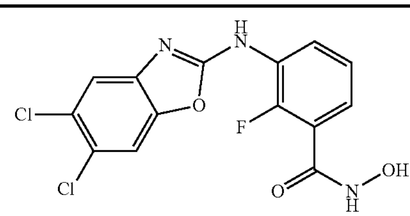 | 3-((5,6-dichlorobenzo[d]oxazol-2-yl)amino)-2-fluoro-N-hydroxybenzamide | (DMSO, 300 MHz, ppm): 11.07 (s, 1H), 10.84 (s, 1H), 9.27 (s, 1H), 8.27-8.22 (m, 1H), 7.95 (s, 1H), 7.73 (s, 1H), 7.34-7.23 (m, 2H) | 356 |
| 4-3 | 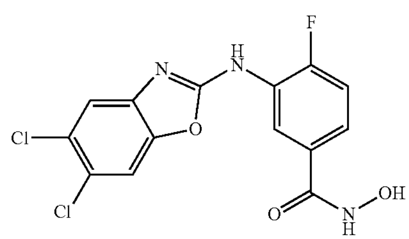 [SMILES: O=C(NO)c1ccc(F)c(Nc2nc3cc(Cl)c(Cl)cc3o2)c1] | 3-((5,6-dichlorobenzo[d]oxazol-2-yl)amino)-4-fluoro-N-hydroxybenzamide | (DMSO, 300 MHz, ppm): 11.25 (s, 1H), 10.83 (s, 1H), 9.10 (s, 1H), 8.51 (d, J = 7.5 Hz, 1H), 7.95 (s, 1H), 7.77 (s, 1H), 7.55-7.50 (m, 1H), 7.43-7.37 (m, 1H) | 356 |
| 4-4 | 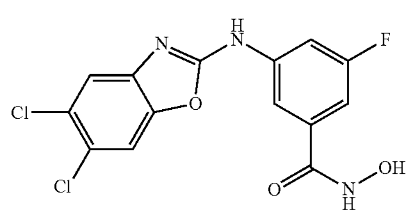 [SMILES: O=C(NO)c1cc(F)cc(Nc2nc3cc(Cl)c(Cl)cc3o2)c1] | 3-((5,6-dichlorobenzo[d]oxazol-2-yl)amino)-5-fluoro-N-hydroxybenzamide | (DMSO, 400 MHz, ppm): 11.31 (s, 1H), 9.18 (s, 1H), 8.19 (s, 1H), 8.04 (d, J = 10.8 Hz, 1H), 7.98-7.89 (m, 1H), 7.82 (s, 2H), 7.20 (d, J = 9.2 Hz, 1H). | 356 |
| 4-5 | 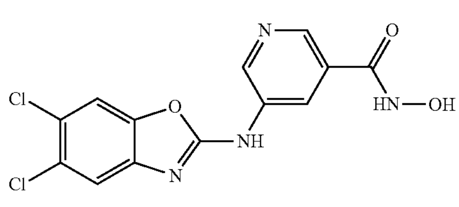 [SMILES: O=C(NO)c1cncc(Nc2nc3cc(Cl)c(Cl)cc3o2)c1] | 5-((5,6-dichlorobenzo[d]oxazol-2-yl)amino)-N-hydroxynicotinamide | (DMSO, 300 MHz, ppm): 10.96 (br, 1H), 9.23 (br, 1H), 8.93 (s, 1H), 8.54-8.51 (m, 2H), 7.94 (s, 1H), 7.78 (s, 1H) | 339 |

| Ex. | Structure | Name | ¹H NMR | (ESI, m/z) [M + H]⁺ |
|---|---|---|---|---|
| 4-6 | 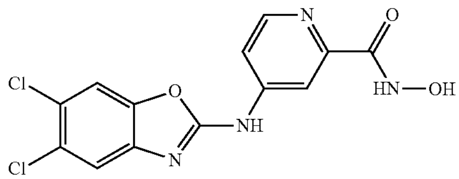 [SMILES: O=C(NO)c1cc(Nc2nc3cc(Cl)c(Cl)cc3o2)ccn1] | 4-((5,6-dichlorobenzo[d]oxazol-2-yl)amino)-N-hydroxypicolinamide | (DMSO, 400 MHz, ppm): 11.57 (br, 1H), 11.39 (br, 1H), 9.08 (s, 1H), 8.50 (d, J = 5.6 Hz, 1H), 8.27 (s, 1H), 8.03 (s, 1H), 7.88 (d, J = 3.2 Hz, 2H) | 339 |
| 4-7 | 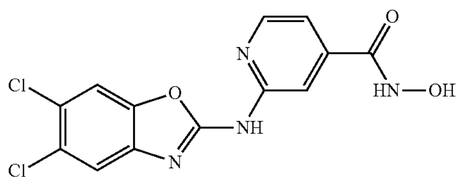 [SMILES: O=C(NO)c1ccnc(Nc2nc3cc(Cl)c(Cl)cc3o2)c1] | 2-((5,6-dichlorobenzo[d]oxazol-2-yl)amino)-N-hydroxyisonicotinamide | (DMSO, 400 MHz, ppm): 11.75 (br, 1H), 11.57 (br, 1H), 9.31 (s, 1H), 8.46-8.38 (m, 2H), 8.03 (s, 1H), 7.86 (s, 1H), 7.32 (d, J = 4.8 Hz, 1H) | 339 |
| 4-8 | 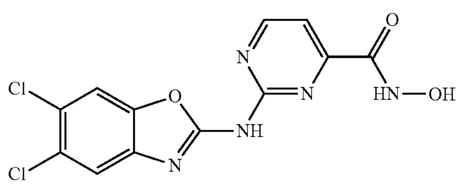 [SMILES: O=C(NO)c1ccnc(Nc2nc3cc(Cl)c(Cl)cc3o2)n1] | 2-((5,6-dichlorobenzo[d]oxazol-2-yl)amino)-N-hydroxypyrimidine-4-carboxamide | (DMSO, 400 MHz, ppm): 11.95 (br, 1H), 11.14 (br, 1H), 9.46 (s, 1H), 8.89-8.84 (m, 1H), 8.03 (s, 1H), 7.86 (s, 1H), 7.53 (d, J = 4.4 Hz, 1H) | 340 |

Example 5-1. 3-(5,6-dichlorobenzo[d]thiazol-2-ylamino)-N-hydroxybenzamide 2,2,2-trifluoroacetate

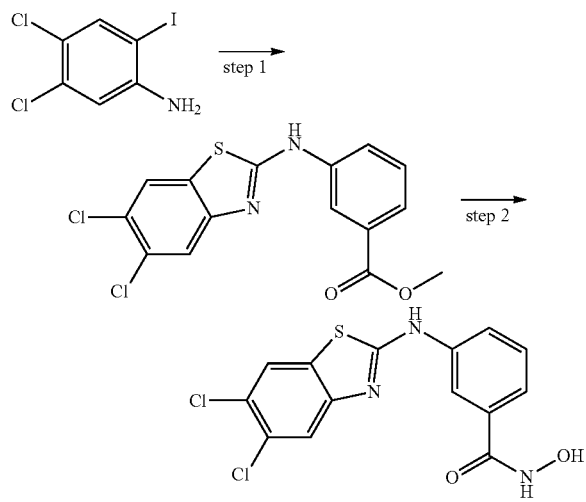

Step 1: methyl 3-(5,6-dichlorobenzo[d]thiazol-2-ylamino)benzoate

A solution of 4,5-dichloro-2-iodoaniline (288 mg, 1 mmol), methyl 3-isothiocyanatobenzoate (193 mg, 1 mmol), copper(I) bromide (14.2 mg, 0.1 mmol), and TBAB (322 mg, 1 mmol) in DMSO (7 mL) stirred overnight at 40° C. The reaction was cooled to room temperature and then poured into of 30 mL of ice/water. The resulting solution was extracted with 2×50 mL of ethyl acetate, and the combined organic phases were washed with 20 mL of brine, dried over anhydrous sodium sulfate, filtered, and concentrated under vacuum. The residue was purified via column chromatography with silica gel (eluting with ethyl acetate/petroleum ether (1:3)) to give methyl 3-(5,6-dichlorobenzo[d]thiazol-2-ylamino)benzoate (238 mg, 67%) as an off-white solid. MS: (ESI, m/z): 353[M+H]⁺.

Step 2: 3-(5,6-dichlorobenzo[d]thiazol-2-ylamino)-N-hydroxybenzamide 2,2,2-trifluoroacetate Hydroxyl amine solution (50% in water, 1.45 mL, 23.9 mmol) and 1 M aqueous sodium hydroxide solution (0.40 mL, 0.40 mmol) were added to a solution of methyl 3-(5,6-dichlorobenzo[d]thiazol-2-ylamino)benzoate (70 mg, 0.20 mmol) in THF/MeOH (4:1, 8 mL), and the resulting solution stirred for 2 h at room temperature. The solids were filtered out and the crude product was purified by Prep-HPLC with the following conditions: Column, Xbridge RP18 5 um, 19×150 mm; mobile phase, water (0.05% TFA) and CH₃CN (5% CH₃CN up to 85% in 8 min); Detector, UV 220/254 nm. The collected fraction was lyophilized to give 3-(5,6-dichlorobenzo[d]thiazol-2-ylamino)-N-hydroxybenzamide 2,2,2-trifluoroacetate (17.7 mg, 19%) as a white solid. ¹H-NMR (DMSO, 400 MHz), δ (ppm): 11.22 (s, 1H), 10.84 (s, 1H), 9.06 (s, 1H), 8.17 (s, 1H), 8.02-8.00 (m, 2H), 7.83 (s, 1H), 7.48-7.37 (m, 2H). MS: (ESI, m/z): 354[M+H]⁺.

Example 6-1. 3-(5-cyano-6-(methylsulfonyl)-1H-benzo[d]imidazol-2-ylamino)-N-hydroxybenzamide

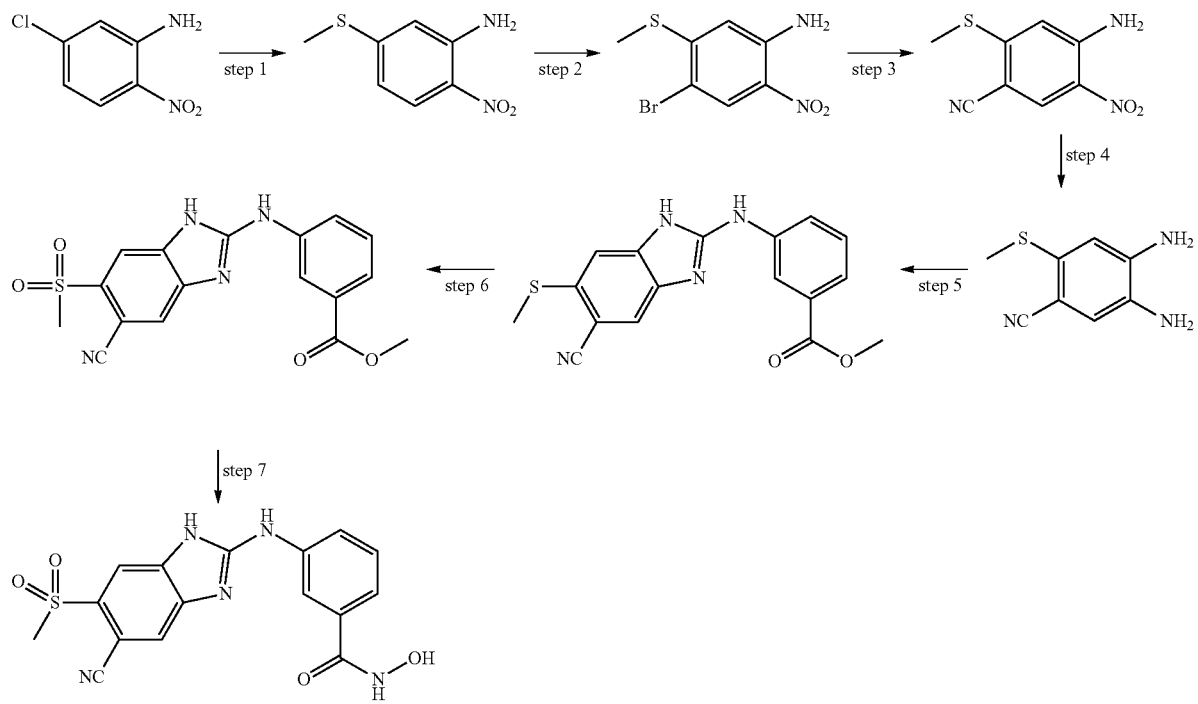

Step 1: 5-(methylthio)-2-nitrobenzenamine

A solution of 5-chloro-2-nitroaniline (15.0 g, 86.7 mmol) and sodium thiomethoxide (24.0 g, 346 mmol) in N,N-dimethylformamide (100 mL) stirred for 20 h at 65° C. in an oil bath. The reaction mixture was cooled to room temperature and diluted with 500 mL of ethyl acetate. The resulting mixture was washed with 5×400 mL of water and 500 mL of brine, dried over anhydrous sodium sulfate, filtered, and concentrated under vacuum. The residue was purified via column chromatography with silica gel (eluting with ethyl acetate/petroleum ether (1:3)) to give 5-(methylthio)-2-nitrobenzenamine (12 g, 75%) as a red solid. MS: (ESI, m/z): 185 [M+H]$^+$.

Step 2: 4-bromo-5-(methylthio)-2-nitrobenzenamine

Bromine (9.87 mL, 30.8 g, 193 mmol) was added dropwise to a solution of 5-(methylthio)-2-nitrobenzenamine (12 g, 65 mmol) in acetic acid (100 mL), and the resulting solution stirred for 12 h at room temperature. The reaction mixture was then added dropwise into 500 mL of saturated aqueous NaHSO$_3$ solution. The resulting mixture was extracted with 3×200 mL of ethyl acetate, and the combined organic phases were washed with 500 mL of brine, dried over anhydrous sodium sulfate, filtered, and concentrated under vacuum to give 4-bromo-5-(methylthio)-2-nitrobenzenamine (9.0 g, 53%) as a red solid. MS: (ESI, m/z): 263[M+H]$^+$.

Step 3: 4-amino-2-(methylthio)-5-nitrobenzonitrile

A solution of 4-bromo-5-(methylthio)-2-nitrobenzenamine (9.0 g, 34 mmol), copper(I) cyanide (7.6 g, 85.4 mmol) and copper(I) iodide (810 mg, 4.25 mmol) in DMF (80 mL) stirred for 12 h at 150° C. in an oil bath. The reaction mixture was cooled to room temperature and then poured into 1000 mL of water. The resulting mixture was extracted with 3×500 mL of ethyl acetate, and the combined organic phases were washed with 500 mL of brine, dried over anhydrous sodium sulfate, filtered, and concentrated under vacuum. The residue was purified via column chromatography with silica gel (eluting with ethyl acetate/petroleum ether (1:3)) to give 4-amino-2-(methylthio)-5-nitrobenzonitrile (3.5 g, 49%) as a yellow solid. MS: (ESI, m/z): 210[M+H]$^+$.

Step 4: 4,5-diamino-2-(methylthio)benzonitrile

A solution of 4-amino-2-(methylthio)-5-nitrobenzonitrile (3.5 g, 16.7 mmol) and tin (II) chloride dehydrate (18.8 g, 83.3 mmol) in ethyl acetate (50 mL) and ethanol (25 mL) stirred for 2 h at 75° C. in an oil bath. The resulting solution was cooled to room temperature and then diluted with 500 mL of ethyl acetate. The resulting mixture was washed with 500 mL of 2 M aqueous sodium bicarbonate solution and 500 mL of brine, dried over anhydrous sodium sulfate, filtered, and concentrated under vacuum. The residue was purified via column chromatography with silica gel (eluting with ethyl acetate/petroleum ether (1:1)) to give 4,5-diamino-2-(methylthio)benzonitrile (1.5 g, 50%) as a yellow solid. MS: (ESI, m/z): 180[M+H]$^+$.

Step 5: methyl 3-(5-cyano-6-(methylthio)-1H-benzo[d]imidazol-2-ylamino)benzoate

A solution of 4,5-diamino-2-(methylthio)benzonitrile (1.00 g, 5.58 mmol), methyl 3-isothiocyanatobenzoate (1.07 g, 5.54 mmol), EDC.HCl (3.2 g, 16.7 mmol) in THF (10 mL) stirred for 3 h at 60° C. in an oil bath. The resulting solution was cooled to room temperature and then diluted with 100 mL of water. The resulting solution was extracted with 3×50 mL of ethyl acetate, and the combined organic phases were washed with 100 mL of brine, dried over anhydrous sodium sulfate, filtered, and concentrated under vacuum. The residue was purified via column chromatography with silica gel (eluting with ethyl acetate/petroleum ether (1:1)) to give methyl 3-(5-cyano-6-(methylthio)-1H-benzo[d]imidazol-2-ylamino)benzoate (400 mg, 21%) as a red solid. MS: (ESI, m/z): 339[M+H]⁺.

Step 6: methyl 3-(5-cyano-6-(methylsulfonyl)-1H-benzo[d]imidazol-2-ylamino)benzoate MCPBA (610 mg, 3.53 mmol) was added portion wise to a solution of methyl 3-(5-cyano-6-(methylthio)-1H-benzo[d]imidazol-2-ylamino)benzoate (400 mg, 1.18 mmol) in dichloromethane (50 mL) and stirred for 12 h at room temperature. The reaction mixture was diluted with 100 mL of dichloromethane, and the resulting solution was washed with 2×100 mL of saturated aqueous NaHSO₃ solution, 2×100 mL of saturated sodium bicarbonate solution, and 100 mL of brine, dried over anhydrous sodium sulfate, filtered, and concentrated under vacuum. The residue was purified via column chromatography with silica gel (eluting with ethyl acetate/petroleum ether (7:10)) to give methyl 3-(5-cyano-6-(methylsulfonyl)-1H-benzo[d]imidazol-2-ylamino) benzoate (100 mg, 23%) as a red solid. MS: (ESI, m/z): 371 [M+H]⁺.

Step 7: 3-(5-cyano-6-(methylsulfonyl)-1H-benzo[d]imidazol-2-ylamino)-N-hydroxybenzamide Hydroxyl amine solution (50% in water, 0.50 mL, 8.1 mmol) and 1 M aqueous sodium hydroxide solution (0.54 mL, 0.54 mmol) were added to a solution of methyl 3-(5-cyano-6-(methylsulfonyl)-1H-benzo[d]imidazol-2-ylamino) benzoate (100 mg, 0.27 mmol) in THF/MeOH (4:1, 2 mL), and the resulting solution stirred for 1 h at room temperature. The crude product was purified by prep-HPLC with the following conditions: Column: XBridge RP C18, 19×150 mm, 5 um; Mobile Phase A: water/0.05% TFA; Mobile Phase B: ACN; Flow rate: 25 mL/min; Gradient: 14% B to 14% B in 13.0 min, 254 nm. The collected fraction was lyophilized to give 3-(5-cyano-6-(methylsulfonyl)-1H-benzo[d]imidazol-2-ylamino)-N-hydroxybenzamide (11.7 mg, 12%) as a brown solid. ¹H-NMR (DMSO, 300 MHz), δ (ppm): 11.22 (s, 1H), 10.35 (s, 1H), 8.05-7.99 (m, 4H), 7.47-7.35 (m, 2H), 3.35 (s, 3H). MS: (ESI, m/z): 372[M+H]⁺.

Example 7-1. N-hydroxy-3-(6-(methylsulfonyl)-5-(trifluoromethyl)-1H-benzo[d]imidazol-2-ylamino)benzamide

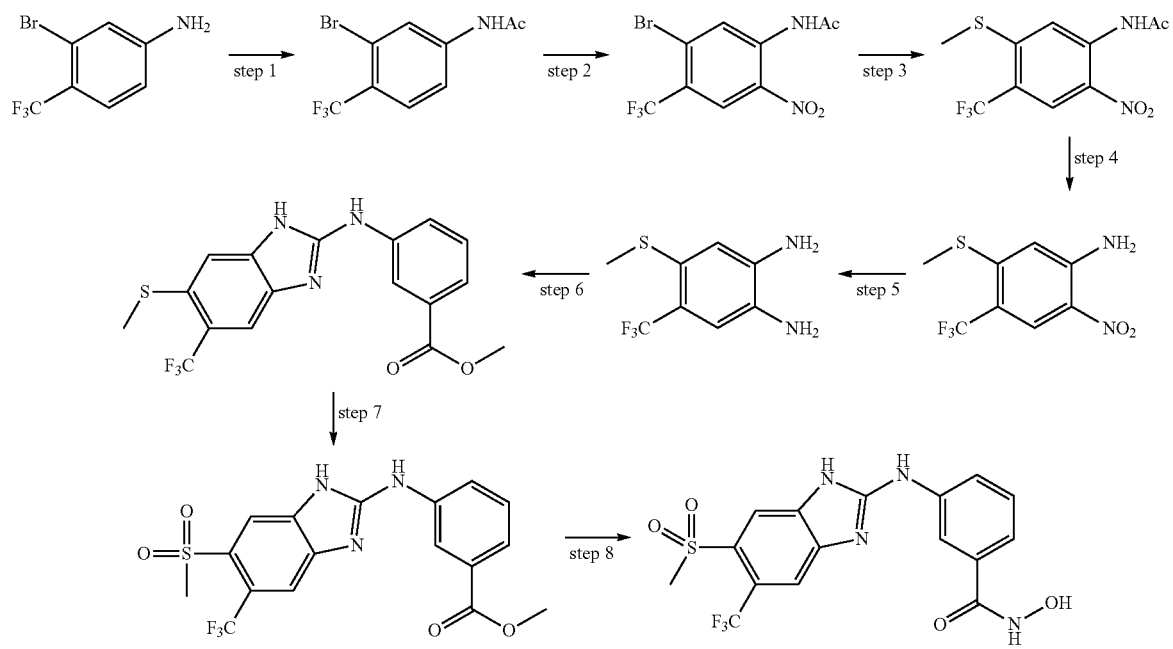

Step 1: N-(3-bromo-4-(trifluoromethyl)phenyl)acetamide

A solution of 3-bromo-4-(trifluoromethyl)aniline (10.0 g, 41.66 mmol) in acetic anhydride (50 mL) stirred for 12 h at room temperature, and was then concentrated under vacuum. The residue was recrystallized from 200 mL of hexane to give N-(3-bromo-4-(trifluoromethyl)phenyl)acetamide (10.3 g, 87%) as a white solid. MS: (ESI, m/z): 282 [M+H]⁺.

Step 2: N-(5-bromo-2-nitro-4-(trifluoromethyl)phenyl)acetamide

N-(3-Bromo-4-(trifluoromethyl)phenyl)acetamide (6.00 g, 21.3 mmol) was added portionwise to sulfuric acid (24 mL), and the mixture was cooled to 0° C. Fuming nitric acid (3.1 mL, 10.7 mmol) was added dropwise at 0° C., and the resulting solution was stirred for 2 hours at 0° C. The reaction mixture was added dropwise to 500 mL of ice/ water, and the resulting mixture was filtered. The filter cake was purified via column chromatography with silica gel (eluting with ethyl acetate/petroleum ether (1:100)) to give N-(5-bromo-2-nitro-4-(trifluoromethyl)phenyl)acetamide (5.0 g, 72%) as a light yellow solid. MS: (ESI, m/z): 325[M−H]⁻.

Step 3: N-(5-(methylthio)-2-nitro-4-(trifluoromethyl)phenyl)acetamide

A solution of N-(5-bromo-2-nitro-4-(trifluoromethyl)phenyl)acetamide (3.000 g, 9.17 mmol) and sodium thiomethoxide (2.6 g, 18.5 mmol) in N,N-dimethylformamide (150 mL) stirred for 12 h at 70° C. in an oil bath. The resulting solution was cooled to room temperature and slowly poured into 1000 mL of water. The solids were collected by filtration and dried under vacuum to give N-(5-(methylthio)-2-nitro-4-(trifluoromethyl)phenyl)acetamide (1.3 g, 48%) as a yellow solid. MS: (ESI, m/z): 293[M−H]⁻.

Step 4: 5-(methylthio)-2-nitro-4-(trifluoromethyl)benzenamine

A solution of N-(5-(methylthio)-2-nitro-4-(trifluoromethyl)phenyl)acetamide (700 mg, 2.38 mmol) in 6 M aqueous HCl solution (100 mL) stirred for 2 h at 98° C. in an oil bath. The reaction was cooled to 0° C. and the pH value of the solution was adjusted to 8-9 with 6 M aqueous sodium hydroxide solution. The resulting solution was extracted with 3×50 mL of ethyl acetate, and the combined organic phases were washed with 1×100 mL of brine, dried over anhydrous sodium sulfate, filtered, and concentrated under vacuum. The residue was purified via column chromatography with silica gel (eluting with ethyl acetate/petroleum ether (5:1)) to give 5-(methylthio)-2-nitro-4-(trifluoromethyl)benzenamine (430 mg, 72%) as a light yellow solid. MS: (ESI, m/z): 251[M−H]⁻.

Step 5: 4-(methylthio)-5-(trifluoromethyl)benzene-1,2-diamine

A mixture of 5-(methylthio)-2-nitro-4-(trifluoromethyl)benzenamine (430 mg, 1.70 mmol) and 10% palladium on carbon (50 mg) in methanol (100 mL) under an atmosphere of hydrogen gas stirred for 2 h at room temperature. The reaction mixture was filtered, and the filtrate was concentrated under vacuum to give 4-(methylthio)-5-(trifluoromethyl)benzene-1,2-diamine (330 mg, 87%) as a dark red solid. MS: (ESI, m/z): 223[M+H]⁺.

Step 6: methyl 3-(6-(methylthio)-5-(trifluoromethyl)-1H-benzo[d]imidazol-2-ylamino)benzoate A solution of 4-(methylthio)-5-(trifluoromethyl)benzene-1,2-diamine (100 mg, 0.45 mmol), and methyl 3-isothiocyanatobenzoate (86 mg, 0.45 mmol) in THF (10 mL) stirred for 4 h at 65° C. in an oil bath. EDC.HCl (260 mg, 1.35 mmol) was added, and the resulting solution stirred for an additional 1 h at 65° C. The reaction mixture was cooled to room temperature and the diluted with 30 mL of ethyl acetate. The resulting mixture was washed with 2×10 mL of brine, dried over anhydrous sodium sulfate and concentrated under vacuum. The residue was purified via column chromatography with silica gel (eluting with dichloromethane/methanol (10:1)) to give methyl 3-(6-(methylthio)-5-(trifluoromethyl)-1H-benzo[d]imidazol-2-ylamino)benzoate (90 mg, 52%) as a yellow solid. MS: (ESI, m/z): 382[M+H]⁺.

Step 7: methyl 3-(6-(methylsulfonyl)-5-(trifluoromethyl)-1H-benzo[d]imidazol-2-ylamino)benzoate A solution of methyl 3-(6-(methylthio)-5-(trifluoromethyl)-1H-benzo[d]imidazol-2-ylamino)benzoate (120 mg, 0.31 mmol) and MCPBA (162.8 mg, 0.94 mmol) in dichloromethane (10 mL) stirred for 12 h at room temperature. The reaction mixture was diluted with 20 mL of dichloromethane, and washed with 2 M aqueous sodium bisulfite solution (10 mL), 2 M aqueous sodium bicarbonate solution (10 mL), and brine (10 mL), dried over anhydrous sodium sulfate, filtered, and concentrated under vacuum to give methyl 3-(6-(methylsulfonyl)-5-(trifluoromethyl)-1H-benzo[d]imidazol-2-ylamino)benzoate (50 mg, 38%) as a white solid. MS: (ESI, m/z): 414[M+H]⁺.

Step 8: N-hydroxy-3-(6-(methylsulfonyl)-5-(trifluoromethyl)-1H-benzo[d]imidazol-2-ylamino)benzamide Hydroxyl amine solution (50% in water, 0.22 mL, 3.6 mmol) and 1 M aqueous sodium hydroxide solution (0.24 mL, 0.24 mmol) were added to a solution of methyl 3-(6-(methylsulfonyl)-5-(trifluoromethyl)-1H-benzo[d]imidazol-2-ylamino)benzoate (50 mg, 0.12 mmol) in THF/MeOH (4:1, 4 mL), and the resulting solution stirred for 1 h at room temperature. The crude product was purified by prep-HPLC with the following conditions: Column: XBridge RP C18, 19×150 mm, 5 um; Mobile Phase A: water/0.05% TFA, Mobile Phase B: ACN; Flow rate: 25 mL/min; Gradient: 5% B to 40% B in 7.0 min, 254 nm. The collected fraction was lyophilized to give N-hydroxy-3-(6-(methylsulfonyl)-5-(trifluoromethyl)-1H-benzo[d]imidazol-2-ylamino)benzamide (2.2 mg, 4%) as a brown solid. ¹H-NMR (DMSO, 300 MHz), δ (ppm): 11.24 (br, 1H), 10.43 (br, 1H), 10.22 (br, 2H), 8.16 (s, 1H), 8.07 (s, 1H), 7.99 (d, J=7.8 Hz, 1H), 7.91 (s, 1H), 7.47-7.35 (m, 2H), 3.26 (s, 3H). MS: (ESI, m/z): 415[M+H]⁺.

Example 8-1. 3-(1H-benzo[d]imidazol-2-ylamino)-N-hydroxybenzamide

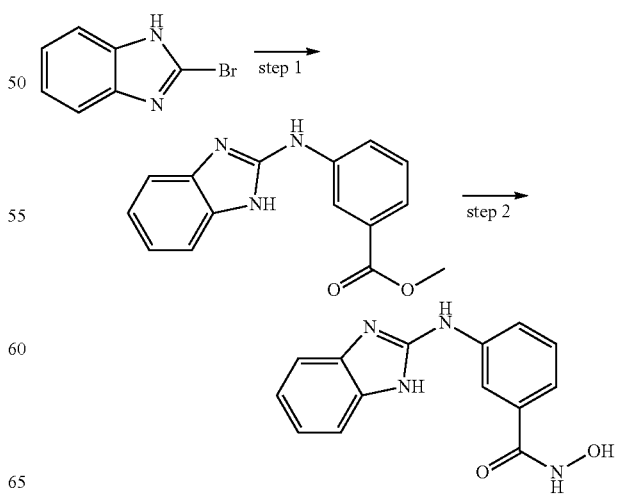

Step 1: methyl 3-(1H-benzo[d]imidazol-2-ylamino)benzoate

A solution of 2-bromo-1H-1,3-benzodiazole (50 mg, 0.25 mmol), methyl 3-aminobenzoate (115 mg, 0.76 mmol), and 6 M aqueous HCl solution (1 drop) in ethanol (3 mL) was irradiated with microwave radiation for 1 h at 120° C. The resulting mixture was cooled to room temperature and then concentrated under vacuum. The residue was purified by preparative thin layer chromatography (eluting with dichloromethane/methanol (20:1)) to afford methyl 3-(1H-benzo[d]imidazol-2-ylamino)benzoate (78 mg, crude) as a yellow solid. MS: (ESI, m/z): 268[M+H]$^+$.

Step 2: 3-(1H-benzo[d]imidazol-2-ylamino)-N-hydroxybenzamide

Hydroxyl amine solution (50% in water, 1.1 mL, 17.5 mmol) and 1 M aqueous sodium hydroxide solution (0.58 mL, 0.58 mmol) were added to a solution of methyl 3-(1H-benzo[d]imidazol-2-ylamino)benzoate (78 mg, 0.29 mmol) in THF/MeOH (4:1, 10 mL), and the resulting solution stirred for 2 h at room temperature. The solids were filtered out, the crude product was purified by prep-HPLC with the following conditions: Column: Waters HSS C18, 2.1×50 mm, 1.8 um; Mobile Phase A: water/0.05% TFA; Mobile Phase B: ACN/0.05% TFA; Flow rate: 0.7 mL/min; Gradient: 5% B to 95% B in 2.0 min, hold 0.6 min; UV 254 nm. The collected fraction was lyophilized to give 3-(1H-benzo[d]imidazol-2-ylamino)-N-hydroxybenzamide (53.2 mg, 68%) as a pink solid. $^1$H-NMR (DMSO, 300 MHz), δ (ppm): 12.95 (br, 1H), 11.28 (br, 1H), 10.94 (br, 1H), 9.13 (br, 1H), 7.87 (s, 1H), 7.69-7.53 (m, 3H), 7.44-7.40 (m, 2H), 7.27-7.24 (m, 2H). MS: (ESI, m/z): 269[M+H]$^+$.

Example 9-1. 3-((5-cyano-6-(trifluoromethyl)-1H-benzo[d]imidazol-2-yl)(methyl)amino)-N-hydroxybenzamide

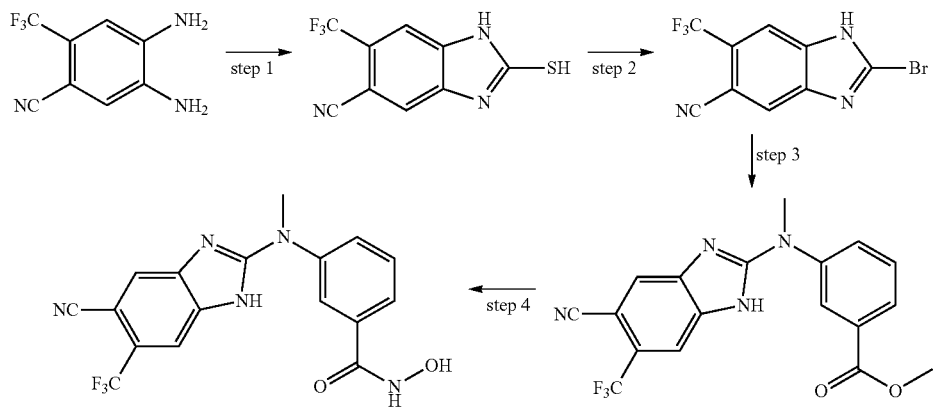

Step 1: 2-mercapto-6-(trifluoromethyl)-1H-benzo[d]imidazole-5-carbonitrile

A solution of 4,5-diamino-2-(trifluoromethyl)benzonitrile (2.00 g, 9.94 mmol), carbon disulfide (6.04 g, 79.52 mmoL) and potassium hydroxide (1.67 g, 29.8 mmol) in ethanol (100 mL) stirred for 5 h at 90° C. in an oil bath. The resulting mixture was cooled to room temperature and concentrated under vacuum. The solution was diluted with 200 mL of water, and the resulting solution was extracted with 3×200 mL of ethyl acetate. The combined organic phases were washed with 100 mL of brine, dried over anhydrous sodium sulfate, filtered, and concentrated under vacuum to give 2-mercapto-6-(trifluoromethyl)-1H-benzo[d]imidazole-5-carbonitrile (1.9 g, 79%) as a red solid. MS: (ESI, m/z): 244[M+H]$^+$.

Step 2: 2-bromo-6-(trifluoromethyl)-1H-benzo[d]imidazole-5-carbonitrile

Bromine (0.2 mL, 4.0 mmol) was added dropwise with stirring over 10 min to a 0° C. solution of 2-mercapto-6-(trifluoromethyl)-1H-benzo[d]imidazole-5-carbonitrile (267 mg, 1.10 mmol) in hydrogen bromide (40% in acetic acid, 12 mL). The resulting solution stirred for 3 h at 0° C. and was then diluted with 1 mL of water. The pH value of the solution was adjusted to 4 with 1 M aqueous sodium hydroxide solution. The resulting solution was extracted with 3×100 mL of ethyl acetate, and the combined organic phases were dried over anhydrous Na$_2$SO$_4$, filtered, and concentrated under vacuum. The residue was purified via column chromatography with silica gel (eluting with ethyl acetate/petroleum ether (3:2)) to give 2-bromo-6-(trifluoromethyl)-1H-benzo[d]imidazole-5-carbonitrile (225 mg, 71%) as a red solid. MS: (ESI, m/z): 290[M+H]$^+$.

Step 3: methyl 3-((5-cyano-6-(trifluoromethyl)-1H-benzo[d]imidazol-2-yl)(methyl)amino)benzoate A solution of 2-bromo-6-(trifluoromethyl)-1H-benzo[d]imidazole-5-carbonitrile (130 mg, 0.45 mmol), methyl 3-(methylamino)benzoate (101.9 mg, 0.62 mmol), and 12 M aqueous HCl solution (1 drop) in ethanol (3 mL) was irradiated with microwave radiation for 1 h at 150° C. The resulting mixture was concentrated under vacuum. The residue was purified via column chromatography with silica gel (eluting with ethyl acetate/petroleum ether (2:3)) to give methyl 3-((5-cyano-6-(trifluoromethyl)-1H-benzo[d]imidazol-2-yl)(methyl)amino)benzoate (160 mg, 95%) as a reddish solid. MS: (ESI, m/z): 375[M+H]$^+$.

Step 4: 3-((5-cyano-6-(trifluoromethyl)-1H-benzo[d]imidazol-2-yl)(methyl)amino)-N-hydroxybenzamide Hydroxyl amine solution (50% in water, 0.87 mL, 14.3 mmol) and 1 M aqueous sodium hydroxide solution (0.95 mL, 0.95 mmol) were added to a solution of methyl 3-((5- cyano-6-(trifluoromethyl)-1H-benzo[d]imidazol-2-yl) (methyl)amino)benzoate (178 mg, 0.48 mmol) in THF/ MeOH (4:1, 2 mL), and the resulting solution stirred for 3 h at room temperature. The crude product was purified by prep-HPLC with the following conditions: Column, XSelect CSH Prep C18 OBD Column, 19×150 mm 5 um 13 nm; mobile phase, Mobile Phase A: water/0.05% TFA, Mobile Phase B: ACN; Gradient: 15% B to 35% B in 7 min; Detector, 254 nm. The collected fraction was lyophilized to give 3-((5-cyano-6-(trifluoromethyl)-1H-benzo[d]imidazol-2-yl)(methyl)amino)-N-hydroxybenzamide (45 mg, 25%) as a white solid. $^1$H-NMR (DMSO, 400 MHz), δ (ppm): 11.29 (s, 1H), 7.86-7.84 (m, 2H), 7.73-7.66 (m, 3H), 7.60-7.56 (m, 1H), 3.57 (s, 3H). MS: (ESI, m/z): 376[M+H]$^+$.

Example 10-1. 3-(5-cyano-1-methyl-6-(trifluoromethyl)-1H-benzo[d]imidazol-2-ylamino)-N-hydroxybenzamide benzo[d]imidazole-5-carbonitrile (180 mg, 86%) as light yellow oil. MS: (ESI, m/z): 304[M+H]$^+$.

Step 2: Synthesis of methyl 3-(5-cyano-1-methyl-6-(trifluoromethyl)-1H-benzo[d]imidazol-2-ylamino) benzoate and methyl 3-(6-cyano-1-methyl-5-(trifluoromethyl)-1H-benzo[d]imidazol-2-ylamino) benzoate A 30-mL microwave tube was charged with the mixture of 2-bromo-1-methyl-6-(trifluoromethyl)-1H-benzo[d]imidazole-5-carbonitrile and 2-bromo-3-methyl-6-(trifluoromethyl)-3H-benzo[d]imidazole-5-carbonitrile (65 mg, 0.21 mmol), ethanol (10 mL), 6 M aqueous HCl solution (1 drop), and methyl 3-aminobenzoate (97 mg, 0.64 mmol). The reaction mixture was irradiated with microwave radiation for 1 h at 150° C. and then cooled to room temperature and concentrated under vacuum. The crude product was purified by Prep-HPLC with the following conditions: Column:

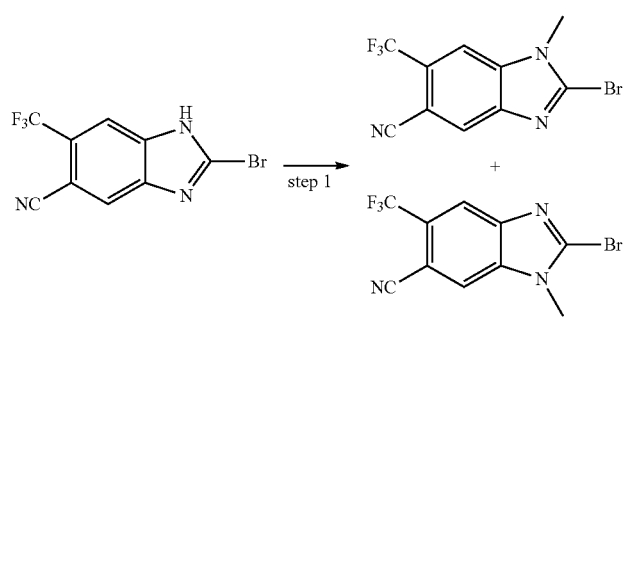
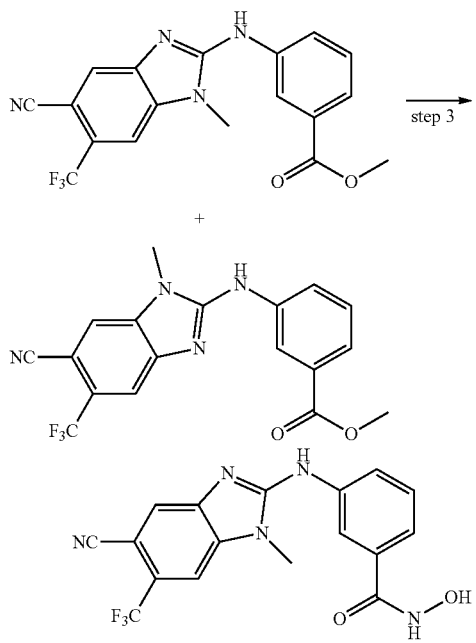

Step 1: Synthesis of 2-bromo-1-methyl-6-(trifluoromethyl)-1H-benzo[d]imidazole-5-carbonitrile and 2-bromo-3-methyl-6-(trifluoromethyl)-3H-benzo[d] imidazole-5-carbonitrile Sodium hydride (60% dispersion in mineral oil, 28 mg, 0.70 mmol) was added to a 0° C. solution of 2-bromo-6-(trifluoromethyl)-1H-benzo[d]imidazole-5-carbonitrile (200 mg, 0.69 mmol) in DMF (5 mL), and the mixture was stirred for 30 minutes. Methyl iodide (0.7 mL, 11.2 mmol) was added at 0° C., and the resulting solution stirred for additional 1 h at 0° C. The reaction was quenched by the addition of 10 mL of water, and the resulting solution was extracted with 3×10 mL of ethyl acetate. The combined organic phases were dried over anhydrous sodium sulfate, filtered, and concentrated under vacuum. The residue was purified via column chromatography with silica gel (eluting with ethyl acetate/petroleum ether (1:2)) to give a mixture of 2-bromo-1-methyl-6-(trifluoromethyl)-1H-benzo[d]imidazole-5-carbonitrile and 2-bromo-3-methyl-6-(trifluoromethyl)-3H-

Waters Sunfire C18, 19×150 mm; Mobile Phase A: water/ 0.1% FA; Mobile Phase B: ACN; Flow rate: 28 mL/min; Gradient: 20% B to 50% B in 10 min; 254 nm. The first eluting isomer was collected and concentrated under vacuum to give methyl 3-(5-cyano-1-methyl-6-(trifluoromethyl)-1H-benzo[d]imidazol-2-ylamino)benzoate (21 mg, 26%) as a white solid. MS: (ESI, m/z): 375[M+H]$^+$. The second eluting isomer was collected and concentrated under vacuum to give methyl 3-(6-cyano-1-methyl-5-(trifluoromethyl)-1H-benzo[d]imidazol-2-ylamino)benzoate (27.6 mg, 34%) as a white solid. MS: (ESI, m/z): 375[M+H]$^+$.

Step 3: 3-(5-cyano-1-methyl-6-(trifluoromethyl)-1H-benzo[d]imidazol-2-ylamino)-N-hydroxybenzamide Hydroxyl amine solution (50% in water, 0.45 mL, 7.3 mmol) and 1 M aqueous sodium hydroxide solution (0.11 mL, 0.11 mmol) were added to a 0° C. solution of methyl 3-(5-cyano-1-methyl-6-(trifluoromethyl)-1H-benzo[d]imidazol-2-ylamino)benzoate (21 mg, 0.06 mmol), in THF/MeOH (4:1, 2 mL), and the resulting solution stirred for 4 h at room temperature. The pH value of the solution was adjusted to 6 with 2 M aqueous HCl solution. The crude product was purified by Prep-HPLC with the following conditions: Column: Water HSS C18, 2.1×50 mm, 1.8 um; Mobile Phase A: water/0.05% TFA; Mobile Phase B: ACN/0.05% TFA; Flow rate: 0.7 mL/min; Gradient: 5% B to 95% B in 2.0 min, hold 0.6 min; 254 nm. The collected fraction was lyophilized to give 3-(5-cyano-1-methyl-6-(trifluoromethyl)-1H-benzo[d]imidazol-2-ylamino)-N-hydroxybenzamide (2.8 mg, 10%) as an off-white solid. $^1$H-NMR (DMSO, 400 MHz), δ (ppm): 11.23 (s, 1H), 9.58 (s, 1H), 9.07 (s, 1H), 8.18-8.02 (m, 4H), 7.47-7.38 (m, 2H), 3.87 (s, 3H). MS: (ESI, m/z): 376[M+H]$^+$.

Example 11-1. 3-(6-cyano-1-methyl-5-(trifluoromethyl)-1H-benzo[d]imidazol-2-ylamino)-N-hydroxybenzamide (45 mL) stirred for 23 h at room temperature. The resulting solution was diluted with 30 mL of water and extracted with 3×30 mL of dichloromethane. The combined organic phases were washed with water (30 mL), dried over anhydrous sodium sulfate, filtered, and concentrated under vacuum. The residue was purified via column chromatography with silica gel (eluting with ethyl acetate/petroleum ether (1:4)) to give 4-amino-5-(methylamino)-2-(trifluoromethyl)benzonitrile (750 mg, 62%) as a brown solid. MS: (ESI, m/z): 216[M+H]$^+$.

Step 3: methyl 3-(6-cyano-1-methyl-5-(trifluoromethyl)-1H-benzo[d]imidazol-2-ylamino)benzoate A solution of 4-amino-5-(methylamino)-2-(trifluoromethyl)benzonitrile (200 mg, 0.93 mmol), methyl 3-isothiocyanatobenzoate (270 mg, 1.40 mmol), and EDC.HCl (370 mg, 1.86 mmol) in tetrahydrofuran (10 mL) stirred for 5 h at 70° C. The resulting mixture was cooled to room temperature and concentrated under vacuum. The residue was

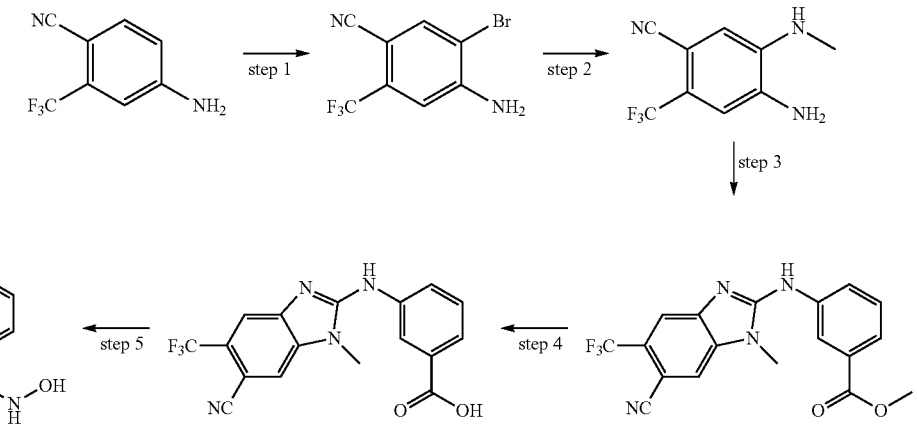

Step 1: 4-amino-5-bromo-2-(trifluoromethyl)benzonitrile

Bromine (4.73 g, 29.6 mmol) was added dropwise to a 0° C. solution of 4-amino-2-(trifluoromethyl)benzonitrile (5.0 g, 26.9 mmol) in methanol (80 mL), and the resulting solution stirred for 3 h at room temperature. The resulting mixture was quenched by the addition of 15 mL of saturated aqueous NaHSO$_3$ solution at 0° C. The methanol was removed under vacuum, and the resulting solution was extracted with 3×20 mL of dichloromethane. The combined organic phases were washed with 3×10 mL of water, dried over anhydrous sodium sulfate, filtered, and concentrated under vacuum. The residue was purified via column chromatography with silica gel (eluting with ethyl acetate/petroleum ether (1:3)) to give 4-amino-5-bromo-2-(trifluoromethyl)benzonitrile (6.5 g, 91%) as a white solid. MS: (ESI, m/z): 263 [M−H]$^-$.

Step 2: 4-amino-5-(methylamino)-2-(trifluoromethyl)benzonitrile

A solution of 4-amino-5-bromo-2-(trifluoromethyl)benzonitrile (1.5 g, 5.68 mmol), methylamine hydrochloride (3.81 g, 56.82 mmol), cesium carbonate (22.23 g, 68.18 mmol), 2,2,6,6-tetramethylheptane-3,5-dione (2.09 g, 11.36 mmol) and copper (I) iodide (1.40 g, 7.34 mmol) in DMSO dissolved in 3 mL of DMF and purified by reversed phase column with the following conditions: Column: C18 column, 40 g, 20-45 um, 100 A; Mobile Phase: water/0.05% TFA and ACN (2% up to 50% in 30 min); Flow rate: 80 mL/min; 254 nm. The collected fraction was concentrated under vacuum to give methyl 3-(6-cyano-1-methyl-5-(trifluoromethyl)-1H-benzo[d]imidazol-2-ylamino)benzoate (60 mg, 17%) as a brown solid. MS: (ESI, m/z): 375[M+H]$^+$.

Step 4: 3-(6-cyano-1-methyl-5-(trifluoromethyl)-1H-benzo[d]imidazol-2-ylamino)benzoic Acid A solution of methyl 3-(6-cyano-1-methyl-5-(trifluoromethyl)-1H-benzo[d]imidazol-2-ylamino)benzoate (100 mg, 0.27 mmol) and lithium hydroxide monohydrate (56 mg, 1.33 mmol) in water (5 mL) and THF (5 mL) stirred for 10 h at room temperature. The resulting mixture was diluted with 10 mL of water and extracted with 10 mL of ethyl acetate. The aqueous layer was separated and the pH value of the solution was adjusted to 5 with 4 M aqueous HCl solution. The resulting solution was extracted with 2×20 mL of dichloromethane, and the combined organic phases were washed with 30 mL of brine, dried over anhydrous sodium sulfate, filtered, and concentrated under vacuum to give 3-(6-cyano-1-methyl-5-(trifluoromethyl)-1H-benzo[d]imidazol-2-ylamino)benzoic acid (90 mg, 94%) as a yellow solid. MS: (ESI, m/z): 361[M+H]$^+$.

Step 5: 3-(6-cyano-1-methyl-5-(trifluoromethyl)-1H-benzo[d]imidazol-2-ylamino)-N-hydroxybenzamide A solution of 3-(6-cyano-1-methyl-5-(trifluoromethyl)-1H-benzo[d]imidazol-2-ylamino)benzoic acid (200 mg, 0.56 mmol), IPCF (0.31 g, 2.78 mmol), NMM (250 mg, 2.47 mmol), and hydroxylamine hydrochloride (0.11 g, 1.59 mmol) in DMA (2 mL) stirred for 10 h at room temperature. The crude product was purified by Prep-HPLC with the following conditions: Column Waters RP 18, 19×150 mm, 5 um; mobile phase, water (0.1% FA)/CH$_3$CN; Solvent B increase from 20 to 41% in 10 min; Detector 220 & 254 nm. The collected fraction was lyophilized to give 3-(6-cyano-1-methyl-5-(trifluoromethyl)-1H-benzo[d]imidazol-2-ylamino)-N-hydroxybenzamide (17 mg, 7%) as a light brown solid. $^1$H-NMR (DMSO, 400 MHz), δ (ppm): 11.22 (br, 1H), 9.71 (br, 1H), 8.24-8.15 (m, 3H), 7.91 (d, J=5.6 Hz, 1H), 7.46-7.38 (m, 2H), 3.83 (s, 3H). MS: (ESI, m/z): 376[M+H]$^+$.

Example 12-1. 3-(6-cyano-5-fluoro-1-methyl-1H-benzo[d]imidazol-2-ylamino)-N-hydroxybenzamide 5-nitrobenzonitrile (4.4 g, 23.95 mmol) in THF (30 mL), and the solution stirred for 30 min at room temperature. Di-tert-butyl dicarbonate (6.36 g, 29.1 mmol) was added, and the solution stirred overnight at room temperature. The reaction was quenched by the addition of 20 mL of water, and the resulting solution was extracted with 3×20 mL of ethyl acetate. The combined organic phases were washed with 3×20 mL of brine, dried over anhydrous Na$_2$SO$_4$, filtered and concentrated under vacuum. The residue was purified via column chromatography with silica gel (eluting with ethyl acetate/petroleum ether (1:4)) to give tert-butyl 4-cyano-5-fluoro-2-nitrophenylcarbamate (4.3 g, 63% two steps) as a white solid. MS: (ESI, m/z): 282[M+H]$^+$.

Step 3: tert-butyl 2-amino-4-cyano-5-fluorophenylcarbamate

A solution of tert-butyl 4-cyano-5-fluoro-2-nitrophenylcarbamate (4.3 g, 15.3 mmol), iron filings (4.28 g, 76.6 mmoL), and ammonium chloride (810 mg, 15.1 mmol) in EtOH/H$_2$O (4:1, 40 mL) stirred for 4 h at 90° C. in an oil bath. The reaction mixture was filtered, and the filtrate was concentrated under vacuum. The residue was diluted with 20 mL of water and extracted with 3×20 mL of ethyl acetate.

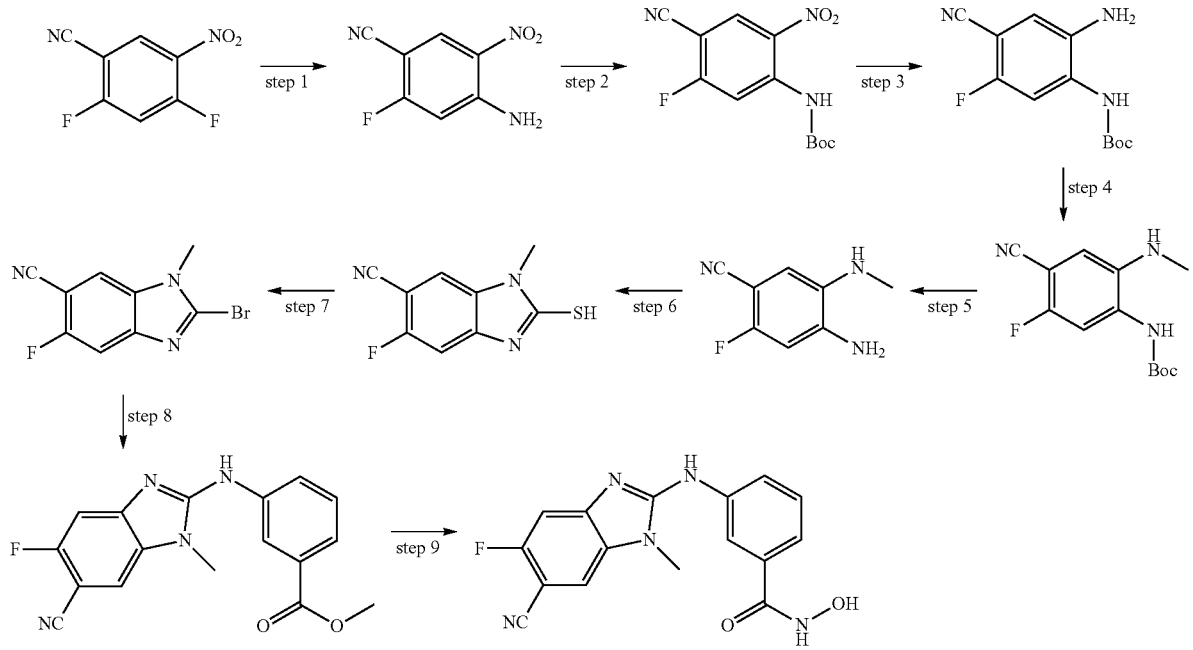

Step 1: 4-amino-2-fluoro-5-nitrobenzonitrile

Ammonium hydroxide (13 mL, 23.9 mmol) was added to a 0° C. solution of 2,4-difluoro-5-nitrobenzonitrile (4.41 g, 23.95 mmol) in ethanol (3 mL), and the resulting solution stirred for 3 h at room temperature. The resulting mixture was filtered and the filter cake was dried to give 4-amino-2-fluoro-5-nitrobenzonitrile (4.4 g, 100%) as a yellow solid. MS: (ESI, m/z): 182[M+H]$^+$.

Step 2: tert-butyl 4-cyano-5-fluoro-2-nitrophenylcarbamate

Sodium hydride (60% dispersion in mineral oil, 1.16 g, 29 mmol) was added to a 0° C. solution of 4-amino-2-fluoro- The combined organic phases were washed with 3×20 mL of brine, dried over anhydrous Na$_2$SO$_4$, filtered and concentrated under vacuum. The residue was purified via column chromatography with silica gel (eluting with dichloromethane/methanol (10:1)) to give tert-butyl 2-amino-4-cyano-5-fluorophenylcarbamate (4 g) as a yellow solid. MS: (ESI, m/z): 252[M+H]$^+$.

Step 4: tert-butyl 4-cyano-5-fluoro-2-(methylamino)phenylcarbamate

A solution of tert-butyl 2-amino-4-cyano-5-fluorophenylcarbamate (4 g, 15.3 mmol), formaldehyde (1.43 g, 47.76 mmol) in MeOH (20 mL) stirred for 2 h, and then sodium cyanoborohydride (5.00 g, 79.6 mmol) was added. The resulting solution stirred overnight at room temperature, and was then quenched by the addition of 20 mL of water. The resulting solution was extracted with 3×20 mL of ethyl acetate, and the combined organic phases were washed with 3×20 mL of brine, dried over anhydrous $Na_2SO_4$, filtered and concentrated under vacuum. The residue was purified via column chromatography with silica gel (eluting with ethyl acetate/petroleum ether (1:1)) to give tert-butyl 4-cyano-5-fluoro-2-(methylamino)phenylcarbamate (2 g, 49% two steps) as a yellow solid. MS: (ESI, m/z): 266[M+H]$^+$.

Step 5: 4-amino-2-fluoro-5-(methylamino)benzonitrile

A solution of tert-butyl 4-cyano-5-fluoro-2-(methylamino)phenylcarbamate (2.00 g, 7.54 mmol) in trifluoroacetic acid/dichloromethane (1:10, 30 mL) stirred overnight at room temperature, and the resulting mixture was concentrated under vacuum. The residue was dissolved in 10 mL of dichloromethane, and the pH value of the solution was adjusted to 7 with saturated aqueous sodium bicarbonate solution. The mixture was extracted with dichloromethane (3×10 mL), and the combined organic phases were dried over anhydrous $Na_2SO_4$, filtered and concentrated under vacuum. The residue was purified via column chromatography with silica gel (eluting with dichloromethane/methanol (10:1)) to give 4-amino-2-fluoro-5-(methylamino)benzonitrile (1.6 g) as a white solid. MS: (ESI, m/z): 166[M+H]$^+$.

Step 6: 6-fluoro-2-mercapto-3-methyl-3H-benzo[d]imidazole-5-carbonitrile

A solution of 4-amino-2-fluoro-5-(methylamino)benzonitrile (1.6 g, 7.54 mmol), potassium hydroxide (1.629 g, 29.03 mmol), and carbon disulfide (1.47 g, 19.3 mmoL) in EtOH (10 mL) stirred for 4 h at 90° C. in an oil bath. The resulting mixture was cooled to room temperature and concentrated under vacuum. Water (10 mL) was added and the mixture was extracted with 3×15 mL of ethyl acetate. The combined organic phases were dried over anhydrous $Na_2SO_4$, filtered and concentrated under vacuum. The residue was purified via column chromatography with silica gel (eluting with ethyl acetate/petroleum ether (1:1)) to give 6-fluoro-2-mercapto-3-methyl-3H-benzo[d]imidazole-5-carbonitrile (550 mg, 35% two steps) as a brown solid. MS: (ESI, m/z): 208[M+H]$^+$.

Step 7: 2-bromo-6-fluoro-3-methyl-3H-benzo[d]imidazole-5-carbonitrile

Bromine (0.54 mL, 10.5 mmol) was added dropwise to a 0° C. solution of 6-fluoro-2-mercapto-3-methyl-3H-benzo[d]imidazole-5-carbonitrile (547 mg, 2.64 mmol) in hydrogen bromide (40% solution in acetic acid, 10 mL), and the resulting solution was stirred for 3 h at 0° C. The reaction was quenched by the addition of water (15 mL) and cooled to 0° C. The pH value of the solution was adjusted to 5 with 2 M aqueous sodium hydroxide solution, and the resulting solution was extracted with 3×20 mL of ethyl acetate. The combined organic phases were dried over anhydrous $Na_2SO_4$, filtered, and concentrated under vacuum. The residue was purified via column chromatography with silica gel (eluting with ethyl acetate/petroleum ether (3:2)) to give 2-bromo-6-fluoro-3-methyl-3H-benzo[d]imidazole-5-carbonitrile (120 mg, 18%) as a yellow solid. MS: (ESI, m/z): 254, 256[M+H]$^+$.

Step 8: methyl 3-(6-cyano-5-fluoro-1-methyl-1H-benzo[d]imidazol-2-ylamino)benzoate A solution of 2-bromo-6-fluoro-3-methyl-3H-benzo[d]imidazole-5-carbonitrile (100 mg, 0.39 mmol), methyl 3-aminobenzoate (119 mg, 0.79 mmol), and 6 M aqueous HCl solution (1 drop) in EtOH (8 mL). The reaction mixture was irradiated with microwave radiation for 2 h at 150° C. and then cooled to room temperature. Water (10 mL) was added, and the resulting solution was extracted with 3×15 mL of ethyl acetate. The combined organic phases were dried over anhydrous $Na_2SO_4$, filtered, and concentrated under vacuum. The residue was purified via column chromatography with silica gel (eluting with dichloromethane/methanol (20:1)) to give methyl 3-(6-cyano-5-fluoro-1-methyl-1H-benzo[d]imidazol-2-ylamino)benzoate (50 mg, 39%) as a brown solid. MS: (ESI, m/z): 325[M+H]$^+$.

Step 9: 3-(6-cyano-5-fluoro-1-methyl-1H-benzo[d]imidazol-2-ylamino)-N-hydroxybenzamide Hydroxyl amine solution (50% in water, 0.45 mL, 7.3 mmol) and 1 M aqueous sodium hydroxide solution (0.24 mL, 0.24 mmol) were added to a 0° C. solution of methyl 3-(6-cyano-5-fluoro-1-methyl-1H-benzo[d]imidazol-2-ylamino)benzoate (40 mg, 0.12 mmol) in THF/MeOH (4:1, 1 mL), and the resulting solution stirred for 2 h at room temperature and was then cooled to 0° C. The pH value of the solution was adjusted to 5 with 6 M aqueous HCl solution. The crude product was purified by Prep-HPLC with the following conditions: Column: Waters HSS C18, 2.1×50 mm, 1.8 um; Mobile Phase A: Water/0.05% TFA, Mobile Phase B: ACN; Flow rate: 0.7 mL/min; Gradient: 5% B to 95% B in 2.0 min, hold 0.6 min; 254 nm. The collected fraction was lyophilized to give 3-(6-cyano-5-fluoro-1-methyl-1H-benzo[d]imidazol-2-ylamino)-N-hydroxybenzamide (13 mg, 24%) as a white solid. $^1$H-NMR (DMSO, 300 MHz), δ (ppm): 11.23 (br, 1H), 9.63 (s, 1H), 8.14-8.07 (m, 2H), 7.92 (d, J=5.7 Hz, 1H), 7.47-7.38 (m, 3H), 3.76 (s, 3H). MS: (ESI, m/z): 326[M+H]$^+$.

Example 13-1. 3-(5,6-dichloro-1-methyl-1H-benzo[d]imidazol-2-ylamino)-N-hydroxybenzamide

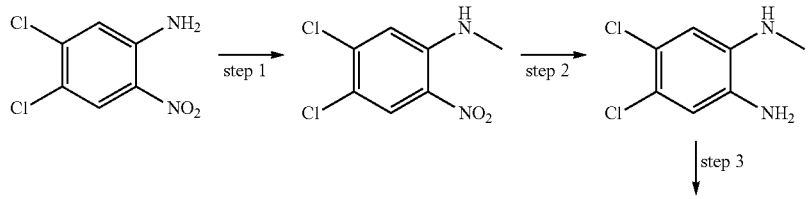

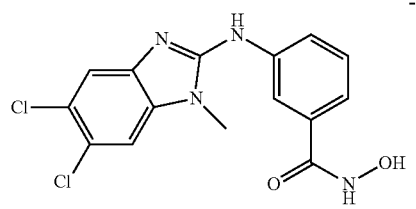 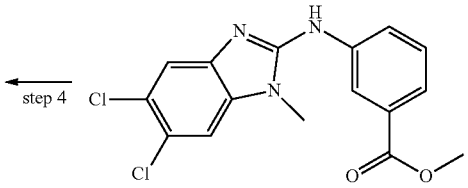

Step 1: 4,5-dichloro-N-methyl-2-nitrobenzenamine

A solution of 4,5-dichloro-2-nitroaniline (2.00 g, 9.66 mmol), dimethyl sulfate (1.4 g, 11.1 mmol), tetrabutylammonium bromide (0.2 g, 0.58 mmol), and sodium hydroxide (4.00 g, 100.0 mmol) in toluene (30 mL) stirred for 5 h at room temperature. The reaction mixture was diluted with saturated aqueous ammonium chloride solution and extracted with 3×50 mL of ethyl acetate. The combined organic phases were dried over anhydrous sodium sulfate, filtered, and concentrated under vacuum. The residue was purified via column chromatography with silica gel (eluting with ethyl acetate/petroleum ether (1:3)) to give 4,5-dichloro-N-methyl-2-nitrobenzenamine (1.9 g, 89%) as a white solid. MS: (ESI, m/z): 219[M−H]$^-$.

Step 2: 4,5-dichloro-N1-methylbenzene-1,2-diamine

Iron filings (0.76 g, 13.56 mmol) were added in portions to a 60° C. solution of 4,5-dichloro-N-methyl-2-nitrobenzenamine (500 mg, 2.26 mmol) and ammonium chloride (244 mg, 4.56 mmol) in ethanol (30 mL) and water (5 mL). The resulting solution stirred for 2 days at 80° C. in an oil bath. The reaction mixture was cooled to room temperature. The reaction mixture was filtered, and the filtrate was concentrated under vacuum. The residue was diluted with 50 mL of water and extracted with 3×30 mL of ethyl acetate. The combined organic phases were dried over anhydrous sodium sulfate, filtered, and concentrated under vacuum. The residue was purified via column chromatography with silica gel (eluting with ethyl acetate/petroleum ether (1:2)) to give 4,5-dichloro-N1-methylbenzene-1,2-diamine (160 mg, 37%) as a brown solid. MS: (ESI, m/z): 191 [M+H]$^+$.

Step 3: methyl 3-(5,6-dichloro-1-methyl-1H-benzo[d]imidazol-2-ylamino)benzoate A solution of 4,5-dichloro-N1-methylbenzene-1,2-diamine (100 mg, 0.52 mmol) methyl 3-isothiocyanatobenzoate (102 mg, 0.53 mmol), N,N'-diisopropylcarbodiimide (132 mg, 1.05 mmol) in THF (50 mL) stirred overnight at 70° C. in an oil bath. The reaction mixture was cooled to room temperature and then concentrated under vacuum. The residue was purified via column chromatography with silica gel (eluting with ethyl acetate/petroleum ether (1:2)) to give methyl 3-(5,6-dichloro-1-methyl-1H-benzo[d]imidazol-2-ylamino)benzoate (70 mg, 38%) as an off-white solid. MS: (ESI, m/z): 350[M+H]$^+$.

Step 4: 3-(5,6-dichloro-1-methyl-1H-benzo[d]imidazol-2-ylamino)-N-hydroxybenzamide Hydroxyl amine solution (50% in water, 0.53 mL, 8.6 mmol) and 1 M aqueous sodium hydroxide solution (0.57 mL, 0.57 mmol) were added to a solution of methyl 3-(5,6-dichloro-1-methyl-1H-benzo[d]imidazol-2-ylamino)benzoate (100 mg, 0.29 mmol) in THF/MeOH (4:1, 2 mL), and the resulting solution stirred for 1 h at room temperature. The pH value of the resulting solution was adjusted to 6 with 6 M aqueous HCl solution. The solids were collected by filtration and recrystallized from 2 mL of MeOH to give 3-(5,6-dichloro-1-methyl-1H-benzo[d]imidazol-2-ylamino)-N-hydroxybenzamide (58 mg, 58%) as a off-white solid. $^1$H-NMR (DMSO, 300 MHz), δ (ppm): 11.18 (s, 1H), 9.29 (s, 1H), 9.02 (s, 1H), 8.03 (d, J=5.7 Hz, 2H), 7.63 (d, J=20.7 Hz, 2H), 7.43-7.31 (m, 2H), 3.72 (s, 3H). MS: (ESI, m/z): 351[M+H]$^+$.

Example 14-1. 3-(6-cyano-1-isopropyl-5-(trifluoromethyl)-1H-benzo[d]imidazol-2-ylamino)-N-hydroxybenzamide

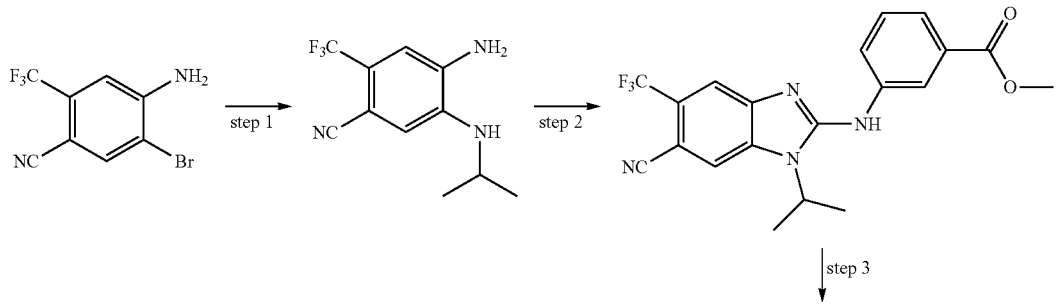

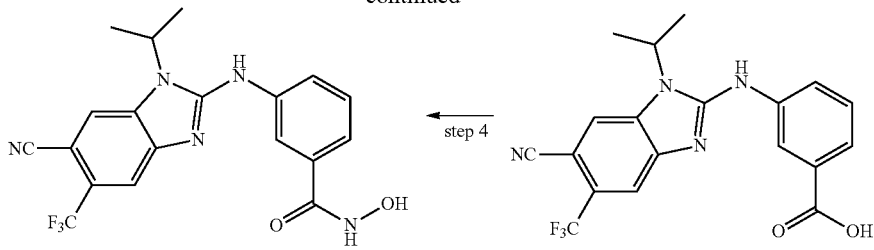

Step 1: 4-amino-5-(isopropylamino)-2-(trifluoromethyl)benzonitrile

A solution of 4-amino-5-bromo-2-(trifluoromethyl)benzonitrile (100 mg, 0.38 mmol), propan-2-amine (230 mg, 3.89 mmol), copper (I) iodide (80 mg, 0.42 mmol), cesium carbonate (370 mg, 1.14 mmol) and 2,2,6,6-tetramethylheptane-3,5-dione (140 mg, 0.76 mmol) in DMSO (2 mL) stirred for 15 h at room temperature. The resulting mixture was concentrated under vacuum. The residue was purified via column chromatography with silica gel (eluting with ethyl acetate/petroleum ether (1:10)) to give 4-amino-5-(isopropylamino)-2-(trifluoromethyl)benzonitrile (30 mg, 33%) as a pink solid. MS: (ESI, m/z): 244[M+H]$^+$.

Step 2: methyl 3-(6-cyano-1-isopropyl-5-(trifluoromethyl)-1H-benzo[d]imidazol-2-ylamino)benzoate A solution of 4-amino-5-(isopropylamino)-2-(trifluoromethyl)benzonitrile (300 mg, 1.23 mmol), methyl 3-isothiocyanatobenzoate (470 mg, 2.45 mmol), and EDC.HCl (708 mg, 3.69 mmol) in THF (30 mL) stirred for 10 h at 70° C. The resulting mixture was cooled to room temperature and concentrated under vacuum. The residue was purified via column chromatography with silica gel (eluting with ethyl acetate/petroleum ether (1:1)) to give methyl 3-(6-cyano-1-isopropyl-5-(trifluoromethyl)-1H-benzo[d]imidazol-2-ylamino)benzoate (200 mg, 40%) as a brown solid. MS: (ESI, m/z): 403[M+H]$^+$.

Step 3: 3-(6-cyano-1-isopropyl-5-(trifluoromethyl)-1H-benzo[d]imidazol-2-ylamino)benzoic Acid A solution of methyl 3-(6-cyano-1-isopropyl-5-(trifluoromethyl)-1H-benzo[d]imidazol-2-ylamino)benzoate (100 mg, 0.25 mmol), lithium hydroxide monohydrate (50 mg, 1.24 mmol) in water (4 mL) and THF (5 mL) stirred for 10 h at room temperature. The resulting mixture was diluted with 10 mL of water and extracted with 10 mL of ethyl acetate. The aqueous layer was separated and the pH value of the solution was adjusted to 5 with 4 M aqueous HCl solution. The resulting solution was extracted with 2×20 mL of dichloromethane, and the combined organic phases were washed with 30 mL of brine, dried over anhydrous sodium sulfate, filtered, and concentrated under vacuum to give 3-(6-cyano-1-isopropyl-5-(trifluoromethyl)-1H-benzo[d]imidazol-2-ylamino)benzoic acid (80 mg, 83%) as a yellow solid. MS: (ESI, m/z): 389[M+H]$^+$.

Step 4: 3-(6-cyano-1-isopropyl-5-(trifluoromethyl)-1H-benzo[d]imidazol-2-ylamino)-N-hydroxybenzamide A solution of 3-(6-cyano-1-isopropyl-5-(trifluoromethyl)-1H-benzo[d]imidazol-2-ylamino)benzoic acid (80 mg, 0.21 mmol), IPCF (129 mg, 1.03 mmol), NMM (104 mg, 1.03 mmol) and hydroxyl amine hydrochloride (71 mg, 1.03 mmol) in DMA (3 mL) stirred for 10 h at room temperature. The crude product was purified by prep-HPLC with the following conditions: Column: XBridge RP C18, 19×150 mm, 5 um; Mobile Phase A: water/0.05% TFA; Mobile Phase B: ACN; Flow rate: 25 mL/min; Gradient: 20% B to 39% B in 10 min, 254 nm. The collected fraction was lyophilized to give 3-(6-cyano-1-isopropyl-5-(trifluoromethyl)-1H-benzo[d]imidazol-2-ylamino)-N-hydroxybenzamide (37.2 mg, 45%) as an off-white solid. $^1$H-NMR (DMSO, 300 MHz), δ (ppm): 11.20 (br, 1H), 9.51 (br, 1H), 8.33 (s, 1H), 8.08-8.03 (m, 2H), 7.86 (s, 1H), 7.42-7.34 (m, 2H), 5.04-4.95 (m, 1H), 1.58 (d, J=6.9 Hz, 6H). MS: (ESI, m/z): 404[M+H]$^+$.

Example 15-1. 3-(5-cyano-1-isopropyl-6-(trifluoromethyl)-1H-benzo[d]imidazol-2-ylamino)-N-hydroxybenzamide

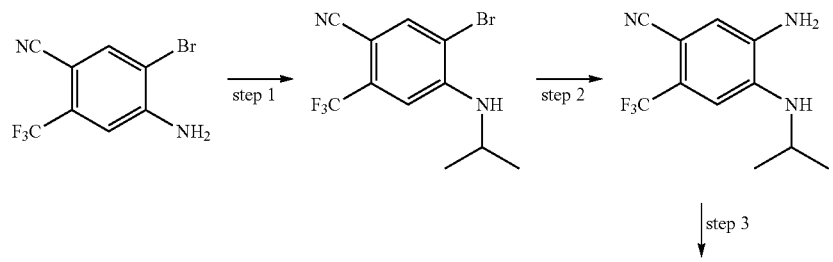

-continued

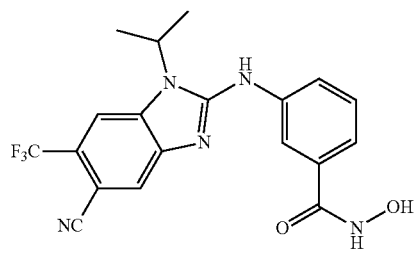 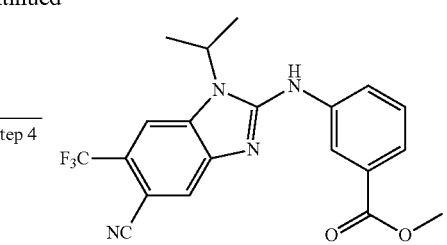

Step 1: 5-bromo-4-(isopropylamino)-2-(trifluoromethyl)benzonitrile

Trifluoroacetic acid (0.60 mL, 7.96 mmol) was added dropwise to a solution of 4-amino-5-bromo-2-(trifluoromethyl)benzonitrile (2.0 g, 7.55 mmol) and 2,2-dimethoxypropane (3.92 g, 37.64 mmol) in toluene (20 mL), and the mixture stirred for 1 h at room temperature. The reaction mixture was cooled to 0° C., and borane dimethyl sulfide complex (10 M, 0.83 mL, 8.31 mmol) was added dropwise. The resulting solution stirred for 18 h at room temperature, and was then added dropwise into 40 mL of methanol. The resulting mixture was concentrated under vacuum. The residue was purified via column chromatography with silica gel (eluting with ethyl acetate/petroleum ether (1:7)) to give 5-bromo-4-(isopropylamino)-2-(trifluoromethyl)benzonitrile (1.583 g, 68%) as a light brown solid. MS: (ESI, m/z): 305[M−H]−.

Step 2: 5-amino-4-(isopropylamino)-2-(trifluoromethyl)benzonitrile

A solution of 5-bromo-4-(isopropylamino)-2-(trifluoromethyl)benzonitrile (1.0 g, 3.26 mmol), pentane-2,4-dione (651 mg, 6.51 mmol), copper (II) acetylacetonate (0.426 g, 1.63 mmol), cesium carbonate (2.12 g, 6.51 mmol), ammonium hydroxide (0.30 mL, 16 mmol) in DMF (15 mL) stirred for 1 day at 90° C. The resulting solution was cooled to room temperature, diluted with 20 mL of water, and extracted with 3×30 mL of ethyl acetate. The combined organic phases were dried over anhydrous sodium sulfate, filtered, and concentrated under vacuum. The residue was purified via column chromatography with silica gel (eluting with ethyl acetate/petroleum ether (1:3)) to give 5-amino-4-(isopropylamino)-2-(trifluoromethyl)benzonitrile (669 mg, 84%) as a blue green oil. MS: (ESI, m/z): 244[M+H]+.

Step 3: methyl 3-(5-cyano-1-isopropyl-6-(trifluoromethyl)-1H-benzo[d]imidazol-2-ylamino)benzoate EDC.HCl (790 mg, 4.12 mmol) was added to a 0° C. solution of 5-amino-4-(isopropylamino)-2-(trifluoromethyl) benzonitrile (400 mg, 1.64 mmol) and methyl 3-isothiocyanatobenzoate (477 mg, 2.47 mmol) in THF (35 mL), and the resulting solution was stirred for 16 h at 75° C. The mixture was cooled to room temperature and concentrated under vacuum. The residue was diluted with 40 mL of ethyl acetate and washed with 3×20 mL of water. The combined organic phases were dried over anhydrous sodium sulfate and concentrated under vacuum. The crude product was purified by reversed phase column with the following conditions: Column: C18 column, 40 g, 20-45 um, 100 A; Mobile Phase: water and ACN (5% up to 50% in 30 min); Flow rate: 80 mL/min; 254 nm. The collected fraction was concentrated under vacuum to give methyl 3-(5-cyano-1-isopropyl-6-(trifluoromethyl)-1H-benzo[d]imidazol-2-ylamino)benzoate (265.9 mg, 40%) as a yellow solid. MS: (ESI, m/z): 403 [M+H]+.

Step 4: 3-(5-cyano-1-isopropyl-6-(trifluoromethyl)-1H-benzo[d]imidazol-2-ylamino)-N-hydroxybenzamide Hydroxyl amine solution (50% in water, 0.59 mL, 9.7 mmol) and 1 M aqueous sodium hydroxide solution (0.65 mL, 0.65 mmol) were added to a solution of methyl 3-(5-cyano-1-isopropyl-6-(trifluoromethyl)-1H-benzo[d]imidazol-2-ylamino)benzoate (130 mg, 0.32 mmol) in THF/MeOH (4:1, 2 mL), and the resulting solution stirred for 3 h at room temperature. The crude product was purified by Prep-HPLC with the following conditions: Column: Xbridge RP18 19×150, 5 um, 19×100 mm; Mobile phase: water with 0.05% TFA and ACN (4% ACN up to 58% in 7 min); Flow rate: 25 ml/min; Detector: 254, 220 nm. The collected fraction was lyophilized to give 3-(5-cyano-1-isopropyl-6-(trifluoromethyl)-1H-benzo[d]imidazol-2-ylamino)-N-hydroxybenzamide (10.7 mg, 8%) as an off-white solid. 1H-NMR (DMSO, 400 MHz), δ (ppm): 11.20 (s, 1H), 9.46 (s, 1H), 8.11-8.05 (m, 3H), 7.96 (s, 1H), 7.46-7.38 (m, 2H), 5.10-5.03 (m, 1H), 1.62 (d, J=6.8 Hz, 6H). MS: (ESI, m/z): 404[M+H]+.

Example 16-1. N-hydroxy-3-(1-isopropyl-6-phenyl-5-(trifluoromethyl)-1H-benzo[d]imidazol-2-ylamino)benzamide

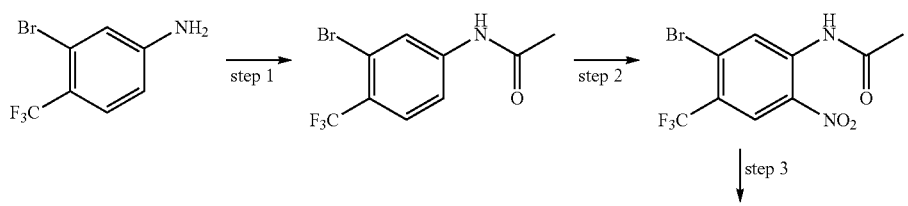

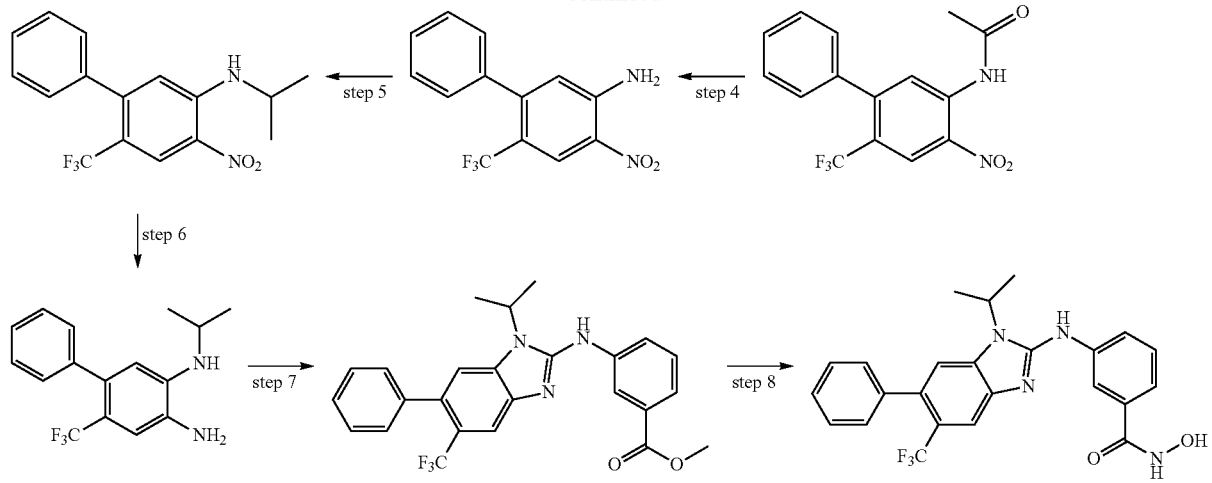

Step 1: N-(3-bromo-4-(trifluoromethyl)phenyl)acetamide

A solution of 3-bromo-4-(trifluoromethyl)aniline (10 g, 41.7 mmol) in acetic anhydride (50 mL) stirred for 2 h at room temperature, and the resulting mixture was concentrated under vacuum. The crude product was re-crystallized from 20 mL of ethyl acetate-petroleum ether (1/10) to give N-(3-bromo-4-(trifluoromethyl)phenyl)acetamide (9.4 g, 80%) as a white solid. MS: (ESI, m/z): 280[M−H]$^-$.

Step 2: N-(5-bromo-2-nitro-4-(trifluoromethyl)phenyl)acetamide

Concentrated nitric acid (4.2 mL) was added dropwise to a 0° C. solution of N-(3-bromo-4-(trifluoromethyl)phenyl) acetamide (8.4 g, 29.8 mmol) in concentrated sulfuric acid (33.6 mL), and the resulting solution stirred for 10 min at room temperature. The reaction was then added dropwise into 1000 mL of ice/water. The solids were collected by filtration and washed with 500 mL of water and dried under vacuum to give N-(5-bromo-2-nitro-4-(trifluoromethyl)phenyl)acetamide (8.4 g, 86%) as a yellow solid. MS: (ESI, m/z): 325[M−H]$^-$.

Step 3: N-(4-nitro-6-(trifluoromethyl)biphenyl-3-yl)

A solution of N-(5-bromo-2-nitro-4-(trifluoromethyl)phenyl)acetamide (8.6 g, 26.3 mmol), phenylboronic acid (6.4 g, 52 mmol), Pd(dppf)Cl$_2$ dichloromethane adduct (1.07 g, 1.31 mmol), and potassium carbonate (10.9 g, 78.8 mmol) in water (20 mL) and 1,4-dioxane (100 mL) stirred overnight at 90° C. The resulting mixture was cooled to room temperature and concentrated under vacuum. The residue was diluted with 200 mL of water and extracted with 2×100 mL of ethyl acetate. The combined organic phases were washed with 1×200 mL of brine, dried over anhydrous sodium sulfate, filtered, and concentrated under vacuum. The residue was purified via column chromatography with silica gel (eluting with ethyl acetate/petroleum ether (1:5)) to give N-(4-nitro-6-(trifluoromethyl)biphenyl-3-yl) (5.4 g, 63%) as a yellow solid. MS: (ESI, m/z): 323[M−H]$^-$.

Step 4: 4-nitro-6-(trifluoromethyl)biphenyl-3-amine

A solution of N-(4-nitro-6-(trifluoromethyl)biphenyl-3-yl)acetamide (5.4 g, 16.65 mmol) in 1,4-dioxane (50 mL) and 6 M aqueous HCl solution (25 mL) stirred for 3 h at 90° C. The resulting mixture was cooled to room temperature and concentrated under vacuum. The residue was diluted with 100 mL of 1 M aqueous NaHCO$_3$ solution, and the resulting solution was extracted with 2×150 mL of ethyl acetate. The combined organic phases were washed with 1×200 mL of brine, dried over anhydrous sodium sulfate, filtered, and concentrated under vacuum. The residue was purified via column chromatography with silica gel (eluting with ethyl acetate/petroleum ether (1:5)) to give 4-nitro-6-(trifluoromethyl)biphenyl-3-amine (4.6 g, 98%) as a yellow solid. MS: (ESI, m/z): 281[M−H]$^-$.

Step 5: N-isopropyl-4-nitro-6-(trifluoromethyl)biphenyl-3-amine

Sodium hydride (60% dispersion in mineral oil, 85 mg, 2.13 mmol) was added in portions to a 0° C. solution of 4-nitro-6-(trifluoromethyl)biphenyl-3-amine (200 mg, 0.71 mmol) in DMF (5 mL), and the resulting solution stirred for 1 h at room temperature. 2-Iodopropane (241 mg, 1.42 mmol) was added dropwise, and the resulting solution stirred overnight at room temperature. The reaction mixture was poured into 50 mL of ice/water and extracted with 2×50 mL of ethyl acetate. The combined organic phases were washed with 2×100 mL of brine, dried over anhydrous sodium sulfate, filtered, and concentrated under vacuum. The residue was purified via column chromatography with silica gel (eluting with ethyl acetate/petroleum ether (1:5)) to give N-isopropyl-4-nitro-6-(trifluoromethyl)biphenyl-3-amine (140 mg, 61%) as a yellow solid. MS: (ESI, m/z): 323 [M−H]$^-$.

Step 6: N3-isopropyl-6-(trifluoromethyl)biphenyl-3,4-diamine

A mixture of N-isopropyl-4-nitro-6-(trifluoromethyl)biphenyl-3-amine (800 mg, 2.47 mmol) and 10% platinum on carbon (150 mg) in methanol (50 mL) stirred for 2 h at room temperature under a hydrogen atmosphere. The reaction mixture was filtered, and the filtrate was concentrated under vacuum to give N3-isopropyl-6-(trifluoromethyl)biphenyl-3,4-diamine (670 mg, 92%) as yellow oil. MS: (ESI, m/z): 295[M+H]$^+$.

Step 7: methyl 3-(1-isopropyl-6-phenyl-5-(trifluoromethyl)-1H-benzo[d]imidazol-2-ylamino)benzoate A solution of N3-isopropyl-6-(trifluoromethyl)biphenyl-3,4-diamine (200 mg, 0.68 mmol) and methyl 3-isothiocyanatobenzoate (144 mg, 0.75 mmol) in THF (20 mL) stirred for 2 h at room temperature. CDI (214 mg, 1.32 mmol) was added, and the resulting solution stirred overnight at 75° C. in an oil bath. The resulting mixture was cooled to room temperature and concentrated under vacuum. The crude product was purified by preparative thin layer chromatography (eluting with ethyl acetate/petroleum ether (1:2)). The collected fraction was concentrated under vacuum to give methyl 3-(1-isopropyl-6-phenyl-5-(trifluoromethyl)-1H-benzo[d]imidazol-2-ylamino)benzoate (90 mg, 30%) as a yellow oil. MS: (ESI, m/z): 454[M+H]$^+$.

Step 8: N-hydroxy-3-(1-isopropyl-6-phenyl-5-(trifluoromethyl)-1H-benzo[d]imidazol-2-ylamino)benzamide Hydroxyl amine solution (50% in water, 0.73 mL, 11.9 mmol) and 1 M aqueous sodium hydroxide solution (0.40 mL, 0.40 mmol) were added to a solution of methyl 3-(1-isopropyl-6-phenyl-5-(trifluoromethyl)-1H-benzo[d]imidazol-2-ylamino)benzoate (90 mg, 0.20 mmol) in THF/MeOH (3:1, 3 mL), and the resulting solution stirred for 2 h at room temperature. The solids were filtered out. The crude product was purified by prep-HPLC with the following conditions: Sunfire C18 Column 19*150 mn; mobile phase, water/0.05% TFA and CH$_3$CN (5% B up to 55% B in 1.1 min); Flow rate: 25 mL/min; Detector, 254 nm. The collected fraction was lyophilized to give N-hydroxy-3-(1-isopropyl-6-phenyl-5-(trifluoromethyl)-1H-benzo[d]imidazol-2-ylamino)benzamide (36.0 mg, 32%) as a pink solid. $^1$H-NMR (CD$_3$OD, 400 MHz), δ (ppm): 7.98 (d, J=1.4 Hz, 1H), 7.79 (s, 1H), 7.73-7.71 (m, 2H), 7.67-7.64 (m, 2H), 7.47-7.44 (m, 3H), 7.39-7.38 (m, 2H), 4.98-4.91 (m, 1H), 1.75 (d, J=6.8 Hz, 6H). MS: (ESI, m/z): 455[M+H]$^+$.

The following compounds were prepared according to the procedures outlined above for N-hydroxy-3-(1-isopropyl-6-phenyl-5-(trifluoromethyl)-1H-benzo[d]imidazol-2-ylamino)benzamide.

| Ex. | Structure | Name | $^1$H NMR | (ESI, m/z) [M + H]$^+$ |
|---|---|---|---|---|
| 16-2 | 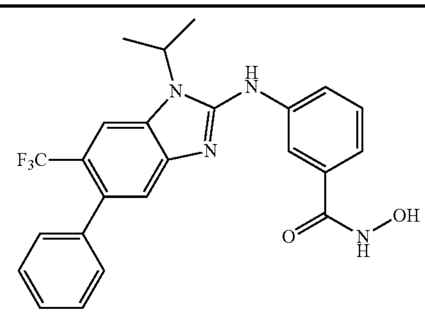 | N-hydroxy-3-((1-isopropyl-5-phenyl-6-(trifluoromethyl)-1H-benzo[d]imidazol-2-yl)amino)benzamide | (DMSO, 400 MHz, ppm): 11.19 (br, 1H), 9.48 (br, 1H), 8.08-8.02 (m, 2H), 7.84 (s, 1H), 7.45-7.32 (m, 8H), 5.07-5.00 (m, 1H), 1.64 (d, J = 6.8 Hz, 6H). | 455 |

Example 17-1. 3-(5,6-dichloro-1-isopropyl-1H-benzo[d]imidazol-2-ylamino)-N-hydroxybenzamide

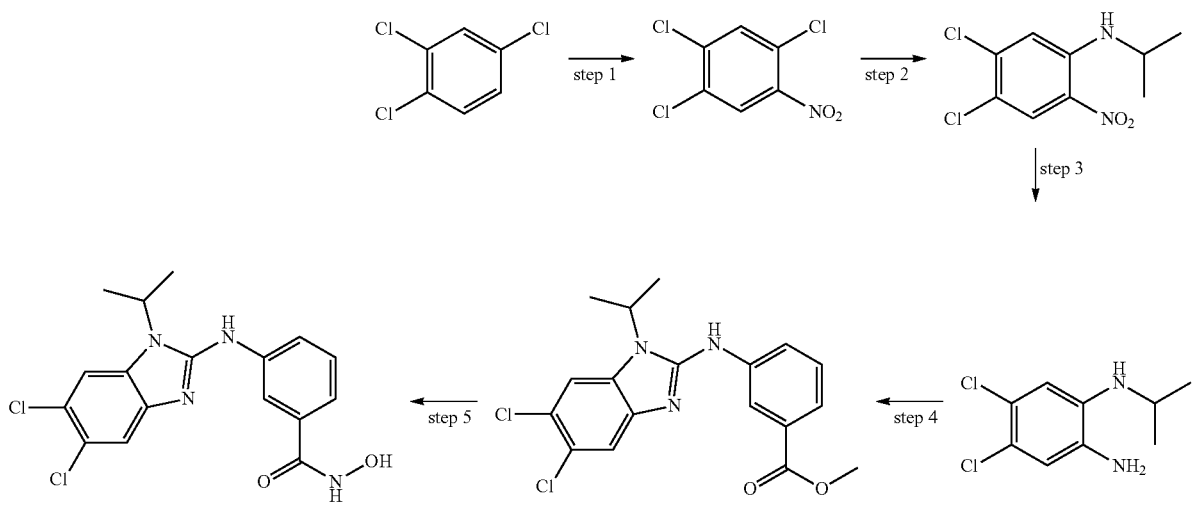

Step 1: 1,2,4-trichloro-5-nitrobenzene 1,2,4-Trichlorobenzene (5.00 g, 27.6 mmol) was added dropwise to a 0° C. solution of nitric acid (98%, 18 mL) and water (2 mL), and the resulting solution stirred for 3 h at room temperature. The reaction mixture was then added dropwise into 30 mL of ice/water and the resulting mixture was filtered. The filter cake was washed with water and dried under vacuum to give 1,2,4-trichloro-5-nitrobenzene (4.9 g, 79%) as a yellow green solid. $^1$H-NMR (DMSO, 400 MHz), δ (ppm): 8.52 (d, J=4.4 Hz, 1H), 8.28 (d, J=4.4 Hz, 1H).

Step 2: 4,5-dichloro-N-isopropyl-2-nitrobenzenamine

A solution of 1,2,4-trichloro-5-nitrobenzene (4.9 g, 21.6 mmol), triethylamine (4.5 mL, 32.6 mmol) and propan-2-amine (6.75 g, 114.19 mmol) in THF (20 mL) stirred for 15 h at 65° C. in an oil bath. The resulting mixture was cooled to room temperature and concentrated under vacuum. The residue was purified via column chromatography with silica gel (eluting with ethyl acetate/petroleum ether (1:10)) to give 4,5-dichloro-N-isopropyl-2-nitrobenzenamine (3.91 g, 73%) as an orange solid. $^1$H-NMR (CDCl$_3$, 400 MHz) δ (ppm): 8.27 (s, 1H), 7.92 (d, J=4.4 Hz, 1H), 6.97 (s, 1H), 3.81-3.73 (m, 1H), 1.34 (d, J=6.4 Hz, 6H).

Step 3: 4,5-dichloro-N1-isopropylbenzene-1,2-diamine

Zinc (5.12 g, 78.8 mmol) was added in portions to a 0° C. solution of 4,5-dichloro-N-isopropyl-2-nitrobenzenamine (3.91 g, 15.7 mmol) in ethanol (15 mL) and ammonium hydroxide (20 mL), and the resulting solution stirred for 5 h at room temperature. The solids were filtered out, and the resulting solution was extracted with 3×100 mL of ether. The combined organic phases were washed with 100 mL of brine, dried over anhydrous sodium sulfate, filtered, and concentrated under vacuum. The residue was purified via column chromatography with silica gel (eluting with ethyl acetate/petroleum ether (1:10)) to give 4,5-dichloro-N1-isopropylbenzene-1,2-diamine (1.03 g, 30%) as a black oil. MS: (ESI, m/z): 219[M+H]$^+$.

Step 4: methyl 3-(5,6-dichloro-1-isopropyl-1H-benzo[d]imidazol-2-ylamino)benzoate A solution of 4,5-dichloro-N1-isopropylbenzene-1,2-diamine (300 mg, 1.37 mmol) and methyl 3-isothiocyanatobenzoate (292 mg, 1.51 mmol) in THF (20 mL) stirred for 3 h at room temperature. N,N'-Diisopropylcarbodiimide (347 mg, 2.75 mmol) was added, and the resulting solution stirred for 16 h at 80° C. in an oil bath. The reaction mixture was cooled to room temperature and concentrated under vacuum. The residue was purified by reversed phase column with the following conditions: Column: C18 column, 40 g, 20-45 um, 100 A; Mobile phase: water with 0.05% NH$_4$HCO$_3$ and CAN (40% up to 50% in 30 minutes), 254 & 220 nm. The collected fraction was concentrated under vacuum to give methyl 3-(5,6-dichloro-1-isopropyl-1H-benzo[d]imidazol-2-ylamino)benzoate (190 mg, 37%) as a pink solid. MS: (ESI, m/z): 378[M+H]$^+$.

Step 5: 3-(5,6-dichloro-1-isopropyl-1H-benzo[d]imidazol-2-ylamino)-N-hydroxybenzamide Hydroxyl amine solution (50% in water, 0.97 mL, 15.9 mmol) and 1 M aqueous sodium hydroxide solution (0.53 mL, 0.53 mmol) were added to a solution of methyl 3-(5,6-dichloro-1-isopropyl-1H-benzo[d]imidazol-2-ylamino)benzoate (100 mg, 0.26 mmol) in THF/MeOH (4:1, 2 mL), and the resulting solution stirred for 4 h at room temperature. The crude product was purified by prep-HPLC with the following conditions: Column,)(Bridge RP C18, 19×150 mm, 5 um; Mobile Phase A: Water/0.05% TFA; Mobile Phase B: ACN; Flow rate: 25 mL/min; Gradient: 5% B to 50% B in 7.0 min, 254 nm. The collected fraction was lyophilized to give 3-(5,6-dichloro-1-isopropyl-1H-benzo[d]imidazol-2-ylamino)-N-hydroxybenzamide (59.3 mg, 45%) as an off-white solid. $^1$H-NMR (DMSO, 400 MHz), δ (ppm): 11.20 (br, 1H), 9.65 (br, 1H), 8.04-7.85 (m, 3H), 7.60 (s, 1H), 7.48-7.39 (m, 2H), 4.95-4.91 (m, 1H), 1.57 (d, J=6.8 Hz, 6H). MS: (ESI, m/z): 379[M+H]$^+$.

Example 18-1. 3-(6-cyano-1-(2-methoxyethyl)-5-(trifluoromethyl)-1H-benzo[d]imidazol-2-ylamino)-N-hydroxybenzamide

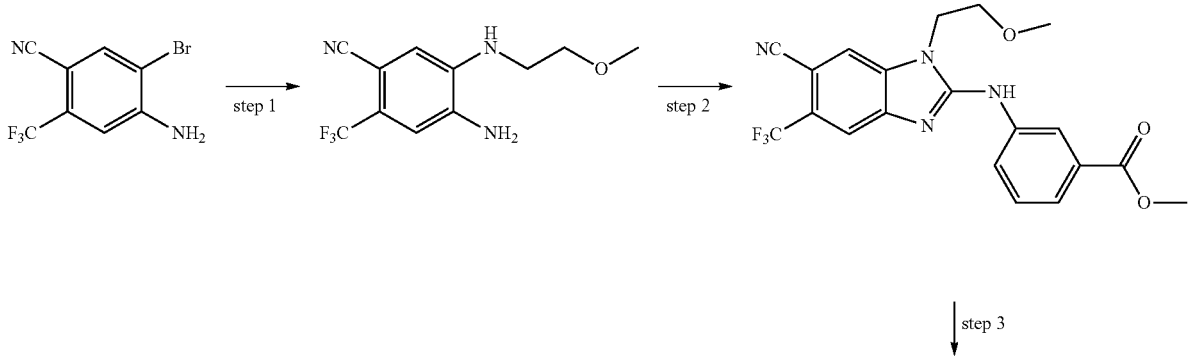

163 164

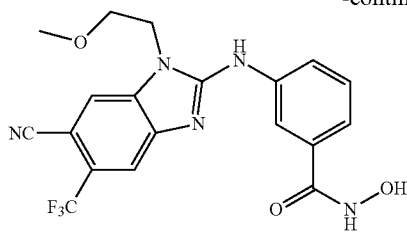 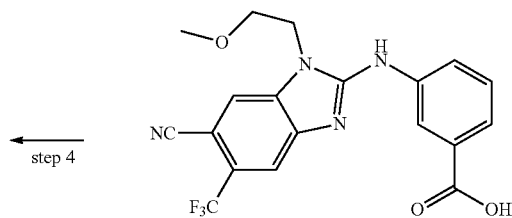

-continued step 4

Step 1: 4-amino-5-(2-methoxyethylamino)-2-(trifluoromethyl)benzonitrile

A solution of 4-amino-5-bromo-2-(trifluoromethyl)benzonitrile (500 mg, 1.89 mmol), 2-methoxyethylamine (1.40 g, 18.6 mmol), cesium carbonate (1.25 g, 3.84 mmol), copper (I) iodide (360 mg, 1.89 mmol), and 2,2,6,6-tetramethylheptane-3,5-dione (500 mg, 2.71 mmol) in DMSO (16 mL) stirred for 18 h at room temperature. The reaction mixture was then poured into water (100 mL) and extracted with 3×30 mL of ethyl acetate. The organic phase was separated and washed with 10×30 mL of water and concentrated under vacuum. The residue was purified via column chromatography with silica gel (eluting with ethyl acetate/petroleum ether (1:1)) give 4-amino-5-(2-methoxyethylamino)-2-(trifluoromethyl)benzonitrile (200 mg, 41%) as a brown solid. MS: (ESI, m/z): 258[M−H]⁻.

Step 2: methyl 3-(6-cyano-1-(2-methoxyethyl)-5-(trifluoromethyl)-1H-benzo[d]imidazol-2-ylamino)benzoate A solution of 4-amino-5-(2-methoxyethylamino)-2-(trifluoromethyl)benzonitrile (300 mg, 1.16 mmol), methyl 3-isothiocyanatobenzoate (267 mg, 1.38 mmol), and DIC (360 mg, 2.85 mmol) in THF (10 mL) stirred for 5.5 h at 70° C. The resulting mixture was cooled to room temperature and concentrated under vacuum. The residue was purified via column chromatography with silica gel (eluting with ethyl acetate/petroleum ether (1:1)) to give methyl 3-(6-cyano-1-(2-methoxyethyl)-5-(trifluoromethyl)-1H-benzo[d]imidazol-2-ylamino)benzoate (70 mg, 14%) as a brown oil. MS: (ESI, m/z): 419[M+H]⁺.

Step 3: 3-(6-cyano-1-(2-methoxyethyl)-5-(trifluoromethyl)-1H-benzo[d]imidazol-2-ylamino)benzoic Acid A solution of lithium hydroxide (57.7 mg, 2.41 mmol) in water (0.5 mL) was added dropwise to a 0° C. solution of methyl 3-(6-cyano-1-(2-methoxyethyl)-5-(trifluoromethyl)-1H-benzo[d]imidazol-2-ylamino)benzoate (48 mg, 0.11 mmol) in THF (3 mL), and the reaction mixture stirred for 26 h at room temperature. The resulting solution was concentrated under vacuum. The residue was purified by reversed phase column with the following conditions: Column: C18 column, 40 g, 20-45 um, 100 A; Mobile phase: water and ACN (5% up to 40% in 30 minutes), 254 & 220 nm. The collected fraction was lyophilized to give 3-(6-cyano-1-(2-methoxyethyl)-5-(trifluoromethyl)-1H-benzo[d]imidazol-2-ylamino)benzoic acid (26 mg, 56%) as a white solid. MS: (ESI, m/z): 405[M+H]⁺.

Step 4: 3-(6-cyano-1-(2-methoxyethyl)-5-(trifluoromethyl)-1H-benzo[d]imidazol-2-ylamino)-N-hydroxybenzamide A solution of 3-(6-cyano-1-(2-methoxyethyl)-5-(trifluoromethyl)-1H-benzo[d]imidazol-2-ylamino)benzoic acid (100 mg, 0.25 mmol), IPCF (160 mg, 1.27 mmol), NMM (130 mg, 1.27 mmol) and hydroxylamine hydrochloride (85 mg, 1.27 mmol) in DMA (3 mL) stirred for 10 h at room temperature. The crude product was purified by Prep-HPLC with the following conditions: Column: Waters HSS C18, 2.1×50 mm, 1.8 um; Mobile Phase A: water/0.05% TFA, Mobile Phase B: ACN; Flow rate: 0.7 mL/min; Gradient: 5% B to 95% B in 2.0 min, hold 0.6 min; 254 nm; Detector). The collected fraction was lyophilized to give 3-(6-cyano-1-(2-methoxyethyl)-5-(trifluoromethyl)-1H-benzo[d]imidazol-2-ylamino)-N-hydroxybenzamide (20.8 mg, 20%) as an off-white solid. ¹H-NMR (DMSO, 400 MHz), δ (ppm): 11.22 (br, 1H), 9.53 (s, 1H), 8.18-8.14 (m, 3H), 7.90 (s, 1H), 7.46-7.38 (m, 2H), 4.59-4.57 (m, 2H), 3.70-3.68 (m, 2H), 3.23 (s, 3H). MS: (ESI, m/z): 420[M+H]⁺.

Example 19-1. 3-(5-cyano-1-(2-methoxyethyl)-6-(trifluoromethyl)-1H-benzo[d]imidazol-2-ylamino)-N-hydroxybenzamide

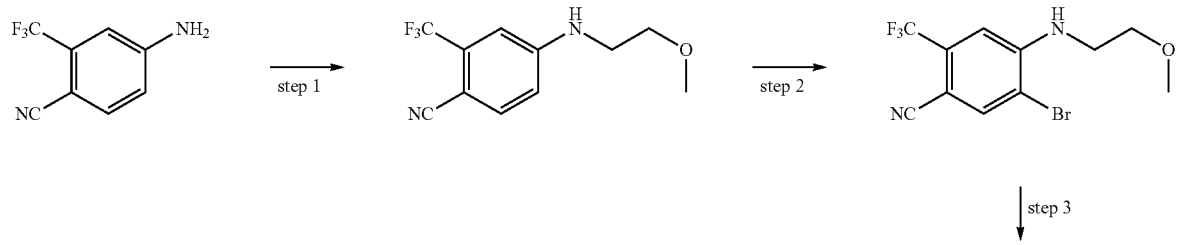

step 1 step 2 step 3

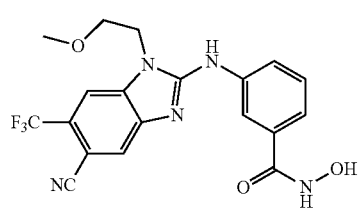 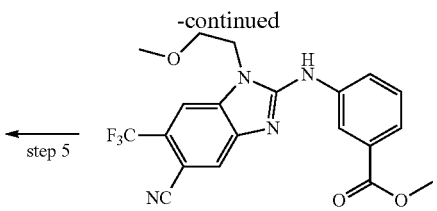

Step 1: 4-(2-methoxyethylamino)-2-(trifluoromethyl)benzonitrile

A solution of 4-amino-2-(trifluoromethyl)benzonitrile (2.00 g, 10.7 mmol), potassium iodide (1.79 g, 10.8 mmol), cesium carbonate (10.51 g, 32.26 mmol) and 1-bromo-2-methoxyethane (7.47 g, 53.7 mmol) in acetonitrile (25 mL) stirred for 18 h at 70° C. The resulting mixture was cooled to room temperature and concentrated under vacuum. The residue was diluted with water (30 mL) and extracted with 3×30 mL of ethyl acetate. The combined organic phases were washed with 2×30 mL of brine, dried over anhydrous sodium sulfate, filtered, and concentrated under vacuum. The residue was purified via column chromatography with silica gel (eluting with ethyl acetate/petroleum ether (1:3)) to give 4-(2-methoxyethylamino)-2-(trifluoromethyl)benzonitrile (2.1 g, 80%) as yellow oil. MS: (ESI, m/z): 243 [M−H]⁻.

Step 2: 5-bromo-4-(2-methoxyethylamino)-2-(trifluoromethyl)benzonitrile

Bromine (0.58 mL, 8.6 mmol) was added dropwise to a 0° C. solution of 4-(2-methoxyethylamino)-2-(trifluoromethyl)benzonitrile (2.1 g, 8.6 mmol) in methanol (30 mL), and the reaction mixture stirred for 4 h at room temperature. The resulting solution was quenched by the addition of 30 mL of saturated aqueous $NaHSO_3$ solution and the methanol was removed under vacuum. The resulting solution was extracted with 3×60 mL of dichloromethane, and the combined organic phases were washed with 2×50 mL of water, dried over anhydrous magnesium sulfate, filtered, and concentrated under vacuum. The residue was purified by reversed phase column with the following conditions: Column: C18 column, 40 g, 20-45 um, 100 A; Mobile phase: water and ACN (5% up to 50% in 30 minutes), 254 & 220 nm. The collected fraction was concentrated under vacuum to give 5-bromo-4-(2-methoxyethylamino)-2-(trifluoromethyl)benzonitrile (1.539 g, 55%) as a light yellow solid. MS: (ESI, m/z): 321[M−H]⁻.

Step 3: 5-amino-4-(2-methoxyethylamino)-2-(trifluoromethyl)benzonitrile

A solution of 5-bromo-4-(2-methoxyethylamino)-2-(trifluoromethyl)benzonitrile (1.0 g, 3.1 mmol), pentane-2,4-dione (619 mg, 6.18 mmol), copper (II) acetylacetonate (405 mg, 1.55 mmol), cesium carbonate (2.017 g, 6.19 mmol), ammonium hydroxide (1.2 mL, 15.44 mmol) in DMF (25 mL) stirred for 2 days at 90° C. The resulting solution was diluted with 25 mL of water and extracted with 3×30 mL of ethyl acetate. The combined organic phases were dried over anhydrous sodium sulfate and concentrated under vacuum. The residue was purified via column chromatography with silica gel (eluting with ethyl acetate/petroleum ether (1:1)) to give 5-amino-4-(2-methoxyethylamino)-2-(trifluoromethyl) benzonitrile (255 mg, 32%) as a black oil. MS: (ESI, m/z): 258[M−H]⁻.

Step 4: methyl 3-(5-cyano-1-(2-methoxyethyl)-6-(trifluoromethyl)-1H-benzo[d]imidazol-2-ylamino) benzoate EDC.HCl (47 mg, 0.25 mmol) was added to a 0° C. solution of 5-amino-4-(2-methoxyethylamino)-2-(trifluoromethyl)benzonitrile (255 mg, 0.98 mmol) and methyl 3-isothiocyanatobenzoate (285 mg, 1.47 mmol) in THF (30 mL), and the reaction stirred for 6 h at 75° C. The resulting mixture was cooled to room temperature and concentrated under vacuum. The residue was dissolved in 25 mL of ethyl acetate and washed with 2×15 mL of water. The combined organic phases were dried over anhydrous sodium sulfate, filtered, and concentrated under vacuum. The residue was purified by reversed phase column with the following conditions: Column: C18 column, 40 g, 20-45 um, 100 A; Mobile phase: water and ACN (5% up to 60% in 30 minutes), 254 & 220 nm. The collected fraction was concentrated under vacuum to give methyl 3-(5-cyano-1-(2-methoxyethyl)-6-(trifluoromethyl)-1H-benzo[d]imidazol-2-ylamino)benzoate (195 mg, 47%) as a yellow oil. MS: (ESI, m/z): 419 [M+H]⁺.

Step 5: 3-(5-cyano-1-(2-methoxyethyl)-6-(trifluoromethyl)-1H-benzo[d]imidazol-2-ylamino)-N-hydroxybenzamide Hydroxyl amine solution (50% in water, 0.86 mL, 14 mmol) and 1 M aqueous sodium hydroxide solution (0.93 mL, 0.93 mmol) were added to a solution of methyl 3-(5-cyano-1-(2-methoxyethyl)-6-(trifluoromethyl)-1H-benzo[d]imidazol-2-ylamino)benzoate (195 mg, 0.47 mmol) in THF/MeOH (4:1, 2 mL), and the resulting solution stirred for 3 h at room temperature. The crude product was purified by prep-HPLC with the following conditions: Column: Xbridge RP18 19×150; mobile phase: water with 0.05% TFA and ACN (5% ACN up to 59% in 7 min); Detector: 254, 220 nm. The collected fraction was lyophilized to give 3-(5-cyano-1-(2-methoxyethyl)-6-(trifluoromethyl)-1H-benzo[d]imidazol-2-ylamino)-N-hydroxybenzamide (12 mg, 6%) as an off-white solid. ¹H-NMR (DMSO, 400 MHz), δ (ppm): 11.22 (s, 1H), 9.46 (s, 1H), 9.05 (s, 1H), 8.18-8.09 (m, 3H), 7.99 (s, 1H), 7.47-7.38 (m, 2H), 4.62-4.60 (m, 2H), 3.69-3.67 (m, 2H), 3.22 (s, 3H). MS: (ESI, m/z): 420[M+H]⁺.

Example 20-1. N-hydroxy-3-(1-(2-methoxyethyl)-6-phenyl-5-(trifluoromethyl)-1H-benzo[d]imidazol-2-ylamino)benzamide

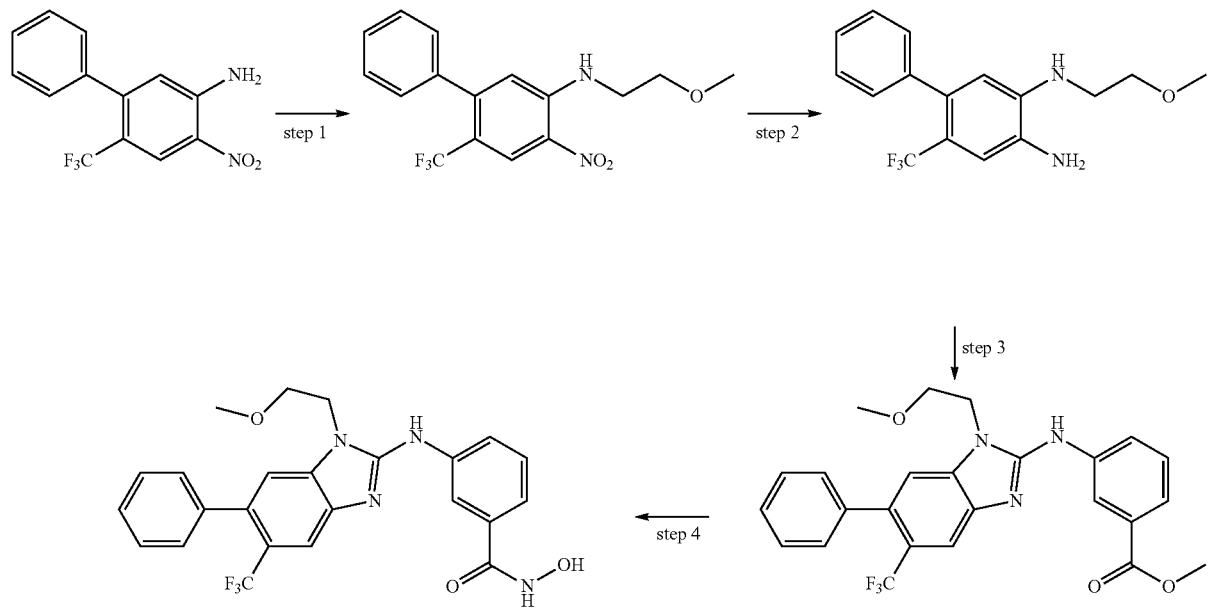

Step 1: N-(2-methoxyethyl)-4-nitro-6-(trifluoromethyl)biphenyl-3-amine

Sodium hydride (60% dispersion in mineral oil, 709 mg, 17.9 mmol) was added in portions to a 0° C. solution of 4-nitro-6-(trifluoromethyl)biphenyl-3-amine (1.00 g, 3.54 mmol) in DMF (50 mL). The reaction mixture stirred for 1 h at room temperature and was then cooled to 0° C. 2-Bromoethyl methyl ether (1.66 g, 17.9 mmol) was added dropwise, and the resulting solution was stirred overnight at room temperature. The reaction was poured into 100 mL of ice/water and extracted with 3×100 mL of ethyl acetate. The combined organic phases were washed with 3×100 mL of brine, dried over anhydrous sodium sulfate, filtered, and concentrated under vacuum. The residue was purified via column chromatography with silica gel (eluting with ethyl acetate/petroleum ether (1:10)) to give N-(2-methoxyethyl)-4-nitro-6-(trifluoromethyl)biphenyl-3-amine (1 g, 83%) as a yellow solid. MS: (ESI, m/z): 341[M+H]$^+$.

Step 2: N3-(2-methoxyethyl)-6-(trifluoromethyl) biphenyl-3,4-diamine

A mixture of N-(2-methoxyethyl)-4-nitro-6-(trifluoromethyl)biphenyl-3-amine (1 g, 2.94 mmol) and 10% palladium on carbon (150 mg) in methanol (50 mL) stirred under an atmosphere of hydrogen for 2 h at room temperature. The reaction mixture was filtered, and the filtrate was concentrated under vacuum to give N3-(2-methoxyethyl)-6-(trifluoromethyl)biphenyl-3,4-diamine (900 mg, crude) as yellow oil. MS: (ESI, m/z): 311[M+H]$^+$.

Step 3: methyl 3-(1-(2-methoxyethyl)-6-phenyl-5-(trifluoromethyl)-1H-benzo[d]imidazol-2-ylamino) benzoate A solution of N3-(2-methoxyethyl)-6-(trifluoromethyl)biphenyl-3,4-diamine (200 mg, 0.64 mmol), methyl 3-isothiocyanatobenzoate (137 mg, 0.71 mmol), and CDI (203 mg, 1.25 mmol) in THF (20 mL) stirred overnight at 75° C. The resulting solution was cooled to room temperature, poured into 50 mL of water, and extracted with 3×50 mL of ethyl acetate. The combined organic phases were washed with 100 mL of brine, dried over anhydrous sodium sulfate, filtered, and concentrated under vacuum. The residue was purified via column chromatography with silica gel (eluting with ethyl acetate/petroleum ether (1:1)) to give N3-(2-methoxyethyl)-6-(trifluoromethyl)biphenyl-3,4-diamine (200 mg, 66%) as yellow oil. MS: (ESI, m/z): 470[M+H]$^+$.

Step 4: N-hydroxy-3-(1-(2-methoxyethyl)-6-phenyl-5-(trifluoromethyl)-1H-benzo[d]imidazol-2-ylamino) benzamide Hydroxyl amine solution (50% in water, 0.78 mL, 12.8 mmol) and 1 M aqueous sodium hydroxide solution (0.42 mL, 0.42 mmol) were added to a solution of methyl 3-(1-(2-methoxyethyl)-6-phenyl-5-(trifluoromethyl)-1H-benzo[d]imidazol-2-ylamino)benzoate (100 mg, 0.21 mmol) in THF/MeOH (4:1, 3 mL), and the resulting solution stirred for 2 h at room temperature. The solids were filtered out. The crude product was purified by prep-HPLC with the following conditions: Sunfire C18 Column 19*150 mn; mobile phase, water with 0.05% TFA and CH$_3$CN (25 mL/min, 5-55% B within 1.1 min); Detector, 254 nm. The collected fraction was lyophilized to give N-hydroxy-3-(1-(2-methoxyethyl)-6-phenyl-5-(trifluoromethyl)-1H-benzo[d]imidazol-2-ylamino)benzamide (72.4 mg, 72%) as a pink solid. $^1$H-NMR (DMSO, 400 MHz), δ (ppm): 11.23 (s, 1H), 9.42 (s, 1H), 8.17-8.12 (m, 2H), 7.76 (s, 1H), 7.48-7.35 (m, 8H), 4.53-4.51 (m, 2H), 3.68-3.65 (m, 2H), 3.23 (s, 3H). MS: (ESI, m/z): 471[M+H]$^+$.

The following compound were prepared according to the procedures outlined above for N-hydroxy-3-(1-(2-methoxyethyl)-6-phenyl-5-(trifluoromethyl)-1H-benzo[d]imidazol-2-ylamino)benzamide

| Ex. | Structure | Name | ¹HNMR | (ESI, m/z) [M + H]⁺ |
|---|---|---|---|---|
| 20-2 | 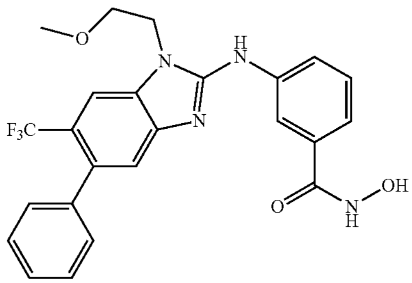 [SMILES: COCCn1c(Nc2cccc(C(=O)NO)c2)nc2cc(-c3ccccc3)c(C(F)(F)F)cc21] | N-hydroxy-3-((1-(2-methoxyethyl)-5-phenyl-6-(trifluoromethyl)-1H-benzo[d]imidazol-2-yl)amino)benzamide | (DMSO, 400 MHz, ppm): 11.22 (br, 1H), 9.56 (br, 1H), 8.09 (s, 2H), 7.87 (s, 1H), 7.48-7.38 (m, 5H), 7.34-7.25 (m, 3H), 4.59-4.70 (m, 2H), 3.73-3.71 (m, 2H), 3.28 (s, 3H) | 471 |

Example 21-1. 3-(1-(5-aminopentyl)-5-cyano-6-(trifluoromethyl)-1H-benzo[d]imidazol-2-ylamino)-N-hydroxybenzamide Formate

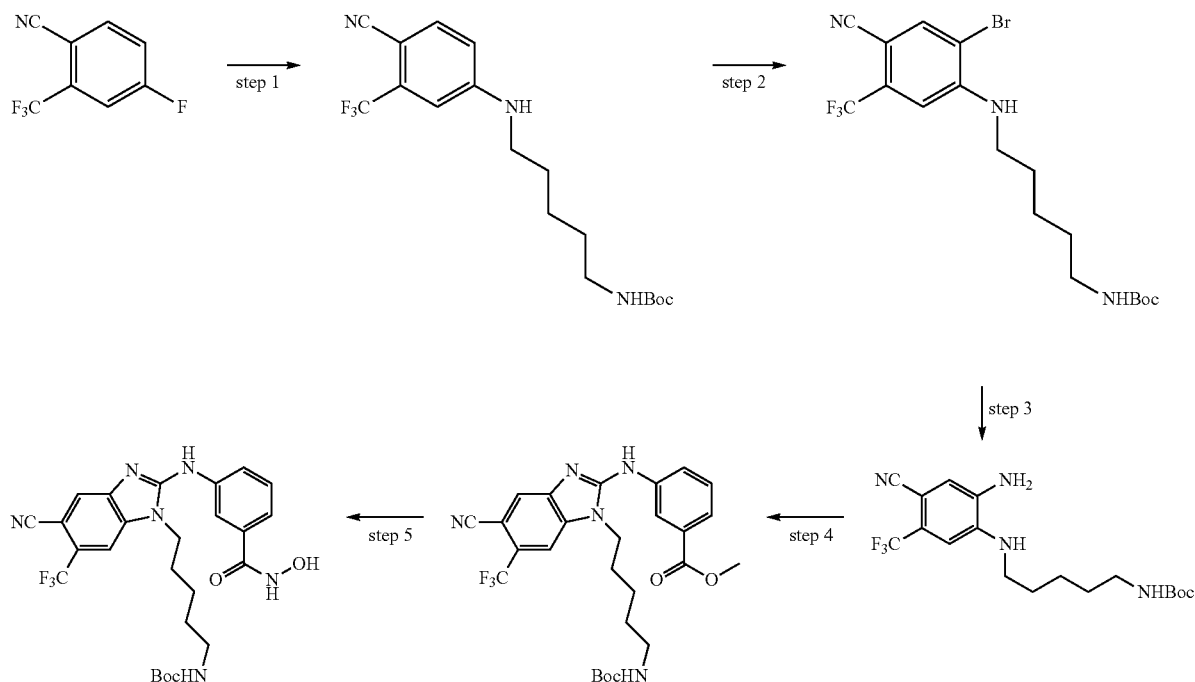

Step 1: tert-butyl 5-(4-cyano-3-(trifluoromethyl)phenylamino)pentylcarbamate

A solution of 4-fluoro-2-(trifluoromethyl)benzonitrile (7.00 g, 37.1 mmol), tert-butyl N-(5-aminopentyl)carbamate (10 g, 49.43 mmol), and N,N-diisopropylethyl amine (11 g, 85.11 mmol) in DMF (100 mL) stirred for 6 h at room temperature. The resulting solution was diluted with 400 mL of ethyl acetate, washed with 2×200 mL brine, dried over anhydrous sodium sulfate, filtered, and concentrated under vacuum. The residue was purified via column chromatography with silica gel (eluting with ethyl acetate/petroleum ether (1:1)) to give tert-butyl 5-(4-cyano-3-(trifluoromethyl)phenylamino)pentylcarbamate (11 g, 60%) as colorless oil. MS: (ESI, m/z): 372[M+H]⁺.

Step 2: tert-butyl 5-(2-bromo-4-cyano-5-(trifluoromethyl)phenylamino)pentylcarbamate A solution of tert-butyl 5-(4-cyano-3-(trifluoromethyl)phenylamino)pentylcarbamate (6.000 g, 16.16 mmol) and NBS (3.450 g, 19.38 mmol) in DMF (30 mL) stirred for 2 h at room temperature. The resulting solution was poured into 100 mL of water and extracted with 2×100 mL of ethyl acetate. The combined organic phases were washed with 3×200 mL of brine, dried over anhydrous sodium sulfate, filtered, and concentrated under vacuum. The residue was purified via column chromatography with silica gel (eluting with ethyl acetate/petroleum ether (1:2)) to give tert-butyl 5-(2-bromo-4-cyano-5-(trifluoromethyl)phenylamino)pentylcarbamate (6 g, 82%) as a colorless solid. MS: (ESI, m/z): 450[M+H]⁺.

Step 3: tert-butyl 5-(2-amino-4-cyano-5-(trifluoromethyl)phenylamino)pentylcarbamate A solution of tert-butyl 5-(2-bromo-4-cyano-5-(trifluoromethyl)phenylamino)pentylcarbamate (3.00 g, 6.67 mmol), copper(II) acetylacetonate (1.74 g, 6.67 mmol), and ammonium hydroxide (15 mL) in DMF (15 mL) stirred for 16 h at 90° C. in an oil bath. The resulting solution was cooled to room temperature and then diluted with 200 mL of ethyl acetate. The resulting solution was washed with 3×100 mL of brine, dried over anhydrous sodium sulfate, filtered, and concentrated under vacuum. The residue was purified via column chromatography with silica gel (eluting with ethyl acetate/petroleum ether (1:1)) to give tert-butyl 5-(2-amino-4-cyano-5-(trifluoromethyl)phenylamino)pentylcarbamate (2.4 g, 93%) as a purple solid. MS: (ESI, m/z): 387[M+H]$^+$.

Step 4: methyl 3-(1-(5-(tert-butoxycarbonylamino)pentyl)-5-cyano-6-(trifluoromethyl)-1H-benzo[d]imidazol-2-ylamino)benzoate Methyl 3-isothiocyanatobenzoate (550 mg, 2.85 mmol) was added to a solution of tert-butyl 5-(2-amino-4-cyano-5-(trifluoromethyl)phenylamino)pentylcarbamate (1.00 g, 2.59 mmol) in DMF (5 mL), and the reaction mixture stirred for 16 h at room temperature. DIC (490 mg, 3.89 mmol) was added, and the resulting solution stirred for 3 h at 80° C. The reaction mixture was cooled to room temperature, diluted with 100 mL of ethyl acetate, washed with 2×50 mL of brine, dried over anhydrous sodium sulfate, filtered, and concentrated under vacuum. The residue was purified via column chromatography with silica gel (eluting with ethyl acetate/petroleum ether (1:1)) to give methyl 3-(1-(5-(tert-butoxycarbonylamino)pentyl)-5-cyano-6-(trifluoromethyl)-1H-benzo[d]imidazol-2-ylamino)benzoate (850 mg, 60%) as a brown solid. MS: (ESI, m/z): 546[M+H]$^+$.

Step 5: 3-(1-(5-aminopentyl)-5-cyano-6-(trifluoromethyl)-1H-benzo[d]imidazol-2-ylamino)-N-hydroxybenzamide Formate Hydroxyl amine solution (50% in water, 2.69 mL, 44.0 mmol) and 1 M aqueous sodium hydroxide solution (0.74 mL, 0.74 mmol) were added to a solution of methyl 3-(1-(5-(tert-butoxycarbonylamino)pentyl)-5-cyano-6-(trifluoromethyl)-1H-benzo[d]imidazol-2-ylamino)benzoate (200 mg, 0.37 mmol) in THF/MeOH (4:1, 5 mL), and the resulting solution stirred for 2 h at room temperature. The pH value of the solution was adjusted to 2 with 6 M aqueous HCl solution and the resulting solution stirred at room temperature for 15 h. The pH value of the solution was adjusted to 6 with 4 M aqueous sodium hydroxide solution and the crude product was purified by prep-HPLC with the following conditions: Column,)(Bridge Prep C18 OBD Column, 150 mm 5 um; mobile phase, water (0.1% FA) and ACN (20.0% ACN up to 30.0% in 8 min); Detector, UV 254 & 220 nm. The collected fraction was lyophilized to give 3-(1-(5-aminopentyl)-5-cyano-6-(trifluoromethyl)-1H-benzo[d]imidazol-2-ylamino)-N-hydroxybenzamide formate (3.1 mg, 2%) as an orange solid. $^1$H-NMR: (DMSO, 300 MHz, ppm): δ 8.50 (s, 1H), 8.27-87.98 (m, 5H), 7.46-7.38 (m, 2H), 4.41-4.35 (m, 2H), 2.66-2.60 (m, 2H), 1.69-1.60 (m, 2H), 1.52-1.39 (m, 4H). MS: (ESI, m/z): 447[M+H]$^+$.

Example 22-1. 3-(1-(5-aminopentyl)-5,6-dichloro-1H-benzo[d]imidazol-2-ylamino)-N-hydroxybenzamide Formate

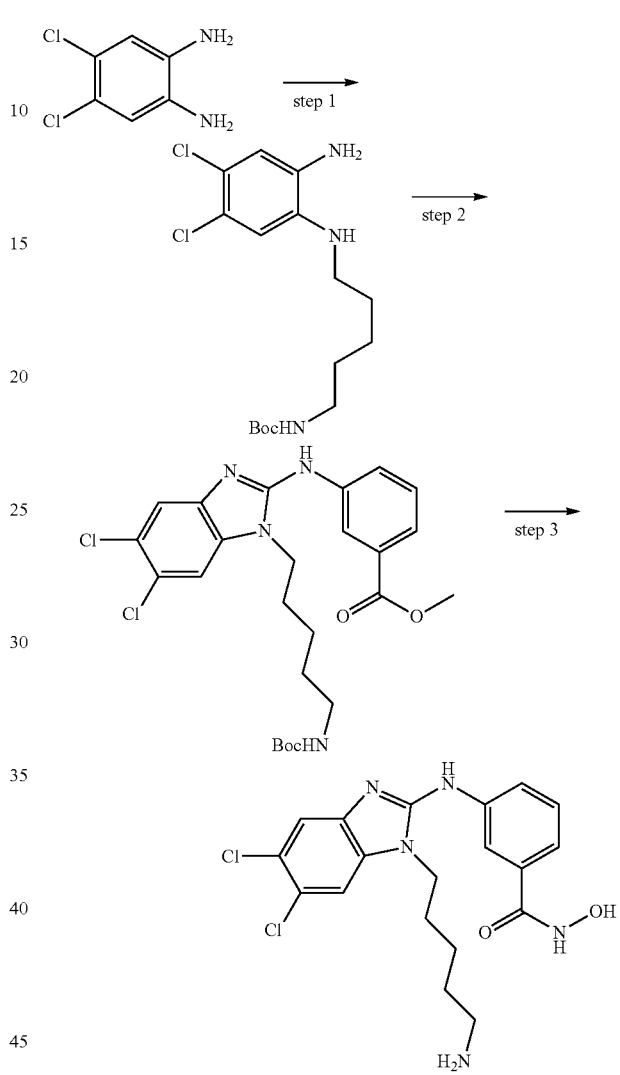

Step 1: tert-butyl 5-(2-amino-4,5-dichlorophenylamino)pentylcarbamate

A solution of 4,5-dichlorobenzene-1,2-diamine (350 mg, 1.99 mmol), tert-butyl N-(5-bromopentyl)carbamate (1.05 g, 3.94 mmol), potassium carbonate (819 mg, 5.93 mmol), and sodium iodide (297 mg, 1.99 mmol) in DMF (20 mL) stirred for 18 h at 80° C. The resulting solution was cooled to room temperature, diluted with 50 mL of water, and extracted with 3×40 mL of ethyl acetate. The combined organic phases were washed with 2×30 mL of brine, dried over anhydrous sodium sulfate, filtered, and concentrated under vacuum. The residue was purified via column chromatography with silica gel (eluting with dichloromethane/methanol (20:1)) to give tert-butyl 5-(2-amino-4,5-dichlorophenylamino)pentylcarbamate (339 mg, 44%) as brown oil. MS: (ESI, m/z): 362[M+H]$^+$.

Step 2: methyl 3-(1-(5-(tert-butoxycarbonylamino)pentyl)-5,6-dichloro-1H-benzo[d]imidazol-2-ylamino)benzoate Methyl 3-isothiocyanatobenzoate (219 mg, 1.13 mmol) was added to a solution of tert-butyl 5-(2-amino-4,5-dichlorophenylamino)pentylcarbamate (339 mg, 0.87 mmol) in DMF (10 mL), and the reaction mixture stirred for 18 h at room temperature. DIC (164 mg, 1.30 mmol) was added, and the resulting solution was stirred for 4 h at 80° C. The reaction mixture was cooled to room temperature, poured into 50 mL of water, and extracted with 3×50 mL of ethyl acetate. The combined organic phases were washed with 3×30 mL of brine, dried over anhydrous sodium sulfate, filtered, and concentrated under vacuum. The residue was purified via column chromatography with silica gel (eluting with ethyl acetate/petroleum ether (1:2)) to give methyl 3-(1-(5-(tert-butoxycarbonylamino)pentyl)-5,6-dichloro-1H-benzo[d]imidazol-2-ylamino)benzoate (300 mg, 38%) as brown oil. MS: (ESI, m/z): 521 [M+H]⁺.

Step 3: 3-(1-(5-aminopentyl)-5,6-dichloro-1H-benzo[d]imidazol-2-ylamino)-N-hydroxybenzamide Formate Hydroxyl amine solution (50% in water, 2.41 mL, 39.4 mmol) and 1 M aqueous sodium hydroxide solution (0.66 mL, 0.66 mmol) were added to a solution of methyl 3-(1-(5-(tert-butoxycarbonylamino)pentyl)-5,6-dichloro-1H-benzo[d]imidazol-2-ylamino)benzoate (300 mg, 0.33 mmol) in THF/MeOH (4:1, 5 mL), and the resulting solution stirred for 5 h at room temperature. The pH value of the solution was adjusted to 2 with 6 M aqueous HCl solution and the resulting solution stirred at room temperature for 15 h. The pH value of the solution was then adjusted to 6 with 4 M aqueous sodium hydroxide solution. The solids were collected by filtration and purified by prep-HPLC with the following conditions: Column, XBridge Shield RP18 OBD Column, 5 um, 19×150 mm; mobile phase, water (0.1% FA) and ACN (3.0% ACN up to 30.0% in 9 min); Detector, UV 220/254 nm. The collected fraction was lyophilized to give 3-(1-(5-aminopentyl)-5,6-dichloro-1H-benzo[d]imidazol-2-ylamino)-N-hydroxybenzamide formate (36.0 mg, 23%) as an off-white solid. ¹H-NMR: (DMSO, 400 MHz) δ (ppm): 8.85 (br, 3H), 8.47 (s, 1H), 8.17-8.15 (m, 2H), 7.68 (s, 1H), 7.57 (s, 1H), 7.40-7.36 (m, 1H), 7.31 (d, J=7.6 Hz, 1H), 4.26-4.22 (m, 2H), 2.71-2.65 (m, 2H), 1.67-1.61 (m, 2H), 1.57-1.50 (m, 2H), 1.40-1.32 (m, 2H). MS: (ESI, m/z): 422[M+H]⁺.

The following compound was prepared according to the procedures outlined above for 3-(1-(5-aminopentyl)-5,6-dichloro-1H-benzo[d]imidazol-2-ylamino)-N-hydroxybenzamide formate

| Ex. | Structure | Name | ¹H NMR | (ESI, m/z) [M + H]⁺ |
|---|---|---|---|---|
| 22-2 | 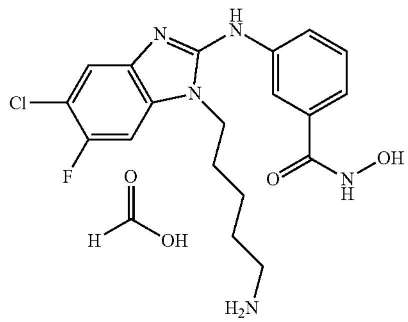 | 3-((1-(5-aminopentyl)-5-chloro-6-fluoro-1H-benzo[d]imidazol-2-yl)amino)-N-hydroxybenzamide formate | (DMSO, 300 MHz, ppm): 8.80 (s, 2H), 8.48 (s, 1H), 8.17-8.15 (m, 2H), 7.59-7.50 (m, 2H), 7.41-7.29 (m, 2H), 4.25-4.21 (m, 2H), 2.69-2.65 (m, 2H), 1.66-1.62 (m, 2H), 1.52-1.50 (m, 2H), 1.34-1.32 (m, 2H) | 406 [M − FA + H]⁺ |

Example 23-1. N-hydroxy-3-((1-(2-methoxyethyl)-1H-benzo[d]imidazol-2-yl)amino)benzamide

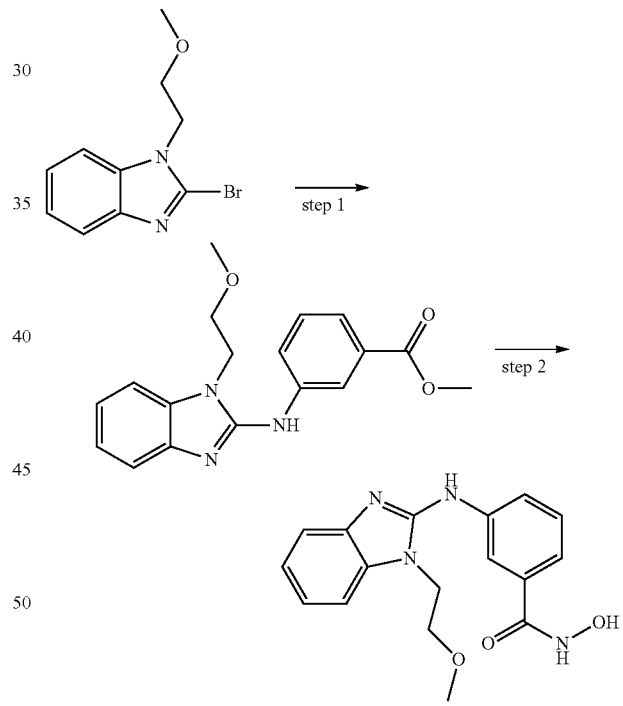

Step 1: methyl 3-((1-(2-methoxyethyl)-1H-benzo[d]imidazol-2-yl)amino)benzoate

A solution of 2-bromo-1-(2-methoxyethyl)-1H-benzo[d]imidazole (150 mg, 0.58 mmol), methyl 3-aminobenzoate (89 mg, 0.58 mmol), and methanesulfonic acid (76 μL, 1.17 mmol) in DMA (3.9 mL) was heated overnight at 80° C. The resulting mixture was cooled to room temperature and diluted with ethyl acetate and water. The resulting white precipitate was collected by suction filtration and dried under vacuum to give methyl 3-((1-(2-methoxyethyl)-1H-benzo[d]imidazol-2-yl)amino)benzoate (150 mg, 78%) as a white solid. $^1$H NMR (300 MHz, DMSO-d$_6$) δ ppm 11.05 (s, 1H) 10.88-11.17 (m, 1H) 8.10 (s, 1H) 7.80-7.93 (m, 2H) 7.58-7.72 (m, 2H) 7.39-7.43 (m, 1H) 7.25-7.37 (m, 2H) 4.58 (br t, J=4.98 Hz, 2H) 3.89 (s, 3H) 3.75 (t, J=5.13 Hz, 2H) 3.27 (s, 3H). MS: (ESI, m/z): 326[M+H]$^+$.

Step 2: N-hydroxy-3-((1-(2-methoxyethyl)-1H-benzo[d]imidazol-2-yl)amino)benzamide Hydroxyl amine solution (50% in water, 2.5 mL, 41.5 mmol) and 1 M aqueous sodium hydroxide solution (1.38 mL, 1.38 mmol) were added to a solution of methyl 3-((1-(2-methoxyethyl)-1H-benzo[d]imidazol-2-yl)amino)benzoate (150 mg, 0.46 mmol) in THF/MeOH (4:1, 4 mL), and the resulting solution stirred for 2 h at room temperature. The reaction mixture was concentrated by half then 1 N aqueous HCl solution was added until the solution became acidic. The resulting white precipitate was collected by suction filtration and dried under high vacuum to give N-hydroxy-3-((1-(2-methoxyethyl)-1H-benzo[d]imidazol-2-yl)amino)benzamide (105 mg, 70%) as a white solid. $^1$H NMR (300 MHz, DMSO-d$_6$) δ ppm 11.11 (s, 1H) 9.79-10.08 (m, 1H) 8.95 (br d, J=1.47 Hz, 1H) 8.00-8.17 (m, 2H) 7.17-7.39 (m, 4H) 6.92-7.05 (m, 2H) 4.37 (t, J=5.42 Hz, 2H) 3.59 (t, J=5.42 Hz, 2H) 3.17 (s, 3H). MS: (ESI, m/z): 327 [M+H]$^+$.

The compounds in the following table were prepared according to the procedures for N-hydroxy-3-((1-(2-methoxyethyl)-1H-benzo[d]imidazol-2-yl)amino)benzamide Example 24-1. N-hydroxy-3-((4-methoxy-1-(2-methoxyethyl)-1H-benzo[d]imidazol-2-yl)amino)benzamide

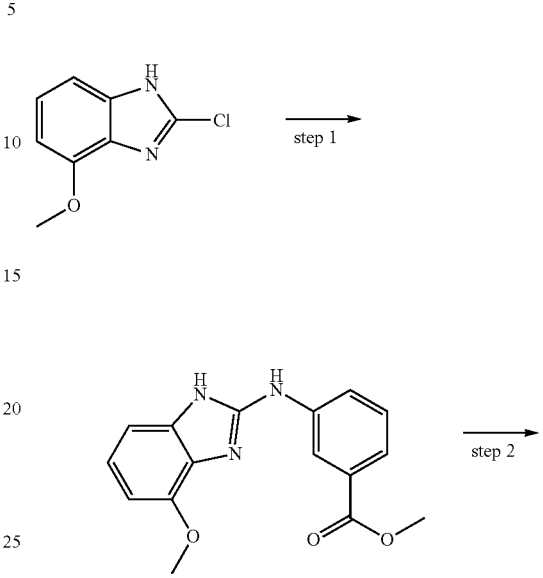

| Ex. | Structure | Name | $^1$HNMR | (ESI, m/z) [M + H]$^+$ |
|---|---|---|---|---|
| 23-2 | 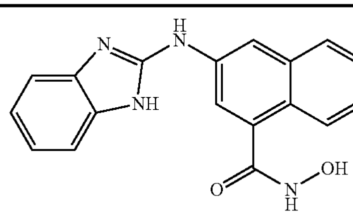 | 3-((1H-benzo[d]imidazol-2-yl)amino)-N-hydroxy-1-naphthamide | $^1$H NMR (300 MHz, DMSO-d$_6$) δ ppm 11.27-11.38 (m, 1 H) 11.11 (br d, J = 2.35 Hz, 1 H) 9.97 (br s, 1 H) 9.18-9.29 (m, 1 H) 8.51 (d, J = 2.05 Hz, 1 H) 8.22 (s, 1 H) 8.01 (d, J = 8.50 Hz, 1 H) 7.82-7.89 (m, 1 H) 7.24-7.53 (m, 4 H) 6.94-7.08 (m, 2 H) | 319 |
| 23-3 | 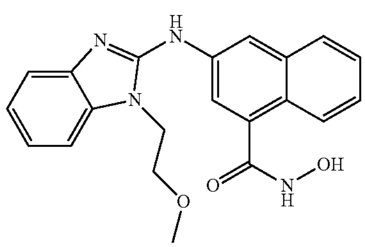 [SMILES: COCCn1c(Nc2cc(C(=O)NO)c3ccccc3c2)nc2ccccc21] | N-hydroxy-3-((1-(2-methoxyethyl)-1H-benzo[d]imidazol-2-yl)amino)-1-naphthamide | $^1$H NMR (300 MHz, DMSO-d$_6$) δ ppm 11.13 (br s, 1 H) 9.23-9.32 (m, 1 H) 9.11-9.15 (m, 1 H) 8.62 (s, 1 H) 7.98-8.05 (m, 2 H) 7.86 (d, J = 7.92 Hz, 1 H) 7.33-7.53 (m, 4 H) 7.01-7.12 (m, 2 H) 4.48 (br t, J = 5.28 Hz, 2 H) 3.68 (t, J = 5.28 Hz, 2 H) 3.25 (s, 3 H) | 377 |
| 23-4 | 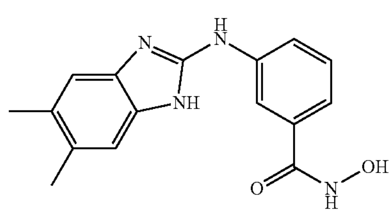 [SMILES: Cc1cc2nc(Nc3cccc(C(=O)NO)c3)[nH]c2cc1C] | 3-((5,6-dimethyl-1H-benzo[d]imidazol-2-yl)amino)-N-hydroxybenzamide | $^1$H NMR (300 MHz, DMSO-d$_6$) δ ppm 11.14 (s, 1 H) 10.74-10.81 (m, 1 H) 9.46 (br d, J = 2.05 Hz, 1 H) 9.01 (br s, 1 H) 8.14 (s, 1 H) 7.98 (s, 1 H) 7.30-7.38 (m, 1 H) 7.20 (br d, J = 7.92 Hz, 1 H) 7.13 (br s, 1 H) 7.06 (br d, J = 2.35 Hz, 1 H) 2.25 (s, 6 H) | 297 |

-continued

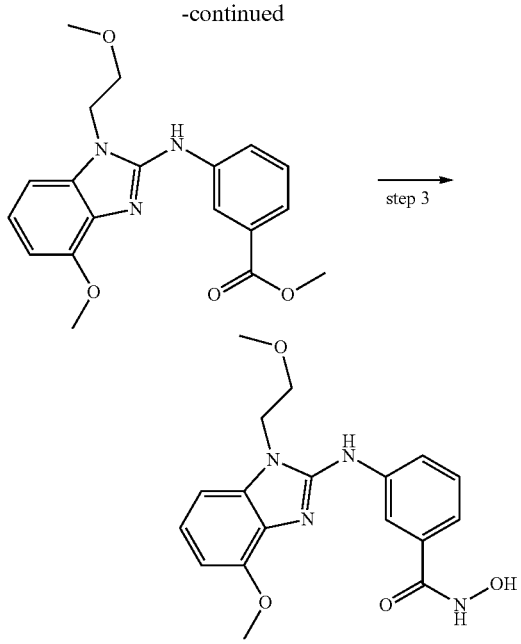

Step 1: methyl 3-((4-methoxy-1H-benzo[d]imidazol-2-yl)amino)benzoate

A solution of 2-chloro-4-methoxy-1H-benzo[d]imidazole (100 mg, 0.54 mmol), methyl 3-aminobenzoate (83 mg, 0.54 mmol), and methanesulfonic acid (71 µL, 1.1 mmol) in NMP (3 mL) was heated overnight at 80° C. The resulting mixture was cooled to room temperature and then diluted with ethyl acetate and water. The resulting white precipitate was collected by suction filtration and dried under vacuum to give methyl 3-((4-methoxy-1H-benzo[d]imidazol-2-yl)amino) benzoate (100 mg, 61%) as a white solid. $^1$H NMR (300 MHz, DMSO-$d_6$) δ ppm 10.76 (s, 1H) 8.07 (br d, J=2.35 Hz, 1H) 7.73-7.87 (m, 2H) 7.54-7.66 (m, 1H) 7.15-7.24 (m, 1H) 7.03 (d, J=7.92 Hz, 1H) 6.91 (br d, J=8.50 Hz, 1H) 3.95 (s, 3H) 3.88 (s, 3H). MS: (ESI, m/z): 298[M+H]$^+$.

Step 2: methyl 3-((4-methoxy-1-(2-methoxyethyl)-1H-benzo[d]imidazol-2-yl)amino)benzoate Sodium hydride (60% dispersion in mineral oil, 13.5 mg, 0.33 mmol) was added to a solution of methyl 3-((4-methoxy-1H-benzo[d]imidazol-2-yl)amino)benzoate (100 mg, 0.33 mmol) in DMF (3 mL), and the mixture stirred for 20 minutes. 1-Bromo-2-methoxyethane (0.031 mL, 0.33 mmol) was added, and the resulting solution stirred overnight. The reaction was quenched by the addition of water (10 mL) and the resulting solution was extracted with 3×10 mL of ethyl acetate. The combined organics were concentrated under vacuum, and the residue was purified via column chromatography on silica gel (gradient elution with 5-40% ethyl acetate/hexane) to give methyl 3-(4-methoxy-1-(2-methoxyethyl)-1H-benzo[d]imidazol-2-ylamino)benzoate (31 mg, 26%) as a colorless oil. MS: (ESI, m/z): 356 [M+H]$^+$.

Step 3: N-hydroxy-3-((4-methoxy-1-(2-methoxyethyl)-1H-benzo[d]imidazol-2-yl)amino)benzamide Hydroxyl amine solution (50% in water, 0.16 mL, 2.6 mmol) and 1 M aqueous sodium hydroxide solution (0.26 mL, 0.26 mmol) were added to a solution of methyl 3-((4-methoxy-1-(2-methoxyethyl)-1H-benzo[d]imidazol-2-yl)amino)benzoate (31 mg, 0.087 mmol) in THF/MeOH (4:1, 2.5 mL), and the resulting solution stirred for 2 h at room temperature. 2 N aqueous HCl solution was added until the solution was acidic, and the resulting solution was concentrated. The residue was purified by Gilson prep-HPLC with acetonitrile and water (0.1% formic acid) and the desired fractions are concentrated and then lyophilized to give N-hydroxy-3-((4-methoxy-1-(2-methoxyethyl)-1H-benzo[d]imidazol-2-yl)amino)benzamide (20 mg, 65%) as a white solid. $^1$H NMR (300 MHz, DMSO-$d_6$) δ ppm 11.17 (s, 1H) 9.02 (d, J=1.47 Hz, 1H) 8.87 (s, 1H) 8.02-8.13 (m, 2H) 7.30-7.41 (m, 1H) 7.25 (br d, J=7.62 Hz, 1H) 7.00 (q, J=8.01 Hz, 2H) 6.69 (br d, J=7.62 Hz, 1H) 4.59 (br t, J=5.72 Hz, 2H) 3.89 (s, 3H) 3.63 (t, J=5.72 Hz, 2H) 3.23 (s, 3H). MS: (ESI, m/z): 357 [M+H]$^+$.

The compound in the following table was prepared according to the procedures for N-hydroxy-3-((4-methoxy-1-(2-methoxyethyl)-1H-benzo[d]imidazol-2-yl)amino)benzamide.

| Ex. | Structure | Name | $^1$H NMR | (ESI, m/z) [M + H]$^+$ |
|---|---|---|---|---|
| 24-2 | 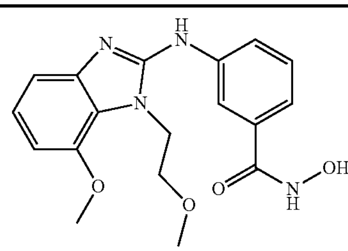 | N-hydroxy-3-((7-methoxy-1-(2-methoxyethyl)-1H-benzo[d]imidazol-2-yl)amino)benzamide | NA | 357 |

Example 25-1. N-hydroxy-3-((4-methoxy-1-(2-methoxyethyl)-1H-benzo[d]imidazol-2-yl)amino) benzamide

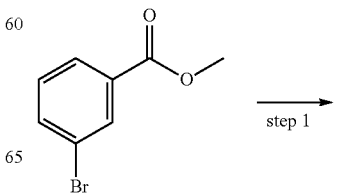

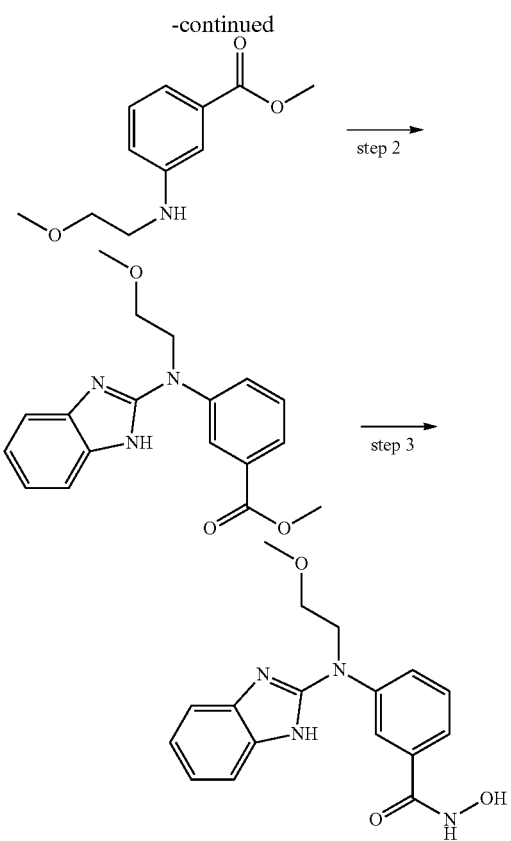

Step 1: methyl 3-((2-methoxyethyl)amino)benzoate

A solution of methyl 3-bromobenzoate (500 mg, 2.32 mmol), cesium carbonate (1.136 g, 3.49 mmol), Pd$_2$(dba)$_3$ (42 mg, 0.047 mmol), BINAP (43 mg, 0.07 mmol), and 2-methoxyethanamine (240 μL, 1.2 mmol) in toluene (10 mL) was heated overnight at 80° C. The resulting mixture was cooled to room temperature, diluted with ethyl acetate, and washed with brine. The organic layer was separated and concentrated, and the residue was purified via column chromatography on silica gel (gradient elution with 20-70% ethyl acetate/hexane) to give methyl 3-((2-methoxyethyl)amino)benzoate (250 mg, 51%) as a yellow semi-solid. $^1$H NMR (300 MHz, DMSO-d$_6$) δ ppm 7.09-7.23 (m, 3H) 6.78-6.89 (m, 1H) 5.96 (t, J=5.72 Hz, 1H) 3.79-3.81 (m, 3H) 3.48 (t, J=5.72 Hz, 2H) 3.27 (s, 3H) 3.15-3.25 (m, 2H). MS: (ESI, m/z): 210[M+H]$^+$.

Step 2: methyl 3-((1H-benzo[d]imidazol-2-yl)(2-methoxyethyl)amino)benzoate

A solution of 2-bromo-1H-benzo[d]imidazole (57 mg, 0.28 mmol), methyl 3-(2-methoxyethylamino)benzoate (60 mg, 0.28 mmol), and 6 M aqueous HCl solution (1 drop) in ethanol (1.5 mL) was irradiated with microwave radiation for 1 h at 150° C. The resulting mixture was cooled to room temperature and then concentrated under vacuum. The residue was purified via prep-HPLC with acetonitrile and water (0.1% formic acid) and the desired fractions were concentrated and then lyophilized to give methyl 3-((1H-benzo[d]imidazol-2-yl)(2-methoxyethyl)amino)benzoate (35 mg, 38%) as a white solid. MS: (ESI, m/z): 326[M+H]$^+$.

Step 3: 3-((1H-benzo[d]imidazol-2-yl)(2-methoxyethyl)amino)-N-hydroxybenzamide Hydroxyl amine solution (50% in water, 0.33 mL, 5.4 mmol) and 1 M aqueous sodium hydroxide solution (0.33 mL, 0.33 mmol) were added to a solution of methyl 3-((1H-benzo[d]imidazol-2-yl)(2-methoxyethyl)amino)benzoate (35 mg, 0.108 mmol) in THF/MeOH (4:1, 2.5 mL), and the resulting solution stirred for 2 h at room temperature. 2 N aqueous HCl solution was added until the solution was acidic, and the resulting solution was concentrated. The residue was purified by Gilson prep-HPLC with acetonitrile and water (0.1% formic acid) and the desired fractions were concentrated and then lyophilized to give 341H-benzo[d]imidazol-2-yl)(2-methoxyethyl)amino)-N-hydroxybenzamide (7 mg, 20%) as a white solid. $^1$H NMR (300 MHz, DMSO-d$_6$) δ ppm 11.27 (br s, 2H) 8.98-9.20 (m, 1H) 8.16 (s, 1H) 7.76 (s, 1H) 7.61 (br d, J=6.74 Hz, 1H) 7.50-7.58 (m, 1H) 7.31-7.50 (m, 1H) 7.21-7.31 (m, 1H) 7.12 (br d, J=3.22 Hz, 1H) 6.93 (s, 1H) 6.93 (br dd, J=11.29, 4.84 Hz, 2H) 4.09 (br d, J=6.16 Hz, 2H) 3.55-3.64 (m, 2H) 3.23 (s, 3H). MS: (ESI, m/z): 327 [M+H]$^+$.

Example 26-1: 3-(5-cyano-6-(trifluoromethyl)-1H-benzo[d]imidazol-2-yloxy)-N-hydroxybenzamide

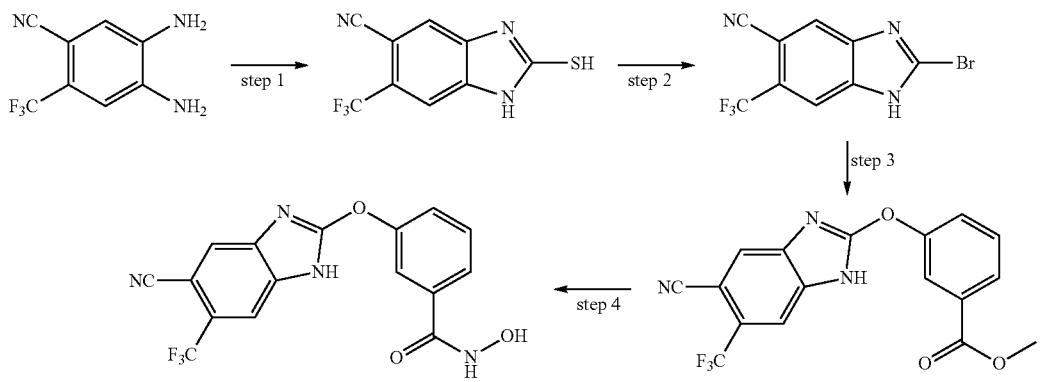

Step 1: 2-mercapto-6-(trifluoromethyl)-1H-benzo[d]imidazole-5-carbonitrile

Carbon disulfide (4.80 mL, 79.6 mmol) was added in portions to a solution of 4,5-diamino-2-(trifluoromethyl)benzonitrile (2.00 g, 9.94 mmol) and potassium hydroxide (1.67 g, 29.76 mmol) in ethanol (100 mL), and the resulting solution stirred for 5 h at 90° C. in an oil bath. The resulting mixture was cooled to room temperature and then concentrated under vacuum. The residue was diluted with 100 mL of water, the pH value of the resulting solution was adjusted to 7 with 2 M aqueous HCl solution, and the mixture was extracted with 3×200 mL of ethyl acetate. The combined organic phases were washed with 1×100 mL of brine, dried over anhydrous sodium sulfate, filtered, and concentrated under vacuum to afford 2-mercapto-6-(trifluoromethyl)-1H-benzo[d]imidazole-5-carbonitrile (1.9 g, 79%) as a red solid. MS: (ESI, m/z): 244[M+H]⁺.

Step 2: 2-bromo-6-(trifluoromethyl)-1H-benzo[d]imidazole-5-carbonitrile

Bromine (0.20 mL, 3.96 mmol) was added dropwise to a 0° C. solution of 2-mercapto-6-(trifluoromethyl)-1H-benzo[d]imidazole-5-carbonitrile (267 mg, 1.10 mmol) in hydrobromic acid (40% in acetic acid, 12 mL), and the resulting solution stirred for 3 h at 0° C. in a water/ice bath. The reaction mixture was concentrated under vacuum, and the residue was diluted with 10 mL of water. The pH value of the solution was adjusted to 4 with 1 M aqueous sodium hydroxide solution. The resulting solution was extracted with 3×20 mL of ethyl acetate, and the combined organic phases were dried over anhydrous sodium sulfate, filtered, and concentrated under vacuum. The residue was purified via column chromatography on silica gel (eluting with ethyl acetate/petroleum ether (1:1)) to afford 2-bromo-6-(trifluoromethyl)-1H-benzo[d]imidazole-5-carbonitrile (225 mg, 71%) as a yellow solid. MS: (ESI, m/z): 331 [M+H+CH₃CN]⁺.

Step 3: methyl 3-(5-cyano-6-(trifluoromethyl)-1H-benzo[d]imidazol-2-yloxy)benzoate A solution of 2-bromo-6-(trifluoromethyl)-1H-benzo[d]imidazole-5-carbonitrile (200 mg, 0.69 mmol), methyl 3-hydroxybenzoate (105 mg, 0.69 mmol), copper (5 mg), and potassium carbonate (286 mg, 2.05 mmol) in pyridine (20 mL) stirred for 24 h at 110° C. in an oil bath. The resulting solution was cooled to room temperature and then concentrated under vacuum. The residue was diluted with 20 mL of water and extracted with 3×20 mL of ethyl acetate. The combined organic phases were washed with 50 mL of water and 50 mL of brine, dried over anhydrous sodium sulfate, filtered, and concentrated under vacuum. The residue was purified via column chromatography on silica gel (eluting with methanol/dichloromethane (1:25)) to afford methyl 3-(5-cyano-6-(trifluoromethyl)-1H-benzo[d]imidazol-2-yloxy)benzoate (95 mg, 38%) as a yellow solid. MS: (ESI, m/z): 362[M+H]⁺

Step 4: 3-(5-cyano-6-(trifluoromethyl)-1H-benzo[d]imidazol-2-yloxy)-N-hydroxybenzamide Hydroxyl amine solution (50% in water, 0.27 mL, 4.2 mmol) and 1 M aqueous sodium hydroxide solution (0.28 mL, 0.28 mmol) were added to a solution of methyl 3-(5-cyano-6-(trifluoromethyl)-1H-benzo[d]imidazol-2-yloxy)benzoate (50 mg, 0.14 mmol) in THF/MeOH (4:1, 1.5 mL), and the resulting solution stirred for 6 h at room temperature. The crude product was purified by Prep-HPLC with the following conditions: Column,)(Bridge RP C18, 19×150 mm, 5 um; mobile phase, Mobile Phase A: water/0.05% TFA, Mobile Phase B: ACN; Flow rate: 25 mL/min; Gradient: 5% B to 54% B in 7.0 min; Detector, 254 nm. The collected fraction was lyophilized to afford 3-(5-cyano-6-(trifluoromethyl)-1H-benzo[d]imidazol-2-yloxy)-N-hydroxybenzamide (4.6 mg, 9%) as a red solid. ¹H-NMR: (DMSO, 300 MHz) δ (ppm): 11.31 (s, 1H), 9.13 (s, 1H), 8.18 (s, 1H), 7.94 (s, 1H), 7.76-7.67 (m, 2H), 7.59-7.57 (m, 2H). MS: (ESI, m/z): 363 [M+H]⁺

Example 27-1: 3-((5-cyano-6-(trifluoromethyl)-1H-benzo[d]imidazol-2-yl)methyl)-N-hydroxybenzamide

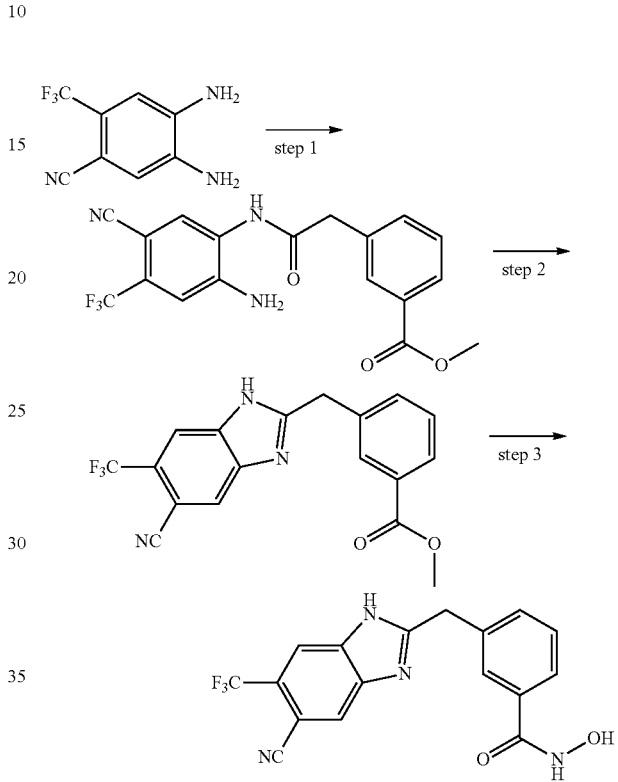

Step 1: methyl 3-(2-(2-amino-5-cyano-4-(trifluoromethyl)phenylamino)-2-oxoethyl)benzoate A solution of 4,5-diamino-2-(trifluoromethyl)benzonitrile (100 mg, 0.50 mmol), DMC (96 mg, 0.57 mmol), 2-[3-(methoxycarbonyl)phenyl]acetic acid (91.9 mg, 0.47 mmol), and N,N-diisopropylethyl amine (0.30 mL, 1.9 mmol) in dichloromethane (10 mL) stirred for 1 h at 25° C. The reaction mixture was then poured into 10 mL of water. The resulting solution was extracted with 3×10 mL of ethyl acetate, and the combined organic phases were dried over anhydrous sodium sulfate, filtered, and concentrated under vacuum. The residue was purified via column chromatography on silica gel (eluting with ethyl acetate/petroleum ether (1:4)) to afford methyl 3-(2-(2-amino-5-cyano-4-(trifluoromethyl)phenylamino)-2-oxoethyl)benzoate (160 mg, 90%) as a white solid. MS: (ESI, m/z): 378[M+H]⁺.

Step 2: methyl 3-((5-cyano-6-(trifluoromethyl)-1H-benzo[d]imidazol-2-yl)methyl)benzoate A solution of methyl 3-(2-(2-amino-5-cyano-4-(trifluoromethyl)phenylamino)-2-oxoethyl)benzoate (100 mg, 0.27 mmol) in toluene (10 mL) and acetic acid (1 mL) stirred for 2 h at 110° C. in an oil bath. The resulting mixture was cooled to room temperature and then concentrated under vacuum. The residue was purified via column chromatography on silica gel (eluting with ethyl acetate/petroleum ether (1:3)) to afford methyl 3-((5-cyano-6-(trifluoromethyl)-1H-benzo[d]imidazol-2-yl)methyl)benzoate (65 mg, 68%) as a yellow solid. MS: (ESI, m/z): 360[M+H]⁺.

Step 3: 3-((5-cyano-6-(trifluoromethyl)-1H-benzo[d]imidazol-2-yl)methyl)-N-hydroxybenzamide Hydroxyl amine solution (50% in water, 0.52 mL, 7.9 mmol) and 1 M aqueous sodium hydroxide solution (0.53 mL, 0.53 mmol) were added to a solution of methyl 3-((5-cyano-6-(trifluoromethyl)-1H-benzo[d]imidazol-2-yl)methyl)benzoate (95 mg, 0.26 mmol) in THF/MeOH (4:1, 2.0 mL), and the resulting solution stirred for 1.5 h at room temperature. The crude product was purified by Prep-HPLC with the following conditions: Column: Waters) (Bridge C18, 19*150 mm; Mobile Phase A: water/0.05% TFA, Mobile Phase B: ACN; Flow rate: 25 mL/min; Gradient: 30% B to 70% B in 10 min; Detector: 254 nm. The collected fraction was lyophilized to afford 3-((5-cyano-6-(trifluoromethyl)-1H-benzo[d]imidazol-2-yl)methyl)-N-hydroxybenzamide (34.3 mg, 36%) as a pink solid. ¹H-NMR: (DMSO, 400 MHz) δ (ppm): 11.20 (br, 1H), 8.38 (s, 1H), 8.12 (s, 1H), 7.74 (s, 1H), 7.62 (d, J=7.6 Hz, 1H), 7.50 (d, J=7.6 Hz, 1H), 7.43-7.39 (m, 1H), 4.36 (s, 2H). MS: (ESI, m/z): 361[M+H]⁺.

The following compound was prepared according to the procedures outlined above 3-((5-cyano-6-(trifluoromethyl)-1H-benzo[d]imidazol-2-yl)methyl)-N-hydroxybenzamide.

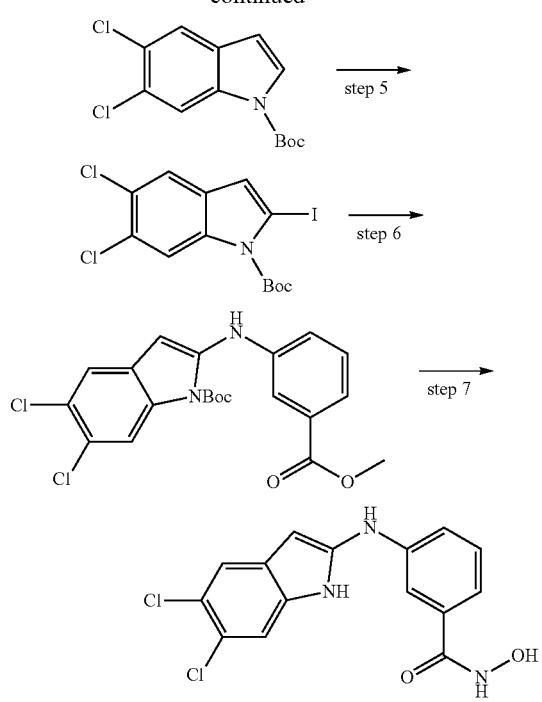

-continued

| Ex. | Structure | Name | ¹H NMR | (ESI, m/z) [M + H]⁺ |
|---|---|---|---|---|
| 27-2 | 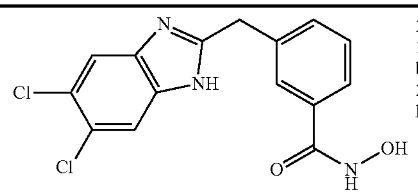 | 3-((5,6-dichloro-1H-benzo[d]imidazol-2-yl)methyl)-N-hydroxybenzamide | (DMSO, 300 MHz, ppm): 7.89 (s, 2H), 7.75 (s, 1H), 7.63 (d, J = 7.5Hz, 1H), 7.51-7.39 (m, 2H), 4.32 (s, 2H) | 336 |

Example 28-1: 3-(5,6-dichloro-1H-indol-2-ylamino)-N-hydroxybenzamide

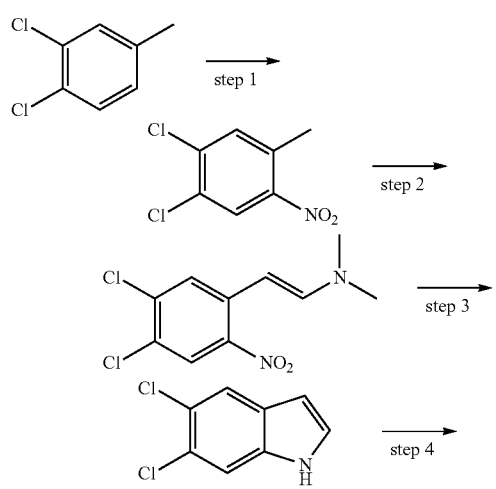

Step 1: 1,2-dichloro-4-methyl-5-nitrobenzene

Fuming nitric acid (40 mL) was added dropwise to 0° C. solution of 1,2-dichloro-4-methylbenzene (20 g, 124.20 mmol), and the resulting solution was stirred for 2 h at room temperature. The reaction mixture was then slowly poured into 200 mL of water/ice. The solids were collected by filtration and dried under vacuum to afford 1,2-dichloro-4-methyl-5-nitrobenzene (25.2 g, 98%) as a yellow solid. ¹H-NMR: (DMSO, 300 MHz) δ (ppm): 8.39 (s, 1H), 7.96 (s, 1H), 2.48 (s, 3H).

Step 2: (E)-2-(4,5-dichloro-2-nitrophenyl)-N,N-dimethylethenamine

A solution of 1,2-dichloro-4-methyl-5-nitrobenzene (25.2 g, 122 mmol), DMF (50 mL), and DMF-dimethyl acetal (19.8 mL, 147.90 mmol) was stirred for 3 h at 130° C. The resulting mixture was concentrated under vacuum. The residue was dissolved in 200 mL of ethyl acetate, washed with 200 mL of water and 200 mL of brine, dried over anhydrous sodium sulfate, filtered, and concentrated under vacuum to afford (E)-2-(4,5-dichloro-2-nitrophenyl)-N,N-dimethylethenamine (37 g) as a red solid. MS: (ESI, m/z): 261[M+H]⁺.

Step 3: 5,6-dichloro-1H-indole

Iron filings (133 g, 2.39 mmol) were added to a 60° C. solution of (E)-2-(4,5-dichloro-2-nitrophenyl)-N,N-dimethylethenamine (37 g, 120 mmol) and acetic acid (500 mL) in ethanol (500 mL), and the resulting solution stirred for 3 h at 90° C. The reaction mixture was cooled to room temperature and filtered. The filtrate was concentrated, and the residue was diluted with 500 mL of water and extracted with 2×500 mL of ethyl acetate. The combined organic phases were washed with 500 mL of brine, dried over anhydrous sodium sulfate, filtered, and concentrated under vacuum. The residue was purified via column chromatography on silica gel (eluting with ethyl acetate/petroleum ether (1:10)) to afford 5,6-dichloro-1H-indole (6 g, 27%) as a brown solid. MS: (ESI, m/z): 186[M+H]⁺.

Step 4: tert-butyl 5,6-dichloro-1H-indole-1-carboxylate

A solution of 5,6-dichloro-1H-indole (1.7 g, 9.14 mmol), 4-dimethylaminopyridine (1.4 g, 11.46 mmol), di-tert-butyl dicarbonate (2.4 g, 11.00 mmol), and THF (50 mL) stirred overnight at room temperature. The mixture was then diluted with 50 mL of ethyl acetate, washed with 50 mL of brine, dried over anhydrous sodium sulfate, filtered, and concentrated under vacuum. The residue was purified via column chromatography on silica gel (eluting with ethyl acetate/petroleum ether (1:30)) to afford tert-butyl 5,6-dichloro-1H-indole-1-carboxylate (2.0 g, 76%) as a light yellow solid. MS: (ESI, m/z): 286[M+H]⁺.

Step 5: tert-butyl 5,6-dichloro-2-iodo-1H-indole-1-carboxylate t-Butyllithium (1.5 M in pentane, 3.0 mL, 4.5 mmol) was added dropwise to a −78° C. solution of tert-butyl 5,6-dichloro-1H-indole-1-carboxylate (1.25 g, 4.37 mmol) in THF (50 mL), and the mixture stirred for 1 h at −78° C. A solution of iodine (3.3 g, 12.99 mmol) in THF (5 mL) was added dropwise, and the resulting solution stirred for 2 h at −78° C. The reaction was quenched by the addition of 5 mL of saturated aqueous ammonium chloride solution and then poured into 100 mL of water. The mixture was extracted with 3×100 mL of ethyl acetate, and the combined organic phases were washed with 100 mL of brine, dried over anhydrous sodium sulfate, filtered, and concentrated under vacuum. The residue was purified via column chromatography on silica gel (eluting with ethyl acetate/petroleum ether (1:20)) to afford tert-butyl 5,6-dichloro-2-iodo-1H-indole-1-carboxylate (1 g, 56%) as a pink solid. MS: (ESI, m/z): 412[M+H]⁺.

Step 6: tert-butyl 5,6-dichloro-2-(3-(methoxycarbonyl)phenylamino)-1H-indole-1-carboxylate A solution of tert-butyl 5,6-dichloro-2-iodo-1H-indole-1-carboxylate (120 mg, 0.29 mmol), methyl 3-aminobenzoate (60 mg, 0.40 mmol), cesium carbonate (180 mg, 0.55 mmol), Pd₂(dba)₃ (5 mg) and Xantphos (5 mg, 0.01 mmol) in toluene (12 mL) stirred for 1 h at 100° C. and was then cooled to room temperature. The mixture was concentrated under vacuum, and the residue was diluted with 20 mL of water and extracted with 2×20 mL of ethyl acetate. The combined organic phases were washed with 50 mL of brine, dried over anhydrous sodium sulfate, filtered, and concentrated. The residue was purified via column chromatography on silica gel (eluting with ethyl acetate/petroleum ether (1:1)) to afford tert-butyl 5,6-dichloro-2-(3-(methoxycarbonyl)phenylamino)-1H-indole-1-carboxylate (70 mg, 55%) as red oil. MS: (ESI, m/z): 335 [M-Boc+H]⁺.

Step 7: 3-(5,6-dichloro-1H-indol-2-ylamino)-N-hydroxybenzamide (PH-FMA-HD-400-0)

Hydroxyl amine solution (50% in water, 0.55 mL, 8.3 mmol) and 1 M aqueous sodium hydroxide solution (0.28 mL, 0.28 mmol) were added to a solution of tert-butyl 5,6-dichloro-2-(3-(methoxycarbonyl)phenylamino)-1H-indole-1-carboxylate (60 mg, 0.14 mmol) in THF/MeOH (4:1, 2.0 mL), and the resulting solution stirred for 4 h at room temperature. The crude product was purified via prep-HPLC with the following conditions: Column: XBridge RP C18, 19×150 mm, 5 um; Mobile Phase A: water/0.05% TFA, Mobile Phase B: ACN; Flow rate: 30 mL/min; Gradient: 5% B to 40% B in 6.0 min, 254 nm. The collected fraction was lyophilized to afford 3-(5,6-dichloro-1H-indol-2-ylamino)-N-hydroxybenzamide (16.6 mg, 36%) as a gray solid. ¹H-NMR: (DMSO, 400 MHz) δ (ppm): 11.17 (br, 1H), 10.87 (s, 1H), 8.93 (s, 1H), 7.61 (s, 2H), 7.40 (s, 1H), 7.35-7.27 (m, 1H), 7.25-7.19 (m, 2H), 5.98 (s, 1H). MS: (ESI, m/z): 336 [M+H]⁺.

Example 29-1: 3-(1H-imidazo[4,5-b]pyrazin-2-ylamino)-N-hydroxybenzamide

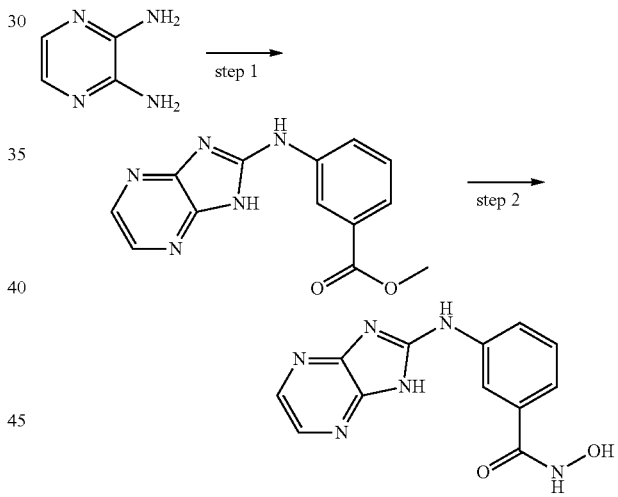

Step 1: methyl 3-(1H-imidazo[4,5-b]pyrazin-2-ylamino)benzoate

A solution of pyrazine-2,3-diamine (540 mg, 4.91 mmol) and methyl 3-isothiocyanatobenzoate (1.04 g, 5.40 mmol) in DMF (10 mL) stirred for 2 h at 100° C. in an oil bath. The resulting mixture was cooled to room temperature and then concentrated under vacuum. The residue was purified via column chromatography on silica gel (eluting with methanol/dichloromethane (1:5)) to afford methyl 3-(1H-imidazo[4,5-b]pyrazin-2-ylamino)benzoate (60 mg, 5%) as a yellow solid. MS: (ESI, m/z): 270 [M+H]⁺.

Step 2: 3-(1H-imidazo[4,5-b]pyrazin-2-ylamino)-N-hydroxybenzamide

Hydroxyl amine solution (50% in water, 0.15 mL, 2.3 mmol) and 1 M aqueous sodium hydroxide solution (0.23 mL, 0.23 mmol) were added to a solution of methyl 3-(1H-imidazo[4,5-b]pyrazin-2-ylamino)benzoate (21 mg, 0.08 mmol) in THF/MeOH (4:1, 2.0 mL), and the resulting solution stirred for 30 minutes at room temperature. The pH value of the solution was adjusted to 5-6 with 1 M aqueous HCl solution. The crude product was purified via Prep-HPLC with conditions: Column: XBridge RP C18, 19×150 mm, 5 um; Mobile Phase A: water/0.05% TFA, Mobile Phase B: ACN; Flow rate: 25 mL/min; Gradient: 4% B to 20% B in 7.0 min, 254 nm. The collected fraction was lyophilized to afford 3-(1H-imidazo[4,5-b]pyrazin-2-ylamino)-N-hydroxybenzamide (16.7 mg, 79%) as a yellow solid. $^{1}$H-NMR: (DMSO, 300 MHz) δ (ppm): 11.19 (br, 1H), 10.26 (br, 1H), 8.16 (s, 1H), 8.02 (s, 2H), 7.96 (d, J=7.5 Hz, 1H), 7.46-7.37 (m, 2H). MS: (ESI, m/z): 271 [M+H]$^{+}$.

Example 30-1:
3-(9H-purin-8-ylamino)-N-hydroxybenzamide

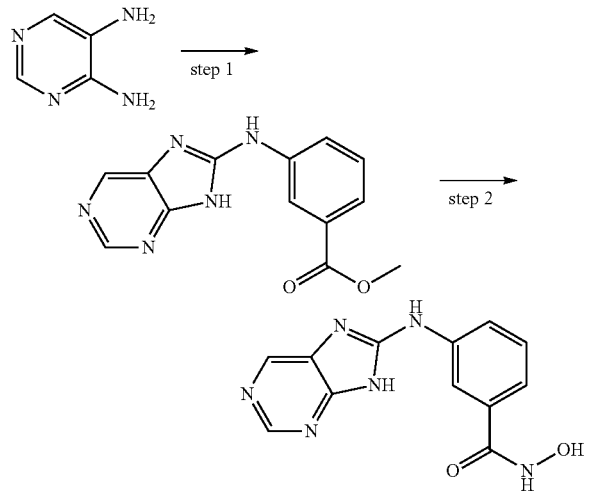

Step 1: methyl 3-(9H-purin-8-ylamino)benzoate

A solution of methyl 3-isothiocyanatobenzoate (170 mg, 0.88 mmol) in THF (2 mL) was added dropwise to a solution of pyrimidine-4,5-diamine (100 mg, 0.91 mmol) in THF (8 mL), and the resulting solution stirred overnight at 65° C. in an oil bath. DIC (0.43 mL, 2.72 mmol) was then dropwise, and the resulting solution was stirred for 5 h at 65° C. in an oil bath. The reaction mixture was cooled to room temperature and then diluted with 25 mL of water. The mixture was extracted with 3×20 of ethyl acetate, and the combined organic phases were washed with 1×10 mL of brine, dried over anhydrous sodium sulfate, filtered, and concentrated under vacuum. The residue was purified via preparative thin layer chromatography (eluting with methanol/dichloromethane (1:10)) to afford methyl 3-(9H-purin-8-ylamino)benzoate (43 mg, 18%) as a light yellow solid. MS: (ESI, m/z): 270 [M+H]$^{+}$.

Step 2: 3-(9H-purin-8-ylamino)-N-hydroxybenzamide

Hydroxyl amine solution (50% in water, 0.26 mL, 3.9 mmol) and 1 M aqueous sodium hydroxide solution (0.39 mL, 0.39 mmol) were added to a solution of methyl 3-(9H-purin-8-ylamino)benzoate in THF/MeOH (4:1, 2.0 mL), and the resulting solution stirred for 30 minutes at room temperature. The pH value of the solution was adjusted to 5-6 with 1 M aqueous HCl solution. The crude product was purified by Prep-HPLC with conditions: Column: XBridge RP C18, 19×150 mm, 5 um; Mobile Phase A: water/0.05% TFA, Mobile Phase B: ACN; Flow rate: 25 mL/min; Gradient: 4% B to 10% B in 7.0 min, 254 nm. The collected fraction was lyophilized to afford 3-(9H-purin-8-ylamino)-N-hydroxybenzamide (8.9 mg, 26%) as a light brown solid. $^{1}$H-NMR: (DMSO, 400 MHz) δ (ppm): 11.21 (br, 1H), 10.72 (br, 1H), 8.84 (s, 1H), 8.64 (s, 1H), 8.12 (s, 1H), 7.94 (d, J=7.6 Hz, 1H), 7.50-7.41 9 m, 2H). MS: (ESI, m/z): 271 [M+H]$^{+}$.

Example 31-1: 6-(5,6-dichlorobenzo[d]oxazol-2-ylamino)-N-hydroxypicolinamide

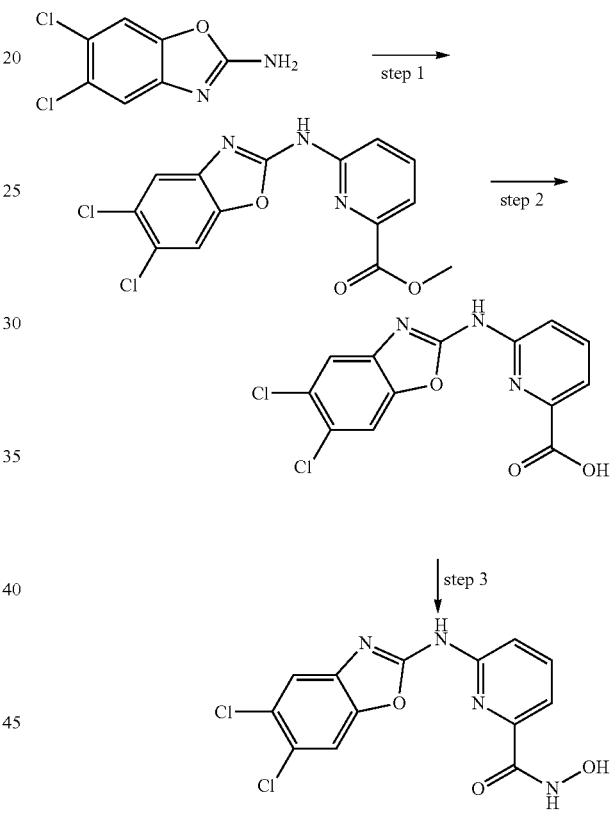

Step 1: methyl 6-(5,6-dichlorobenzo[d]oxazol-2-ylamino)picolinate

A solution of Pd(OAc)$_{2}$ (3 mg, 0.01 mmol) and t-Bu-BrettPhos (12 mg, 0.02 mmol) in tert-butanol (1 mL) and water (1 drop) stirred for 1.5 min at 110° C. in an oil bath and was then added dropwise via cannula to a solution of 5,6-dichloro-1,3-benzoxazol-2-amine (50 mg, 0.25 mmol), methyl 6-bromopyridine-2-carboxylate (53 mg, 0.25 mmol), and potassium carbonate (47.6 mg, 0.34 mmol) in tert-butanol (2 mL). The resulting solution stirred for 3 h at 110° C. and was then cooled to room temperature and concentrated under vacuum. The residue was diluted with 10 mL of water and extracted with 3×10 mL of ethyl acetate. The combined organic phases were dried over anhydrous sodium sulfate, filtered, and concentrated under vacuum to afford methyl 6-(5,6-dichlorobenzo[d]oxazol-2-ylamino)picolinate (95 mg) as a yellow solid. MS: (ESI, m/z): 338[M+H]$^+$.

Step 2: 6-(5,6-dichlorobenzo[d]oxazol-2-ylamino) picolinic Acid

A solution of lithium hydroxide (71 mg, 2.97 mmol) in water (2 mL) was added to a solution of methyl 6-(5,6-dichlorobenzo[d]oxazol-2-ylamino)picolinate (110 mg, 0.30 mmol) in THF (2 mL), and the resulting solution stirred for 2 h at room temperature. THF was removed under vacuum and the reaction mixture was diluted with 5 mL of water. The resulting solution was washed with 5 mL of ethyl acetate and the aqueous layer was separated and cooled to 0° C. The pH value of the solution was adjusted to 5 with 2 M aqueous HCl solution, and the resulting solution was extracted with 3×10 mL of ethyl acetate. The combined organic phases were dried over anhydrous sodium sulfate, filtered, and concentrated under vacuum to afford 6-(5,6-dichlorobenzo [d]oxazol-2-ylamino)picolinic acid (65 mg) as a yellow solid. MS: (ESI, m/z): 324[M+H]$^+$.

Step 3: 6-(5,6-dichlorobenzo[d]oxazol-2-ylamino)-N-hydroxypicolinamide

IPCF (20 μL, 0.18 mmol) was added dropwise to a 0° C. solution of 6-(5,6-dichlorobenzo[d]oxazol-2-ylamino)picolinic acid (65 mg, 0.18 mmol) and NMM (99 μL, 0.91 mmol) in DMA (5 mL). Hydroxylamine hydrochloride (14 mg, 0.20 mmol) was added, and the resulting solution stirred overnight at room temperature. The solids were filtered out. The crude product was purified by Prep-HPLC with the following conditions: Column: Waters HSS C18, 2.1×50 mm, 1.8 um; Mobile Phase A: water/0.05% TFA, Mobile Phase B: ACN; Flow rate: 0.7 mL/min; Gradient: 5% B to 95% B in 2.0 min, hold 0.6 min; Detector: UV 254 nm. The collected fraction was lyophilized to afford 6-(5,6-dichlorobenzo[d]oxazol-2-ylamino)-N-hydroxypicolinamide (6.4 mg, 11%) as a white solid. $^1$H-NMR: (DMSO, 300 MHz) δ (ppm): 11.59 (s, 1H), 10.73 (s, 1H), 9.27 (s, 1H), 8.29 (d, J=8.1 Hz, 1H), 8.08-8.00 (m, 2H), 7.80 (s, 1H), 7.60 (d, J=7.5 Hz, 1H). MS: (ESI, m/z): 339[M+H]$^+$.

Example 32-1: Preparation of N-hydroxy-3-(oxazolo[4,5-b]pyridin-2-ylamino)benzamide

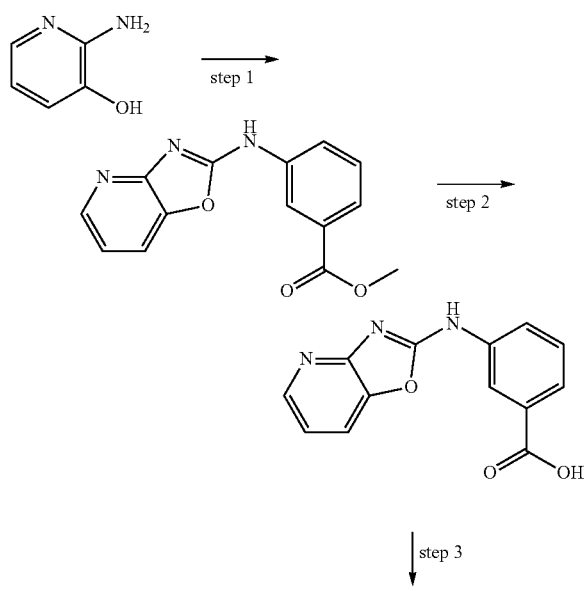

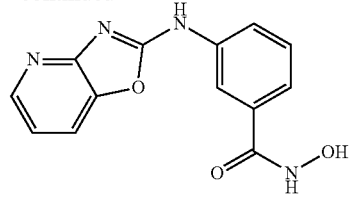

Step 1: methyl 3-(oxazolo[4,5-b]pyridin-2-ylamino) benzoate

A solution of 2-aminopyridin-3-ol (440 mg, 4.00 mmol), methyl 3-isothiocyanatobenzoate (0.63 mL, 4.00 mmol), copper (I) iodide (38 mg, 0.20 mmol), and triethylamine (2.22 mL, 16.0 mmol) in ethanol (8 mL) was irradiated with microwave radiation for 10 min at 100° C. The resulting mixture was cooled to room temperature and then concentrated under vacuum. The residue was purified via Prep-HPLC with the following conditions: Column, XBridge RP18 19*250 mm; Mobile phase A: water (0.1% FA), Mobile Phase B: ACN; Flow rate: 30 mL/min; Gradient: 20% B to 80% B in 10 min; 254&220 nm. The collected fraction was concentrated under vacuum to afford methyl 3-(oxazolo[4,5-b]pyridin-2-ylamino)benzoate (150 mg, 14%) as a light yellow solid. MS: (ESI, m/z): 270[M+H]$^+$.

Step 2: 3-(oxazolo[4,5-b]pyridin-2-ylamino)benzoic Acid

A solution of lithium hydroxide (22 mg, 0.92 mmol) in water (1 mL) was added to a solution of methyl 3-(oxazolo[4,5-b]pyridin-2-ylamino)benzoate (50 mg, 0.19 mmol) in THF (1 mL), and the resulting solution stirred for 12 h at room temperature. The pH value of the solution was adjusted to 7 with 6 M aqueous HCl solution, and the mixture was extracted with 3×10 mL of ethyl acetate. The combined organic phases were dried over anhydrous sodium sulfate, filtered, and concentrated under vacuum to afford 3-(oxazolo[4,5-b]pyridin-2-ylamino)benzoic acid (35 mg, 74%) as yellow oil. MS: (ESI, m/z): 256[M+H]$^+$.

Step 3: N-hydroxy-3-(oxazolo[4,5-b]pyridin-2-ylamino)benzamide

IPCF (76 μL, 0.68 mmol) was added dropwise to a 0° C. solution of 3-(oxazolo[4,5-b]pyridin-2-ylamino)benzoic acid (35 mg, 0.14 mmol) and NMM (75 μL, 0.91 mmol) in DMA (5 mL). The mixture stirred for 1 h at room temperature and then a solution of hydroxylamine hydrochloride (47 mg, 0.68 mmol) in DMA (1 mL) was added. The resulting solution was stirred for 14 h at room temperature. The solids were filtered out. The crude product was purified by Prep-HPLC with the following conditions: Column: XBridge BEH C18 OBD Prep Column, 5 um, 19×250 mm; Mobile Phase A: water (0.1% FA), Mobile Phase B: ACN; Flow rate: 30 mL/min; Gradient: 5% B to 30% B in 6 min; 254 & 220 nm. The collected fraction was lyophilized to afford N-hydroxy-3-(oxazolo[4,5-b]pyridin-2-ylamino)benzamide (10.6 mg, 29%) as a white solid. $^1$H-NMR (DMSO, 400 MHz) δ (ppm): 11.16 (br, 2H), 9.08 (br, 1H), 8.27-8.25 (m, 1H), 8.17 (s, 1H), 7.94-7.87 (m, 2H), 7.50-7.41 (m, 2H), 7.17-7.13 (m, 1H). MS: (ESI, m/z): 271[M+H]$^+$.

The following compound was prepared according to the procedures outlined N-hydroxy-3-(oxazolo[4,5-b]pyridin-2-ylamino)benzamide.

| Ex. | Structure | Name | $^1$H NMR | (ESI, m/z) [M + H]$^+$ |
|---|---|---|---|---|
| 32-2 | ![structure] | N-hydroxy-3-((6-(trifluoromethyl)oxazolo[4,5-b]pyridin-2-yl)amino)benzamide | (DMSO, 300 MHz, ppm): 11.33 (br, 2H), 9.08 (br, 1H), 8.60 (s, 1H), 8.30 (s, 1H), 8.14 (s, 1H), 7.92-7.85 (m, 1H), 7.51-7.39 (m, 2H) | 339 |

Example 33-1. 3-((6-chloro-5-fluoro-1H-benzo[d]imidazol-2-yl)amino)-N-hydroxybenzamide

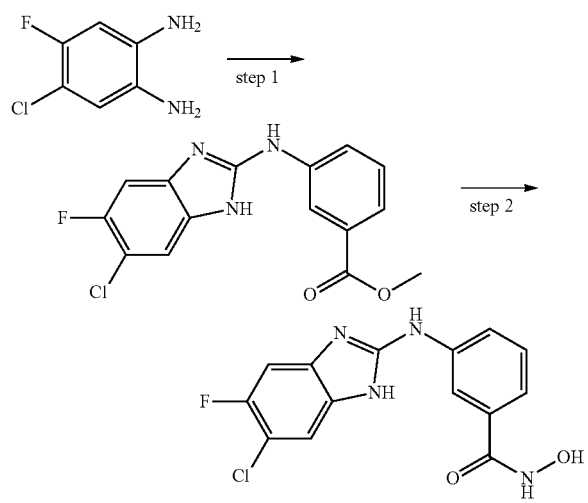

A 2 mL reaction vial was charged with 4-chloro-5-fluorobenzene-1,2-diamine (0.2 M in DMF, 150 μL, 30 umol), triethylamine (42 μL, 300 μmol) and methyl 3-isothiocyanatobenzoate (0.2 M in DMF, 150 μL, 30 μmol). 1-Ethyl-3-(3-dimethylaminopropyl)carbodiimide (0.4 M in DMF, 225 μL, 90 μmol) was added, and the resulting mixture was shaken at room temperature for 30 minutes and then at 90° C. overnight. The solvent was removed under a stream of nitrogen. The residue was diluted with ethyl acetate (0.7 mL) and brine (0.5 mL), and the mixture was shaken. The organic layer was separated and the aqueous phase was extracted with ethyl acetate (0.7 mL). The combined organic layers were concentrated under a stream of nitrogen and THF/methanol (3:1, 200 μL) was added to the residue. The vial was sealed and shaken at 50° C. for 15 min to dissolve the residue and then cooled to room temperature. Hydroxylamine (50% v/v solution in water, 150 μL) was added followed by 1 N aqueous NaOH solution (100 and the vial was sealed and shaken at room temperature for 16 h. The reaction mixture was concentrated under a stream of nitrogen at room temperature. The residue was dissolved in 500 μL of DMSO and purified by prep-HPLC with the following conditions: Column: Waters SunFire C18, 5 um, 19×150 mm; mobile phase, A: water with 0.1% formic acid, B: CH$_3$CN with 0.1% formic acid; Flow rate, 23 mL/min; Gradient, 0% B to 5% B in 5 min; Detector, 254, 220 nm. The collected fractions were concentrated to give 3-((6-chloro-5-fluoro-1H-benzo[d]imidazol-2-yl)amino)-N-hydroxybenzamide (1.5 mg, 15.6% yield) as an off-white solid. MS: (ESI, m/z): 321[M+H]$^+$.

The following compounds were prepared according to the procedures outlined 3-((6-chloro-5-fluoro-1H-benzo[d]imidazol-2-yl)amino)-N-hydroxybenzamide:

| Example | Structure | Name | (ESI, m/z) [M + H]+ |
|---|---|---|---|
| 33-2 | ![structure] | 3-((5-chloro-6-methyl-1H-benzo[d]imidazol-2-yl)amino)-N-hydroxybenzamide | 317 |
| 33-3 | ![structure] | 3-((5,6-difluoro-1H-benzo[d]imidazol-2-yl)amino)-N-hydroxybenzamide | 305 |

-continued

| Example | Structure | Name | (ESI, m/z) [M + H]+ |
|---|---|---|---|
| 33-4 | 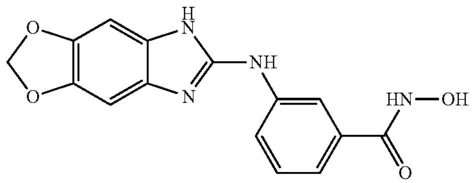 [SMILES: O=C(NO)c1cccc(Nc2nc3cc4c(cc3[nH]2)OCO4)c1] | 3-((5H-[1,3]dioxolo[4',5':4,5]benzo[1,2-d]imidazol-6-yl)amino)-N-hydroxybenzamide | 313 |
| 33-5 | 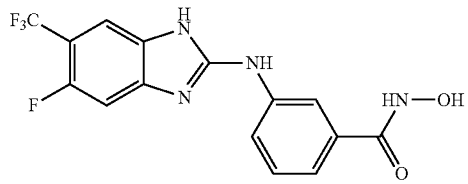 [SMILES: O=C(NO)c1cccc(Nc2nc3cc(F)c(C(F)(F)F)cc3[nH]2)c1] | 3-((5-fluoro-6-(trifluoromethyl)-1H-benzo[d]imidazol-2-yl)amino)-N-hydroxybenzamide | 355 |
| 33-6 | 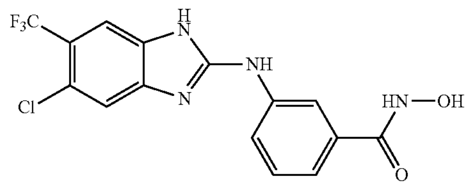 [SMILES: O=C(NO)c1cccc(Nc2nc3cc(Cl)c(C(F)(F)F)cc3[nH]2)c1] | 3-((5-chloro-6-(trifluoromethyl)-1H-benzo[d]imidazol-2-yl)amino)-N-hydroxybenzamide | 371 |
| 33-7 | 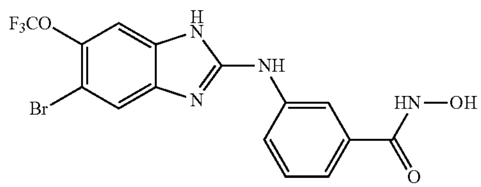 [SMILES: O=C(NO)c1cccc(Nc2nc3cc(Br)c(OC(F)(F)F)cc3[nH]2)c1] | 3-((5-bromo-6-(trifluoromethoxy)-1H-benzo[d]imidazol-2-yl)amino)-N-hydroxybenzamide | 431 |
| 33-8 | 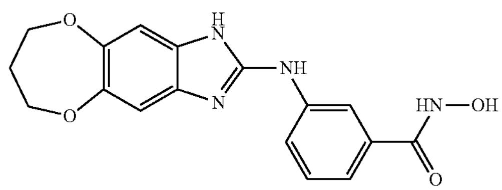 [SMILES: O=C(NO)c1cccc(Nc2nc3cc4c(cc3[nH]2)OCCCO4)c1] | 3-((7,8-dihydro-1H,6H-[1,4]dioxepino[2',3':4,5]benzo[1,2-d]imidazol-2-yl)amino)-N-hydroxybenzamide | 341 |
| 33-9 | 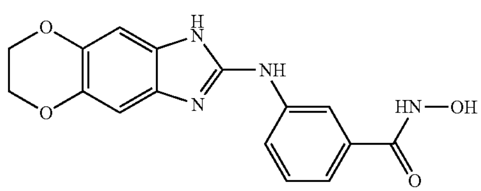 [SMILES: O=C(NO)c1cccc(Nc2nc3cc4c(cc3[nH]2)OCCO4)c1] | 3-((6,7-dihydro-1H-[1,4]dioxino[2',3':4,5]benzo[1,2-d]imidazol-2-yl)amino)-N-hydroxybenzamide | 327 |
| 33-10 | 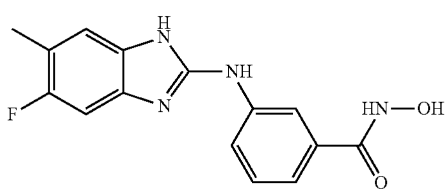 | 3-((5-fluoro-6-methyl-1H-benzo[d]imidazol-2-yl)amino)-N-hydroxybenzamide | 301 |
| 33-11 | 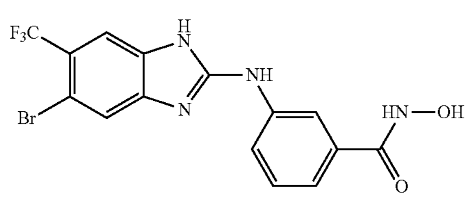 [SMILES: O=C(NO)c1cccc(Nc2nc3cc(Br)c(C(F)(F)F)cc3[nH]2)c1] | 3-((5-bromo-6-(trifluoromethyl)-1H-benzo[d]imidazol-2-yl)amino)-N-hydroxybenzamide | 415 |

-continued

| Example | Structure | Name | (ESI, m/z) [M + H]+ |
|---|---|---|---|
| 33-12 | 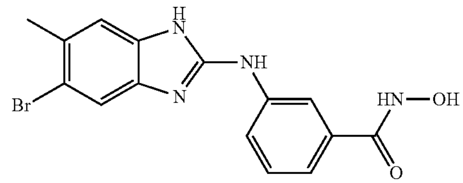 | 3-((5-bromo-6-methyl-1H-benzo[d]imidazol-2-yl)amino)-N-hydroxybenzamide | 361 |
| 33-13 | 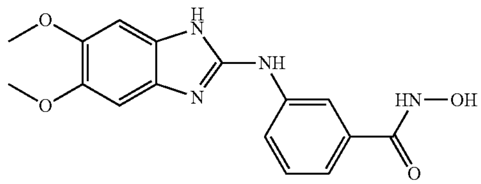 | 3-((5,6-dimethoxy-1H-benzo[d]imidazol-2-yl)amino)-N-hydroxybenzamide | 329 |
| 33-14 | 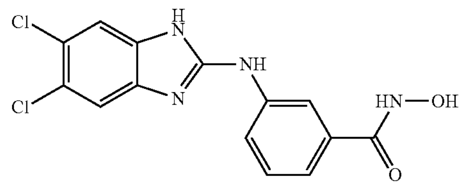 | 3-((5,6-dichloro-1H-benzo[d]imidazol-2-yl)amino)-N-hydroxybenzamide | 337 |
| 33-15 | 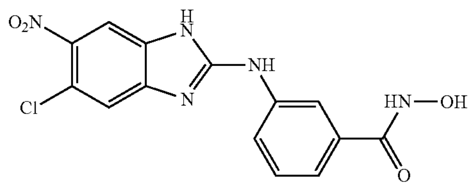 [SMILES: O=C(NO)c1cccc(Nc2nc3cc(Cl)c([N+](=O)[O-])cc3[nH]2)c1] | 3-((5-chloro-6-nitro-1H-benzo[d]imidazol-2-yl)amino)-N-hydroxybenzamide | 348 |
| 33-16 | 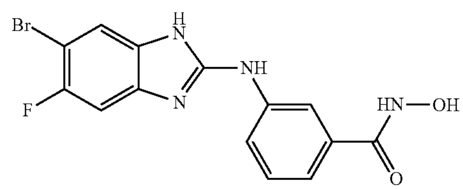 | 3-((6-bromo-5-fluoro-1H-benzo[d]imidazol-2-yl)amino)-N-hydroxybenzamide | 365 |
| 33-17 | 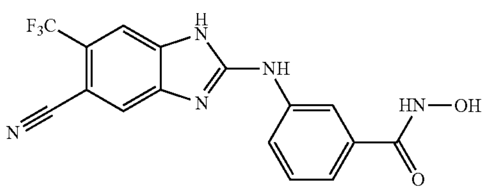 [SMILES: N#Cc1cc2nc(Nc3cccc(C(=O)NO)c3)[nH]c2cc1C(F)(F)F] | 3-((5-cyano-6-(trifluoromethyl)-1H-benzo[d]imidazol-2-yl)amino)-N-hydroxybenzamide | 355 |
| 33-18 | 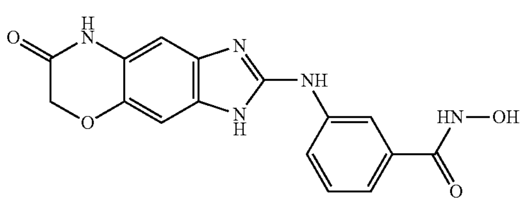 [SMILES: O=C1COc2cc3[nH]c(Nc4cccc(C(=O)NO)c4)nc3cc2N1] | N-hydroxy-3-((7-oxo-3,6,7,8-tetrahydroimidazo[4',5':4,5]benzo[1,2-b][1,4]oxazin-2-yl)amino)benzamide | 340 |
| 33-19 | 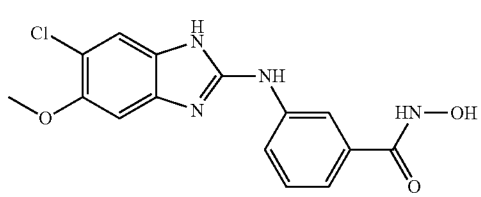 [SMILES: COc1cc2nc(Nc3cccc(C(=O)NO)c3)[nH]c2cc1Cl] | 3-((6-chloro-5-methoxy-1H-benzo[d]imidazol-2-yl)amino)-N-hydroxybenzamide | 333 |

| Example | Structure | Name | (ESI, m/z) [M + H]+ |
|---|---|---|---|
| 33-20 | 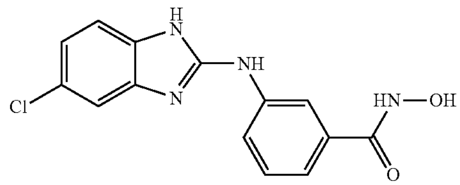 [SMILES: O=C(NO)c1cccc(Nc2nc3cc(Cl)ccc3[nH]2)c1] | 3-((5-chloro-1H-benzo[d]imidazol-2-yl)amino)-N-hydroxybenzamide | 303 |
| 33-21 | 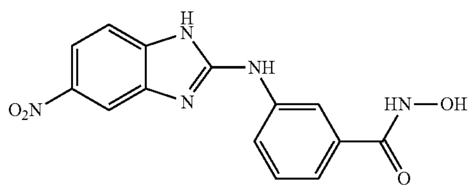 [SMILES: O=C(NO)c1cccc(Nc2nc3cc([N+](=O)[O-])ccc3[nH]2)c1] | N-hydroxy-3-((5-nitro-1H-benzo[d]imidazol-2-yl)amino)benzamide | 314 |
| 33-22 | 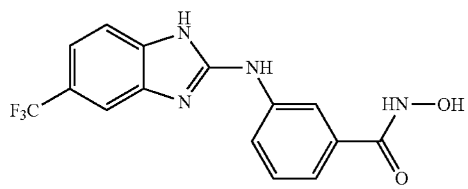 [SMILES: O=C(NO)c1cccc(Nc2nc3cc(C(F)(F)F)ccc3[nH]2)c1] | N-hydroxy-3-((5-(trifluoromethyl)-1H-benzo[d]imidazol-2-yl)amino)benzamide | 337 |
| 33-23 | 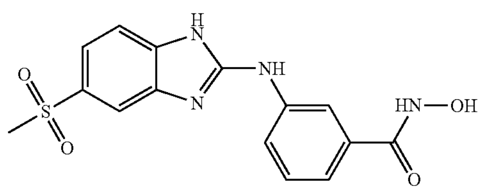 [SMILES: CS(=O)(=O)c1ccc2[nH]c(Nc3cccc(C(=O)NO)c3)nc2c1] | N-hydroxy-3-((5-(methylsulfonyl)-1H-benzo[d]imidazol-2-yl)amino)benzamide | 347 |
| 33-24 | 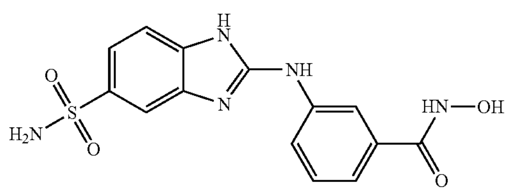 [SMILES: NS(=O)(=O)c1ccc2[nH]c(Nc3cccc(C(=O)NO)c3)nc2c1] | N-hydroxy-3-((5-sulfamoyl-1H-benzo[d]imidazol-2-yl)amino)benzamide | 348 |

Example 34-1. N-hydroxy-3-(methyl(1-methyl-5-(pyridin-3-yl)-6-(trifluoromethyl)-1H-benzo[d]imidazol-2-yl)amino)benzamide

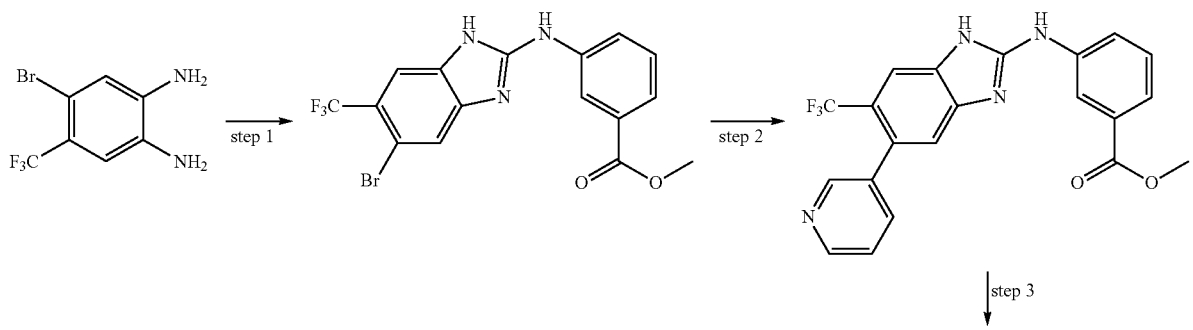

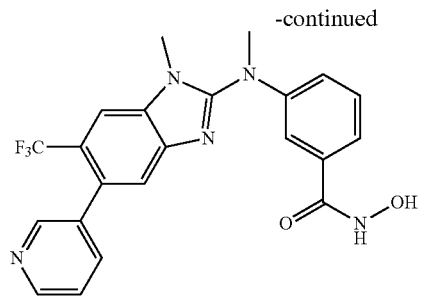 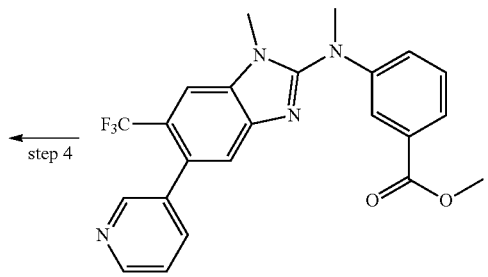

Step 1: Methyl 3-((5-bromo-6-(trifluoromethyl)-1H-benzo[d]imidazol-2-yl)amino)benzoate A solution of 4-bromo-5-(trifluoromethyl)benzene-1,2-diamine (700 mg, 2.74 mmol), triethylamine (1.4 mL, 10 mmol) and methyl 3-isothiocyanatobenzoate (530 mg, 2.74 mmol) in DMF (8 mL) stirred at room temperature for 15 minutes and then 1-ethyl-3-(3-dimethylaminopropyl)carbodiimide (1.063 g, 6.85 mmol) was added. The resulting mixture was stirred at room temperature for 30 min then at 90° C. for 4 h. The solvent was evaporated under reduce pressure, and the residue was diluted with ethyl acetate (10 mL) and brine (5 mL). The aqueous phase was separated and extracted with ethyl acetate (10 mL). The combined organic layers were dried over anhydrous sodium sulfate, filtered, and concentrated under reduce pressure. The residue was purified via column chromatography on silica gel (eluting with ethyl acetate/hexane (2:1)) to afford methyl 3-((5-bromo-6-(trifluoromethyl)-1H-benzo[d]imidazol-2-yl)amino)benzoate (706 mg, 62%) as white solid. MS: (ESI, m/z): 415[M+H]$^+$.

Step 2: Methyl 3-((5-(pyridin-3-yl)-6-(trifluoromethyl)-1H-benzo[d]imidazol-2-yl)amino)benzoate Potassium phosphate tribasic (2 M in water, 200 μL, 400 μmol) and Pd(PPh$_3$)$_4$ (11.6 mg, 10 μmol) were added to a solution of methyl 3-((5-bromo-6-(trifluoromethyl)-1H-benzo[d]imidazol-2-yl)amino)benzoate (41.4 mg, 100 μmol), and 3-(4,4,5,5-tetramethyl-1,3,2-dioxaborolan-2-yl)pyridine (51.2 mg, 250 μmol) in 1,4-dioxane (600 μL) and water (60 μL) and stirred at 120° C. overnight. The mixture was cooled to room temperature and ethyl acetate (1 mL) and brine (500 μL) were added. The aqueous phase was separated and extracted with ethyl acetate (1 mL). The combined organic layers were dried and concentrated. The crude product was purified by preparative thin layer chromatography (eluting with DCM/MeOH/NH$_4$OH=10:1:0.1) to give methyl 3-((5-(pyridin-3-yl)-6-(trifluoromethyl)-1H-benzo[d]imidazol-2-yl)amino)benzoate (29 mg, 72%) as a light yellow solid. MS: (ESI, m/z): 413 [M+H]$^+$).

Step 3: Methyl 3-(methyl(1-methyl-5-(pyridin-3-yl)-6-(trifluoromethyl)-1H-benzo[d]imidazol-2-yl)amino)benzoate and methyl 3-(methyl(1-methyl-6-(pyridin-3-yl)-5-(trifluoromethyl)-1H-benzo[d]imidazol-2-yl)amino)benzoate A 2 mL reaction vial was charged with methyl 3-((5-(pyridin-3-yl)-6-(trifluoromethyl)-1H-benzo[d]imidazol-2-yl)amino)benzoate (29 mg, 72 μmol) and acetonitrile (400 μL). Iodomethane (0.4 M in acetonitrile, 500 μL, 200 μmol) was added followed by cesium carbonate (130 mg, 400 μmol). The mixture was shaken at room temperature overnight, and the solvent was removed under reduced pressure. The residue was diluted with ethyl acetate (0.7 mL) and brine (0.5 mL), and the mixture was shaken. The aqueous phase was separated and extracted with ethyl acetate (0.7 mL), and the combined organic layers were concentrated under a stream of nitrogen. The crude product was purified by preparative thin layer chromatography (eluting with 10:0.5:0.05 DCM/MeOH/NH$_4$OH). The top band on the TLC plate was assumed as methyl 3-(methyl(1-methyl-5-(pyridin-3-yl)-6-(trifluoromethyl)-1H-benzo[d]imidazol-2-yl)amino)benzoate (9.5 mg, 31%) MS: (ESI, m/z): 441[M+H]$^+$. The lower band was assumed as methyl 3-(methyl(1-methyl-6-(pyridin-3-yl)-5-(trifluoromethyl)-1H-benzo[d]imidazol-2-yl)amino)benzoate (3.7 mg, 12%) MS: (ESI, m/z): 441[M+H]$^+$.

Step 4: (N-hydroxy-3-(methyl(1-methyl-5-(pyridin-3-yl)-6-(trifluoromethyl)-1H-benzo[d]imidazol-2-yl)amino)benzamide)

A solution of methyl 3-(methyl(1-methyl-5-(pyridin-3-yl)-6-(trifluoromethyl)-1H-benzo[d]imidazol-2-yl)amino)benzoate (9.5 mg, 22 μmol) in THF/methanol (3:1, 200 μL) was heated at 50° C. for 15 minutes (to dissolve the solids) and then cooled to room temperature. Hydroxylamine (50% v/v solution in water, 150 μL) and 1 N aqueous NaOH solution (100 μL) were added, and the mixture was shaken at room temperature for 16 h. The reaction mixtures was concentrated under a stream of nitrogen at room temperature. The residue was dissolved in 500 μL of DMSO and purified by prep-HPLC with the following conditions: Column: Waters SunFire C18, 5 um, 19×150 mm; mobile phase, A: water with 0.1% formic acid, B: CH$_3$CN with 0.1% formic acid; Flow rate, 23 mL/min; Gradient, 0% B to 5% B in 5 min; Detector, 254, 220 nm. The collected fractions were concentrated to give (N-hydroxy-3-(methyl(1-methyl-5-(pyridin-3-yl)-6-(trifluoromethyl)-1H-benzo[d]imidazol-2-yl)amino)benzamide) (5.8 mg, 61% yield), MS: (ESI, m/z): 442[M+H]$^+$ The following compounds were prepared according to the procedures outlined N-hydroxy-3-(methyl(1-methyl-5-(pyridin-3-yl)-6-(trifluoromethyl)-1H-benzo[d]imidazol-2-yl)amino)benzamide:

| Example | Structure | IUPAC Name | (ESI, m/z) [M + H]+ |
|---|---|---|---|
| 34-2 | 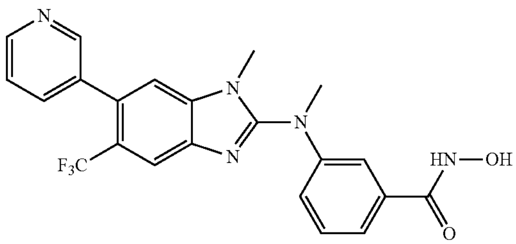 [SMILES: CN(c1cccc(C(=O)NO)c1)c1nc2cc(C(F)(F)F)c(-c3cccnc3)cc2n1C] | (N-hydroxy-3-(methyl(1-methyl-6-(pyridin-3-yl)-5-(trifluoromethyl)-1H-benzo[d]imidazol-2-yl)amino)benzamide) | 442 |
| 34-3 | 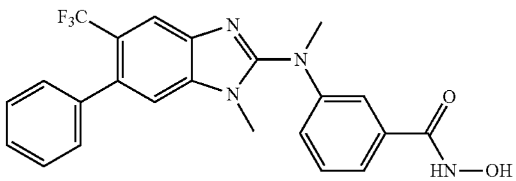 [SMILES: CN(c1cccc(C(=O)NO)c1)c1nc2cc(C(F)(F)F)c(-c3ccccc3)cc2n1C] | N-hydroxy-3-(methyl(1-methyl-6-phenyl-5-(trifluoromethyl)-1H-benzo[d]imidazol-2-yl)amino)benzamide | 441 |

Example 35-1. N-hydroxy-3-((1-methyl-5-(pyridin-3-yl)-6-(trifluoromethyl)-1H-benzo[d]imidazol-2-yl)amino)benzamide

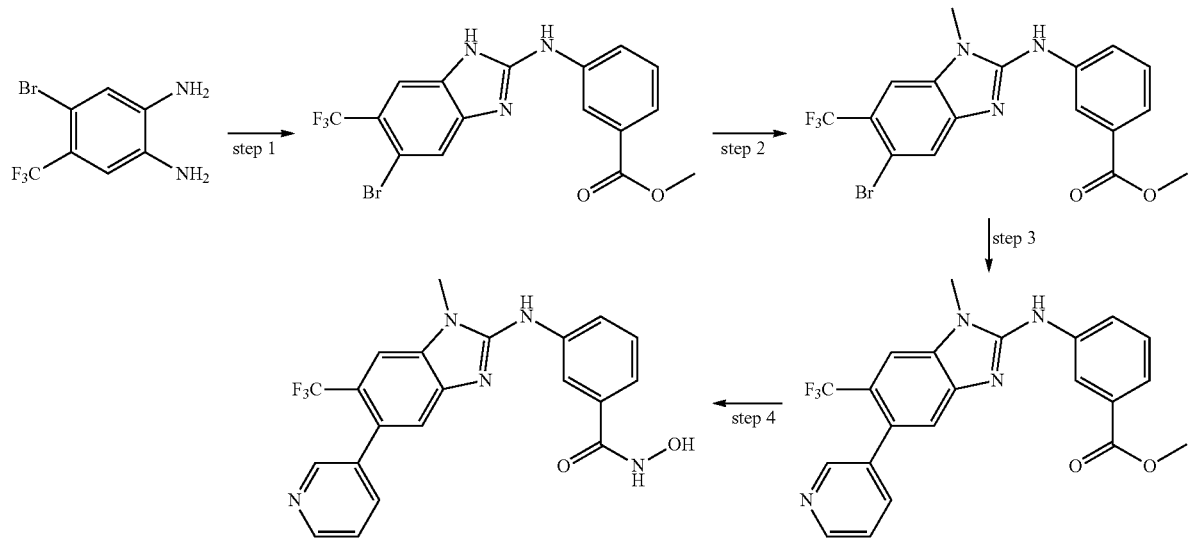

Step 1. Methyl 3-((5-bromo-6-(trifluoromethyl)-1H-benzo[d]imidazol-2-yl)amino)benzoate A 25 mL reaction vial was charged with 4-bromo-5-(trifluoromethyl)benzene-1,2-diamine (700 mg, 2.74 mmol), DMF (8 mL), triethylamine (1.4 mL, 10 mmol) and methyl 3-isothiocyanatobenzoate (530 mg, 2.74 mmol), and the mixture was stirred at room temperature for 15 minutes. 1-Ethyl-3-(3-dimethylaminopropyl)carbodiimide (1.06 g, 6.85 mmol) was added, and the resulting reaction mixture was stirred at room temperature for 30 min then at 90° C. for 4 h. DMF was removed under reduce pressure, and ethyl acetate (10 mL) and brine (5 mL) were added to the residue. The mixture was shaken and the layers were separated. The aqueous phase was extracted with ethyl acetate (10 mL), and the combined organic layers were evaporated under reduce pressure. The residue purified via column chromatography on silica gel (eluting with 2:1 ethyl acetate/hexanes) to give methyl 3-((5-bromo-6-(trifluoromethyl)-1H-benzo[d]imidazol-2-yl)amino)benzoate (706 mg, 62%) as white solid. MS: (ESI, m/z): 415 [M+H]+.

Step 2. (methyl 3-((5-bromo-1-methyl-6-(trifluoromethyl)-1H-benzo[d]imidazol-2-yl)amino)benzoate and methyl 3-((6-bromo-1-methyl-5-(trifluoromethyl)-1H-benzo[d]imidazol-2-yl)amino)benzoate)

A 4 mL reaction vial was charged with methyl 3-((5-bromo-6-(trifluoromethyl)-1H-benzo[d]imidazol-2-yl)amino)benzoate (100 mg, 0.242 mmol), acetonitrile (2 mL) and iodomethane (1M in acetonitrile, 315 µL, 0.315 mmol). Cesium carbonate (95 mg, 0.29 mmol) was added, and the mixture was shaken at room temperature overnight. The solvent was evaporated under reduce pressure, the residue was diluted with ethyl acetate (2 mL) and brine (1 mL), and the mixture was shaken. The organic layer was separated and the aqueous phase was extracted with ethyl acetate (1 mL). The combined organic layers were concentrated under a stream of nitrogen. The crude product was purified via column chromatography on silica gel (eluting with 2:1 ethyl acetate/hexanes) to afford a mixture of methyl 3-((5-bromo-1-methyl-6-(trifluoromethyl)-1H-benzo[d]imidazol-2-yl)amino)benzoate and methyl 3-((6-bromo-1-methyl-5-(trifluoromethyl)-1H-benzo[d]imidazol-2-yl)amino)benzoate) (92 mg, 89%) as a white solid. MS: (ESI, m/z): 429[M+H]$^+$.

Step 3. Methyl 3-((1-methyl-5-(pyridin-3-yl)-6-(trifluoromethyl)-1H-benzo[d]imidazol-2-yl)amino)benzoate and methyl 3-((1-methyl-6-(pyridin-3-yl)-5-(trifluoromethyl)-1H-benzo[d]imidazol-2-yl)amino)benzoate A 4 mL reaction vial was charged with the mixture of methyl 3-((5-bromo-1-methyl-6-(trifluoromethyl)-1H-benzo[d]imidazol-2-yl)amino)benzoate and methyl 3-((6-bromo-1-methyl-5-(trifluoromethyl)-1H-benzo[d]imidazol-2-yl)amino)benzoate (42.8 mg, 100 μmol), 3-(4,4,5,5-tetramethyl-1,3,2-dioxaborolan-2-yl)pyridine (51.2 mg, 250 μmol), 1,4-dioxane (600 μL) and water (60 μL). Potassium phosphate tribasic (2 M in water, 200 μL, 400 μmol) and Pd(PPh$_3$)$_4$ (11.6 mg, 10 μmol) were added, and the vial was sealed and shaken at 120° C. overnight. Ethyl acetate (1 mL) and brine (500 μL) were added, and the mixture was shaken. The organic layer was separated and the aqueous phase was extracted with ethyl acetate (1 mL). The combined organic layers were concentrated under a stream of nitrogen and the crude product was purified by preparative thin layer chromatography (eluting with 4:1 ethyl acetate/hexanes). The top band on TLC plate was assumed as methyl 3-((1-methyl-5-(pyridin-3-yl)-6-(trifluoromethyl)-1H-benzo[d]imidazol-2-yl)amino)benzoate (6.2 mg, 14%) MS: (ESI, m/z): 427[M+H]$^+$. The lower band was assumed as methyl 3-((1-methyl-6-(pyridin-3-yl)-5-(trifluoromethyl)-1H-benzo[d]imidazol-2-yl)amino)benzoate (8.1 mg, 18.7%), MS: (ESI, m/z): 427[M+H]$^+$.

Step 4. N-hydroxy-3-((1-methyl-5-(pyridin-3-yl)-6-(trifluoromethyl)-1H-benzo[d]imidazol-2-yl)amino)benzamide A 2 mL reaction vial was charged with methyl 3-((1-methyl-5-(pyridin-3-yl)-6-(trifluoromethyl)-1H-benzo[d]imidazol-2-yl)amino)benzoate (6.2 mg, 14 μmol) and THF/methanol (3:1, 200 and the vial was sealed and shaken at 50° C. for 15 minutes and then cooled to room temperature. Hydroxylamine (50% v/v solution in water, 150 μL) was added, followed by 1 N aqueous NaOH solution (100 The vial was sealed and then shaken at room temperature for 16 h. The reaction mixture was concentrated under a stream of nitrogen at room temperature, dissolved in 500 μL of DMSO, and purified by prep-HPLC with the following conditions: Column: Waters SunFire C18, 5 um, 19×150 mm; mobile phase, A: water with 0.1% formic acid, B: CH$_3$CN with 0.1% formic acid; Flow rate, 23 mL/min; Gradient, 0% B to 5% B in 5 min; Detector, 254, 220 nm. The collected fractions were concentrated to give N-hydroxy-3-((1-methyl-5-(pyridin-3-yl)-6-(trifluoromethyl)-1H-benzo[d]imidazol-2-yl)amino)benzamide (1.3 mg, 20.9%) MS: (ESI, m/z): 428[M+H]$^+$.

The following compounds were prepared according to the procedures outlined N-hydroxy-3-((1-methyl-5-(pyridin-3-yl)-6-(trifluoromethyl)-1H-benzo[d]imidazol-2-yl)amino)benzamide:

| Example | Structure | Name | (ESI, m/z) [M + H]+ |
|---|---|---|---|
| 35-2 | 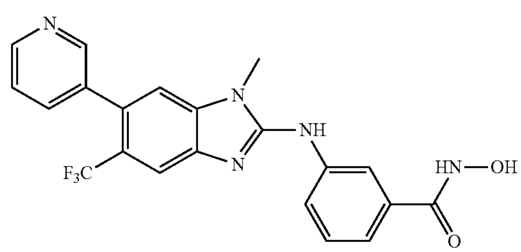 [SMILES: Cn1c(Nc2cccc(C(=O)NO)c2)nc2cc(C(F)(F)F)c(-c3cccnc3)cc21] | N-hydroxy-3-((1-methyl-6-(pyridin-3-yl)-5-(trifluoromethyl)-1H-benzo[d]imidazol-2-yl)amino)benzamide | |
| 35-3 | 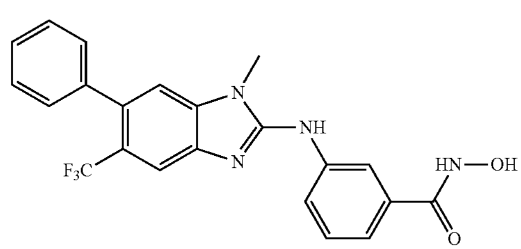 [SMILES: Cn1c(Nc2cccc(C(=O)NO)c2)nc2cc(C(F)(F)F)c(-c3ccccc3)cc21] | N-hydroxy-3-((1-methyl-6-phenyl-5-(trifluoromethyl)-1H-benzo[d]imidazol-2-yl)amino)benzamide | 427 |

Example 36-1. N-hydroxy-3-((5-phenyl-6-(trifluoromethyl)-1H-benzo[d]imidazol-2-yl)amino)benzamide

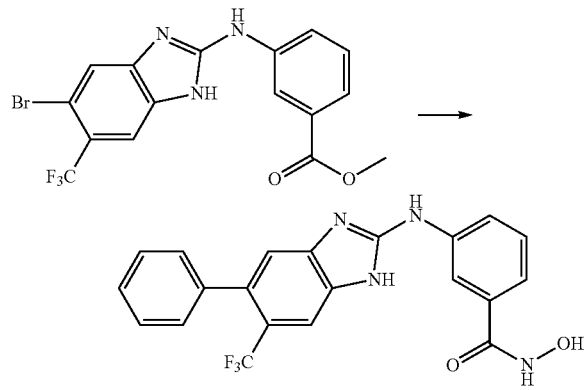

A 2 mL reaction vial was charged with methyl 3-((5-bromo-6-(trifluoromethyl)-1H-benzo[d]imidazol-2-yl)amino)benzoate (0.2 M in 1,4-dioxane, 150 μL, 30 μmol), phenylboronic acid (0.2 M in 1,4-dioxane, 275 μL, 45 μmol), potassium phosphate tribasic (1 M in water, 120 μL, 120 μmol), and Pd(PPh$_3$)$_4$ (0.02 M in toluene, 75 μL, 1.5 μmol). The vial was sealed and heated at 110° C. overnight. The mixture was concentrated under a stream of N$_2$. The residue was diluted with ethyl acetate (0.7 mL) and brine (0.5 mL), and the mixture was shaken. The organic layer was separated and the aqueous phase was extracted with ethyl acetate (0.7 mL). The combined organic layers were concentrated under a stream of nitrogen, and THF/methanol (3:1, 200 μL) was added to the residue. The vial was sealed and shaken at 50° C. for 15 minutes to dissolve the residue. Hydroxylamine (50% v/v solution in water, 150 μL) was added followed by 1 N aqueous NaOH solution (100 μL). The vial was sealed and shaken at room temperature for 16 h, and then concentrated under a stream of nitrogen at room temperature. The residue was dissolved in 500 μL of DMSO and purified by prep-HPLC with the following conditions: Column: Waters SunFire C18, 5 um, 19×150 mm; mobile phase, A: water with 0.1% formic acid, B: CH$_3$CN with 0.1% formic acid; Flow rate, 23 mL/min; Gradient, 0% B to 5% B in 5 min; Detector, 254, 220 nm. The collected fractions were concentrated to give N-hydroxy-3-((5-phenyl-6-(trifluoromethyl)-1H-benzo[d]imidazol-2-yl)amino)benzamide (2.6 mg, 20.6% yield) as an off-white solid. MS: (ESI, m/z): 413[M+H]$^+$.

The following compounds were prepared according to the procedures outlined N-hydroxy-3-((1-methyl-5-(pyridin-3-yl)-6-(trifluoromethyl)-1H-benzo[d]imidazol-2-yl)amino)benzamide:

| Example | Structure | Name | (ESI, m/z) [M + H]+ |
|---|---|---|---|
| 36-2 | 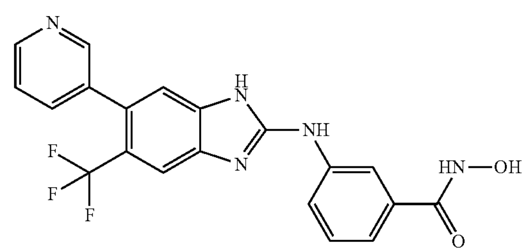 [SMILES: O=C(NO)c1cccc(Nc2nc3cc(C(F)(F)F)c(-c4cccnc4)cc3[nH]2)c1] | N-hydroxy-3-((6-(pyridin-3-yl)-5-(trifluoromethyl)-1H-benzo[d]imidazol-2-yl)amino)benzamide | 414 |
| 36-3 | 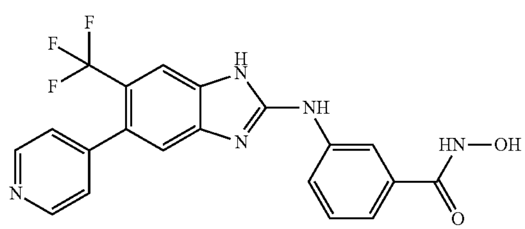 [SMILES: O=C(NO)c1cccc(Nc2nc3cc(-c4ccncc4)c(C(F)(F)F)cc3[nH]2)c1] | N-hydroxy-3-((5-(pyridin-4-yl)-6-(trifluoromethyl)-1H-benzo[d]imidazol-2-yl)amino)benzamide | 414 |
| 36-4 | 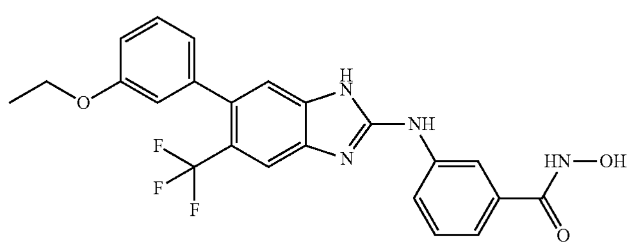 [SMILES: CCOc1cccc(-c2cc3[nH]c(Nc4cccc(C(=O)NO)c4)nc3cc2C(F)(F)F)c1] | 3-((6-(3-ethoxyphenyl)-5-(trifluoromethyl)-1H-benzo[d]imidazol-2-yl)amino)-N-hydroxybenzamide | 457 |

-continued

| Example | Structure | Name | (ESI, m/z) [M + H]+ |
|---|---|---|---|
| 36-5 | 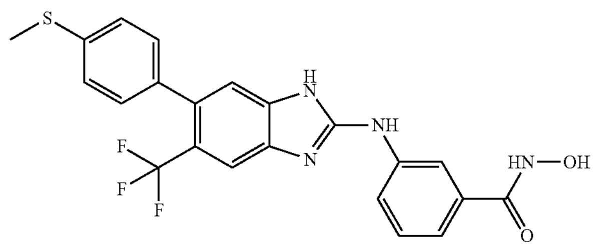 [SMILES: CSc1ccc(-c2cc3[nH]c(Nc4cccc(C(=O)NO)c4)nc3cc2C(F)(F)F)cc1] | N-hydroxy-3-((6-(4-(methylthio)phenyl)-5-(trifluoromethyl)-1H-benzo[d]imidazol-2-yl)amino)benzamide | 459 |
| 36-6 | 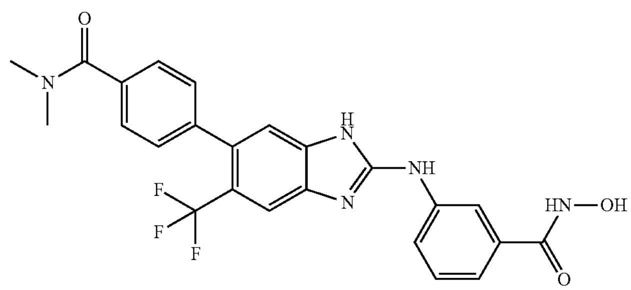 [SMILES: CN(C)C(=O)c1ccc(-c2cc3[nH]c(Nc4cccc(C(=O)NO)c4)nc3cc2C(F)(F)F)cc1] | 4-(2-((3-(hydroxycarbamoyl)phenyl)amino)-5-(trifluoromethyl)-1H-benzo[d]imidazol-6-yl)-N,N-dimethylbenzamide | 484 |
| 36-7 | 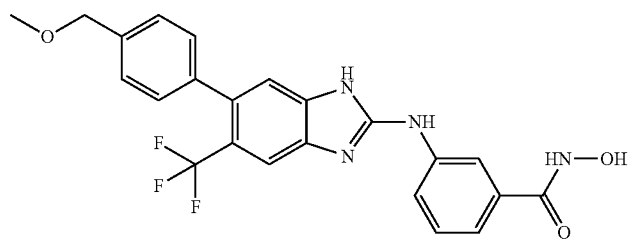 [SMILES: COCc1ccc(-c2cc3[nH]c(Nc4cccc(C(=O)NO)c4)nc3cc2C(F)(F)F)cc1] | N-hydroxy-3-((6-(4-(methoxymethyl)phenyl)-5-(trifluoromethyl)-1H-benzo[d]imidazol-2-yl)amino)benzamide | 457 |
| 36-8 | 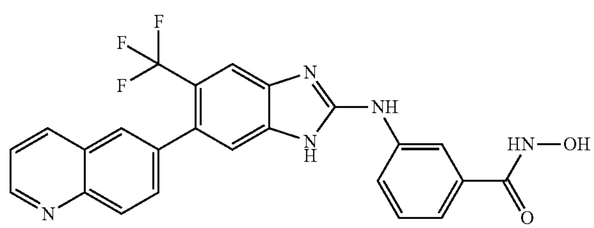 | N-hydroxy-3-((6-(quinolin-6-yl)-5-(trifluoromethyl)-1H-benzo[d]imidazol-2-yl)amino)benzamide | 464 |
| 36-9 | 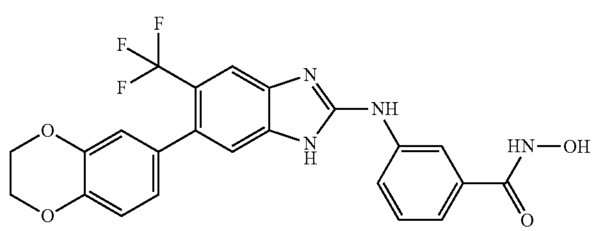 | 3-((6-(2,3-dihydrobenzo[b][1,4]dioxin-6-yl)-5-(trifluoromethyl)-1H-benzo[d]imidazol-2-yl)amino)-N-hydroxybenzamide | 471 |
| 36-10 | 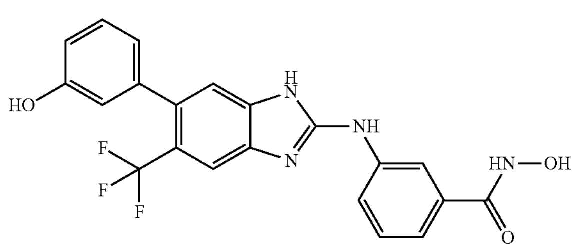 [SMILES: O=C(NO)c1cccc(Nc2nc3cc(C(F)(F)F)c(-c4cccc(O)c4)cc3[nH]2)c1] | N-hydroxy-3-((6-(3-hydroxyphenyl)-5-(trifluoromethyl)-1H-benzo[d]imidazol-2-yl)amino)benzamide | 429 |

| Example | Structure | Name | (ESI, m/z) [M + H]+ |
|---|---|---|---|
| 36-11 | 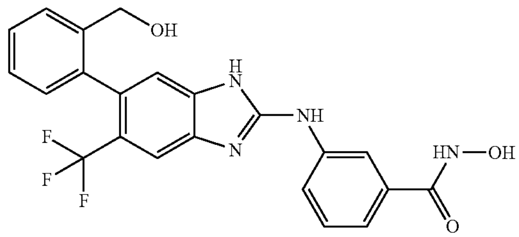 [SMILES: O=C(NO)c1cccc(Nc2nc3cc(C(F)(F)F)c(-c4ccccc4CO)cc3[nH]2)c1] | N-hydroxy-3-((6-(2-(hydroxymethyl)phenyl)-5-(trifluoromethyl)-1H-benzo[d]imidazol-2-yl)amino)benzamide | 443 |
| 36-12 | 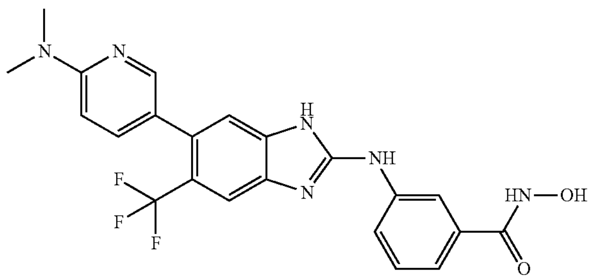 [SMILES: CN(C)c1ccc(-c2cc3[nH]c(Nc4cccc(C(=O)NO)c4)nc3cc2C(F)(F)F)cn1] | 3-((6-(6-(dimethylamino)pyridin-3-yl)-5-(trifluoromethyl)-1H-benzo[d]imidazol-2-yl)amino)-N-hydroxybenzamide | 457 |
| 36-13 | 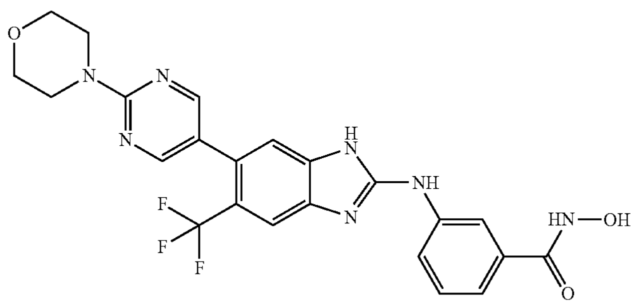 [SMILES: O=C(NO)c1cccc(Nc2nc3cc(C(F)(F)F)c(-c4cnc(N5CCOCC5)nc4)cc3[nH]2)c1] | N-hydroxy-3-((6-(2-morpholinopyrimidin-5-yl)-5-(trifluoromethyl)-1H-benzo[d]imidazol-2-yl)amino)benzamide | 500 |
| 36-14 | 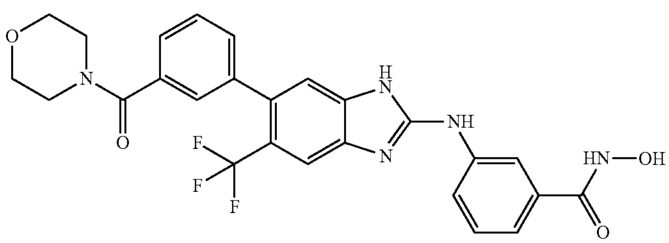 [SMILES: O=C(NO)c1cccc(Nc2nc3cc(C(F)(F)F)c(-c4cccc(C(=O)N5CCOCC5)c4)cc3[nH]2)c1] | N-hydroxy-3-((6-(3-(morpholine-4-carbonyl)phenyl)-5-(trifluoromethyl)-1H-benzo[d]imidazol-2-yl)amino)benzamide | 526 |
| 36-15 | 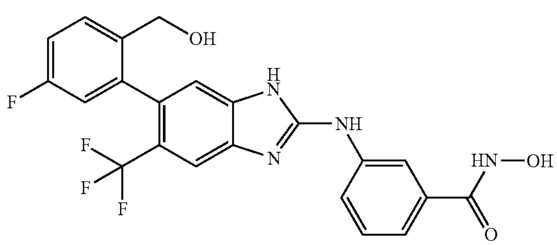 [SMILES: O=C(NO)c1cccc(Nc2nc3cc(C(F)(F)F)c(-c4cc(F)ccc4CO)cc3[nH]2)c1] | 3-((6-(5-fluoro-2-(hydroxymethyl)phenyl)-5-(trifluoromethyl)-1H-benzo[d]imidazol-2-yl)amino)-N-hydroxybenzamide | 461 |
| 36-16 | 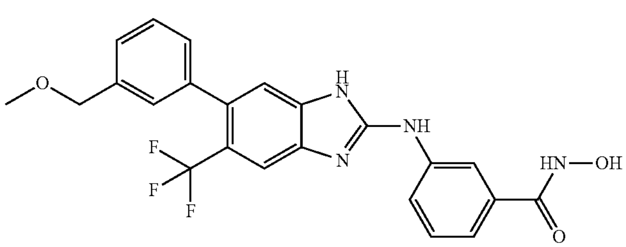 | N-hydroxy-3-((6-(3-(methoxymethyl)phenyl)-5-(trifluoromethyl)-1H-benzo[d]imidazol-2-yl)amino)benzamide | 457 |

| Example | Structure | Name | (ESI, m/z) [M + H]+ |
|---|---|---|---|
| 36-17 | 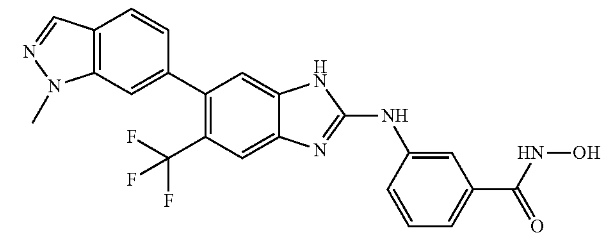 [SMILES: Cn1ncc2ccc(-c3cc4[nH]c(Nc5cccc(C(=O)NO)c5)nc4cc3C(F)(F)F)cc21] | N-hydroxy-3-((6-(1-methyl-1H-indazol-6-yl)-5-(trifluoromethyl)-1H-benzo[d]imidazol-2-yl)amino)benzamide | 467 |
| 36-18 | 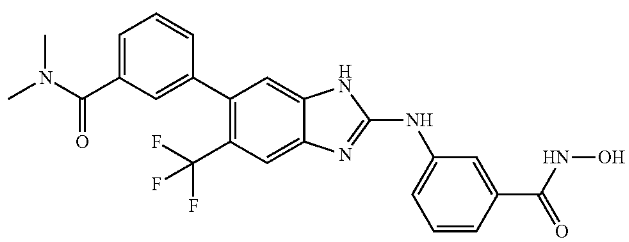 [SMILES: CN(C)C(=O)c1cccc(-c2cc3[nH]c(Nc4cccc(C(=O)NO)c4)nc3cc2C(F)(F)F)c1] | 3-(2-((3-(hydroxycarbamoyl)phenyl)amino)-5-(trifluoromethyl)-1H-benzo[d]imidazol-6-yl)-N,N-dimethylbenzamide | 484 |
| 36-19 | 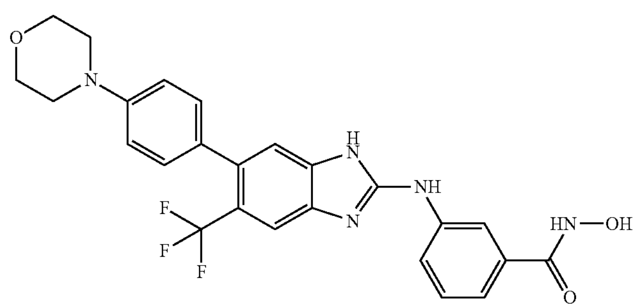 [SMILES: O=C(NO)c1cccc(Nc2nc3cc(C(F)(F)F)c(-c4ccc(N5CCOCC5)cc4)cc3[nH]2)c1] | N-hydroxy-3-((6-(4-morpholinophenyl)-5-(trifluoromethyl)-1H-benzo[d]imidazol-2-yl)amino)benzamide | 498 |
| 36-20 | 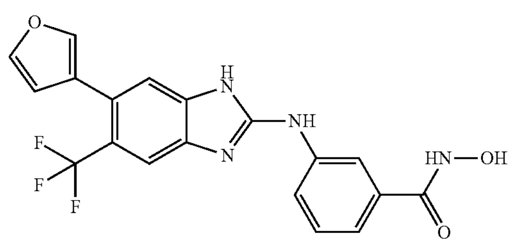 [SMILES: O=C(NO)c1cccc(Nc2nc3cc(C(F)(F)F)c(-c4ccoc4)cc3[nH]2)c1] | 3-((6-(furan-3-yl)-5-(trifluoromethyl)-1H-benzo[d]imidazol-2-yl)amino)-N-hydroxybenzamide | 403 |

Example 37-1. N-((benzylcarbamoyl)oxy)-3-((5-phenyl-6-(trifluoromethyl)-1H-benzo[d]imidazol-2-yl)amino)benzamide

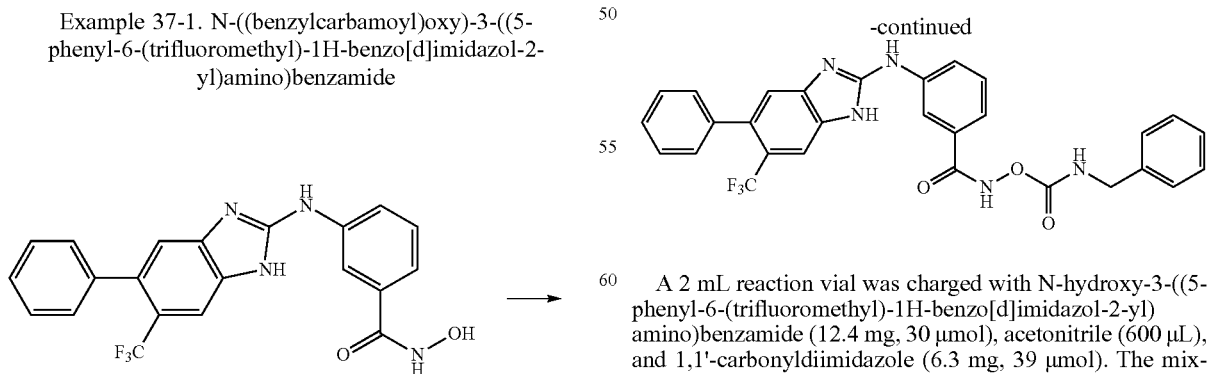

A 2 mL reaction vial was charged with N-hydroxy-3-((5-phenyl-6-(trifluoromethyl)-1H-benzo[d]imidazol-2-yl)amino)benzamide (12.4 mg, 30 µmol), acetonitrile (600 µL), and 1,1'-carbonyldiimidazole (6.3 mg, 39 µmol). The mixture was shaken at room temperature for 30 minutes and then benzylamine (4.8 mg, 45 µmol) was added. The vial was shaken at room temperature for 16 h and then concentrated under a stream of nitrogen. The residue was dissolved in 500

µL of DMSO and purified by prep-HPLC with the following conditions: Column: Waters SunFire C18, 5 um, 19×150 mm; mobile phase, A: water with 0.1% formic acid, B: CH$_3$CN with 0.1% formic acid; Flow rate, 23 mL/min; Gradient, 0% B to 5% B in 5 min; Detector, 254, 220 nm. The collected fractions were concentrated to yield N-((benzylcarbamoyl)oxy)-3-((5-phenyl-6-(trifluoromethyl)-1H-benzo[d]imidazol-2-yl)amino)benzamide (4 mg, 24%) as an off-white solid. MS: (ESI, m/z): 546[M+H]$^+$.

The following compound was synthesized according to the above protocol:

| Example | Structure | Name | (ESI, m/z) [M + H]+ |
|---|---|---|---|
| 37-2 | 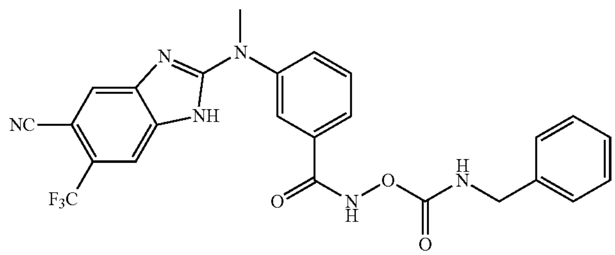 [SMILES: CN(c1cccc(C(=O)NOC(=O)NCc2ccccc2)c1)c1nc2cc(C#N)c(C(F)(F)F)cc2[nH]1] | N-((benzylcarbamoyl)oxy)-3-((5-cyano-6-(trifluoromethyl)-1H-benzo[d]imidazol-2-yl)(methyl)amino)benzamide | 509 |

Example 38-1. In Vitro Histone Deacetylase Assay

The probe binding HDAC11 assay was performed using a time resolved fluorescence (TRF) assay format. Recombinant N-terminal GST tag full-length human HDAC11 was expressed and purified from baculovirus in Sf9 insect cells (SignalChem, # H93-30G-1000). Each assay was performed in 1536 black well microplates (Corning, #3936) in a final volume of 8 µL in assay buffer containing 50 mM HEPES (pH 7.5), 50 mM KCl, 50 mM NaCl, 0.5 mM GSH (L-Glutathione reduced, Sigma #G4251), 0.03% BGG (0.22 µM filtered, Sigma, #G7516-25G), and 0.01% Triton X-100 (Sigma, #T9284-10L). 100 nL of 10-point, 3-fold serial dilution in DMSO was pre-dispensed into respective wells of 1536 assay plates for a final test concentration range of 25 µM to 1.3 nM respectively. The final concentration in the assay of HDAC11 and probe (a fluorescein labeled HDAC 11 inhibitor) was 2.5 nM and 20 nM respectively. 4 µL of 2× probe and 2× anti-GST Terbium (Cisbio, #61GSTXLB) was added to assay plates followed by 4 µL of 2×HDAC11. Plates were incubated for 16 hours at room temperature before time resolved fluorescence was read on the Envision (Excitation at 340 nm, and Emission at 485 nm and 535 nm, Perkin Elmer).

Data from HDAC11 Assays were reported as percent inhibition (inh) compared with control wells based on the following equation: % inh=1−((FLU−AveLow)/(AveHigh−AveLow)) where FLU=measured time resolved fluorescence. AveLow=average time resolved fluorescence of no enzyme control (n=32). AveHigh=average time resolved fluorescence of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm.

As set forth in Table I-2 below, "+++" indicates an IC$_{50}$ below 0.5 µM; "++" indicates an IC$_{50}$ between 0.5 µM and 1 µM; and "+" indicates an IC$_{50}$ above 1 µM.

TABLE I-2

IC$_{50}$ Ranges for Compounds of the Disclosure

| Compound No. | HDAC11 IC$_{50}$ Range |
|---|---|
| 1-1 | +++ |
| 2-1 | +++ |
| 3-1 | +++ |
| 4-1 | +++ |
| 4-2 | +++ |

TABLE I-2-continued

IC$_{50}$ Ranges for Compounds of the Disclosure

| Compound No. | HDAC11 IC$_{50}$ Range |
|---|---|
| 4-3 | +++ |
| 4-5 | +++ |
| 4-6 | +++ |
| 4-7 | +++ |
| 4-8 | + |
| 5-1 | +++ |
| 6-1 | ++ |
| 7-1 | +++ |
| 8-1 | + |
| 9-1 | +++ |
| 10-1 | +++ |
| 11-1 | +++ |
| 12-1 | +++ |
| 13-1 | +++ |
| 14-1 | +++ |
| 15-1 | +++ |
| 16-1 | +++ |
| 16-2 | +++ |
| 17-1 | +++ |
| 18-1 | +++ |
| 19-1 | +++ |
| 20-1 | +++ |
| 20-2 | +++ |
| 21-1 | +++ |
| 22-1 | +++ |
| 22-2 | +++ |
| 23-1 | + |
| 23-2 | + |
| 23-3 | + |
| 23-4 | +++ |
| 24-1 | + |
| 24-2 | + |
| 25-1 | + |
| 26-1 | + |
| 27-1 | +++ |
| 27-2 | +++ |
| 28-1 | +++ |
| 29-1 | + |
| 30-1 | + |
| 31-1 | +++ |
| 32-1 | + |

TABLE I-2-continued

IC$_{50}$ Ranges for Compounds of the Disclosure

| Compound No. | HDAC11 IC$_{50}$ Range |
|---|---|
| 32-2 | +++ |
| 33-1 | +++ |
| 33-2 | +++ |
| 33-3 | ++ |
| 33-4 | + |
| 33-5 | +++ |
| 33-6 | +++ |
| 33-7 | +++ |
| 33-8 | + |
| 33-9 | ++ |
| 33-10 | +++ |
| 33-11 | +++ |
| 33-12 | +++ |
| 33-13 | + |
| 33-14 | +++ |
| 33-15 | +++ |
| 33-16 | +++ |
| 33-17 | +++ |
| 33-18 | + |
| 33-19 | ++ |
| 33-20 | + |
| 33-21 | ++ |
| 33-22 | +++ |
| 33-23 | + |
| 33-24 | + |
| 34-1 | + |
| 34-2 | + |
| 34-3 | ++ |
| 35-1 | ++ |
| 35-2 | +++ |
| 35-3 | +++ |
| 36-1 | +++ |
| 36-2 | +++ |
| 36-3 | +++ |
| 36-4 | +++ |
| 36-5 | +++ |
| 36-6 | +++ |
| 36-7 | +++ |
| 36-8 | +++ |
| 36-9 | +++ |
| 36-10 | +++ |
| 36-11 | +++ |
| 36-12 | +++ |
| 36-13 | +++ |
| 36-14 | +++ |
| 36-15 | +++ |
| 36-16 | +++ |
| 36-17 | +++ |
| 36-18 | +++ |
| 36-19 | +++ |
| 36-20 | +++ |
| 37-1 | +++ |
| 37-2 | + |

Synthesis of Spiro Compounds

Example 1-2—Preparation of 1'-(4-chlorobenzyl)-N-hydroxy-2'-oxo-1,3-dihydrospiro[indene-2,3'-pyrrolidine]-4-carboxamide (II-1)

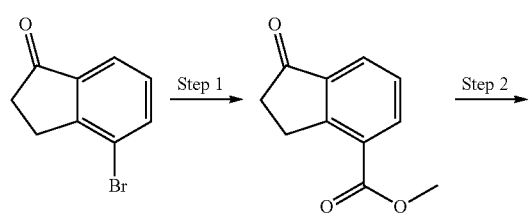

Step-1: Methyl 1-oxo-2,3-dihydro-1H-indene-4-carboxylate

Into a 1000-mL pressure tank reactor was placed 4-bromo-2,3-dihydro-1H-inden-1-one (30 g, 142 mmol, 1 equiv), MeOH (450 mL), Pd(dppf)Cl$_2$·CH$_2$Cl$_2$ (25 g, 0.1 equiv), and Et$_3$N (150 mL). The resulting mixture was stirred for 24 h at 100° C. under an atmosphere of 50 MPa CO (g). After cooling to room temperature, the mixture was filtered through a pad of celite and then concentrated under vacuum. The residue was purified by normal phase chromatography on silica gel using EtOAc/petroleum ether (1:10). The collected fractions were concentrated under vacuum to afford 17 g (63% yield) of the title compound as a white solid. MS: (ES, m/z): 191 [M+H]$^+$.

Step-2: Dimethyl 1-oxo-2,3-dihydro-1H-indene-2,4-dicarboxylate

Into a 500-mL 3-necked round-bottom flask purged and maintained with an inert atmosphere of nitrogen, was placed dimethyl carbonate (180 mL) and methyl 1-oxo-2,3-dihydro-1H-indene-4-carboxylate (30 g, 0.158 mol, 1 equiv). To this mixture, NaH (60% dispersion in oil, 12.6 g, 0.316 mol, 2 equiv) was added at room temperature. The resulting solution was stirred for 2 h at 80° C. The reaction was quenched by the addition of 40 mL of water and extracted with 3×200 mL of EtOAc. The combined organic layers were dried over $Na_2SO_4$ and concentrated under vacuum. The residue was purified by normal phase chromatography on silica gel using EtOAc/petroleum ether (1:10). The collected fractions were concentrated under vacuum to afford 8 g of the title compound as a white solid. MS: (ES, m/z): 249 [M+H]$^+$.

Step-3: Dimethyl 2-(cyanomethyl)-1-oxo-2,3-dihydro-1H-indene-2,4-dicarboxylate

Into a 500-mL 3-necked round-bottom flask was placed dimethyl 1-oxo-2,3-dihydro-1H-indene-2,4-dicarboxylate (7 g, 28.2 mmol, 1 equiv), $Et_3N$ (15 g, 148 mmol, 5 equiv), 2-bromoacetonitrile (10 g, 83 mmol, 3 equiv) and THF (200 mL). The resulting solution was stirred for 16 h at room temperature and then concentrated under vacuum. The residue was diluted with 250 mL of water and extracted with 3×100 mL of EtOAc. The combined organic layers were dried over $Na_2SO_4$ and concentrated under vacuum. The residue was purified by normal phase chromatography on silica gel using EtOAc/petroleum ether (1:10). The collected fractions were concentrated under vacuum to afford 5 g (62% yield) of the title compound as a white solid. MS: (ES, m/z): 288 [M+H]$^+$.

Step-4: Dimethyl 2-(2-aminoethyl)-1-hydroxy-2,3-dihydro-1H-indene-2,4-dicarboxylate Acetate Into a 250-mL round-bottom flask equipped with a balloon of $H_2$ (g), was placed a solution of dimethyl 2-(cyanomethyl)-1-oxo-2,3-dihydro-1H-indene-2,4-dicarboxylate (3 g, 10.44 mmol, 1 equiv) in MeOH (100 mL), AcOH (60 mL), and $PtO_2$ (1.28 g). The resulting solution was stirred for 16 h at room temperature under an atmosphere of $H_2$ (g). The resulting mixture was filtered. The filtrate was concentrated under vacuum to give 3.7 g (crude) of the title compound as yellow oil which was used without further purification. MS: (ES, m/z): 294 [M+H]$^+$.

Step-5: Methyl 1-hydroxy-2'-oxo-1,3-dihydrospiro[indene-2,3'-pyrrolidine]-4-carboxylate Into a 250-mL round-bottom flask was placed a solution of dimethyl 2-(2-aminoethyl)-1-hydroxy-2,3-dihydro-1H-indene-2,4-dicarboxylate acetate (3.7 g, 10.48 mmol, 1 equiv) in MeOH (60 mL), and $NH_3$ solution in MeOH (40 mL). The resulting solution was stirred for 4 h at room temperature and then concentrated under vacuum. The residue was purified by normal phase chromatography on silica gel using $MeOH/CH_2Cl_2$ (1:10). The collected fractions were concentrated under vacuum to afford 1.3 g (48% yield) of the title compound as a white solid. MS: (ES, m/z): 262 [M+H]$^+$.

Step-6: Methyl 2'-oxo-1,3-dihydrospiro[indene-2,3'-pyrrolidine]-4-carboxylate

Into a 250-mL round-bottom flask was placed methyl 1-hydroxy-2'-oxo-1,3-dihydrospiro[indene-2,3'-pyrrolidine]-4-carboxylate (1.3 g, 4.98 mmol, 1 equiv), triethylsilane (10 mL) and TFA (60 mL). The resulting solution was stirred for 48 h at room temperature and then concentrated under vacuum. The residue was purified by normal phase chromatography on silica gel using $MeOH/CH_2Cl_2$ (1:10). The collected fractions were concentrated under vacuum to afford 700 mg (57% yield) of the title compound as a white solid. $^1H$ NMR (300 MHz, DMSO-d6) δ (ppm): 7.76-7.73 (d, J=7.2 Hz, 2H), 7.47-7.45 (d, J=7.2 Hz, 1H), 7.32-7.27 (t, J=7.6 Hz, 1H), 3.82 (s, 3H), 3.39-3.12 (m, 5H), 2.92-2.87 (d, J=16.2 Hz, 1H), 2.03-1.90 (m, 2H). MS: (ES, m/z): 246 [M+H]$^+$.

Step-7: 1'-(4-Chlorobenzyl)-2'-oxo-1,3-dihydrospiro[indene-2,3'-pyrrolidine]-4-carboxylic Acid Into a 50-mL round-bottom flask was placed a solution of methyl 2'-oxo-1,3-dihydrospiro[indene-2,3'-pyrrolidine]-4-carboxylate (60 mg, 0.24 mmol, 1 equiv) in DMF (3 mL), and NaH (60% dispersion in oil, 30 mg, 0.75 mmol, 3.12 equiv) was added at room temperature. The mixture was stirred for 20 min at room temperature and 1-(bromomethyl)-4-chlorobenzene (48 mg, 0.23 mmol, 0.95 equiv) was added. The resulting solution was stirred for 3 h at room temperature. The reaction was then quenched by the addition of 0.5 mL of water. The crude product was purified by reverse phase chromatography with the following conditions: Column: C18, 40 g, 20-35 μm; Mobile Phase A: Water/0.05% formic acid, Mobile Phase B: $CH_3CN$; Flow rate: 40 mL/min; Gradient: 5% B to 70% B in 25 min; Detector: UV 254 nm. The collected fractions were lyophilized to afford 50 mg (57% yield) of the title compound as a white solid. MS: (ES, m/z): 356 [M+H]$^+$.

Step-8: 1'-(4-Chlorobenzyl)-N-hydroxy-2'-oxo-1,3-dihydrospiro[indene-2,3'-pyrrolidine]-4-carboxamide Into a 25-mL round-bottom flask was placed a solution of 1'-[(4-chlorophenyl)methyl]-2'-oxo-1,3-dihydrospiro[indene-2,3'-pyrrolidine]-4-carboxylic acid (50 mg, 0.14 mmol, 1 equiv) in DMF (3 mL), isopropyl chloroformate (17 mg, 0.14 mmol, 1 equiv), and NMM (14 mg, 0.14 mmol, 0.98 equiv). The mixture was stirred for 1 h and $NH_2OH \cdot HCl$ (30 mg, 0.43 mmol, 3.1 equiv) was added. The resulting solution was stirred overnight at room temperature. The crude product was purified by Prep-HPLC with the following conditions: Column: X Bridge C18, 19×150 mm, 5 μm; Mobile Phase A: Water/0.05% TFA, Mobile Phase B: $CH_3CN$; Flow rate: 20 mL/min; Gradient: 30% B to 70% B in 10 min; Detector: UV 254 nm. The collected fractions were lyophilized to afford 16 mg (28% yield) of the title compound as a white solid. $^1H$ NMR (400 MHz, DMSO-d6) δ (ppm): 10.91 (s, 1H), 7.46-7.42 (m, 2H), 7.34-7.31 (m, 2H), 7.28-7.20 (m, 3H), 4.47-4.39 (m, 2H), 3.36-2.87 (m, 6H), 2.07-1.94 (m, 2H). MS: (ES, m/z): 371 [M+H]$^+$.

TABLE 1-2

| Ex. | Structure | 1H-NMR δ (ppm) | Found (ES, m/z) [M + H]+ |
|---|---|---|---|
| II-2 | 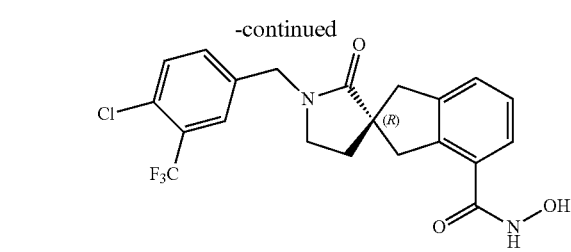 | (400 MHz, DMSO-d6): 10.90 (br s, 1H), 7.33-7.31 (m, 2H), 7.24-7.20 (m, 1H), 3.35-3.26 (m, 3H), 3.14 (d, J = 16 Hz, 1H), 3.02 (d, J = 16 Hz, 1H), 2.85 (d, J = 16 Hz, 1H), 2.80 (s, 3H), 1.94 (t, J = 5.8 Hz, 2H) | 261 |

The following compound was prepared according to the method of Example 1-2, with the following modification: In Step 7, the halide used was methyl iodide.

Example 2-2—Preparation of (R)-1'-(4-chloro-3-(trifluoromethyl)benzyl)-N-hydroxy-2'-oxo-1,3-dihydrospiro[indene-2,3'-pyrrolidine]-4-carboxamide and (S)-1'-(4-chloro-3-(trifluoromethyl)benzyl)-N-hydroxy-2'-oxo-1,3-dihydrospiro[indene-2,3'-pyrrolidine]-4-carboxamide (II-3 and HDTK054)

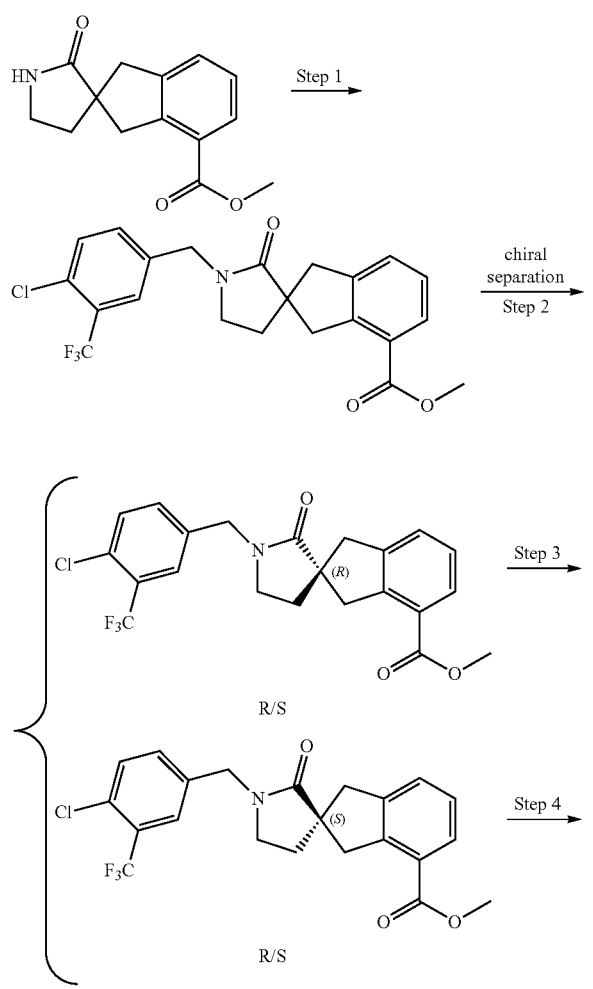

Step-1: Methyl 1'-(3-chloro-4-(trifluoromethyl)benzyl)-2'-oxo-1,3-dihydrospiro[indene-2,3'-pyrrolidine]-4-carboxylate Into a 25-mL round-bottom flask was placed a solution of methyl 2'-oxo-1,3-dihydrospiro[indene-2,3'-pyrrolidine]-4-carboxylate (300 mg, 1.22 mmol, 1 equiv) in THF (10 mL). Then NaH (60% dispersion in oil, 100 mg, 2.50 mmol, 2 equiv) was added at 0° C. over 15 min, followed by 4-(bromomethyl)-1-chloro-2-(trifluoromethyl)benzene (655 mg, 2.40 mmol, 2 equiv). The resulting solution was stirred for 3 h at room temperature and then concentrated under vacuum. The residue was purified by normal phase chromatography on silica gel using EtOAc/petroleum ether (2:1). The collected fractions were concentrated under vacuum to afford 300 mg (56% yield) of the title compound as a white solid. MS: (ES, m/z): 438 [M+H]+.

Step-2: Chiral separation of methyl (R)-1'-(4-chloro-3-(trifluoromethyl)benzyl)-2'-oxo-1,3-dihydrospiro[indene-2,3'-pyrrolidine]-4-carboxylate and methyl (S)-1'-(4-chloro-3-(trifluoromethyl)benzyl)-2'-oxo-1,3-dihydrospiro[indene-2,3'-pyrrolidine]-4-carboxylate The racemate of methyl 1'-(3-chloro-4-(trifluoromethyl)benzyl)-2'-oxo-1,3-dihydrospiro[indene-2,3'-pyrrolidine]-4-carboxylate was separated by Prep-SFC with the following conditions: Column: Chiralpak IA 2×25 cm, 5 μm; Mobile Phase A: $CO_2$, 70%, Mobile Phase B: MeOH, 30%; Flow rate: 40 mL/min; Detector: UV 220 nm. The first eluting isomer (Rt 4.87 min) was collected and concentrated under vacuum to give 110 mg (56% yield) of a white solid which was assigned as the R isomer of methyl 1'-(3-chloro-4-(trifluoromethyl)benzyl)-2'-oxo-1,3-dihydrospiro[indene-2,3'-pyrrolidine]-4-carboxylate. MS: (ES, m/z): 438 [M+H]$^+$. The second eluting isomer (Rt 6.24 min) was collected and concentrated under vacuum to give 120 mg (61% yield) of a white solid which was assigned as the S isomer of methyl 1'-(3-chloro-4-(trifluoromethyl)benzyl)-2'-oxo-1,3-dihydrospiro[indene-2,3'-pyrrolidine]-4-carboxylate. MS: (ES, m/z): 438 [M+H]$^+$.

Step-3: (R)-1'-(4-Chloro-3-(trifluoromethyl)benzyl)-N-hydroxy-2'-oxo-1,3-dihydrospiro[indene-2,3'-pyrrolidine]-4-carboxamide Into a 25-mL round-bottom flask was placed a solution of the first eluted isomer from Step 2, which was assigned as methyl (R)-1'-(4-chloro-3-(trifluoromethyl)benzyl)-2'-oxo-1,3-dihydrospiro[indene-2,3'-pyrrolidine]-4-carboxylate as described above, (110 mg, 0.25 mmol, 1 equiv) in THF/MeOH (4:1, 2 mL), NH$_2$OH (50% in H$_2$O, 2 mL, 30.21 mmol, 120 equiv), and aq. 1N NaOH (0.50 mL, 0.50 mmol, 2 equiv). The resulting solution was stirred for 16 h at room temperature. The solids were filtered out. The crude product was purified by Prep-HPLC with the following conditions: Column: XBridge Prep C18 OBD, 19×150 mm, 5 μm; Mobile Phase A: water/0.1% formic acid, Mobile Phase B: CH$_3$CN; Flow rate: 20 mL/min; Gradient: 5% B to 80% B in 8 min; Detector: UV 254 nm, 220 nm. The collected fractions were lyophilized to give 48 mg (44% yield) of the title compound as an off-white solid. $^1$H NMR (400 MHz, DMSO-d6) δ (ppm): 10.91 (br s, 1H), 8.97 (br s, 1H), 7.74 (d, J=8.8 Hz, 2H), 7.55 (d, J=8.4 Hz, 1H), 7.33-7.32 (m, 2H), 7.24-7.21 (m, 1H), 4.58-4.48 (m, 2H), 3.37-3.25 (m, 3H), 3.18-3.08 (m, 2H), 2.92 (d, J=16.0 Hz, 1H), 1.98 (t, J=6.4 Hz, 2H). MS: (ES, m/z): 439 [M+H]$^+$. Chiral HPLC (Column: Chiralpak AS-3, 0.46×5 cm, 3 μm; Mobile Phase A: hexanes/0.5% TFA, Mobile Phase B: EtOH; Flow rate: 1 mL/min; Gradient: 20% B hold for 8 min; Detector: UV 254 nm): Rt 2.25 min; >99%.

Step-4: (S)-1'-(4-Chloro-3-(trifluoromethyl)benzyl)-N-hydroxy-2'-oxo-1,3-dihydrospiro[indene-2,3'-pyrrolidine]-4-carboxamide The procedure from Step 3 was followed using the second eluted isomer from Step 2, which was assigned as methyl (S)-1'-(4-chloro-3-(trifluoromethyl)benzyl)-2'-oxo-1,3-dihydrospiro[indene-2,3'-pyrrolidine]-4-carboxylate as described above, (120 mg, 0.27 mmol, 1 equiv) to afford 51.3 mg (43% yield) of the title compound as an off-white solid. $^1$H NMR (400 MHz, DMSO-d6) δ (ppm): 10.91 (br s, 1H), 8.97 (br s, 1H), 7.75 (d, J=8.8 Hz, 2H), 7.55 (d, J=8.4 Hz, 1H), 7.33-7.32 (m, 2H), 7.24-7.21 (m, 1H), 4.58-4.48 (m, 2H), 3.37-3.25 (m, 3H), 3.20-3.06 (m, 2H), 2.92 (d, J=16.0 Hz, 1H), 1.98 (t, J=6.4 Hz, 2H). MS: (ES, m/z): 439 [M+H]$^+$. Chiral HPLC: Rt 3.94 min; >99%.

Example 3-2—Preparation of 1'-(3-fluoro-4-(trifluoromethyl)benzyl)-N-hydroxy-2'-oxo-1,3-dihydrospiro[indene-2,3'-pyrrolidine]-4-carboxamide (II-5)

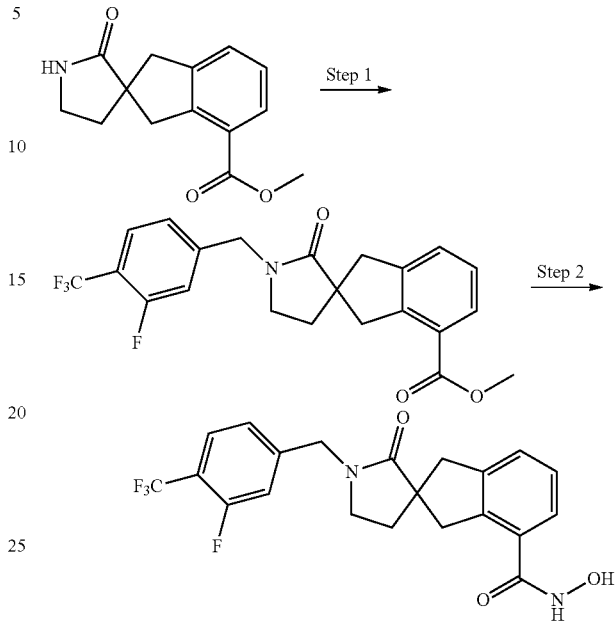

Step-1: Methyl 1'-(3-fluoro-4-(trifluoromethyl)benzyl)-2'-oxo-1,3-dihydrospiro[indene-2,3'-pyrrolidine]-4-carboxylate Into a 25-mL round-bottom flask was placed a solution of methyl 2'-oxo-1,3-dihydrospiro[indene-2,3'-pyrrolidine]-4-carboxylate (50 mg, 0.20 mmol, 1 equiv) in THF (5 mL). Then NaH (60% dispersion in oil, 10 mg, 0.25 mmol, 1.25 equiv) was added at room temperature. After stirring for 15 min, 4-(bromomethyl)-2-fluoro-1-(trifluoromethyl)benzene (60 mg, 0.23 mmol, 1.2 equiv) was added. The resulting solution was stirred for 2 h at room temperature and then concentrated under vacuum. The residue was purified by normal phase chromatography on silica gel using EtOAc/petroleum ether (1:1). The collected fractions were concentrated under vacuum to afford 48 mg (56% yield) of the title compound as a colorless oil. MS: (ES, m/z): 422 [M+H]$^+$.

Step-2: 1'-(3-Fluoro-4-(trifluoromethyl)benzyl)-N-hydroxy-2'-oxo-1,3-dihydrospiro[indene-2,3'-pyrrolidine]-4-carboxamide Into a 25-mL round-bottom flask was placed methyl 1'-(3-fluoro-4-(trifluoromethyl)benzyl)-2'-oxo-1,3-dihydrospiro[indene-2,3'-pyrrolidine]-4-carboxylate (43 mg, 0.10 mmol, 1 equiv), THF/MeOH (1:1, 3 mL), NH$_2$OH (50% in H$_2$O, 0.2 mL), and aq. NaOH (8 mg in 0.2 mL). The resulting solution was stirred for 2 h at room temperature. The crude product was purified by Prep-HPLC with the following conditions: Column: XBridge Prep C18, 19×150 mm, 5 μm; Mobile Phase A: water/0.05% TFA, Mobile Phase B: CH$_3$CN; Flow rate: 20 mL/min; Gradient: 10% B to 80% B in 15 min; Detector: UV 254 nm. The collected fractions were lyophilized to afford 10.2 mg (24% yield) of the title compound as a white solid. $^1$H NMR (400 MHz, DMSO-d6) δ (ppm): 10.91 (s, 1H), 9.00 (br s, 1H), 7.91 (t, J=7.6 Hz, 2H), 7.42-7.20 (m, 5H), 4.55 (s, 2H), 3.47-3.28 (m, 4H), 3.20 (d, J=16 Hz, 1H), 3.10 (d, J=16 Hz, 1H), 2.94 (d, J=16 Hz, 1H), 2.01 (t, J=8.4 Hz, 2H). MS: (ES, m/z): 423 [M+H]$^+$.

TABLE 2-2

| Ex. | Structure | ¹H-NMR δ (ppm) | Found (ES, m/z) [M + H]⁺ |
|---|---|---|---|
| II-6 | 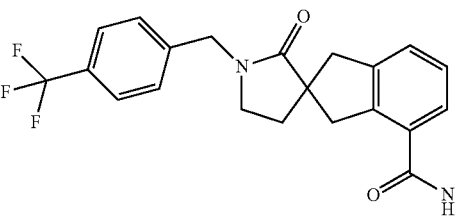 | (400 MHz, DMSO-d6): 10.90 (br s, 1H), 9.08 (br s, 1H), 7.76-7.74 (m, 2H), 7.48-7.45 (m, 2H), 7.35-7.31 (m, 2H), 7.24-7.20 (m, 1H), 4.55 (t, J = 3.6 Hz, 2H), 3.35-3.26 (m, 3H), 3.20 (d, J = 16 Hz, 1H), 3.08 (d, J = 16.8 Hz, 1H), 2.92 (d, J = 16 Hz. 1H), 1.98 (t, J = 6.4 Hz, 2H) | 405 |
| II-7 | 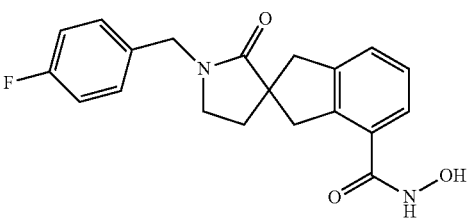 [SMILES: O=C(NO)c1cccc2c1CC1(CCN(Cc3ccc(F)cc3)C1=O)C2] | (400 MHz, DMSO-d6): 10.92 (br s, 1H), 9.03-8.90 (m, 1H), 7.34-7.13 (m, 7H), 4.48 (s, 2H), 3.34 (d, J = 16.8 Hz, 1H), 3.24-3.16 (m, 3H), 3.06 (d, J = 17.2 Hz, 1H), 2.89 (d, J = 16 Hz, 1H), 1.95-1.93 (m, 2H) | 355 |
| II-8 | 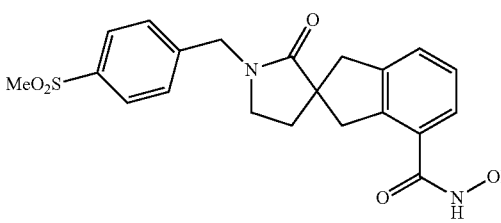 | (400 MHz, DMSO-d6): 9.00 (br s, 1H), 7.94 (d, J = 8.4 Hz, 2H), 7.51 (d, J = 8.4 Hz, 2H), 7.35-7.32 (m, 2H), 7.25-7.21 (m, 1H), 4.56 (s, 2H), 3.39-3.07 (m, 8H), 2.94 (d, J = 17 Hz, 1H), 2.00 (t, J = 6.8 Hz, 2H) | 415 |

The following compounds were prepared according to the method of Example 3-2, with the following modification: In Step 2, the solvent system can be MeOH or a 1:1 mixture of THF/MeOH.

Example 4-2—Preparation of 1'-cyclopropyl-N-hydroxy-2'-oxo-1,3-dihydrospiro[indene-2,3'-pyrrolidine]-4-carboxamide (II-9)

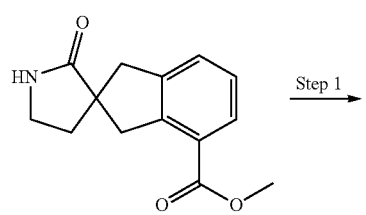

Step 1 →

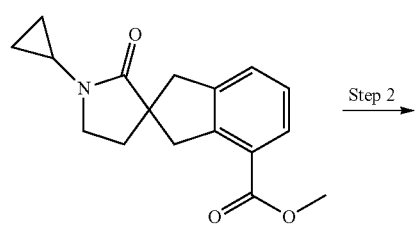

Step 2 →

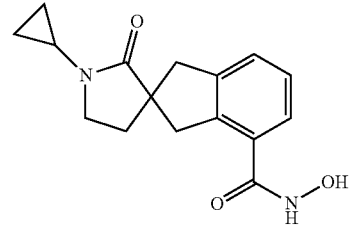

Step-1: Methyl 1'-cyclopropyl-2'-oxo-1,3-dihydrospiro[indene-2,3'-pyrrolidine]-4-carboxylate Into a 50-mL round-bottom flask was placed methyl 2'-oxo-1,3-dihydrospiro[indene-2,3'-pyrrolidine]-4-carboxylate (50 mg, 0.20 mmol, 1 equiv), cyclopropylboronic acid (150 mg, 1.75 mmol, 10 equiv), Cu(OAc)$_2$ (100 mg, 0.55 mmol, 2.7 equiv), Et$_3$N (150 mg, 1.48 mmol, 7.27 equiv), pyridine (75 mg, 0.95 mmol, 4.65 equiv), and THF (10 mL). The resulting solution was stirred for 48 h at 60° C. The solids were filtered out and the filtrate was concentrated under vacuum. The residue was purified by normal phase chromatography on silica gel with EtOAc/petroleum ether (1:1). The collected fractions were concentrated to give 38 mg (65% yield) of the title compound as a white solid. MS: (ES, m/z): 286 [M+H]⁺.

Step-2: 1'-Cyclopropyl-N-hydroxy-2'-oxo-1,3-dihydrospiro[indene-2,3'-pyrrolidine]-4-carboxamide Into a 25-mL round-bottom flask was placed a solution of methyl 1'-cyclopropyl-2'-oxo-1,3-dihydrospiro[indene-2,3'- pyrrolidine]-4-carboxylate (38 mg, 0.13 mmol, 1 equiv) in THF/MeOH (4:1, 3 mL), NH₂OH (50% in H₂O, 0.2 mL, 3.03 mmol, 23 equiv), and aq. 1N NaOH (0.27 mL, 0.27 mmol, 2 equiv). The resulting solution was stirred for 2 h at room temperature. The solids were filtered out. The crude product was purified by Prep-HPLC with the following conditions: Column: SunFire Prep C18 OBD, 19×150 mm, 5 μm; Mobile Phase A: water/0.1% formic acid, Mobile Phase B: CH₃CN; Flow rate: 20 mL/min; Gradient: 5% B to 48% B in 10 min; Detector: UV 254 nm, 220 nm. The collected fractions were lyophilized to give 2.8 mg (7% yield) of the title compound as a white solid. ¹H NMR (400 MHz, DMSO-d6) δ (ppm): 10.90 (s, 1H), 8.98 (s, 1H), 7.32 (d, J=7.2 Hz, 2H), 7.22 (t, J=7.2 Hz, 1H), 3.29-3.22 (m, 3H), 3.14 (d, J=16 Hz, 1H), 3.02 (d, J=16 Hz, 1H), 2.84 (d, J=16 Hz, 1H), 2.74-2.70 (m, 1H), 1.90 (t, J=6.8 Hz, 2H), 0.69-0.67 (m, 4H). MS: (ES, m/z): 287 [M+H]⁺.

Example 5-2—Preparation of 1'-(cyclobutylmethyl)-N-hydroxy-2'-oxo-1,3-dihydrospiro[indene-2,3'-pyrrolidine]-4-carboxamide (II-10)

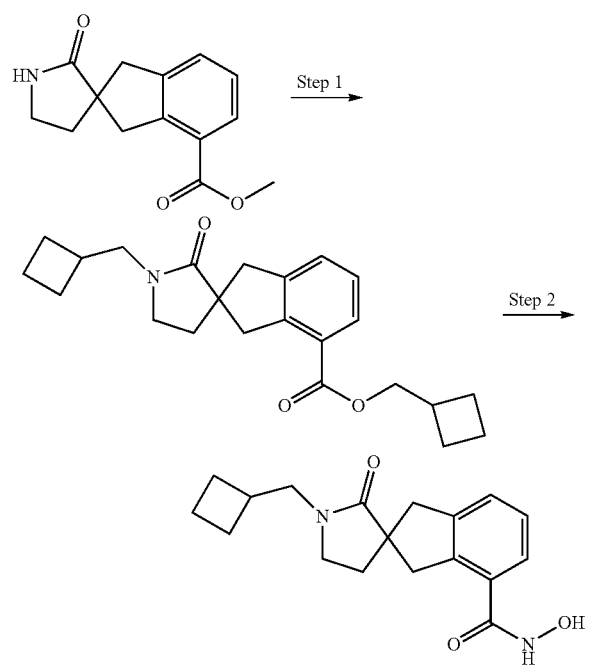

Step-1: Cyclobutylmethyl 1'-(cyclobutylmethyl)-2'-oxo-1,3-dihydrospiro[indene-2,3'-pyrrolidine]-4-carboxylate Into a 10-mL vial was placed methyl 2'-oxo-1,3-dihydrospiro[indene-2,3'-pyrrolidine]-4-carboxylate (80 mg, 0.33 mmol, 1 equiv), (bromomethyl)cyclobutane (480 mg, 3.22 mmol, 10 equiv), NaOᵗBu (80 mg, 0.71 mmol, 2.16 equiv), and DMF (3 mL). The reaction mixture was heated at 100° C. for 1 h in a microwave reactor. After cooling, the solids were filtered out. The crude product was purified by reverse phase chromatography with the following conditions: Column: C18, 40 g, 20-35 μm; Mobile Phase A: Water/0.05% TFA, Mobile Phase B: CH₃CN; Flow rate: 40 mL/min; Gradient: 5% B to 95% B in 35 min; Detector: UV 254 nm. The collected fractions were lyophilized to give 40 mg (33% yield) of the title compound as a white solid. MS: (ES, m/z): 368 [M+H]⁺.

Step-2: 1'-(Cyclobutylmethyl)-N-hydroxy-2'-oxo-1,3-dihydrospiro[indene-2,3'-pyrrolidine]-4-carboxamide Into a 25-mL round-bottom flask was placed a solution of cyclobutylmethyl 1'-(cyclobutylmethyl)-2'-oxo-1,3-dihydrospiro[indene-2,3'-pyrrolidine]-4-carboxylate (40 mg, 0.11 mmol, 1 equiv) in THF/MeOH (4:1, 3 mL), NH₂OH (50% in H₂O, 0.72 mL, 10.9 mmol, 100 equiv), and aq. 1N NaOH (0.44 mL, 0.44 mmol, 4 equiv). The resulting solution was stirred for 10 h at room temperature. The solids were filtered out. The crude product was purified by Prep-HPLC with the following conditions: Column: SunFire Prep C18 OBD, 19×150 mm, 5 μm; Mobile Phase A: water/0.1% formic acid, Mobile Phase B: CH₃CN; Flow rate: 20 mL/min; Gradient: 5% B to 85% B in 10 min; Detector: UV 254 nm, 220 nm. The collected fractions were lyophilized to give 3.0 mg (8% yield) of the title compound as a white solid. ¹H NMR (400 MHz, DMSO-d6) δ (ppm): 10.90 (s, 1H), 8.97 (s, 1H), 7.33-7.30 (m, 2H), 7.24-7.21 (m, 1H), 3.31-3.25 (m, 4H), 3.14 (d, J=16 Hz, 1H), 3.02 (d, J=16 Hz, 1H), 2.85 (d, J=16 Hz, 1H), 2.52-2.50 (m, 1H), 2.03-1.81 (m, 7H), 1.73-1.61 (m, 2H). MS: (ES, m/z): 315 [M+H]⁺.

Example 6-2—Preparation of N-hydroxy-2'-oxo-1'-(4-(trifluoromethyl)phenyl)-1,3-dihydrospiro[indene-2,3'-pyrrolidine]-4-carboxamide (II-11)

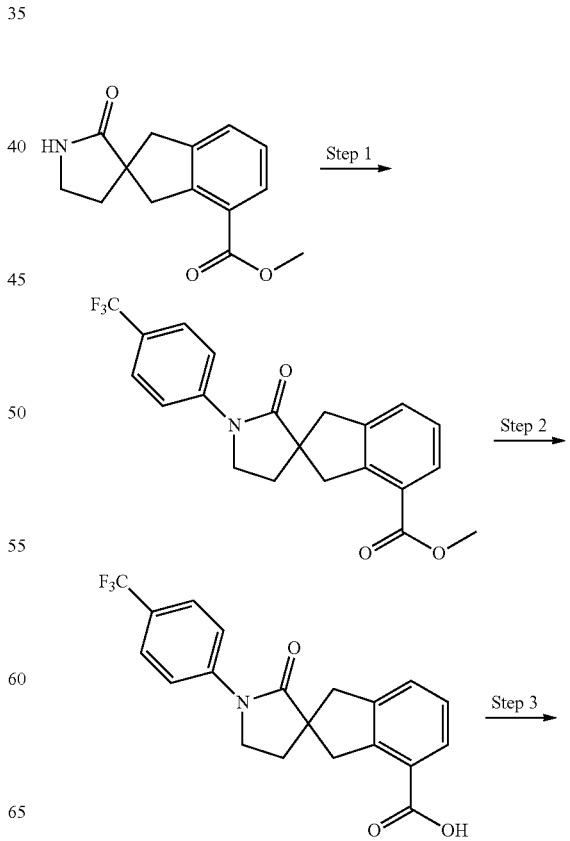

-continued

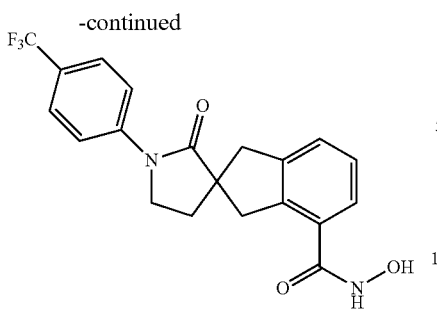

Step-1: Methyl 2'-oxo-1'-(4-(trifluoromethyl)phenyl)-1,3-dihydrospiro[indene-2,3'-pyrrolidine]-4-carboxylate Into a 50-mL round-bottom flask was placed methyl 2'-oxo-1,3-dihydrospiro[indene-2,3'-pyrrolidine]-4-carboxylate (100 mg, 0.41 mmol, 1 equiv), 1-iodo-4-(trifluoromethyl)benzene (100 mg, 0.37 mmol, 1.2 equiv), methyl [2-(methylamino)ethyl]amine (40 mg, 0.45 mmol, 0.4 equiv), CuI (40 mg, 0.21 mmol, 0.2 equiv), $Cs_2CO_3$ (400 mg, 1.23 mmol, 3 equiv), and DMSO (15 mL). The resulting solution was stirred for 12 h at 130° C. After cooling, 10 mL of $H_2O$ was added to the solution. The resulting solution was extracted with 20 mL of EtOAc, dried over $Na_2SO_4$, and concentrated under vacuum. The residue was purified by normal phase chromatography on silica gel with EtOAc/petroleum ether (1:10). The collected fractions were concentrated to give 70 mg (44% yield) of the title compound as a yellow solid. MS: (ES, m/z): 390 [M+H]$^+$.

Step-2: 2'-Oxo-1'-(4-(trifluoromethyl)phenyl)-1,3-dihydrospiro[indene-2,3'-pyrrolidine]-4-carboxylic Acid Into a 25-mL round-bottom flask was placed a solution of methyl 2'-oxo-1'-(4-(trifluoromethyl)phenyl)-1,3-dihydrospiro[indene-2,3'-pyrrolidine]-4-carboxylate (50 mg, 0.13 mmol, 1 equiv) in THF (10 mL), and NaOH (40 mg, 1.00 mmol, 7.6 equiv). The resulting solution was stirred for 18 h at 70° C. The pH value of the solution was adjusted to 4 with 1N HCl. The solids were filtered out. The crude product was purified by reverse phase chromatography with the following conditions: Column: C18, 40 g, 20-35 μm; Mobile Phase A: Water/0.05% TFA, Mobile Phase B: $CH_3CN$; Flow rate: 40 mL/min; Gradient: 25% B to 50% B in 10 min; Detector: UV 254 nm. The collected fractions were lyophilized to give 20 mg (41% yield) of the title compound as a white solid. MS: (ES, m/z): 376 [M+H]$^+$.

Step-3: N-Hydroxy-2'-oxo-1'-(4-(trifluoromethyl)phenyl)-1,3-dihydrospiro[indene-2,3'-pyrrolidine]-4-carboxamide Into a 25-mL round-bottom flask was placed a solution of 2'-oxo-1'-(4-(trifluoromethyl)phenyl)-1,3-dihydrospiro[indene-2,3'-pyrrolidine]-4-carboxylic acid (50 mg, 0.13 mmol, 1 equiv) in DMA (3 mL), NMM (10 mg, 0.10 mmol, 1 equiv), isopropyl chloroformate (10 mg, 0.08 mmol, 0.8 equiv) and $NH_2OH \cdot HCl$ (100 mg, 1.45 mmol, 14.5 equiv). The resulting solution was stirred for 12 h at 25° C. The solids were filtered out. The crude product was purified by Prep-HPLC with the following conditions: Column: XBridge Prep C18 OBD, 19×150 mm, 5 μm; Mobile Phase A: water/0.1% formic acid, Mobile Phase B: $CH_3CN$; Flow rate: 20 mL/min; Gradient: 5% B to 60% B in 8 min; Detector: UV 254 nm, 220 nm. The collected fractions were lyophilized to give 16 mg (32% yield) of the title compound as a light yellow solid. $^1$H NMR (400 MHz, DMSO-d6) δ (ppm): 10.91 (br s, 1H), 9.01 (br s, 1H), 7.97 (d, J=8.4 Hz, 2H), 7.77 (d, J=8.4 Hz, 2H), 7.37-7.34 (m, 2H), 7.28-7.23 (m, 1H), 3.93 (t, J=6.4 Hz, 2H), 3.44 (d, J=16.1 Hz, 1H), 3.33-3.19 (m, 2H), 3.05 (d, J=16.1 Hz, 1H), 2.15 (t, J=6.4 Hz, 2H). MS: (ES, m/z): 391 [M+H]$^+$.

Example 7-2—Preparation of N-hydroxy-2'-oxo-1'-(3-(trifluoromethyl)phenyl)-1,3-dihydrospiro[indene-2,3'-pyrrolidine]-4-carboxamide (II-12)

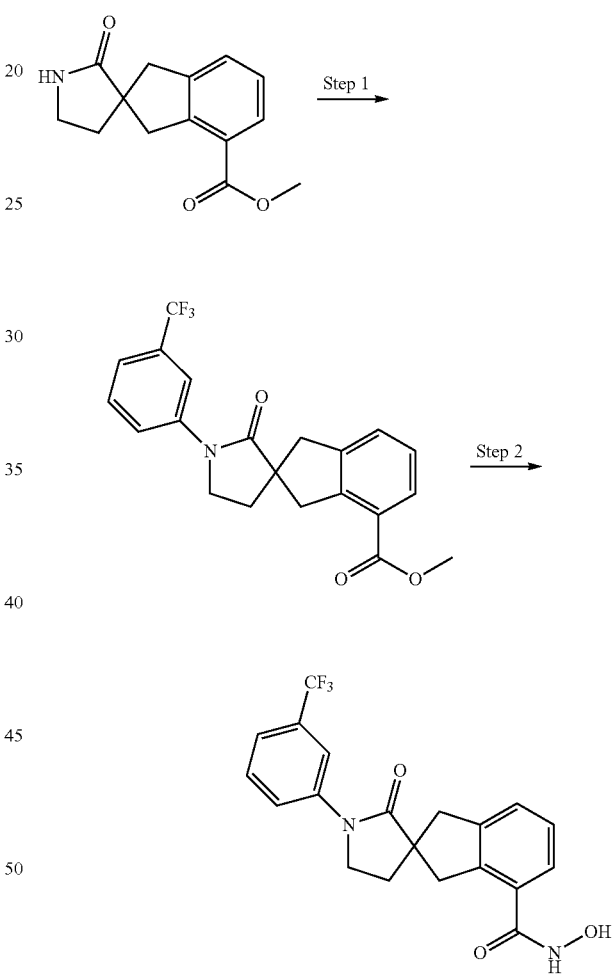

Step-1: Methyl 2'-oxo-1'-(3-(trifluoromethyl)phenyl)-1,3-dihydrospiro[indene-2,3'-pyrrolidine]-4-carboxylate Into a 25-mL round-bottom flask was placed methyl 2'-oxo-1,3-dihydrospiro[indene-2,3'-pyrrolidine]-4-carboxylate (200 mg, 0.82 mmol, 1 equiv), 1-iodo-3-(trifluoromethyl)benzene (200 mg, 0.74 mmol, 1.2 equiv), CuI (40 mg, 0.21 mmol, 0.2 equiv), methyl[2-(methylamino)ethyl]amine (40 mg, 0.45 mmol, 0.4 equiv), $Cs_2CO_3$ (400 mg, 1.23 mmol, 3 equiv), and DMSO (5 mL). The resulting solution was stirred for 24 h at 130° C. After cooling, 10 mL of H₂O was added to the solution. The resulting solution was extracted with 15 mL of EtOAc, dried over anhydrous Na₂SO₄, and concentrated under vacuum. The residue was purified by normal phase chromatography on silica gel with EtOAc/petroleum ether (1:1). The collected fractions were concentrated to give 80 mg (25% yield) of the title compound as a white solid. MS: (ES, m/z): 390 [M+H]⁺.

Step-2: N-Hydroxy-2'-oxo-1'-(3-(trifluoromethyl) phenyl)-1,3-dihydrospiro[indene-2,3'-pyrrolidine]-4-carboxamide Into a 25-mL round-bottom flask was placed a solution of methyl 2'-oxo-1'-(3-(trifluoromethyl)phenyl)-1,3-dihydrospiro[indene-2,3'-pyrrolidine]-4-carboxylate (66 mg, 0.17 mmol, 1 equiv) in THF/MeOH (4:1, 4 mL), NH₂OH (50% in H₂O, 1.12 mL, 17 mmol, 100 equiv), and aq. 1N NaOH (0.34 mL, 0.34 mmol, 2 equiv). The resulting solution was stirred for 24 h at room temperature. The solids were filtered out. The crude product was purified by Prep-HPLC with the following conditions: Column: XBridge Prep C18 OBD, 19×150 mm, 5 µm; Mobile Phase A: water/0.1% formic acid, Mobile Phase B: CH₃CN; Flow rate: 20 mL/min; Gradient: 18% B to 76% B in 8 min; Detector: UV 254 nm, 220 nm. The collected fractions were lyophilized to give 24.2 mg (37% yield) of the title compound as a white solid. ¹H NMR (400 MHz, DMSO-d6) δ (ppm): 10.93 (br s, 1H), 9.00 (br s, 1H), 8.28 (s, 1H), 7.89 (d, J=8.4 Hz, 1H), 7.66 (t, J=8.0 Hz, 1H), 7.52 (d, J=8.0 Hz, 1H), 7.36-7.34 (m, 2H), 7.27-7.24 (m, 1H), 3.98-3.90 (m, 2H), 3.41 (d, J=16.0 Hz, 1H), 3.30-3.19 (m, 2H), 3.04 (d, J=16.0 Hz, 1H), 2.15 (t, J=6.8 Hz, 2H). MS: (ES, m/z): 391 [M+H]⁺.

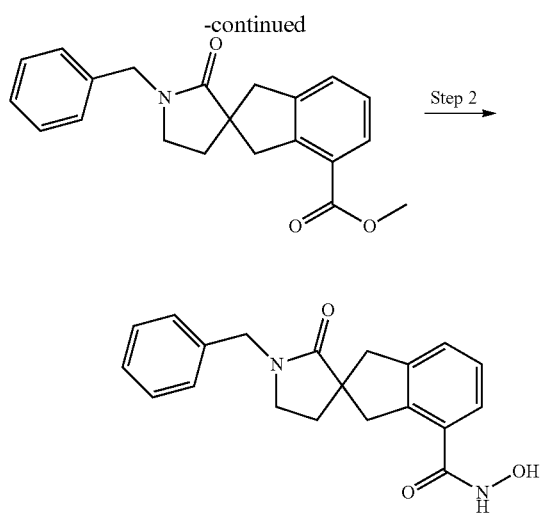

A solution of methyl 2'-oxo-1,3-dihydrospiro[indene-2,3'-pyrrolidine]-4-carboxylate in DMA (0.2M, 331 mg, 1.35 mmol) was deprotonated with an equimolar quantity of NaH (60% dispersion in oil, 54 mg). This solution (150 µL, 30 µmol, 1 equiv) was added to a solution of benzyl bromide (0.2M in CH₃CN, 300 µL, 60 µmol, 2 equiv) in a 2-dram vial. NaI (18 mg, 120 µmol, 4 equiv) was added as a solid in one portion. The vial was sealed and shaken at 50° C. for 24 h, then the solvent was removed under a stream of N₂ (g). The residue was diluted with brine (500 µL) and extracted with EtOAc (2×500 µL). The combined organic layers were dried under a stream of N₂ (g). THF/MeOH (3:1, 200 µL) was added to the residue. The vial was sealed and shaken at

TABLE 3-2

| Ex. | Structure | ¹H-NMR δ (ppm) | Found (ES, m/z) [M + H]⁺ |
|---|---|---|---|
| II-13 | 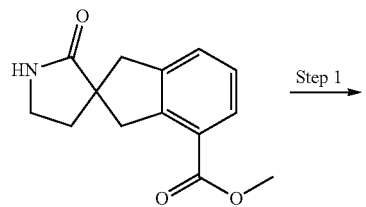 | (300 MHz, DMSO-d6): 10.9 (br s, 1H), 7.86-7.78 (m, 2H), 7.66-7.56 (m, 2H), 7.44-7.19 (m, 3H), 3.80-3.71 (m, 2H), 3.41 (d, J = 22.8 Hz, 1H), 3.3-3.17 (m, 2H), 3.04 (d, J = 21.6 Hz, 1H), 2.19 (t, J = 8.8 Hz, 2H) | 391 |

Example 8-2—Preparation of 1'-benzyl-N-hydroxy-2'-oxo-1,3-dihydrospiro[indene-2,3'-pyrrolidine]-4-carboxamide (II-14)

50° C. for 15 min to dissolve the residue, then cooled to room temperature. NH₂OH (50% v/v solution in water, 150 µL) was added, followed by aq. 1N NaOH (100 µL). The mixture was sealed and then shaken at room temperature for 18 h. The reaction mixture was concentrated under a stream of N₂ (g) at room temperature, then dissolved in 500 of DMSO and purified by mass triggered Prep-HPLC using the following conditions: Column: Waters Sunfire C18, 19×50 mm, 5 µm; Mobile Phase A: water/0.1% formic acid, Mobile Phase B: CH₃CN/0.1% formic acid; Gradient; 15% B up to 100% B in 6 min; Flow rate: 23 mL/min; Detector: UV 254 nm, 220 nm. The product-containing fractions were combined and concentrated under vacuum to afford 2.0 mg (20% yield) the title compound. MS: (ES, m/z): 337 [M+H]⁺.

TABLE 4-2

| Ex. | Structure | Found (ES, m/z) [M + H]+ |
|---|---|---|
| II-15 | 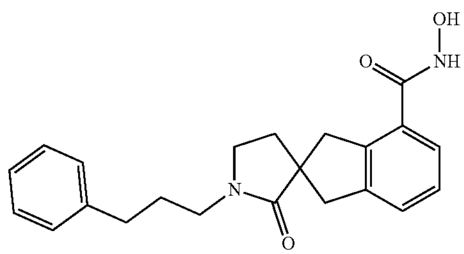 [SMILES: O=C(NO)c1cccc2c1CC1(CCN(CCCc3ccccc3)C1=O)C2] | 365 |
| II-16 | 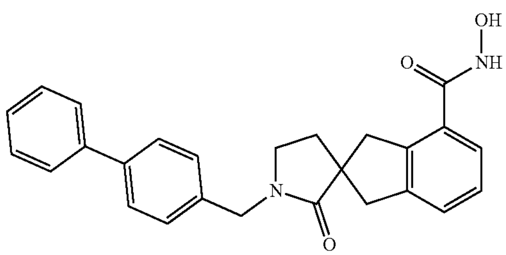 [SMILES: O=C(NO)c1cccc2c1CC1(CCN(Cc3ccc(-c4ccccc4)cc3)C1=O)C2] | 413 |
| II-17 | 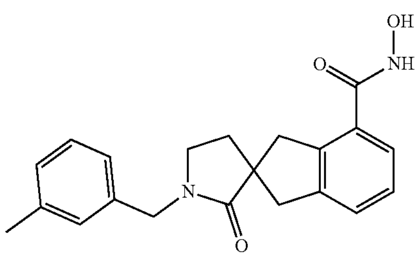 [SMILES: Cc1cccc(CN2CCC3(Cc4cccc(C(=O)NO)c4C3)C2=O)c1] | 351 |
| II-18 | 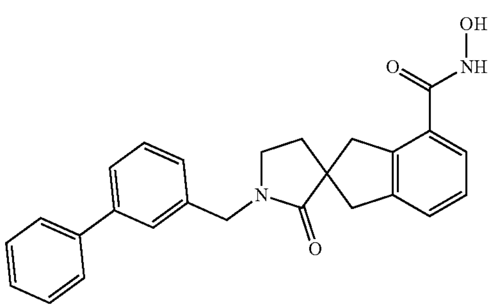 [SMILES: O=C(NO)c1cccc2c1CC1(CCN(Cc3cccc(-c4ccccc4)c3)C1=O)C2] | 413 |
| II-19 | 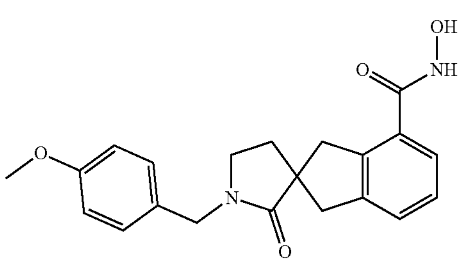 [SMILES: COc1ccc(CN2CCC3(Cc4cccc(C(=O)NO)c4C3)C2=O)cc1] | 367 |

TABLE 4-2-continued

| Ex. | Structure | Found (ES, m/z) [M + H]+ |
|---|---|---|
| II-20 | 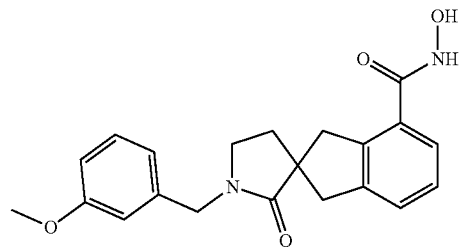 [SMILES: COc1cccc(CN2CCC3(Cc4cccc(C(=O)NO)c4C3)C2=O)c1] | 367 |
| II-21 | 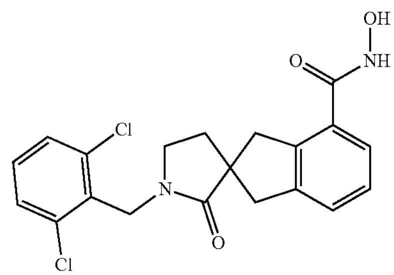 [SMILES: O=C(NO)c1cccc2c1CC1(CCN(Cc3c(Cl)cccc3Cl)C1=O)C2] | 405 |
| II-22 | 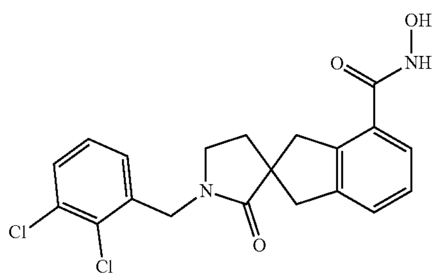 [SMILES: O=C(NO)c1cccc2c1CC1(CCN(Cc3cccc(Cl)c3Cl)C1=O)C2] | 405 |
| II-23 | 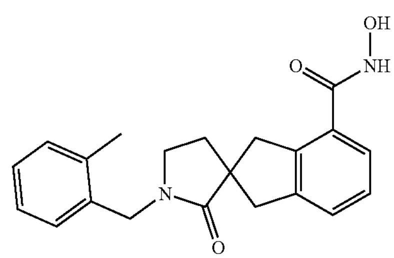 [SMILES: Cc1ccccc1CN1CCC2(Cc3cccc(C(=O)NO)c3C2)C1=O] | 351 |
| II-24 | 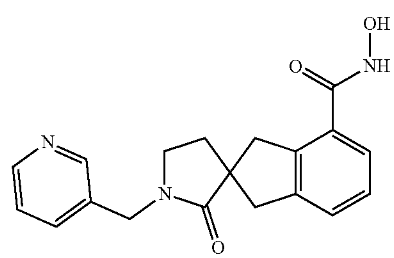 [SMILES: O=C(NO)c1cccc2c1CC1(CCN(Cc3cccnc3)C1=O)C2] | 338 |
| II-25 | 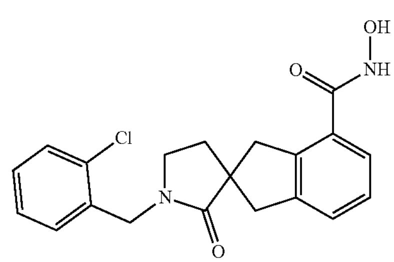 [SMILES: O=C(NO)c1cccc2c1CC1(CCN(Cc3ccccc3Cl)C1=O)C2] | 371 |

TABLE 4-2-continued

| Ex. | Structure | Found (ES, m/z) [M + H]+ |
|---|---|---|
| II-26 | 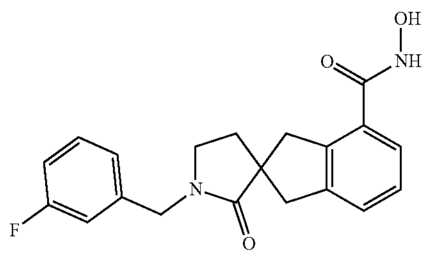 [SMILES: O=C(NO)c1cccc2c1CC1(CCN(Cc3cccc(F)c3)C1=O)C2] | 355 |
| II-27 | 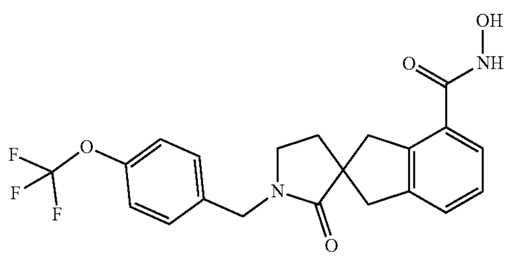 [SMILES: O=C(NO)c1cccc2c1CC1(CCN(Cc3ccc(OC(F)(F)F)cc3)C1=O)C2] | 421 |
| II-28 | 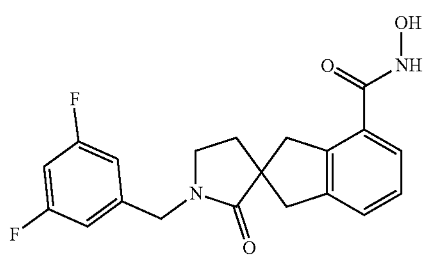 [SMILES: O=C(NO)c1cccc2c1CC1(CCN(Cc3cc(F)cc(F)c3)C1=O)C2] | 373 |
| II-29 | 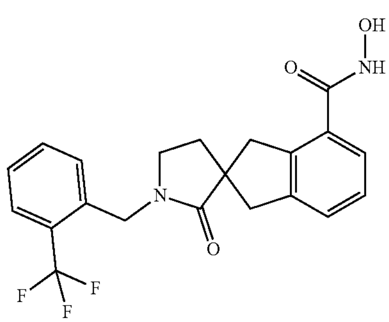 [SMILES: O=C(NO)c1cccc2c1CC1(CCN(Cc3ccccc3C(F)(F)F)C1=O)C2] | 405 |
| II-30 | 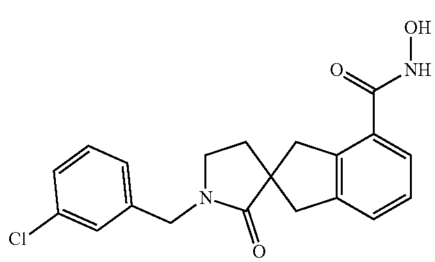 [SMILES: O=C(NO)c1cccc2c1CC1(CCN(Cc3cccc(Cl)c3)C1=O)C2] | 371 |

TABLE 4-2-continued

| Ex. | Structure | Found (ES, m/z) [M + H]+ |
|---|---|---|
| II-31 | 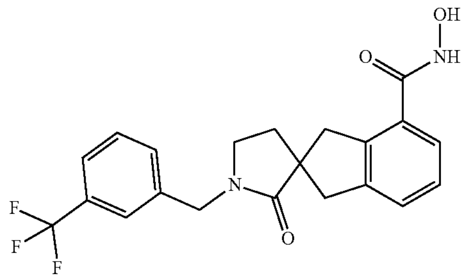 [SMILES: O=C(NO)c1cccc2c1CC1(CCN(Cc3cccc(C(F)(F)F)c3)C1=O)C2] | 405 |
| II-32 | 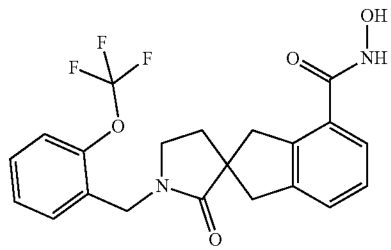 [SMILES: O=C(NO)c1cccc2c1CC1(CCN(Cc3ccccc3OC(F)(F)F)C1=O)C2] | 421 |
| II-33 | 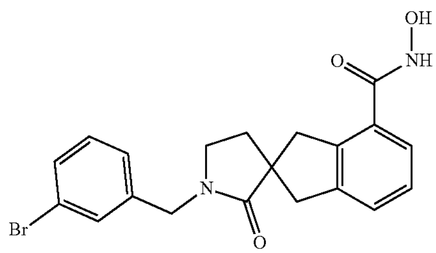 | 415 |
| II-34 | 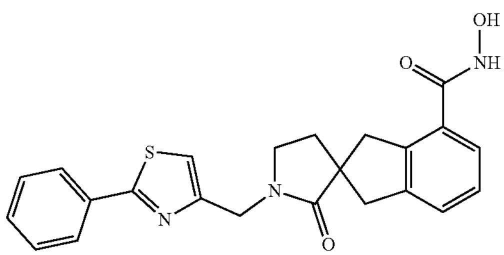 [SMILES: O=C(NO)c1cccc2c1CC1(CCN(Cc3csc(-c4ccccc4)n3)C1=O)C2] | 420 |
| II-35 | 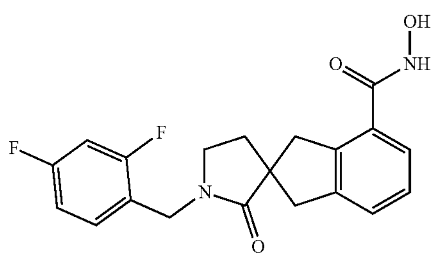 [SMILES: O=C(NO)c1cccc2c1CC1(CCN(Cc3ccc(F)cc3F)C1=O)C2] | 373 |
| II-36 | 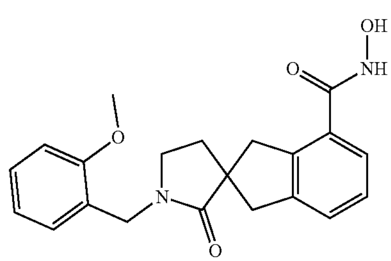 [SMILES: COc1ccccc1CN1CCC2(Cc3cccc(C(=O)NO)c3C2)C1=O] | 367 |

TABLE 4-2-continued

| Ex. | Structure | Found (ES, m/z) [M + H]+ |
|---|---|---|
| II-37 | 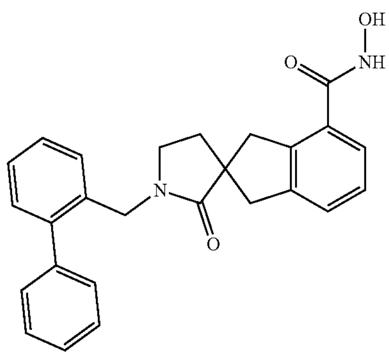 [SMILES: O=C(NO)c1cccc2c1CC1(CCN(Cc3ccccc3-c3ccccc3)C1=O)C2] | 413 |
| II-38 | 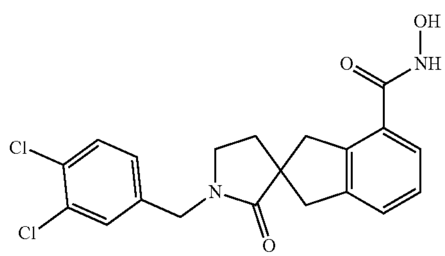 [SMILES: O=C(NO)c1cccc2c1CC1(CCN(Cc3ccc(Cl)c(Cl)c3)C1=O)C2] | 405 |
| II-39 | 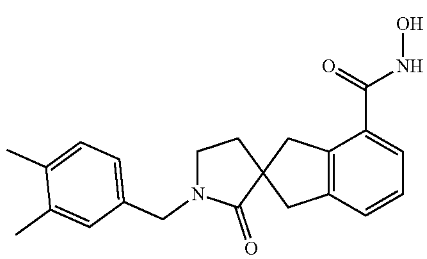 [SMILES: Cc1ccc(CN2CCC3(Cc4cccc(C(=O)NO)c4C3)C2=O)cc1C] | 365 |
| II-40 | 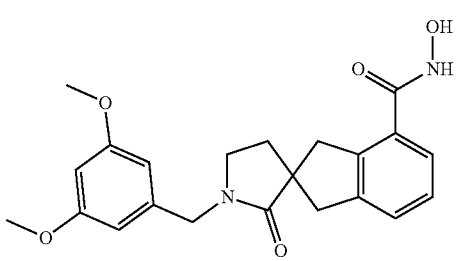 [SMILES: COc1cc(CN2CCC3(Cc4cccc(C(=O)NO)c4C3)C2=O)cc(OC)c1] | 397 |
| II-41 | 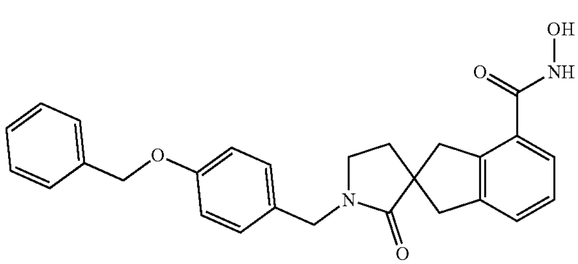 [SMILES: O=C(NO)c1cccc2c1CC1(CCN(Cc3ccc(OCc4ccccc4)cc3)C1=O)C2] | 443 |

TABLE 4-2-continued

| Ex. | Structure | Found (ES, m/z) [M + H]+ |
|---|---|---|
| II-42 | 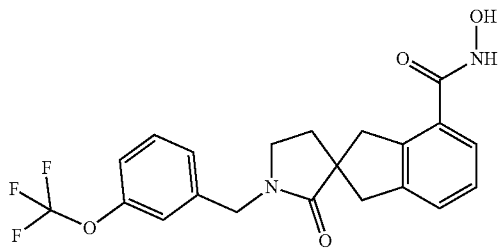 [SMILES: O=C(NO)c1cccc2c1CC1(CCN(Cc3cccc(OC(F)(F)F)c3)C1=O)C2] | 421 |
| II-43 | 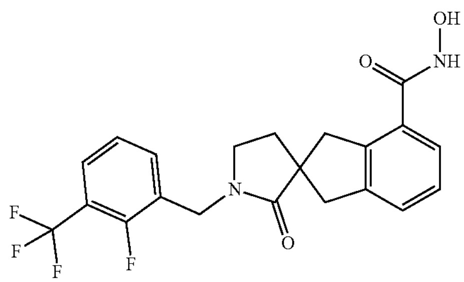 [SMILES: O=C(NO)c1cccc2c1CC1(CCN(Cc3cccc(C(F)(F)F)c3F)C1=O)C2] | 423 |
| II-44 | 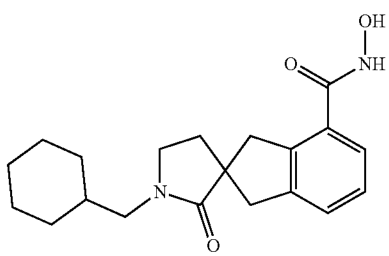 [SMILES: O=C(NO)c1cccc2c1CC1(CCN(CC3CCCCC3)C1=O)C2] | 343 |
| II-45 | 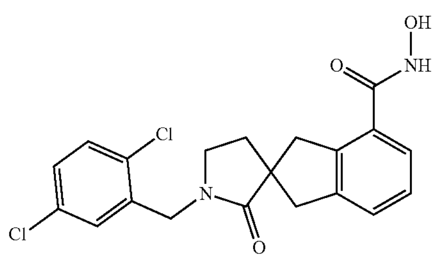 [SMILES: O=C(NO)c1cccc2c1CC1(CCN(Cc3cc(Cl)ccc3Cl)C1=O)C2] | 405 |
| II-46 | 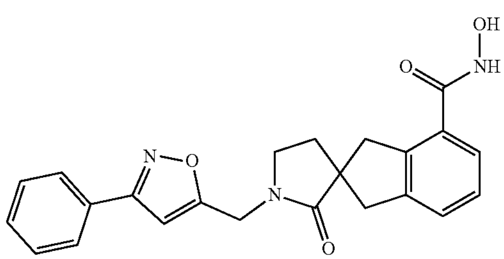 [SMILES: O=C(NO)c1cccc2c1CC1(CCN(Cc3cc(-c4ccccc4)no3)C1=O)C2] | 404 |
| II-47 | 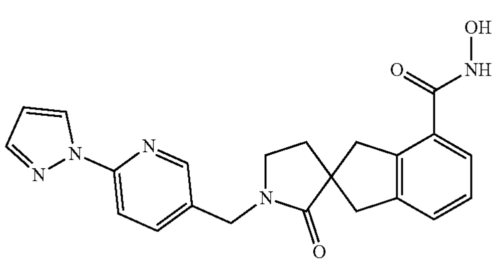 [SMILES: O=C(NO)c1cccc2c1CC1(CCN(Cc3ccc(-n4cccn4)nc3)C1=O)C2] | 404 |

TABLE 4-2-continued
| Ex. | Structure | Found (ES, m/z) [M + H]+ |
|---|---|---|
| II-48 | 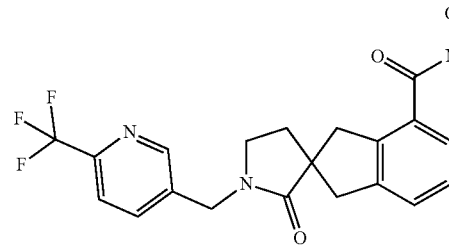 | 406 |
| II-49 | 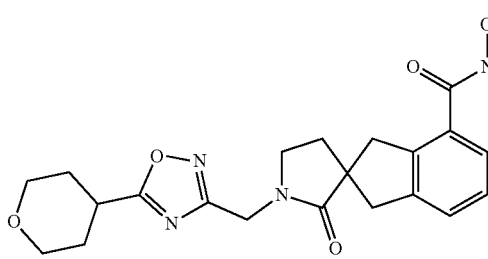 | 413 |
| II-50 | 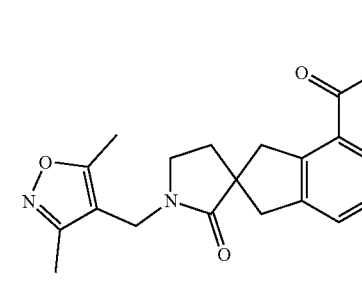 | 356 |
| II-51 | 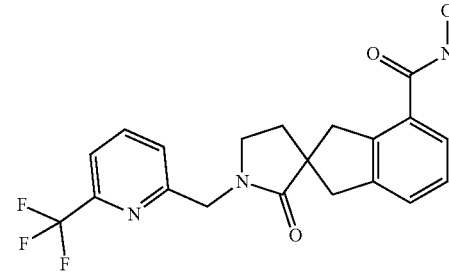 | 406 |
| II-52 | 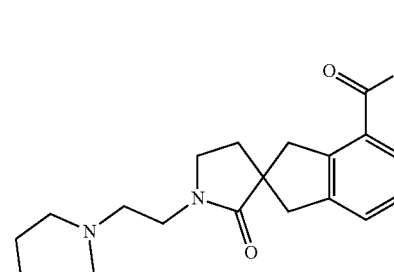 | 360 |

TABLE 4-2-continued

| Ex. | Structure | Found (ES, m/z) [M + H]+ |
|---|---|---|
| II-53 | 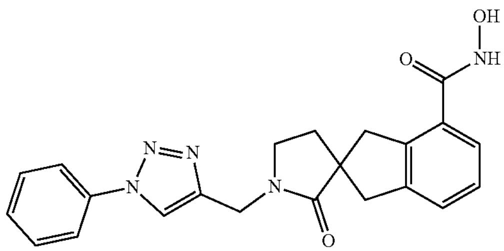 [SMILES: O=C(NO)c1cccc2c1CC1(CCN(Cc3cn(-c4ccccc4)nn3)C1=O)C2] | 404 |
| II-54 | 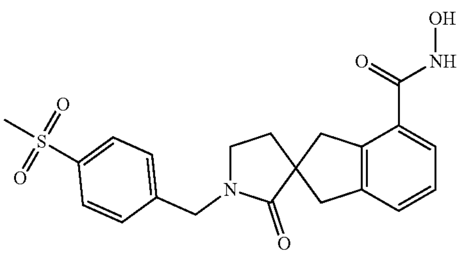 [SMILES: CS(=O)(=O)c1ccc(CN2CCC3(Cc4cccc(C(=O)NO)c4C3)C2=O)cc1] | 415 |
| II-55 | 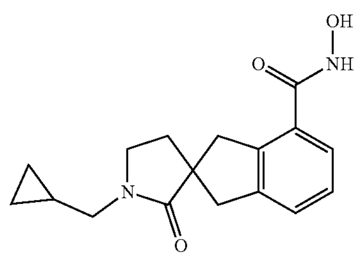 [SMILES: O=C(NO)c1cccc2c1CC1(CCN(CC3CC3)C1=O)C2] | 301 |

The following compounds were prepared according to the parallel synthesis method of Example 8-2.

Example 9-2—Preparation of N-hydroxy-1'-(4-(trifluoromethyl)benzyl)-1,3-dihydrospiro[indene-2,3'-pyrrolidine]-4-carboxamide (II-56)

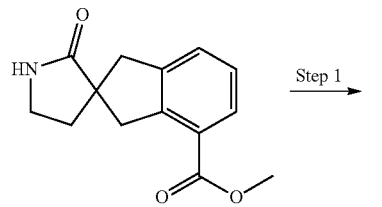

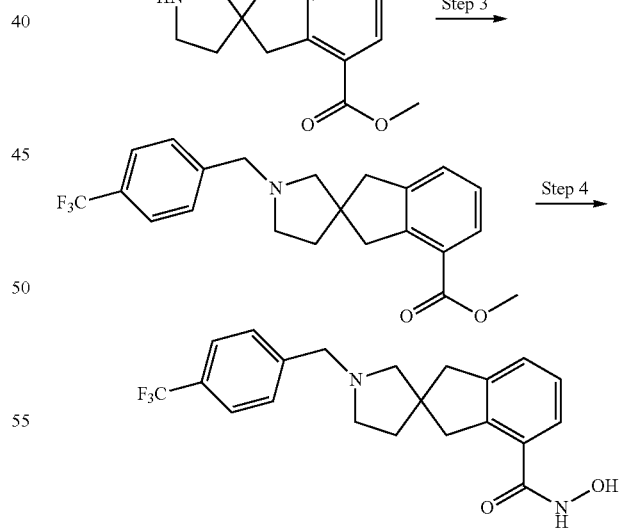

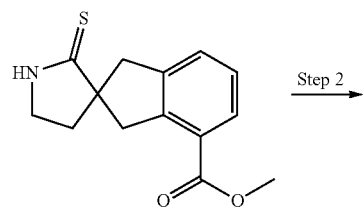

Step-1: Methyl 2'-thioxo-1,3-dihydrospiro[indene-2,3'-pyrrolidine]-4-carboxylate Into a 25-mL round-bottom flask was placed methyl 2'-oxo-1,3-dihydrospiro[indene-2,3'-pyrrolidine]-4-carboxylate (1.5 g, 6.12 mmol, 1 equiv), 2,4-bis(4-methoxyphenyl)-2,4-dithioxo-1,3,2,4-dithiadiphosphetane (Lawesson reagent) (2.37 g, 5.87 mmol, 0.96 equiv), and THF (15 mL). The resulting solution was stirred for 12 h at room temperature and then concentrated under vacuum. The residue was purified by normal phase chromatography on silica gel with EtOAc/petroleum ether (1:3). The collected fractions were concentrated to afford 600 mg (38% yield) of the title compound as a white solid. MS: (ES, m/z): 262 [M+H]⁺.

Step-2: Methyl 1,3-dihydrospiro[indene-2,3'-pyrrolidine]-4-carboxylate

Into a 250-mL round-bottom flask was placed methyl 2'-thioxo-1,3-dihydrospiro[indene-2,3'-pyrrolidine]-4-carboxylate (600 mg, 2.30 mmol, 1 equiv), NiCl$_2$.6H$_2$O (1.9 g, 7.98 mmol, 3.5 equiv), MeOH (30 mL), and THF (20 mL). Then NaBH$_4$ (400 mg, 10.57 mmol, 4.66 equiv) was added in portions at 0° C. The resulting solution was stirred for 1 h at room temperature. The solids were filtered out and the filtrate was concentrated under vacuum. The residue was purified by normal phase chromatography on silica gel using MeOH/CH$_2$Cl$_2$ (1:10). The collected fractions were concentrated to afford 400 mg (75% yield) of the title compound as white solid. MS: (ES, m/z): 232 [M+H]⁺.

Step-3: Methyl 1'-(4-(trifluoromethyl)benzyl)-1,3-dihydrospiro[indene-2,3'-pyrrolidine]-4-carboxylate Into a 25-mL round-bottom flask was placed 1-(bromomethyl)-4-(trifluoromethyl)benzene (81 mg, 0.34 mmol, 1.1 equiv), methyl 1,3-dihydrospiro[indene-2,3'-pyrrolidine]-4-carboxylate (69 mg, 0.30 mmol, 1 equiv), THF (10 mL), and a drop of DMF. This was followed by the addition of NaH (30 mg, 1.25 mmol, 2.1 equiv). The resulting solution was stirred for 12 h at room temperature. The resulting mixture was concentrated under vacuum. The residue was purified by normal phase chromatography on silica gel using EtOAc/petroleum ether (1:1). The collected fractions were concentrated to afford 20 mg (17% yield) of the title compound as colorless oil. MS: (ES, m/z): 390 [M+H]⁺.

Step-4: N-Hydroxy-1'-(4-(trifluoromethyl)benzyl)-1,3-dihydrospiro[indene-2,3'-pyrrolidine]-4-carboxamide Into a 25-mL round-bottom flask was placed methyl 1'-(4-(trifluoromethyl)benzyl)-1,3-dihydrospiro[indene-2,3'-pyrrolidine]-4-carboxylate (20 mg, 0.05 mmol, 1 equiv) in THF/MeOH (4:1, 2 mL), NH$_2$OH (50% in H$_2$O, 0.1 mL, 1.52 mmol, 30 equiv) and aq. 1N NaOH (0.1 mL, 0.1 mmol, 2 equiv). The resulting solution was stirred for 2 h at room temperature. The solids were filtered out. The crude product was purified by Prep-HPLC with the following conditions: Column: Gemini-NX C18 110 A, AXIA Packed 150×21.2 mm, 5 µm; Mobile Phase A: water/0.05% TFA, Mobile Phase B: CH$_3$CN; Flow rate: 20 mL/min; Gradient: 10% B to 42% B in 12 min; Detector: UV 254 nm, 220 nm. Aqueous 1N HCl (0.05 mL) was added to the collected fractions and lyophilized to give 3 mg (15% yield) of the title compound as the HCl salt as a white solid. ¹H NMR (400 MHz, DMSO-d6) δ (ppm): 10.92 (br s, 1H), 9.01 (br s, 1H), 7.88-7.83 (m, 4H), 7.24-7.05 (m, 3H), 4.58-4.45 (m, 2H), 3.55-3.53 (m, 2H), 3.44-3.14 (m, 4H), 3.14-2.90 (m, 2H), 2.14-2.00 (m, 1H), 1.98-1.90 (m, 1H). MS: (ES, m/z): 391 [M−HCl+H]⁺.

Example 10-2—Preparation of 1'-cyclopropyl-N-hydroxy-1,3-dihydrospiro[indene-2,3'-pyrrolidine]-4-carboxamide (II-57)

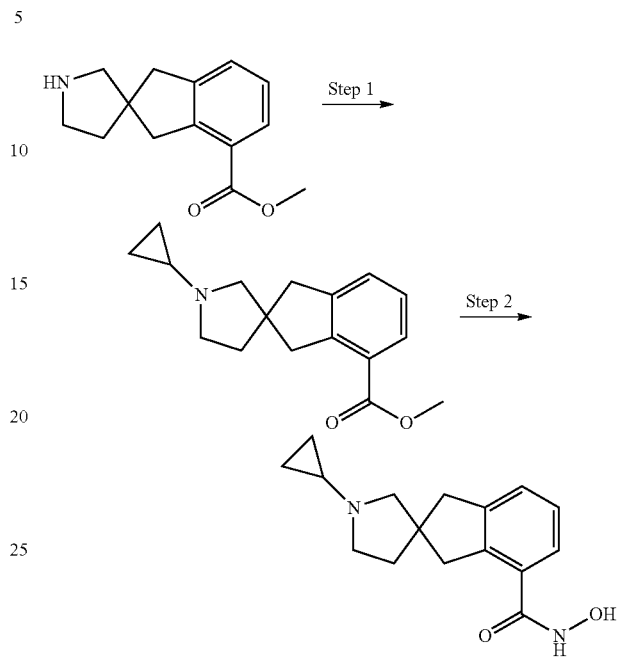

Step-1: Methyl 1'-cyclopropyl-1,3-dihydrospiro[indene-2,3'-pyrrolidine]-4-carboxylate Into a 50-mL round-bottom flask was placed a solution of methyl 1,3-dihydrospiro[indene-2,3'-pyrrolidine]-4-carboxylate (180 mg, 0.78 mmol, 1 equiv) in CH$_2$Cl$_2$ (5 mL), (1-ethoxycyclopropoxy)trimethylsilane (720 mg, 4.13 mmol, 5.3 equiv), AcOH (416 mg, 6.93 mmol, 8.9 equiv), and NaBH$_3$CN (224 mg, 3.56 mmol, 4.6 equiv). The resulting solution was stirred overnight at 40° C. The reaction mixture was cooled to room temperature and concentrated under vacuum. The crude product was purified by reverse phase chromatography with the following conditions: Column: C18, 40 g, 20-35 µm; Mobile Phase A: Water/0.05% TFA, Mobile Phase B: CH$_3$CN; Flow rate: 40 mL/min; Gradient: 5% B to 65% B in 30 min. The collected fractions were lyophilized to give 60 mg (28% yield) of the title compound as white solid. MS: (ES, m/z): 272 [M+H]⁺.

Step-2: 1'-Cyclopropyl-N-hydroxy-1,3-dihydrospiro[indene-2,3'-pyrrolidine]-4-carboxamide Into a 25-mL round-bottom flask was placed a solution of 1'-cyclopropyl-1,3-dihydrospiro[indene-2,3'-pyrrolidine]-4-carboxylate (60 mg, 0.22 mmol, 1 equiv) in THF/MeOH (4:1, 3 mL), NH$_2$OH (50% in H$_2$O, 1.40 mL, 21 mmol, 96 equiv) and aq. 1N NaOH (0.44 mL, 0.44 mmol, 2 equiv). The resulting solution was stirred for 4 h at room temperature. The solids were filtered out. The crude product was purified by Prep-HPLC with the following conditions: Column: X Bridge C18, 19×150 mm, 5 µm; Mobile Phase A: Water/0.05% TFA, Mobile Phase B: CH$_3$CN; Flow rate: 20 mL/min; Gradient: 30% B to 70% B in 10 min; Detector: UV 254 nm. The collected fractions were lyophilized to give 1.4 mg (2% yield) of the title compound as a white solid. ¹H NMR (300 MHz, DMSO-d6) δ (ppm): 10.80 (br s, 1H), 8.95

(br s, 1H), 7.27-7.23 (m, 2H), 7.16-7.12 (m, 1H), 3.07-2.79 (m, 4H), 2.73-2.70 (m, 2H), 2.65-2.57 (m, 2H), 1.75-1.65 (m, 3H), 0.35-0.25 (m, 4H). MS: (ES, m/z): 273 [M+H]+.

Example 11-2—Preparation of N-hydroxy-1'-(4-(trifluoromethyl)benzoyl)-1,3-dihydrospiro[indene-2,3'-pyrrolidine]-4-carboxamide (II-58)

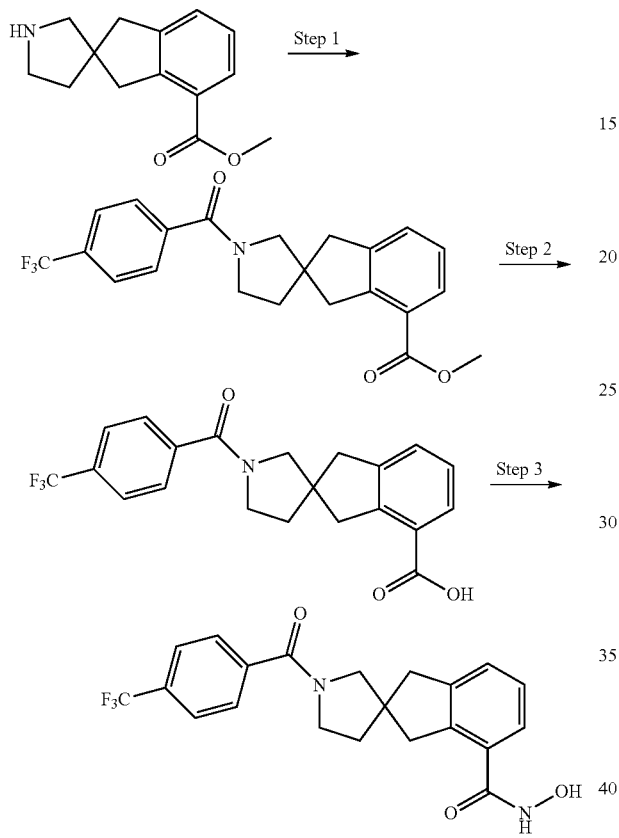

Step-1: Methyl 1'-(4-(trifluoromethyl)benzoyl)-1,3-dihydrospiro[indene-2,3'-pyrrolidine]-4-carboxylate Into a 50-mL round-bottom flask was placed a solution of methyl 1,3-dihydrospiro[indene-2,3'-pyrrolidine]-4-carboxylate (30 mg, 0.13 mmol, 1 equiv) in CH$_2$Cl$_2$ (5 mL), and pyridine (60 mg, 0.76 mmol, 5.85 equiv). The reaction mixture was stirred for 30 min at room temperature, and then 4-(trifluoromethyl)benzoyl chloride (45 mg, 0.22 mmol, 1.66 equiv) was added. The resulting solution was stirred for 1 h at room temperature, then concentrated under vacuum. The residue was purified by normal phase chromatography on silica gel using EtOAc/petroleum ether (1:2). The collected fractions were concentrated to afford 30 mg (57% yield) of the title compound as colorless oil. MS: (ES, m/z): 404 [M+H]+.

Step-2: 1'-(4-(Trifluoromethyl)benzoyl)-1,3-dihydrospiro[indene-2,3'-pyrrolidine]-4-carboxylic Acid Into a 50-mL round-bottom flask was placed methyl 1'-(4-(trifluoromethyl)benzoyl)-1,3-dihydrospiro[indene-2,3'-pyrrolidine]-4-carboxylate (30 mg, 0.07 mmol, 1 equiv), aq. 1N NaOH (0.2 mL, 0.2 mmol, 2.8 equiv), and THF (3 mL). The resulting solution was stirred overnight at 80° C. The reaction mixture was cooled to room temperature. The crude product was purified by reverse phase chromatography with the following conditions: Column: C18, 40 g, 20-35 μm; Mobile Phase A: Water/0.05% TFA, Mobile Phase B: CH$_3$CN; Flow rate: 40 mL/min; Gradient: 5% B to 95% B in 35 min; Detector: UV 254 nm. The collected fractions were lyophilized to give 25 mg (86% yield) of the title compound as an off-white solid. MS: (ES, m/z): 390 [M+H]+.

Step-3: N-Hydroxy-1'-(4-(trifluoromethyl)benzoyl)-1,3-dihydrospiro[indene-2,3'-pyrrolidine]-4-carboxamide Into a 25-mL round-bottom flask was placed a solution of 1'-(4-(trifluoromethyl)benzoyl)-1,3-dihydrospiro[indene-2,3'-pyrrolidine]-4-carboxylic acid (25 mg, 0.06 mmol, 1 equiv) in DMF (3 mL), isopropyl chloroformate (11 mg, 0.10 mmol, 1.54 equiv) and NMM (10 mg, 0.10 mmol, 1.54 equiv). The mixture was stirred for 5 min at room temperature and then NH$_2$OH.HCl (6 mg, 0.1 mmol, 1.54 equiv) was added. The resulting solution was stirred overnight at room temperature. The crude product was purified by Prep-HPLC with the following conditions: Column: X Bridge RP, 19×150 mm, 5 μm; Mobile Phase A: Water/0.05% formic acid, Mobile Phase B: CH$_3$CN; Flow rate: 20 mL/min; Gradient: 12% B to 34% B in 9 min; Detector: UV 254 nm. The collected fractions were lyophilized to give 4 mg (15% yield) of the title compound as an off-white solid. $^1$H NMR (400 MHz, DMSO-d6) δ (ppm): 10.91-10.83 (m, 1H), 9.11 (br s, 1H), 7.83-7.71 (m, 4H), 7.35-7.14 (m, 3H), 3.65-3.61 (m, 1H), 3.52-3.49 (m, 2H), 3.38-3.32 (m, 1H), 3.16-2.87 (m, 4H), 1.97-1.86 (m, 2H). MS: (ES, m/z): 405 [M+H]+.

Example 12-2—Preparation of 1'-acetyl-N-hydroxy-1,3-dihydrospiro[indene-2,3'-pyrrolidine]-4-carboxamide (II-59)

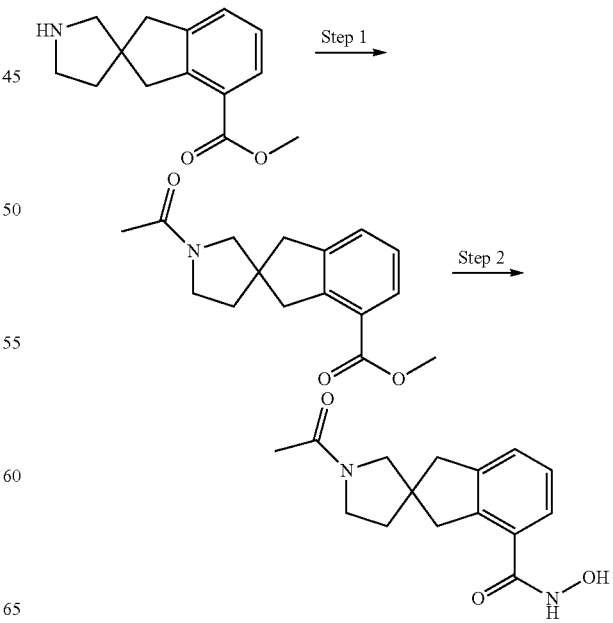

Step-1: Methyl 1'-acetyl-1,3-dihydrospiro[indene-2,3'-pyrrolidine]-4-carboxylate Into a 25-mL round-bottom flask was placed a solution of methyl 1,3-dihydrospiro[indene-2,3'-pyrrolidine]-4-carboxylate (70 mg, 0.30 mmol, 1 equiv) in CH$_2$Cl$_2$ (3 mL), and pyridine (240 mg, 3.03 mmol, 10 equiv). The solution was stirred for 20 min at room temperature and then acetyl chloride (35 mg, 0.45 mmol, 1.47 equiv) was added. The resulting solution was stirred for 1 h at room temperature and then concentrated under vacuum. The residue was purified by normal phase chromatography on silica gel using EtOAc/petroleum ether (1:10). The collected fractions were concentrated to afford 50 mg (60% yield) of the title compound as colorless oil. MS: (ES, m/z): 274 [M+H]$^+$.

Step-2: 1'-Acetyl-N-hydroxy-1,3-dihydrospiro[indene-2,3'-pyrrolidine]-4-carboxamide Into a 25-mL round-bottom flask was placed methyl 1'-acetyl-1,3-dihydrospiro[indene-2,3'-pyrrolidine]-4-carboxylate (40 mg, 0.15 mmol, 1 equiv) in THF/MeOH (4:1, 4 mL), NH$_2$OH (50% in H$_2$O, 0.93 mL, 14.07 mmol, 96 equiv), and aq. 1N NaOH (0.29 mL, 0.29 mmol, 2 equiv). The resulting solution was stirred for 1 h at room temperature. The solids were filtered out. The crude product was purified by Prep-HPLC with the following conditions: Column: X Bridge RP, 19×150 mm, 5 μm; Mobile Phase A: Water/0.05% formic acid, Mobile Phase B: CH$_3$CN; Flow rate: 20 mL/min; Gradient: 12% B to 34% B in 9 min; Detector: UV 254 nm. The collected fractions were lyophilized to give 2.2 mg (5% yield) of the title compound as a brown solid. $^1$H NMR (300 MHz, DMSO-d6) δ (ppm): 10.86 (br s, 1H), 7.38-7.17 (m, 3H), 3.56-3.52 (m, 1H), 3.41-3.38 (m, 2H), 3.36 (s, 1H), 3.14-3.00 (m, 2H), 2.91-2.85 (m, 2H), 1.95-1.82 (m, 5H). MS: (ES, m/z): 275 [M+H]$^+$.

Example 13-2—Preparation of 1'-acetyl-N-hydroxy-1,3-dihydrospiro[indene-2,4'-piperidine]-4-carboxamide (II-60)

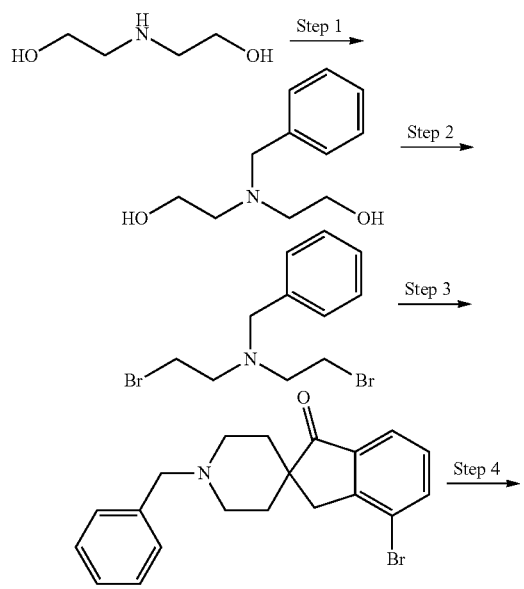

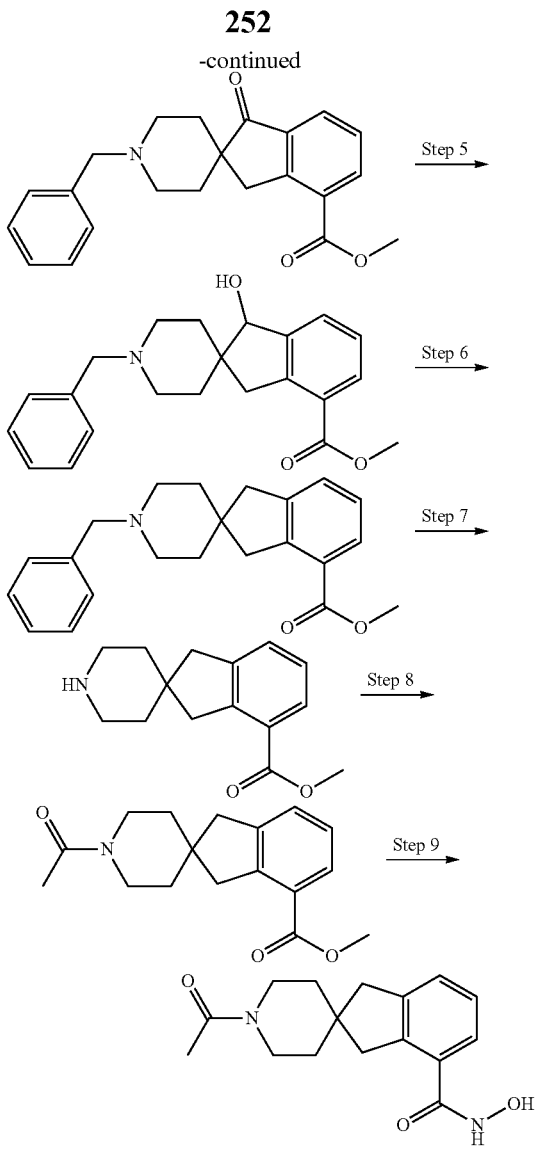

Step-1: 2,2'-(Benzylazanediyl)diethanol

Into a 500-mL round-bottom flask was placed 2,2'-azanediyldiethanol (10 g, 95 mmol, 1 equiv), MeCN (140 mL), (bromomethyl)benzene (12 mL), and K$_2$CO$_3$ (26.7 g, 193 mmol, 2 equiv). The resulting solution was stirred overnight at 85° C. The reaction mixture was cooled. The solids were filtered out and the filtrate was concentrated under vacuum. The residue was diluted with 60 mL of water. The resulting solution was extracted with 3×60 mL of CH$_2$Cl$_2$. The combined organic layers were washed with 2×60 mL of water, dried over anhydrous Na$_2$SO$_4$, filtered, and concentrated under vacuum. The residue was purified by normal phase chromatography on silica gel using MeOH/CH$_2$Cl$_2$ (1:10). The collected fractions were concentrated under vacuum to afford 7.53 g (41% yield) of the title compound as yellow oil. MS: (ES, m/z): 196 [M+H]$^+$.

Step-2: N-Benzyl-2-bromo-N-(2-bromoethyl)ethanamine

Into a 500-mL round-bottom flask was placed 2,2'-(benzylazanediyl)diethanol (11.3 g, 57.9 mmol, 1 equiv) and CH₂Cl₂ (100 mL). This was followed by the dropwise addition of phosphorus tribromide (34.6 g, 128 mmol, 2.2 equiv) at 0° C. The resulting solution was stirred for 8 h at room temperature. The reaction was then quenched by the addition of 80 mL of ice-water. The pH value of the solution was adjusted to 7 with sat. aq. Na₂CO₃ solution. The resulting solution was extracted with 3×80 mL of CH₂Cl₂. The combined organic layers were dried over anhydrous Na₂SO₄, filtered, and concentrated under vacuum. The residue was purified by normal phase chromatography on silica gel using CH₂Cl₂/petroleum ether (1:3). The collected fractions were concentrated under vacuum to afford 3.3 g (18% yield) of the title compound as yellow oil. ¹H NMR (400 MHz, CDCl₃) δ (ppm): 7.34-7.27 (m, 5H), 3.73 (s, 2H), 3.43 (t, J=7.2 Hz, 4H), 2.98 (t, J=7.2 Hz, 1H).

Step-3: 1'-Benzyl-4-bromospiro[indene-2,4'-piperidin]-1(3H)-one

Into a 500-mL 3-necked round-bottom flask was placed 4-bromo-2,3-dihydro-1H-inden-1-one (7.23 g, 34.3 mmol, 1 equiv), DMF (70 mL), and N-benzyl-2-bromo-N-(2-bromoethyl)ethanamine (16.5 g, 53.8 mmol, 1.57 equiv). This was followed by the addition of NaH (60% dispersion in oil, 5.72 g, 143 mmol, 4.17 equiv), in portions at 0° C. The resulting solution was stirred for 1 h at 0° C. The reaction mixture was quenched by the addition of 80 mL of ice-water and the resulting solution was extracted with 2×100 mL of EtOAc. The combined organic layers were dried over anhydrous Na₂SO₄, filtered, and concentrated under vacuum. The residue was purified by normal phase chromatography on silica gel using EtOAc/petroleum ether (1:5). The collected fractions were concentrated under vacuum to afford 4.87 g (38% yield) of the title compound as a brown solid. MS: (ES, m/z): 370 [M+H]⁺.

Step-4: Methyl 1'-benzyl-1-oxo-1,3-dihydrospiro[indene-2,4'-piperidine]-4-carboxylate Into a 30-mL pressure tank reactor (40 atm), was placed 1'-benzyl-4-bromospiro[indene-2,4'-piperidin]-1(3H)-one (1.15 g, 3.1 mmol, 1 equiv), MeOH (15 mL), Pd(dppf)Cl₂ (575 mg, 0.79 mmol, 0.25 equiv), and Et₃N (5 mL). CO (g) was introduced into the reactor and the resulting solution was stirred for 2 days at 100° C. The reaction mixture was cooled. The solids were filtered out and the filtrate was concentrated under vacuum. The residue was purified by normal phase chromatography on silica gel using EtOAc/petroleum ether (1:1). The collected fractions were concentrated under vacuum to afford 518 mg (48% yield) of the title compound as a brown solid. MS: (ES, m/z): 350 [M+H]⁺.

Step-5: Methyl 1'-benzyl-1-hydroxy-1,3-dihydrospiro[indene-2,4'-piperidine]-4-carboxylate Into a 500-mL round-bottom flask was placed methyl 1'-benzyl-1-oxo-1,3-dihydrospiro[indene-2,4'-piperidine]-4-carboxylate (2.16 g, 6.2 mmol, 1 equiv) and MeOH (70 mL). This was followed by the addition of NaBH₄ (707 mg, 18.7 mmol, 3 equiv) in portions at 0° C. The resulting solution was stirred for 4 h at 0° C. The resulting mixture was concentrated under vacuum. The residue was purified by normal phase chromatography on silica gel using MeOH/CH₂Cl₂ (1:10). The collected fractions were concentrated under vacuum to afford 1.85 g (85% yield) of the title compound as a brown oil. MS: (ES, m/z): 352 [M+H]⁺.

Step-6: Methyl 1'-benzyl-1,3-dihydrospiro[indene-2,4'-piperidine]-4-carboxylate

Into a 250-mL round-bottom flask was placed methyl 1'-benzyl-1-hydroxy-1,3-dihydrospiro[indene-2,4'-piperidine]-4-carboxylate (1.6 g, 4.5 mmol, 1 equiv), TFA (60 mL), and triethylsilane (15 mL). The resulting solution was stirred for 3 days at room temperature. The resulting mixture was concentrated under vacuum. The residue was purified by normal phase chromatography on silica gel using MeOH/CH₂Cl₂ (1:10). The collected fractions were concentrated under vacuum to afford 1.84 g (crude) of the title compound as a yellow oil. MS: (ES, m/z): 336 [M+H]⁺.

Step-7: Methyl 1,3-dihydrospiro[indene-2,4'-piperidine]-4-carboxylate acetate

Into a 30-mL pressure tank reactor (60 atm), was placed methyl 1'-benzyl-1,3-dihydrospiro[indene-2,4'-piperidine]-4-carboxylate (1.58 g, crude), AcOH (15 mL), and Pd(OH)₂ on carbon (Pearlman's catalyst) (20 wt. %, 960 mg). H₂ (g) was introduced into the reactor and the resulting solution was stirred for 2 days at room temperature. The solids were filtered out and the filtrate was concentrated under vacuum to afford 0.9 g (82% yield over two steps) of the title compound as the acetate salt as a yellow solid. ¹H NMR (400 MHz, CDCl₃) δ (ppm): 9.38 (br s, 2H), 7.86-7.84 (m, 1H), 7.39-7.36 (m, 1H), 7.26-7.23 (m, 1H), 3.97 (s, 3H), 3.27-3.14 (m, 6H), 2.91-2.83 (m, 2H), 1.92-1.90 (m, 4H). MS: (ES, m/z): 246 [M+H]⁺.

Step-8: Methyl 1'-acetyl-1,3-dihydrospiro[indene-2,4'-piperidine]-4-carboxylate

Into a 25-mL round-bottom flask was placed methyl 1,3-dihydrospiro[indene-2,4'-piperidine]-4-carboxylate acetate (40 mg, 0.13 mmol, 1 equiv), CH₂Cl₂ (3 mL), pyridine (64.5 mg, 0.82 mmol, 6.3 equiv), and acetyl chloride (28 mg, 0.36 mmol, 2.8 equiv). The resulting solution was stirred for 2 h at room temperature. The resulting mixture was concentrated under vacuum. The residue was purified by reverse phase chromatography with the following conditions: Column: C18, 40 g, 20-35 µm; Mobile Phase A: Water/0.05% TFA, Mobile Phase B: CH₃CN; Flow rate: 40 mL/min; Gradient: 5% B to 50% B in 25 min; Detector: UV 254 nm. The collected fractions were lyophilized to afford 25.7 mg (68% yield) of the title compound as a colorless oil. MS: (ES, m/z): 288 [M+H]⁺.

Step-9: 1'-Acetyl-N-hydroxy-1,3-dihydrospiro[indene-2,4'-piperidine]-4-carboxamide Into a 25-mL round-bottom flask was placed methyl 1'-acetyl-1,3-dihydrospiro[indene-2,4'-piperidine]-4-carboxylate (25.7 mg, 0.09 mmol, 1 equiv), THF/MeOH (4:1, 2 mL), NH₂OH (50% in H₂O, 591 mg, 8.95 mmol, 100 equiv), and aq. 1N NaOH (0.18 mL, 0.18 mmol, 2 equiv). The resulting solution was stirred for 7 h at room temperature. The crude product was purified by Prep-HPLC with the following conditions: Column: XBridge Prep C18 OBD, 19×150 mm, 5 µm; Mobile Phase A: water/0.05% formic acid, Mobile Phase B: CH₃CN; Detector: UV 254 nm, 220 nm. The collected fractions were lyophilized to give 9 mg (35% yield) of the title compound as a light brown solid. ¹H NMR (400 MHz, DMSO-d6) δ (ppm): 10.91-10.83 (m, 1H), 7.32-7.21 (m, 2H), 7.21-7.15 (m, 1H), 3.61-3.37 (m, 4H), 3.02-2.93 (m, 2H), 2.85-2.79 (m, 2H), 2.00 (s, 3H), 1.57-1.50 (m, 2H), 1.49-1.38 (m, 2H). MS: (ES, m/z): 289 [M+H]+.

Example 14-2—Preparation of 1'-(4-chlorobenzoyl)-N-hydroxy-1,3-dihydrospiro[indene-2,4'-piperidine]-4-carboxamide (II-61)

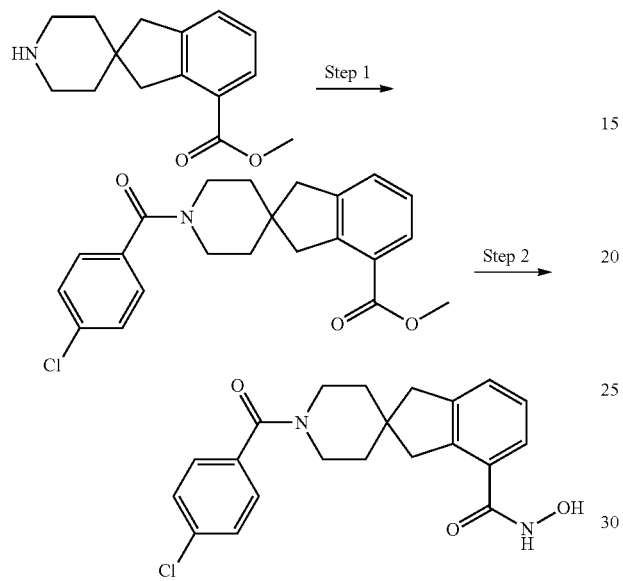

Step-1: Methyl 1'-(4-chlorobenzoyl)-1,3-dihydrospiro[indene-2,4'-piperidine]-4-carboxylate Into a 25-mL round-bottom flask was placed 4-chlorobenzoic acid (95.5 mg, 0.61 mmol, 1.85 equiv), DMF (3 mL), EDC (130.7 mg, 0.84 mmol, 2.55 equiv), HOBt (55.2 mg, 0.41 mmol, 1.24 equiv), Et$_3$N (136.3 mg, 1.35 mmol, 4.09 equiv), and methyl 1,3-dihydrospiro[indene-2,4'-piperidine]-4-carboxylate acetate (100 mg, 0.33 mmol, 1 equiv). The resulting solution was stirred overnight at room temperature. The resulting solution was diluted with 10 mL of water and extracted with 3×10 mL of EtOAc. The combined organic layers were dried over anhydrous Na$_2$SO$_4$, filtered, and concentrated under vacuum. The residue was purified by normal phase chromatography on silica gel using EtOAc/petroleum ether (1:5). The collected fractions were concentrated under vacuum to afford 58.2 mg (46% yield) of the title compound as a yellow oil. MS: (ES, m/z): 384 [M+H]+.

Step-2: 1'-(4-Chlorobenzoyl)-N-hydroxy-1,3-dihydrospiro[indene-2,4'-piperidine]-4-carboxamide Into a 25-mL round-bottom flask was placed methyl 1'-(4-chlorobenzoyl)-1,3-dihydrospiro[indene-2,4'-piperidine]-4-carboxylate (58.2 mg, 0.15 mmol, 1 equiv), THF/MeOH (4:1, 2 mL), NH$_2$OH (50% in H$_2$O, 1003 mg, 15 mmol, 100 equiv), and aq. 1N NaOH (0.3 mL, 0.30 mmol, 2 equiv). The resulting solution was stirred for 5 h at room temperature. The crude product was purified by Prep-HPLC with the following conditions: Column: XBridge Prep C18 OBD, 19×150 mm, 5 μm; Mobile Phase A: water/0.05% TFA, Mobile Phase B: CH$_3$CN; Detector: UV 254 nm. The collected fractions were lyophilized to give 17.3 mg (30% yield) of the title compound as a pink solid. $^1$H NMR (400 MHz, DMSO-d6) δ (ppm): 10.91-10.81 (m, 1H), 7.52-7.50 (m, 2H), 7.49-7.43 (m, 2H), 7.30-7.18 (m, 3H), 3.79-3.51 (m, 2H), 3.41-3.25 (m, 2H), 2.99 (s, 2H), 2.84 (s, 2H), 1.69-1.42 (m, 4H). MS: (ES, m/z): 385 [M+H]+.

Example 15-2—Preparation of 1'-(4-chlorobenzyl)-N-hydroxy-1,3-dihydrospiro[indene-2,4'-piperidine]-4-carboxamide (II-62)

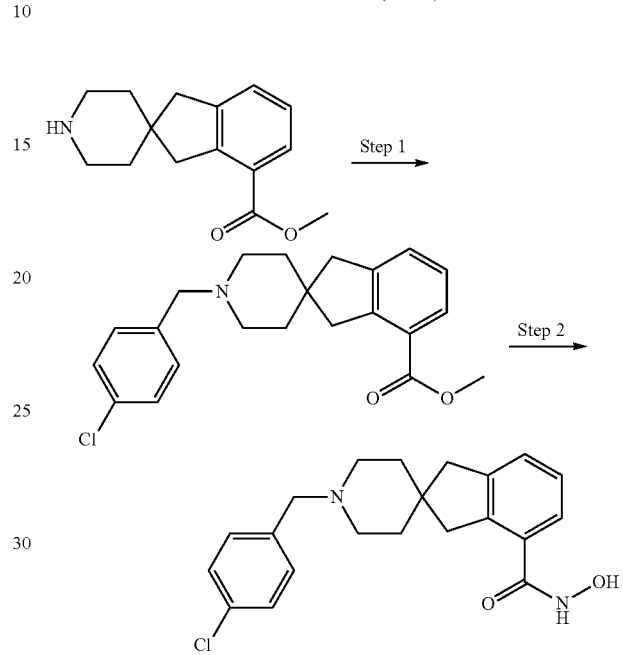

Step-1: Methyl 1'-(4-chlorobenzyl)-1,3-dihydrospiro[indene-2,4'-piperidine]-4-carboxylate Into a 25-mL round-bottom flask was placed methyl 1,3-dihydrospiro[indene-2,4'-piperidine]-4-carboxylate acetate (100 mg, 0.33 mmol, 1 equiv), CH$_2$Cl$_2$ (3 mL), and 4-chlorobenzaldehyde (60 mg, 0.43 mmol, 1.3 equiv). The resulting solution was stirred for 1 h at room temperature. Then NaBH(OAc)$_3$ (129.8 mg, 0.61 mmol, 1.85 equiv) was added. The resulting solution was allowed to react, with stirring, overnight at room temperature. The reaction mixture was then quenched with 20 mL of water and extracted with 3×20 mL of CH$_2$Cl$_2$. The combined organic layers were dried over anhydrous Na$_2$SO$_4$, filtered, and concentrated under vacuum. The residue was purified by normal phase chromatography on silica gel using EtOAc/petroleum ether (1:5). The collected fractions were concentrated under vacuum to afford 60 mg (50% yield) of the title compound as a white solid. MS: (ES, m/z): 370 [M+H]+.

Step-2: 1'-(4-Chlorobenzyl)-N-hydroxy-1,3-dihydrospiro[indene-2,4'-piperidine]-4-carboxamide Into a 25-mL round-bottom flask was placed methyl 1'-(4-chlorobenzyl)-1,3-dihydrospiro[indene-2,4'-piperidine]-4-carboxylate (60 mg, 0.16 mmol, 1 equiv), THF/MeOH (4:1, 2 mL), NH$_2$OH (50% in H$_2$O, 1073 mg, 16 mmol, 100 equiv), and aq. 1N NaOH (0.8 mL, 0.8 mmol, 5 equiv). The resulting solution was stirred for 8 h at room temperature. The crude product was purified by Prep-HPLC with the following conditions: Column: XBridge Prep C18

OBD, 19×150 mm, 5 μm; Mobile Phase A: water/0.05% TFA, Mobile Phase B: CH₃CN; Detector: UV 254 nm. The collected fractions were lyophilized to give 13.5 mg (20% yield) of the title compound as a white solid. $^1$H NMR (400 MHz, DMSO-d6) δ (ppm): 10.91-10.88 (d, J=12 Hz, 1H), 10.44-10.38 (m, 1H), 9.05-8.69 (m, 1H), 7.68-7.62 (m, 2H), 7.56-7.52 (m, 2H), 7.32-7.25 (m, 2H), 7.21-7.17 (m, 1H), 4.34-4.29 (m, 2H), 3.25-3.17 (m, 2H), 3.12-3.00 (m, 3H), 2.93 (d, J=12 Hz, 2H), 2.78 (s, 1H), 1.93-1.84 (m, 2H), 1.78-1.66 (m, 2H). MS: (ES, m/z): 371 [M+H]⁺.

Example 16-2—Preparation of 1'-cyclopropyl-N-hydroxy-1,3-dihydrospiro[indene-2,4'-piperidine]-4-carboxamide (II-63)

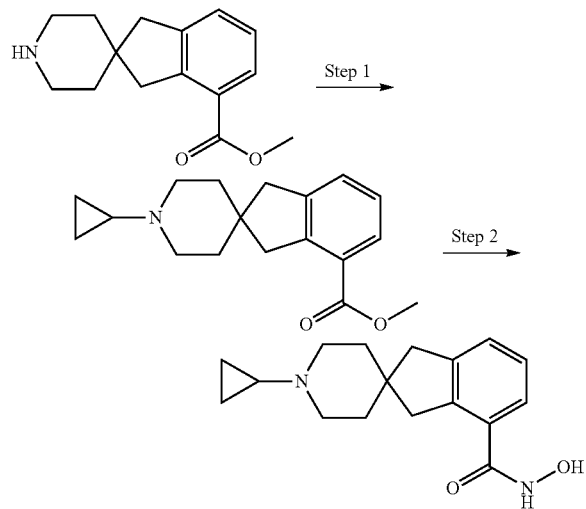

Step-1: Methyl 1'-cyclopropyl-1,3-dihydrospiro[indene-2,4'-piperidine]-4-carboxylate Into an 8-mL round-bottom flask was placed methyl 1,3-dihydrospiro[indene-2,4'-piperidine]-4-carboxylate acetate (100 mg, 0.33 mmol, 1 equiv), (1-ethoxycyclopropoxy)trimethylsilane (430 mg, 2.47 mmol, 7.48 equiv), CH₂Cl₂ (5 mL), and AcOH (240 mg, 4.00 mmol, 12.12 equiv). The resulting solution was stirred for 30 min at room temperature. Then NaBH₃CN (130 mg, 2.07 mmol, 6.27 equiv) was added. The resulting solution was allowed to react, with stirring, overnight at 40° C. The reaction mixture was then cooled to room temperature, diluted with 20 mL of water, and extracted with 3×20 mL of CH₂Cl₂. The combined organic layers were dried with anhydrous Na₂SO₄, filtered, and concentrated under vacuum. The residue was purified by normal phase chromatography on silica gel using MeOH/CH₂Cl₂ (1:5). The collected fractions were concentrated under vacuum to afford 50 mg (crude) of the title compound as yellow oil. MS: (ES, m/z): 286 [M+H]⁺.

Step-2: 1'-Cyclopropyl-N-hydroxy-1,3-dihydrospiro[indene-2,4'-piperidine]-4-carboxamide Into a 100-mL round-bottom flask was placed methyl 1'-cyclopropyl-1,3-dihydrospiro[indene-2,4'-piperidine]-4-carboxylate (66 mg, 0.23 mmol, 1 equiv), THF/MeOH (4:1, 2 mL), NH₂OH (50% in H₂O, 1.53 g, 23 mmol, 100 equiv), and aq. 1N NaOH (0.46 mL, 0.46 mmol, 2 equiv). The resulting solution was stirred overnight at room temperature. The crude product was purified by Prep-HPLC with the following conditions: Column: XBridge Prep C18 OBD, 19×250 mm, 5 μm; Mobile Phase A: water/0.05% TFA, Mobile Phase B: CH₃CN; Gradient: 5% B to 23% B in 9 min; Detector: UV 254 nm, 220 nm. The collected fractions were concentrated under vacuum to afford 12.2 mg (18% yield) of the title compound as a colorless oil. $^1$H NMR (400 MHz, DMSO-d6) δ (ppm): 10.88 (br s, 1H), 10.32 (m, 1H), 7.37-7.11 (m, 3H), 3.38-3.26 (m, 2H), 3.24-3.22 (m, 2H), 3.08 (s, 1H), 2.98-2.76 (m, 4H), 1.98-1.91 (m, 2H), 1.72-1.67 (m, 2H), 1.10 (s, 2H), 0.77 (s 2H). MS: (ES, m/z): 287 [M+H]⁺.

Example 17-2—Preparation of 1'-benzyl-N-hydroxy-1,3-dihydrospiro[indene-2,4'-piperidine]-4-carboxamide (II-64)

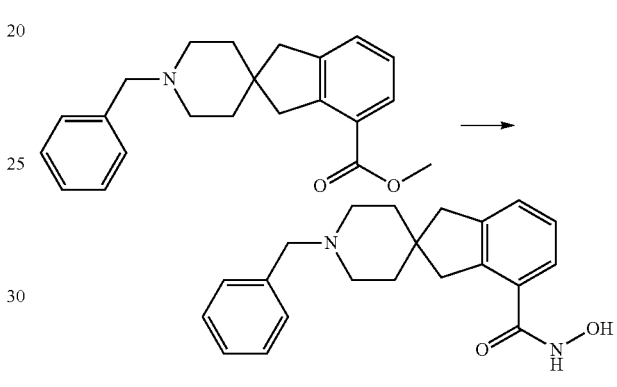

Into a 25-mL round-bottom flask was placed methyl 1'-benzyl-1,3-dihydrospiro[indene-2,4'-piperidine]-4-carboxylate (50 mg, 0.15 mmol, 1 equiv), THF/MeOH (4:1, 2 mL), NH₂OH (50% in H₂O, 985 mg, 15 mmol, 100 equiv), and aq. 1N NaOH (0.3 mL, 0.30 mmol, 2 equiv). The resulting solution was stirred for 8.5 h at room temperature. The crude product was purified by Prep-HPLC with the following conditions: Column: XBridge Prep C18 OBD, 19×150 mm, 5 μm; Mobile Phase A: water/0.05% TFA, Mobile Phase B: CH₃CN; Detector: UV 254 nm, 220 nm. The collected fractions were concentrated under vacuum to afford 6.4 mg (12% yield) of the title compound as a as a pink solid. $^1$H NMR (400 MHz, DMSO-d6) δ (ppm): 10.88-10.87 (m, 1H), 10.36-10.29 (m, 1H), 9.15-8.82 (m, 1H), 7.63-7.58 (m, 2H), 7.47 (s, 3H), 7.32-7.24 (m, 2H), 7.22-7.18 (m, 1H), 4.35-4.31 (m, 2H), 3.22-3.19 (m, 2H), 3.12-3.02 (m, 3H), 2.94-2.91 (m, 2H), 2.78 (s, 1H), 1.94-1.88 (m, 2H), 1.75-1.70 (m, 2H). MS: (ES, m/z): 337 [M+H]⁺.

Example 18-2—Preparation of 1'-benzyl-N-hydroxy-1-oxo-1,3-dihydrospiro[indene-2,4'-piperidine]-4-carboxamide (II-65)

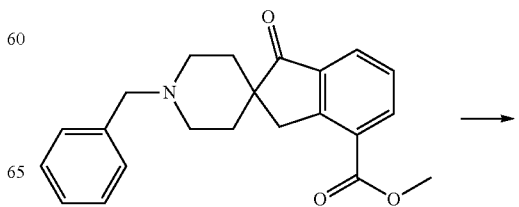

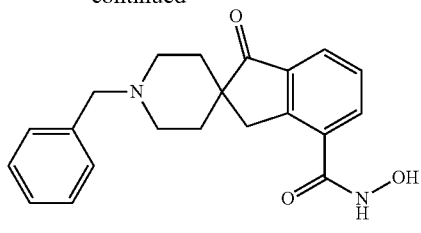

Into a 25-mL round-bottom flask was placed methyl 1'-benzyl-1-oxo-1,3-dihydrospiro[indene-2,4'-piperidine]-4-carboxylate (50 mg, 0.14 mmol, 1 equiv), THF/MeOH (4:1, 2 mL), NH$_2$OH (50% in H$_2$O, 946 mg, 14 mmol, 100 equiv), and aq. 1N NaOH (0.29 mL, 0.29 mmol, 2 equiv). The resulting solution was stirred for 2 h at room temperature. The crude product was purified by Prep-HPLC with the following conditions: Column: XBridge Prep C18 OBD, 19×150 mm, 5 μm; Mobile Phase A: water/0.05% TFA, Mobile Phase B: CH$_3$CN; Detector: UV 254 nm. The collected fractions were concentrated under vacuum to afford 3.6 mg (7% yield) of the title compound as a as a pink solid. $^1$H NMR (400 MHz, DMSO-d6) δ (ppm): 11.19 (s, 1H), 10.02 (br s, 1H), 9.18 (s, 1H), 7.86-7.63 (m, 2H), 7.58-7.48 (m, 6H), 4.39 (s, 2H), 3.39-3.34 (m, 4H), 3.20-3.11 (m, 2H), 2.11-1.95 (m, 2H), 1.66-1.63 (m, 2H). MS: (ES, m/z): 351 [M+H]$^+$.

Example 19-2—Preparation of 1'-benzyl-N,1-dihydroxy-1,3-dihydrospiro[indene-2,4'-piperidine]-4-carboxamide (II-66)

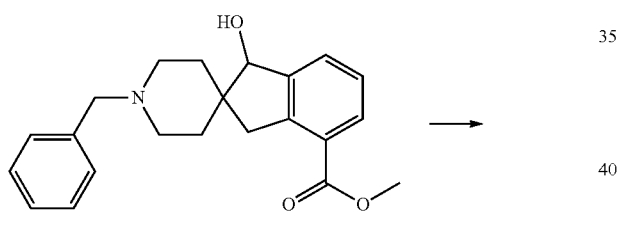

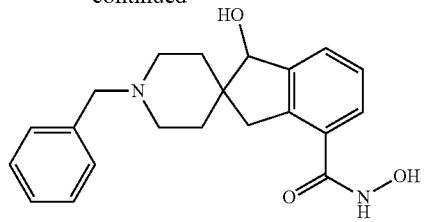

Into a 25-mL round-bottom flask was placed methyl 1'-benzyl-1-hydroxy-1,3-dihydrospiro[indene-2,4'-piperidine]-4-carboxylate (50 mg, 0.14 mmol, 1 equiv), THF/MeOH (4:1, 2 mL), NH$_2$OH (50% in H$_2$O, 940 mg, 14 mmol, 100 equiv), and aq. 1N NaOH (0.28 mL, 0.28 mmol, 2 equiv). The resulting solution was stirred for 4 h at room temperature. The crude product was purified by Prep-HPLC with the following conditions: Column: XBridge Prep C18 OBD, 19×150 mm, 5 μm; Mobile Phase A: water/0.1% formic acid, Mobile Phase B: CH$_3$CN; Detector: UV 254 nm, 220 nm. The collected fractions were concentrated under vacuum to afford 14.5 mg (26% yield) of the title compound as a pink solid. $^1$H NMR (400 MHz, DMSO-d6) δ (ppm): 10.95 (s, 1H), 10.42-10.01 (m, 1H), 8.99 (s, 1H), 7.63-7.09 (m, 8H), 5.65-5.44 (m, 1H), 4.83-4.59 (m, 1H), 4.33 (s, 2H), 3.29-2.73 (m, 6H), 2.11-1.22 (m, 4H). MS: (ES, m/z): 353 [M+H]$^+$.

Example 20-2—Preparation of 1'-(4-chloro-3-(trifluoromethyl)benzyl)-N-hydroxy-2'-oxo-3,4-dihydro-1H-spiro[naphthalene-2,3'-pyrrolidine]-8-carboxamide (II-67)

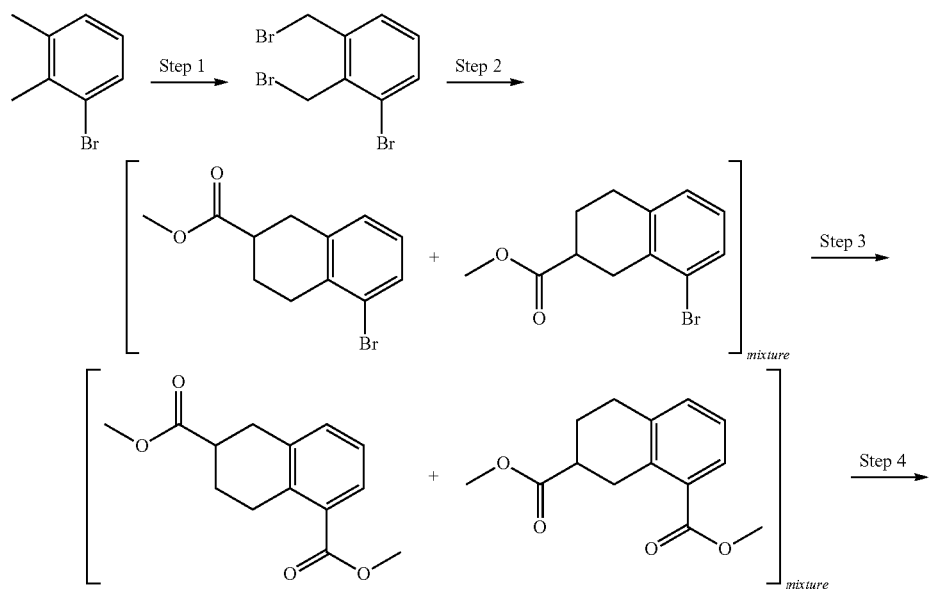

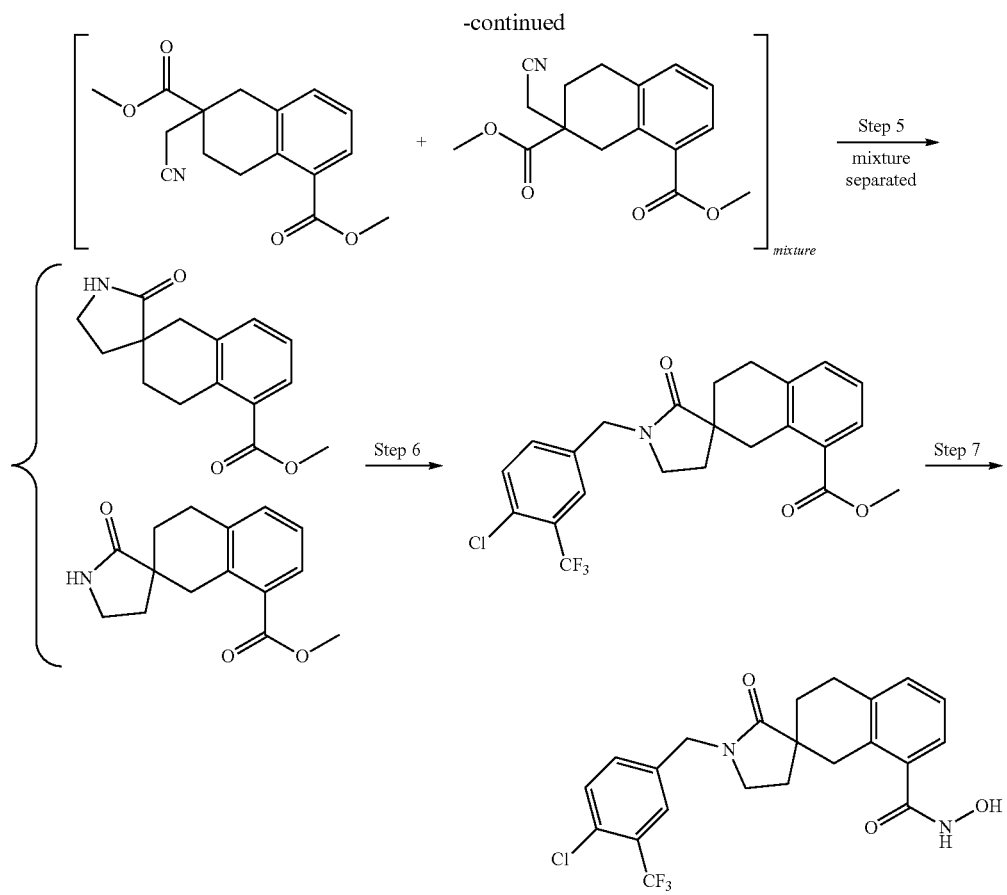

Step-1: 1-Bromo-2,3-bis(bromomethyl)benzene

Into a 250-mL 3-necked round-bottom flask was placed 1-bromo-2,3-dimethylbenzene (10 g, 54 mmol, 1 equiv), carbon tetrachloride (60 mL), N-bromosuccinimide (38 g, 213.5 mmol, 3.95 equiv), AIBN (253 mg, 1.54 mmol, 0.03 equiv). The resulting solution was stirred for 15 h at 85° C. in an oil bath. The reaction mixture was cooled to room temperature. The solids were filtered out and the filtrate was washed with 2×200 mL of water and 200 mL of brine, dried over anhydrous $Na_2SO_4$, filtered, and concentrated under vacuum to give 22 g (crude) of the title compound as a brown oil. GCMS: (ES, m/z): 340.

Step-2: Mixture of methyl 5-bromo-1,2,3,4-tetrahydronaphthalene-2-carboxylate and methyl 8-bromo-1,2,3,4-tetrahydronaphthalene-2-carboxylate Into a 500-mL round-bottom flask purged and maintained with an inert atmosphere of nitrogen was placed 1-bromo-2,3-bis(bromomethyl)benzene (22 g, 64 mmol, 1 equiv), DMF (100 mL), methyl prop-2-enoate (27.5 g, 319 mmol, 5 equiv), and sodium iodide (38.4 g, 256 mmol, 4 equiv). The resulting solution was stirred for 18 h at 90° C. in an oil bath. The reaction mixture was cooled to room temperature and then quenched by the addition of 100 mL of water. The resulting solution was decolorized by the addition of aq. 5% $Na_2S_2O_3$ solution and extracted with 3×150 mL of EtOAc. The combined organic layers were washed with 200 mL of brine, dried over anhydrous $Na_2SO_4$, filtered, and concentrated under vacuum. The residue was purified by normal phase chromatography on silica gel using EtOAc/petroleum ether (1:20). The collected fractions were concentrated under vacuum to afford 10.5 g (61% yield) of the title compounds as a light brown oil. GCMS: (ES, m/z): 268.

Step-3: Mixture of dimethyl 5,6,7,8-tetrahydronaphthalene-1,6-dicarboxylate and dimethyl 5,6,7,8-tetrahydronaphthalene-1,7-dicarboxylate Into a 50-mL pressure tank reactor (60 atm), was placed the mixture of methyl 5-bromo-1,2,3,4-tetrahydronaphthalene-2-carboxylate and methyl 8-bromo-1,2,3,4-tetrahydronaphthalene-2-carboxylate (6.95 g, 25.84 mmol, 1 equiv), MeOH (20 mL), Pd(dppf)Cl$_2$ (2.30 g, 3.14 mmol, 0.12 equiv), and Et$_3$N (10.44 g, 103.17 mmol, 4.00 equiv). CO (g) was introduced and the resulting solution was stirred for 24 h at 120° C. The resulting mixture was cooled to room temperature and concentrated under vacuum. The residue was purified by normal phase chromatography on silica gel using EtOAc/petroleum ether (1:10). The collected fractions were concentrated under vacuum to afford 3.14 g (49% yield) of the title compounds as a greenish oil. MS: (ES, m/z): 249 [M+H]$^+$.

Step-4: Mixture of dimethyl 6-(cyanomethyl)-5,6,7,8-tetrahydronaphthalene-1,6-dicarboxylate and dimethyl 7-(cyanomethyl)-5,6,7,8-tetrahydronaphthalene-1,7-dicarboxylate Into a 250-mL 3-necked round-bottom flask purged and maintained with an inert atmosphere of nitrogen, was placed the mixture of dimethyl 5,6,7,8-tetrahydronaphthalene-1,6-dicarboxylate and dimethyl 5,6,7,8-tetrahydronaphthalene-1,7-dicarboxylate (3.14 g, 12.66 mmol, 1 equiv) in THF (25 mL). This was followed by the addition of lithium diisopropylamide solution (2M in THF, 12.6 mL, 25.32 mmol, 2 equiv) dropwise with stirring at −78° C. and then the mixture was stirred for 1 hr at −78° C. To this was added 2-bromoacetonitrile (4.56 g, 38.02 mmol, 3 equiv) dropwise with stirring at −78° C. The resulting solution was stirred for 3 h at −78° C. The reaction mixture was then quenched by the addition of 5 mL of aq. sat. $NH_4Cl$ solution and slowly warmed to room temperature. The resulting mixture was poured into 50 mL of water and extracted with 3×50 mL of EtOAc. The combined organic layers were washed with 100 mL of brine, dried over anhydrous $Na_2SO_4$, filtered, and concentrated under vacuum. The residue was purified by normal phase chromatography on silica gel using EtOAc/petroleum ether (1:5). The collected fractions were concentrated under vacuum to give 2.22 g (61% yield) of the title compound as a brown oil. MS: (ES, m/z): 288 [M+H]+.

Step-5: Methyl 2'-oxo-3,4-dihydro-1H-spiro[naphthalene-2,3'-pyrrolidine]-5-carboxylate and Methyl 2'-oxo-3,4-dihydro-1H-spiro[naphthalene-2,3'-pyrrolidine]-8-carboxylate Into a 250-mL round-bottom flask was placed the mixture of dimethyl 6-(cyanomethyl)-5,6,7,8-tetrahydronaphthalene-1,6-dicarboxylate and dimethyl 7-(cyanomethyl)-5,6,7,8-tetrahydronaphthalene-1,7-dicarboxylate (2.22 g, 7.74 mmol, 1 equiv), MeOH (60 mL), AcOH (14 mL), and $PtO_2$ (2 g, 8.81 mmol, 1.14 equiv). $H_2$ (g) was introduced and the resulting solution was stirred for 3.5 h at room temperature. The solids were filtered out and the filtrate was concentrated under vacuum. The residue was dissolved in 20 mL of $NH_3$ solution (7M in MeOH) and stirred for 18 h at room temperature. The resulting mixture was concentrated under vacuum. The crude product was purified by reversed phase chromatography with the following conditions: Column: C18, 120 g, 20-45 μm, 100 Å; Mobile Phase A: Water/0.1% formic acid, Mobile Phase B: $CH_3CN$; Gradient: 15% B to 45% B in 50 min; Detector: UV 254 nm. The first eluting isomer was collected and concentrated under vacuum to give 100 mg (7% yield) of the title compound methyl 2'-oxo-3,4-dihydro-1H-spiro[naphthalene-2,3'-pyrrolidine]-5-carboxylate as a white solid. Structure assignment based on NOESY, HSQC, and HMBC NMR experiments: $^1H$ NMR (400 MHz, DMSO-d6) δ (ppm): 7.68 (s, 1H, NH), 7.61 (d, 1H, $CH^2$), 7.32 (d, 1H, $CH^4$), 7.22 (t, 1H, $CH^3$), 3.81 (s, 3H, $CH_3$), 3.19-3.22 (m, 2H, $CH^9$), 2.92-3.18 (m, 2H, $CH^7$), 2.76 (dd, 2H, $CH^5$), 1.70-1.95 (m, 4H, $CH^6$ and $CH^{10}$). $^{13}C$ NMR (100 MHz, DMSO-d6) δ (ppm): 180.1, 167.6, 136.22, 136.18, 133.5, 129.6, 127.7, 125.4, 51.9, 41.1, 37.9, 36.2 ($C^5$), 31.1, 28.5, 23.9 ($C^7$). NOESY correlation observed between $H^4$ and $H^5$. HMBC correlation observed between $H^4$ and $C^5$. MS: (ES, m/z): 260 [M+H]+.

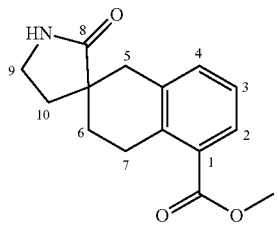

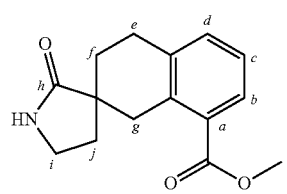

The second eluting isomer was collected and concentrated under vacuum to give 800 mg (53% yield) of the title compound methyl 2'-oxo-3,4-dihydro-1H-spiro[naphthalene-2,3'-pyrrolidine]-8-carboxylate as a light yellow solid. Structure assignment based on NOESY, HSQC, and HMBC NMR experiments: $^1H$ NMR (400 MHz, DMSO-d6) δ (ppm): 7.68 (s, 1H, NH), 7.60 (d, 1H, $CH^b$), 7.34 (d, 1H, $CH^d$), 7.23 (app t, 1H, $CH^c$), 3.80 (s, 3H, $CH_3$), 3.17-3.21 (m, 2H, $CH^i$), 2.87-2.94 (m, 2H, $CH^g$), 2.80-2.85 (m, 2H, $CH^e$), 1.61-1.93 (m, 4H, $CH^f$ and $CH^j$). $^{13}C$ NMR (100 MHz, DMSO-d6) δ (ppm): 180.3, 167.6, 136.8, 135.5, 132.7, 130.4, 127.6, 125.4, 51.9, 41.6, 37.9, 34.1 ($C^g$), 31.5, 27.9, 25.8 ($C^e$). NOESY correlation observed between $H^d$ and $H^e$. HMBC correlation observed between $H^d$ and $C^e$. MS: (ES, m/z): 260 [M+H]+.

Step-6: Methyl 1'-(4-chloro-3-(trifluoromethyl)benzyl)-2'-oxo-3,4-dihydro-1H-spiro[naphthalene-2,3'-pyrrolidine]-8-carboxylate Into an 8-mL vial was placed methyl 2'-oxo-3,4-dihydro-1H-spiro[naphthalene-2,3'-pyrrolidine]-8-carboxylate (50 mg, 0.19 mmol, 1 equiv), DMF (3 mL). This was followed by the addition of NaH (60% dispersion in oil, 23 mg, 0.58 mmol, 3 equiv), in portions at 0° C. The mixture was stirred for 30 min at room temperature. To this was added a solution of 4-(bromomethyl)-1-chloro-2-(trifluoromethyl)benzene (158 mg, 0.58 mmol, 3 equiv) in DMF (0.5 mL) dropwise with stirring at 0° C. The resulting solution was stirred for 2 h at room temperature. The reaction mixture was then poured into 20 mL of ice-water and extracted with 3×20 mL of EtOAc. The combined organic layers were washed with 30 mL of brine, dried over anhydrous $Na_2SO_4$, filtered, and concentrated under vacuum. The residue was purified by normal phase chromatography on silica gel with EtOAc/petroleum ether (1:3). The collected fractions were concentrated under vacuum to give 100 mg (crude) of the title compound as light yellow oil. MS: (ES, m/z): 452 [M+H]+.

Step-7: 1'-(4-Chloro-3-(trifluoromethyl)benzyl)-N-hydroxy-2'-oxo-3,4-dihydro-1H-spiro[naphthalene-2,3'-pyrrolidine]-8-carboxamide Into a 25-mL round-bottom flask was placed methyl 1'-(4-chloro-3-(trifluoromethyl)benzyl)-2'-oxo-3,4-dihydro-1H-spiro[naphthalene-2,3'-pyrrolidine]-8-carboxylate (100 mg, 0.13 mmol, 1 equiv), THF/MeOH (4:1, 3 mL), $NH_2OH$ (50% in $H_2O$, 0.26 mL, 4 mmol, 30 equiv), and aq. 1N NaOH (0.26 mL, 0.26 mmol, 2 equiv). The resulting solution was stirred for 4 h at room temperature. The crude product was purified by Prep-HPLC with the following conditions: Column: XBridge Prep C18 OBD, 19×150 mm, 5 μm; Mobile Phase A: water/0.1% formic acid, Mobile Phase B: $CH_3CN$; Gradient: 35% B to 50% B in 8 min, up to 52% B in 1 min; Detector: UV 254 nm, 220 nm. The collected fractions were lyophilized to give 20.5 mg (20% yield) of the title compound as an off-white solid. $^1H$ NMR (300 MHz, DMSO-d6) δ (ppm): 10.79 (br s, 1H), 9.03 (br s, 1H), 7.76-14 (m, 2H), 7.76-7.74 (m, 2H), 7.55-7.52 (m, 1H), 7.22-7.07 (m, 3H), 4.60 (d, J=15.3 Hz, 1H), 4.43 (d, J=15.3 Hz, 1H), 3.27-3.22 (m, 2H), 2.98-2.88 (m, 3H), 2.66 (d, J=17.4 Hz, 1H), 1.93-1.81 (m, 2H), 1.70-1.63 (m, 2H). MS: (ES, m/z): 453 [M+H]+.

TABLE 5-2

| Ex. | Structure | $^1$H-NMR δ (ppm) | Found (ES, m/z) [M + H]$^+$ |
|---|---|---|---|
| II-68 | 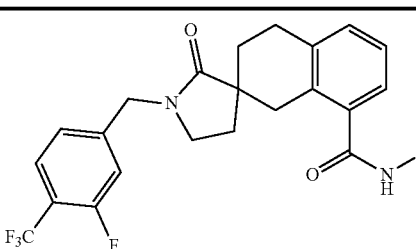 | (400 MHz, DMSO-d6): 10.79 (br s, 1H), 9.01 (br s, 1H), 7.82-7.78 (m, 1H), 7.37 (d, J = 12.0 Hz, 1H), 7.27 (d, J = 8.0 Hz, 1H), 7.21-7.14 (m, 2H), 7.08 (d, J = 6.4 Hz, 1H), 4.60-4.44 (m, 2H), 3.27-3.21 (m, 2H), 2.97-2.84 (m, 3H), 2.69-2.64 (m, 1H), 1.98-1.92 (m, 1H), 1.87-1.82 (m, 1H), 1.77-1.59 (m, 2H) | 437 |
| II-69 | 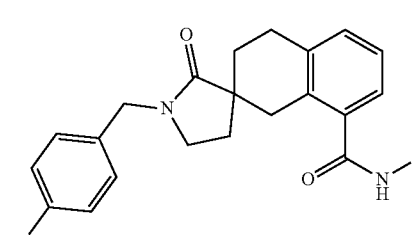 | (400 MHz, DMSO-d6): 10.80 (br s, 1H), 9.08 (br s, 1H), 7.43 (d, J = 8.4 Hz, 2H), 7.28 (d, J = 8.0 Hz, 2H), 7.25-7.13 (m, 2H), 7.09-7.07 (m, 1H), 4.47-4.35 (m, 2H), 3.23-3.16 (m, 2H), 2.95-2.83 (m, 3H), 2.67-2.61 (m, 1H), 1.94-1.79 (m, 2H), 1.68-1.61 (m, 2H) | 385 |

The following compounds were prepared according to the method of Example 20-2.

TABLE 6-2

| Ex. | Structure | $^1$H-NMR δ (ppm) | Found (ES, m/z) [M + H]$^+$ |
|---|---|---|---|
| II-84 | 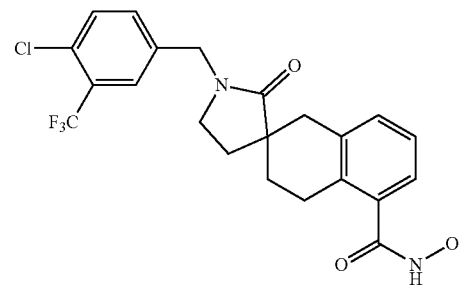 | (300 MHz, DMSO-d6): 10.80 (br s, 1H), 9.03 (br s, 1H), 7.77-7.73 (m, 2H), 7.57-7.54 (m, 1H), 7.19-7.08 (m, 3H), 4.51 (s, 1H), 3.28-3.24 (m, 2H), 2.95-2.81 (m, 3H), 2.68-2.63 (m, 1H), 1.97-1.69 (m, 4H) | 453 |
| II-85 | 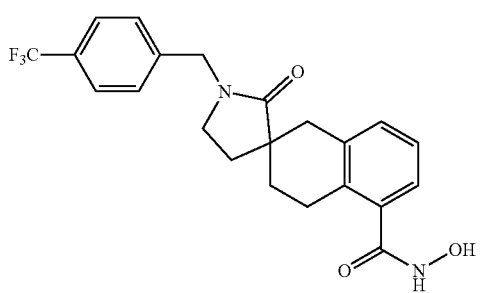 [SMILES: O=C(NO)c1cccc2c1CCC1(CCN(Cc3ccc(C(F)(F)F)cc3)C1=O)C2] | (400 MHz, DMSO-d6): 11.79 (br s, 1H), 9.02 (br s, 1H), 7.73 (d, J = 8.4 Hz, 2H), 7.45 (d, J = 8 Hz, 2H), 7.17-7.06 (m, 3H), 4.51 (s, 2H), 3.25-3.22 (m, 2H), 2.93-2.79 (m, 3H), 2.67-2.65 (m, 1H), 1.94-1.87 (m, 1H), 1.84-1.76 (m, 1H), 1.73-1.65 (m, 2H) | 419 |

TABLE 6-2-continued

| Ex. | Structure | ¹H-NMR δ (ppm) | Found (ES, m/z) [M + H]⁺ |
|---|---|---|---|
| II-86 | 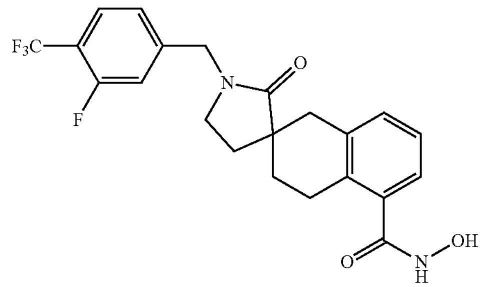 [SMILES: O=C(NO)c1cccc2c1CCC1(CCN(Cc3ccc(C(F)(F)F)c(F)c3)C1=O)C2] | (300 MHz, DMSO-d6): 10.78 (br s, 1H), 9.03 (br s, 1H), 7.83-7.77 (m, 1H), 7.38-7.27 (m, 2H), 7.20-7.07 (m, 3H), 4.53 (2, 3H), 3.29-3.27 (m, 2H), 2.95-2.81 (m, 3H), 2.68 (d, J = 16.2 Hz, 1H), 1.99-1.89 (m, 1H), 1.86-1.69 (m, 3H) | 437 |
| II-87 | 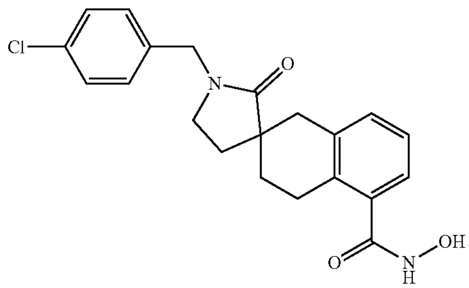 [SMILES: O=C(NO)c1cccc2c1CCC1(CCN(Cc3ccc(Cl)cc3)C1=O)C2] | (300 MHz, DMSO-d6): 10.77 (br s, 1H), 9.04 (br s, 1H), 7.43 (d, J = 8.1 Hz, 2H), 7.23 (d, J = 8.4 Hz, 2H), 7.17-7.07 (m, 3H), 4.41 (s, 2H), 3.24-3.19 (m, 2H), 2.95-2.85 (m, 3H), 2.63 (d, J = 16.8 Hz, 1H), 1.91-1.67 (m, 4H) | 385 |

The following compounds were prepared according to the method of Example 20-2, with the following modification: In Step 6, methyl 2'-oxo-3,4-dihydro-1H-spiro[naphthalene-2,3'-pyrrolidine]-5-carboxylate was used.

Example 21-2—Preparation of N-hydroxy-2'-oxo-1'-(4-(trifluoromethyl)benzyl)-3,4-dihydro-1H-spiro[naphthalene-2,3'-pyrrolidine]-8-carboxamide (II-70)

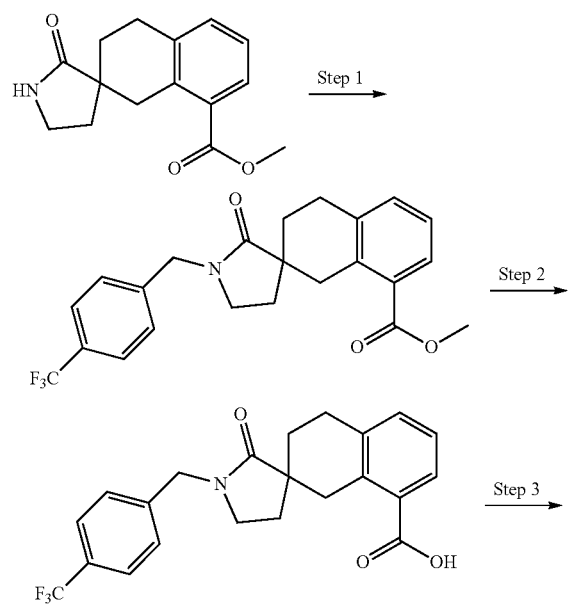

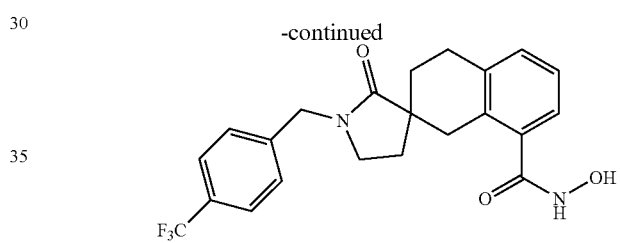

Step-1: Methyl 2'-oxo-1'-(4-(trifluoromethyl)benzyl)-3,4-dihydro-1H-spiro[naphthalene-2,3'-pyrrolidine]-8-carboxylate Into an 8-mL vial was placed methyl 2'-oxo-3,4-dihydro-1H-spiro[naphthalene-2,3'-pyrrolidine]-8-carboxylate (150 mg, 0.58 mmol, 1 equiv) and DMF (4 mL). This was followed by the addition of NaH (60% dispersion in oil, 69 mg, 1.74 mmol, 3 equiv), in portions at 0° C. The resulting mixture was stirred for 30 min at room temperature. To this was added 1-(bromomethyl)-4-(trifluoromethyl)benzene (276 mg, 1.16 mmol, 2 equiv) dropwise with stirring at 0° C. The resulting solution was stirred for 2 h at room temperature. The reaction mixture was then poured into 20 mL of aq. sat. NH₄Cl solution. The resulting solution was extracted with 3×20 mL of EtOAc. The combined organic layers were dried over anhydrous Na₂SO₄, filtered, and concentrated under vacuum. The residue was purified by normal phase chromatography on silica gel using EtOAc/petroleum ether (1:2). The collected fraction was concentrated under vacuum to give 76 mg (31% yield) of the title compound as light yellow oil. MS: (ES, m/z): 418 [M+H]⁺.

Step-2: 2'-Oxo-1'-(4-(trifluoromethyl)benzyl)-3,4-dihydro-1H-spiro[naphthalene-2,3'-pyrrolidine]-8-carboxylic Acid Into a 25-mL round-bottom flask was placed methyl 2'-oxo-1'-(4-(trifluoromethyl)benzyl)-3,4-dihydro-1H-spiro

[naphthalene-2,3'-pyrrolidine]-8-carboxylate (76 mg, 0.18 mmol, 1 equiv) and THF (3 mL). This was followed by the addition of LiOH (40 mg, 1.67 mmol, 9 equiv) in water (3 mL) dropwise with stirring at 0° C. The resulting solution was stirred for 20 h at room temperature. The pH value of the solution was adjusted to 3 with 2N HCl and the resulting solution was extracted with 3×20 mL of EtOAc. The combined organic layers were dried over anhydrous $Na_2SO_4$, filtered, and concentrated under vacuum. The collected fraction was concentrated under vacuum to give 29 mg (39% yield) of the title compound as off-white solid. MS: (ES, m/z): 404 [M+H]$^+$.

Step-3: N-Hydroxy-2'-oxo-1'-(4-(trifluoromethyl) benzyl)-3,4-dihydro-1H-spiro[naphthalene-2,3'-pyrrolidine]-8-carboxamide Into an 8-mL vial was placed 2'-oxo-1'-(4-(trifluoromethyl)benzyl)-3,4-dihydro-1H-spiro[naphthalene-2,3'-pyrrolidine]-8-carboxylic acid (29 mg, 0.07 mmol, 1 equiv) and DMA (3 mL). This was followed by the addition of isopropyl chloroformate (88 mg, 0.72 mmol, 10 equiv) dropwise with stirring at 0° C. To this was added NMM (73 mg, 0.72 mmol, 10 equiv) dropwise with stirring at 0° C. The mixture was stirring for 5 min at 0° C. To the mixture was added a solution of $NH_2OH \cdot HCl$ (50 mg, 0.72 mmol, 10 equiv) in DMA (1 mL) dropwise with stirring at 0° C. The resulting solution was stirred for 24 h at room temperature. The crude product was purified by Prep-HPLC with the following conditions: Column: XBridge Prep C18 OBD, 19×150 mm, 5 μm; Mobile Phase A: water/0.1% formic acid, Mobile Phase B: $CH_3CN$; Gradient: 25% B to 39% B in 7 min, hold at 39% B for 5 min; Detector: UV 254 nm, 220 nm. The collected fractions were lyophilized to give 8.3 mg (27% yield) of the title compound as an off-white solid. $^1$H NMR (300 MHz, DMSO-d6) δ (ppm): 10.80 (br s, 1H), 9.03 (br s, 1H), 7.74 (d, J=8.1 Hz, 2H), 7.45 (d, J=7.8 Hz, 2H), 7.21-7.07 (m, 3H), 4.59-4.44 (m, 2H), 3.23-3.21 (m, 2H), 2.98-2.83 (m, 3H), 2.72-2.63 (m, 1H), 1.97-1.79 (m, 2H), 1.69-1.64 (m, 2H). MS: (ES, m/z): 419 [M+H]$^+$.

Example 22-2—Preparation of N-hydroxy-2'-oxo-1'-(4-(trifluoromethyl)phenyl)-3,4-dihydro-1H-spiro[naphthalene-2,3'-pyrrolidine]-8-carboxamide (II-71)

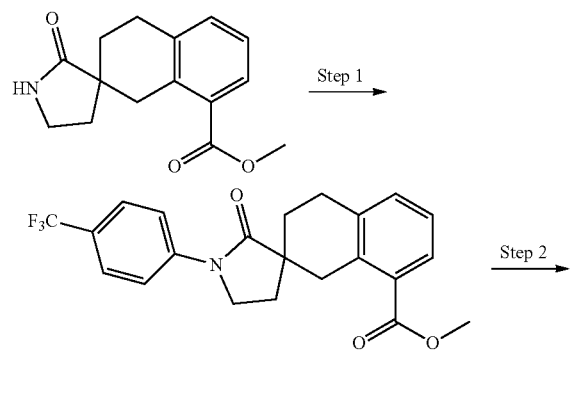

-continued

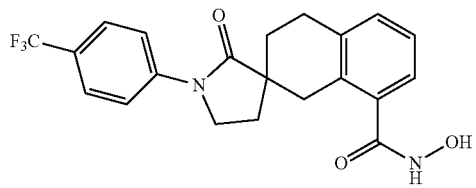

Step-1: Methyl 2'-oxo-1'-(4-(trifluoromethyl)phenyl)-3,4-dihydro-1H-spiro[naphthalene-2,3'-pyrrolidine]-8-carboxylate Into a 50-mL round-bottom flask was placed methyl 2'-oxo-3,4-dihydro-1H-spiro[naphthalene-2,3'-pyrrolidine]-8-carboxylate (50 mg, 0.19 mmol, 1 equiv), $CH_2Cl_2$ (10 mL), [4-(trifluoromethyl)phenyl]boronic acid (72.2 mg, 0.38 mmol, 2 equiv), $Cu(OAc)_2$ (69.2 mg, 0.38 mmol, 2 equiv), pyridine (22.5 mg, 0.28 mmol, 1.5 equiv), $Et_3N$ (57.6 mg, 0.57 mmol, 3 equiv), and 4 Å molecular sieves (100 mg). $O_2$ (g) was introduced and the resulting solution was stirred for 36 h at 60° C. The reaction mixture was then cooled to room temperature. The solids were filtered out and the filtrate was concentrated under vacuum. The residue was purified by prep-TLC with EtOAc/petroleum ether (1:3). The collected fractions were concentrated under vacuum to give 30 mg (38% yield) of the title compound as a white solid. MS: (ES, m/z): 404 [M+H]$^+$.

Step-2: N-Hydroxy-2'-oxo-1'-(4-(trifluoromethyl) phenyl)-3,4-dihydro-1H-spiro[naphthalene-2,3'-pyrrolidine]-8-carboxamide Into a 25-mL round-bottom flask was placed methyl 2'-oxo-1'-(4-(trifluoromethyl)phenyl)-3,4-dihydro-1H-spiro[naphthalene-2,3'-pyrrolidine]-8-carboxylate (50 mg, 0.12 mmol, 1 equiv), THF/MeOH (4:1, 3 mL), $NH_2OH$ (50% in $H_2O$, 491 mg, 7.44 mmol, 60 equiv). This was followed by the addition of aq. 1N NaOH (0.25 mL, 0.25 mmol, 2 equiv) dropwise with stirring. The resulting solution was stirred for 2 h at room temperature. The solids were filtered out. The crude product was purified by Prep-HPLC with the following conditions: Column: XBridge Prep C18 OBD, 19×150 mm, 5 μm; Mobile Phase A: water/0.05% $NH_3 \cdot H_2O$, Mobile Phase B: $CH_3CN$; Gradient: 27% B to 48% B in 7 min, hold at 48% B for 2 min; Detector: UV 254 nm, 220 nm. The collected fractions were lyophilized to give 4.2 mg (8% yield) of the title compound as a white solid. $^1$H NMR (300 MHz, DMSO-d6) δ (ppm): 7.97 (d, J=8.7 Hz, 2H), 7.77 (d, J=8.7 Hz, 2H), 7.20-7.13 (m, 3H), 3.92-3.83 (m, 2H), 2.92-2.76 (m, 4H), 2.08-1.75 (m, 4H), MS: (ES, m/z): 405 [M+H]$^+$.

TABLE 7-2

| Ex. | Structure | ¹H-NMR δ (ppm) | Found (ES, m/z) [M + H]⁺ |
|---|---|---|---|
| II-88 | (structure) | (300 MHz, DMSO-d6): 10.79 (br s, 1H), 9.03 (br s, 1H), 7.95 (d, J = 8.7 Hz, 2H), 7.76 (d, J = 9 Hz, 2H), 7.21-7.09 (m, 3H), 3.94-3.89 (m, 2H), 2.99-2.78 (m, 4H), 2.11-2.05 (m, 1H), 1.92-1.85 (m, 3H) | 405 |
| II-89 | (structure) | (300 MHz, DMSO-d6): 10.80 (br s, 1H), 9.04 (br s, 1H), 8.27 (s, 1H), 7.87 (d, J = 8.7 Hz, 1H), 7.67-7.62 (m, 1H), 7.50 (d, J = 7.8 Hz, 1H), 7.19-7.09 (m, 3H), 3.95-3.90 (m, 2H), 2.99-2.72 (m, 4H), 2.11-2.02 (m, 1H), 1.91-1.83 (m, 3H) | 405 |

The following compounds were prepared according to the method of Example 22-2, with the following modification: In Step 1, methyl 2'-oxo-3,4-dihydro-1H-spiro[naphthalene-2,3'-pyrrolidine]-5-carboxylate was used.

Example 23-2—Preparation of N-hydroxy-2'-oxo-1'-(3-(trifluoromethyl)phenyl)-3,4-dihydro-1H-spiro[naphthalene-2,3'-pyrrolidine]-8-carboxamide (II-72)

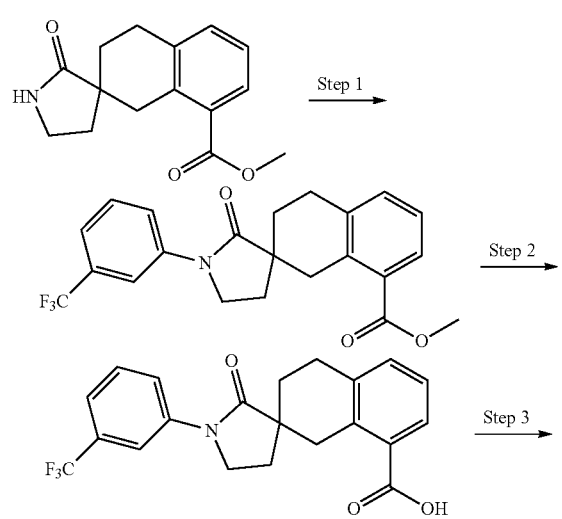

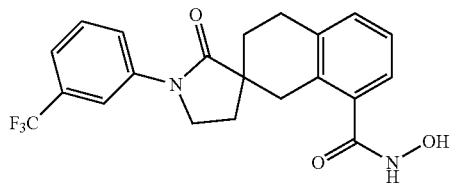

Step-1: Methyl 2'-oxo-1'-(3-(trifluoromethyl)phenyl)-3,4-dihydro-1H-spiro[naphthalene-2,3'-pyrrolidine]-8-carboxylate Into a 50-mL round-bottom flask was placed methyl 2'-oxo-3,4-dihydro-1H-spiro[naphthalene-2,3'-pyrrolidine]-8-carboxylate (50 mg, 0.19 mmol, 1 equiv), THF (10 mL), [3-(trifluoromethyl)phenyl]boronic acid (183.116 mg, 0.96 mmol, 5 equiv), Cu(OAc)₂ (35 mg, 0.19 mmol, 1 equiv), Et₃N (59 mg, 0.58 mmol, 3 equiv), pyridine (22.879 mg, 0.29 mmol, 1.5 equiv) and 4 Å molecular sieves (100 mg). O₂ (g) was introduced and the resulting solution was stirred for 18 h at 60° C. in an oil bath. The solids were filtered out. The resulting mixture was concentrated under vacuum. The residue was purified by normal phase chromatography on silica gel using EtOAc/petroleum ether (2:3). The collected fractions were concentrated under vacuum to give 32 mg (41% yield) of the title compound as light brown oil. MS: (ES, m/z): 404 [M+H]⁺.

Step-2: 2'-Oxo-1'-(3-(trifluoromethyl)phenyl)-3,4-dihydro-1H-spiro[naphthalene-2,3'-pyrrolidine]-8-carboxylic Acid Into a 25-mL round-bottom flask was placed methyl 2'-oxo-1'-(3-(trifluoromethyl)phenyl)-3,4-dihydro-1H-spiro[naphthalene-2,3'-pyrrolidine]-8-carboxylate (32 mg, 0.08 mmol, 1 equiv) and THF (5 mL). This was followed by the addition of a solution of LiOH (19 mg, 0.79 mmol, 10 equiv) in water (4 mL) dropwise with stirring at 0° C. The resulting solution was stirred for 1.5 days at room temperature. The pH value of the solution was adjusted to 3 with 2N HCl at 0° C. and was extracted with 3×15 mL of EtOAc The combined organic layers were dried over anhydrous $Na_2SO_4$, filtered, and concentrated under vacuum. The collected fraction was concentrated under vacuum to give 30 mg (85% yield) of the title compound as a light yellow solid. MS: (ES, m/z): 390 [M+H]$^+$.

Step-3: N-Hydroxy-2'-oxo-1'-(3-(trifluoromethyl)phenyl)-3,4-dihydro-1H-spiro[naphthalene-2,3'-pyrrolidine]-8-carboxamide Into an 8-mL vial was placed a solution of 2'-oxo-1'-(3-(trifluoromethyl)phenyl)-3,4-dihydro-1H-spiro[naphthalene-2,3'-pyrrolidine]-8-carboxylic acid (30 mg, 0.08 mmol, 1 equiv) in DMA (3 mL). This was followed by the addition of isopropyl chloroformate (95 mg, 0.78 mmol, 10 equiv) dropwise with stirring at 0° C. To this was added NMM (78 mg, 0.77 mmol, 10 equiv) dropwise with stirring at 0° C. The mixture was stirring for 5 min. To the mixture was added a solution of $NH_2OH·HCl$ (54 mg, 0.78 mmol, 10 equiv) in DMA (1 mL) dropwise with stirring at 0° C. The resulting solution was stirred for 24 h at room temperature. The crude product was purified by Prep-HPLC with the following conditions: Column: XBridge Prep C18 OBD, 19×150 mm, 5 μm; Mobile Phase A: water/0.1% formic acid, Mobile Phase B: $CH_3CN$; Gradient: 20% B to 41% B in 8 min, hold at 41% B for 4 min; Detector: UV 254 nm, 220 nm. The collected fractions were lyophilized to give 12.6 mg (40% yield) of the title compound as an orange solid. $^1$H NMR (400 MHz, DMSO-d6) δ (ppm): 10.84 (br s, 1H), 9.04 (br s, 1H), 8.27 (s, 1H), 7.89 (d, J=8.0 Hz, 1H), 7.67-7.63 (m, 1H), 7.51 (d, J=7.6 Hz, 1H), 7.24-7.09 (m, 3H), 3.95-3.84 (m, 2H), 2.97-2.74 (m, 4H), 2.09-2.03 (m, 1H), 1.95-1.79 (m, 3H). MS: (ES, m/z): 405 [M+H]$^+$.

Example 24-2—Preparation of N-hydroxy-2'-oxo-1'-(2-(trifluoromethyl)phenyl)-3,4-dihydro-1H-spiro[naphthalene-2,3'-pyrrolidine]-8-carboxamide (II-73)

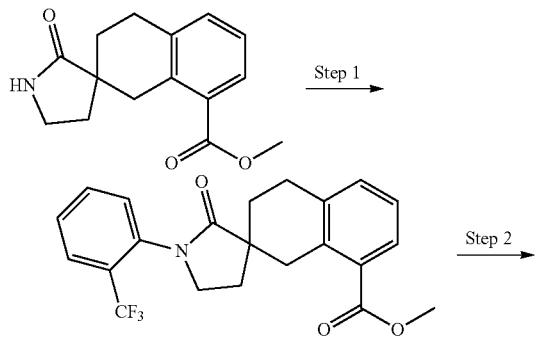

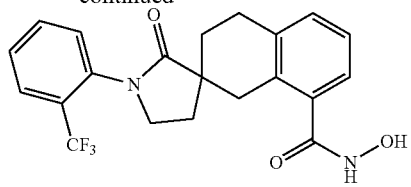

Step-1: Methyl 2'-oxo-1'-(2-(trifluoromethyl)phenyl)-3,4-dihydro-1H-spiro[naphthalene-2,3'-pyrrolidine]-8-carboxylate Into a 20-mL microwave tube purged and maintained with an inert atmosphere of nitrogen, was placed a solution of methyl 2'-oxo-3,4-dihydro-1H-spiro[naphthalene-2,3'-pyrrolidine]-8-carboxylate (100 mg, 0.39 mmol, 1 equiv) in toluene (5 mL), 1-iodo-2-(trifluoromethyl)benzene (210 mg, 0.77 mmol, 2 equiv), CuI (7 mg, 0.04 mmol, 0.1 equiv), methyl[2-(methylamino)ethyl]amine (7 mg, 0.08 mmol, 0.2 equiv) and $K_3PO_4$ (250 mg, 1.18 mmol, 3 equiv). The resulting solution was stirred overnight at 110° C. The reaction mixture was cooled to room temperature and then poured into 20 mL of water. The resulting solution was extracted with 3×20 mL of EtOAc. The combined organic layers were dried over anhydrous $Na_2SO_4$, filtered, and concentrated under vacuum. The residue was purified by preparative TLC with EtOAc/petroleum ether (1:3). The collected fractions were concentrated under vacuum to give 50 mg (32% yield) of the title compound as yellow oil. MS: (ES, m/z): 404 [M+H]$^+$.

Step-2: N-Hydroxy-2'-oxo-1'-(2-(trifluoromethyl)phenyl)-3,4-dihydro-1H-spiro[naphthalene-2,3'-pyrrolidine]-8-carboxamide Into a 10-mL round-bottom flask was placed a solution of methyl 2'-oxo-1'-(2-(trifluoromethyl)phenyl)-3,4-dihydro-1H-spiro[naphthalene-2,3'-pyrrolidine]-8-carboxylate (50 mg, 0.12 mmol, 1 equiv), THF/MeOH (4:1, 3 mL), $NH_2OH$ (50% in $H_2O$, 491 mg, 7.2 mmol, 60 equiv), and aq. 1N NaOH (0.24 mL, 0.24 mmol, 2 equiv). The resulting solution was stirred for 2 h at room temperature. The solids were filtered out. The crude product was purified by Prep-HPLC with the following conditions: Column: XBridge Prep C18 OBD, 19×150 mm, 5 μm; Mobile Phase A: water/10 mM $NH_4HCO_3$, Mobile Phase B: $CH_3CN$; Gradient: 30% B to 40% B in 7 min; Detector: UV 254 nm, 220 nm. The collected fractions were lyophilized to give 11.5 mg (23% yield) of the title compound as a white solid. $^1$H NMR (300 MHz, DMSO-d6) δ (ppm): 10.80 (br s, 1H), 9.05 (br s, 1H), 7.85-7.77 (m, 2H), 7.65-7.52 (m, 2H), 7.23-7.09 (m, 3H), 3.69-3.59 (m, 2H), 3.01-2.77 (m, 4H), 2.17-2.07 (m, 1H), 1.91-1.81 (m, 3H). MS: (ES, m/z): 405 [M+H]$^+$.

TABLE 8-2

| Ex. | Structure | ¹H-NMR δ (ppm) | Found (ES, m/z) [M + H]⁺ |
|---|---|---|---|
| II-90 | 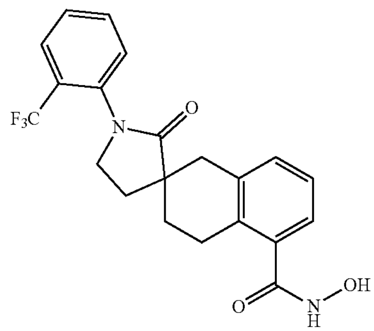 [SMILES: O=C(NO)c1cccc2c1CCC1(CCN(c3ccccc3C(F)(F)F)C1=O)C2] | (300 MHz, DMSO-d6): 10.81 (br s, 1H), 9.04 (br s, 1H), 7.85-7.78 (m, 2H), 7.65-7.54 (m, 2H), 7.24-7.09 (m, 3H), 3.70-3.65 (m, 2H), 2.98-2.83 (m, 4H), 2.13-2.05 (m, 1H), 1.93-1.81 (m, 3H) | 405 |

The following compound was prepared according to the method of Example 24-2, with the following modification: In Step 1, methyl 2'-oxo-3,4-dihydro-1H-spiro[naphthalene-2,3'-pyrrolidine]-5-carboxylate was used.

Example 25-2—Preparation of methyl spiro[chromane-2,4'-piperidine]-8-carboxylate (Intermediate)

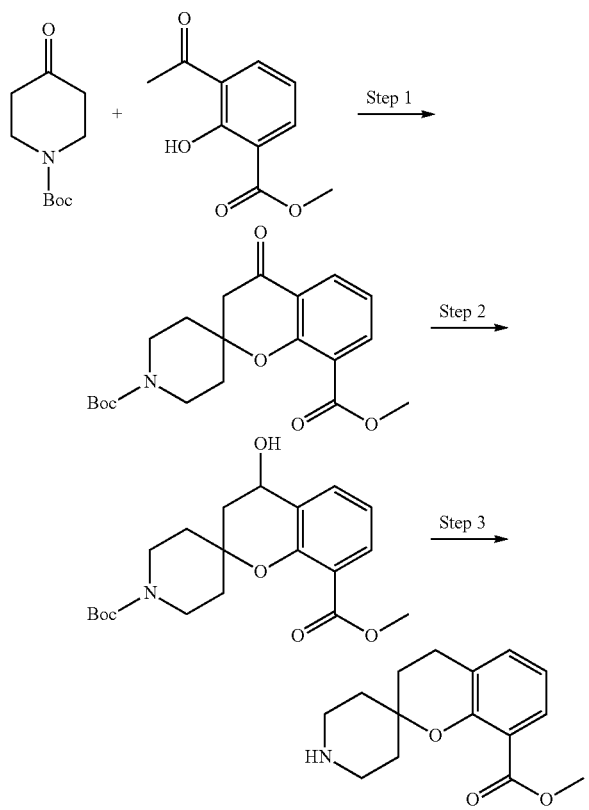

Step-1: 1'-(tert-Butyl) 8-methyl 4-oxospiro[chromane-2,4'-piperidine]-1',8-dicarboxylate N-tert-Butoxycarbonyl-4-piperidone (1.0 g, 5.0 mmol, 1 equiv) was added to a stirred solution of methyl 3-acetyl-2-hydroxybenzoate (0.97 g, 5.0 mmol, 1 equiv) and pyrrolidine (418 µL, 5.0 mmol, 1 equiv) in MeOH (10 mL) at room temperature. The reaction mixture was stirred at room temperature for 24 h. The reaction mixture was then concentrated and partitioned between EtOAc (75 mL) and 2N HCl (75 mL). The layers were separated and the aqueous layer was extracted with EtOAc (2×150 mL). The combined organic layers were washed with water (50 mL) and brine (50 mL), dried over Na₂SO₄, filtered, and concentrated under reduced pressure. The crude product was purified by flash column chromatography on silica gel (30% EtOAc/hexanes) to afford 1.71 g (91% yield) of the title compound as a pale yellow solid. ¹H NMR (400 MHz, CDCl₃) δ (ppm): 8.08-8.04 (m, 2H), 7.05 (t, J=7.4 Hz, 1H), 3.96 (br s, 2H), 3.91 (s, 3H), 3.28 (br s, 2H), 2.75 (s, 2H), 2.05 (app d, J=12.5 Hz, 2H), 1.59 (dt, J=13.2, 4.9 Hz, 2H), 1.45 (s, 9H). MS: (ES, m/z): 276 [M+H-Boc]⁺.

Step-2: 1'-(tert-Butyl) 8-methyl 4-hydroxyspiro[chromane-2,4'-piperidine]-1',8-dicarboxylate NaBH₄ (190 mg, 5.01 mmol, 1.1 equiv) was added to a stirred solution of 1'-(tert-butyl)-8-methyl-4-oxospiro[chromane-2,4'-piperidine]-1',8-dicarboxylate (1.71 g, 4.55 mmol, 1 equiv) in MeOH (15 mL), cooled to 0° C. The reaction warmed to room temperature over 15 min, then was quenched with 60 mL of aq. sat. NH₄Cl solution. The mixture was extracted with EtOAc (4×50 mL) and dried over Na₂SO₄. The Na₂SO₄ was filtered off and the solvent was removed in vacuo to afford the title compound as an off-white solid, which was carried forward without further purification.

Step-3: Methyl spiro[chromane-2,4'-piperidine]-8-carboxylate

1'-(tert-Butyl)-8-methyl-4-hydroxyspiro[chromane-2,4'-piperidine]-1',8-dicarboxylate was dissolved in 3 mL of triethylsilane. Then 2 mL of TFA was added. The mixture was stirred for 48 h at room temperature. The reaction mixture was then diluted with EtOAc (100 mL) and the excess acid was quenched with aq. 10% K₂CO₃ (30 mL). Then layers were separated and the organic phase was dried over Na₂SO₄. After filtration, the organic phase was reduced to 10 mL and 4N HCl in dioxane was added. A white precipitate formed. Hexanes (50 mL) was added and the mixture was triturated and filtered to afford 1.48 g (85% yield over 2 steps) of the title compound as the TFA salt as a white solid. $^1$H NMR (400 MHz, DMSO-d6) δ (ppm): 8.87 (br s, 1H), 8.55 (br s, 1H), 7.54 (d, J=9.0 Hz, 1H), 7.33 (d, J=7.4 Hz, 1H), 6.93 (t, J=7.8 Hz, 1H), 3.82 (s, 3H), 3.26-3.14 (m, 4H), 2.82 (t, J=6.6 Hz, 2H), 1.92-1.75 (m, 6H). $^{13}$C NMR (100 MHz, DMSO-d6) δ (ppm): 166.3, 151.6, 133.8, 129.1, 122.8, 119.8, 119.4, 71.8, 51.9, 30.6, 30.1, 20.6. MS: (ES, m/z): 262 [M+H-TFA]$^+$.

Example 26-2—Preparation of methyl spiro[chromane-2,4'-piperidine]-5-carboxylate (Intermediate)

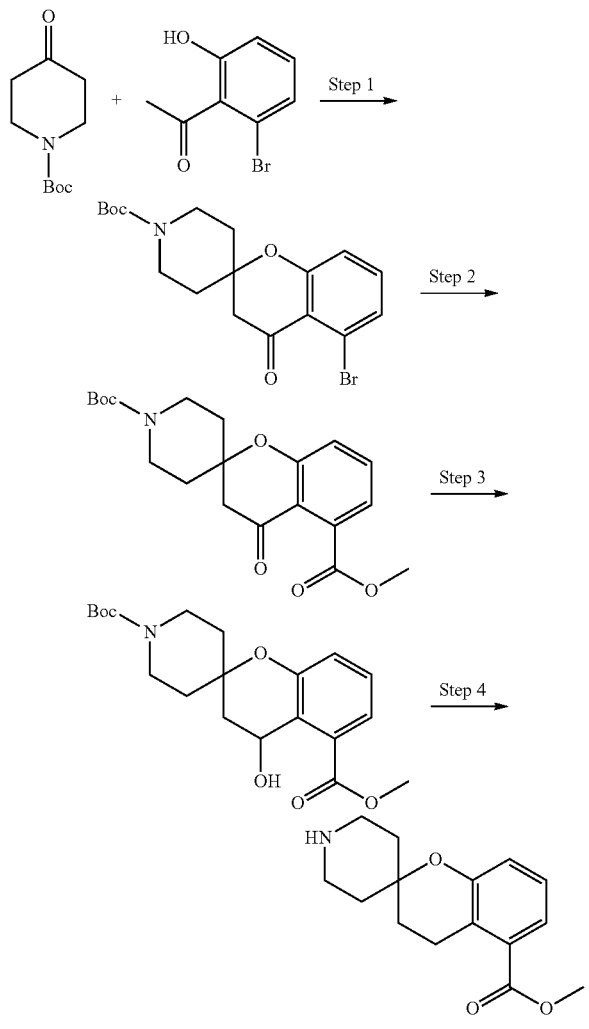

Step-1: tert-Butyl 5-bromo-4-oxospiro[chromane-2,4'-piperidine]-1'-carboxylate

N-tert-butoxycarbonyl-4-piperidone (0.996 g, 5 mmol) was added to a stirred solution of 1-(2-bromo-6-hydroxyphenyl)ethanone (1.08 g, 5 mmol) in 5 mL of MeOH, followed by pyrrolidine (0.82 mL, 10 mmol). The reaction mixture was sealed and followed at room temperature for 48 h. The mixture was then diluted with 75 mL of EtOAc and washed with 1N HCl (2×50 mL) and brine (1×50 mL). The organic phase was dried over Na$_2$SO$_4$. After filtration, the organic solvent was removed in vacuo. The viscous red residue was purified by flash column chromatography on silica gel (40% EtOAc/hexanes) to afford 1.19 g (60% yield) of the title compound as an off-white solid. $^1$H NMR (400 MHz, DMSO-d6) δ (ppm): 7.41 (t, J=8.2 Hz, 1H), 7.28 (dd, J=8.2, 1.0 Hz, 1H), 7.10 (dd, J=8.6, 1.0 Hz, 1H), 3.69 (app d, 2H), 3.12 (br s, 2H), 2.88 (s, 2H), 1.85-1.82 (m, 2H), 1.66-1.58 (m, 2H). $^{13}$C NMR (100 MHz, DMSO-d6) δ (ppm): 189.8, 160.2, 153.8, 153.9, 127.6, 119.8, 118.4, 118.3, 78.8, 77.8, 47.3, 32.9, 28.1. MS: (ES, m/z): 296 [M+H-Boc]$^+$.

Step-2: 1'-(tert-Butyl) 5-methyl 4-oxospiro[chromane-2,4'-piperidine]-1',5-dicarboxylate tert-Butyl-5-bromo-4-oxospiro[chromane-2,4'-piperidine]-1'-carboxylate (1.31 g, 3.3 mmol) was added to a stirred solution of palladium (II) chloride (47 mg, 0.26 mmol) and 1,3-bis(diphenylphosphanyl)propane (110 mg, 0.26 mmol) in anhydrous MeOH (10 mL) and anhydrous DMF (1.5 mL) in a pressure vessel. CO (g) was vigorously bubbled through the reaction mixture while Et$_3$N (1.5 mL) was added. The vessel was sealed under CO (g) and heated at 75° C. for 24 h. The reaction mixture was then cooled to room temperature and diluted with EtOAc (100 mL) and washed with 1M HCl (2×50 mL) and brine (1×50 mL). The organic phase was dried over Na$_2$SO$_4$. After filtration, the organic solvent was removed in vacuo and the residue was purified by flash column chromatography on silica gel (40% EtOAc/hexanes) to afford 400 mg (32% yield) of the title compound as an off-white solid. $^1$H NMR (400 MHz, CDCl$_3$) δ (ppm): 7.50 (dd, J=8.2, 0.8 Hz, 1H), 7.07 (dd, J=8.2, 0.8 Hz, 1H), 6.97 (dd, J=7.4, 1.2 Hz, 1H), 3.93 (s, 3H), 3.87 (br s, 2H), 3.21 (app t, J=11.7 Hz, 2H), 2.75 (s, 2H), 2.02 (app d, J=13.3 Hz, 2H), 1.62 (dt, J=12.9, 5.1 Hz, 2H), 1.46 (s, 9H). $^{13}$C NMR (100 MHz, CDCl$_3$) δ (ppm): 190.1, 169.8, 158.9, 154.6, 135.7, 133.9, 120.0, 117.7, 79.8, 78.3, 52.8, 47.9, 33.9, 28.4. MS: (ES, m/z): 398 [M+Na]$^+$.

Step-3: 1'-(tert-Butyl) 5-methyl 4-hydroxyspiro[chromane-2,4'-piperidine]-1',5-dicarboxylate NaBH$_4$ (161 mg, 4.28 mmol) was added to a stirred solution of 1'-(tert-butyl)-5-methyl-4-oxospiro[chromane-2,4'-piperidine]-1',5-dicarboxylate (0.400 g, 1.07 mmol) in 10 mL of MeOH, cooled to 0° C. The reaction warmed to room temperature over 15 min, then was quenched with 60 mL of aq. sat. NH$_4$Cl solution. The mixture was extracted with EtOAc (4×50 mL) and dried over Na$_2$SO$_4$. The Na$_2$SO$_4$ was filtered off and the solvent was removed in vacuo to afford the title compound as an off-white solid, which was carried forward without further purification.

Step-4: Methyl spiro[chromane-2,4'-piperidine]-5-carboxylate

1'-(tert-Butyl)-5-methyl-4-hydroxyspiro[chromane-2,4'-piperidine]-1',5-dicarboxylate was dissolved in 3 mL of triethylsilane. Then 2 mL of TFA was added. The mixture stirred for 48 h at room temperature. The reaction mixture was then diluted with EtOAc (100 mL) and the excess acid was quenched with aq. 10% K$_2$CO$_3$ (30 mL). The layers were separated and the organic phase was dried over Na$_2$SO$_4$. After filtration, the organic phase was concentrated to 10 mL and 4N HCl in dioxane was added. A white precipitate formed. 50 mL of hexanes was added and the mixture was triturated and filtered to afford 236 mg (75% yield over 2 steps) of the title compound as the HCl salt as a white solid. $^1$H NMR (400 MHz, CDCl$_3$) δ (ppm): 10.0 (br s, 1H), 8.63 (br s, 1H), 7.54 (dd, J=7.8, 1.1 Hz, 1H), 7.19 (t, J=8.2 Hz, 1H), 7.04 (dd, J=7.8, 1.0 Hz, 1H), 3.88 (s, 3H), 3.23 (br s, 4H), 3.13 (t, J=7.0 Hz, 2H), 1.98 (br s, 4H), 1.88 (t, J=7.0 Hz, 2H). $^{13}$C NMR (100 MHz, CDCl$_3$) δ (ppm): 167.5, 152.9, 130.2, 127.1, 123.4, 122.9, 121.7, 70.5, 51.9, 39.3, 31.6, 31.2, 20.1. MS: (ES, m/z): 262 [M+H]$^+$.

Example 27-2—Preparation of N8-hydroxy-N1', N1'-dimethylspiro[chromane-2,4'-piperidine]-1',8-dicarboxamide (II-74)

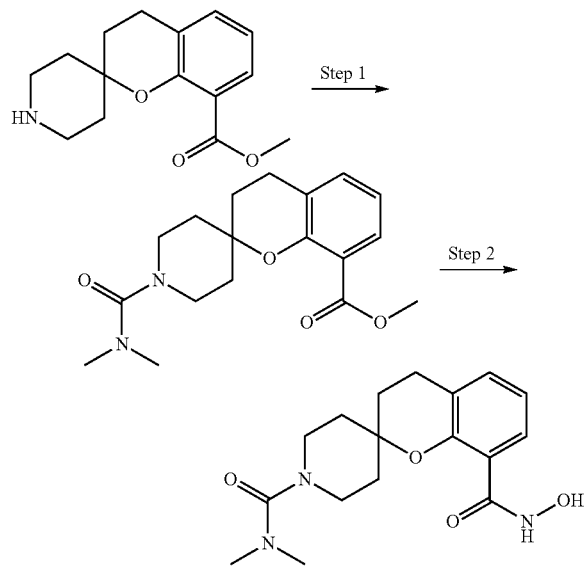

Step-1: Methyl 1'-(dimethylcarbamoyl)spiro[chromane-2,4'-piperidine]-8-carboxylate A 2-mL vial was charged with a solution of methyl spiro[chromane-2,4'-piperidine]-8-carboxylate TFA (0.2M in DCE/DIPEA (10:1), 200 μL, 0.040 mmol, 1 equiv) followed by dimethylcarbamyl chloride (0.2M in DCE, 200 μL, 0.040 mmol, 1 equiv). The vial was sealed and shaken at room temperature for 18 h, then the solvent was removed under a stream of N$_2$ (g). The residue was diluted with brine (500 μL) and extracted with EtOAc (2×500 μL). The combined organic layers were dried under a stream of N$_2$ (g) revealing a pale yellow residue, which was used without further purification. $^1$H NMR (400 MHz, CDCl$_3$) δ (ppm): 7.65 (dd, J=7.8, 1.6 Hz, 1H), 7.20 (d, J=7.4 Hz, 1H), 6.86 (t, J=7.4 Hz, 1H), 3.89 (s, 3H), 3.57-3.52 (m, 2H), 3.67 (dt, J=12.5, 2.0 Hz, 2H), 2.84-2.80 (m, 8H), 1.84-1.79 (m, 4H), 1.67-1.59 (m, 2H). MS: (ES, m/z): 333 [M+H]$^+$.

Step-2: N8-Hydroxy-N1',N1'-dimethylspiro[chromane-2,4'-piperidine]-1',8-dicarboxamide The residue from Step 1 was dissolved in THF/MeOH (3:1, 200 μL). The vial was sealed and shaken at 50° C. for 15 min to dissolve the residue, then cooled to room temperature. NH$_2$OH (50% v/v solution in water, 150 μL) was added, followed by aq. 1N NaOH (100 μL). The mixture was sealed and shaken at room temperature for 18 h. The reaction mixture was concentrated under a stream of N$_2$ (g) at room temperature, then dissolved in 500 μL of DMSO and purified by Prep-HPLC using the following conditions: Column: Waters Sunfire C18, 19×50 mm, 5 μm; Mobile Phase A: water/0.1% formic acid, Mobile Phase B: CH$_3$CN/0.1% formic acid; Gradient: 15% B up to 100% B in 6 min; Flow Rate: 23 mL/min; Detector: UV 254 nm, 220 nm. The product-containing fractions were combined and concentrated to afford 2.5 mg (19% over 2 steps) of the title compound. $^1$H NMR (400 MHz, CDCl$_3$) δ (ppm): 8.08 (s, 1H), 8.01 (dd, J=7.8, 1.6 Hz, 1H), 7.23 (d, J=7.4 Hz, 1H), 7.01 (t, J=7.8 Hz, 1H), 3.55 (dt, J=13.7, 3.9 Hz, 1H), 3.22 (ddd, J=13.9, 11.3, 2.9 Hz, 1H), 2.88-2.83 (m, 8H), 1.94-1.88 (m, 4H), 1.81-1.73 (m, 2H). MS: (ES, m/z): 334 [M+H]$^+$.

TABLE 9-2

| Ex. | Structure | Found (ES, m/z) [M + H]$^+$ |
|---|---|---|
| II-75 | 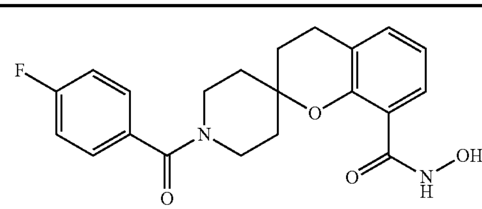 | 385 |
| II-76 | 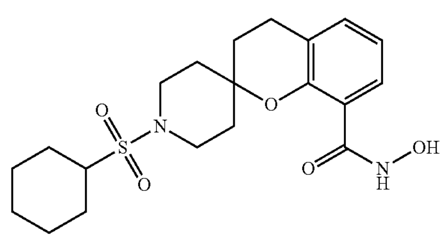 [SMILES: O=C(NO)c1cccc2c1OC1(CC2)CCN(S(=O)(=O)C2CCCCC2)CC1] | 409 |

TABLE 9-2-continued

| Ex. | Structure | Found (ES, m/z) [M + H]+ |
|---|---|---|
| II-77 | 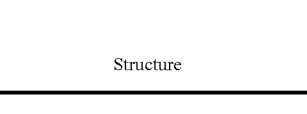 | 389 |
| II-78 | 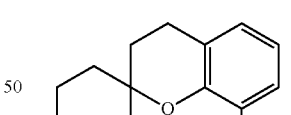 | 475 |
| II-79 | 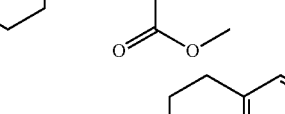 | 381 |

The following compounds were prepared according to the parallel synthesis method of Example 27-2.

TABLE 10-2

| Ex. | Structure | Found (ES, m/z) [M + H]+ |
|---|---|---|
| II-91 | 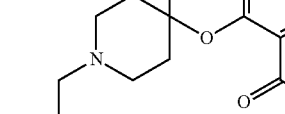 | 305 |

The following compound was prepared according to the parallel synthesis method of Example 27-2, with the following modification: In Step 1, methyl spiro[chromane-2,4'-piperidine]-5-carboxylate HCl was used.

Example 28-2—Preparation of 1'-(4-fluorobenzyl)-N-hydroxyspiro[chromane-2,4'-piperidine]-8-carboxamide (II-80)

283
-continued

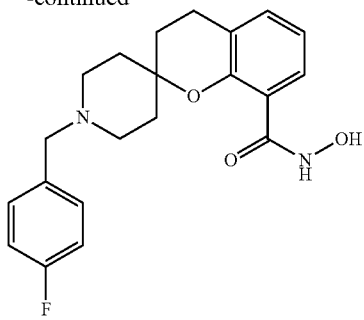

Step-1: Methyl 1'-(4-fluorobenzyl)spiro[chromane-2,4'-piperidine]-8-carboxylate

A 2-mL vial was charged with a solution of methyl spiro[chromane-2,4'-piperidine]-8-carboxylate TFA (0.2M in DCE/DIPEA (10:1), 200 µL, 0.040 mmol, 1 equiv), followed by a solution of 4-fluorobenzaldehyde (0.2M in DCE, 200 µL, 0.040 mmol, 1 equiv). Then NaBH(OAc)₃ (42 mg, 0.080 mmol, 2 equiv) was added in one portion. The vial was sealed and shaken at room temperature for 18 h, then the solvent was removed under a stream of N₂ (g). The residue was diluted with brine (500 µL) and extracted with EtOAc (2×500 The combined organic layers were dried under a stream of N₂ (g) revealing a pale yellow residue, which was used without further purification. ¹H NMR (400 MHz, CDCl₃) δ (ppm): 7.64 (dd, J=7.8, 2.0 Hz, 1H), 7.41 (dd, J=8.4, 5.3 Hz, 2H), 7.20 (d, J=7.8 Hz, 1H), 7.05 (t, J=8.6 Hz, 2H), 6.87 (t, J=7.6 Hz, 1H), 3.88 (s, 3H), 3.84 (br s, 2H), 2.97-2.86 (m, 4H), 2.82 (t, J=8.6 Hz, 2H), 1.96-1.85 (m, 6H). MS: (ES, m/z): 370 [M+H]⁺.

Step-2: 1'-(4-Fluorobenzyl)-N-hydroxyspiro[chromane-2,4'-piperidine]-8-carboxamide The residue from Step 1 was dissolved in THF/MeOH (3:1, 200 The vial was sealed and shaken at 50° C. for 15 min to dissolve the residue, then cooled to room temperature. NH₂OH (50% v/v solution in water, 150 µL) was added, followed by aq. 1N NaOH (100 The mixture was sealed and shaken at room temperature for 18 h. The reaction mixture was concentrated under a stream of N₂ (g) at room temperature, then dissolved in 500 µL of DMSO and purified by Prep-HPLC using the following conditions: Column: Waters Sunfire C18, 19×50 mm, 5 µm; Mobile Phase A: water/0.1% formic acid, Mobile Phase B: CH₃CN/0.1% formic acid; Gradient: 15% B up to 100% B in 6 min; Flow Rate: 23 mL/min; Detector: UV 254 nm, 220 nm. The product-containing fractions were combined and concentrated to afford the title compound. MS: (ES, m/z): 371 [M+H]⁺.

TABLE 11-2

| Ex. | Structure | Found (ES, m/z) [M + H]⁺ |
|---|---|---|
| II-81 | ![structure] | 345 |

284

The following compound was prepared according to the parallel synthesis method of Example 28-2.

Example 29-2—Preparation of N-hydroxy-1'-(5-(trifluoromethyl)pyridin-2-yl)spiro[chromane-2,4'-piperidine]-8-carboxamide (II-82)

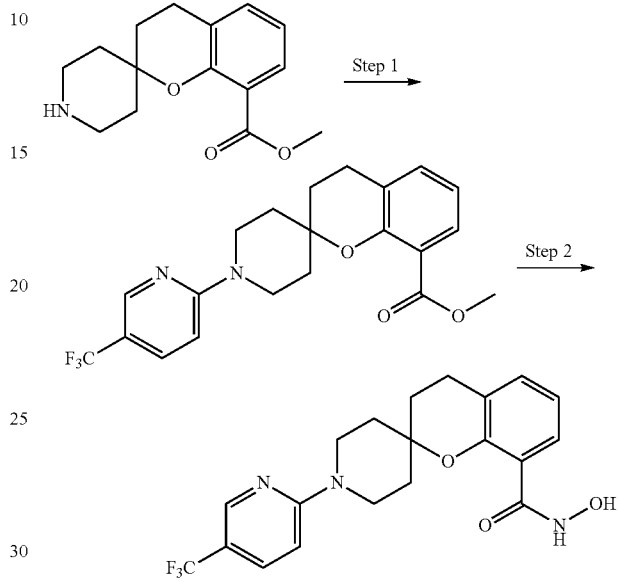

Step-1: Methyl 1'-(5-(trifluoromethyl)pyridin-2-yl)spiro[chromane-2,4'-piperidine]-8-carboxylate A 2-mL vial was charged methyl spiro[chromane-2,4'-piperidine]-8-carboxylate TFA (0.2M in dioxane, 200 µL, 40 µmol, 1 equiv) and Cs₂CO₃ (39 mg, 120 µmol, 3 equiv). Then a solution of 2-chloro-5-(trifluoromethyl)pyridine (0.2M in dioxane, 400 µL, 80 µmol, 2 equiv) was added. The vial was sealed and brought into a glovebox. Then a degassed solution of the copper(I) bromide and N,N-dimethylethane-1,2-diamine ligand (0.02M in DMA, 150 µL, 3.0 µmol) was added. The vial was sealed and heated at 105° C. for 18 h. The solvent was removed under a stream of N₂ (g). The residue was diluted with brine (500 µL) and extracted with EtOAc (2×500 µL). The combined organic layers were dried under a stream of N₂ (g). The residue was carried forward without further purification. ¹H NMR (400 MHz, CDCl₃) δ (ppm): 8.39 (s, 1H), 7.67 (dd, J=7.8, 2.0 Hz, 1H), 7.60 (dd, J=9.0, 2.3 Hz, 1H), 7.22 (d, J=7.4 Hz, 1H), 6.89 (t, J=7.8 Hz, 1H), 6.68 (d, J=9.0 Hz, 1H), (dt, J=13.4, 2.3 Hz, 2H), 3.87 (s, 3H), 3.59-3.51 (m, 2H), 2.86 (t, J=6.8 Hz, 2H), 1.93 (dd, J=14.3, 2.2 Hz, 2H), 1.85 (t, J=7.0 Hz, 2H), 1.67-1.59 (m, 2H). MS: (ES, m/z): 407 [M+H]⁺.

Step-2: N-Hydroxy-1'-(5-(trifluoromethyl)pyridin-2-yl)spiro[chromane-2,4'-piperidine]-8-carboxamide The residue from Step 1 was taken up in THF/MeOH (3:1, 200 µL). The vial was sealed and shaken at 50° C. for 15 min to dissolve the residue, then cooled to room temperature. NH₂OH (50% v/v solution in water, 150 µL) was added, followed by aq. 1N NaOH (100 µL). The mixture was sealed and then shaken at room temperature for 18 h. The reaction mixture was concentrated under a stream of N₂ (g) at room temperature, then dissolved in 500 μL of DMSO and purified by Prep-HPLC using the following conditions: Column: Waters Sunfire C18, 19×50 mm, 5 μm; Mobile Phase A: water/0.1% formic acid, Mobile Phase B: CH₃CN/0.1% formic acid; Gradient: 15% B up to 100% B in 6 min; Flow Rate: 23 mL/min; Detector: UV 254 nm, 220 nm. The product-containing fractions were combined and concentrated to afford 4.0 mg (25% yield) of the title compound. $^1$H NMR (400 MHz, DMSO-d6) δ (ppm): 10.52 (s, 1H), 9.07 (s, 1H), 8.41 (s, 7.78 (dd, J=9.2, 2.5 Hz, 1H), 7.27 (dd, J=7.6, 1.4 Hz, 1H), 7.20 (d, J=7.8 Hz, 1H), 7.01 (d, J=9.4 Hz, 1H), 6.89 (t, J=7.4 Hz, 1H), 4.23 (d, J=13.3 Hz, 2H), 3.39 (t, J=11.3 Hz, 2H), 2.79 (t, J=6.6 Hz, 2H), 1.84-1.80 (m, 4H), 1.65-1.57 (m, 2H). MS: (ES, m/z): 408 [M+H]$^+$.

TABLE 12-2

| Ex. | Structure | Found (ES, m/z) [M + H]$^+$ |
|---|---|---|
| II-83 | [structure] | 371 |

The following was prepared according to the parallel synthesis method of Example 29-2.

TABLE 13-2

| Ex. | Structure | Found (ES, m/z) [M + H]$^+$ |
|---|---|---|
| II-92 | [structure] | 339 |
| II-93 | [structure] | 357 |

The following compounds were prepared according to the parallel synthesis method of Example 29-2, with the following modification: In Step 1, methyl spiro[chromane-2,4'-piperidine]-5-carboxylate HCl was used.

Example 30-2—In Vitro Histone Deacetylase Assay

The enzymatic HDAC11 assay was performed using electrophoretic mobility shift assay. Full length human recombinant HDAC11 protein was expressed in baculoviral system and purified by affinity chromatography. The enzymatic reactions were assembled in 384 well plates in a total volume of 25 μL in a reaction buffer composing: 100 mM HEPES, pH 7.5, 25 mM KCl, 0.1% bovine serum albumin, 0.01% Triton X-100, 1% DMSO (from compounds) 2 μM of the fluorescently labeled peptide substrate and enzyme. The enzyme was added at a final concentration of 10 nM. The peptide substrate FAM-RHKK(tri-fluor-Ac)-NH₂ was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 μL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR):P/(S+P), where P is the peak height of the product peptide and S is the peak height of the substrate peptide. Percent inhibition ($P_{inh}$) is determined using the following equation:

$$P_{inh} = (PSR0\% - PSR_{inh})/(PSR0\% - PSR100\%)*100,$$

where $PSR_{inh}$ is the product sum ratio in the presence of inhibitor, PSR0% is the average product sum ration in the absence of inhibitor and PSR100% is the average product sum ratio in 100%-inhibition control samples. The $IC_{50}$ values of inhibitors were determined by fitting the percent inhibition curves with 4 parameter dose-response model using XLfit 4 software.

As set forth in Table 14-2 below, "+++" indicates an $IC_{50}$ below 0.5 µM; "++" indicates an $IC_{50}$ between 0.5 µM and 1 µM; and "+" indicates an $IC_{50}$ above 1 µM.

TABLE 14-2

$IC_{50}$ Ranges for Compounds of the Disclosure

| Compound No. | HDAC11 $IC_{50}$ Range |
|---|---|
| II-1 | +++ |
| II-2 | + |
| II-3 | +++ |
| II-4 | +++ |
| II-5 | +++ |
| II-6 | +++ |
| II-7 | ++ |
| II-8 | + |
| II-9 | + |
| II-10 | + |
| II-11 | + |
| II-12 | ++ |
| II-13 | + |
| II-14 | + |
| II-15 | + |
| II-16 | +++ |
| II-17 | ++ |
| II-18 | +++ |
| II-19 | + |
| II-20 | + |
| II-21 | ++ |
| II-22 | +++ |
| II-23 | + |
| II-24 | + |
| II-25 | + |
| II-26 | + |
| II-27 | +++ |
| II-28 | + |
| II-29 | ++ |
| II-30 | +++ |
| II-31 | +++ |
| II-32 | ++ |
| II-33 | +++ |
| II-34 | + |
| II-35 | + |
| II-36 | + |
| II-37 | +++ |
| I-38 | +++ |
| II-39 | ++ |
| II-40 | + |
| II-41 | +++ |
| II-42 | +++ |
| II-43 | +++ |
| II-44 | + |
| II-45 | ++ |
| II-46 | + |
| II-47 | + |
| II-48 | + |
| II-49 | + |
| II-50 | + |
| II-51 | + |
| II-52 | + |
| II-53 | + |
| II-54 | + |
| II-55 | + |
| II-56 | ++ |
| II-57 | + |
| II-58 | + |
| II-59 | + |
| II-60 | + |
| II-61 | + |
| II-62 | + |
| II-63 | + |
| II-64 | + |
| II-65 | + |
| II-66 | + |
| II-67 | +++ |
| II-68 | +++ |
| II-69 | + |
| II-70 | ++ |
| II-71 | ++ |
| II-72 | + |
| II-73 | + |
| II-74 | + |
| II-75 | + |
| II-76 | + |
| II-77 | + |
| II-78 | +++ |
| II-79 | + |
| II-80 | + |
| II-81 | + |
| II-82 | + |
| II-83 | + |
| II-84 | +++ |
| II-85 | +++ |
| II-86 | +++ |
| II-87 | + |
| II-88 | +++ |
| II-89 | ++ |
| II-90 | + |
| II-91 | + |
| II-92 | + |
| II-93 | + |

What is claimed is:

1. A compound of Formula I-A or a pharmaceutically acceptable salt thereof,

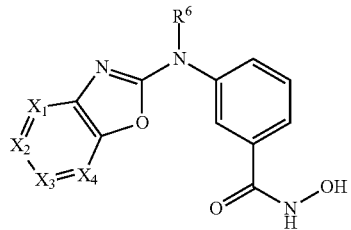

I-A wherein:

$X_1$, $X_2$, $X_3$, and $X_4$ are each independently, at each occurrence, N or $CR^1$;

wherein (i) $X_1$ and $X_4$ are both N, and $X_2$ and $X_3$ are each independently $CR^1$;

(ii) $X_2$ and $X_4$ are both N, and $X_1$ and $X_3$ are each independently $CR^1$;

(iii) $X_1$ is N and $X_2$, $X_3$, and $X_4$ are each independently $CR^1$; or (iv) $X_1$, $X_2$, $X_3$, and $X_4$ are each $CR^1$;

$R^1$ is independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, —$OR^3$, halogen, —$NO_2$, —CN, —$NHC_1$-$C_6$alkyl, —$N(C_1$-$C_6$alkyl$)_2$, —$S(O)_2NH_2$, —$S(O)_2N(C_1$-$C_6$alkyl$)_2$, —$N(C_1$-$C_6$alkyl$)S(O)_2R^5$, —$S(O)_2(C_1$-$C_6$alkyl), —$(C_1$-$C_6$alkyl$)S(O)_2R^5$, —$C(O)C_1$-$C_6$alkyl, —$C(O)OC_1$-$C_6$alkyl, —$N(C_1$-$C_6$alkyl$)S(O)_2C_1$-$C_6$alkyl, or —$(CHR^5)_pNR^3R^4$, wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^3$, —$R^5$, —$SR^3$, —$OR^3$, —$NHR^3$, —$NR^3R^4$, —$S(O)_2N(R^3)_2$—, —$S(O)_2R^5$, —$C(O)R^5$, —$C(O)OR^5$, —$NR^3S(O)_2R^5$, —$S(O)R^5$, —$S(O)NR^3R^4$, —$NR^3S(O)R^5$, heterocycle, aryl, or heteroaryl;

or two occurrences of $R^1$, when on adjacent atoms, can combine to form a cycloalkyl, a heterocycle, aryl, heteroaryl containing 1-5 heteroatoms selected from the group consisting of N, S, P and O, or a cycloalkenyl, each optionally substituted with one or more independent occurrences of $R^3$ and $R^4$;

$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —$S(O)_2N(C_1$-$C_6$alkyl$)_2$, —$S(O)_2(C_1$-$C_6$alkyl), —$(C_1$-$C_6$alkyl$)S(O)_2R^5$, —$C(O)C_1$-$C_6$alkyl, —$C(O)OC_1$-$C_6$alkyl, oxo, or —$(CHR^5)_pN(C_1$-$C_6$alkyl$)_2$, wherein each alkyl, alkenyl, cycloalkenyl, alkynyl, cycloalkyl, heterocyclyl, aryl, and heteroaryl is optionally substituted with one or more substituents selected from —OH, halogen, —$NO_2$, oxo, —CN, —$R^5$, —$O(C_1$-$C_6)$alkyl, —$NH(C_1$-$C_6)$alkyl, —$N(C_1$-$C_6$alkyl$)_2$, —$S(O)_2N(C_1$-$C_6$alkyl$)_2$, —$S(O)_2NHC_1$-$C_6$alkyl, —$C(O)C_1$-$C_6$alkyl, —$C(O)OC_1$-$C_6$alkyl, —$N(C_1$-$C_6$alkyl$)S(O)_2C_1$-$C_6$alkyl, —$S(O)R^5$, —$S(O)N(C_1$-$C_6$alkyl$)_2$, —$N(C_1$-$C_6$alkyl$)S(O)R^5$, heterocycle, aryl, or heteroaryl;

$R^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —$NO_2$, —CN, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$C(O)OC_1$-$C_6$alkyl, —$N(C_1$-$C_6$alkyl$)SO_2C_1$-$C_6$alkyl, —$S(O)(C_1$-$C_6$alkyl), —$S(O)N(C_1$-$C_6$alkyl$)_2$, —$N(C_1$-$C_6$alkyl$)S(O)(C_1$-$C_6$alkyl) or —$(CH_2)_pN(C_1$-$C_6$alkyl$)_2$;

$R^6$ is —H, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —$S(O)_2N(C_1$-$C_6$alkyl$)_2$, —$S(O)_2(C_1$-$C_6$alkyl), —$(C_1$-$C_6$alkyl$)S(O)_2R^5$, —$C(O)C_1$-$C_6$alkyl, —$C(O)OC_1$-$C_6$alkyl, or —$(CHR^5)_pNR^3R^4$ wherein each alkyl, alkenyl, cycloalkenyl, alkynyl, cycloalkyl, heterocyclyl, aryl, and heteroaryl is optionally substituted with one or more substituents selected from —OH, halogen, —$NO_2$, oxo, —CN, —$R^5$, —$O(C_1$-$C_6)$alkyl, —NH$(C_1$-$C_6)$alkyl, —$N(C_1$-$C_6$alkyl$)_2$, —$S(O)_2N(C_1$-$C_6$alkyl$)_2$, —$S(O)_2NHC_1$-$C_6$alkyl, —$C(O)C_1$-$C_6$alkyl, —$C(O)OC_1$-$C_6$alkyl, —$N(C_1$-$C_6$alkyl$)S(O)_2C_1$-$C_6$alkyl, —$S(O)R^5$, —$S(O)N(C_1$-$C_6$alkyl$)_2$, —$N(C_1$-$C_6$alkyl$)S(O)R^5$, heterocycle, aryl, or heteroaryl;

and p is 0, 1, 2, 3, 4, 5, or 6.

2. The compound of claim 1, wherein $X_1$, $X_2$, $X_3$, and $X_4$ are each $CR^1$.

3. The compound of claim 2, wherein each $R^1$ is independently H, halogen, —$CF_3$, —OH, —CN, —$SO_2(C_1$-$C_3$alkyl), phenyl, $C_1$-$C_3$alkyl, $C_1$-$C_3$alkoxy, pyridyl, —$C(O)C_1$-$C_3$alkyl, —$OC_1$-$C_3$alkyl, —$(C_1$-$C_3$alkyl$)O(C_1$-$C_3$alkyl), —$OCF_3$ or —$OCH_2$phenyl.

4. The compound of claim 3, wherein each $R^1$ is independently H or halogen.

5. The compound of claim 1, wherein $R^6$ is H, —$(CHR^5)_pNR^3R^4$, or —$C_1$-$C_6$alkyl optionally substituted with one or more substituents selected from —OH, halogen, —$NO_2$, oxo, —CN, —$R^5$, —$O(C_1$-$C_6)$alkyl, —NH$(C_1$-$C_6)$ alkyl, —N(C$_1$-C$_6$alkyl)$_2$, —S(O)$_2$N(C$_1$-C$_6$alkyl)$_2$, —S(O)$_2$NHC$_1$-C$_6$alkyl, —C(O)C$_1$-C$_6$alkyl, —C(O)OC$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, or —N(C$_1$-C$_6$alkyl)S(O)R$^5$.
6. The compound of claim 5, wherein R$^6$ is H.
7. A compound selected from
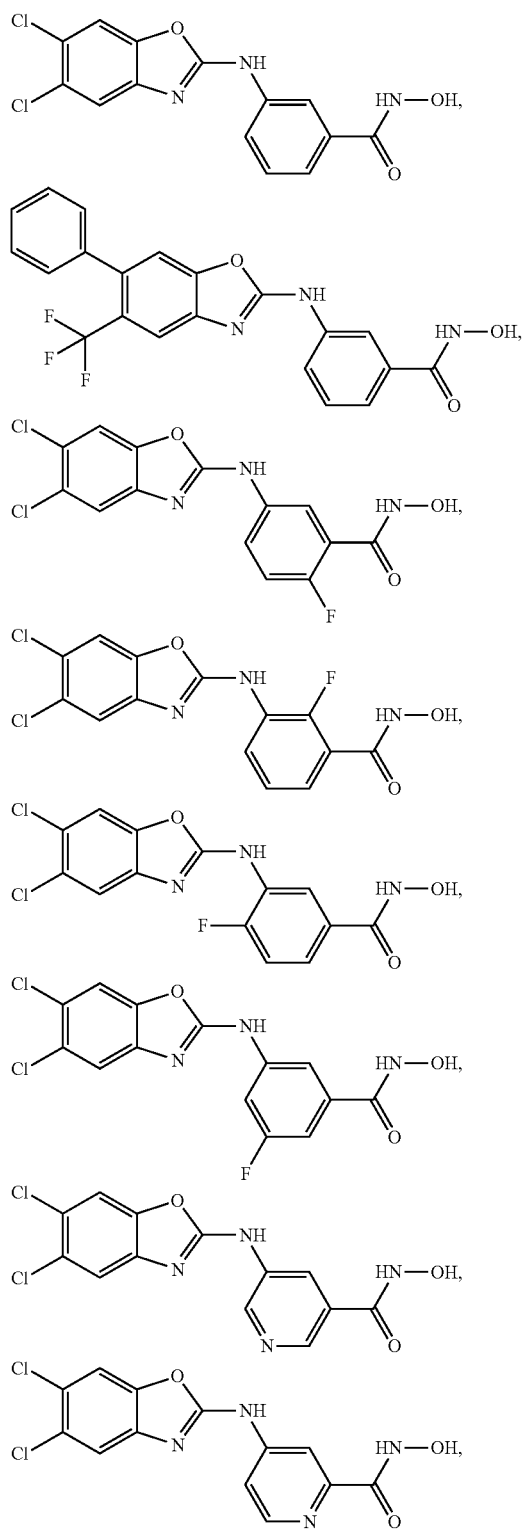
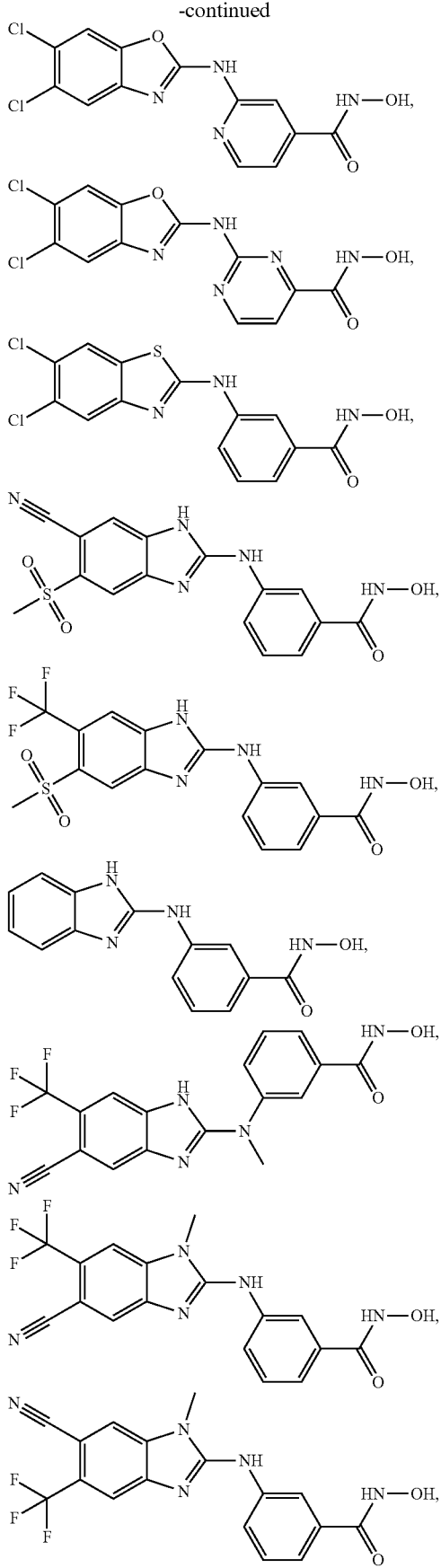

-continued
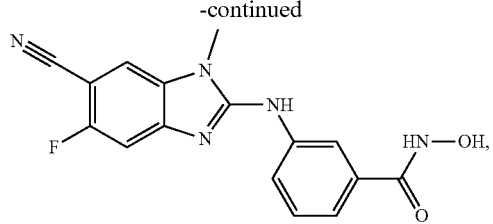
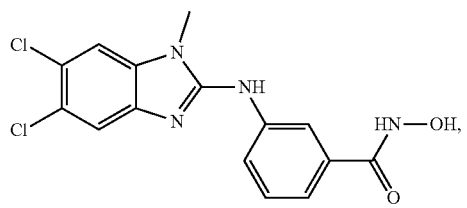
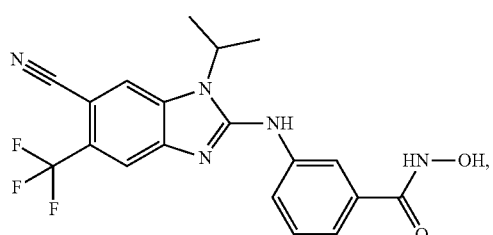
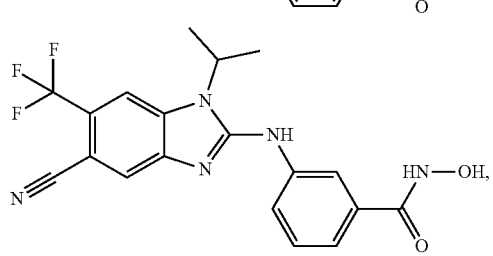
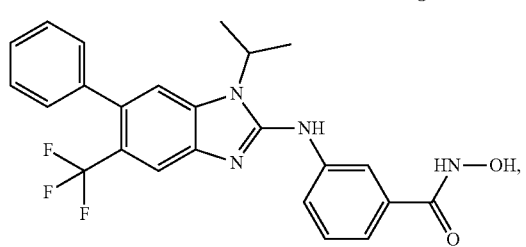
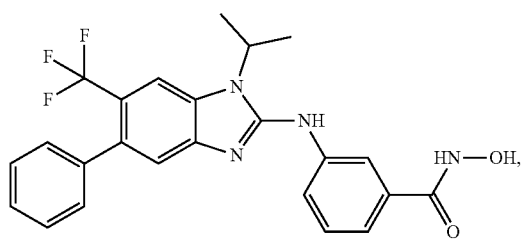
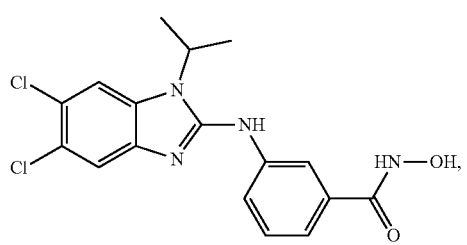
-continued
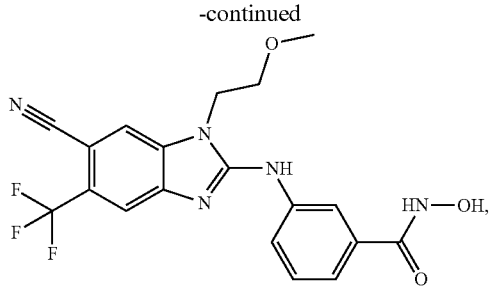
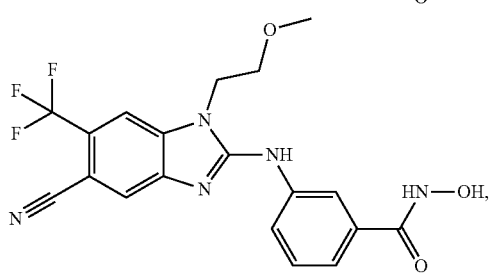
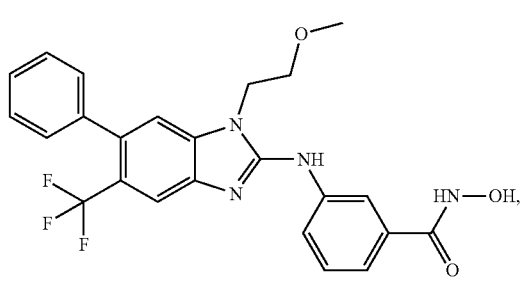
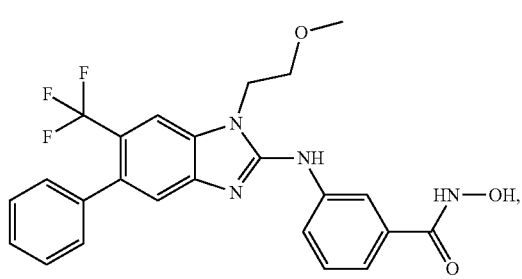
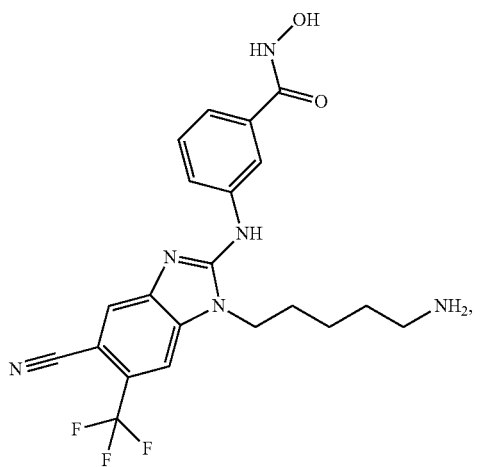

303
-continued
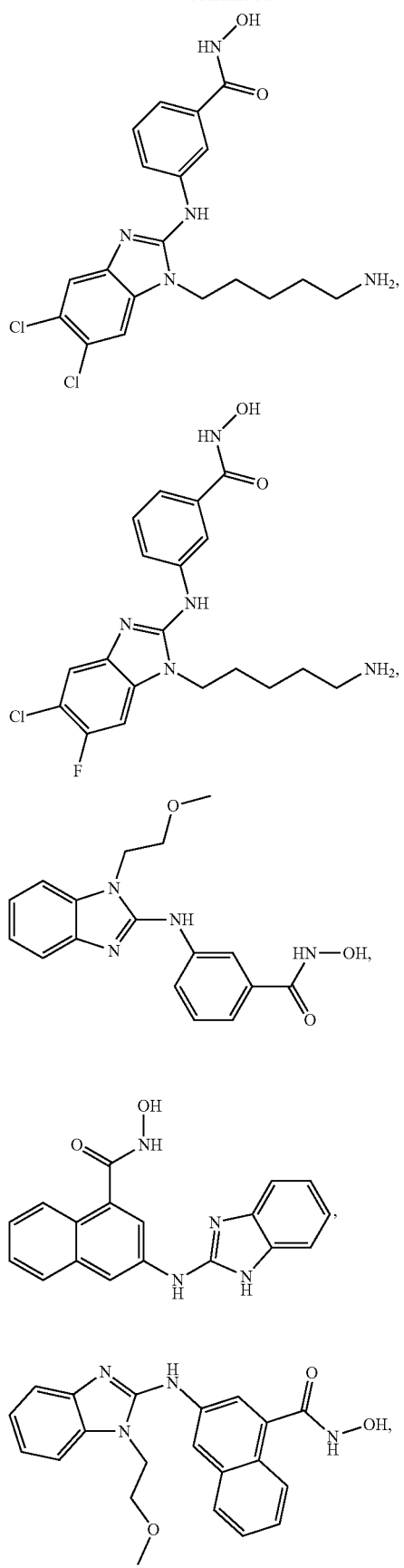
304
-continued
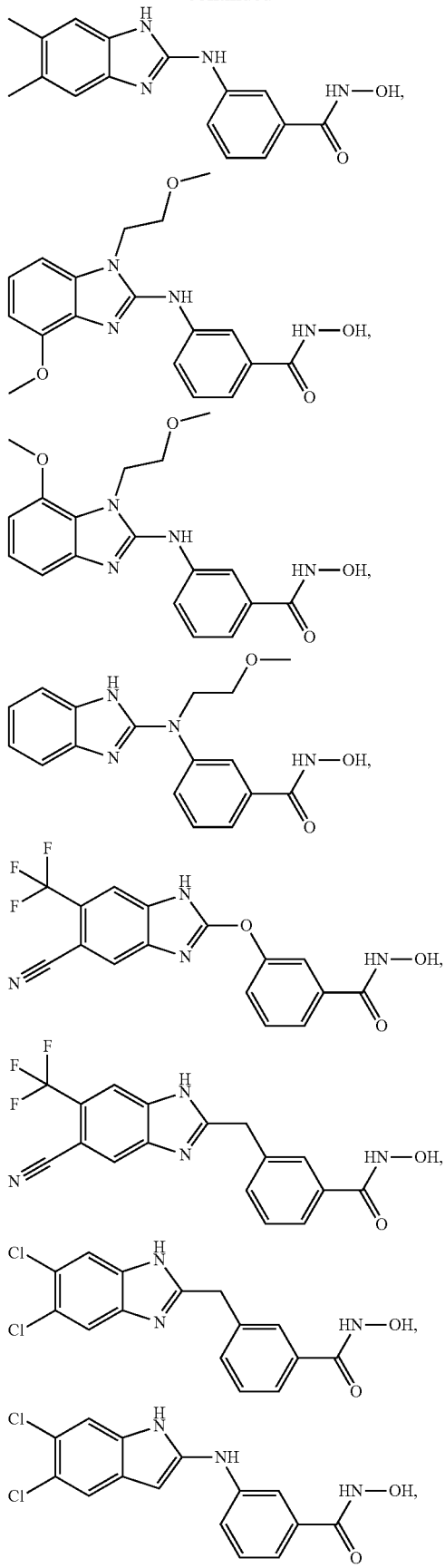

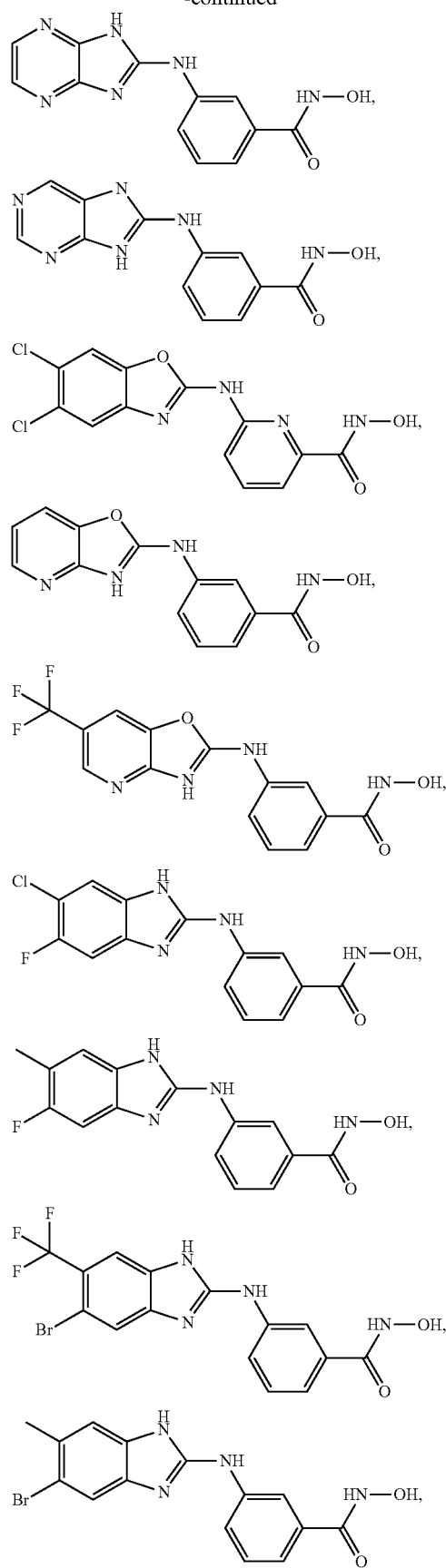
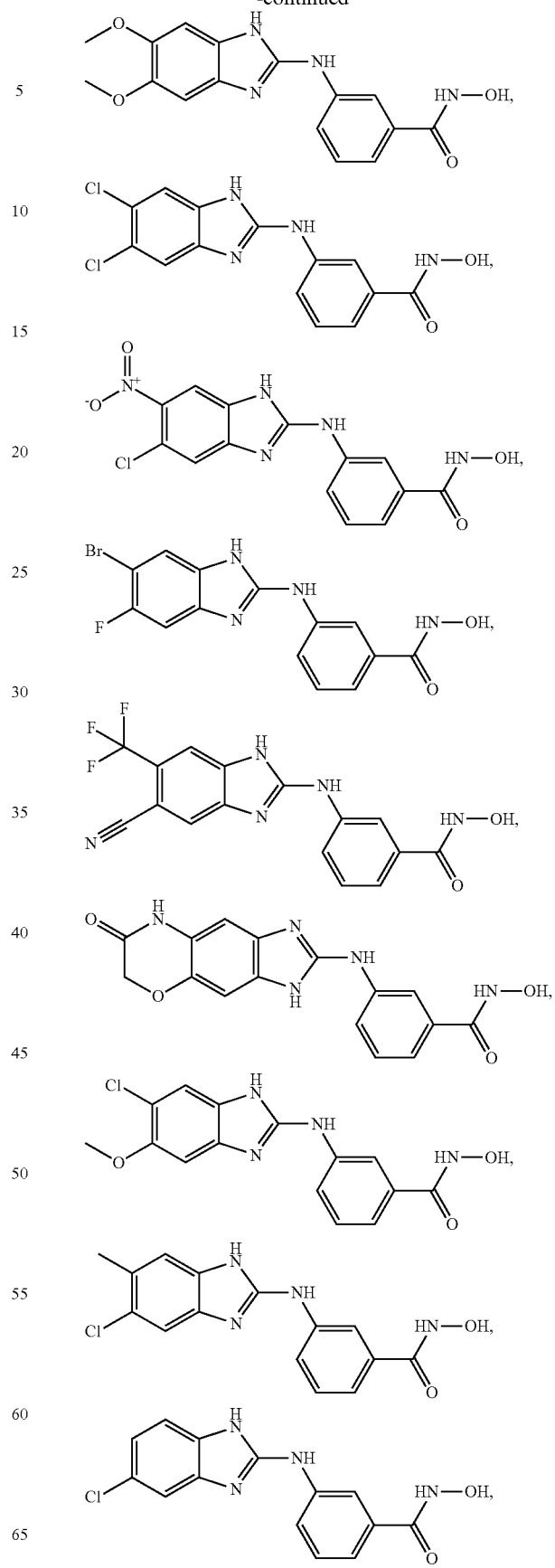

307
-continued
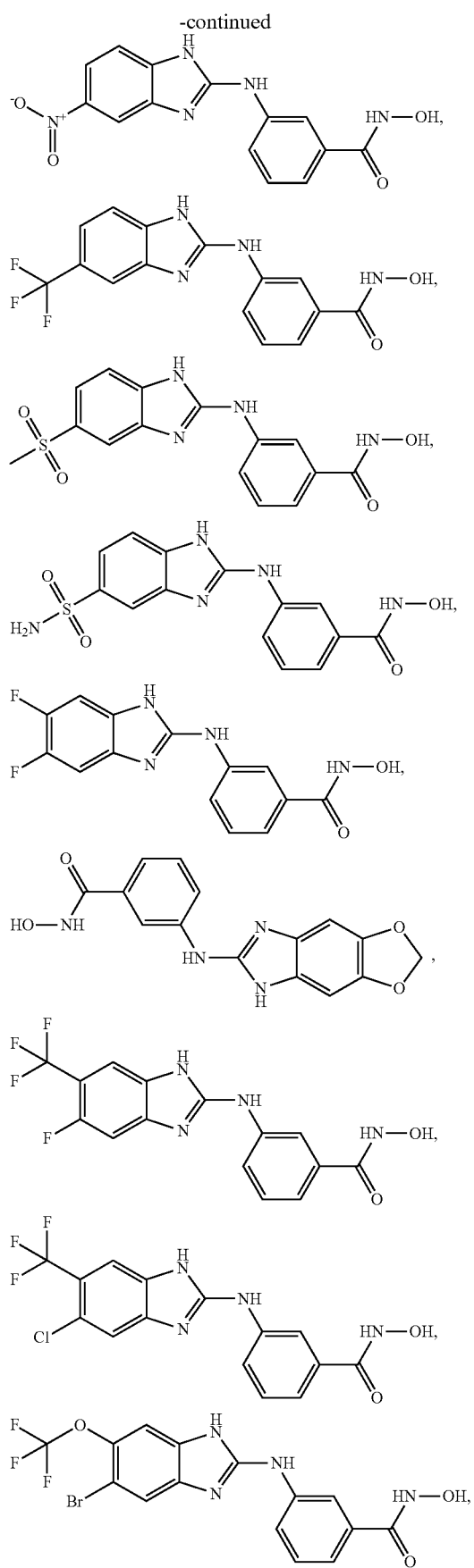
308
-continued
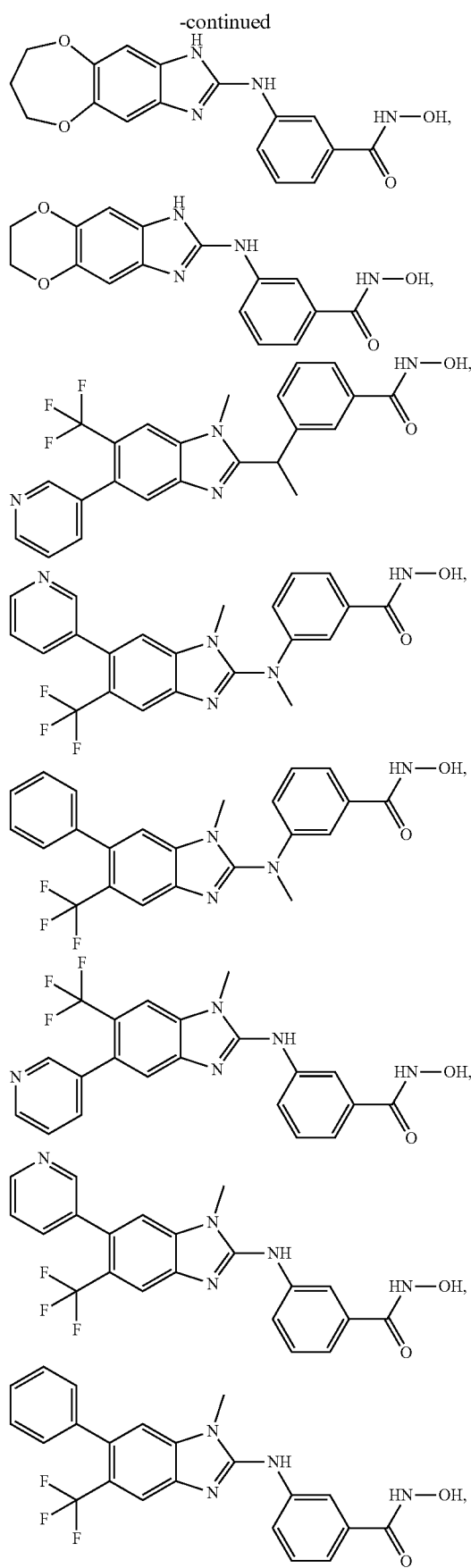

309
-continued
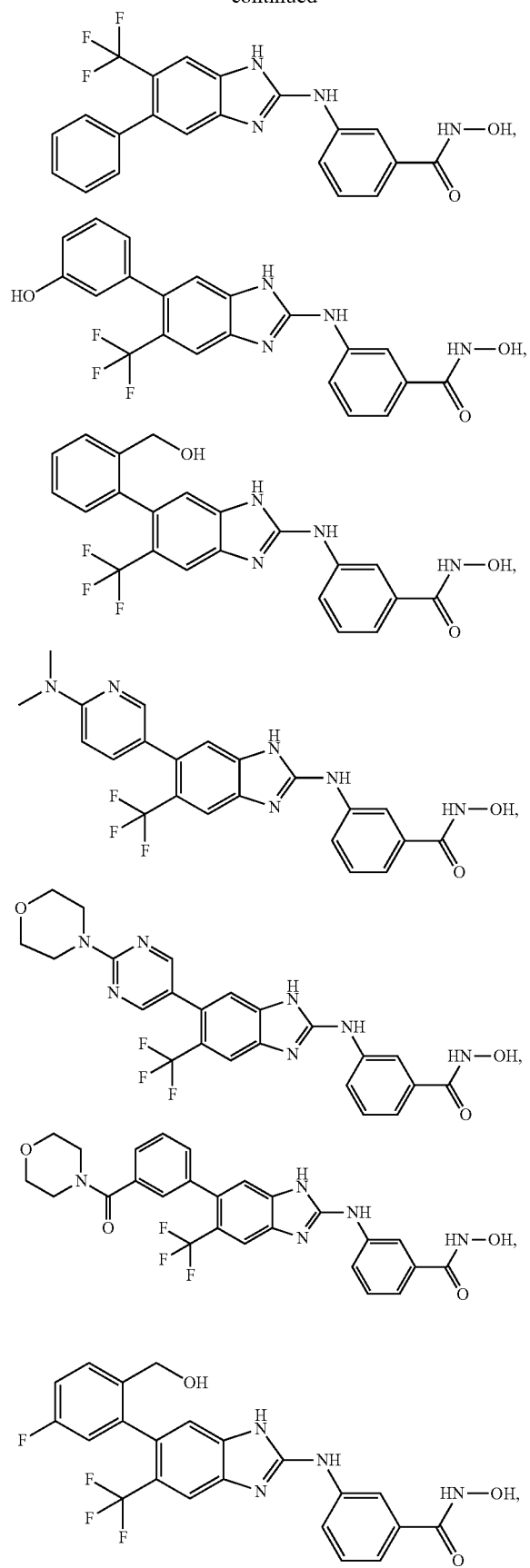
310
-continued
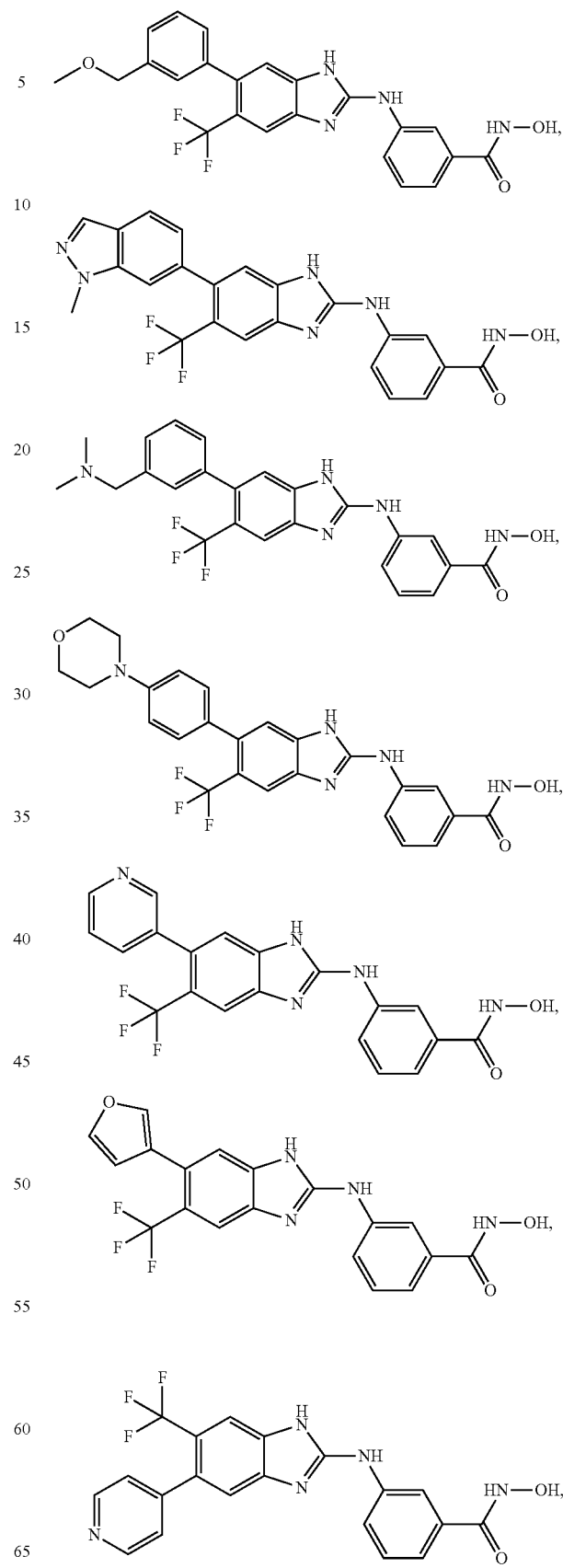

311
-continued
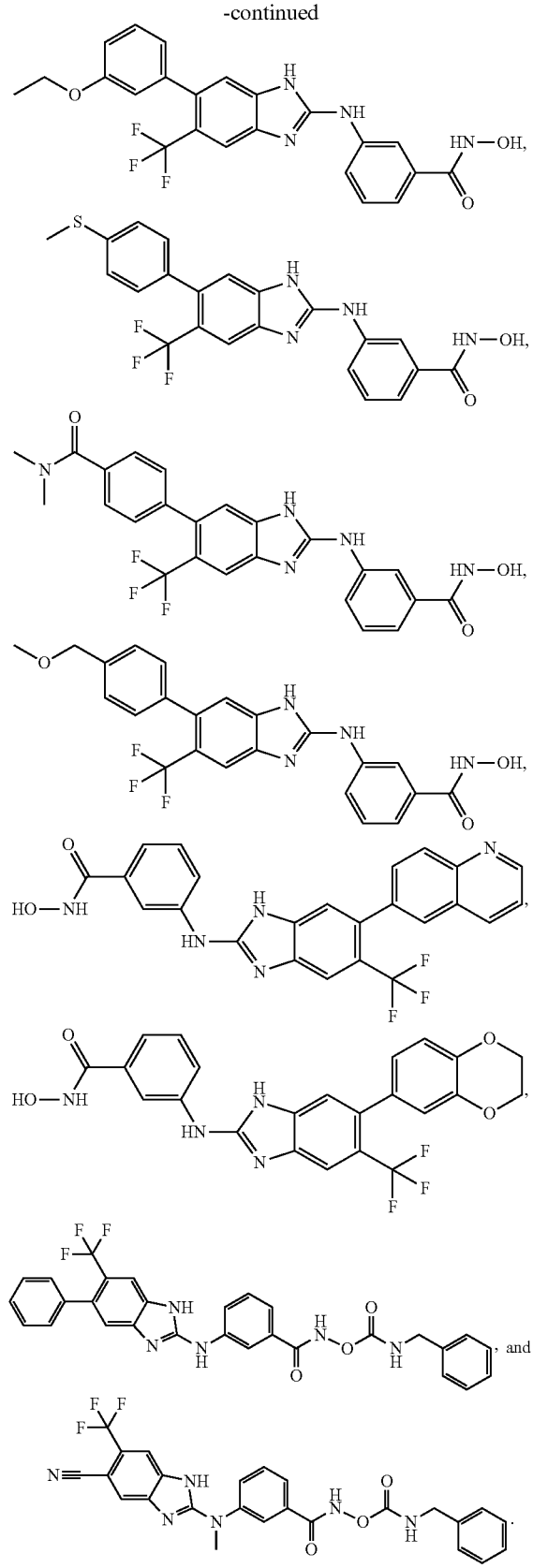
8. The compound of claim 7, wherein the compound is selected from:
312
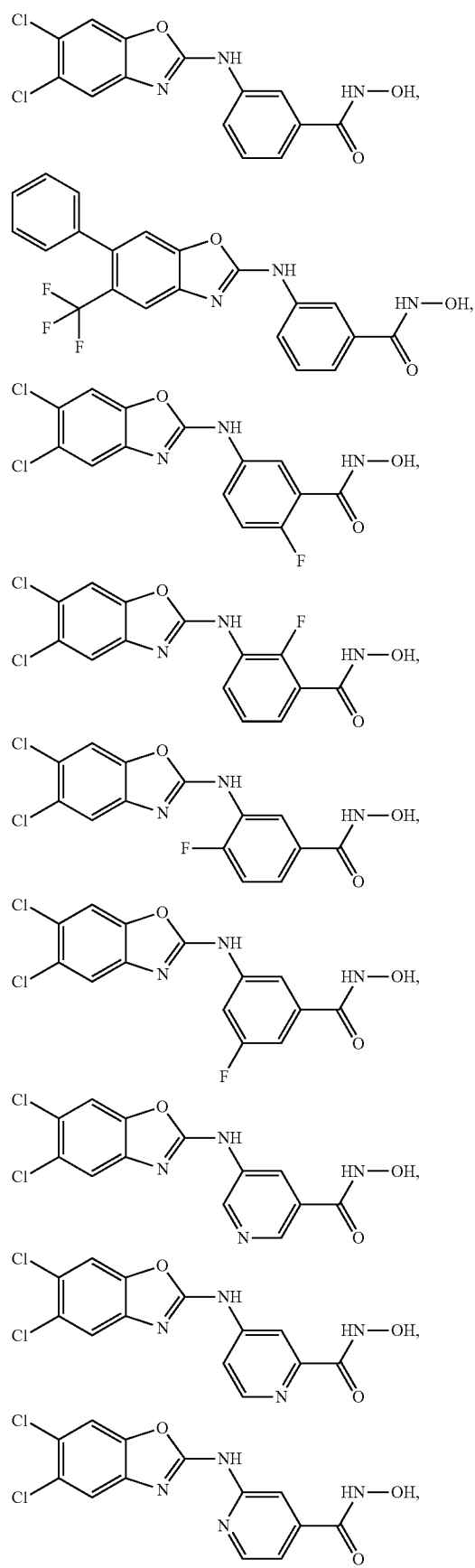

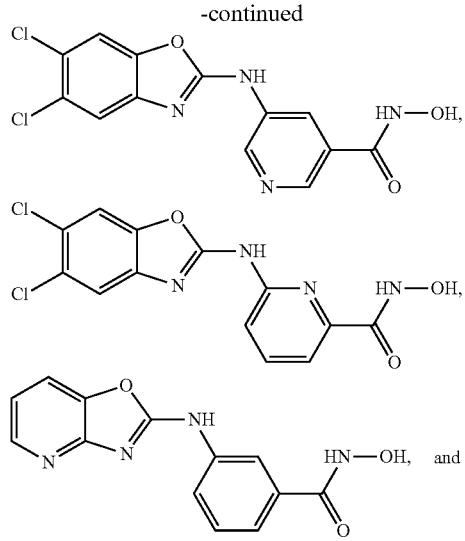

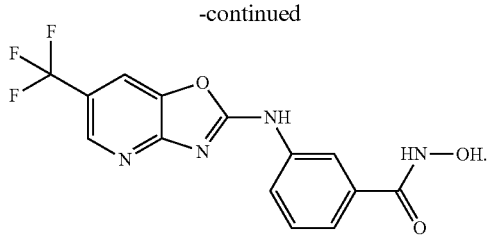

9. A pharmaceutical composition comprising a compound of claim 1, or a pharmaceutically accepted salt thereof, and a pharmaceutically accepted carrier.

10. A pharmaceutical composition comprising a compound of claim 7, or a pharmaceutically accepted salt thereof, and a pharmaceutically accepted carrier.

11. A pharmaceutical composition comprising a compound of claim 8, or a pharmaceutically accepted salt thereof, and a pharmaceutically accepted carrier.

* * * * *

UNITED STATES PATENT AND TRADEMARK OFFICE
CERTIFICATE OF CORRECTION

PATENT NO. : 10,508,088 B2
APPLICATION NO. : 16/202207
DATED : December 17, 2019
INVENTOR(S) : Jennifer Lee et al.

Page 1 of 1

It is certified that error appears in the above-identified patent and that said Letters Patent is hereby corrected as shown below:

In the Claims

In Claim 1, Column 298, at Line 37, please delete:
"$R^6$ is –H, –$C_2$-$C_6$alkenyl,"
And insert:
-- $R^6$ is –H, –$C_1$-$C_6$alkyl, –$C_2$-$C_6$alkenyl, --

In Claim 7, Column 310, beginning at Line 20 and ending at Line 25, please delete:

" 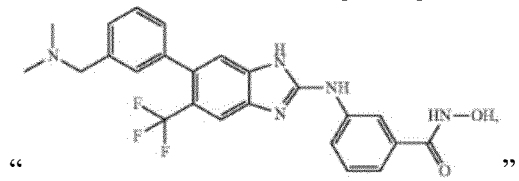 "

And insert:

-- 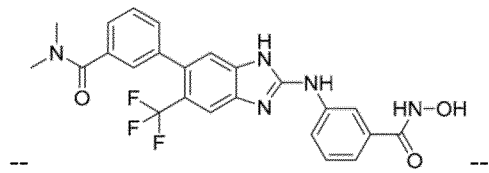 --

Signed and Sealed this
Seventeenth Day of March, 2020

Andrei Iancu
*Director of the United States Patent and Trademark Office*

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide sequence, YAP1 FP

<400> SEQUENCE: 1
cccaagacgg ccaacgtgcc                20

<210> SEQ ID NO 2
<211> LENGTH: 20
<212> TYPE: DNA

```
<213> ORGANISM: Artificial Sequence
<220> FEATURE:
<223> OTHER INFORMATION: Synthetic polynucleotide sequence, YAP1 RP

<400> SEQUENCE: 2
actggcctgt cgggagtggg                                                  20

<210> SEQ ID NO 3
<211> LENGTH: 24
<212> TYPE: DNA
<213> ORGANISM: Artificial Sequence
<220> FEATURE:
<223> OTHER INFORMATION: Synthetic polynucleotide sequence, Sox2 FP

<400> SEQUENCE: 3
gggaaatggg agggtgcaa aaga                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic polynucleotide sequence, Sox2 RP

<400> SEQUENCE: 4
ttgcgtgagt gtggatggga ttgg                                             24

<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide sequence, Oct4 FP

<400> SEQUENCE: 5
acatcaaagc tctgcagaaa gaact                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic polynucleotide sequence, Oct4 RP

<400> SEQUENCE: 6
ctgaatacct tcccaaatag aaccc                                            25

<210> SEQ ID NO 7
<211> LENGTH: 18
<212> TYPE: DNA
<213> ORGANISM: Artificial Sequence
<220> FEATURE:
<223> OTHER INFORMATION: Synthetic polynucleotide sequence, Nanog FP

<400> SEQUENCE: 7
agaaggcctc agcaccta                                                    18

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide sequence, Nanog RP

<400> SEQUENCE: 8
ggcctgattg ttccaggatt                                                  20
```

<210> SEQ ID NO 9
<211> LENGTH: 23
<212> TYPE: DNA
<213> ORGANISM: Artificial Sequence
<220> FEATURE:
<223> OTHER INFORMATION: Synthetic polynucleotide sequence, GAPDH FP

<400> SEQUENCE: 9
ggtggtctcc tctgacttca aca                                             23

<210> SEQ ID NO 10
<211> LENGTH: 23
<212> TYPE: DNA
<213> ORGANISM: Artificial Sequence
<220> FEATURE:
<223> OTHER INFORMATION: Synthetic polynucleotide sequence, GAPDH RP

<400> SEQUENCE: 10
gttgctgtag ccaaattcgt tgt                                             23

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide sequence, Gli1 FP

<400> SEQUENCE: 11
cccaatcaca agtcaggttc ct                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic polynucleotide sequence, Gli1 RP

<400> SEQUENCE: 12
cctatgtgaa gccctatttg cc                                              22

<210> SEQ ID NO 13
<211> LENGTH: 347
<212> TYPE: PRT
<213> ORGANISM: Homo sapiens

<400> SEQUENCE: 13

Met Leu His Thr Thr Gln Leu Tyr Gln His Val Pro Glu Thr Arg Trp
1               5                   10                  15

Pro Ile Val Tyr Ser Pro Arg Tyr Asn Ile Thr Phe Met Gly Leu Glu
            20                  25                  30

Lys Leu His Pro Phe Asp Ala Gly Lys Trp Gly Lys Val Ile Asn Phe
        35                  40                  45

Leu Lys Glu Glu Lys Leu Leu Ser Asp Ser Met Leu Val Glu Ala Arg
    50                  55                  60

Glu Ala Ser Glu Glu Asp Leu Leu Val Val His Thr Arg Arg Tyr Leu
65                  70                  75                  80

Asn Glu Leu Lys Trp Ser Phe Ala Val Ala Thr Ile Thr Glu Ile Pro
                85                  90                  95

Pro Val Ile Phe Leu Pro Asn Phe Leu Val Gln Arg Lys Val Leu Arg
            100                 105                 110

Pro Leu Arg Thr Gln Thr Gly Gly Thr Ile Met Ala Gly Lys Leu Ala

```
            115                 120                 125
Val Glu Arg Gly Trp Ala Ile Asn Val Gly Gly Phe His His Cys
    130                 135                 140

Ser Ser Asp Arg Gly Gly Gly Phe Cys Ala Tyr Ala Asp Ile Thr Leu
145                 150                 155                 160

Ala Ile Lys Phe Leu Phe Glu Arg Val Glu Gly Ile Ser Arg Ala Thr
                165                 170                 175

Ile Ile Asp Leu Asp Ala His Gln Gly Asn Gly His Glu Arg Asp Phe
            180                 185                 190

Met Asp Asp Lys Arg Val Tyr Ile Met Asp Val Tyr Asn Arg His Ile
        195                 200                 205

Tyr Pro Gly Asp Arg Phe Ala Lys Gln Ala Ile Arg Arg Lys Val Glu
    210                 215                 220

Leu Glu Trp Gly Thr Glu Asp Glu Tyr Leu Asp Lys Val Glu Arg
225                 230                 235                 240

Asn Ile Lys Lys Ser Leu Gln Glu His Leu Pro Asp Val Val Tyr
                245                 250                 255

Asn Ala Gly Thr Asp Ile Leu Glu Gly Asp Arg Leu Gly Gly Leu Ser
            260                 265                 270

Ile Ser Pro Ala Gly Ile Val Lys Arg Asp Glu Leu Val Phe Arg Met
        275                 280                 285

Val Arg Gly Arg Val Pro Ile Leu Met Val Thr Ser Gly Gly Tyr
    290                 295                 300

Gln Lys Arg Thr Ala Arg Ile Ile Ala Asp Ser Ile Leu Asn Leu Phe
305                 310                 315                 320

Gly Leu Gly Leu Ile Gly Pro Glu Ser Pro Ser Val Ser Ala Gln Asn
                325                 330                 335

Ser Asp Thr Pro Leu Leu Pro Pro Ala Val Pro
            340                 345

<210> SEQ ID NO 14
<211> LENGTH: 296
<212> TYPE: PRT
<213> ORGANISM: Homo sapiens

<400> SEQUENCE: 14

Met Gly Leu Glu Lys Leu His Pro Phe Asp Ala Gly Lys Trp Gly Lys
1               5                   10                  15

Val Ile Asn Phe Leu Lys Glu Lys Leu Leu Ser Asp Ser Met Leu
                20                  25                  30

Val Glu Ala Arg Glu Ala Ser Glu Glu Asp Leu Leu Val Val His Thr
            35                  40                  45

Arg Arg Tyr Leu Asn Glu Leu Lys Arg Lys Val Leu Arg Pro Leu Arg
        50                  55                  60

Thr Gln Thr Gly Gly Thr Ile Met Ala Gly Lys Leu Ala Val Glu Arg
65                  70                  75                  80

Gly Trp Ala Ile Asn Val Gly Gly Phe His His Cys Ser Ser Asp
                85                  90                  95

Arg Gly Gly Gly Phe Cys Ala Tyr Ala Asp Ile Thr Leu Ala Ile Lys
            100                 105                 110

Phe Leu Phe Glu Arg Val Glu Gly Ile Ser Arg Ala Thr Ile Ile Asp
        115                 120                 125

Leu Asp Ala His Gln Gly Asn Gly His Glu Arg Asp Phe Met Asp Asp
    130                 135                 140
```

```
Lys Arg Val Tyr Ile Met Asp Val Tyr Asn Arg His Ile Tyr Pro Gly
145                 150                 155                 160

Asp Arg Phe Ala Lys Gln Ala Ile Arg Arg Lys Val Glu Leu Glu Trp
                165                 170                 175

Gly Thr Glu Asp Asp Glu Tyr Leu Asp Lys Val Glu Arg Asn Ile Lys
            180                 185                 190

Lys Ser Leu Gln Glu His Leu Pro Asp Val Val Tyr Asn Ala Gly
        195                 200                 205

Thr Asp Ile Leu Glu Gly Asp Arg Leu Gly Gly Leu Ser Ile Ser Pro
210                 215                 220

Ala Gly Ile Val Lys Arg Asp Glu Leu Val Phe Arg Met Val Arg Gly
225                 230                 235                 240

Arg Arg Val Pro Ile Leu Met Val Thr Ser Gly Gly Tyr Gln Lys Arg
                245                 250                 255

Thr Ala Arg Ile Ile Ala Asp Ser Ile Leu Asn Leu Phe Gly Leu Gly
            260                 265                 270

Leu Ile Gly Pro Glu Ser Pro Ser Val Ser Ala Gln Asn Ser Asp Thr
        275                 280                 285

Pro Leu Leu Pro Pro Ala Val Pro
    290                 295

<210> SEQ ID NO 15
<211> LENGTH: 268
<212> TYPE: PRT
<213> ORGANISM: Homo sapiens

<400> SEQUENCE: 15

Met Leu His Thr Thr Gln Leu Tyr Gln His Val Pro Glu Thr Arg Trp
1               5                   10                  15

Pro Ile Val Tyr Ser Pro Arg Tyr Asn Ile Thr Phe Met Gly Leu Glu
                20                  25                  30

Lys Leu His Pro Phe Asp Ala Gly Lys Trp Gly Lys Val Ile Asn Phe
            35                  40                  45

Leu Lys Glu Glu Lys Leu Leu Ser Asp Ser Met Leu Val Glu Ala Arg
50                  55                  60

Glu Ala Ser Glu Glu Asp Leu Val Val His Thr Arg Arg Tyr Leu
65                  70                  75                  80

Asn Glu Leu Lys Phe Leu Phe Glu Arg Val Glu Gly Ile Ser Arg Ala
                85                  90                  95

Thr Ile Ile Asp Leu Asp Ala His Gln Gly Asn Gly His Glu Arg Asp
            100                 105                 110

Phe Met Asp Asp Lys Arg Val Tyr Ile Met Asp Val Tyr Asn Arg His
        115                 120                 125

Ile Tyr Pro Gly Asp Arg Phe Ala Lys Gln Ala Ile Arg Arg Lys Val
130                 135                 140

Glu Leu Glu Trp Gly Thr Glu Asp Asp Glu Tyr Leu Asp Lys Val Glu
145                 150                 155                 160

Arg Asn Ile Lys Lys Ser Leu Gln Glu His Leu Pro Asp Val Val Val
                165                 170                 175

Tyr Asn Ala Gly Thr Asp Ile Leu Glu Gly Asp Arg Leu Gly Gly Leu
            180                 185                 190

Ser Ile Ser Pro Ala Gly Ile Val Lys Arg Asp Glu Leu Val Phe Arg
        195                 200                 205

Met Val Arg Gly Arg Arg Val Pro Ile Leu Met Val Thr Ser Gly Gly
210                 215                 220
```

```
Tyr Gln Lys Arg Thr Ala Arg Ile Ile Ala Asp Ser Ile Leu Asn Leu
225                 230                 235                 240

Phe Gly Leu Gly Leu Ile Gly Pro Glu Ser Pro Ser Val Ser Ala Gln
                245                 250                 255

Asn Ser Asp Thr Pro Leu Leu Pro Pro Ala Val Pro
                260                 265
```